(12) United States Patent
Tansey et al.

(10) Patent No.: US 12,398,097 B2
(45) Date of Patent: Aug. 26, 2025

(54) WDR5-MYC INHIBITORS

(71) Applicant: Vanderbilt University, Nashville, TN (US)

(72) Inventors: William P. Tansey, Brentwood, TN (US); Stephen W. Fesik, Nashville, TN (US); Shaun R. Stauffer, Brentwood, TN (US); Alex G. Waterson, Nashville, TN (US); Changho Han, Nashville, TN (US); Joseph R. Alvarado, Cleveland Heights, OH (US); Jonathan D. MacDonald, Nashville, TN (US); Selena Chacon Simon, Nashville, TN (US); Sameer S. Nikhar, Nashville, TN (US); Alexey Kuznetsov, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 861 days.

(21) Appl. No.: 17/631,114

(22) PCT Filed: Jul. 29, 2020

(86) PCT No.: PCT/US2020/044097
§ 371 (c)(1),
(2) Date: Aug. 11, 2022

(87) PCT Pub. No.: WO2021/021951
PCT Pub. Date: Feb. 4, 2021

(65) Prior Publication Data
US 2022/0289673 A1    Sep. 15, 2022

Related U.S. Application Data

(60) Provisional application No. 62/880,032, filed on Jul. 29, 2019.

(51) Int. Cl.
| | |
|---|---|
| *C07C 311/21* | (2006.01) |
| *C07C 311/29* | (2006.01) |
| *C07C 311/39* | (2006.01) |
| *C07C 311/43* | (2006.01) |
| *C07C 317/34* | (2006.01) |
| *C07C 317/38* | (2006.01) |
| *C07C 317/48* | (2006.01) |
| *C07C 323/49* | (2006.01) |

(Continued)

(52) U.S. Cl.
CPC .......... *C07C 311/21* (2013.01); *C07C 311/29* (2013.01); *C07C 311/39* (2013.01); *C07C 311/43* (2013.01); *C07C 317/34* (2013.01); *C07C 317/38* (2013.01); *C07C 317/48* (2013.01); *C07C 323/49* (2013.01); *C07C 381/00* (2013.01); *C07D 205/04* (2013.01); *C07D 207/08* (2013.01); *C07D 207/12* (2013.01); *C07D 207/27* (2013.01); *C07D 211/48* (2013.01); *C07D 213/40* (2013.01); *C07D 213/56* (2013.01); *C07D 213/64* (2013.01); *C07D 215/36* (2013.01); *C07D 233/36* (2013.01); *C07D 239/26* (2013.01); *C07D 241/04* (2013.01); *C07D 249/14* (2013.01); *C07D 265/30* (2013.01); *C07D 305/08* (2013.01); *C07D 307/14* (2013.01); *C07D 307/18* (2013.01); *C07D 307/22* (2013.01); *C07D 307/52* (2013.01); *C07D 307/79* (2013.01); *C07D 309/04* (2013.01); *C07D 309/10* (2013.01); *C07D 309/14* (2013.01); *C07D 309/22* (2013.01); *C07D 333/20* (2013.01); *C07D 333/24* (2013.01)

(58) Field of Classification Search
CPC ... C07C 311/21; C07C 311/29; C07C 311/39; C07C 311/43; C07C 317/34; C07C 317/38; C07C 317/48; C07C 323/49; C07C 381/00; C07D 205/04; C07D 207/08; C07D 207/12; C07D 207/27; C07D 211/48; C07D 213/40; C07D 213/56; C07D 213/64; C07D 215/36; C07D 233/36; C07D 239/26; C07D 241/04; C07D 249/14; C07D 265/30; C07D 305/08; C07D 307/14; C07D 307/18; C07D 307/22; C07D 307/52; C07D 307/79; C07D 309/04; C07D 309/10; C07D 309/14; C07D 309/22; C07D 333/20; C07D 333/24
USPC .................................................. 514/210.17
See application file for complete search history.

(56) References Cited

U.S. PATENT DOCUMENTS

| | | |
|---|---|---|
| 4,282,375 A | 8/1981 | Bernstein et al. |
| 2004/0024258 A1 | 2/2004 | Drent et al. |

(Continued)

FOREIGN PATENT DOCUMENTS

| | | |
|---|---|---|
| CN | 104000824 A | 8/2014 |
| DE | 3613009 A1 | 10/1986 |

(Continued)

OTHER PUBLICATIONS

Cancer [online], [retrieved on Jul. 6, 2007] Retrieved from the Internet, URL: http://www.nim.nih.gov/medlineplus/cancer.html (Year: 2007).*

(Continued)

Primary Examiner — Kristin A Vajda
(74) Attorney, Agent, or Firm — Michael Best & Friedrich LLP

(57) ABSTRACT

Substituted N-phenyl sulfonamide compounds inhibit WDR5-MYC interactions, and the compounds and their pharmaceutical compositions are useful for treating disorders and conditions in a subject, such as cancer cell proliferation.

18 Claims, 2 Drawing Sheets

(51) Int. Cl.

| | | |
|---|---|---|
| C07C 381/00 | (2006.01) | |
| C07D 205/04 | (2006.01) | |
| C07D 207/08 | (2006.01) | |
| C07D 207/12 | (2006.01) | |
| C07D 207/27 | (2006.01) | |
| C07D 211/48 | (2006.01) | |
| C07D 213/40 | (2006.01) | |
| C07D 213/56 | (2006.01) | |
| C07D 213/64 | (2006.01) | |
| C07D 215/36 | (2006.01) | |
| C07D 233/36 | (2006.01) | |
| C07D 239/26 | (2006.01) | |
| C07D 241/04 | (2006.01) | |
| C07D 249/14 | (2006.01) | |
| C07D 265/30 | (2006.01) | |
| C07D 305/08 | (2006.01) | |
| C07D 307/14 | (2006.01) | |
| C07D 307/18 | (2006.01) | |
| C07D 307/22 | (2006.01) | |
| C07D 307/52 | (2006.01) | |
| C07D 307/79 | (2006.01) | |
| C07D 309/04 | (2006.01) | |
| C07D 309/10 | (2006.01) | |
| C07D 309/14 | (2006.01) | |
| C07D 309/22 | (2006.01) | |
| C07D 333/20 | (2006.01) | |
| C07D 333/24 | (2006.01) | |

(56) References Cited

U.S. PATENT DOCUMENTS

| | | |
|---|---|---|
| 2006/0069269 A1 | 3/2006 | Amrein et al. |
| 2007/0042997 A1* | 2/2007 | Itai .................. A61P 43/00 514/408 |
| 2007/0191603 A1 | 8/2007 | Ackermann et al. |
| 2009/0163545 A1 | 6/2009 | Goldfarb |
| 2010/0120779 A1 | 5/2010 | Haydar et al. |
| 2023/0022304 A1 | 1/2023 | Simon et al. |

FOREIGN PATENT DOCUMENTS

| | | | |
|---|---|---|---|
| DE | 19509950 A1 | 9/1996 | |
| JP | H02111943 A | 4/1990 | |
| JP | H07219177 A | 8/1995 | |
| JP | 2001066745 A | 3/2001 | |
| JP | 2003292485 A | 10/2003 | |
| WO | 2002032863 A1 | 4/2002 | |
| WO | 2004064728 A2 | 8/2004 | |
| WO | 2004073634 A2 | 9/2004 | |
| WO | 2004103980 A1 | 12/2004 | |
| WO | 2005097764 A1 | 10/2005 | |
| WO | 2006010629 A1 | 2/2006 | |
| WO | 2006020830 A2 | 2/2006 | |
| WO | 2006051662 A1 | 5/2006 | |
| WO | 2006137376 A1 | 12/2006 | |
| WO | WO-2007076055 A2 * | 7/2007 | ............. A61K 31/44 |
| WO | 2007093507 A1 | 8/2007 | |
| WO | 2007100066 A1 | 9/2007 | |
| WO | 2007110171 A1 | 10/2007 | |
| WO | 2010026365 A1 | 3/2010 | |
| WO | 2011161201 A1 | 12/2011 | |
| WO | 2012064744 A2 | 5/2012 | |
| WO | 2012177668 A1 | 12/2012 | |
| WO | 2015088000 A1 | 6/2015 | |
| WO | 2016130818 A1 | 8/2016 | |
| WO | 2016133160 A1 | 8/2016 | |
| WO | 2016199906 A1 | 12/2016 | |
| WO | 2016203112 A1 | 12/2016 | |
| WO | 2017075185 A1 | 5/2017 | |
| WO | 2021101927 A1 | 5/2021 | |

OTHER PUBLICATIONS

Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Patel et al., "Structure of WDR5 Bound to Mixed Lineage Leukemia Protein-1 Peptide", J. Biol. Chem., 2008, vol. 283, No. 47, pp. 32158-32161.
Pubchem SID 227036496, available Feb. 12, 2015, <https://pubchem.ncbi.nlm.nih.gov/substance/227036496>, 8 pages.
Pubchem SID 315001332, available Jun. 16, 2016, <https://pubchem.ncbi.nlm.nih.gov/substance/315001332>, 6 pages.
Richards et al., "Structural Basis of N-Myc Binding by Aurora-A and Its Destabilization by Kinase Inhibitors", PNAS, 2016, vol. 113, No. 48, pp. 13726-13731.
Sackton et al., "Synergistic Blockade of Mitotic Exit by Two Chemical Inhibitors of the APC/C", Nature, 2014, vol. 514, No. 7524, pp. 646-649.
Schanda et al., "SOFAST-HMQC Experiments for Recording Two-Dimensional Deteronuclear Correlation Spectra of Proteins within a Few Seconds", J. Biomol. NMR, 2005, vol. 33, No. 4, pp. 199-211.
Schapira et al., "WD40 Repeat Domain Proteins: A Novel Target Class?", Nat. Publ. Gr. 2017, 773-786.
Scozzafava, A., et al. "Carbonic anhydrase inhibitors: perfluoroalkyl/aryl-substituted derivatives of aromatic/heterocyclic sulfonamides as topical intraocular pressure-lowering agents with prolonged duration of action." Journal of medicinal chemistry 43.23 (2000): 4542-4551.
Singh, J. et al. "Estimation of human carbonic anhydrase II inhibition using topological indices and their combination with quantum-theoretical descriptors." Medicinal Chemistry 4.1 (2008): 30-66.
Smith et al., "The WD Repeat: A Common Architecture for Diverse Functions", Trends Biochem. Sci., 1999, vol. 24, No. 5, pp. 181-185.
Song et al., "Disease Association and Druggability of WD40 Repeat Proteins", J. Proteome Res., 2017, vol. 16, No. 10, pp. 3766-3773.
Song et al., "WDR5 Interacts with Mixed Lineage Leukemia (MLL) Protein via the Histone H3-Binding Pocket", J. Biol. Chem., 2008, vol. 283, No. 50, pp. 35258-35264.
Soucek et al., "Inhibition of Myc family proteins eradicates KRas-driven lung cancer in mice", Genes Dev, 2013, vol. 27, pp. 504-513.
Southall et al., "Structural Basis for the Requirement of Additional Factors for MLL1 Set Domain Activity and Recognition of Epigenetic Marks", Mol. Cell, 2009, vol. 33 No. 2, pp. 181-191.
Spencer CA; et al. Control of C-Myc Regulation in Normal and Neoplastic Cells. Adv. Cancer Res 1991, 56, 1-48.
Stirnimann et al., "WD40 Proteins Propel Cellular Networks", Trends Biochem. Sci., 2010, vol. 35, pp. 565-574.
Sun et al., "WDR5 supports an N-Myc transcriptional complex that drives a pro-tumorigenic gene expression signature in neuroblastoma", Cancer Res., 2015, vol. 75, pp. 5143-5154.
Supuran, C. T., et al. "Sulfonylamido derivatives of 2-aminophenoxathiin-10, 10-dioxide and related compounds possess antifungal action due to the possible inhibition of lanosterol-14-α-demethylase." Journal of enzyme inhibition 13.4 (1998): 291-310.
Tansey, "Mammalian MYC proteins and cancer", New Journal of Science, 2014, pp. 1-27.
Thomas et al., "Interaction with WDR5 Promotes Target Gene Recognition and Tumorigenesis by MYC", Mol. Cell, 2015, vol. 58, pp. 440-452.
Thomas, L. R., et al. "The MYC-WDR5 nexus and cancer." Cancer research 75.19 (2015): 4012-4015.
Wang et al., "Discovery of Potent 2-Aryl-6,7-Dihydro-5H-Pyrrolo[1,2-a]Imidazoles as WDR5-WIN-Site Inhibitors Using Fragment-Based Methods and Structure-Based Design", J. Med. Chem., 2018, vol. 61, No. 13, pp. 5623-5642.

(56) References Cited

OTHER PUBLICATIONS

Wang H; et al. Disruption of Myc-Max Heterodimerization with Improved Cell-Penetrating Analogs of the Small Molecule 10074-G5. Oncotarget 2013, 4 (6), 936-949.
Wang, T. et al. "Hexadehydro-Diels-Alder (HDDA)-enabled carbazolyne chemistry: single step, de novo construction of the pyranocarbazole core of alkaloids of the Murraya koenigii (curry tree) family." Journal of the American Chemical Society 138.42 (2016): 13870-13873.
Wenglowsky, S., et al. "Pyrazolopyridine inhibitors of B-RafV600E. Part 2: Structure-activity relationships." Bioorganic & medicinal chemistry letters 21.18 (2011): 5533-5537.
Whitfield Jr; et al. Strategies to Inhibit Myc and Their Clinical Applicability. Front. Cell Dev. Biol 2017, 5, 10.
Winn et al., "Overview of the CCP4 Suite and Current Developments", Acta Crystallogr. Sect. D, 2011, vol. 67, pp. 235-242.
Xu et al., "Structure and Function of WD40 Domain Proteins", Protein Cell, 2011, vol. 2, No. 3, pp. 202-214.
Yang et al., "Essential Role of LncRNA Binding for WDR5 Maintenance of Active Chromatin and Embryonic Stem Cell Pluripotency", Elife, 2014, 3, e02046.
Yang F; et al. Interactive Association of Drugs Binding to Human Serum Albumin. Int. J. Mol. Sci 2014, 15 (3), 3580-3595.
Yin X; et al. Low Molecular Weight Inhibitors of Myc-Max Interaction and Function. Oncogene 2003, 22 (40), 6151-6159.
Adams et al., "PHENIX: Building New Software for Automated Crystallographic Structure Determination", Acta Crystallogr. Sect. D, 2002, vol. 58, pp. 1948-1954.
Aho et al., "Displacement of WDR5 from Chromatin by a WIN Site Inhibitor with Picomolar Affinity", Cell Rep., 2019, vol. 26, No. 11, pp. 2916-2928.
Allen, B. K., et al. "Identification of a novel class of BRD4 inhibitors by computational screening and binding simulations." ACS omega 2.8 (2017): 4760-4771.
Allen, B. K., et al. "Large-Scale Computational Screening Identifies First in Class Multitarget Inhibitor of EGFR Kinase and BRD4." Scientific reports 5 (2015): 16924.
Altomonte S; et al. Synthetic Chemistry and Biological Activity of Pentafluorosulphanyl Organic Molecules. J. Fluor. Chem 2012, 143, 57-93.
Avdic et al., "Structural and Biochemical Insights into MLL1 Core Complex Assembly", Structure, 2011, vol. 19, No. 1, pp. 101-108.
Bano, B., et al. "Synthesis, in vitro β-glucuronidase inhibitory potential and molecular docking studies of quinolines." European Journal of Medicinal Chemistry 139 (2017): 849-864.
Barnes-Seeman D et al. Metabolically Stable Tert-Butyl Replacement. ACS Med. Chem. Lett 2013, 4, 514-516.
Bayliss et al., "A Moving Target: Structure and Disorder in Pursuit of Myc Inhibitors", Biochem. Soc. Trans., 2017, vol. 45, No. 3, pp. 709-717.
Berg T; et al. Small-Molecule Antagonists of Myc/Max Dimerization Inhibit Myc-Induced Transformation of Chicken Embryo Fibroblasts. Proc. Natl. Acad. Sci. U. S. A 2002, 99 (6), 3830-3835.
Beroukhim R; et al. The Landscape of Somatic Copy-Number Alteration across Human Cancers. Nature 2010, 463 (7283), 899-905.
Blus, K. et al. "Synthesis and properties of aminoarylsulphonanilide-3', 5'-dicarboxylic acids." Dyes and pigments 13.3 (1990): 233-240.
Blus, K., et al. "The influence of arylamide groups on the properties of acid dyes." Dyes and pigments 22.3 (1993): 163-172.
Cao F; et al. Targeting MLL1 H3K4 Methyltransferase Activity in Mixed-Lineage Leukemia. Mol. Cell 2014, 53 (2), 247-261.
Chacon Simon, S., et al. "Discovery of WD repeat-containing protein 5 (WDR5)-MYC inhibitors using fragment-based methods and structure-based design." Journal of medicinal chemistry 63.8 (2020): 4315-4333.
Clare, B. W., et al. "Predictive flip regression: A technique for QSAR of derivatives of symmetric molecules." Journal of chemical information and modeling 45.5 (2005): 1385-1391.

Conacci-Sorrell et al., "An overview of MYC and its interactome", Perspectives in Medicine, 2014, vol. 4, a014357.
Cyr P; et al. Mild and Diazo-Free Synthesis of Trifluoromethyl-Cyclopropanes Using Sulfonium Ylides. Org. Lett 2019, 21, 2265-2268.
Dang CV; et al. Drugging the "undruggable" Cancer Targets. Nat. Rev. Cancer 2017, 17 (8), 502-508.
Dang, "Therapeutic targeting of Myc-reprogrammed cancer cell metabolism", Symposia on Quantitative Biology, 2011, vol. 76, pp. 369-374.
Delmore et al., "ET bromodomain inhibition as a therapeutic strategy to target c-Myc", Cell, 2011, vol. 146, pp. 904-917.
Dias et al., "Structural Analysis of the KANSL1/WDR5/ KANSL2 Complex Reveals That WDR5 Is Required for Efficient Assembly and Chromatin Targeting of the NSL Complex", Genes Dev., 2014, vol. 28, No. 9, pp. 929-942.
Emsley et al., "Coot: Model-Building Tools for Molecular Graphics", Acta Crystallogr. Sect. D, 2004, vol. 60, pp. 2126-2132.
English, J. P., et al. "Studies in Chemotherapy. XIV. Antimalarials. The Synthesis of Substituted Metanilamides and Related Compounds1." Journal of the American Chemical Society 68.6 (1946): 1039-1049.
Getlik et al., "Structure-Based Optimization of a Small Molecule Antagonist of the Interaction Between WD Repeat-Containing Protein 5 (WDR5) and Mixed-Lineage Leukemia 1 (MLL1)", J. Med. Chem., 2016, vol. 59, No. 6, pp. 2478-2496.
Grebien et al., "Pharmacological Targeting of the Wdr5-MLL Interaction in C/EBPα N-Terminal Leukemia", Nat. Chem. Biol., 2015, vol. 11, No. 8, pp. 571-578.
Guarnaccia et al., "Moonlighting with WDR5: A Cellular Multitasker", J. Clin. Med., 2018, vol. 7, No. 2, 21.
Gustafson et al., "Drugging MYCN through an Allosteric Transition in Aurora Kinase A", Cancer Cell, 2014, vol. 26, No. 3, pp. 414-427.
Hart Jr et al. Inhibitor of MYC Identified in a Krohnke Pyridine Library. Proc. Natl. Acad. Sci 2014, 111 (34), 12556-12561.
Hultquist, M. E., et al. "N-Heterocyclic benzenesulfonamides." Journal of the American Chemical Society 73.6 (1951): 2558-2566.
International Search Report and Written Opinion for Application No. PCT/US2020/044097 dated Dec. 14, 2020 (14 pages).
Kalkat M; et al. MYC Protein Interactome Profiling Reveals Functionally Distinct Regions That Cooperate to Drive Tumorigenesis. Mol. Cell 2018, 72 (5), 836-848.
Karatas et al., "Discovery of a Highly Potent, Cell-Permeable Macrocyclic Peptidomimetic (MM-589) Targeting the WD Repeat Domain 5 Protein (WDR5)-Mixed Lineage Leukemia (MLL) Protein-Protein Interaction", J. Med. Chem., 2017, vol. 60, No. 12, pp. 4818-4839.
Karatas et al., "High-Affinity, Small-Molecule Peptidomimetic Inhibitors of MLL1/WDR5 Protein-Protein Interaction", J. Am. Chem. Soc., 2013, vol. 135, No. 2, pp. 669-682.
Kiessling A; et al. Selective Inhibition of C-Myc/Max Dimerization and DNA Binding by Small Molecules. Chem. Biol 2006, 13 (7), 745-751.
Kramer SE et al. The Binding of Salicylic Acid and Acetylsalicylic Acid to Human Serum Albumin. Clin. Biochem 1973, 6 (C), 98-105.
Li et al., "Structural Basis for Activity Regulation of MLL Family Methyltransferases", Nature 2016, vol. 530 , No. 7591, pp. 447-452.
Li, D.-D., et al. "High-affinity small molecular blockers of mixed lineage leukemia 1 (MLL1)-WDR5 interaction inhibit MLL1 complex H3K4 methyltransferase activity." European journal of medicinal chemistry 124 (2016): 480-489.
Li, Y., et al. "Insight into the Structural Features of Pyrazolopyrimidine- and Pyrazolopyridine-based B-RafV600E Kinase Inhibitors by Computational Explorations." Chemical Biology & Drug Design 83.6 (2014): 643-655.
Lorenzin et al., "Different promoter affinities account for specificity in MYC-dependent gene regulation", eLife 5, 2016, e15161.
MacDonald, J. D., et al. "Discovery and optimization of salicylic acid-derived sulfonamide inhibitors of the WD repeat-containing protein 5-MYC protein-protein interaction." Journal of medicinal chemistry 62.24 (2019): 11232-11259.

(56) References Cited

OTHER PUBLICATIONS

Mattioni, B. E., et al. "Development of quantitative structure-activity relationship and classification models for a set of carbonic anhydrase inhibitors." Journal of chemical information and computer sciences 42.1 (2002): 94-102.

McKeown MR; et al. Therapeutic Strategies to Inhibit MYC. Cold Spring Harb. Perspect. Med 2014, 4 (10), 1-16.

Nagahara, T., et al. "Design and synthesis of non-peptide, selective orexin receptor 2 agonists." Journal of medicinal chemistry 58.20 (2015): 7931-7937.

Nicholls A; et al. Molecular Shape and Medicinal Chemistry: A Perspective. J. Med. Chem 2010, 53 (10), 3862-3886.

Odho et al., "Characterization of a Novel WDR5-Binding Site That Recruits RbBP5 through a Conserved Motif to Enhance Methylation of Histone H3 Lysine 4 by Mixed Lineage Leukemia Protein-1", J. Biol. Chem., 2010, vol. 285, No. 43, pp. 32967-32976.

Orlicky et al., "An Allosteric Inhibitor of Substrate Recognition by the SCFCdc4 Ubiquitin Ligase", Nat. Biotechnol 2010, 28 (4), 733-738.

Otwinowski et al., "Processing of X-Ray Diffraction Data Collected in Oscillation Mode", Methods Enzymol., 1997, vol. 276, pp. 307-326.

Patel A; et al. On the Mechanism of Multiple Lysine Methylation by the Human Mixed Lineage Leukemia Protein-1 (MLL1) Core Complex. J. Biol. Chem 2009, 284 (36), 24242-24256.

Patel et al., "A Conserved Arginine-Containing Motif Crucial for the Assembly and Enzymatic Activity of the Mixed Lineage Leukemia Protein-1 Core Complex", J. Biol. Chem., 2008, vol. 283, No. 47, pp. 32162-32175.

\* cited by examiner

WDR5-MYC INHIBITORS

RELATED APPLICATIONS

This patent application is the U.S. national stage entry, under 35 U.S.C. § 371, of International Application Number PCT/US2020/044097, filed Jul. 29, 2020, which claims priority to U.S. Provisional Application No. 62/880,032, filed Jul. 29, 2019, the entire contents of each of which are hereby incorporated by reference.

STATEMENT OF GOVERNMENT INTEREST

This invention was made with government support under Contract No. HHSN261200800001E, awarded by the National Institutes of Health. The government has certain rights in the invention.

TECHNICAL FIELD

The present disclosure relates to compounds, compositions, and methods for treating MYC-related cancers, such as ovarian cancer, breast cancer, colorectal cancer, pancreatic cancer, gastric cancer, stomach cancer, lung cancer, cervical cancer, uterine cancer, cancers of the blood, and cancers of the lymphatic system.

BACKGROUND

The MYC oncogenes (c-, N-, and L-MYC) encode a family of related transcription factors (hereafter "MYC") that are overexpressed in the majority of malignancies and contribute to ~100,000 cancer related deaths annually in the USA alone. MYC drives tumorigenesis by dimerizing with its obligate partner MAX to form a sequence-specific transcription factor that controls the expression of genes linked to cell growth, metabolism, proliferation, and genome instability (Tansey 2014). Unlike many oncogenes, activation of MYC is not dependent on changes to its protein sequence, but instead results from mutations that increase MYC expression, either by altering MYC gene copy number or location, or by subverting regulatory mechanisms that normally restrict MYC accumulation. The advantages of MYC overexpression to a cancer cell—together with the myriad of ways this can occur-means that increased MYC levels are common in cancer, and has led to the concept that loss of control of MYC underlies the etiology of all malignancies (Conacci-Sorrell et al. 2014).

The pervasive involvement of MYC in cancer has fueled interest in the notion that MYC can be targeted to treat malignancies. It is clear that attenuating MYC expression or activity in the context of an existing cancer promotes tumor regression in mice (Conacci-Sorrell et al. 2014), even in cases where MYC is not the primary oncogenic driver (Soucek et al. 2013). A number of strategies have been developed to mitigate MYC overexpression in cancer (Delmore et al. 2011), or to interfere with processes hijacked by MYC in the malignant state (Dang 2011), but in terms of directly blocking MYC function, there appears to be few if any viable options. Indeed, the obvious route to direct MYC inhibition-disrupting interaction with MAX—is daunting, as the MYC:MAX interface is large and tight, and not readily amenable to inhibition by drug-like molecules. Accordingly, there exists a need for small molecule modulators of MYC that selectively interact with and disrupt the oncogenic activity of MYC.

Recently, it emerged that target gene recognition by MYC does not solely depend on the DNA-binding characteristics of MYC:MAX dimers, and that additional factors can facilitate MYC recruitment to chromatin. Modeling reveals that upwards of 90% of MYC binding events cannot be accounted for in terms of the affinity of MYC:MAX dimers for DNA (Lorenzin et al. 2016), and that even weak interactions ($K_d$ ~10 µM) with chromatin resident-proteins could stabilize MYC:MAX dimers and explain MYC binding patterns observed in vivo. If the factors that facilitate recruitment of MYC to chromatin can be identified, they could serve as novel therapeutic targets for blocking this basic MYC function in cancer cells. One such factor that facilitates recruitment of MYC to chromatin is the WD40-repeat protein WDR5 (Thomas et al. 2015).

WD40-repeat proteins are a ubiquitous family of scaffolding proteins, containing ß-propeller domains that form donut-shaped structures which participate in many multi-protein complexes. WDR5 scaffolds the assembly of protein complexes related to chromatin structure and epigenetic modifications. Like most WD40-repeat proteins, WDR5 is involved in many direct and indirect protein-protein interactions, but all known direct partners of WDR5 interact through one of two sites, referred to as the "WDR5-interaction" (WIN) site and the "WDR5 binding motif" (WBM) site.

The interaction of c-MYC and L-MYC with the WBM site of WDR5 has been previously described (Thomas et al., 2015), and it has been further reported that WDR5 is a crucial partner in the facilitated recruitment of MYC to chromatin. N-MYC also binds WDR5 (Sun et al. 2015). Co-immunoprecipitation and X-ray crystallography confirmed that WDR5 binds to the central-portion of MYC via the conserved 'MYC box' MbIIIb motif that is invariant in all MYC proteins throughout evolution. Within MbIIIb is a consensus WBM (sequence "EEIDVV") that engages the shallow hydrophobic WBM site on WDR5. Mutations in MYC that disrupt interaction with WDR5 disrupt binding of MYC to chromatin and disable its tumorigenic potential in mice, defining the MYC-WDR5 interaction as critical for MYC-driven cancer. The identification of WDR5 as a universal MYC co-factor, and the characterization of a defined WDR5-MYC interaction site, presents a potentially tractable target for small molecule inhibition of MYC-driven tumors.

SUMMARY

Disclosed herein are inhibitors or disruptors of the WDR5-MYC protein-protein interaction. The inhibitors can be compounds of formula (I) or (II). Compounds of formula (I) or (II) may bind to the WBM site of WDR5 and prevent MYC from binding to WDR5. Targeting the WBM site of WDR5 with a small molecule inhibitor may disrupt the association of MYC with WDR5 and block MYC's recruitment to key target genes required for the onset or maintenance of the tumorigenic state. As a result, inhibitors of the WDR5-MYC protein-protein interaction can result in inhibition of oncogenic processes governed by MYC and provide therapeutic benefits for cancers caused by MYC dysregulation. Overexpression and dysregulation of MYC has been implicated in a number of different cancers including, but not limited to, ovarian cancer, breast cancer, colorectal cancer, pancreatic cancer, gastric cancer, uterine cancer, and cancers of the blood. Accordingly, compounds of formula (I) or (II) can be used to treat cancers associated with MYC by preventing association of MYC with WDR5.

In one aspect, disclosed are compounds of formula (I), or pharmaceutically acceptable salts thereof,

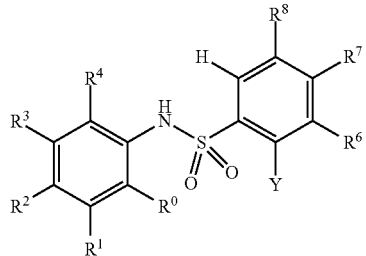

(I)

wherein
Y is —$XR^{5b}$, C(O)OH, or C(O)O$C_{1-4}$alkyl;
X is O, S, N, or $NR^{5a}$;
$R^0$ is hydrogen or halogen;
$R^1$ is halogen, cyano, $SF_5$, $C_{1-6}$alkyl, $C_{2-6}$alkenyl, $C_{1-4}$haloalkyl, —O$C_{1-4}$-alkyl, —O$C_{1-4}$haloalkyl, or $R^{1G}$;
$R^{1G}$ is $C_{3-6}$cycloalkyl, $C_{5-6}$cycloalkenyl, phenyl, a 4- to 6-membered heterocyclyl, or a 5- to 6-membered heteroaryl, wherein $R^{1G}$ is optionally substituted with 1-4 substituents independently selected from the group consisting of halogen, cyano, oxo or a cyclic ketal thereof, $C_{1-4}$alkyl, and $C_{1-4}$haloalkyl;
$R^2$ is hydrogen, $C_{1-4}$alkyl, —O$C_{1-4}$alkyl, —O$C_{1-4}$haloalkyl, halogen, or OH;
$R^3$ is C(O)O$R^{3a}$, C(O)N$R^{3b}R^{3c}$, C(O)$R^{3a}$, S$R^{3d}$, S(O)$R^{3d}$, S(O)$_2R^{3d}$, S(O)$_2$N$R^{3b}R^{3c}$, NO$_2$, N$R^{3b}$C(O)$R^{3c}$, or N$R^{3b}$C(O)N$R^{3b}R^{3c}$;
$R^{3a}$ is hydrogen, $C_{1-8}$alkyl, $C_{1-8}$haloalkyl, -$L^1$-$R^{30}$, $G^1$, or -$L^1$-$G^2$;
$R^{3b}$ and $R^{3c}$ are independently hydrogen, $C_{1-8}$alkyl, $C_{1-8}$haloalkyl, -$L^1$-$R^{30}$, $G^1$, or -$L^1$-$G^2$, wherein
$R^{3b}$ and $R^{3c}$ together with the nitrogen to which they attach optionally form a 3- to 8-membered heterocyclyl, the heterocyclyl being optionally substituted with 1-4 substituents independently selected from the group consisting of halogen, cyano, $C_{1-4}$alkyl, $C_{1-4}$haloalkyl, oxo, OH, —O$C_{1-4}$alkyl, —O$C_{1-4}$haloalkyl, —$C_{1-6}$alkylene-OH, —$C_{1-6}$alkylene-O$C_{1-4}$alkyl, NH$_2$, —NH$C_{1-4}$alkyl, —N($C_{1-4}$alkyl)$_2$, and —S(O)$_2C_{1-4}$alkyl; or
$R^{3b}$ and $R^{3c}$ together with the intervening —NC(O)— or —NC(O)N($R^{3b}$)—, optionally form a 5- to 8-membered heterocyclyl, the heterocyclyl being optionally substituted with 1-4 substituents independently selected from the group consisting of halogen, cyano, $C_{1-4}$alkyl, $C_{1-4}$haloalkyl, oxo, OH, —O$C_{1-4}$alkyl, —O$C_{1-4}$haloalkyl, NH$_2$, —NH$C_{1-4}$alkyl, and —N($C_{1-4}$alkyl)$_2$;
$R^{3d}$ is $C_{1-8}$alkyl, $C_{1-8}$haloalkyl, -$L^1$-$R^{30}$, $G^1$, or -$L^1$-$G^2$;
$L^1$ is $C_{1-6}$alkylene, wherein the $C_{1-6}$alkylene is optionally substituted with halogen, OH, COOH, —C(O)O$C_{1-4}$alkyl, C(O)NH$_2$, —C(O)NH$C_{1-4}$alkyl, or —C(O)N($C_{1-4}$ alkyl)$_2$;
$R^{3d}$ is —O$R^{30a}$, —S$R^{30a}$, —N$R^{30b}R^{30c}$, COOH, —C(O)O$C_{1-4}$alkyl, C(O)NH$_2$, —C(O)NH$C_{1-4}$alkyl, or —C(O)N($C_{1-4}$alkyl)$_2$;

$R^{30a}$, $R^{30b}$, and $R^{30c}$ are independently hydrogen, $C_{1-4}$alkyl, $C_{1-4}$haloalkyl, $G^1$, or -$L^2$-$G^2$;
$L^2$ is $C_{1-3}$alkylene;
$G^1$, at each occurrence, is independently $C_{3-10}$carbocyclyl, a 6- to 12-membered aryl, a 5- to 12-membered heteroaryl, or a 4- to 12-membered heterocyclyl, wherein $G^1$ is attached to the parent molecular moiety at a carbon atom of $G^1$ and optionally substituted with 1-5 substituents independently selected from the group consisting of halogen, cyano, $C_{1-4}$alkyl, $C_{1-4}$haloalkyl, oxo, ON, —O$C_{1-4}$alkyl, —O$C_{1-4}$haloalkyl, NH$_2$, —NH$C_{1-4}$alkyl, and —N($C_{1-4}$alkyl)$_2$;
$G^2$, at each occurrence, is independently $C_{3-10}$carbocyclyl, a 6- to 12-membered aryl, a 5- to 12-membered heteroaryl, or a 4- to 12-membered heterocyclyl, wherein $G^2$ is optionally substituted with 1-5 substituents independently selected from the group consisting of halogen, cyano, $C_{1-4}$alkyl, $C_{1-4}$haloalkyl, oxo, OH, —O$C_{1-4}$alkyl, —O$C_{1-4}$haloalkyl, NH$_2$, —NH$C_{1-4}$alkyl, and —N($C_{1-4}$alkyl)$_2$;
$R^4$ is hydrogen, halogen, OH, —O$C_{1-4}$alkyl, —O$C_{1-4}$haloalkyl, —O$C_{3-6}$cycloalkyl, NH$_2$, —NH$C_{1-4}$alkyl, —N($C_{1-4}$alkyl)$_2$, —NH$C_{3-6}$cycloalkyl, —N($C_{1-4}$alkyl)($C_{3-6}$cycloalkyl), or —N($C_{3-6}$cycloalkyl)$_2$;
$R^{5a}$ is hydrogen, $C_{1-6}$alkyl, $C_{1-6}$haloalkyl, $C_{3-6}$cycloalkyl, or —$C_{1-3}$alkylene-$C_{3-6}$cycloalkyl;
$R^{5b}$ is hydrogen, $C_{1-6}$alkyl, $C_{1-6}$haloalkyl, $C_{3-6}$cycloalkyl, or —$C_{1-3}$alkylene-$C_{3-6}$cycloalkyl; alternatively, $R^{5a}$ and $R^{5b}$, together with the nitrogen to which they attach form a 3- to 8-membered heterocyclyl, the heterocyclyl being optionally substituted with 1-4 substituents independently selected from the group consisting of halogen, cyano, $C_{1-4}$alkyl, $C_{1-4}$haloalkyl, OH, —O$C_{1-4}$alkyl, —O$C_{1-4}$haloalkyl, —$C_{1-6}$alkylene-OH, and —$C_{1-6}$alkylene-O$C_{1-4}$alkyl;
$R^6$ is hydrogen, halogen, cyano, C(O)OH, $SF_5$, NO$_2$, $C_{1-4}$alkyl, $C_{1-4}$haloalkyl, —O$C_{1-4}$alkyl, —O$C_{1-4}$haloalkyl, —$C_{1-6}$alkylene-OH, —$C_{1-6}$alkylene-O$C_{1-4}$alkyl, $C_{3-6}$cycloalkyl, or a 4- to 7-membered heterocyclyl, wherein the cycloalkyl and heterocyclyl are optionally substituted with 1-4 substituents independently selected from the group consisting of halogen, cyano, $C_{1-4}$alkyl, and $C_{1-4}$haloalkyl;
alternatively, $R^{5b}$ and $R^6$, together with the intervening atoms form a 5- to 6-membered heteroaryl or a 5- to 7-membered heterocycle, wherein the heteroaryl and heterocycle are optionally substituted with 1-4 substituents independently selected from the group consisting of halogen, cyano, $C_{1-4}$alkyl, and $C_{1-4}$haloalkyl;
$R^7$ is hydrogen, halogen, cyano, $C_{1-4}$alkyl, $C_{1-4}$haloalkyl, —O$C_{1-4}$alkyl, or —O$C_{1-4}$haloalkyl; and
$R^8$ is halogen, cyano, $C_{1-2}$alkyl, $C_{1-2}$haloalkyl, —O$C_{1-2}$alkyl, or —O$C_{1-2}$haloalkyl; provided the compound of formula (I) is not
3-[[(6-methyl-8-quinolinyl)sulfonyl]amino]-5-(trifluoromethyl)-benzoic acid;
3-[[(5-bromo-2-methoxyphenyl)sulfonyl]amino]-5-(trifluoromethyl)-benzoic acid; or
3-[[(3-bromo-5-chloro-2-methoxyphenyl)sulfonyl] amino]-5-(trifluoromethyl)-benzoic acid.
In another aspect, disclosed are compounds of formula (II), or pharmaceutically acceptable salts thereof,

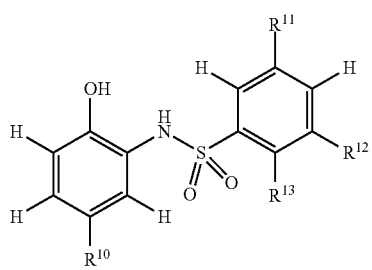

(II)

wherein
$R^{10}$ is halogen, cyano, —$C_{1-3}$alkylene-cyano, $SF_5$, $C_{1-4}$alkyl, $C_{1-4}$haloalkyl, —$OC_{1-4}$alkyl, —$OC_{1-4}$haloalkyl, or $C_{3-6}$cycloalkyl, wherein the cycloalkyl is optionally substituted with 1-4 substituents independently selected from the group consisting of halogen, cyano, $C_{1-4}$alkyl, and $C_{1-4}$haloalkyl;
$R^{11}$ is halogen;
$R^{12}$ is hydrogen or halogen; and
$R^{13}$ is hydrogen or OH.

In another aspect, the invention provides a pharmaceutical composition comprising a compound of formula (I) or (II), or a pharmaceutically acceptable salt thereof, and a pharmaceutically acceptable carrier.

In another aspect, the invention provides a method for the treatment of cancer, comprising administering to a subject in need thereof a therapeutically effective amount of a compound of formula (I) or (II), or a pharmaceutically acceptable salt or composition thereof.

In another aspect, the invention provides a method for inhibiting the binding of MYC to WDR5, comprising administering to a subject in need thereof a therapeutically effective amount of a compound of formula (I) or (II), or a pharmaceutically acceptable salt or composition thereof.

In another aspect, the invention provides a compound of formula (I) or (II), or a pharmaceutically acceptable salt or composition thereof, for use in the treatment of cancer.

In another aspect, the invention provides a compound of formula (I) or (II), or a pharmaceutically acceptable salt or composition thereof, for use in the inhibition of binding of MYC to WDR5.

In another aspect, the invention provides the use of a compound of formula (I) or (II), or a pharmaceutically acceptable salt or composition thereof, in the manufacture of a medicament for the treatment of cancer.

In another aspect, the invention provides the use of a compound of formula (I) or (II), or a pharmaceutically acceptable salt or composition thereof, in the manufacture of a medicament for the inhibition of binding of MYC to WDR5.

In another aspect, the invention provides a kit comprising a compound of formula (I) or (II), or a pharmaceutically acceptable salt or composition thereof, and instructions for use.

DETAILED DESCRIPTION

1. Definitions

Figure 1:
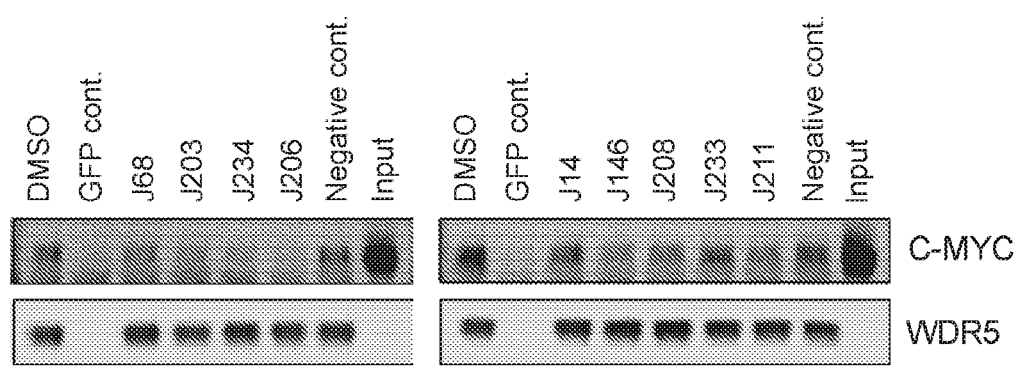
FIG. 1 shows the inhibition of binding between MYC and WDR5 for selected example compounds at a concentration of 50 µM, as described in Biological Example 2.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain saturated hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched saturated chain hydrocarbon, for example, of 1 to 6 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkenylene," as used herein, refers to a divalent group derived from a straight or branched chain hydrocarbon having at least one carbon-carbon double bond The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a carbocyclic ring system containing zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic all-carbon ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic, saturated, or partially saturated carbocyclic ring, a monocyclic heteroaryl, or a monocyclic heterocycle. The bicyclic heteroaryl group includes a 9-membered fused bicyclic aromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinvl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a heteroatom-containing ring atom (e.g., indolin-1-yl, hexahydrocyclopenta[b]pyrrol-1 (2H)-yl). Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3] heptan-2-yl, 2-oxa-6-azaspiro[3.3]heptan-6-yl, azabicyclo [2.2.1]heptyl (including 2-azabicyclo[2.2.]hept-2-yl), azabicyclo[3.1.0]hexanyl (including 3-azabicyclo[3.1.0] hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety at a heteroatom-containing ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$ alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

Aspects of the invention provide compounds of formula (I) or (II), wherein $R^0$-$R^4$, $R^6$-$R^8$, $R^{10}$-$R^{13}$, and Y are as defined herein.

In the following, embodiments of the invention are disclosed. The first embodiment is denoted E1, the second embodiment is denoted E2 and so forth.

E1. A compound of formula (I), or a pharmaceutically acceptable salt thereof,

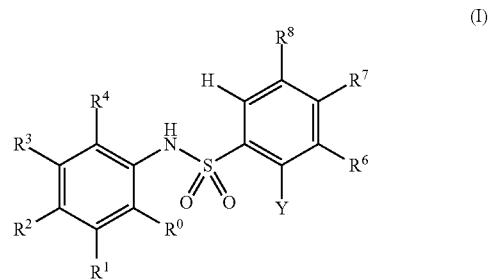

(I)

wherein
Y is —$XR^{5b}$, C(O)OH, or C(O)O$C_{1-4}$alkyl;
X is O, S, N, or $NR^{5a}$;
$R^0$ is hydrogen or halogen;
$R^1$ is halogen, cyano, $SF_5$, $C_{1-6}$alkyl, $C_{2-6}$alkenyl, $C_{1-4}$haloalkyl, —O$C_{1-4}$alkyl, —O$C_{1-4}$haloalkyl, or $R^{1G}$;
$R^{1G}$ is $C_{3-6}$cycloalkyl, $C_{5-6}$cycloalkenyl, phenyl, a 4- to 6-membered heterocyclyl, or a 5- to 6-membered heteroaryl, wherein $R^{1G}$ is optionally substituted with 1-4 substituents independently selected from the group consisting of halogen, cyano, oxo or a cyclic ketal thereof, $C_{1-4}$alkyl, and $C_{1-4}$haloalkyl;
$R^2$ is hydrogen, $C_{1-4}$alkyl, —O$C_{1-4}$alkyl, —O$C_{1-4}$haloalkyl, halogen, or OH;
$R^3$ is C(O)O$R^{3a}$, C(O)N$R^{3b}R^{3c}$, C(O)$R^{3a}$, S$R^{3d}$, S(O)$R^{3d}$, S(O)$_2R^{3d}$, S(O)$_2$N$R^{3b}R^{3c}$, $NO_2$, N$R^{3b}$C(O)$R^{3c}$, or N$R^{3b}$C(O)N$R^{3b}R^{3c}$;
$R^{3a}$ is hydrogen, $C_{1-8}$alkyl, $C_{1-8}$haloalkyl, -$L^1$-$R^{30}$, $G^1$, or -$L^1$-$G^2$;
$R^{3b}$ and $R^{3c}$ are independently hydrogen, $C_{1-8}$alkyl, $C_{1-8}$haloalkyl, -$L^1$-$R^{30}$, $G^1$, or -$L^1$-$G^2$, wherein
$R^{3b}$ and $R^{3c}$ together with the nitrogen to which they attach optionally form a 3- to 8-membered heterocyclyl, the heterocyclyl being optionally substituted with 1-4 substituents independently selected from the group consisting of halogen, cyano, $C_{1-4}$alkyl, $C_{1-4}$haloalkyl, oxo, OH, —O$C_{1-4}$alkyl, —O$C_{1-4}$haloalkyl, —$C_{1-6}$alkylene-OH, —$C_{1-6}$alkylene-O$C_{1-4}$alkyl, $NH_2$, —NH$C_{1-4}$alkyl, —N($C_{1-4}$alkyl)$_2$, and —S(O)$_2C_{1-4}$alkyl; or
$R^{3b}$ and $R^{3c}$ together with the intervening —NC(O)— or —NC(O)N($R^{3b}$)—, optionally form a 5- to 8-membered heterocyclyl, the heterocyclyl being optionally substituted with 1-4 substituents independently selected from the group consisting of halogen, cyano, $C_{1-4}$alkyl, $C_{1-4}$haloalkyl, oxo, OH, —O$C_{1-4}$alkyl, —O$C_{1-4}$haloalkyl, $NH_2$, —NH$C_{1-4}$alkyl, and —N($C_{1-4}$alkyl)$_2$;
$R^{3d}$ is $C_{1-8}$alkyl, $C_{1-8}$haloalkyl, -$L^1$-$R^{30}$, $G^1$, or -$L^1$-$G^2$;
$L^1$ is $C_{1-6}$alkylene, wherein the $C_{1-6}$alkylene is optionally substituted with halogen, OH, COOH, —C(O)O$C_{1-4}$alkyl, C(O)$NH_2$, —C(O)NH$C_{1-4}$alkyl, or —C(O)N($C_{1-4}$ alkyl)$_2$;
$R^{30}$ is —O$R^{30a}$, —S$R^{30a}$, —N$R^{30b}R^{31c}$, COOH, —C(O)O$C_{1-4}$alkyl, C(O)$NH_2$, —C(O)NH$C_{1-4}$alkyl, or —C(O)N($C_{1-4}$alkyl)$_2$;
$R^{30a}$, $R^{30b}$, and $R^{30c}$ are independently hydrogen, $C_{1-4}$alkyl, $C_{1-4}$haloalkyl, $G^1$, or -$L^2$-$G^2$; $L^2$ is $C_{1-3}$alkylene;

G$^1$, at each occurrence, is independently C$_{3-10}$carbocyclyl, a 6- to 12-membered aryl, a 5- to 12-membered heteroaryl, or a 4- to 12-membered heterocyclyl, wherein G$^1$ is attached to the parent molecular moiety at a carbon atom of G$^1$ and optionally substituted with 1-5 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, NH$_2$, —NHC$_{1-4}$alkyl, and —N(C$_{1-4}$alkyl)$_2$;

G$^2$, at each occurrence, is independently C$_{3-10}$carbocyclyl, a 6- to 12-membered aryl, a 5- to 12-membered heteroaryl, or a 4- to 12-membered heterocyclyl, wherein G$^2$ is optionally substituted with 1-5 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, NH$_2$, —NHC$_{1-4}$alkyl, and —N(C$_{1-4}$alkyl)$_2$;

R$^4$ is hydrogen, halogen, OH, —OC$_{1-4}$alkyl, —OC$_{1-4}$haloalkyl, —OC$_{3-6}$cycloalkyl, NH$_2$, —NHC$_{1-4}$alkyl, —N(C$_{1-4}$alkyl)$_2$, —NHC$_{3-6}$cycloalkyl, —N(C$_{1-4}$alkyl)(C$_{3-6}$cycloalkyl), or —N(C$_{3-6}$cycloalkyl)$_2$;

R$^{5a}$ is hydrogen, C$_{1-6}$alkyl, C$_{1-6}$haloalkyl, C$_{3-6}$cycloalkyl, or —C$_{1-3}$alkylene-C$_{3-6}$cycloalkyl;

R$^{5b}$ is hydrogen, C$_{1-6}$alkyl, C$_{1-6}$haloalkyl, C$_{3-6}$cycloalkyl, or —C$_{1-3}$alkylene-C$_{3-6}$cycloalkyl; alternatively, R$^{5a}$ and R$^{5b}$, together with the nitrogen to which they attach form a 3- to 8-membered heterocyclyl, the heterocyclyl being optionally substituted with 1-4 substituents independently selected from the group consisting of halogen, cyano, C$_{1-4}$alkyl, C$_{1-4}$haloalkyl, OH, —OC$_{1-4}$alkyl, —OC$_{1-4}$haloalkyl, —C$_{1-6}$alkylene-OH, and —C$_{1-6}$alkylene-OC$_{1-4}$alkyl;

R$^6$ is hydrogen, halogen, cyano, C(O)OH, SF$_5$, NO$_2$, C$_{1-4}$alkyl, C$_{1-4}$haloalkyl, —OC$_{1-4}$alkyl, —OC$_{1-4}$haloalkyl, —C$_{1-6}$alkylene-OH, —C$_{1-6}$alkylene-OC$_{1-4}$alkyl, C$_{3-6}$cycloalkyl, or a 4- to 7-membered heterocyclyl, wherein the cycloalkyl and heterocyclyl are optionally substituted with 1-4 substituents independently selected from the group consisting of halogen, cyano, C$_{1-4}$alkyl, and C$_{1-4}$haloalkyl;

alternatively, R$^{5b}$ and R$^6$, together with the intervening atoms form a 5- to 6-membered heteroaryl or a 5- to 7-membered heterocycle, wherein the heteroaryl and heterocycle are optionally substituted with 1-4 substituents independently selected from the group consisting of halogen, cyano, C$_{1-4}$alkyl, and C$_{1-4}$haloalkyl;

R$^7$ is hydrogen, halogen, cyano, C$_{1-4}$alkyl, C$_{1-4}$haloalkyl, —OC$_{1-4}$alkyl, or —OC$_{1-4}$haloalkyl; and R$^8$ is halogen, cyano, C$_{1-2}$alkyl, C$_{1-2}$haloalkyl, —OC$_{1-2}$alkyl, or —OC$_{1-2}$haloalkyl; provided the compound of formula (I) is not
3-[[(6-methyl-8-quinolinyl)sulfonyl]amino]-5-(trifluoromethyl)-benzoic acid;
3-[[(5-bromo-2-methoxyphenyl)sulfonyl]amino]-5-(trifluoromethyl)-benzoic acid; or
3-[[(3-bromo-5-chloro-2-methoxyphenyl)sulfonyl]amino]-5-(trifluoromethyl)-benzoic acid.

E2. The compound of embodiment 1, or a pharmaceutically acceptable salt thereof, wherein R$^4$ is OH.

E3. The compound of embodiment 1, or a pharmaceutically acceptable salt thereof, wherein R$^4$ is hydrogen E4. The compound of embodiment 1 or 3, or a pharmaceutically acceptable salt thereof, wherein R$^2$ is OH.

E5. The compound of any of embodiments 1-3, or a pharmaceutically acceptable salt thereof, wherein R$^2$ is hydrogen or C$_{1-4}$alkyl.

E6. The compound of any of embodiments 1-5, or a pharmaceutically acceptable salt thereof, wherein R$^3$ is C(O)OR$^{3a}$, C(O)NR$^{3b}$R$^{3c}$, S(O)R$^{3d}$, S(O)$_2$R$^{3d}$, NO$_2$, NR$^{3b}$C(O)R$^{3c}$, or NR$^{3b}$C(O)NR$^{3b}$R$^{3c}$.

E7. The compound of embodiment 6, or a pharmaceutically acceptable salt thereof, wherein R$^3$ is C(O)OH.

E7.1. The compound of embodiment 6, or a pharmaceutically acceptable salt thereof, wherein R$^3$ is C(O)OC$_{1-4}$alkyl.

E8. The compound of embodiment 6, or a pharmaceutically acceptable salt thereof, wherein R$^3$ is C(O)NR$^{3b}$R$^{3c}$.

E8.1. The compound of any of embodiments 1-5, or a pharmaceutically acceptable salt thereof, wherein R$^3$ is S(O)$_2$NR$^{3b}$R$^{3c}$.

E9. The compound of embodiment 6, 8, or 8.1, or a pharmaceutically acceptable salt thereof, wherein R$^{3b}$ is hydrogen.

E9.1. Compound of embodiment 6, 8, or 8.1, or a pharmaceutically acceptable salt thereof, wherein R$^{3b}$ is methyl.

E10. The compound of embodiment 9 or 9.1, or a pharmaceutically acceptable salt thereof, wherein R$^{3c}$ is hydrogen.

E11. The compound of embodiment 9 or 9.1, or a pharmaceutically acceptable salt thereof, wherein R$^{3c}$ is C$_{1-8}$alkyl.

E11.1. The compound of embodiment 9 or 9.1, or a pharmaceutically acceptable salt thereof, wherein R$^{3c}$ is C$_{1-8}$fluoroalkyl.

E12. The compound of embodiment 9 or 9.1, or a pharmaceutically acceptable salt thereof, wherein R$^{3c}$ is -L$^1$-R$^{30}$.

E13. The compound of embodiment 12, or a pharmaceutically acceptable salt thereof, wherein R$^{30}$ is COOH, CONH$_2$, OH, —OC$_{1-4}$alkyl, NH$_2$, or —N(C$_{1-4}$alkyl)$_2$.

E14. The compound of embodiment 9 or 9.1, or a pharmaceutically acceptable salt thereof, wherein R$^{3c}$ is G$^1$.

E15. The compound of embodiment 9 or 9.1, or a pharmaceutically acceptable salt thereof, wherein R$^{3c}$ is -L$^1$-G$^2$.

E16. The compound of embodiment 14 or 15, or a pharmaceutically acceptable salt thereof, wherein G$^1$ or G$^2$ is a 4- to 8-membered monocyclic heterocyclyl containing one oxygen atom (e.g., oxetanyl, tetrahydrofuranyl, tetrahydropyranyl) and optionally substituted with 1-4 substituents independently selected from the group consisting of halogen, OH, and C$_{1-4}$alkyl.

E16.1. The compound of embodiment 14 or 15, or a pharmaceutically acceptable salt thereof, wherein G$^1$ or G$^2$ is a C$_{3-6}$cycloalkyl (e.g., cyclopropyl, cyclobutyl) and optionally substituted with 1-4 substituents independently selected from the group consisting of halogen, OH, OC$_{1-4}$alkyl, and C$_{1-4}$alkyl.

E17. The compound of embodiment 15, or a pharmaceutically acceptable salt thereof, wherein G$^2$ is a 4- to 8-membered monocyclic heterocyclyl containing 1-2 heteroatoms independently selected from the group consisting of oxygen and nitrogen (e.g., oxetanyl, tetrahydrofuranyl, tetrahydropyranyl, morpholino, piperazinyl, piperidinyl, 2-oxo-1,2-dihydropyridin-4-yl, 6-oxo-1,6-dihydropyridin-3-yl), and optionally substituted with 1-4 substituents independently selected from the group consisting of halogen and C$_{1-4}$alkyl.

E18. The compound of embodiment 14, or a pharmaceutically acceptable salt thereof, wherein G$^1$ is a 5- to 6-membered heteroaryl optionally substituted with 1-3 substituents independently selected from the group consisting of halogen and C$_{1-4}$alkyl.

E18.1. The compound of embodiment 15, or a pharmaceutically acceptable salt thereof, wherein G$^2$ is a 5- to 6-membered heteroaryl (e.g., pyridinyl, pyrimidinyl, thienyl, furanyl) optionally substituted with 1-3 substituents independently selected from the group consisting of halogen and $C_{1-4}$alkyl.

E18.2. The compound of embodiment 15, or a pharmaceutically acceptable salt thereof, wherein $G^2$ is a phenyl optionally substituted with 1-3 substituents independently selected from the group consisting of halogen and $C_{1-4}$alkyl.

E19. The compound of embodiment 8 or 8.1, or a pharmaceutically acceptable salt thereof, wherein $R^{3b}$ and $R^{3c}$ together with the nitrogen to which they attach form the 3- to 8-membered heterocyclyl (e.g., azetidine, pyrrolidine, piperidine, morpholine, piperazine).

E20. The compound of embodiment 6, or a pharmaceutically acceptable salt thereof, wherein $R^3$ is $S(O)_2R^{3d}$.

E21. The compound of embodiment 6 or 20, or a pharmaceutically acceptable salt thereof, wherein $R^{3d}$ is $C_{1-8}$alkyl.

E22. The compound of embodiment 6 or 20, or a pharmaceutically acceptable salt thereof, wherein $R^{3d}$ is -$L^1$-$R^{30}$.

E23. The compound of embodiment 22, or a pharmaceutically acceptable salt thereof, wherein $R^{30}$ is —N($C_{1-4}$alkyl)$_2$.

E23.1. The compound of embodiment 22, or a pharmaceutically acceptable salt thereof, wherein $R^{30}$ is —O$C_{1-4}$alkyl.

E24. The compound of embodiment 6, or a pharmaceutically acceptable salt thereof, wherein $R^3$ is $S(O)R^{3d}$.

E25. The compound of embodiment 24, or a pharmaceutically acceptable salt thereof, wherein $R^{3d}$ is $C_{1-8}$alkyl.

E26. The compound of embodiment 6, or a pharmaceutically acceptable salt thereof, wherein $R^3$ is $NO_2$.

E27. The compound of embodiment 6, or a pharmaceutically acceptable salt thereof, wherein $R^3$ is $NR^{3b}C(O)R^{3c}$, wherein $R^{3b}$ and $R^{3c}$ together with the intervening —NC(O)— form the 5- to 8-membered heterocyclyl.

E28. The compound of embodiment 6, or a pharmaceutically acceptable salt thereof, wherein $R^3$ is $NR^{3b}C(O)NR^{3b}R^{3c}$, wherein $R^{3b}$ and $R^{3c}$ together with the intervening —NC(O)N($R^{3b}$)— form the 5- to 8-membered heterocyclyl.

E29. The compound of embodiment 6, or a pharmaceutically acceptable salt thereof, wherein $R^3$ is C(O)OH, C(O)OCH$_3$, C(O)NH$_2$, C(O)NHCH$_3$, C(O)N(CH$_3$)$_2$, C(O)NH(CH$_2$)$_3$CH$_3$, C(O)NHCH$_2$CHF$_2$, C(O)NHCH$_2$CH$_2$OH, C(O)NHCH$_2$CH$_2$CH$_2$OH, C(O)NHCH$_2$CH(OH)CH$_2$CH$_3$, C(O)NHCH$_2$CH(OH)CH(CH$_3$)$_2$, C(O)NHCH$_2$C(CH$_3$)(OH)CH$_2$CH$_3$, C(O)NHCH$_2$CH$_2$OCH$_3$, C(O)N(CH$_3$)CH$_2$CH$_2$OCH$_3$, C(O)NHCH$_2$CH$_2$OCH$_3$, C(O)NHCH$_2$CH$_2$CH$_2$OCH$_3$, C(O)NHCH$_2$CH$_2$NH$_2$, C(O)NHCH$_2$CH$_2$N(CH$_3$)$_2$, C(O)NHCH$_2$COOH, C(O)NHCH(CH$_3$)CONH$_2$, C(O)NHCH(CH$_2$OH)CONH$_2$, C(O)NHCH(CH$_2$OH)CONHCH$_3$, NO$_2$, SCH$_2$CH$_2$N(CH$_2$CH$_3$)$_2$, SCH$_2$CH$_2$N(CH(CH$_3$)$_2$)$_2$, S(O)$_2$CH$_3$, S(O)$_2$CH$_2$CH$_3$, S(O)$_2$CH(CH$_3$)$_2$, S(O)$_2$CH$_2$CH$_2$N(CH$_2$CH$_3$)$_2$, S(O)$_2$CH$_2$CH$_2$N(CH(CH$_3$)$_2$)$_2$, S(O)$_2$CH$_2$CH$_2$CH$_2$N(CH$_3$)$_2$, S(O)$_2$CH$_2$CH$_2$CH$_2$N(CH(CH$_3$)$_2$)$_2$, S(O)CH$_3$, S(O)CH$_2$CH$_3$, S(O)CH(CH$_3$)$_2$, S(O)$_2$NH$_2$, S(O)$_2$NHCH$_3$, S(O)$_2$NHCH$_2$CH$_2$OCH$_3$, NHC(O)CH$_3$,

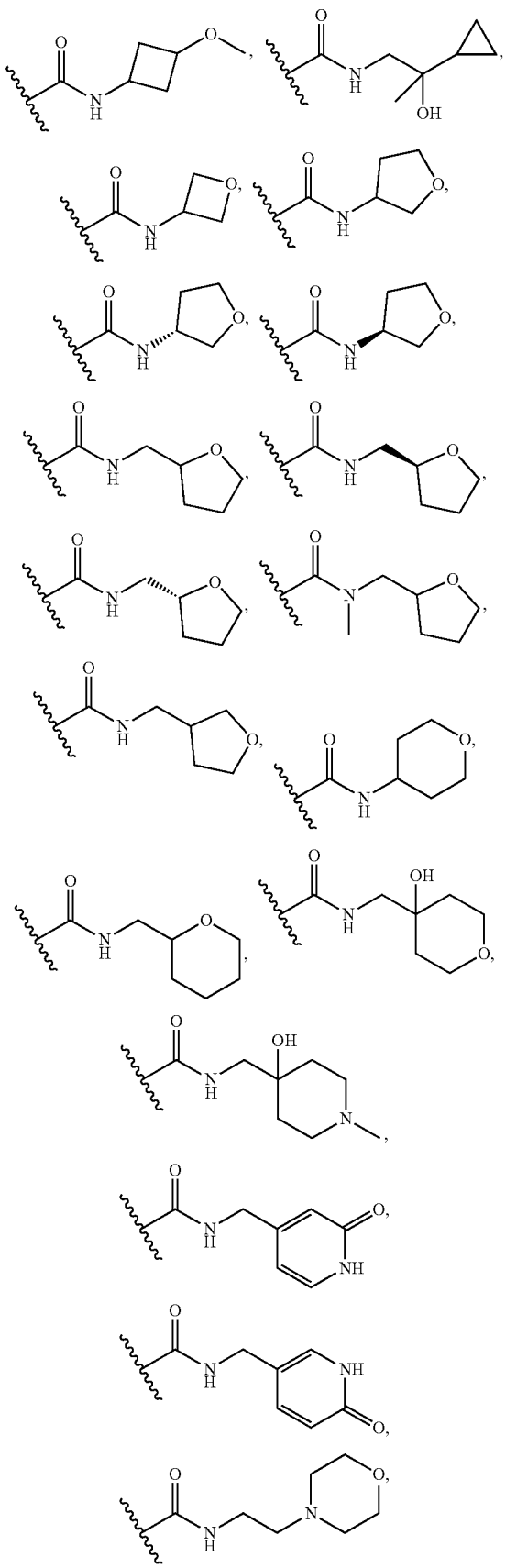

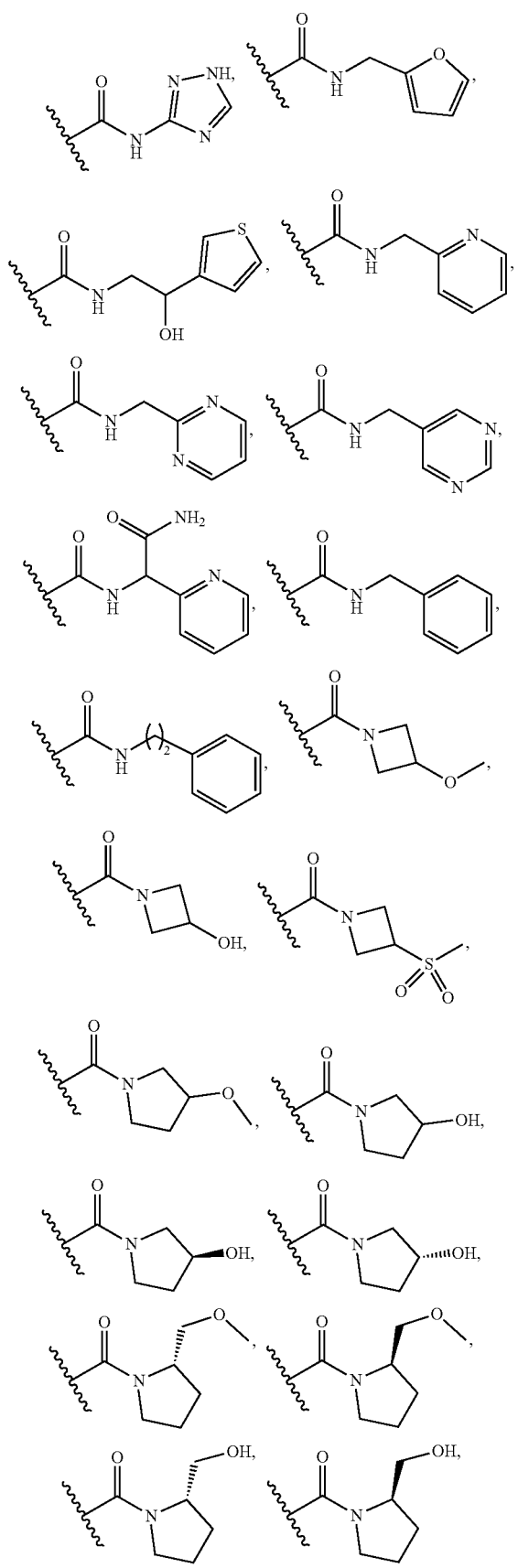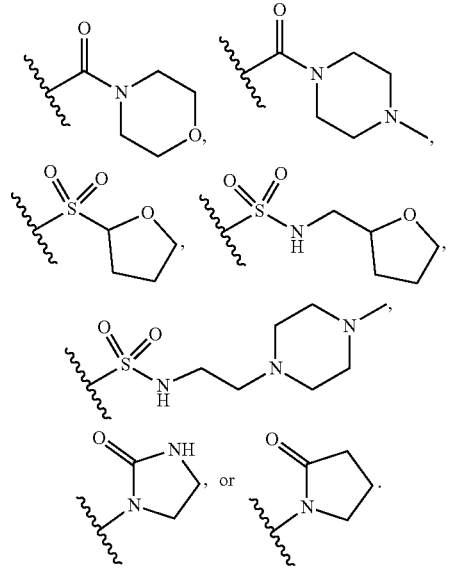

E30. The compound of any of embodiments 1-29, or a pharmaceutically acceptable salt thereof, wherein $R^1$ is halogen, $SF_5$, $C_{1-4}$alkyl, $C_{1-4}$haloalkyl, —$OC_{1-4}$haloalkyl, or $R^{1G}$, wherein $R^{1G}$ is optionally substituted with 1-4 substituents independently selected from the group consisting of halogen, cyano, $C_{1-4}$alkyl, and $C_{1-4}$haloalkyl.

E31. The compound of any of embodiments 1-29, or a pharmaceutically acceptable salt thereof, wherein $R^1$ is chloro, $SF_5$, tert-butyl, $OCF_3$, cyclopropyl, 1-cyanocyclobut-1-yl, 1-cyanocyclohex-1-yl, phenyl, 2-chlorophenyl,

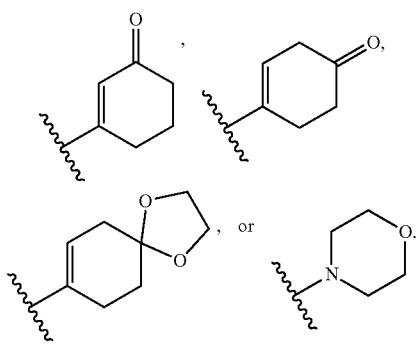

E31.1. The compound of any of embodiments 1-29, or a pharmaceutically acceptable salt thereof, wherein $R^1$ is ethyl, fluoro, bromo,

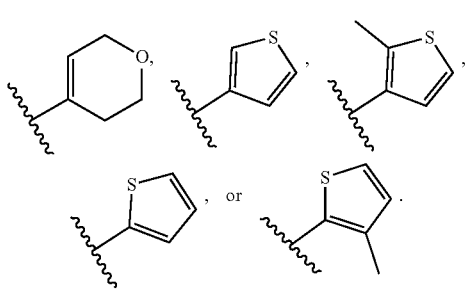

E32. The compound of any of embodiments 1-31.1, or a pharmaceutically acceptable salt thereof, wherein Y is —$XR^{5b}$; X is O; and $R^{5b}$ is hydrogen of $C_{1-4}$alkyl.

E33. The compound of any of embodiments 1-31.1, or a pharmaceutically acceptable salt thereof, wherein Y is —$XR^{5b}$; X is O; and $R^{5b}$ and $R^6$, together with the intervening atoms form a 5- to 7-membered heterocycle containing 1-2 oxygen atoms (e.g., 2,3-dihydrofuran to form a benzofuran ring system), the heterocycle being optionally substituted with 1-4 substituents independently selected from the group consisting of halogen, cyano, $C_{1-4}$alkyl, and $C_{1-4}$haloalkyl.

E34. The compound of any of embodiments 1-31.1, or a pharmaceutically acceptable salt thereof, wherein Y is —$XR^{5b}$; X is N; and $R^{5b}$ and $R^6$, together with the intervening atoms form a 6-membered heteroaryl containing 1-2 nitrogen atoms (e.g., pyridine to form a quinoline ring system), the heteroaryl being optionally substituted with 1-4 substituents independently selected from the group consisting of halogen, cyano, $C_{1-4}$alkyl, and $C_{1-4}$haloalkyl.

E35. The compound of any of embodiments 1-31.1, or a pharmaceutically acceptable salt thereof, wherein Y is C(O)OH or C(O)O$C_{1-4}$alkyl.

E36. The compound of any of embodiments 1-32 or 35, or a pharmaceutically acceptable salt thereof, wherein $R^6$ is hydrogen or halogen.

E37. The compound of embodiment 36, or a pharmaceutically acceptable salt thereof, wherein $R^6$ is chloro.

E38. The compound of any of embodiments 1-32 or 35, or a pharmaceutically acceptable salt thereof, wherein $R^6$ is hydrogen, halogen, $C_{1-4}$alkyl, —$OC_{1-4}$alkyl, —$OC_{1-4}$haloalkyl, or C(O)OH.

E39. The compound of any of embodiments 1-38, or a pharmaceutically acceptable salt thereof, wherein $R^7$ is hydrogen, $C_{1-4}$alkyl, or —$OC_{1-4}$alkyl;

E40. The compound of any of embodiments 1-39, or a pharmaceutically acceptable salt thereof, wherein $R^8$ is halogen.

E41. The compound of embodiment 40, or a pharmaceutically acceptable salt thereof, wherein $R^8$ is bromo.

E41.1. The compound of any of embodiments 1-41, or a pharmaceutically acceptable salt thereof, wherein $L^1$ is —$CH_2$—, —$CH_2CH_2$—, —$CH_2CH_2CH_2$—, —$CH_2CH(CH_2CH_3)$—, —$CH_2CH(CH(CH_3)_2)$—, —$CH_2C(CH_3)(CH_2CH_3)$—, —$CH(CH_3)$—, —$CH(CH_2OH)$—, —$CH_2CH(OH)$—, —$CH_2C(CH_3)(OH)$—, —$CH_2CH_2CH_2$—, —$CH_2CH(CH_2CH_3)$—, —$CH_2CH(CH(CH_3)_2)$—, —$CH_2C(CH_3)(CH_2CH_3)$—, or —$CH(C(O)NH_2)$—.

E42. A compound of formula (II), or a pharmaceutically acceptable salt thereof,

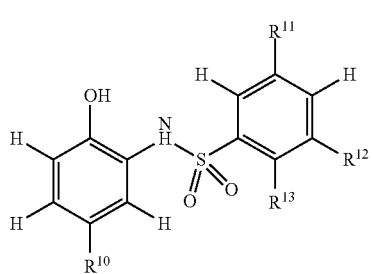

(II)

wherein
$R^{10}$ is halogen, cyano, —$C_{1-3}$alkylene-cyano, $SF_5$, $C_{1-4}$alkyl, $C_{1-4}$haloalkyl, —$OC_{1-4}$alkyl, —$OC_{1-4}$haloalkyl, or $C_{3-6}$cycloalkyl, wherein the cycloalkyl is optionally substituted with 1-4 substituents independently selected from the group consisting of halogen, cyano, $C_{1-4}$alkyl, and $C_{1-4}$haloalkyl;

$R^{11}$ is halogen;
$R^{12}$ is hydrogen or halogen; and
$R^{13}$ is hydrogen or OH.

E43. The compound of embodiment 42, or a pharmaceutically acceptable salt thereof, wherein
$R^{10}$ is chloro, cyano, —$CH_2$-cyano, $SF_5$, $CF_3$, —$OCF_3$, or

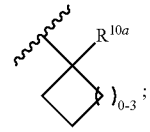

and
$R^{10a}$ is cyano or $CF_3$.

E44. The compound of embodiment 43, or a pharmaceutically acceptable salt thereof, wherein $R^{10}$ is chloro, cyano, —$CH_2$-cyano, $SF_5$, $CF_3$, —$OCF_3$,

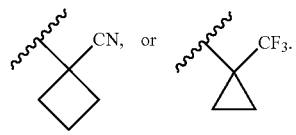 [SMILES: *C1(C#N)CCC1 ; *C1(C(F)(F)F)CC1]

E45. The compound of any of embodiments 42-44, or a pharmaceutically acceptable salt thereof, wherein $R^{11}$ is bromo.

E46. The compound of any of embodiments 42-45, or a pharmaceutically acceptable salt thereof, wherein $R^{12}$ is hydrogen.

E47. The compound of any of embodiments 42-45, or a pharmaceutically acceptable salt thereof, wherein $R^{12}$ is chloro.

E48. The compound of any of embodiments 42-47, or a pharmaceutically acceptable salt thereof, wherein $R^{13}$ is hydrogen.

E49. The compound of any of embodiments 42-47, or a pharmaceutically acceptable salt thereof, wherein $R^{13}$ is OH.

E49.1. Throughout the embodiments and description of the compounds of the invention, all instances of haloalkyl may be fluoroalkyl (e.g., any $C_{1-4}$haloalkyl may be $C_{1-4}$fluoroalkyl).

E49.2. Representative compounds of the invention include:
3-((5-Bromo-2-hydroxyphenyl)sulfonamido)-5-chloro-2-hydroxybenzoic acid;
3-((5-Bromo-2-methoxyphenyl)sulfonamido)-5-chloro-2-hydroxybenzoic acid;
3-((5-Bromo-3-chloro-2-hydroxyphenyl)sulfonamido)-5-chloro-2-hydroxybenzoic acid;
3-((5-Bromo-3-fluoro-2-hydroxyphenyl)sulfonamido)-5-chloro-2-hydroxybenzoic acid;
3-((5-Bromo-2-hydroxy-3-nitrophenyl)sulfonamido)-5-chloro-2-hydroxybenzoic acid;
3-((5-Bromo-4-chloro-2-methoxyphenyl)sulfonamido)-5-chloro-2-hydroxybenzoic acid;
3-((5-Bromo-4-fluoro-2-methoxyphenyl)sulfonamido)-5-chloro-2-hydroxybenzoic acid;

3-((5-Bromo-4-fluoro-2-hydroxyphenyl)sulfonamido)-5-chloro-2-hydroxybenzoic acid;
5-Chloro-3-((5-chloro-4-fluoro-2-hydroxyphenyl)sulfonamido)-2-hydroxybenzoic acid;
5-Chloro-3-((4,5-dichloro-2-hydroxyphenyl)sulfonamido)-2-hydroxybenzoic acid;
5-Chloro-3-((5-chloro-4-ethyl-2-hydroxyphenyl)sulfonamido)-2-hydroxybenzoic acid;
3-((5-Bromo-3-ethyl-2-hydroxyphenyl)sulfonamido)-5-chloro-2-hydroxybenzoic acid;
3-((5-bromo-3-ethyl-2-hydroxyphenyl)sulfonamido)-5-ethyl-2-hydroxybenzoic acid;
3-((5-Bromo-2-hydroxy-3-(trifluoromethoxy)phenyl)sulfonamido)-5-ethyl-2-hydroxybenzoic acid;
3-((5-Bromo-3-ethyl-2-hydroxyphenyl)sulfonamido)-2-hydroxy-5-(trifluoromethoxy)benzoic acid;
3-((5-Bromo-3-ethyl-2-hydroxyphenyl)sulfonamido)-2-hydroxy-5-(trifluoromethoxy)benzoic acid;
3-((5-Bromo-2-hydroxy-3-propylphenyl)sulfonamido)-2-hydroxy-5-(trifluoromethoxy)benzoic acid;
3-((5-Bromo-2-hydroxy-3-propylphenyl)sulfonamido)-5-chloro-2-hydroxybenzoic acid;
3-((5-Bromo-2-hydroxyphenyl)sulfonamido)-5-ethyl-2-hydroxybenzoic acid;
3-((5-Bromo-3-fluoro-2-hydroxyphenyl)sulfonamido)-5-ethyl-2-hydroxybenzoic acid;
3-((5-Bromo-3-chloro-2-hydroxyphenyl)sulfonamido)-5-ethyl-2-hydroxybenzoic acid;
3-((5-Bromo-3-chloro-2-hydroxyphenyl)sulfonamido)-2-hydroxy-5-(trifluoromethoxy)benzoic acid;
3-((5-Bromo-2-hydroxy-3-(3-hydroxypropyl)phenyl)sulfonamido)-2-hydroxy-5-(trifluoromethoxy)benzoic acid;
3-((6-Bromoquinoline)-8-sulfonamido)-5-chloro-2-hydroxybenzoic acid;
3-((5-Bromo-2-hydroxyphenyl)sulfonamido)-5-chloro-2-hydroxy-N-methylbenzamide;
3-((5-Bromo-2-hydroxyphenyl)sulfonamido)-5-chloro-2-hydroxy-N-(2-methoxyethyl)benzamide;
3-((5-Bromo-2-hydroxyphenyl)sulfonamido)-5-chloro-2-hydroxy-N-(2-hydroxyethyl)benzamide;
3-((5-Bromo-2-hydroxyphenyl)sulfonamido)-5-chloro-2-hydroxy-N-(3-hydroxypropyl)benzamide;
3-((5-Bromo-2-hydroxyphenyl)sulfonamido)-5-chloro-2-hydroxy-N-(tetrahydrofuran-3-yl)benzamide;
3-((5-Bromo-2-hydroxyphenyl)sulfonamido)-5-chloro-2-hydroxy-N-(2-morpholinoethyl)benzamide;
3-((5-Bromo-2-hydroxyphenyl)sulfonamido)-5-chloro-2-hydroxy-N-(oxetan-3-yl)benzamide;
(S)-3-((5-Bromo-2-hydroxyphenyl)sulfonamido)-5-chloro-2-hydroxy-N-(tetrahydrofuran-3-yl)benzamide;
3-((5-Bromo-2-hydroxyphenyl)sulfonamido)-5-chloro-2-hydroxy-N-((tetrahydrofuran-3-yl)methyl)benzamide;
5-Bromo-N-(5-chloro-2-hydroxy-3-(3-methoxypyrrolidine-1-carbonyl)phenyl)-2-hydroxybenzenesulfonamide;
3-((5-Bromo-2-hydroxyphenyl)sulfonamido)-5-chloro-2-hydroxy-N-((tetrahydrofuran-2-yl)methyl)benzamide;
(R)-3-((5-Bromo-2-hydroxyphenyl)sulfonamido)-5-chloro-2-hydroxy-N-((tetrahydrofuran-2-yl)methyl)benzamide;
(S)-3-((5-Bromo-2-hydroxyphenyl)sulfonamido)-5-chloro-2-hydroxy-N-((tetrahydrofuran-2-yl)methyl)benzamide;
(R)-5-Bromo-N-(5-chloro-2-hydroxy-3-(2-(methoxymethyl)pyrrolidine-1-carbonyl)phenyl)-2-hydroxybenzenesulfonamide;
(S)-5-Bromo-N-(5-chloro-2-hydroxy-3-(2-(methoxymethyl)pyrrolidine-1-carbonyl)phenyl)-2-hydroxybenzenesulfonamide;
5-Bromo-N-(5-chloro-2-hydroxy-3-(morpholine-4-carbonyl)phenyl)-2-hydroxybenzenesulfonamide;
3-((5-Bromo-2-hydroxyphenyl)sulfonamido)-5-chloro-2-hydroxy-N-(pyridin-2-ylmethyl)benzamide;
3-((5-Bromo-2-hydroxyphenyl)sulfonamido)-5-chloro-2-hydroxy-N-(pyrimidin-2-ylmethyl)benzamide;
3-((5-Bromo-2-hydroxyphenyl)sulfonamido)-5-chloro-2-hydroxy-N-(pyrimidin-5-ylmethyl)benzamide;
3-((5-Bromo-2-hydroxyphenyl)sulfonamido)-5-chloro-N-(furan-2-ylmethyl)-2-hydroxybenzamide;
3-((5-Bromo-2-hydroxyphenyl)sulfonamido)-5-chloro-2-hydroxy-N-((6-oxo-1,6-dihydropyridin-3-yl)methyl)benzamide;
3-((5-Bromo-2-hydroxyphenyl)sulfonamido)-5-chloro-2-hydroxy-N-((2-oxo-1,2-dihydropyridin-4-yl)methyl)benzamide;
3-((5-Bromo-2-hydroxyphenyl)sulfonamido)-5-chloro-2-hydroxy-N-methyl-N-((tetrahydrofuran-2-yl)methyl)benzam ide;
3-((5-Bromo-2-hydroxyphenyl)sulfonamido)-5-chloro-N-(3,3-difluorocyclobutyl)-2-hydroxybenzamide;
3-((5-Bromo-2-hydroxyphenyl)sulfonamido)-5-chloro-N-(2,2-difluoroethyl)-2-hydroxybenzamide;
3-((5-Bromo-3-chloro-2-hydroxyphenyl)sulfonamido)-5-chloro-2-hydroxybenzamide;
3-((5-Bromo-3-chloro-2-hydroxyphenyl)sulfonamido)-5-chloro-2-hydroxy-N-methylbenzamide;
3-((5-Bromo-3-chloro-2-hydroxyphenyl)sulfonamido)-5-chloro-2-hydroxy-N-(2-hydroxyethyl)benzamide;
3-((5-Bromo-3-chloro-2-hydroxyphenyl)sulfonamido)-5-chloro-2-hydroxy-N-(2-methoxyethyl)benzamide;
3-((5-Bromo-2-methoxyphenyl)sulfonamido)-5-chloro-2-hydroxybenzamide;
3-((5-Bromo-2-methoxyphenyl)sulfonamido)-5-chloro-2-hydroxy-N-methylbenzamide;
3-((5-Bromo-2-methoxyphenyl)sulfonamido)-5-chloro-2-hydroxy-N-(2-methoxyethyl)benzamide;
3-((5-Bromo-2-methoxyphenyl)sulfonamido)-N-butyl-5-chloro-2-hydroxybenzamide;
N-Benzyl-3-((5-bromo-2-methoxyphenyl)sulfonamido)-5-chloro-2-hydroxybenzamide;
5-Bromo-N-(5-chloro-2-hydroxy-3-(morpholine-4-carbonyl)phenyl)-2-methoxybenzenesulfonamide;
3-((5-Bromo-2-methoxyphenyl)sulfonamido)-5-chloro-2-hydroxy-N-phenethylbenzamide;
3-((5-Bromo-2-methoxyphenyl)sulfonamido)-5-chloro-2-hydroxy-N,N-dimethylbenzamide;
3-((5-Bromo-2-methoxyphenyl)sulfonamido)-5-chloro-2-hydroxy-N-(3-methoxypropyl)benzamide;
3-((5-Bromo-2-methoxyphenyl)sulfonamido)-5-chloro-2-hydroxy-N-(tetrahydro-2H-pyran-4-yl)benzamide;
3-((5-Bromo-2-methoxyphenyl)sulfonamido)-5-chloro-2-hydroxy-N-(3-hydroxypropyl)benzamide;
(S)-5-Bromo-N-(5-chloro-2-hydroxy-3-(2-(hydroxymethyl)pyrrolidine-1-carbonyl)phenyl)-2-methoxybenzenesulfonamide;
(R)-5-Bromo-N-(5-chloro-2-hydroxy-3-(2-(hydroxymethyl)pyrrolidine-1-carbonyl)phenyl)-2-methoxybenzenesulfonamide;
(S)-5-Bromo-N-(5-chloro-2-hydroxy-3-(2-(methoxymethyl)pyrrolidine-1-carbonyl)phenyl)-2-methoxybenzenesulfonamide;
(R)-5-Bromo-N-(5-chloro-2-hydroxy-3-(2-(methoxymethyl)pyrrolidine-1-carbonyl)phenyl)-2-methoxybenzenesulfonamide;
3-((5-Bromo-2-methoxyphenyl)sulfonamido)-5-chloro-2-hydroxy-N-(2-methoxyethyl)-N-methylbenzamide;

3-((5-Bromo-2-methoxyphenyl)sulfonamido)-5-chloro-2-hydroxy-N-(2-hydroxyethyl)benzamide;
3-((5-Bromo-2-methoxyphenyl)sulfonamido)-5-chloro-2-hydroxy-N-(tetrahydrofuran-3-yl)benzamide;
N-(2-Aminoethyl)-3-((5-bromo-2-methoxyphenyl)sulfonamido)-5-chloro-2-hydroxybenzamide;
5-Bromo-N-(5-chloro-2-hydroxy-3-(3-methoxyazetidine-1-carbonyl)phenyl)-2-methoxybenzenesulfonamide;
5-Bromo-N-(5-chloro-2-hydroxy-3-(3-hydroxyazetidine-1-carbonyl)phenyl)-2-methoxybenzenesulfonamide;
5-Bromo-N-(5-chloro-2-hydroxy-3-(3-(methylsulfonyl)azetidine-1-carbonyl)phenyl)-2-methoxybenzenesulfonamide;
3-((5-Bromo-2-methoxyphenyl)sulfonamido)-5-chloro-2-hydroxy-N-((tetrahydrofuran-2-yl)methyl)benzamide;
3-((5-Bromo-2-hydroxyphenyl)sulfonamido)-5-chlorobenzoic acid;
3-((5-Bromo-2-hydroxyphenyl)sulfonamido)-5-chloro-N-(1H-1,2,4-triazol-3-yl)benzamide;
(3-((5-Bromo-2-hydroxyphenyl)sulfonamido)-2-hydroxy-5-(trifluoromethoxy)benzoyl)glycine;
3-((5-Bromo-3-ethyl-2-hydroxyphenyl)sulfonamido)-5-chloro-2-hydroxy-N-((4-hydroxy-1-methylpiperidin-4-yl)methyl)benzamide;
3-((5-Bromo-2-hydroxyphenyl)sulfonamido)-2-hydroxy-N-(3-hydroxycyclobutyl)-5-(trifluoromethoxy)benzamide;
3-((5-Bromo-2-hydroxyphenyl)sulfonamido)-2-hydroxy-N-(oxetan-3-yl)-5-(trifluoromethoxy)benzamide;
3-((5-Bromo-2-hydroxyphenyl)sulfonamido)-2-hydroxy-N-(2-hydroxyethyl)-5-(trifluoromethoxy)benzamide;
3-((5-Bromo-2-hydroxy-3-(3-hydroxypropyl)phenyl)sulfonamido)-2-hydroxy-5-(trifluoromethoxy)benzamide;
3-((5-Bromo-3-fluoro-2-hydroxyphenyl)sulfonamido)-2-hydroxy-N-(2-hydroxybutyl)-5-(trifluoromethoxy)benzamide;
3-((5-Bromo-3-ethyl-2-hydroxyphenyl)sulfonamido)-2-hydroxy-N-(2-hydroxybutyl)-5-(trifluoromethoxy)benzamide;
3-((5-Bromo-3-chloro-2-hydroxyphenyl)sulfonamido)-2-hydroxy-N-(2-hydroxybutyl)-5-(trifluoromethoxy)benzamide;
3-((5-Bromo-2-hydroxyphenyl)sulfonamido)-2-hydroxy-N-(2-hydroxy-2-(thiophen-3-yl)ethyl)-5-(trifluoromethoxy)benzamide;
3-((5-Bromo-2-hydroxyphenyl)sulfonamido)-N-(2-cyclopropyl-2-hydroxypropyl)-2-hydroxy-5-(trifluoromethoxy)benzamide;
3-((5-Bromo-2-hydroxyphenyl)sulfonamido)-2-hydroxy-N-(2-hydroxy-2-methylbutyl)-5-(trifluoromethoxy)benzamide;
3-((5-Bromo-2-hydroxyphenyl)sulfonamido)-2-hydroxy-N-(3-hydroxy-1-(methylamino)-1-oxopropan-2-yl)-5-(trifluoromethoxy)benzamide;
(S)—N-(1-Amino-3-hydroxy-1-oxopropan-2-yl)-3-((5-bromo-2-hydroxyphenyl)sulfonamido)-2-hydroxy-5-(trifluoromethoxy)benzamide;
N-(1-Amino-1-oxopropan-2-yl)-3-((5-bromo-2-hydroxyphenyl)sulfonamido)-2-hydroxy-5-(trifluoromethoxy)benzamide;
N-(2-Amino-2-oxo-1-(pyridin-2-yl)ethyl)-3-((5-bromo-2-hydroxyphenyl)sulfonamido)-2-hydroxy-5-(trifluoromethoxy)benzamide;
3-((5-Bromo-3-chloro-2-hydroxyphenyl)sulfonamido)-2-hydroxy-N-((4-hydroxy-1-methylpiperidin-4-yl)methyl)-5-(trifluoromethoxy)benzamide;
3-((5-Bromo-3-chloro-2-hydroxyphenyl)sulfonamido)-N-(2-cyclopropyl-2-hydroxypropyl)-2-hydroxy-5-(trifluoromethoxy)benzamide;
3-((5-Bromo-3-chloro-2-hydroxyphenyl)sulfonamido)-2-hydroxy-N-(2-hydroxy-3-methylbutyl)-5-(trifluoromethoxy)benzamide;
3-((5-Bromo-3-chloro-2-hydroxyphenyl)sulfonamido)-2-hydroxy-N-((4-hydroxytetrahydro-2H-pyran-4-yl)methyl)-5-(trifluoromethoxy)benzamide;
3-((5-Bromo-3-chloro-2-hydroxyphenyl)sulfonamido)-2-hydroxy-N-(oxetan-3-yl)-5-(trifluoromethoxy)benzamide;
3-((5-Bromo-2-hydroxyphenyl)sulfonamido)-N-(3,3-difluorocyclobutyl)-2-hydroxy-5-(trifluoromethoxy)benzamide;
(S)—N-(1-Amino-3-hydroxy-1-oxopropan-2-yl)-3-((5-bromo-3-chloro-2-hydroxyphenyl)sulfonamido)-2-hydroxy-5-(trifluoromethoxy)benzamide;
N-(1-Amino-1-oxopropan-2-yl)-3-((5-bromo-3-chloro-2-hydroxyphenyl)sulfonamido)-2-hydroxy-5-(trifluoromethoxy)benzamide;
3-((5-Bromo-3-ethyl-2-hydroxyphenyl)sulfonamido)-5-chloro-2-hydroxy-N-(oxetan-3-yl)benzamide;
N-(1-Amino-1-oxopropan-2-yl)-3-((5-bromo-3-ethyl-2-hydroxyphenyl)sulfonamido)-5-chloro-2-hydroxybenzamide;
3-((5-Bromo-3-chloro-2-hydroxyphenyl)sulfonamido)-2-hydroxy-N-(3-methoxycyclobutyl)-5-(trifluoromethoxy)benzamide;
3-((5-Bromo-3-chloro-2-hydroxyphenyl)sulfonamido)-2-hydroxy-N-(3-hydroxycyclobutyl)-5-(trifluoromethoxy)benzamide;
3-((5-Bromo-3-chloro-2-hydroxyphenyl)sulfonamido)-2-hydroxy-5-(trifluoromethoxy)benzamide;
3-((5-Bromo-3-chloro-2-hydroxyphenyl)sulfonamido)-2-hydroxy-N-methyl-5-(trifluoromethoxy)benzamide;
3-((5-Bromo-2-hydroxyphenyl)sulfonamido)-5-cyclopropyl-2-hydroxybenzoic acid;
3-((5-Bromo-2-methoxyphenyl)sulfonamido)-5-cyclopropyl-2-hydroxybenzoic acid;
3-((5-Bromo-3-chloro-2-hydroxyphenyl)sulfonamido)-5-cyclopropyl-2-hydroxybenzoic acid;
3-((5-Bromo-4-chloro-2-methoxyphenyl)sulfonamido)-5-cyclopropyl-2-hydroxybenzoic acid;
3-((5-Bromo-4-fluoro-2-methoxyphenyl)sulfonamido)-5-cyclopropyl-2-hydroxybenzoic acid;
3-((5-Bromo-2-(cyclopropylamino)phenyl)sulfonamido)-5-cyclopropyl-2-hydroxybenzoic acid;
3-((5-Bromo-2-(isobutylamino)phenyl)sulfonamido)-5-cyclopropyl-2-hydroxybenzoic acid;
(R)-3-((5-Bromo-2-((3-methylbutan-2-yl)amino)phenyl)sulfonamido)-5-cyclopropyl-2-hydroxybenzoic acid;
(S)-3-((5-Bromo-2-((3-methylbutan-2-yl)amino)phenyl)sulfonamido)-5-cyclopropyl-2-hydroxybenzoic acid;
(R)-3-((5-Bromo-2-((1-cyclopropylethyl)amino)phenyl)sulfonamido)-5-cyclopropyl-2-hydroxybenzoic acid;
(R)-3-((5-Bromo-2-(2-(methoxymethyl)pyrrolidin-1-yl)phenyl)sulfonamido)-5-cyclopropyl-2-hydroxybenzoic acid;
3-((5-Bromo-2-((cyclopropylmethyl)amino)phenyl)sulfonamido)-5-cyclopropyl-2-hydroxybenzoic acid;
3-((5-Bromo-2-hydroxyphenyl)sulfonamido)-5-cyclopropyl-2-hydroxybenzamide;
3-((5-Bromo-2-hydroxyphenyl)sulfonamido)-5-cyclopropyl-2-hydroxy-N-methylbenzamide;
3-((5-Bromo-2-hydroxyphenyl)sulfonamido)-5-cyclopropyl-2-hydroxy-N-(2-hydroxyethyl)-N-methylbenzamide;

3-((5-Bromo-2-hydroxyphenyl)sulfonamido)-5-cyclopropyl-2-hydroxy-N-(2-methoxyethyl)-N-methylbenzamide;
3-((5-Bromo-2-hydroxyphenyl)sulfonamido)-5-cyclopropyl-2-hydroxy-N-(2-morpholinoethyl)benzamide;
5-Bromo-N-(5-cyclopropyl-2-hydroxy-3-(morpholine-4-carbonyl)phenyl)-2-hydroxybenzenesulfonamide;
3-((5-Bromo-2-hydroxyphenyl)sulfonamido)-5-cyclopropyl-2-hydroxy-N-(2-methoxyethyl)benzamide;
3-((5-Bromo-2-hydroxyphenyl)sulfonamido)-5-cyclopropyl-2-hydroxy-N-(2-hydroxyethyl)benzamide;
3-((5-Bromo-2-hydroxyphenyl)sulfonamido)-5-cyclopropyl-2-hydroxy-N-(3-methoxypropyl)benzamide;
5-Bromo-2-hydroxyphenyl)sulfonamido)-5-cyclopropyl-N-(2-(dimethylamino)ethyl)-2-hydroxybenzamide;
3-((5-Bromo-2-hydroxyphenyl)sulfonamido)-5-cyclopropyl-2-hydroxy-N-(tetrahydrofuran-3-yl)benzamide;
3-((5-Bromo-2-hydroxyphenyl)sulfonamido)-5-cyclopropyl-2-hydroxy-N-(3-hydroxypropyl)benzamide;
5-Bromo-N-(5-cyclopropyl-2-hydroxy-3-(4-methylpiperazine-1-carbonyl)phenyl)-2-hydroxybenzenesulfonamide;
3-((5-Bromo-2-hydroxyphenyl)sulfonamido)-5-cyclopropyl-2-hydroxy-N-(oxetan-3-yl)benzamide;
3-((5-Bromo-3-chloro-2-hydroxyphenyl)sulfonamido)-5-cyclopropyl-2-hydroxybenzamide;
3-((5-Bromo-3-chloro-2-hydroxyphenyl)sulfonamido)-5-cyclopropyl-2-hydroxy-N-methylbenzamide;
3-((5-Bromo-3-chloro-2-hydroxyphenyl)sulfonamido)-5-cyclopropyl-2-hydroxy-N-(2-methoxyethyl)benzamide;
(S)-3-((5-Bromo-3-chloro-2-hydroxyphenyl)sulfonamido)-5-cyclopropyl-2-hydroxy-N-(tetrahydrofuran-3-yl)benzamide;
3-((5-Bromo-3-fluoro-2-hydroxyphenyl)sulfonamido)-5-cyclopropyl-2-hydroxy-N-methylbenzamide;
3-((5-Bromo-3-fluoro-2-hydroxyphenyl)sulfonamido)-5-cyclopropyl-2-hydroxy-N-(2-methoxyethyl)benzamide;
3-((5-Bromo-2-(isobutylamino)phenyl)sulfonamido)-5-cyclopropyl-2-hydroxy-N-methylbenzamide;
(R)-3-((5-Bromo-2-((3-methylbutan-2-yl)amino)phenyl)sulfonamido)-5-cyclopropyl-2-hydroxy-N-methylbenzamide;
(S)-3-((5-Bromo-2-((3-methylbutan-2-yl)amino)phenyl)sulfonamido)-5-cyclopropyl-2-hydroxy-N-methylbenzamide;
3-((5-Bromo-2-(cyclopropylamino)phenyl)sulfonamido)-5-cyclopropyl-2-hydroxy-N-methylbenzamide;
3-((5-Bromo-2-hydroxy-3-nitrophenyl)sulfonamido)-5-cyclopropyl-2-hydroxybenzamide;
3-((5-Bromo-4-chloro-2-methoxyphenyl)sulfonamido)-5-cyclopropyl-2-hydroxybenzamide;
3-((5-Bromo-4-fluoro-2-methoxyphenyl)sulfonamido)-5-cyclopropyl-2-hydroxybenzamide;
3-((5-Bromo-2-hydroxyphenyl)sulfonamido)-5-fluoro-2-hydroxybenzoic acid;
3-((5-Bromo-2-hydroxyphenyl)sulfonamido)-5-fluoro-2-hydroxybenzamide;
3-((5-Bromo-2-hydroxyphenyl)sulfonamido)-5-fluoro-2-hydroxy-N-methylbenzamide;
3-((5-Bromo-2-hydroxyphenyl)sulfonamido)-5-fluoro-2-hydroxy-N-(2-methoxyethyl)benzamide;
3-((5-Bromo-2-hydroxyphenyl)sulfonamido)-5-fluoro-2-hydroxy-N-(2-hydroxyethyl)benzamide;
3-((5-Bromo-2-hydroxyphenyl)sulfonamido)-5-cyclopropyl-2-fluorobenzoic acid;
3-((6-Bromoquinoline)-8-sulfonamido)-5-cyclopropyl-2-fluorobenzoic acid;
5-((5-Bromo-2-hydroxyphenyl)sulfonamido)-3-cyclopropyl-2-fluorobenzoic acid;
5-((5-Bromo-3-chloro-2-hydroxyphenyl)sulfonamido)-3-cyclopropyl-2-fluorobenzoic acid;
5-((6-Bromoquinoline)-8-sulfonamido)-3-cyclopropyl-2-fluorobenzoic acid;
3-((5-Bromo-2-hydroxyphenyl)sulfonamido)-5-cyclopropyl-6-fluoro-2-hydroxybenzoic acid;
3-((5-Bromo-3-chloro-2-hydroxyphenyl)sulfonamido)-5-cyclopropyl-6-fluoro-2-hydroxybenzoic acid;
3-((5-Bromo-3-fluoro-2-hydroxyphenyl)sulfonamido)-5-cyclopropyl-6-fluoro-2-hydroxybenzoic acid;
3-((5-Chloro-4-fluoro-2-hydroxyphenyl)sulfonamido)-5-cyclopropyl-6-fluoro-2-hydroxybenzoic acid;
3-((6-Bromoquinoline)-8-sulfonamido)-5-cyclopropyl-6-fluoro-2-hydroxybenzoic acid;
3-((5-Bromo-2-hydroxyphenyl)sulfonamido)-5-cyclopropyl-6-fluoro-2-hydroxybenzamide;
3-((5-Bromo-2-hydroxyphenyl)sulfonamido)-5-cyclopropyl-6-fluoro-2-hydroxy-N-methylbenzamide;
3-((5-Bromo-2-hydroxyphenyl)sulfonamido)-5-cyclopropyl-6-fluoro-2-hydroxy-N-(2-morpholinoethyl)benzamide;
3-((5-Bromo-2-hydroxyphenyl)sulfonamido)-5-cyclopropyl-6-fluoro-2-hydroxy-N-(2-hydroxyethyl)benzamide;
3-((5-Bromo-2-hydroxyphenyl)sulfonamido)-5-cyclopropyl-6-fluoro-2-hydroxy-N-(2-methoxyethyl)benzamide;
3-((5-Bromo-2-hydroxyphenyl)sulfonamido)-5-cyclopropyl-6-fluoro-2-hydroxy-N-(oxetan-3-yl)benzamide;
3-((5-Bromo-2-hydroxyphenyl)sulfonamido)-5-cyclopropyl-6-fluoro-2-hydroxy-N-(tetrahydrofuran-3-yl)benzamide;
(R)-3-((5-Bromo-2-hydroxyphenyl)sulfonamido)-5-cyclopropyl-6-fluoro-2-hydroxy-N-(tetrahydrofuran-3-yl)benzamide;
(S)-3-((5-Bromo-2-hydroxyphenyl)sulfonamido)-5-cyclopropyl-6-fluoro-2-hydroxy-N-(tetrahydrofuran-3-yl)benzamide;
3-((6-Bromoquinoline)-8-sulfonamido)-5-cyclopropyl-6-fluoro-2-hydroxy-N-methylbenzamide;
5-((5-Bromo-2-hydroxyphenyl)sulfonamido)-3-cyclopropyl-2-fluoro-N-methylbenzamide;
5-((5-Bromo-2-hydroxyphenyl)sulfonamido)-3-cyclopropyl-2-fluoro-N-(2-methoxyethyl)benzamide;
5-((5-Bromo-2-hydroxyphenyl)sulfonamido)-3-cyclopropyl-2-fluoro-N-(2-morpholinoethyl)benzamide;
5-((5-Bromo-2-hydroxyphenyl)sulfonamido)-3-cyclopropyl-2-fluoro-N-(oxetan-3-yl)benzamide;
5-((5-Bromo-2-hydroxyphenyl)sulfonamido)-3-cyclopropyl-2-fluoro-N-(tetrahydrofuran-3-yl)benzamide;
5-((6-Bromoquinoline)-8-sulfonamido)-3-cyclopropyl-2-fluoro-N-methylbenzamide;
3-((5-Bromo-2-hydroxyphenyl)sulfonamido)-5-cyclopropyl-2-fluoro-N-methylbenzamide;
3-((5-Bromo-2-hydroxyphenyl)sulfonamido)-5-cyclopropyl-2-fluoro-N-(2-methoxyethyl)benzamide;
3-((5-Bromo-2-hydroxyphenyl)sulfonamido)-5-cyclopropyl-2-fluoro-N-(2-morpholinoethyl)benzamide;
3-((5-Bromo-2-hydroxyphenyl)sulfonamido)-5-cyclopropyl-2-fluoro-N-(oxetan-3-yl)benzamide;
3-((5-Bromo-2-hydroxyphenyl)sulfonamido)-5-cyclopropyl-4-fluoro-2-hydroxy-N-methylbenzamide;
3-((5-Bromo-3-chloro-2-hydroxyphenyl)sulfonamido)-5-cyclopropyl-6-fluoro-2-hydroxy-N-methylbenzamide;
3-((5-Bromo-3-chloro-2-hydroxyphenyl)sulfonamido)-5-cyclopropyl-6-fluoro-2-hydroxy-N-(2-methoxyethyl)benzamide;

3-((5-Bromo-3-chloro-2-hydroxyphenyl)sulfonamido)-5-cyclopropyl-6-fluoro-2-hydroxy-N-(2-morpholinoethyl)benzamide;

3-((5-Bromo-3-chloro-2-hydroxyphenyl)sulfonamido)-5-cyclopropyl-6-fluoro-2-hydroxy-N-(oxetan-3-yl)benzamide;

3-((5-Bromo-3-fluoro-2-hydroxyphenyl)sulfonamido)-5-cyclopropyl-6-fluoro-2-hydroxy-N-methylbenzamide;

5-((5-Bromo-3-chloro-2-hydroxyphenyl)sulfonamido)-3-cyclopropyl-2-fluoro-N-methylbenzamide;

5-((5-Bromo-3-chloro-2-hydroxyphenyl)sulfonamido)-3-cyclopropyl-2-fluoro-N-(2-methoxyethyl)benzamide;

5-((5-Bromo-3-chloro-2-hydroxyphenyl)sulfonamido)-3-cyclopropyl-2-fluoro-N-(2-morpholinoethyl)benzamide;

5-((5-Bromo-3-chloro-2-hydroxyphenyl)sulfonamido)-3-cyclopropyl-2-fluoro-N-(1H-1,2,4-triazol-3-yl)benzamide;

5-((5-Bromo-3-chloro-2-hydroxyphenyl)sulfonamido)-3-cyclopropyl-2-fluoro-N-(oxetan-3-yl)benzamide;

3-((5-Bromo-3-chloro-2-hydroxyphenyl)sulfonamido)-5-cyclopropyl-2-fluoro-N-methylbenzamide;

3-((5-Bromo-3-chloro-2-hydroxyphenyl)sulfonamido)-5-cyclopropyl-2-fluoro-N-(2-methoxyethyl)benzamide;

3-((5-Bromo-3-chloro-2-hydroxyphenyl)sulfonamido)-5-cyclopropyl-2-fluoro-N-(2-morpholinoethyl)benzamide;

3-((5-Bromo-3-chloro-2-hydroxyphenyl)sulfonamido)-5-cyclopropyl-2-fluoro-N-(oxetan-3-yl)benzamide;

3-((5-Bromo-2-hydroxyphenyl)sulfonamido)-2-hydroxy-5-(trifluoromethoxy)benzoic acid;

3-((6-Bromoquinoline)-8-sulfonamido)-2-hydroxy-5-(trifluoromethoxy)benzoic acid;

3-((5-Bromo-2-hydroxyphenyl)sulfonamido)-2-hydroxy-N-methyl-5-(trifluoromethoxy)benzamide;

3-((5-Bromo-2-hydroxyphenyl)sulfonamido)-2-hydroxy-N-(2-methoxyethyl)-5-(trifluoromethoxy)benzamide;

3-((5-Bromo-2-hydroxyphenyl)sulfonamido)-2-hydroxy-N-(2-morpholinoethyl)-5-(trifluoromethoxy)benzamide;

3-((5-Bromo-2-hydroxyphenyl)sulfonamido)-2-hydroxy-N-((tetrahydrofuran-2-yl)methyl)-5-(trifluoromethoxy)benzamide;

3-((5-Bromo-2-hydroxyphenyl)sulfonamido)-2-hydroxy-N-((tetrahydrofuran-3-yl)methyl)-5-(trifluoromethoxy)benzamide;

3-((5-Bromo-2-hydroxyphenyl)sulfonamido)-2-hydroxy-N-(tetrahydrofuran-3-yl)-5-(trifluoromethoxy)benzamide;

(S)-3-((5-Bromo-2-hydroxyphenyl)sulfonamido)-2-hydroxy-N-(tetrahydrofuran-3-yl)-5-(trifluoromethoxy)benzamide;

(S)-5-Bromo-2-hydroxy-N-(2-hydroxy-3-(2-(hydroxymethyl)pyrrolidine-1-carbonyl)-5-(trifluoromethoxy)phenyl)benzenesulfonamide;

(R)-5-Bromo-2-hydroxy-N-(2-hydroxy-3-(2-(hydroxymethyl)pyrrolidine-1-carbonyl)-5-(trifluoromethoxy)phenyl)benzenesulfonamide;

(S)-5-Bromo-2-hydroxy-N-(2-hydroxy-3-(2-(methoxymethyl)pyrrolidine-1-carbonyl)-5-(trifluoromethoxy)phenyl)benzenesulfonamide;

(R)-5-Bromo-2-hydroxy-N-(2-hydroxy-3-(2-(methoxymethyl)pyrrolidine-1-carbonyl)-5-(trifluoromethoxy)phenyl)benzenesulfonamide;

(R)-5-Bromo-2-hydroxy-N-(2-hydroxy-3-(3-hydroxypyrrolidine-1-carbonyl)-5-(trifluoromethoxy)phenyl)benzenesulfonamide;

5-Bromo-2-hydroxy-N-(2-hydroxy-3-(3-methoxypyrrolidine-1-carbonyl)-5-(trifluoromethoxy)phenyl)benzenesulfonamide;

3-((5-Chloro-2-hydroxyphenyl)sulfonamido)-2-hydroxy-N-methyl-5-(trifluoromethoxy)benzamide;

(S)-5-Chloro-2-hydroxy-N-(2-hydroxy-3-(2-(methoxymethyl)pyrrolidine-1-carbonyl)-5-(trifluoromethoxy)phenyl)benzenesulfonamide;

(R)-5-Chloro-2-hydroxy-N-(2-hydroxy-3-(2-(methoxymethyl)pyrrolidine-1-carbonyl)-5-(trifluoromethoxy)phenyl)benzenesulfonamide;

3-((5-Chloro-2-hydroxyphenyl)sulfonamido)-2-hydroxy-N-((tetrahydrofuran-2-yl)methyl)-5-(trifluoromethoxy)benzamide;

3-((5-Bromo-2-methoxyphenyl)sulfonamido)-2-hydroxy-N-((tetrahydrofuran-2-yl)methyl)-5-(trifluoromethoxy)benzamide;

(S)-5-Bromo-N-(2-hydroxy-3-(2-(methoxymethyl)pyrrolidine-1-carbonyl)-5-(trifluoromethoxy)phenyl)-2-methoxybenzenesulfonamide;

(R)-5-bromo-N-(2-hydroxy-3-(2-(methoxymethyl)pyrrolidine-1-carbonyl)-5-(trifluoromethoxy)phenyl)-2-methoxybenzenesulfonamide;

3-((6-Bromoquinoline)-8-sulfonamido)-2-hydroxy-N-methyl-5-(trifluoromethoxy)benzamide;

5-((5-Bromo-2-methoxyphenyl)sulfonamido)-4-hydroxy-[1,1'-biphenyl]-3-carboxylic acid;

5-((5-Bromo-2-hydroxyphenyl)sulfonamido)-4-hydroxy-2-methyl-[1,1'-biphenyl]-3-carboxylic acid;

3-((5-Bromo-2-hydroxyphenyl)sulfonamido)-5-cyclopropyl-2-hydroxy-6-methylbenzoic acid;

3-((5-Bromo-2-methoxyphenyl)sulfonamido)-5-(3,6-dihydro-2H-pyran-4-yl)benzoic acid;

3-((5-Bromo-2-methoxyphenyl)sulfonamido)-2-hydroxy-5-morpholinobenzoic acid;

3-((5-Bromo-2-hydroxyphenyl)sulfonamido)-2-hydroxy-5-(thiophen-3-yl)benzoic acid;

3-((5-bromo-2-hydroxyphenyl)sulfonamido)-2-hydroxy-5-(thiophen-2-yl)benzoic acid;

3-((5-Bromo-2-hydroxyphenyl)sulfonamido)-2-hydroxy-5-(3-methylthiophen-2-yl)benzoic acid;

3-((5-Bromo-2-hydroxyphenyl)sulfonamido)-2-hydroxy-5-(2-methylthiophen-3-yl)benzoic acid;

3-((5-Bromo-2-hydroxyphenyl)sulfonamido)-6-fluoro-2-hydroxy-5-(thiophen-3-yl)benzoic acid;

N-(3-((5-Bromo-2-methoxyphenyl)sulfonamido)-5-chloro-2-hydroxyphenyl)acetamide;

3-((5-Bromo-2-hydroxyphenyl)sulfonamido)-5-(tert-butyl)-2-hydroxybenzoic acid;

3-((5-Bromo-2-hydroxyphenyl)sulfonamido)-5-(tert-butyl)-2-hydroxy-N-methylbenzamide;

3-((5-Bromo-2-hydroxyphenyl)sulfonamido)-5-(1-cyanocyclobutyl)-2-hydroxybenzoic acid;

3-((5-Bromo-2-methoxyphenyl)sulfonamido)-5-(1-cyanocyclobutyl)-2-hydroxybenzoic acid;

3-((5-Bromo-3-chloro-2-hydroxyphenyl)sulfonamido)-5-(1-cyanocyclobutyl)-2-hydroxybenzoic acid;

3-((5-Bromo-4-chloro-2-methoxyphenyl)sulfonamido)-5-(1-cyanocyclobutyl)-2-hydroxybenzoic acid;

3-((5-Bromo-2-hydroxyphenyl)sulfonamido)-5-(1-cyanocyclobutyl)-2-hydroxy-N-methylbenzamide;

3-((5-Bromo-2-methoxyphenyl)sulfonamido)-5-(1-cyanocyclobutyl)-2-hydroxy-N-methylbenzamide;

3-((5-Bromo-3-chloro-2-hydroxyphenyl)sulfonamido)-5-(1-cyanocyclobutyl)-2-hydroxy-N-methylbenzamide;

3-((5-Bromo-2-hydroxy-3-methylphenyl)sulfonamido)-5-(1-cyanocyclobutyl)-2-hydroxy-N-methylbenzamide;

3-((5-Bromo-3-ethyl-2-hydroxyphenyl)sulfonamido)-5-(1-cyanocyclobutyl)-2-hydroxy-N-methylbenzamide;

3-((5-Bromo-2-hydroxy-3-(trifluoromethoxy)phenyl)sulfonamido)-5-(1-cyanocyclobutyl)-2-hydroxy-N-methylbenzamide;

3-((5-Bromo-4-chloro-2-methoxyphenyl)sulfonamido)-5-(1-cyanocyclobutyl)-2-hydroxy-N-methylbenzamide;

5-(1-Cyanocyclobutyl)-3-((3,5-dichloro-2-hydroxyphenyl)sulfonamido)-2-hydroxy-N-methylbenzamide;

3-((6-Bromoquinoline)-8-sulfonamido)-5-(1-cyanocyclobutyl)-2-hydroxy-N-methylbenzamide;

3-((5-Bromo-2-hydroxyphenyl)sulfonamido)-5-(1-cyanocyclobutyl)-2-hydroxybenzamide;

3-((5-Bromo-2-hydroxyphenyl)sulfonamido)-5-(1-cyanocyclobutyl)-2-hydroxy-N-(2-methoxyethyl)benzamide;

3-((5-Bromo-2-hydroxyphenyl)sulfonamido)-5-(1-cyanocyclobutyl)-2-hydroxy-N-((tetrahydrofuran-2-yl)methyl)benzamide;

5-Bromo-N-(5-(1-cyanocyclobutyl)-2-hydroxy-3-(3-methoxypyrrolidine-1-carbonyl)phenyl)-2-hydroxybenzenesulfonamide;

3-((5-Bromo-2-hydroxyphenyl)sulfonamido)-5-(1-cyanocyclobutyl)-2-hydroxy-N-((2-oxo-1,2-dihydropyridin-4-yl)methyl)benzamide;

5-Bromo-N-(5-(1-cyanocyclobutyl)-2-hydroxy-3-(3-methoxyazetidine-1-carbonyl)phenyl)-2-hydroxybenzenesulfonamide;

5-Bromo-N-(5-(1-cyanocyclobutyl)-2-hydroxy-3-(3-hydroxyazetidine-1-carbonyl)phenyl)-2-hydroxybenzenesulfonamide;

3-((5-Bromo-2-hydroxyphenyl)sulfonamido)-5-(1-cyanocyclobutyl)-2-hydroxy-N-(2-morpholinoethyl)benzamide;

3-((5-Bromo-2-hydroxyphenyl)sulfonamido)-5-(1-cyanocyclobutyl)-N-(2-(dimethylamino)ethyl)-2-hydroxybenzamide;

3-((5-Bromo-2-hydroxyphenyl)sulfonamido)-5-(1-cyanocyclobutyl)-2-hydroxy-N-(1H-1,2,4-triazol-3-yl)benzamide;

3-((5-Bromo-2-hydroxyphenyl)sulfonamido)-5-(1-cyanocyclobutyl)-2-hydroxy-N-(2-hydroxyethyl)benzamide;

3-((5-Bromo-2-hydroxyphenyl)sulfonamido)-5-(1-cyanocyclobutyl)-2-hydroxy-N-((tetrahydro-2H-pyran-2-yl)methyl)benzamide;

3-((5-Bromo-2-hydroxyphenyl)sulfonamido)-5-(1-cyanocyclobutyl)-2-hydroxy-N-((6-oxo-1,6-dihydropyridin-3-yl)methyl)benzamide;

3-((5-Bromo-2-hydroxyphenyl)sulfonamido)-5-(1-cyanocyclohexyl)-2-hydroxybenzoic acid;

3-((5-Bromo-2-hydroxyphenyl)sulfonamido)-5-(1-cyanocyclohexyl)-2-hydroxybenzamide;

3-((5-Bromo-2-hydroxyphenyl)sulfonamido)-5-(1-cyanocyclohexyl)-2-hydroxy-N-methylbenzamide;

3-((5-Bromo-3-chloro-2-hydroxyphenyl)sulfonamido)-5-(1-cyanocyclohexyl)-2-hydroxybenzoic acid;

3-((5-Bromo-3-chloro-2-hydroxyphenyl)sulfonamido)-5-(1-cyanocyclohexyl)-2-hydroxybenzamide;

3-((5-Bromo-3-chloro-2-hydroxyphenyl)sulfonamido)-5-(1-cyanocyclohexyl)-2-hydroxy-N-methylbenzamide;

3-((5-bromo-3-chloro-2-methoxyphenyl)sulfonamido)-5-(1-cyanocyclobutyl)-2-hydroxy-N-methylbenzamide;

3-((5-bromo-3-chloro-2-methoxyphenyl)sulfonamido)-5-(1-cyanocyclobutyl)-2-hydroxybenzoic acid;

3-((5-bromo-4-fluoro-2-methoxyphenyl)sulfonamido)-5-(1-cyanocyclobutyl)-2-hydroxy-N-methylbenzamide;

3-((6-bromoquinoline)-8-sulfonamido)-5-(1-cyanocyclobutyl)-2-hydroxybenzoic acid;

3-((5-bromo-2,3-dihydrobenzofuran)-7-sulfonamido)-5-(1-cyanocyclobutyl)-2-hydroxy-N-methylbenzamide;

3-((5-bromo-2,3-dihydrobenzofuran)-7-sulfonamido)-5-(1-cyanocyclobutyl)-2-hydroxybenzoic acid;

3-((5-Bromo-3-chloro-2-hydroxyphenyl)sulfonamido)-2-hydroxy-N-methyl-5-(pentafluoro-$\lambda^6$-sulfaneyl)benzamide;

3-((5-Bromo-3-chloro-2-hydroxyphenyl)sulfonamido)-2-hydroxy-5-(pentafluoro-$\lambda^1$-sulfaneyl)benzoic acid;

3-((5-Bromo-2-hydroxyphenyl)sulfonamido)-2-hydroxy-5-(pentafluoro-$\lambda^1$-sulfaneyl)benzoic acid;

3-((5-Bromo-2-hydroxyphenyl)sulfonamido)-2-hydroxy-N-methyl-5-(pentafluoro-$\lambda^6$-sulfaneyl)benzamide;

3-((6-Bromoquinoline)-8-sulfonamido)-2-hydroxy-N-methyl-5-pentafluoro-$\lambda^6$-sulfaneyl)benzamide;

3-((6-Bromoquinoline)-8-sulfonamido)-2-hydroxy-5-pentafluoro-$\lambda^6$-sulfaneyl)benzoic acid;

3-((5-Bromo-3-chloro-2-hydroxyphenyl)sulfonamido)-5-chloro-N-methylbenzamide;

3-((5-Bromo-2-hydroxyphenyl)sulfonamido)-5-chloro-N-methylbenzamide;

3-((5-Bromo-3-chloro-2-hydroxyphenyl)sulfonamido)-5-(1-cyanocyclobutyl)benzoic acid;

5-Bromo-2-hydroxy-N-(3-(methylsulfonyl)phenyl)-3-(trifluoromethoxy)benzenesulfonamide;

5-Bromo-N-(3-bromo-5-(methylsulfonyl)phenyl)-2-hydroxy-3-(trifluoromethoxy)benzenesulfonamide;

N-(3-chloro-5-(methylsulfonyl)phenyl)-2-hydroxy-3-(trifluoromethoxy)benzenesulfonamide;

5-Bromo-N-(3-chloro-5-(methylsulfonyl)phenyl)-3-ethyl-2-hydroxybenzenesulfonamide;

5-Bromo-N-(3-chloro-5-(methylsulfonyl)phenyl)-2-hydroxybenzenesulfonamide;

5-Bromo-3-chloro-N-(3-chloro-5-(methylsulfonyl)phenyl)-2-hydroxybenzenesulfonamide;

5-Bromo-N-(3-cyclopropyl-5-(methylsulfonyl)phenyl)-2-hydroxybenzenesulfonamide;

5-Bromo-3-chloro-N-(3-cyclopropyl-5-(methylsulfonyl)phenyl)-2-hydroxybenzenesulfonamide;

5-Bromo-2-hydroxy-N-(3-(methylsulfonyl)-5-(trifluoromethoxy)phenyl)benzenesulfonamide;

5-Bromo-3-chloro-2-hydroxy-N-(3-(methylsulfonyl)-5-(trifluoromethoxy)phenyl)benzenesulfonamide;

5-Bromo-2-hydroxy-N-(3-(methylsulfonyl)-5-(pentafluoro-$\lambda^6$-sulfaneyl)phenyl)benzenesulfonamide;

5-Bromo-3-chloro-2-hydroxy-N-(3-(methylsulfonyl)-5-(pentafluoro-$\lambda^6$-sulfaneyl)phenyl)benzenesulfonamide;

5-Bromo-N-(3-bromo-5-((tetrahydrofuran-2-yl)sulfonyl)phenyl)-3-chloro-2-hydroxybenzenesulfonamide;

5-Bromo-3-chloro-N-(3-cyclopropyl-5-((tetrahydrofuran-2-yl)sulfonyl)phenyl)-2-hydroxybenzenesulfonamide;

5-Bromo-N-(3-bromo-5-((tetrahydrofuran-2-yl)sulfonyl)phenyl)-2-hydroxybenzenesulfonamide;

5-Bromo-3-chloro-N-(5-chloro-2-hydroxy-3-(methylsulfonyl)phenyl)-2-hydroxybenzenesulfonamide;

5-Bromo-N-(5-chloro-2-hydroxy-3-(methylsulfonyl)phenyl)-2-hydroxybenzenesulfonamide;

5-Bromo-3-chloro-2-hydroxy-N-(2-hydroxy-3-(methylsulfonyl)-5-(pentafluoro-$\lambda^6$-sulfaneyl)phenyl)benzenesulfonamide;

5-Bromo-2-hydroxy-N-(2-hydroxy-3-(methylsulfonyl)-5-(pentafluoro-$\lambda^6$-sulfaneyl)phenyl)benzenesulfonamide;

4-Bromo-2-hydroxy-N-(2-hydroxy-3-(methylsulfonyl)-5-(pentafluoro-$\lambda$6-sulfaneyl)phenyl)benzenesulfonamide;

5-Bromo-3-Chloro-N-(5-chloro-3-(ethylsulfonyl)-2-hydroxyphenyl)-2-hydroxybenzenesulfonamide;

5-Bromo-N-(5-chloro-3-(ethylsulfonyl)-2-hydroxyphenyl)-2-hydroxybenzenesulfonamide;

5-Bromo-3-chloro-N-(5-chloro-2-hydroxy-3-(isopropylsulfonyl)phenyl)-2-hydroxybenzenesulfonamide;
5-Bromo-3-chloro-N-(5-chloro-2-hydroxy-3-(isopropylsulfinyl)phenyl)-2-hydroxybenzenesulfonamide;
5-Bromo-N-(5-chloro-2-hydroxy-3-(isopropylsulfinyl)phenyl)-2-hydroxybenzenesulfonamide;
5-Bromo-3-chloro-2-hydroxy-N-(2-hydroxy-3-(methylsulfinyl)-5-(trifluoromethyl)phenyl)benzenesulfonamide;
5-Bromo-3-2-hydroxy-N-(2-hydroxy-3-(methylsulfonyl)-5-(trifluoromethyl)phenyl)benzenesulfonamide;
5-Bromo-3-chloro-N-(5-cyclopropyl-2-hydroxy-3-(methylsulfonyl)phenyl)-2-hydroxybenzenesulfonamide;
5-Bromo-N-(5-cyclopropyl-2-hydroxy-3-(methylsulfonyl)phenyl)-2-hydroxybenzenesulfonamide;
5-Bromo-3-chloro-N-(5-chloro-2-hydroxy-3-sulfamoylphenyl)-2-hydroxybenzenesulfonamide;
5-Bromos-N-(5-chloro-2-hydroxy-3-sulfamoylphenyl)-2-hydroxybenzenesulfonamide;
5-bromo-3-chloro-N-(5-chloro-2-hydroxy-3-(N-methylsulfamoyl)phenyl)-2-hydroxybenzenesulfonamide;
5-bromo-N-(5-chloro-2-hydroxy-3-(N-methylsulfamoyl)phenyl)-2-hydroxybenzenesulfonamide;
5-bromo-3-chloro-N-(5-chloro-2-hydroxy-3-(N-(2-methoxyethyl)sulfamoyl)phenyl)-2-hydroxybenzenesulfonamide;
5-bromo-N-(5-chloro-2-hydroxy-3-(N-(2-methoxyethyl)sulfamoyl)phenyl)-2-hydroxybenzenesulfonamide;
5-Bromo-3-chloro-N-(5-chloro-2-hydroxy-3-(N-((tetrahydrofuran-2-yl)methyl)sulfamoyl)phenyl)-2-hydroxybenzenesulfonamide;
5-Bromo-N-(5-chloro-2-hydroxy-3-(N-((tetrahydrofuran-2-yl)methyl)sulfamoyl)phenyl)-2-hydroxybenzenesulfonamide;
5-Bromo-3-chloro-N-(5-chloro-2-hydroxy-3-(N-(2-(4-methylpiperazin-1-yl)ethyl)sulfamoyl)phenyl)-2-hydroxybenzenesulfonamide;
5-Bromo-3-chloro-N-(3-chloro-5-((2-(diethylamino)ethyl)thio)phenyl)-2-hydroxybenzenesulfonamide;
5-Bromo-3-chloro-N-(3-chloro-5-((2-(diethylamino)ethyl)sulfonyl)phenyl)-2-hydroxybenzenesulfonamide;
5-Bromo-3-chloro-N-(3-chloro-5-((2-(diisopropylamino)ethyl)thio)phenyl)-2-hydroxybenzenesulfonamide;
5-Bromo-3-chloro-N-(3-chloro-5-((2-(diisopropylamino)ethyl)sulfonyl)phenyl)-2-hydroxybenzenesulfonamide;
5-Bromo-N-(3-chloro-5-((2-(diethylamino)ethyl)sulfonyl)phenyl)-2-hydroxybenzenesulfonamide;
5-Bromo-N-(3-chloro-5-((2-(diisopropylamino)ethyl)sulfonyl)phenyl)-2-hydroxybenzenesulfonamide;
6-Bromo-N-(3-chloro-5-((2-(diethylamino)ethyl)sulfonyl)phenyl)quinoline-8-sulfonamide;
6-Bromo-N-(3-chloro-5-((2-(diisopropylamino)ethyl)sulfonyl)phenyl)quinoline-8-sulfonamide;
5-Bromo-N-(3-chloro-5-((2-(diethylamino)ethyl)sulfonyl)phenyl)-2-methoxybenzenesulfonamide;
5-Bromo-N-(3-chloro-5-((2-(diisopropylamino)ethyl)sulfonyl)phenyl)-2-methoxybenzenesulfonamide;
5-Bromo-3-chloro-N-(5-chloro-2-hydroxy-3-(methylsulfonyl)phenyl)-2-methoxybenzenesulfonamide;
5-Bromo-N-(5-chloro-2-hydroxy-3-(methylsulfonyl)phenyl)-2-methoxybenzenesulfonamide;
5-Bromo-3-chloro-N-(3-chloro-5-((3-(dimethylamino)propyl)sulfonyl)phenyl)-2-hydroxybenzenesulfonamide;
5-Bromo-N-(3-chloro-5-((3-(dimethylamino)propyl)sulfonyl)phenyl)-2-hydroxybenzenesulfonamide;
5-Bromo-3-chloro-N-(5-chloro-2-fluoro-3-(methylsulfonyl)phenyl)-2-hydroxybenzenesulfonamide;
5-Bromo-N-(5-chloro-2-hydroxy-3-(methylsulfonyl)phenyl)-2,3-dihydrobenzofuran-7-sulfonamide;
5-Bromo-N-(5-(1-cyanocyclobutyl)-2-hydroxy-3-(methylsulfonyl)phenyl)-2-methoxybenzenesulfonamide;
5-Bromo-3-chloro-N-(5-(1-cyanocyclobutyl)-2-hydroxy-3-(methylsulfonyl)phenyl)-2-hydroxybenzenesulfonamide;
6-Bromo-N-(5-(1-cyanocyclobutyl)-2-hydroxy-3-(methylsulfonyl)phenyl)quinoline-8-sulfonamide;
5-Bromo-3-chloro-N-(5-(1-cyanocyclobutyl)-2-hydroxy-3-(methylsulfonyl)phenyl)-2-methoxybenzenesulfonamide;
5-Bromo-3-chloro-N-(3-(1-cyanocyclobutyl)-5-(methylsulfonyl)phenyl)-2-hydroxybenzenesulfonamide;
5-bromo-N-(3-(1-cyanocyclobutyl)-5-(methylsulfonyl)phenyl)-2-hydroxybenzenesulfonamide;
5-Bromo-N-(5-chloro-2-hydroxy-3-nitrophenyl)-2-methoxybenzenesulfonamide;
5-Bromo-N-(5-chloro-2-hydroxy-3-nitrophenyl)-2-methoxybenzenesulfonamide;
2-Bromo-N-(5-chloro-2-hydroxy-3-nitrophenyl)-4-ethyl-5-hydroxybenzenesulfonamide;
Methyl 4-chloro-2-(N-(5-chloro-2-hydroxy-3-nitrophenyl)sulfamoyl)benzoate;
Methyl 4-chloro-2-(N-(5-chloro-2-hydroxy-3-nitrophenyl)sulfamoyl)benzoate;
5-Bromo-N-(5-chloro-2-hydroxy-3-nitrophenyl)-2-hydroxybenzenesulfonamide;
5-Bromo-N-(5-chloro-2-hydroxy-3-nitrophenyl)-2,3-dihydrobenzofuran-7-sulfonamide;
5-Bromo-N-(5-chloro-2-hydroxy-3-nitrophenyl)-2,4-dimethoxybenzenesulfonamide;
5-Bromo-N-(5-chloro-2-hydroxy-3-nitrophenyl)-2-hydroxy-3-(trifluoromethoxy)benzenesulfonamide;
5-Bromo-N-(5-chloro-2-hydroxy-3-nitrophenyl)-2-hydroxy-3-propylbenzenesulfonamide;
3-Bromo-5-(N-(5-chloro-2-hydroxy-3-nitrophenyl)sulfamoyl)benzoic acid;
5-Bromo-3-chloro-N-(3-chloro-5-(2-oxopyrrolidin-1-yl)phenyl)-2-hydroxybenzenesulfonamide;
5-Bromo-3-chloro-N-(3-chloro-5-(2-oxoimidazolidin-1-yl)phenyl)-2-hydroxybenzenesulfonamide;
3-Bromo-N-(5-chloro-2-hydroxyphenyl)benzenesulfonamide;
5-Bromo-N-(5-chloro-2-hydroxyphenyl)-2-hydroxybenzenesulfonamide;
5-Bromo-N-(5-cyclopropyl-2-hydroxyphenyl)-2-hydroxybenzenesulfonamide;
5-Bromo-2-hydroxy-N-(2-hydroxy-5-(trifluoromethoxy)phenyl)benzenesulfonamide;
5-Bromo-2-hydroxy-N-(2-hydroxy-5-(pentafluorosulfanyl)phenyl)benzenesulfonamide;
5-Bromo-2-hydroxy-N-(2-hydroxy-5-(1-(trifluoromethyl)cyclopropyl)phenyl)benzenesulfonamide;
5-Bromo-N-(5-(1-cyanocyclopropyl)-2-hydroxyphenyl)-2-hydroxybenzenesulfonamide;
5-Bromo-N-(5-(1-cyanocyclobutyl)-2-hydroxyphenyl)-2-hydroxybenzenesulfonamide;
5-Bromo-N-(5-(1-cyanocyclopentyl)-2-hydroxyphenyl)-2-hydroxybenzenesulfonamide;
5-Bromo-N-(5-(1-cyanocyclohexyl)-2-hydroxyphenyl)-2-hydroxybenzenesulfonamide;
or a pharmaceutically acceptable salt thereof.

E50. The compound of any of embodiments 1-49.2, or a pharmaceutically acceptable salt thereof, wherein the compound is isotopically labeled.

E51. A pharmaceutical composition comprising the compound of any of embodiments 1-50, or a pharmaceutically acceptable salt thereof, and a pharmaceutically acceptable carrier.

E52. A method of treating cancer comprising administering to a subject in need thereof, a therapeutically effective amount of the compound of any of embodiments 1-50, or a pharmaceutically acceptable salt thereof, or the pharmaceutical composition of embodiment 51.

E53. A method of inhibiting cancer cell proliferation, comprising administering to a subject in need thereof, the compound of any of embodiments 1-50, or a pharmaceutically acceptable salt thereof, or the pharmaceutical composition of embodiment 51, in an amount effective to inhibit the cancer cell proliferation.

E54. Use of the compound of any of embodiments 1-50, or a pharmaceutically acceptable salt thereof, or the pharmaceutical composition of embodiment 51, in the manufacture of a medicament for the treatment of cancer.

E55. Use of the compound of any of embodiments 1-50, or a pharmaceutically acceptable salt thereof, or the pharmaceutical composition of embodiment 51, in the manufacture of a medicament for the inhibition of cancer cell proliferation.

E56. The compound of any of embodiments 1-50, or a pharmaceutically acceptable salt thereof, or the pharmaceutical composition of embodiment 51, for use in the treatment of cancer.

E57. The compound of any of embodiments 1-50, or a pharmaceutically acceptable salt thereof, or the pharmaceutical composition of embodiment 51, for use in the inhibition of cancer cell proliferation.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I) or (II), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) or (II) are $^{11}C$, $^{13}N$, $^{15}O$, and $^{18}F$. Isotopically-labeled compounds of formula (I) or (II) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. BINDING TO WDR5

The disclosed compounds may bind to WDR5 and prevent the association of MYC. The compounds may bind to WDR5 and prevent oncogenic processes associated with MYC.

Compounds of formula (I) or (II) can bind to WDR5 resulting in a $K_i$ ranging from about 0.01 nM to about 250 µM. The compounds may have a $K_i$ of about 250 µM, about 200 µM, about 150 µM, about 100 µM, about 90 µM, about 80 µM, about 70 µM, about 60 µM, about 50 µM, about 40 µM, about 30 µM, about 20 µM, about 10 µM, about 9 µM, about 8 µM, about 7 µM, about 6 µM, about 5 µM, about 4 µM, about 3 µM, about 2 µM, about 1 µM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) or (II) can bind to WDR5 resulting in a $K_i$ of less than 250 µM, less than 200 µM, less than 150 µM, less than 100 µM, less than 90 µM, less than 80 µM, less than 70 µM, less than 60 µM, less than 50 µM, less than 40 µM, less than 30 µM, less than 20 µM, less than 10 µM, less than 9 µM, less than 8 µM, less than 7 µM, less than 6 µM, less than 5 µM, less than 4 µM, less than 3 µM, less than 2 µM, less than 1 µM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. GENERAL SYNTHESIS

Compounds of formula (I) or (II) may be prepared by synthetic processes or by metabolic processes. Preparation of the compounds by metabolic processes includes those occurring in the human or animal body (in vivo) or processes occurring in vitro.

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein. Compounds of formula (I) or (II) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

Compounds of the current invention can be readily synthesized using a number of techniques known to those of skill in the art. In one convenient procedure, compounds of the current invention can be prepared by reacting an appropriately substituted aniline with an appropriately substituted sulfonyl chloride.

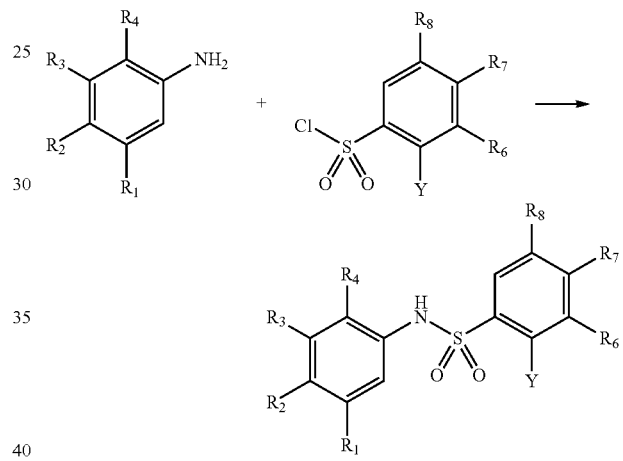

It will be recognized by those of ordinary skill in the art that the anilines and sulfonyl chlorides required for this procedure can be prepared using a number of techniques. In one such technique, appropriately substituted aromatic compounds can be reacted with chlorosulfonic acid, as shown in Scheme 1, and as exemplified by General Procedure A.

Scheme 1. Synthesis of sulfonyl chlorides

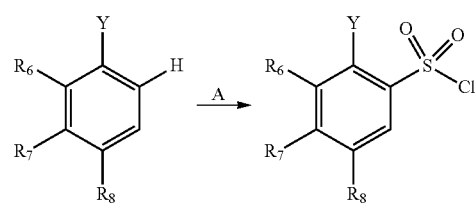

General Procedure A (Chlorosulfonation). Chlorosulfonic acid (7-10 eq) was cooled to −10° C. in a bath of ice/saturated aqueous NaCl. To this was added the corresponding aromatic species (1 eq), portion-wise, as required; the mixture was stirred for 1-16 h. The mixture was quenched by careful addition to a slurry of ice (with or without the addition of saturated aqueous NaCl) and $CH_2Cl_2$, extracting with $CH_2Cl_2$. The crude material was purified by ISCO flash chromatography or used directly with no purification.

Likewise, those of skill in the art will recognize that the anilines required to synthesize compounds of the present invention can be prepared using several known techniques. In one such convenient procedure, appropriately substituted aromatic compounds can be reacted with nitric acid in the presence of sulfuric and in an appropriate solvent, such as dichoromethane, dichloroethane, or the like. Subsequently, the resulting nitro aromatic compound can be converted to the aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 2 and exemplified with General Procedures B followed by C or D.

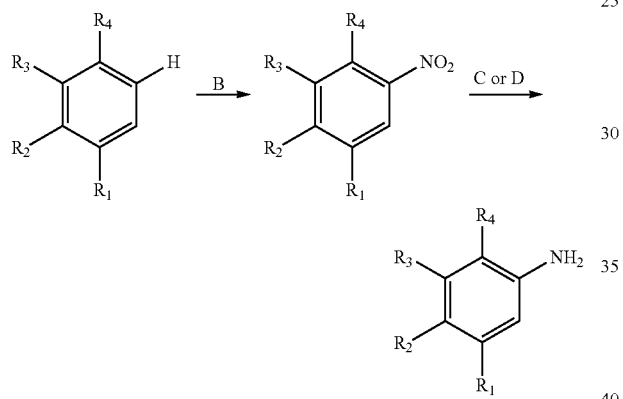

Scheme 2. Synthesis of anilines

General Procedure B (Nitration). A 0.2-0.4 M solution containing the appropriate reactant (1 eq) in $CH_2Cl_2$ was cooled to –20° C. or to 0° C. in an ice/water bath. To this was added a pre-mixed solution of $HNO_3$ (conc., 1.5-1.6 eq) and $H_2SO_4$ (conc., 1.5-2.7 eq). The mixture was stirred for 1-16 h, allowing to warm to r.t., then poured over ice water and extracted with $CH_2Cl_2$. The crude material was purified by ISCO flash chromatography.

General Procedure C (Hydrogenation). To a solution containing the appropriate reactant (1 eq) and EtOAc (with or without added MeOH), was added Pd/C (5% C by wt., 10 mol %) and the mixture was stirred under a $H_2$ atmosphere for 16 h. The mixture was filtered through celite, concentrated, and purified by ISCO flash chromatography if required.

General Procedure D (Nitro Reduction). To a mixture containing the corresponding nitrobenzene and HOAc, iron powder was added. The reaction mixture was allowed to stir overnight at room temperature, then filtered and concentrated. The crude material was purified by ISCO chromatography or preparative HPLC.

Some compounds of the current invention, in which the aniline is substituted with an ester, can be conveniently prepared by first reacting an appropriately substituted aniline with an appropriately substituted sulfonyl chloride in an appropriate solvent, such as dichloromethane, tetrahydrofuran, or the like, and using an appropriate base, such as pyridine, triethyl amine, diisopropylethyl amine, or the like. Then, the ester can be converted to a compound of the present invention by reacting the ester-substituted compound with a reagent capable of hydrozyling the ester, such as lithium hydroxide, sodium hydroxide, or the like, in a suitable solvent, such as ether, tetrahydrofuran, methanol, water, or the like. This procedure is shown in Scheme 3 and exemplified by General Procedures E and F.

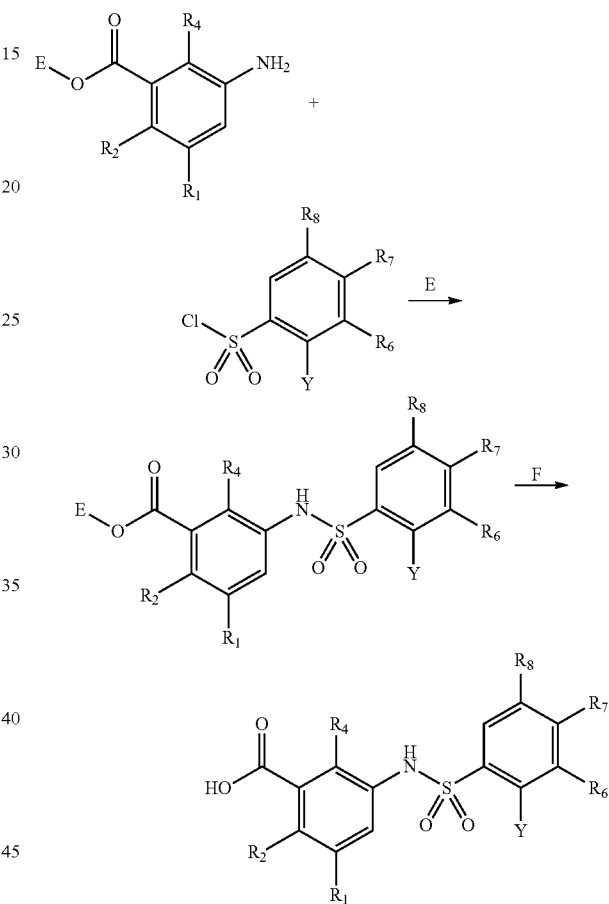

Scheme 3. Sulfonamide coupling and acid hydrolysis.

E = Methyl, ethyl, or similar

General Procedure E (Sulfonamide Coupling). To a solution containing the corresponding aniline (1-1.5 eq), sulfonyl chloride (1.0-1.5 eq), and $CH_2Cl_2$, at 0.2 M at r.t., was added pyridine (3 eq). The mixture was allowed to stir for 1-16 h, then concentrated under reduced pressure and purified by ISCO flash chromatography or preparative HPLC, unless otherwise stated.

General Procedure F (Ester Hydrolysis). A ~0.2 M solution containing the corresponding ester (1 eq) and THF or a THF/MeOH mixture was added a 2 M aqueous solution of LiOH or a 1 M aqueous solution of NaOH. The reaction mixture was heated at 45-65° C. for 1-16 h, unless otherwise stated. The mixture was acidified with hydrochloric acid, extracted with EtOAc and washed with brine. The crude material was purified by preparative HPLC.

Some compounds of the present invention can be conveniently synthesized by reacting an ester-containing compound with an appropriate amine in a suitable solvent, such as tetrahydrofuran, dioxane, dimethylsulfoxide, or the like, and at a temperature of 30-150° C., optionally in the presence of a suitable base, such as potassium carbonate, trimethylamine, diisopropylethyl amine, or the like. Similar compounds can also be conveniently prepared by converting an acid-containing compound to an amide-containing compound using a suitable amine. Those of skill in the art will recognize that there are numerous ways to accomplish this transformation. Methods useful for the preparation of compounds of the current invention which contain an amide include treating an appropriately substituted acid-containing compound with a suitable coupling agent, such as EDC, HATU, or Pybrop, in a suitable solvent, such as dicholoromethane, tetrahydrofuran, dimethylformamide, or the like, in the presence of an appropriately substituted amine, and using a suitable base, such as triethyl amine or diisopropyl amine. These procedures for converting an ester- or acid-containing compound to an amide-containing compound are shown in Scheme 4 and exemplified by General Procedures G, H, I, and J.

General Procedure G (Methyl Amide Synthesis). To the corresponding salicylate ester (1 eq) was added a 2.0 M solution of methylamine in THF (10 eq) and the mixture was heated at 65° C. for 1-16 h. The mixture was concentrated under reduced pressure and purified by preparative HPLC.

General Procedure H (Amide Coupling—Thermal). To the corresponding salicylate ester (1 eq) was added the corresponding amine (1.5-15 eq), NEt$_3$ or DIPEA (3-30 eq), and THF or 1,4-dioxane. The reaction mixture was heated at 90-100° C. for 1-16 h. DMSO was added to aid dissolution where required. The mixture was concentrated in vacuo and purified by preparative HPLC.

General Procedure I (HATU Mediated Amide Coupling). A 0.2 M solution containing the corresponding carboxylic acid (1 eq) and DIPEA (3 eq) in CH$_2$Cl$_2$ was cooled to 0° C. in an ice/water bath. HATU (1.5 eq) was added and the reaction mixture was stirred for 30 mins, followed by the addition of amine (1.1 eq). The solution was warmed to r.t. and stirred for 16 h, then diluted with CH$_2$Cl$_2$ and washed with H$_2$O. Crude product was purified by ISCO flash chromatography or preparative HPLC.

General Procedure J (PyBrop Mediated Amide Coupling). To a 0.2 M solution containing the corresponding carboxylic acid (1 eq), PyBrop (1.5 eq) and DIPEA (2 eq) in CH$_2$Cl$_2$ was added the corresponding amine (1.5 eq). The reaction mixture was stirred at r.t. for 16 h, then diluted with CH$_2$Cl$_2$ and washed with saturated aqueous NaHCO$_3$ and concentrated. Crude product was purified by ISCO flash chromatography, or preparative HPLC.

Some compounds of the present invention can be conveniently synthesized by reacting an ester-containing compound with an ammonia or an ammonia equivalent, such as ammonium hydroxide, in the presence of an appropriate solvent, such as ether, tetrahydrofuran, or water. This procedure is shown in Scheme 4a and exemplified by General Procedure K.

Scheme 4. Synthesis of amides.

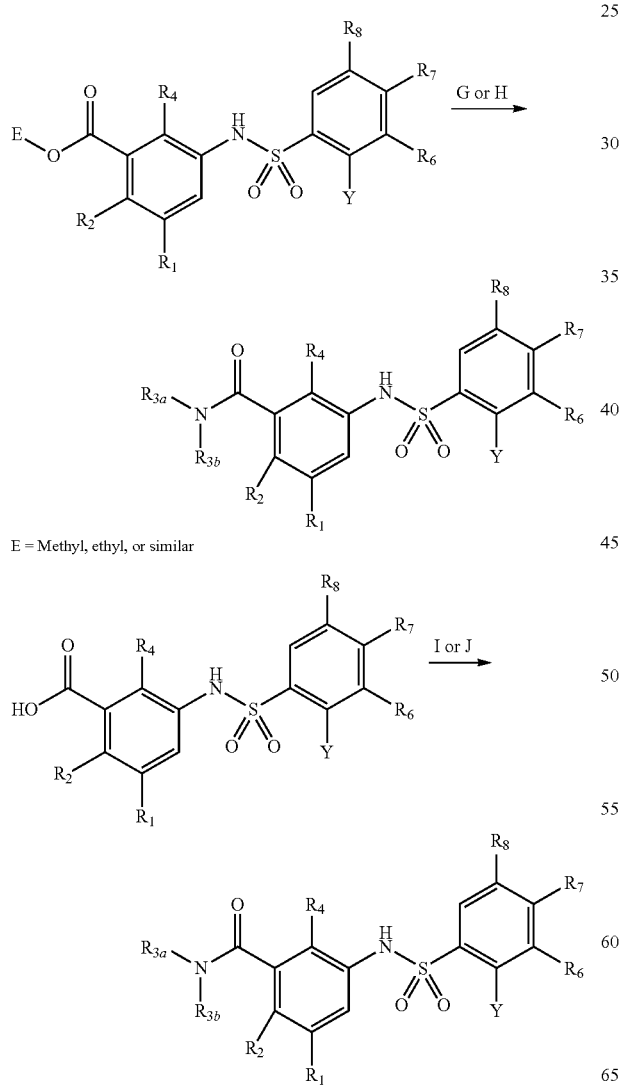

E = Methyl, ethyl, or similar

Scheme 4a. Synthesis of carboxamides.

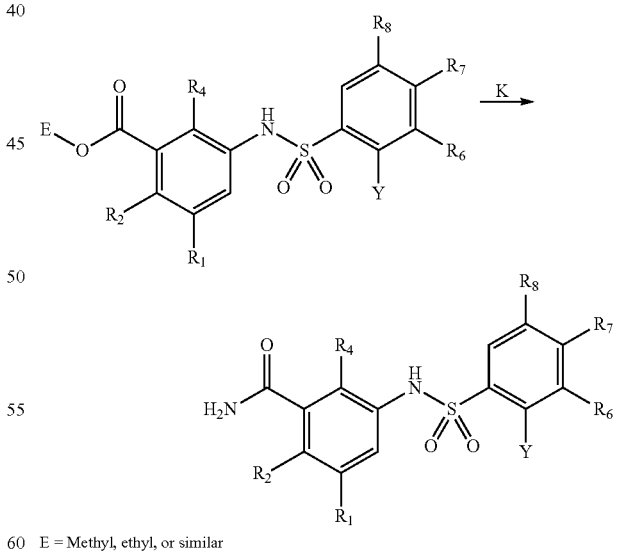

E = Methyl, ethyl, or similar

General Procedure K (Carboxamide synthesis). To the salicylate ester intermediate (1 eq) was added a 30% NH$_4$OH solution. The reaction mixture was allowed to stir at rt for 16 h, then concentrated under reduced pressure and purified by preparative HPLC.

The synthesis of some compounds of the present invention requires anilines with specific substitutions that are not readily available. The preparation of many of these can be conveniently accomplished via the reaction of an appropriately substituted aromatic halide, such as a bromide, with an appropriately substituted boronic acid or boronate ester in the presence of an appropriate palladium catalyst and suitable ligand, such as triphenyl phosphine, dppf, Xantphos, or the like, in an appropriate solvent, such as tetrahydrofuran, dioxane, water, or the like, and in the presence of a suitable base, such as sodium carbonate, cesium carbonate, or potassium phosphate, at a temperature of 50-150° C. The anilines can be prepared from the resulting nitro aromatic using many different conditions. One such set of conditions includes exposing the compound in an appropriate solvent, such as ethyl acetate, methanol, isopropanol, or the like to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 5a, and exemplified by General Procedures J and C or D. Such anilines can be reacted with appropriately substituted sulfonyl chlorides to synthesize compounds of the present invention.

Scheme 5a. Synthesis of elaborated anilines by palladium coupling.

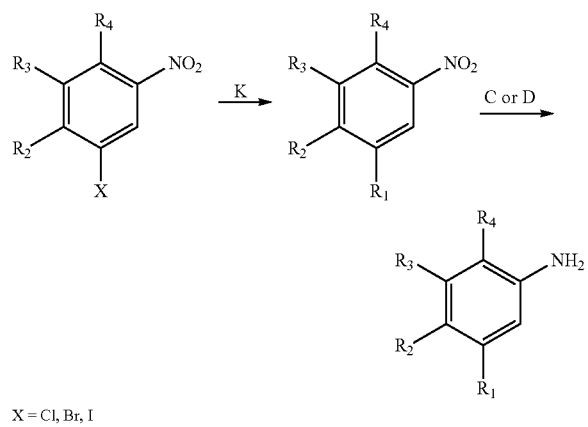

X = Cl, Br, I

General Procedure L (Suzuki-Miyaura Coupling—(Hetero)Aromatic Boronic Acids). To a solution containing the corresponding bromide (1 eq), (hetero)aromatic boronic acid or pinacol ester (1.2 eq), and Pd(dppf)Cl$_2$·DCM (0.05 eq) in de-gassed anhydrous dioxane was added a 2 M aqueous solution of Na$_2$CO$_3$ (2 eq). The reaction mixture was heated at 80° C. for 1-16 h. The cooled mixture was filtered through celite, washing with CH$_2$Cl$_2$, and purified by ISCO flash chromatography.

The synthesis of some compounds of the present invention requires an aniline substituted with a cyclopropyl ring. These anilines can be prepared by reacting an appropriately substituted aromatic halide, such as a bromide, with cyclopropyl boronic acid, in the presence of an appropriate palladium catalyst and a suitable ligand, such as triphenyl phosphine, tricyclohexylphosphine, dppf, Xantphos, or the like, in an appropriate solvent, such as tetrahydrofuran, dioxane, toluene, water, or the like, and in the presence of a suitable base, such as sodium carbonate, cesium carbonate, or potassium phosphate, at a temperature of 50-150° C. This procedure is shown in Scheme 5b, and exemplified by General Procedure M. Such anilines can be reacted with appropriately substituted sulfonyl chlorides to synthesize compounds of the present invention.

Scheme 5b. Synthesis of cyclopropyl substituted anilines.

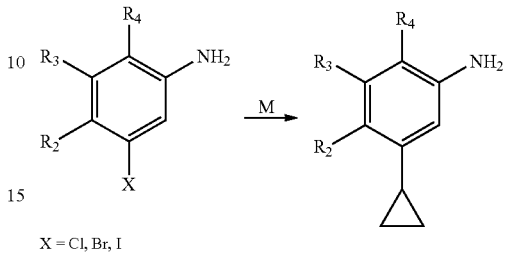

X = Cl, Br, I

General Procedure M (Suzuki Coupling—Cyclopropylboronic Acid). A mixture containing the intermediate bromide (1 eq), cyclopropylboronic acid (1.2 eq), Pd(OAc)$_2$ (0.05 eq), PCy$_3$·HBF$_4$ (0.1 eq), and K$_3$PO$_4$ (2.5 eq) in a mixture of toluene:H$_2$O (10:1, 0.2 M final concentration) was heated at 110° C. for 1-16 h. The cooled reaction mixture was filtered through celite, washed with CH$_2$Cl$_2$, and purified by ISCO flash chromatography.

Some anilines required for the synthesis of some compounds of the present invention can be prepared by reacting an appropriately substituted aromatic bromide with phenyl formate in the presence of an appropriate palladium catalyst and a suitable ligand, such as tricyclohexylphosphine, tributylphosphine, or Xantphos, in an appropriate solvent, such as toluene, tetrahydrofuran, acetonitrile, or the like, at a temperature of 50-150° C. and using an appropriate base, such as triethylamine, cesium carbonate, potassium phosphate, or the like. The phenol can be revealed by reacting the resulting aromatic ether with boron tribromide in a suitable solvent, such as dichloromethane, dichloroethane, toluene, or the like. The phenol resulting from this set of procedures can then be reacted with nitric acid in the presence of sulfuric and in an appropriate solvent, such as dichoromethane, dichloroethane, or the like. Subsequently, the resulting nitro aromatic compound can be converted to the aniline using many different conditions. One such set of conditions includes exposing the compound in an appropriate solvent, such as ethyl acetate, methanol, isopropanol, or the like to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 6 and exemplified with General Procedures N, O, B, and C or D. Such anilines can be reacted with appropriately substituted sulfonyl chlorides to synthesize compounds of the present invention.

Scheme 6. Synthesis of elaborated anilines by carbonylation.

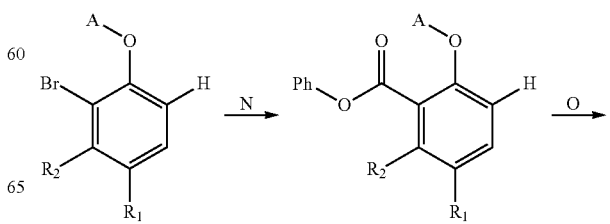

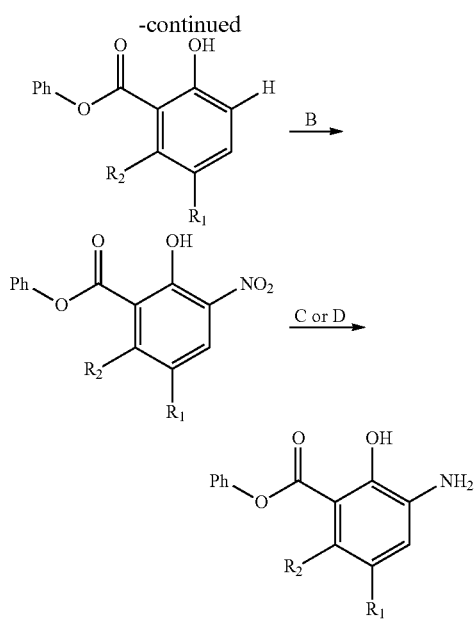

A = alkyl, such as methyl or benzyl

General Procedure N (Palladium Mediated Carbonylation—Phenyl Formate). To a mixture containing the corresponding bromide (1 eq), Pd(OAc)$_2$ (0.05 eq), P($^t$Bu).HBF$_4$ (0.2 eq) and phenol (1 eq) in anhydrous MeCN (at 0.25 M final concentration) in a sealed tube was added phenyl formate (1.67 eq) and NEt$_3$ (3 eq). The reaction mixture was heated at 90° C. for 18 h. Upon cooling, the mixture was filtered through celite and concentrated in vacuo. The residue was dissolved in EtOAc and washed with water. Crude product was purified by ISCO flash chromatography.

General Procedure O (Boron Tribromide Demethylation/Debenzylation). A 0.4 M solution containing the corresponding intermediate (1 eq) in anhydrous DCM was cooled to −78° C. in an acetone/dry ice bath under an inert atmosphere. To this was added a 1.0 M solution of BBr$_3$ in DCM (2 eq) drop-wise, and the mixture was stirred for 1 h at −78° C., then allowed to warm to r.t. The reaction mixture was poured over an ice-water slurry, extracted with EtOAc, washed with water and brine, and purified by ISCO flash chromatography.

Those of skill in the art will recognize that there are many ways to prepare intermediates needed to synthesize the anilines necessary to synthesize compounds of the present invention. In some instances, an appropriately substituted hydroxybenzoic acid can be converted to the corresponding methyl ester using a variety of techniques. One such technique involves the reaction of the carboxylic acid with trimethylsilyldiazomethane in an appropriate solvent, such as ether, tetrahydrofuran, water, or the like. Subsequently, the free phenol can be masked using a number of protecting groups that will be evident to those of ordinary skill. One such protecting group is a benzyl ether, which can be installed by reacting the phenol with benzyl bromide in an appropriate solvent, such as tetrahydrofuran, acetonitrile, toluene, or the like, and in the presence of a suitable base, such as triethyl amine, potassium carbonate, sodium hydride, or the like. The aromatic compound produced in this way can be brominated using reagents evident to those of skill in the art. One such brominating reagent is N-bromosuccinimide. The bromo-aromatic produced in this way can be reacted with an appropriate boronic acid or boronate ester, in the presence of an appropriate palladium catalyst and suitable ligand, such as triphenyl phosphine, tricyclohexylphosphine, dppf, Xantphos, or the like, in an appropriate solvent, such as tetrahydrofuran, dioxane, toluene, water, or the like, and in the presence of a suitable base, such as sodium carbonate, cesium carbonate, or potassium phosphate, at a temperature of 50-150° C. Those of skill in the art will recognize that there are numerous ways to remove the benzyl group. One such method involves the reaction of the benzyl ether with boron tribromide in a suitable solvent, such as dichloromethane, dichloroethane, toluene, or the like. The phenol resulting from this set of procedures can then be reacted with nitric acid in the presence of sulfuric and in an appropriate solvent, such as dichoromethane, dichloroethane, or the like. Subsequently, the resulting nitro aromatic compound can be converted to the aniline using many different conditions. One such set of conditions includes exposing the compound in an appropriate solvent, such as ethyl acetate, methanol, isopropanol, or the like to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 7 and exemplified with General Procedures P, Q, L or M, B, O, and C or D. Such anilines can be reacted with appropriately substituted sulfonyl chlorides to synthesize compounds of the present invention.

Scheme 7. Synthesis of bromoaromatics.

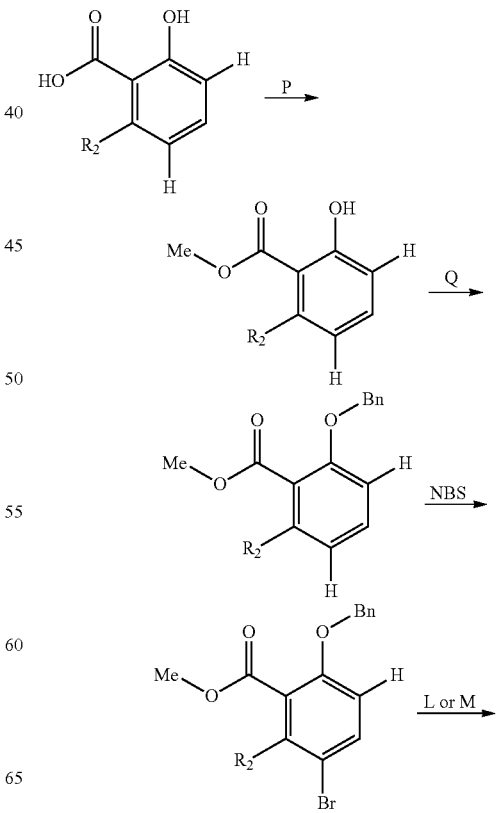

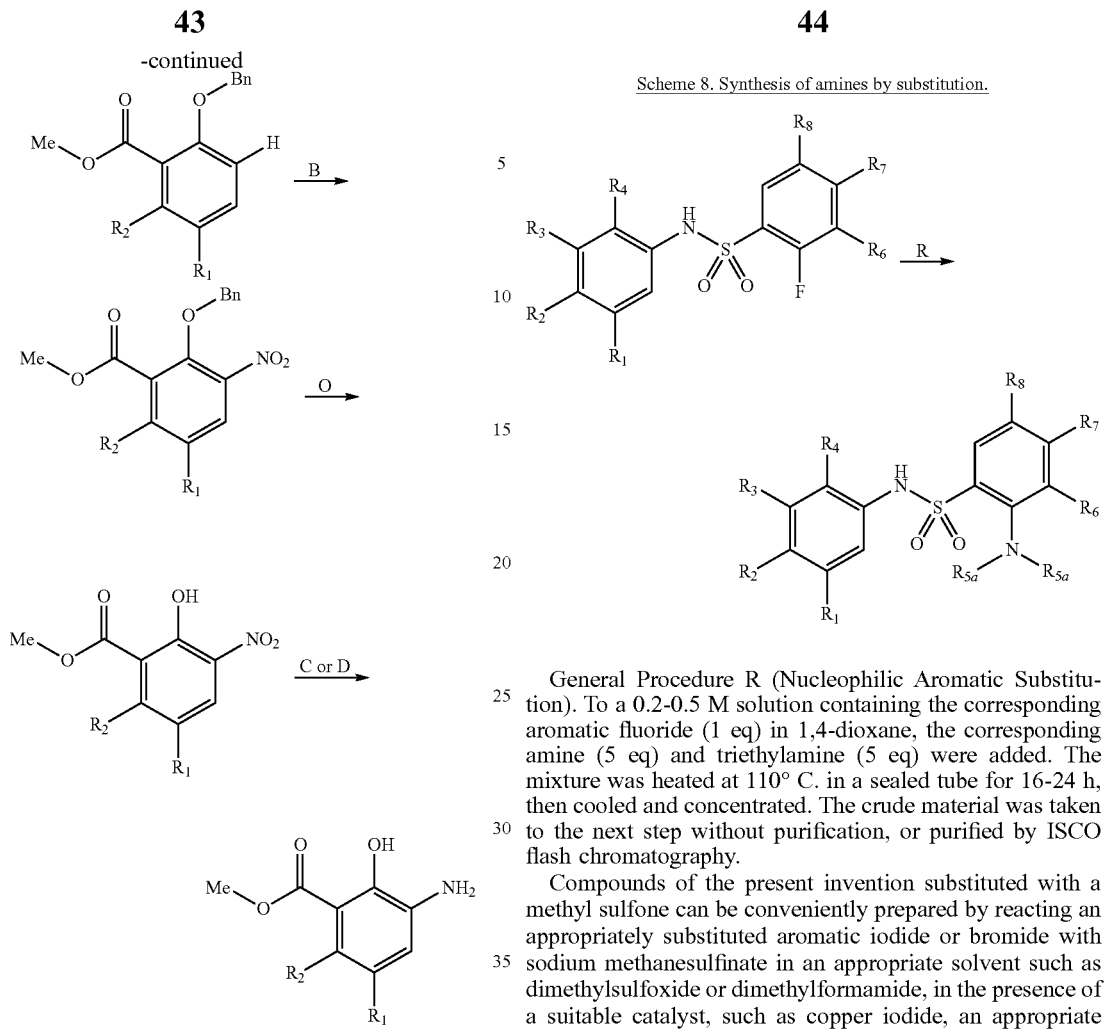

General Procedure P (TMS Diazomethane Esterification). A 0.2 M mixture containing the corresponding carboxylic acid (1 eq) and a 5:1 mixture of THF:MeOH was cooled to 0° C. in an ice/water bath. A 2.0 M solution of TMS Diazomethane in Et$_2$O (1.1 eq) was added drop-wise and the mixture was stirred for 1-16 h. The completed reaction was concentrated in vacuo, and the residue was re-dissolved in EtOAc and washed with H$_2$O, and brine. If required, the crude residue was purified by ISCO flash chromatography.

General Procedure Q (Benzyl Protection). A mixture containing the corresponding phenol (1 eq), benzyl bromide (1.05 eq), and potassium carbonate (1.1 eq) in acetonitrile was heated at reflux for 18 h. Upon cooling, the mixture was concentrated in vacuo, and the residue was re-dissolved in EtOAc and washed with water and brine. The crude residue was purified by ISCO flash chromatography.

Some compounds of the present invention can be synthesized by converting an appropriate molecule, synthesized as described above, and containing a fluorine in the appropriate position, to a compound of the present invention containing an amine in the appropriate position. This can be accomplished by reaction with a suitable amine in an appropriate solvent, such as tetrahydrofuran, dioxane, dimethylformamide, or the like, in the presence of a suitable base, such as trimethylamine, diisopropylamine, or the like. This procedure is shown in Scheme 8 and exemplified by General Procedure R.

Scheme 8. Synthesis of amines by substitution.

General Procedure R (Nucleophilic Aromatic Substitution). To a 0.2-0.5 M solution containing the corresponding aromatic fluoride (1 eq) in 1,4-dioxane, the corresponding amine (5 eq) and triethylamine (5 eq) were added. The mixture was heated at 110° C. in a sealed tube for 16-24 h, then cooled and concentrated. The crude material was taken to the next step without purification, or purified by ISCO flash chromatography.

Compounds of the present invention substituted with a methyl sulfone can be conveniently prepared by reacting an appropriately substituted aromatic iodide or bromide with sodium methanesulfinate in an appropriate solvent such as dimethylsulfoxide or dimethylformamide, in the presence of a suitable catalyst, such as copper iodide, an appropriate ligand, such as proline, and using a suitable base, such as sodium hydroxide, at a temperature of 40-100° C. The resulting nitroaromatic can be converted to the aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. The resulting aniline can be reacted with an appropriately substituted sulfonyl chloride in an appropriate solvent, such as dichloromethane, tetrahydrofuran, or the like, and using an appropriate base, such as pyridine, triethyl amine, diisopropylethyl amine, or the like. These procedures are shown in Scheme 9 and exemplified by General Procedures S, C or D, and E.

Scheme 9. Methyl sulfone synthesis

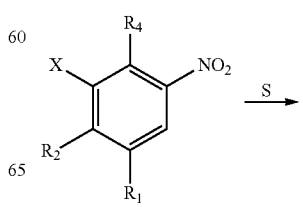

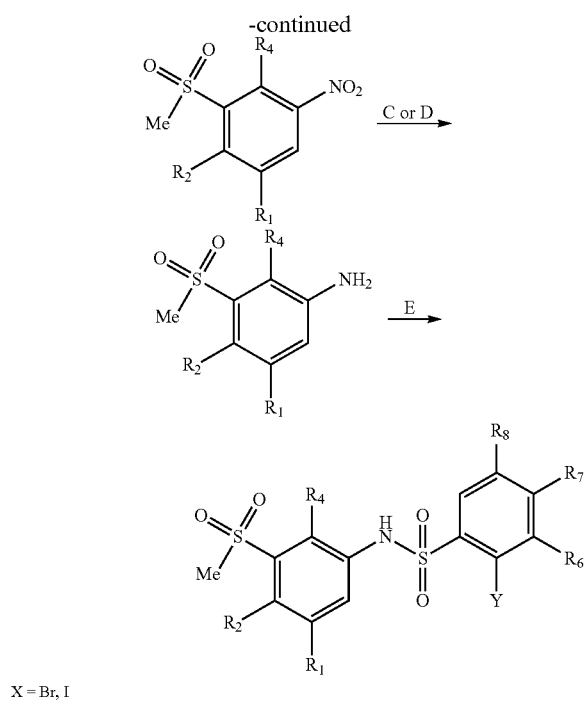

X = Br, I

General Procedure S (Sulfone Coupling). The corresponding aryl iodide or bromide (1 eq) was combined with sodium methanesulfinate (1.2 eq), CuI (0.10 eq), L-proline (0.20 eq) and NaOH (0.2 eq). The reaction vessel was purged with Ar, sufficient DMSO to produce a 0.5 M concentration was added, and the mixture was heated at 57-85° C. for 16-20 h. Upon cooling, the mixture was diluted with water and extracted with $CH_2Cl_2$. The organic phase was dried and concentrated. The crude material was taken forward without purification.

Compounds of the present invention which are substituted with a sulfoxide or sulfone can be conveniently prepared by first reacting an appropriately substituted aromatic halide with an appropriate disulfide in a suitable solvent, such toluene or pyridine, and in presence of a suitable catalyst, such as copper, at a temperature of 50-130° C. The aromatic sulfides produced in this way can be converted to the corresponding sulfones via the use of an oxidizing agent, such as Oxone or sodium periodate, in a suitable solvent, such as tetrahydrofuran, methanol, ethanol, water, or the like. Alternatively, the aromatic sulfides produced in this way can be converted to the corresponding sulfoxides via the use of an oxidizing agent, such as Oxone, sodium periodate, or meta-chloroperbenzoic acid, in a suitable solvent, such as tetrahydrofuran, methanol, ethanol, water, or the like, but with fewer equivalents of oxidizing agent and shorter reaction times compared to the synthesis of the sulfones. Appropriately substituted nitro-substituted aromatic compounds synthesized in this way can be converted to the corresponding aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like Alternatively, the nitroaromatic can be converted to the corresponding aniline by treatment with iron powder in an appropriate solvent, such as acetic acid. The resulting aniline can be reacted with an appropriately substituted sulfonyl chloride in an appropriate solvent, such as dichloromethane, tetrahydrofuran, or the like, and using an appropriate base, such as pyridine, triethyl amine, diisopropylethyl amine, or the like. These procedures are shown in Scheme 10 and exemplified by General Procedures T, U or V, C or D, and E.

Scheme 10. Alternative synthesis of sulfone and sulfoxide analogs.

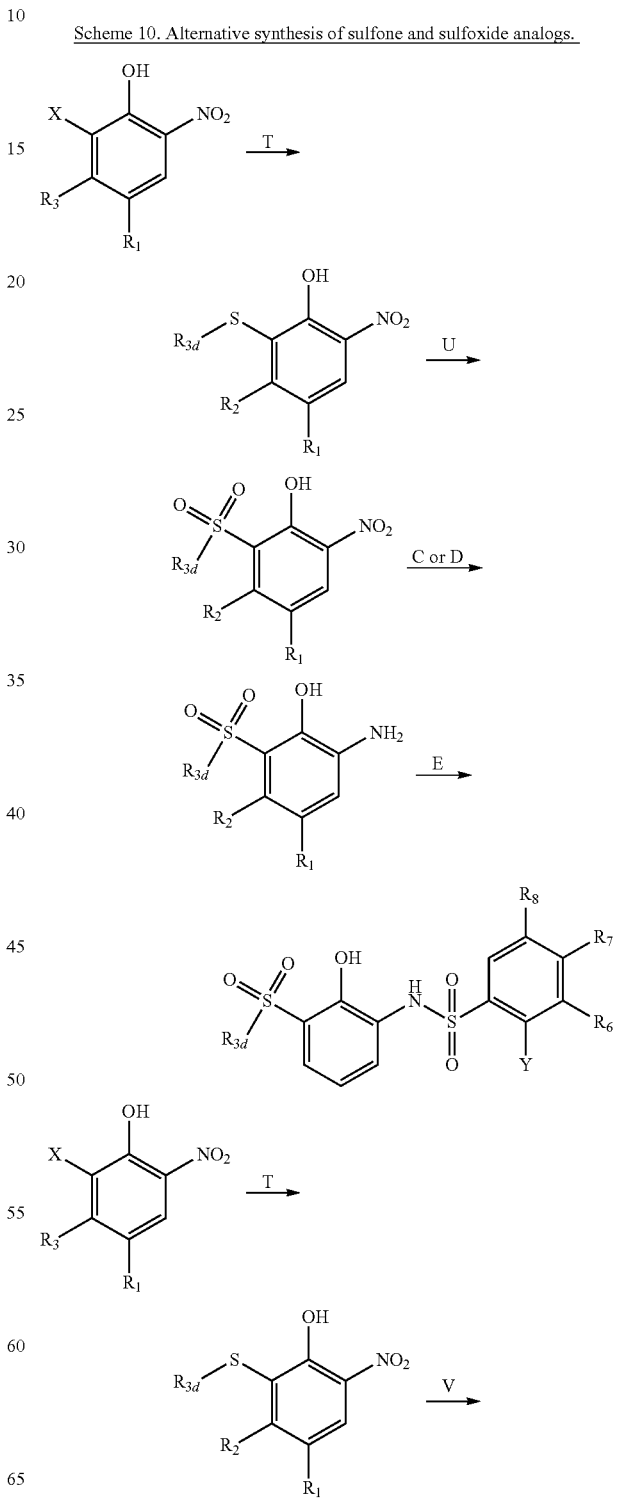

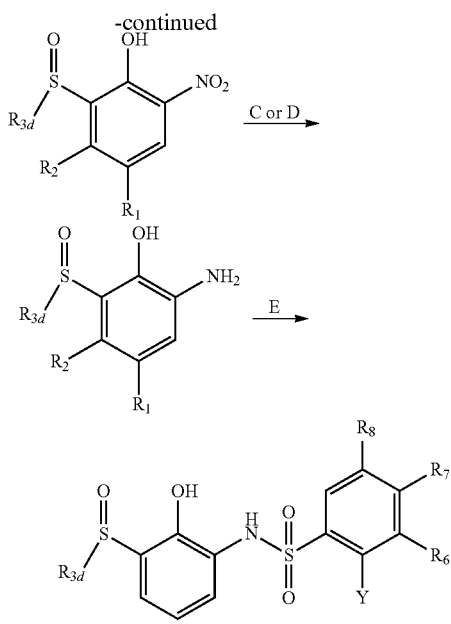

X = Cl, Br, or I

General Procedure T (Sulfide Coupling). To a 0.4 M solution containing the corresponding aryl bromide (1 eq) in pyridine was added Cu (2 eq) and dialkyl disulfide (2 eq). The reaction mixture was stirred at 90-115° C. for 16-20 h. The mixture was allowed to reach room temperature and then filtered. The filter cake was washed with $CH_2Cl_2$ and the filtrate was concentrated to dryness and then re-suspended in a 3 M aqueous solution of HCl. This mixture was extracted with $CH_2Cl_2$ and the organic phase was separated, and concentrated and the residue was purified by ISCO flash chromatography.

General Procedure U (Sulfide-Sulfone Oxidation). To a 0.32 M solution of the corresponding sulfide in a 1:mixture of $H_2O$:EtOH was added Oxone (2 eq). The reaction mixture was stirred at r.t. for 4-20 h. Water was added to the mixture and it was extracted with $CH_2Cl_2$. The organic phase was dried using a phase separator and the solvent was removed under vacuum. If required, the residue was purified by ISCO flash chromatography.

General Procedure V (Sulfide-Sulfoxide Oxidation). To a 0.32 M solution of the corresponding sulfide in a 1:mixture of $H_2O$:EtOH was added Oxone (1 eq). The reaction mixture was stirred at r.t. for 1 h. Water was added to the mixture and it was extracted with $CH_2Cl_2$. The organic phase was dried using a phase separator and the solvent was removed under vacuum. If required, the residue was purified by ISCO flash chromatography.

Some anilines required for the synthesis of some compounds of the present invention can be conveniently prepared by reacting an appropriately substituted aromatic halide, such as an aromatic bromide, with an appropriately substituted disulfide, in a suitable solvent, such as tetrahydrofuran, dimethylsulfoxide, water, or the like, in the presence of a suitable catalyst, such as copper sulfate, and an appropriate base, such as sodium hydroxide or potassium hydroxide. aromatic sulfides produced in this way can be converted to the corresponding sulfones via the use of an oxidizing agent, such as Oxone or sodium periodate, in a suitable solvent, such as tetrahydrofuran, methanol, ethanol, water, or the like. Alternatively, the aromatic sulfides produced in this way can be converted to the corresponding sulfoxides via the use of an oxidizing agent, such as Oxone, sodium periodate, or meta-chloroperbenzoic acid, in a suitable solvent, such as tetrahydrofuran, methanol, ethanol, water, or the like, but with fewer equivalents of oxidizing agent and shorter reaction times compared to the synthesis of the sulfones. Appropriately substituted nitro-substituted aromatic compounds synthesized in this way can be converted to the corresponding aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like. The resulting aniline can be reacted with an appropriately substituted sulfonyl chloride in an appropriate solvent, such as dichloromethane, tetrahydrofuran, or the like, and using an appropriate base, such as pyridine, triethyl amine, diisopropylethyl amine, or the like. These procedures are shown in Scheme 10 and exemplified by General Procedures W and U or V. Such anilines can be reacted with appropriately substituted sulfonyl chlorides to synthesize compounds of the present invention.

Scheme 10a. Alternative sulfide synthesis and oxidation.

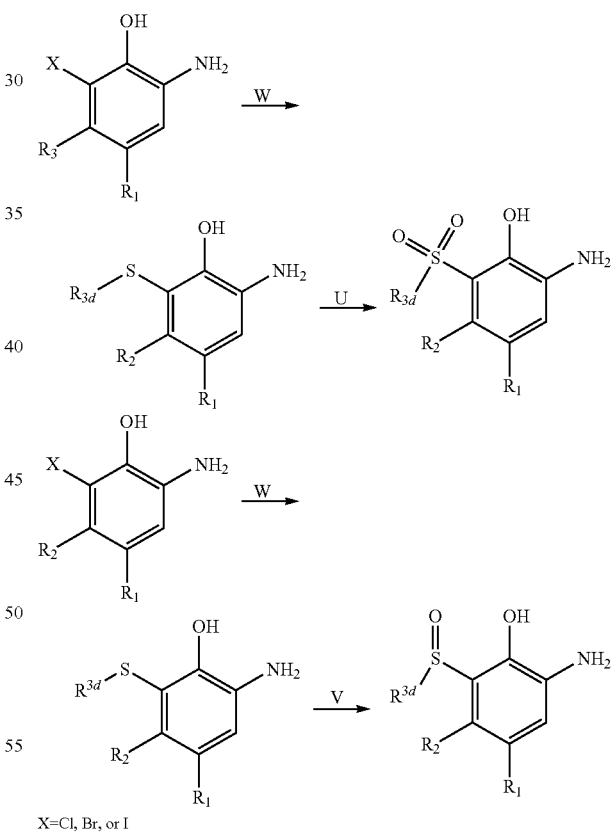

X=Cl, Br, or I

General Procedure W (Thiol Coupling and alkylation). A mixture containing the corresponding aryl bromide (1 eq), $CUSO_4·5H_2O$ (0.05 eq), and KOH (5 eq) in DMSO:$H_2O$ (9:1, [0.45 M] final) was purged by bubbling Argon for 10 min and then 2 eq of 1,2-dithioethane were added. The vial was sealed and was heated at 110° C. for 20 h. To isolate the thiol, the mixture was treated with 3 M HCl and then extracted with EtOAc. The organic phase was dried over a phase separator and the solvent removed under vacuum. The crude material was purified using ISCO flash chromatography. When the alkylated thiol was desired, the reaction mixture was treated with a solution made of the corresponding alkyl bromide (3 eq) in DMF ([3 M]) and Et$_3$N (3 eq) and reaction mixture was allowed to stir overnight at room temperature. The reaction mixture was quenched by the addition of water and extracted with EtOAc. The organic phase was dried over a phase separator and the solvent removed under vacuum. The crude was purified using ISCO flash chromatography.

Appropriately substituted anilines required for the synthesis of compounds of the present invention can be conveniently prepared by reacting an appropriately substituted aromatic iodide or bromide with sodium methanesulfinate in an appropriate solvent such as dimethylsulfoxide or dimethylformamide, in the presence of a suitable catalyst, such as copper iodide, an appropriate ligand, such as proline, and using a suitable base, such as sodium hydroxide, at a temperature of 40-100° C. In the instances in which the resulting aromatic compounds are substituted with an appropriate ester, the corresponding aniline can be synthesized by initial reaction with diphenylphosphoryl azide along with tert-butanol in an appropriate solvent, such as dioxane, dimethoxyethane, and the like, and at a temperature of 50-110° C. Those of skill in the art will recognize that this reaction produces a tert-butyl carbamate, which can be converted to the corresponding aniline by treatment with a number of acid reagents, such as hydrochloric acid or trifluoroacetic acid, in an appropriate solvent, such as dichloromethane, dichloroethane, or the like. These procedures are shown in Scheme 11 and exemplified by General Procedures S and X. Such anilines can be reacted with appropriately substituted sulfonyl chlorides to synthesize compounds of the present invention.

t-BuOH (5 eq), diphenylphosphoryl azide (DPPA, 1.2 eq), and 1,2-dimethoxyethane was heated at 100° C. for 16-20 h. The reaction mixture was allowed to reach room temperature, quenched with a saturated solution of NH$_4$Cl, and extracted with EtOAc. The organic phase was washed with a saturated solution of NaHCO$_3$ and then with water. The organic phase was dried over Na$_2$SO$_4$ and filtered, and the solvent removed under vacuum.

The crude residue was resuspended in CH$_2$Cl$_2$ (at 0.2 M) and trifluoroacetic acid (TFA, 0.007 eq) was added. The reaction mixture was stirred at room temperature for 1-16 h, quenched by the addition of a saturated solution of NaHCO$_3$, and then extracted with CH$_2$Cl$_2$. The organic phase was dried over a phase separator and the solvent removed under vacuum. The crude residue was purified using ISCO flash chromatography.

Some anilines required for the synthesis of compounds of the current invention can be obtained by first reacting an appropriately substituted phenol with chlorosulfonic acid. The sulfonyl chlorides obtained in this way can be reacted with an appropriate amine in an appropriate solvent, such as ether, tetrahydrofuran, dichloromethane, dichloroethane, or the like, in the presence of a suitable base, such as triethylamine, diisopropylethylamine, potassium carbonate, or the like. The corresponding sulfonamides can then be converted to the corresponding aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 12 and exemplified by General Procedures A, Y, and C or D. Such anilines can be reacted with appropriately substituted sulfonyl chlorides to synthesize compounds of the present invention.

Scheme 11. Alternative synthesis of anilines using a Curtius rearrangement.

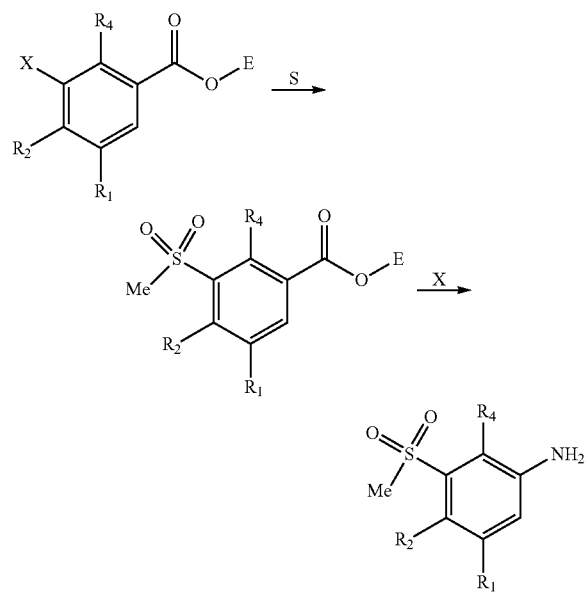

E = Methyl, ethyl, or similar
X = Cl, Br, or I

Scheme 12. Synthesis of sulfonamide-containing anilines.

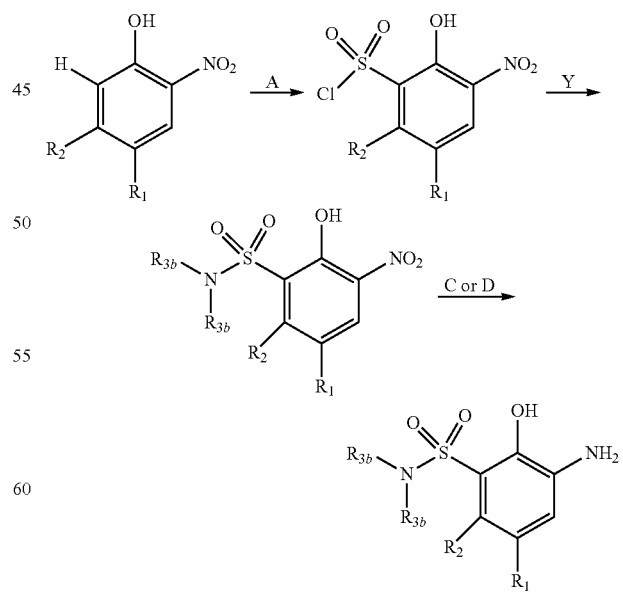

General Procedure X (Curtius rearrangement). A 0.2 M mixture containing the corresponding carboxylic acid (1 eq), General Procedure Y (Sulfonamide Coupling B). To a mixture containing the corresponding amine (1.5 eq) in THF (at [0.8 M]) was added Et$_3$N (1.5 eq) was added. The reaction mixture was cooled to 0° C. in an ice/water bath. Then, the corresponding sulfonyl chloride (1 eq) was added and the reaction mixture allowed to come to rt and stir for 1-4 h at room temperature. Upon completion of the reaction, the mixture was cooled to 0° C. was quenched by the addition of 3 M aqueous HCl. The mixture was extracted using CH$_2$Cl$_2$. The organic phase was dried over phase separator and the solvent removed under reduced pressure. The crude material was purified using ISCO flash chromatography.

Compounds of the present invention which are substituted with a methylsulfoxide or methylsulfone can be conveniently prepared by first reacting an appropriately substituted aromatic halide with sodium methanethiolate in an appropriate solvent, such as tetrahydrofuran or dioxane, in the presence of an appropriate palladium catalyst and a suitable ligand, such as Xantphos, at a temperature of 50-110° C. The aromatic sulfides produced in this way can be converted to the corresponding sulfones via the use of an oxidizing agent, such as Oxone or sodium periodate, in a suitable solvent, such as tetrahydrofuran, methanol, ethanol, water, or the like. Alternatively, the aromatic sulfides produced in this way can be converted to the corresponding sulfoxides via the use of an oxidizing agent, such as Oxone, sodium periodate, or meta-chloroperbenzoic acid, in a suitable solvent, such as tetrahydrofuran, methanol, ethanol, water, or the like, but with fewer equivalents of oxidizing agent and shorter reaction times compared to the synthesis of the sulfones. Aromatic compounds synthesized in this way can be reacted with nitric acid in the presence of sulfuric and in an appropriate solvent, such as dichoromethane, dichloroethane, or the like. Appropriately substituted nitro-substituted aromatic compounds synthesized in this way can be converted to the corresponding aniline using many different conditions. One such set of conditions includes exposing the compound, in an appropriate solvent, such as ethyl acetate, methanol, isopropanol, or the like, to an atmosphere of hydrogen gas and in the presence of an appropriate catalyst, such as palladium on carbon, platinum on carbon, or the like. Alternatively, the nitroaromatic can be converted to the corresponding aniline by treatment with iron powder in an appropriate solvent, such as acetic acid. These procedures are shown in Scheme 10 and exemplified by General Procedures Z, U or V, B, and C or D. Such anilines can be reacted with appropriately substituted sulfonyl chlorides to synthesize compounds of the present invention.

Scheme 13. Methyl sulfide synthesis and oxidation.

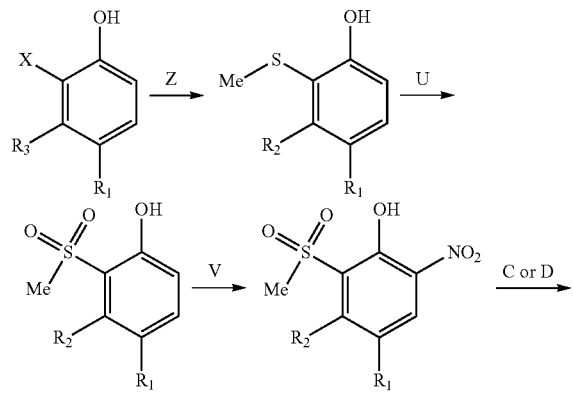

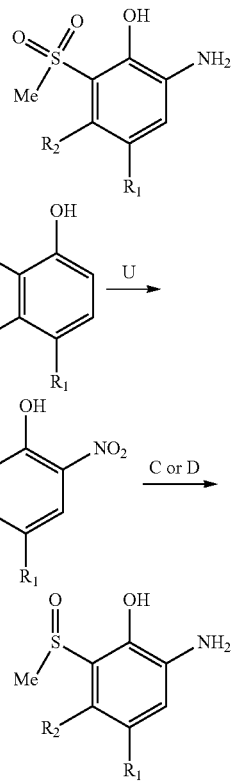

X = Cl, Br, or I

General Procedure Z (Methyl sulfide Coupling). A vial/container containing the corresponding aryl/heteroaryl iodide or bromide (1 eq), sodium methanethiolate (1.05 eq), Pd$_2$(dba)$_3$ (0.025 eq), and xantphos (0.05 eq) was purged with Ar. Then, THF (to [0.34 M]) and Et$_3$N (1.25 eq) were added and the reaction mixture was heated at 76° C. for 18 h. Upon cooling, the mixture was filtered and the solvent was removed under vacuum. The crude was purified using ISCO Flash chromatography.

C. EXAMPLES

All chemical reagents and reaction solvents were purchased from commercial suppliers and used as received. All microwave-assisted reactions were performed using a Biotage Initiator 2.0 microwave reactor. Hydrogenation reactions are performed using an atmospheric balloon, or using a Parr hydrogenation shaker apparatus where stated. Analytical thin-layer chromatography (TLC) was performed on Kieselgel 60 F254 glass plates precoated with a 0.25 mm thick silica gel. TLC plates were visualized with UV light and iodine.

All compounds were obtained at 95% purity or higher, unless otherwise noted, as measured by analytical reversed-phase HPLC. Analytical HPLC was performed on an Agilent 1200 series system with UV detection at 214 and 254 nm, along with evaporative light-scattering detection (ELSD). Low-resolution mass spectra were obtained on an Agilent 6140 mass spectrometer with electrospray ionization (ESI). For LCMS characterization of the compounds in the present invention, one of the following methods were used: Method A: A Phenomenex Kinetex 2.6 µm XB-C18 100 Å LC column (50 Å~2.1 mm) was used with a 2 min gradient of 5-95% MeCN in H$_2$O and 0.1% TFA. Method B: A Phenomenex Kinetex 2.6 μm XB-C18 100 Å LC column (50 Å~2.1 mm) was used with a 1 min gradient of 5-95% MeCN in H$_2$O and 0.1% TFA. Normal phase flash silica gel-based column chromatography was performed using ready-to-connect cartridges from ISCO, on irregular silica gel, particle size 15-40 μm using a Teledyne ISCO Combiflash Rf system. Preparative reverse-phase HPLC was performed on a Gilson instrument equipped with a Phenomenex Kinetex C18 column, using varying concentrations of MeCN in H$_2$O and 0.1% TFA, unless otherwise stated.

Proton nuclear magnetic resonance ($^1$H NMR) spectra were recorded at either 400 or 600 MHz on a Bruker spectrometer, as stated. For $^1$H NMR spectra, chemical shifts are reported in parts per million (ppm) relative to residual nondeuterated solvent signals. Coupling constants are reported in hertz (Hz). The following abbreviations (or a combination thereof) are used to describe splitting patterns: s, singlet; d, doublet; t, triplet; q, quartet; pent, pentet; sxt, sextet; m, multiplet; br, broad.

Compounds obtained as a TFA salt after purification were afforded as free base, unless salt form stated, by dissolving the salt in EtOAc and washing with saturated aqueous K$_2$CO$_3$.

Abbreviations sat.=saturated
aq.=aqueous
eq=equivalents
h=hours
conc.=concentrated
r.t.=room temperature
rt=room temperature
wt.=weight
MeOH=methanol
EtOAc=ethyl acetate
DIPEA=di-isopropyl ethyl amine
min=minutes
HATU=1-[Bis(dimethylamino)methylene]-1H-1,2,3-triazolo[4,5-b]pyridinium 3-oxid hexafluorophosphate,
PyBrop=Bromotripyrrolidinophosphonium hexafluorophosphate
MeCN=acetonitrile
DCM=dichloromethane, CH$_2$Cl$_2$
DMSO=dimethylsulfoxide
TFA=trifluoroacetic acid
THF=tetrahydrofuran
TMS=trimethylsilyl Example J1: 3-((5-Bromo-2-hydroxyphenyl)sulfonamido)-5-chloro-2-hydroxybenzoic acid

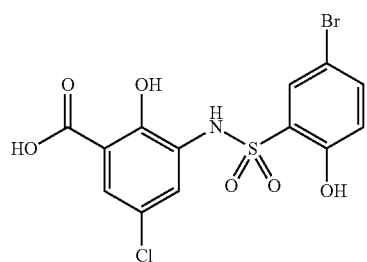 [SMILES: O=C(O)c1cc(Cl)cc(NS(=O)(=O)c2cc(Br)ccc2O)c1O]

Step A: 5-Bromo-2-hydroxybenzenesulfonyl chloride. Using a procedure analogous to General Procedure A, starting with 4-Bromophenol (1.73 g, 10 mmol), 5-bromo-2-hydroxybenzenesulfonyl chloride was obtained as a pale brown oily solid (1.50 g, 5.53 mmol, 55%) after purification. $^1$H NMR (400 MHz, CDCl$_3$) $\delta_H$ 7.95 (d, J=2.4 Hz, 1H), 7.71 (dd, J=8.9, 2.4 Hz, 1H), 7.04 (d, J=8.9 Hz, 1H); LCMS (Method A) t$_R$=1.39 min; Purity (AUC) >90%.

Step B: Methyl 3-((5-bromo-2-hydroxyphenyl)sulfonamido)-5-chloro-2-hydroxybenzoate. Using a procedure analogous to General Procedure E, starting with methyl 3-amino-5-chloro-2-hydroxybenzoate (605 mg, 3.0 mmol) and 5-bromo-2-hydroxybenzenesulfonyl chloride, which was prepared by a procedure analogous to the procedure used to prepare Example J1 Step A, methyl 3-((5-bromo-2-hydroxyphenyl)sulfonamido)-5-chloro-2-hydroxybenzoate was obtained as a colorless solid (918 mg, 2.1 mmol, 70%). LCMS (Method A): t$_R$=1.15 min, m/z=437.8 [M+H]$^+$; Purity (AUC) ≥95%.

Step C: 3-((5-Bromo-2-hydroxyphenyl)sulfonamido)-5-chloro-2-hydroxybenzoic acid. Using a procedure analogous to General Procedure F, starting with methyl 3-((5-bromo-2-hydroxyphenyl)sulfonamido)-5-chloro-2-hydroxybenzoate (918 mg, 2.10 mmol), which was prepared by a procedure analogous to the procedure used to prepare Example J1 Step B, the title compound was obtained as a colorless solid (425 mg, 1.0 mmol, 48%). $^1$H NMR (400 MHz, MeOH-d$_4$) $\delta_H$ 7.81 (d, J=2.5 Hz, 1H), 7.62 (d, J=2.6 Hz, 1H), 7.55 (d, J=2.6 Hz, 1H), 7.53 (dd, J=8.7, 2.5 Hz, 1H), 6.87 (d, J=8.7 Hz, 1H); LCMS (Method A) t$_R$=1.53 min, m/z=421.7, 423.7 [M+H]$^+$; Purity (AUC) ≥95%.

Example J2: 3-((5-Bromo-2-methoxyphenyl)sulfonamido)-5-chloro-2-hydroxybenzoic acid

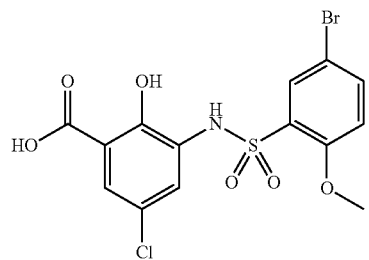 [SMILES: COc1ccc(Br)cc1S(=O)(=O)Nc1cc(Cl)cc(C(=O)O)c1O]

Step A: Methyl 3-((5-bromo-2-methoxyphenyl)sulfonamido)-5-chloro-2-hydroxybenzoate. Using a procedure analogous to General Procedure E, starting from methyl 3-amino-5-chloro-2-hydroxybenzoate (202 mg, 1.0 mmol) and 5-bromo-2-methoxybenzenesulfonyl chloride, which was prepared by a procedure analogous to the procedure used to prepare Example J1 Step A, methyl 3-((5-bromo-2-methoxyphenyl)sulfonamido)-5-chloro-2-hydroxybenzoate was obtained as a colorless solid (370 mg, 0.82 mmol, 82%). $^1$H NMR (DMSO-d$_6$) $\delta_H$ 7.81-7.76 (m, 2H), 7.55 (d, J=2.7 Hz, 1H), 7.49 (d, J=2.6 Hz, 1H), 7.19 (dt, J=8.6, 1.0 Hz, 1H), 3.88 (s, 3H), 3.76 (s, 3H); LCMS (Method A) t$_R$=1.77 min, m/z=450, 452 [M+H]$^+$; Purity (AUC) ≥95%.

Step B: 3-((5-Bromo-2-methoxyphenyl)sulfonamido)-5-chloro-2-hydroxybenzoic acid. Using a procedure analogous to General Procedure F, starting from methyl 3-((5-bromo-2-methoxyphenyl)sulfonamido)-5-chloro-2-hydroxybenzoate (370 mg, 0.82 mmol), which was prepared by a procedure analogous to the procedure used to prepare Example J2

Step A, the title compound was obtained as a colorless solid (260 mg, 0.59 mmol, 72%). $^1$H NMR (DMSO-d$_6$) δ$_H$ 9.52 (s, 1H), 7.80-7.75 (m, 2H), 7.52 (d, J=2.7 Hz, 1H), 7.43 (d, J=2.7 Hz, 1H), 7.18 (d, J=9.6 Hz, 1H), 3.77 (s, 3H); LCMS (Method A) t$_R$=1.55 min, m/z=436.0, 438.0 [M+H]$^+$; Purity (AUC) ≥95%.

Example J4: 3-((5-Bromo-3-chloro-2-hydroxyphenyl)sulfonamido)-5-chloro-2-hydroxybenzoic acid

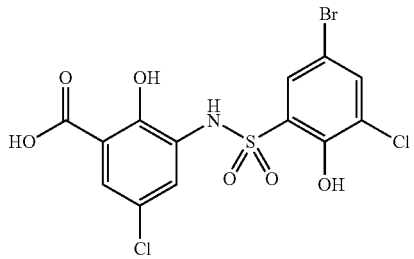 [SMILES: O=C(O)c1cc(Cl)cc(NS(=O)(=O)c2cc(Br)cc(Cl)c2O)c1O]

Step A: 5-Bromo-3-chloro-2-hydroxybenzenesulfonyl chloride. Using a procedure analogous to General Procedure A, starting with 2-chloro-4-bromophenol (2.08 g, 10 mmol), 5-bromo-3-chloro-2-hydroxybenzenesulfonyl chloride was obtained as a colorless solid (2.19 g, 7.15 mmol, 72%). $^1$H NMR (400 MHz, CDCl$_3$) δ$_H$ 7.92 (1H, d, J=2.4 Hz), 7.86 (1H, d, J=2.4 Hz); LCMS (Method A) t$_R$=1.50 min; Purity (AUC) ≥95%.

Step B: Methyl 3-((5-bromo-3-chloro-2-hydroxyphenyl)sulfonamido)-5-chloro-2-hydroxybenzoate. Using a procedure analogous to General Procedure E, starting with methyl 3-amino-5-chloro-2-hydroxybenzoate (192 mg, 0.95 mmol) and 5-bromo-3-chloro-2-hydroxybenzenesulfonyl chloride, which was prepared by a procedure analogous to the procedure used to prepare Example J4 Step A, and methyl 3-((5-bromo-3-chloro-2-hydroxyphenyl)sulfonamido)-5-chloro-2-hydroxybenzoate was obtained as a colorless solid (374 mg, 0.91 mmol, 91%). $^1$H NMR (400 MHz, CDCl$_3$) δ$_H$ 11.03 (s, 1H), 7.71-7.68 (m, 2H), 7.64 (d, J=2.5 Hz, 1H), 7.62 (d, J=2.5 Hz, 1H), 3.95 (s, 3H); LCMS (Method B) t$_R$=1.22 min, m/z=471.6 [M+H]$^+$; Purity (AUC) ≥95%.

Step C: 3-((5-Bromo-3-chloro-2-hydroxyphenyl)sulfonamido)-5-chloro-2-hydroxybenzoic acid. Using a procedure analogous to General Procedure F, starting with methyl 3-((5-bromo-3-chloro-2-hydroxyphenyl)sulfonamido)-5-chloro-2-hydroxybenzoate (298 mg, 0.63 mmol), which was prepared by a procedure analogous to the procedure used to prepare Example J4 Step C, the title compound was obtained as a colorless solid (231 mg, 0.51 mmol, 80%). $^1$H NMR (400 MHz, CDCl$_3$) δ$_H$ 7.76 (s, 2H), 7.63 (d, J=2.5 Hz, 1H), 7.61 (d, J=2.6 Hz, 1H); LCMS (Method A) t$_R$=1.68 min, m/z=457.6 [M+H]$^+$; Purity (AUC) ≥95%.

Example J5: 3-((5-Bromo-3-fluoro-2-hydroxyphenyl)sulfonamido)-5-chloro-2-hydroxybenzoic acid [HCH-3-70-2:]

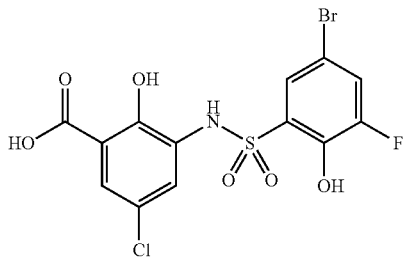 [SMILES: O=C(O)c1cc(Cl)cc(NS(=O)(=O)c2cc(Br)cc(F)c2O)c1O]

Step A: 5-Bromo-3-fluoro-2-hydroxybenzenesulfonyl chloride. Using a procedure analogous to General Procedure A, starting with 2-fluoro-4-bromophenol (1.1 mL, 10 mmol), 5-bromo-3-fluoro-2-hydroxybenzenesulfonyl chloride was obtained as an off-white solid (1.47 g, 5.1 mmol, 51%). $^1$H NMR (400 MHz, CDCl$_3$) δ$_H$ 7.90 (s, 1H), 7.80 (t, J=2.1 Hz, 1H), 7.60 (dd, J=9.4, 2.3 Hz, 1H); $^{19}$F NMR (376 MHz, CDCl$_3$) δ$_F$ −127.1; LCMS (Method A) t$_R$=1.50 min; Purity (AUC) ≥95%.

Step B. Methyl 3-((5-bromo-3-fluoro-2-hydroxyphenyl)sulfonamido)-5-chloro-2-hydroxybenzoate (HCH-3-67-5). Using a procedure analogous to General Procedure E, starting from 5-bromo-3-fluoro-2-hydroxybenzenesulfonyl chloride (50.0 mg, 0.17 mmol), which was prepared by a procedure analogous to the procedure used to prepare Example J5 Step A, and methyl 3-amino-5-chloro-2-hydroxybenzoate (52.2 mg, 0.26 mmol, 1.5 eq), methyl 3-((5-bromo-3-fluoro-2-hydroxyphenyl)sulfonamido)-5-chloro-2-hydroxybenzoate was obtained as a solid (16.9 mg, 0.04 mmol, 21%). LCMS (Method A) t$_R$=1.68 min, m/z=455.7 [M+H]$^+$.

Step C. 3-((5-Bromo-3-fluoro-2-hydroxyphenyl)sulfonamido)-5-chloro-2-hydroxybenzoic acid (HCH-3-70-2). Using a procedure analogous to General Procedure F, starting from methyl 3-((5-bromo-3-fluoro-2-hydroxyphenyl)sulfonamido)-5-chloro-2-hydroxybenzoate (14.6 mg, 0.03 mmol) and 1 M NaOH (0.5 mL)/THF (1.0 mL)/MeOH (0.5 mL), the title compound was obtained as a solid (8.3 mg, 0.02 mmol, 58%). $^1$H NMR (400 MHz, Methanol-d$_4$) δ 7.65-7.63 (m, 1H), 7.60 (d, J=2.5 Hz, 1H), 7.56 (d, J=2.6 Hz, 1H), 7.53 (dd, J=10.1, 2.3 Hz, 1H). $^{19}$F NMR (376 MHz, Methanol-d$_4$) δ −133.10 (dd, J=10.1, 1.3 Hz). LCMS (Method A) t$_R$=1.50 min, m/z=463.6 [M+Na]$^+$; Purity (AUC) ≥95%.

Example J6: 3-((5-Bromo-2-hydroxy-3-nitrophenyl)sulfonamido)-5-chloro-2-hydroxybenzoic acid

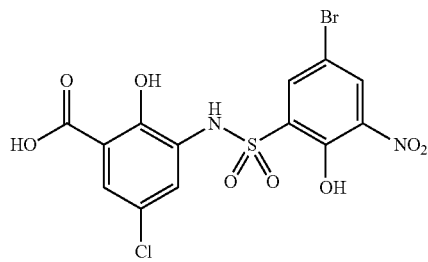 [SMILES: O=C(O)c1cc(Cl)cc(NS(=O)(=O)c2cc(Br)cc([N+](=O)[O-])c2O)c1O]

Step A: 5-Bromo-2-hydroxy-3-nitrobenzenesulfonyl chloride. Using a procedure analogous to General Procedure B, starting with 5-bromo-2-hydroxybenzenesulfonyl chloride (844 mg, 3.1 mmol), which was prepared by a procedure analogous to the procedure used to prepare Example J1 Step A, 5-bromo-2-hydroxy-3-nitrobenzenesulfonyl chloride was obtained as a yellow oil (489 mg, 1.55 mmol, 50%). $^1$H NMR (400 MHz, DMSO-d$_6$) $\delta_H$ 8.13 (d, J=2.5 Hz, 1H), 7.83 (d, J=2.5 Hz, 1H).

Step B: Methyl 3-((5-bromo-2-hydroxy-3-nitrophenyl)sulfonamido)-5-chloro-2-hydroxybenzoate. Using a procedure analogous to General Procedure E, starting with methyl 3-amino-5-chloro-2-hydroxybenzoate (40 mg, 0.20 mmol) and 5-bromo-2-hydroxy-3-nitrobenzenesulfonyl chloride, which was prepared by a procedure analogous to the procedure used to prepare Example J6 Step A, methyl 3-((5-bromo-2-hydroxy-3-nitrophenyl)sulfonamido)-5-chloro-2-hydroxybenzoate was obtained as a yellow solid (13 mg, 0.027 mmol, 14%). LCMS (Method A) $t_R$=1.72 min; Purity (AUC) >90%.

Step C: 3-((5-bromo-2-hydroxy-3-nitrophenyl)sulfonamido)-5-chloro-2-hydroxybenzoic acid. Using a procedure analogous to General Procedure F, starting with methyl 3-((5-bromo-2-hydroxy-3-nitrophenyl)sulfonamido)-5-chloro-2-hydroxybenzoate (13 mg, 0.027 mmol), which was prepared by a procedure analogous to the procedure used to prepare Example J6 Step B, the title compound was obtained as a yellow solid (10 mg, 0.021 mmol, 80%). $^1$H NMR (400 MHz, DMSO-d$_6$) $\delta_H$ 8.21 (d, J=2.7 Hz, 1H), 7.93 (d, J=2.7 Hz, 1H), 7.53 (d, J=2.7 Hz, 1H), 7.49 (d, J=2.7 Hz, 1H); LCMS (Method A) $t_R$=1.70 min; m/z=466.8, 468.8 [M+H]$^+$; Purity (AUC) ≥95%.

Example J7: 3-((5-Bromo-4-chloro-2-methoxyphenyl)sulfonamido)-5-chloro-2-hydroxybenzoic acid

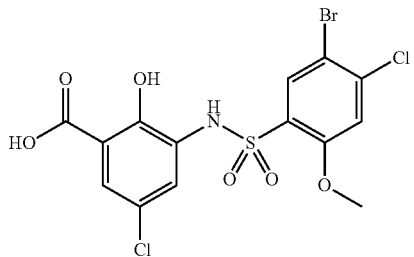 [SMILES: COc1cc(Cl)c(Br)cc1S(=O)(=O)Nc1cc(Cl)cc(C(=O)O)c1O]

Step A: 5-Bromo-4-chloro-2-methoxybenzenesulfonyl chloride. Using a procedure analogous to General Procedure A, starting with 4-bromo-3-chloroanisole (1.42 mL, 10 mmol), 5-bromo-4-chloro-2-methoxybenzenesulfonyl chloride was obtained as a colorless solid (3.2 g, quant.). $^1$H NMR (400 MHz, DMSO-d$_6$) $\delta_H$ 7.90 (s, 1H), 7.23 (s, 1H), 3.79 (s, 3H); LCMS (Method A) $t_R$=1.69 min; Purity (AUC) >90%.

Step B: Methyl 3-((5-bromo-4-chloro-2-methoxyphenyl)sulfonamido)-5-chloro-2-hydroxybenzoate. Using a procedure analogous to General Procedure E, starting with methyl 3-amino-5-chloro-2-hydroxybenzoate (40 mg, 0.20 mmol and 5-bromo-4-chloro-2-methoxybenzenesulfonyl chloride and 5-bromo-4-chloro-2-methoxybenzenesulfonyl chloride), which was prepared by a procedure analogous to the procedure used to prepare Example J7 Step A, methyl 3-((5-bromo-4-chloro-2-methoxyphenyl)sulfonamido)-5-chloro-2-hydroxybenzoate was obtained as a colorless solid (76 mg, 0.16 mmol, 81%). LCMS (Method A) $t_R$=1.86 min, m/z=485.7 [M+H]$^+$; Purity (AUC) ≥95%.

Step C: 3-((5-Bromo-4-chloro-2-methoxyphenyl)sulfonamido)-5-chloro-2-hydroxybenzoic acid. Using a procedure analogous to General Procedure F, starting with methyl 3-((5-bromo-4-chloro-2-methoxyphenyl)sulfonamido)-5-chloro-2-hydroxybenzoate (49 mg, 0.10 mmol), which was prepared by a procedure analogous to the procedure used to prepare Example J7 Step A, the title compound was obtained as a colorless solid (33 mg, 0.07 mmol, 70%). $^1$H NMR (400 MHz, MeOH-d$_4$) $\delta_H$ 8.01 (s, 1H), 7.61 (d, J=2.6 Hz, 1H), 7.60 (d, J=2.6 Hz, 1H), 7.37 (s, 1H), 3.89 (s, 3H); LCMS (Method A) $t_R$=1.66 min, m/z=471.7 [M+H]$^+$; Purity (AUC) ≥95%.

Example J8: 3-((5-Bromo-4-fluoro-2-methoxyphenyl)sulfonamido)-5-chloro-2-hydroxybenzoic acid

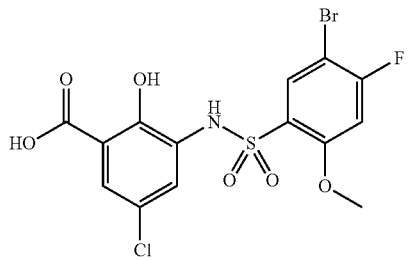 [SMILES: COc1cc(F)c(Br)cc1S(=O)(=O)Nc1cc(Cl)cc(C(=O)O)c1O]

Step A: 5-Bromo-4-fluoro-2-methoxybenzenesulfonyl chloride. Using a procedure analogous to General Procedure A, starting with 4-bromo-3-fluoroanisole (1.34 mL, 10 mmol), 5-bromo-4-fluoro-2-methoxybenzenesulfonyl chloride was obtained as a colorless solid (2.2 g, 7.2 mmol, 72%). $^1$H NMR (400 MHz, DMSO-d$_6$) $\delta_H$ 7.85 (d, J=8.6 Hz, 1H), 7.07 (d, J=11.3 Hz, 1H), 3.77 (s, 3H); $^{19}$F NMR (376 MHz, DMSO-d$_6$) $\delta_F$ —105.4; LCMS (Method A) $t_R$=1.60 min, Purity (AUC) >90%.

Step B: Methyl 3-((5-bromo-4-fluoro-2-methoxyphenyl)sulfonamido)-5-chloro-2-hydroxybenzoate. Using a procedure analogous to General Procedure E, starting with methyl 3-amino-5-chloro-2-hydroxybenzoate (40 mg, 0.20 mmol) and 5-bromo-4-fluoro-2-methoxybenzenesulfonyl chloride, which was prepared by a procedure analogous to the procedure used to prepare Example J8 Step A, methyl 3-((5-bromo-4-fluoro-2-methoxyphenyl)sulfonamido)-5-chloro-2-hydroxybenzoate was obtained as a colorless solid (72 mg, 0.16 mmol, 79%). LCMS (Method A) $t_R$=1.80 min, m/z=468, 470 [M+H]$^+$.

Step C: 3-((5-Bromo-4-fluoro-2-methoxyphenyl)sulfonamido)-5-chloro-2-hydroxybenzoic acid. Using a procedure analogous to General Procedure F, starting with methyl 3-((5-bromo-4-fluoro-2-methoxyphenyl)sulfonamido)-5-chloro-2-hydroxybenzoate (46 mg, 0.10 mmol), which was prepared by a procedure analogous to the procedure used to prepare Example J8 Step B, the title compound was obtained as a colorless solid (26 mg, 0.057 mmol, 57%). $^1$H NMR (400 MHz, MeOH-d$_4$) $\delta_H$ 8.00 (d, J=7.7 Hz, 1H), 7.62 (d, J=2.6 Hz, 1H), 7.59 (d, J=2.6 Hz, 1H), 7.13 (d, J=10.5 Hz, 1H), 3.90 (s, 3H); $^{19}$F NMR (376 MHz, MeOH-d$_4$) $\delta_F$ –97.7; LCMS (Method A) $t_R$=1.60 min, m/z=453.7, 455.7 [M+H]$^+$; Purity (AUC) ≥95%.

Example J9: 3-((5-Bromo-4-fluoro-2-hydroxyphenyl)sulfonamido)-5-chloro-2-hydroxybenzoic acid

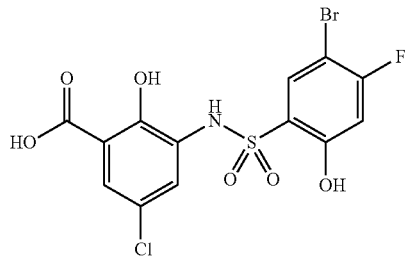 [SMILES: O=C(O)c1cc(Cl)cc(NS(=O)(=O)c2cc(Br)c(F)cc2O)c1O]

Step A: 5-Bromo-4-fluoro-2-hydroxybenzenesulfonyl chloride. Using a procedure analogous to General Procedure A, starting with 4-bromo-3-fluorophenol (1.91 g, 10 mmol), 5-bromo-4-fluoro-2-hydroxybenzenesulfonyl chloride was obtained as a colorless solid (1.2 g, 4.1 mmol, 41%). $^1$H NMR (400 MHz, CDCl$_3$) $\delta_H$ 8.08 (d, J=7.1 Hz, 1H), 6.94 (d, J=9.2 Hz, 1H); $^{19}$F NMR (376 MHz, CDCl$_3$) $\delta_F$ −89.7; LCMS (Method A) $t_R$=1.45 min; Purity (AUC) >85%.

Step B: 3-((5-Bromo-4-fluoro-2-hydroxyphenyl)sulfonamido)-5-chloro-2-hydroxybenzoic acid. Using a procedure analogous to General Procedure E, starting with methyl 3-amino-5-chloro-2-hydroxybenzoate (80 mg, 0.40 mmol) and 5-bromo-4-fluoro-2-hydroxybenzenesulfonyl chloride, which was prepared by a procedure analogous to the procedure used to prepare Example J9 Step A, methyl 3-((5-bromo-4-fluoro-2-hydroxyphenyl)sulfonamido)-5-chloro-2-hydroxybenzoate was obtained and used without purification in a procedure analogous to General Procedure F, the title compound was obtained as a pale brown solid (36 mg, 0.08 mmol, 20% over two steps). $^1$H NMR (400 MHz, DMSO-d$_6$) $\delta_H$ 7.87 (d, J=7.9 Hz, 1H), 7.50 (d, J=2.7 Hz, 1H), 7.45 (d, J=2.7 Hz, 1H), 6.89 (d, J=10.2 Hz, 1H); $^{19}$F NMR (376 MHz, DMSO-d$_6$) $\delta_F$ −99.1; LCMS (Method A) $t_R$=1.50 min, m/z=461.7, 463.6 [M+Na]$^+$; Purity (AUC) ≥95%.

Example J10: 5-Chloro-3-((5-chloro-4-fluoro-2-hydroxyphenyl)sulfonamido)-2-hydroxybenzoic acid

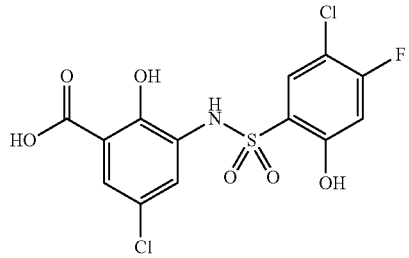 [SMILES: O=C(O)c1cc(Cl)cc(NS(=O)(=O)c2cc(Cl)c(F)cc2O)c1O]

Step A: 5-Chloro-4-fluoro-2-hydroxybenzenesulfonyl chloride. Using a procedure analogous to General Procedure A, starting with 4-chloro-3-fluorophenol (1.91 g, 10 mmol), 5-chloro-4-fluoro-2-hydroxybenzenesulfonyl chloride was obtained as a colorless solid (190 mg, 0.78 mmol, 8%). LCMS (Method A) $t_R$=1.41 min; Purity (AUC) >90%.

Step B: 5-Chloro-3-((5-chloro-4-fluoro-2-hydroxyphenyl)sulfonamido)-2-hydroxybenzoic acid. Using a procedure analogous to General Procedure E, starting with methyl 3-amino-5-chloro-2-hydroxybenzoate (142 mg, 0.70 mmol) and 5-chloro-4-fluoro-2-hydroxybenzenesulfonyl chloride, which was prepared by a procedure analogous to the procedure used to prepare Example J10 Step B, methyl 5-chloro-3-((5-chloro-4-fluoro-2-hydroxyphenyl)sulfonamido)-2-hydroxybenzoate was obtained and used without purification in a procedure analogous to General Procedure F to afford the title compound as a pale brown solid (54 mg, 0.13 mmol, 19% over two steps). $^1$H NMR (400 MHz, DMSO-d$_6$) $\delta_H$ 11.39 (s, 1H), 9.36 (s, 1H), 7.64 (d, J=8.7 Hz, 1H), 7.50 (d, J=2.6 Hz, 1H), 7.44 (d, J=2.7 Hz, 1H), 7.08 (d, J=6.0 Hz, 1H); $^{19}$F NMR (376 MHz, DMSO-d$_6$) $\delta_F$ −127.9; LCMS (Method A) $t_R$=1.43 min, m/z=418.1 [M+Na]$^+$; Purity (AUC) ≥95%.

Example J11: 5-Chloro-3-((4,5-dichloro-2-hydroxyphenyl)sulfonamido)-2-hydroxybenzoic acid

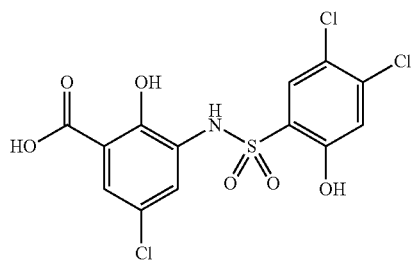 [SMILES: O=C(O)c1cc(Cl)cc(NS(=O)(=O)c2cc(Cl)c(Cl)cc2O)c1O]

Step A: 4,5-Dichloro-2-hydroxybenzenesulfonyl chloride. Using a procedure analogous to General Procedure A, starting with 3,4-dichlorophenol (1.63 g, 10 mmol) 4,5-dichloro-2-hydroxybenzenesulfonyl chloride was obtained as a colorless solid (897 mg, 3.43 mmol, 34%). LCMS (Method A) $t_R$=1.51 min; Purity (AUC) >90%.

Step B: 5-Chloro-3-((4,5-dichloro-2-hydroxyphenyl)sulfonamido)-2-hydroxybenzoic acid. Using a procedure analogous to General Procedure E, starting with methyl 3-amino-5-chloro-2-hydroxybenzoate (142 mg, 0.70 mmol) and 4,5-dichloro-2-hydroxybenzenesulfonyl chloride, which was prepared by a procedure analogous to the procedure used to prepare Example J11 Step A, the title compound was obtained as a colorless solid (24 mg, 0.06 mmol, 11% over two steps). $^1$H NMR (400 MHz, DMSO-d$_6$) $\delta_H$ 7.79 (s, 1H), 7.49 (d, J=2.7 Hz, 1H), 7.43 (d, J=2.7 Hz, 1H), 7.15 (s, 1H); LCMS (Method A) $t_R$=1.52 min, m/z=434.1 [M+Na]$^+$; Purity (AUC) ≥95%.

Example J12: 5-Chloro-3-((5-chloro-4-ethyl-2-hydroxyphenyl)sulfonamido)-2-hydroxybenzoic acid

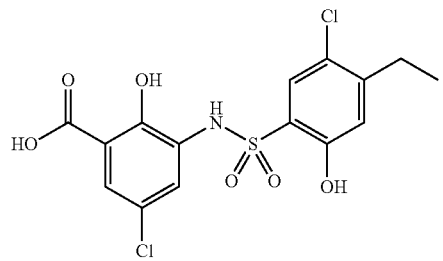 [SMILES: CCc1cc(O)c(S(=O)(=O)Nc2cc(Cl)cc(C(=O)O)c2O)cc1Cl]

Step A: 5-Chloro-4-ethyl-2-hydroxybenzenesulfonyl chloride. Using a procedure analogous to General Procedure A, starting with 4-chloro-3-ethylphenol (1.57 g, 10 mmol), 5-chloro-4-ethyl-2-hydroxybenzenesulfonyl chloride was obtained as a colorless solid (939 mg, 3.68 mmol, 37%). LCMS (Method A) $t_R$=1.56 min: Purity (AUC) >90%.

Step B: 5-Chloro-3-((5-chloro-4-ethyl-2-hydroxyphenyl)sulfonamido)-2-hydroxybenzoic acid. Using a procedure analogous to General Procedure E, starting with methyl 3-amino-5-chloro-2-hydroxybenzoate (142 mg, 0.70 mmol) and 5-chloro-4-ethyl-2-hydroxybenzenesulfonyl chloride, which was prepared by a procedure analogous to the procedure used to prepare Example J12 Step A, 5-chloro-3-((5-chloro-4-ethyl-2-hydroxyphenyl)sulfonamido)-2-hydroxybenzoate was obtained and used without purification in a procedure analogous to General Procedure F to afford the title compound as a colorless solid (85 mg, 0.20 mmol, 40% over two steps). $^1$H NMR (400 MHz, DMSO-$d_6$) $\delta_H$ 11.14 (s, 1H), 9.15 (s, 1H), 7.60 (s, 1H), 7.48 (d, J=2.7 Hz, 1H), 7.46 (d, J=2.7 Hz, 1H), 6.92 (s, 1H), 2.63 (q, J=7.5 Hz, 2H), 1.13 (t, J=7.5 Hz, 3H); LCMS (Method A) $t_R$=1.60 min, m/z=428.1 [M+Na]$^+$; Purity (AUC) ≥95%.

Example HCH-11 (HCH-2-81) 3-((5-Bromo-3-ethyl-2-hydroxyphenyl)sulfonamido)-5-chloro-2-hydroxybenzoic acid

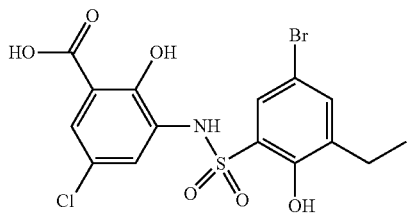 [SMILES: CCc1cc(Br)cc(S(=O)(=O)Nc2cc(Cl)cc(C(=O)O)c2O)c1O]

Step A. Methyl 3-((5-bromo-3-ethyl-2-hydroxyphenyl)sulfonamido)-5-chloro-2-hydroxybenzoate (HCH-2-58-3). Using a procedure analogous to General Procedure E, starting from 5-bromo-3-ethyl-2-hydroxybenzenesulfonyl chloride (80.0 mg, 0.27 mmol), which was prepared by a procedure analogous to the procedure used to prepare Example HCH-2 Step A, and methyl 3-amino-5-chloro-2-hydroxybenzoate (80.8 mg, 0.40 mmol, 1.5 eq), methyl 3-((5-bromo-3-ethyl-2-hydroxyphenyl)sulfonamido)-5-chloro-2-hydroxybenzoate was obtained as a solid (27.4 mg, 0.06 mmol, 22%). $^1$H NMR (400 MHz, Methanol-$d_4$) δ 7.63-7.60 (m, 2H), 7.55 (d, J=2.4 Hz, 1H), 7.44 (d, J=2.3 Hz, 1H), 3.93 (s, 3H), 2.61 (q, J=7.5 Hz, 2H), 1.13 (t, J=7.5 Hz, 3H). LCMS (Method A) $t_R$=1.88 min, m/z=465.7 [M+H]$^+$.

Step B. 3-((5-Bromo-3-ethyl-2-hydroxyphenyl)sulfonamido)-5-chloro-2-hydroxybenzoic acid (HCH-2-81). Using a procedure analogous to General Procedure F, except that the reaction ran at 50° C. overnight, starting from methyl 3-((5-bromo-3-ethyl-2-hydroxyphenyl)sulfonamido)-5-chloro-2-hydroxybenzoate (30.0 mg, 0.06 mmol), which was prepared by a procedure analogous to the procedure used to prepare Example HCH-11 Step A, and 1 M NaOH (0.5 mL)/THF (1.0 mL)/MeOH (0.5 mL), the title compound was obtained as a solid (15.6 mg, 0.03 mmol, 53%). $^1$H NMR (400 MHz, Methanol-$d_4$) δ 7.61 (d, J=2.6 Hz, 1H), 7.58 (d, J=2.5 Hz, 1H), 7.54 (d, J=2.4 Hz, 1H), 7.44 (d, J=2.3 Hz, 1H), 2.60 (q, J=7.5 Hz, 2H), 1.13 (t, J=7.5 Hz, 3H). LCMS (Method A) $t_R$=1.66 min, m/z=451.7 [M+H]$^+$; Purity (AUC) ≥98%.

Example HCH-12 (HCH-2-118-1) 3-((5-bromo-3-ethyl-2-hydroxyphenyl)sulfonamido)-5-ethyl-2-hydroxybenzoic acid

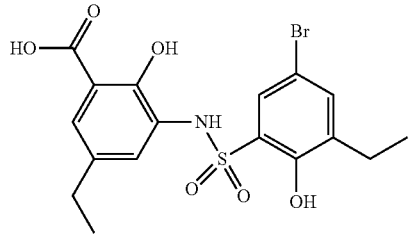 [SMILES: CCc1cc(NS(=O)(=O)c2cc(Br)cc(CC)c2O)c(O)c(C(=O)O)c1]

Step A. Methyl 5-ethyl-2-hydroxybenzoate (HCH-2-110). Using a procedure analogous to the procedure used to prepare Example HCH-42 Step B, starting from 5-ethyl-2-hydroxybenzoic acid (300.0 mg, 1.81 mmol) and MeOH (20.0 mL), methyl 5-ethyl-2-hydroxybenzoate (231.7 mg, 1.28 mmol, 71%) was obtained. LCMS (Method A) $t_R$=1.55 min, m/z=181.2 [M+H]$^+$.

Step B. Methyl 5-ethyl-2-hydroxy-3-nitrobenzoate (HCH-2-111). Using a procedure analogous to General Procedure B, starting from methyl 5-ethyl-2-hydroxybenzoate (231.7 mg, 1.29 mmol), methyl 5-ethyl-2-hydroxy-3-nitrobenzoate was obtained as a crude mixture, which was used for the next step without further purification. $^1$H NMR (400 MHz, Chloroform-d) δ 8.00 (d, J=2.3 Hz, 1H), 7.97 (d, J=2.3 Hz, 1H), 4.00 (s, 3H), 2.66 (q, J=7.6 Hz, 2H), 1.26 (t, J=7.6 Hz, 3H). LCMS (Method A) $t_R$=1.49 min, m/z=226.2 [M+H]$^+$.

Step C. Methyl 3-amino-5-ethyl-2-hydroxybenzoate (HCH-2-112). Using a procedure analogous to General Procedure C, except that Pt/C (50.1 mg) was used, starting from methyl 5-ethyl-2-hydroxy-3-nitrobenzoate (289.6 mg, 1.29 mmol) utilizing General Procedure C, methyl 3-amino-5-ethyl-2-hydroxybenzoate was obtained (209.6 mg, 1.07 mmol, 83%). LCMS (Method A) $t_R$=0.95 min, m/z=196.2 [M+H]$^+$.

Step D. Methyl 3-((5-bromo-3-ethyl-2-hydroxyphenyl)sulfonamido)-5-ethyl-2-hydroxybenzoate (HCH-2-115-1). Using a procedure analogous to General Procedure C, except that Pyridine (54.0 μL, 0.67 mmol, 5.0 eq) was used, starting from 5-bromo-3-ethyl-2-hydroxybenzenesulfonyl chloride (40.0 mg, 0.13 mmol) and methyl 3-amino-5-ethyl-2-hydroxybenzoate (31.3 mg, 0.16 mmol, 1.2 eq), methyl 3-((5-bromo-3-ethyl-2-hydroxyphenyl)sulfonamido)-5-ethyl-2-hydroxybenzoate was obtained as a solid (27.9 mg, 0.06 mmol, 45%). LCMS (Method A) $t_R$=1.89 min, m/z=459.3 [M+H]$^+$.

Step E. 3-((5-Bromo-3-ethyl-2-hydroxyphenyl)sulfonamido)-5-ethyl-2-hydroxybenzoic acid (HCH-2-118-1). Using a procedure analogous to General Procedure F, starting from methyl 3-((5-bromo-3-ethyl-2-hydroxyphenyl)sulfonamido)-5-ethyl-2-hydroxybenzoate (24.0 mg, 0.05 mmol) and 1 M NaOH (0.5 mL)/THF (1.0 mL)/MeOH (0.5 mL), the title compound was obtained as a solid (14.1 mg, 0.03 mmol, 60%). LCMS (Method A) $t_R$=1.68 min, m/z=445.3 [M+H]$^+$; Purity (AUC) ≥98%.

Example HCH-13 (HCH-2-118-3) 3-((5-Bromo-2-hydroxy-3-(trifluoromethoxy)phenyl)sulfonamido)-5-ethyl-2-hydroxybenzoic acid

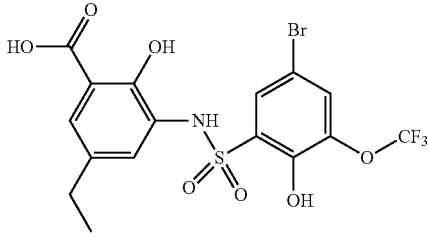 [SMILES: CCc1cc(NS(=O)(=O)c2cc(Br)cc(OC(F)(F)F)c2O)c(O)c(C(=O)O)c1]

Step A. 5-Bromo-2-hydroxy-3-(trifluoromethoxy)benzenesulfonyl chloride (HCH-2-114-2). Using a procedure analogous to General Procedure A, 4-bromo-2-(trifluoromethoxy)phenol (500.0 mg 1.95 mmol) was reacted with chlorosulfonic acid (10.0 mL), to afford a crude mixture of 5-bromo-2-hydroxy-3-(trifluoromethoxy)benzenesulfonyl chloride. The crude material was used for the next step without further purification.

Step B. Methyl 3-((5-bromo-2-hydroxy-3-(trifluoromethoxy)phenyl)sulfonamido)-5-ethyl-2-hydroxybenzoate (HCH-2-115-6). Using a procedure analogous to General Procedure E, starting from 5-bromo-2-hydroxy-3-(trifluoromethoxy)benzenesulfonyl chloride (45.0 mg, 0.13 mmol) and methyl 3-amino-5-ethyl-2-hydroxybenzoate (29.6 mg, 0.15 mmol, 1.2 eq), which was prepared by a procedure analogous to the procedure used to prepare Example HCH-12 Step C, methyl 3-((5-bromo-2-hydroxy-3-(trifluoromethoxy)phenyl)sulfonamido)-5-ethyl-2-hydroxybenzoate was obtained as a solid (30.9 mg, 0.06 mmol, 47%). LCMS (Method A) $t_R$=1.80 min, m/z=515.3 [M+H]$^+$.

Step C. 3-((5-Bromo-2-hydroxy-3-(trifluoromethoxy)phenyl)sulfonamido)-5-ethyl-2-hydroxybenzoic acid (HCH-2-118-3). Using a procedure analogous to General Procedure F, starting from methyl 3-((5-bromo-2-hydroxy-3-(trifluoromethoxy)phenyl)sulfonamido)-5-ethyl-2-hydroxybenzoate (28.9 mg, 0.06 mmol) and 1 M NaOH (0.5 mL)/THF (1.0 mL)/MeOH (0.5 mL), the title compound was obtained as a solid (18.7 mg, 0.04 mmol, 66%). LCMS (Method A) $t_R$=1.62 min, m/z=501.2 [M+H]$^+$; Purity (AUC) ≥98%.

Example HCH-14 (HCH-2-135-5-F11) 3-((5-Bromo-3-ethyl-2-hydroxyphenyl)sulfonamido)-2-hydroxy-5-(trifluoromethoxy)benzoic acid

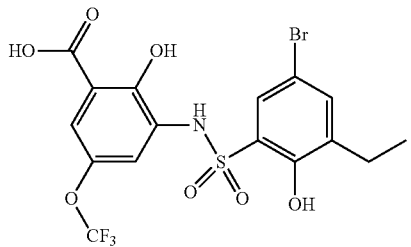 [SMILES: CCc1cc(Br)cc(S(=O)(=O)Nc2cc(OC(F)(F)F)cc(C(=O)O)c2O)c1O]

Step A. Methyl 3-((5-bromo-3-ethyl-2-hydroxyphenyl)sulfonamido)-2-hydroxy-5-(trifluoromethoxy)benzoate (HCH-2-129-5). Using a procedure analogous to General Procedure E, starting from 5-bromo-3-ethyl-2-hydroxybenzenesulfonyl chloride (40.0 mg, 0.13 mmol), which was prepared by a procedure analogous to the procedure used to prepare Example HCH-2 Step A, and methyl 3-amino-2-hydroxy-5-(trifluoromethoxy)benzoate (40.2 mg, 0.16 mmol, 1.2 eq), which was prepared by a procedure analogous to the procedure used to prepare Example HCH-1 Step C, methyl 3-((5-bromo-3-ethyl-2-hydroxyphenyl)sulfonamido)-2-hydroxy-5-(trifluoromethoxy)benzoate was obtained as a solid (24.4 mg, 0.05 mmol, 35%). Pyridine (54.0 μL, 0.67 mmol, 5.0 eq) was used. $^1$H NMR (400 MHz, Methanol-d$_4$) δ 7.57 (d, J=2.1 Hz, 1H), 7.55 (d, J=2.4 Hz, 1H), 7.50 (d, J=2.2 Hz, 1H), 7.43 (d, J=2.4 Hz, 1H), 3.94 (s, 3H), 2.59 (q, J=7.5 Hz, 2H), 1.11 (t, J=7.5 Hz, 3H). $^{19}$F NMR (376 MHz, Methanol-d$_4$) δ −60.27. LCMS (Method A) $t_R$=1.89 min, m/z=515.2 [M+H]$^+$.

Step B. 3-((5-Bromo-3-ethyl-2-hydroxyphenyl)sulfonamido)-2-hydroxy-5-(trifluoromethoxy)benzoic acid (HCH-2-135-5). Using a procedure analogous to General Procedure F, starting from methyl 3-((5-bromo-3-ethyl-2-hydroxyphenyl)sulfonamido)-2-hydroxy-5-(trifluoromethoxy)benzoate (24.4 mg, 0.05 mmol) and 1M NaOH (0.5 mL)/THF (1.0 mL)/MeOH (0.5 mL) the title compound was obtained as a solid (16.2 mg, 0.03 mmol, 68%). LCMS (Method A) $t_R$=1.88 min, m/z=555.2 [M+H]$^+$; Purity (AUC) ≥95%.

Example HCH-15 (HCH-2-135-4) 3-((5-Bromo-2-hydroxy-3-(trifluoromethoxy)phenyl)sulfonamido)-2-hydroxy-5-(trifluoromethoxy)benzoic acid

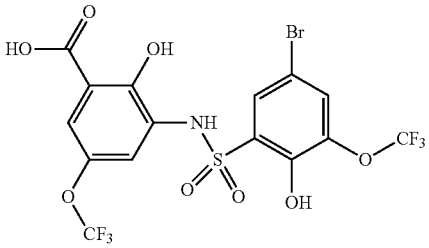 [SMILES: O=C(O)c1cc(OC(F)(F)F)cc(NS(=O)(=O)c2cc(Br)cc(OC(F)(F)F)c2O)c1O]

Step A. Methyl 3-((5-bromo-2-hydroxy-3-(trifluoromethoxy)phenyl)sulfonamido)-2-hydroxy-5-(trifluoromethoxy)benzoate (HCH-2-129-4). Using a procedure analogous to General Procedure E, starting from 5-bromo-2-hydroxy-3-(trifluoromethoxy)benzenesulfonyl chloride (40.0 mg, 0.11 mmol), which was prepared by a procedure analogous to the procedure used to prepare Example HCH-13 Step A, and methyl 3-amino-2-hydroxy-5-(trifluoromethoxy)benzoate (33.9 mg, 0.14 mmol, 1.2 eq), which was prepared by a procedure analogous to the procedure used to prepare Example HCH-1 Step C, methyl 3-((5-bromo-2-hydroxy-3-(trifluoromethoxy)phenyl)sulfonamido)-2-hydroxy-5-(trifluoromethoxy)benzoate was obtained as a solid (18.9 mg, 0.03 mmol, 29%). LCMS (Method A) $t_R$=1.83 min, m/z=571.2 [M+H]$^+$.

Step B. 3-((5-Bromo-2-hydroxy-3-(trifluoromethoxy)phenyl)sulfonamido)-2-hydroxy-5-(trifluoromethoxy)benzoic acid (HCH-2-135-4). Using a procedure analogous to General Procedure F, starting from methyl 3-((5-bromo-2-hydroxy-3-(trifluoromethoxy)phenyl)sulfonamido)-2-hydroxy-5-(trifluoromethoxy)benzoate (18.9 mg, 0.03 mmol) and 1 M NaOH (0.5 mL)/THF (1.0 mL)/MeOH (0.5 mL), the title compound was obtained as a solid (11.3 mg, 0.02 mmol, 61%). 1H NMR (400 MHz, Methanol-d$_4$) δ 7.81 (d, J=2.3 Hz, 1H), 7.66-7.62 (m, 1H), 7.54 (d, J=2.2 Hz, 1H), 7.48 (d, J=2.2 Hz, 1H). $^{19}$F NMR (376 MHz, Methanol-d$_4$) δ −60.30, −60.38. LCMS (Method A) $t_R$=1.68 min, m/z=557.2 [M+H]$^+$; Purity (AUC) ≥95%.

Example HCH-16 (HCH-2-148-2) 3-((5-Bromo-2-hydroxy-3-propylphenyl)sulfonamido)-2-hydroxy-5-(trifluoromethoxy)benzoic acid

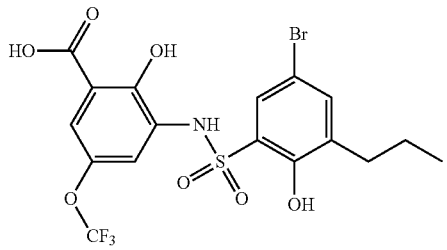 [SMILES: CCCc1cc(Br)cc(S(=O)(=O)Nc2cc(OC(F)(F)F)cc(C(=O)O)c2O)c1O]

Step A. 4-Bromo-2-propylphenol (HCH-2-137-1). Using a procedure analogous to the procedure used to prepare Example HCH-4 Step B, starting from 2-propylphenol (500.0 mg, 3.67 mmol) and tetrabutyl ammonium tribromide (2124.3 mg, 4.41 mmol), 4-bromo-2-propylphenol was obtained (766.3 mg, 3.56 mmol, 97%). $^1$H NMR (400 MHz, Chloroform-d) δ 7.23 (d, J=2.4 Hz, 1H), 7.17 (dd, J=8.5, 2.5 Hz, 1H), 6.64 (d, J=8.5 Hz, 1H), 2.59-2.48 (m, 2H), 1.63 (dq, J=14.8, 7.4 Hz, 2H), 0.97 (t, J=7.4 Hz, 3H). LCMS (Method A) $t_R$=1.55 min, m/z=216.1 [M+H]$^+$.

Step B. 5-Bromo-2-hydroxy-3-propylbenzenesulfonyl chloride (HCH-2-144-5). Using a procedure analogous to General Procedure A, 4-bromo-2-propylphenol (413.0 mg 2.05 mmol) was reacted with chlorosulfonic acid (6.0 mL) to afford 5-bromo-2-hydroxy-3-propylbenzenesulfonyl chloride as a crude mixture that was used for the next step without further purification. x Step C. Methyl 3-((5-bromo-2-hydroxy-3-propylphenyl)sulfonamido)-2-hydroxy-5-(trifluoromethoxy)benzoate (HCH-2-144-5). Using a procedure analogous to General Procedure E, starting from 5-bromo-2-hydroxy-3-propyl-benzenesulfonyl chloride (50.0 mg, 0.16 mmol), which was prepared by a procedure analogous to the procedure used to prepare Example HCH-16 Step B, and methyl 3-amino-2-hydroxy-5-(trifluoromethoxy)benzoate (60.1 mg, 0.24 mmol, 1.5 eq), which was prepared by a procedure analogous to the procedure used to prepare Example HCH-1 Step C, methyl 3-((5-bromo-2-hydroxy-3-propylphenyl)sulfonamido)-2-hydroxy-5-(trifluoromethoxy)benzoate was obtained as a solid (56.0 mg, 0.11 mmol, 66%). LCMS (Method A) $t_R$=1.95 min, m/z=529.3 [M+H]$^+$.

Step D. 3-((5-bromo-2-hydroxy-3-propylphenyl)sulfonamido)-2-hydroxy-5-(trifluoromethoxy)benzoic acid % (HCH-2-148-2). Using a procedure analogous to General Procedure F, starting from methyl 3-((5-bromo-2-hydroxy-3-propylphenyl)sulfonamido)-2-hydroxy-5-(trifluoromethoxy)benzoate (25.0 mg, 0.05 mmol) and 1 M NaOH (0.5 mL)/THF (1.0 mL)/MeOH (0.5 mL), the title compound was obtained as a solid (18.4 mg, 0.04 mmol, 75%). $^1$H NMR (400 MHz, Methanol-d$_4$) δ 7.56 (d, J=2.5 Hz, 1H), 7.54 (d, J=2.4 Hz, 1H), 7.50 (d, J=2.2 Hz, 1H), 7.41 (d, J=2.4 Hz, 1H), 2.59-2.51 (m, 2H), 1.52 (h, J=7.4 Hz, 2H), 0.85 (t, J=7.4 Hz, 4H). $^{19}$F NMR (376 MHz, Methanol-d$_4$) δ −60.27. LCMS (Method A) $t_R$=1.75 min, m/z=515.3 [M+H]$^+$; Purity (AUC) ≥98%.

Example HCH-17 (HCH-2-148-1) 3-((5-Bromo-2-hydroxy-3-propylphenyl)sulfonamido)-5-chloro-2-hydroxybenzoic acid (HCH-2-144-4)

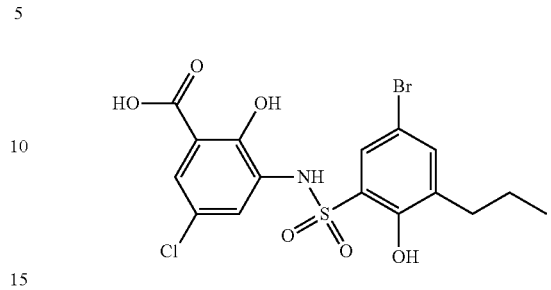

Step A. Methyl 3-((5-bromo-2-hydroxy-3-propylphenyl)sulfonamido)-5-chloro-2-hydroxybenzoate. Using a procedure analogous to General Procedure E, starting from 5-bromo-2-hydroxy-3-propylbenzenesulfonyl chloride (50.0 mg, 0.16 mmol), which was prepared by a procedure analogous to the procedure used to prepare Example HCH-16 Step B, and methyl 3-amino-5-chloro-2-hydroxybenzoate (48.2 mg, 0.24 mmol, 1.5 eq), methyl 3-((5-bromo-2-hydroxy-3-propylphenyl)sulfonamido)-5-chloro-2-hydroxybenzoate was obtained as a solid (63.9 mg, 0.13 mmol, 83%). LCMS (Method A) $t_R$=1.90 min, m/z=479.7 [M+H]$^+$.

Step B. 3-((5-Bromo-2-hydroxy-3-propylphenyl)sulfonamido)-5-chloro-2-hydroxybenzoic acid (HCH-2-148-1). Using a procedure analogous to General Procedure F, starting from methyl 3-((5-bromo-2-hydroxy-3-propylphenyl)sulfonamido)-5-chloro-2-hydroxybenzoate (25.0 mg, 0.05 mmol) and 1 M NaOH (0.5 mL)/THF (1.0 mL)/MeOH (0.5 mL), the title compound was obtained as a solid (18.9 mg, 0.04 mmol, 77%). $^1$H NMR (400 MHz, Methanol-d$_4$) δ 7.61 (d, J=2.6 Hz, 1H), 7.58 (d, J=2.6 Hz, 1H), 7.55 (d, J=2.4 Hz, 1H), 7.41 (d, J=2.4 Hz, 1H), 2.60-2.51 (m, 2H), 1.53 (h, J=7.4 Hz, 2H), 0.87 (t, J=7.4 Hz, 3H). LCMS (Method A) $t_R$=1.71 min, m/z=465.7 [M+H]$^+$; Purity (AUC) ≥98%.

Example HCH-18 (HCH-3-33) 3-((5-Bromo-2-hydroxyphenyl)sulfonamido)-5-ethyl-2-hydroxybenzoic acid

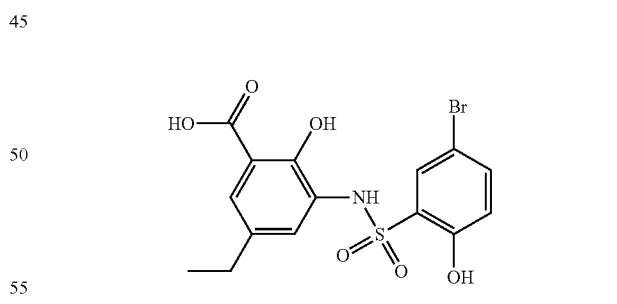

Step A. tert-Butyl 3-((5-bromo-2-hydroxyphenyl)sulfonamido)-5-ethyl-2-hydroxybenzoate (HCH-3-28-1). Using a procedure analogous to General Procedure E, starting from 5-bromo-2-hydroxybenzenesulfonyl chloride (70.0 mg, 0.26 mmol), which was prepared by a procedure analogous to the procedure used to prepare Example J1 Step A, and tert-butyl 3-amino-5-ethyl-2-hydroxybenzoate (91.8 mg, 0.39 mmol, 1.5 eq), tert-butyl 3-((5-bromo-2-hydroxyphenyl)sulfonamido)-5-ethyl-2-hydroxybenzoate was obtained as a solid (92.2 mg, 0.19 mmol, 75%). $^1$H NMR (400 MHz, Methanol-d$_4$) δ 7.77 (d, J=2.5 Hz, 1H), 7.51-7.45 (m, 2H), 7.33 (d, J=2.1 Hz, 1H), 6.85 (d, J=8.8 Hz, 1H), 2.53 (q, J=7.6 Hz, 2H), 1.60 (s, 9H), 1.15 (t, J=7.6 Hz, 3H). LCMS (Method A) $t_R$=2.02 min, m/z=495.4 [M+H]$^+$.

Step B. 3-((5-Bromo-2-hydroxyphenyl)sulfonamido)-5-ethyl-2-hydroxybenzoic acid (HCH-3-33). Using a procedure analogous to the procedure used to prepare Example HCH-1 Step G, starting from tert-butyl 3-((5-bromo-2-hydroxyphenyl)sulfonamido)-5-ethyl-2-hydroxybenzoate (23.4 mg, 0.05 mmol), TFA (0.1 mL), and 1 drop of concentrated HCl, the title compound was obtained as a solid (18.0 mg, 0.04 mmol, 87%). LCMS (Method A) $t_R$=1.81 min, m/z=417.2 [M+H]$^+$; Purity (AUC) ≥98%.

Example HCH-21 (HCH-3-71) 3-((5-Bromo-3-fluoro-2-hydroxyphenyl)sulfonamido)-5-ethyl-2-hydroxybenzoic acid

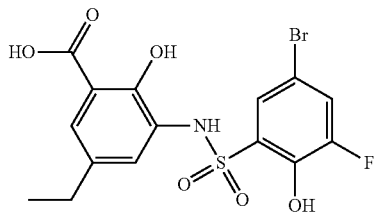 [SMILES: CCc1cc(NS(=O)(=O)c2cc(Br)cc(F)c2O)c(O)c(C(=O)O)c1]

Step A. tert-Butyl 3-((5-bromo-3-fluoro-2-hydroxyphenyl)sulfonamido)-5-ethyl-2-hydroxybenzoate (HCH-3-67-1). Using a procedure analogous to General Procedure E, starting from 5-bromo-3-fluoro-2-hydroxybenzenesulfonyl chloride (50.0 mg, 0.17 mmol), which was prepared by a procedure analogous to the procedure used to prepare Example J5 Step A, and tert-butyl 3-amino-5-ethyl-2-hydroxybenzoate (61.5 mg, 0.26 mmol), tert-butyl 3-((5-bromo-3-fluoro-2-hydroxyphenyl)sulfonamido)-5-ethyl-2-hydroxybenzoate was obtained as a solid (41.6 mg, 0.09 mmol, 54%). $^1$H NMR (400 MHz, Methanol-d$_4$) δ 7.60-7.56 (m, 1H), 7.46 (dd, J=10.7, 2.1 Hz, 2H), 7.33 (d, J=2.1 Hz, 1H), 2.51 (q, J=7.6 Hz, 2H), 1.58 (s, 9H), 1.13 (t, J=7.6 Hz, 3H). LCMS (Method A) $t_R$=1.91 min, m/z=434.2 [M+H–tBu]$^+$.

Step B. 3-((5-Bromo-3-fluoro-2-hydroxyphenyl)sulfonamido)-5-ethyl-2-hydroxybenzoic acid (HCH-3-71). Using a procedure analogous to the procedure used to prepare Example HCH-1 Step G, starting from tert-butyl 3-((5-bromo-3-fluoro-2-hydroxyphenyl)sulfonamido)-5-ethyl-2-hydroxybenzoate (41.6 mg, 0.08 mmol), the title compound was obtained as a solid (13.4 mg, 0.03 mmol, 36%). 1H NMR (400 MHz, Methanol-d$_4$) δ 7.60-7.58 (m, 1H), 7.49 (dd, J=10.0, 2.3 Hz, 1H), 7.45 (d, J=4.8 Hz, 2H), 2.54 (q, J=7.6 Hz, 2H), 1.16 (t, J=7.6 Hz, 3H). $^{19}$F NMR (376 MHz, Methanol-d$_4$) δ −133.24 (dd, J=10.0, 1.3 Hz). LCMS (Method A) $t_R$=1.53 min, m/z=435.2 [M+H]$^+$; Purity (AUC) ≥95%.

Example HCH-22 (HCH-3-79) 3-((5-Bromo-3-chloro-2-hydroxyphenyl)sulfonamido)-5-ethyl-2-hydroxybenzoic acid

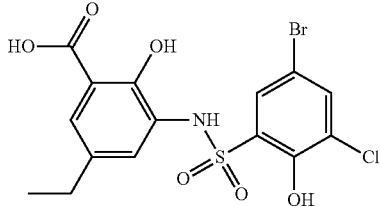 [SMILES: CCc1cc(NS(=O)(=O)c2cc(Br)cc(Cl)c2O)c(O)c(C(=O)O)c1]

Step A. tert-Butyl 3-((5-bromo-3-chloro-2-hydroxyphenyl)sulfonamido)-5-ethyl-2-hydroxybenzoate (HCH-3-77-1). Using a procedure analogous to General Procedure E, starting from 5-bromo-3-chloro-2-hydroxybenzenesulfonyl chloride (24.0 mg, 0.05 mmol), which was prepared by a procedure analogous to the procedure used to prepare Example J4 Step A, and tert-butyl 3-amino-5-ethyl-2-hydroxybenzoate (50.4 mg, 0.21 mmol, 1.3 eq), tert-butyl 3-((5-bromo-3-chloro-2-hydroxyphenyl)sulfonamido)-5-ethyl-2-hydroxybenzoate was obtained as a solid (27.0 mg, 0.05 mmol, 32%). LCMS (Method A) $t_R$=2.02 min, m/z=450.7 [M+H–tBu]$^+$.

Step B. 3-((5-Bromo-3-chloro-2-hydroxyphenyl)sulfonamido)-5-ethyl-2-hydroxybenzoic acid (HCH-3-79). Using a procedure analogous to the procedure used to prepare Example HCH-1 Step G, starting from tert-butyl 3-((5-bromo-3-chloro-2-hydroxyphenyl)sulfonamido)-5-ethyl-2-hydroxybenzoate (24.0 mg, 0.05 mmol), the title compound was obtained as a solid (7.9 mg, 0.02 mmol, 37%). $^1$H NMR (400 MHz, Methanol-d$_4$) δ 7.71 (d, J=2.4 Hz, 1H), 7.67 (d, J=2.4 Hz, 1H), 7.47 (s, 1H), 7.46 (d, J=1.8 Hz, 1H), 2.56 (q, J=7.6 Hz, 2H), 1.17 (t, J=7.6 Hz, 4H). LCMS (Method A) $t_R$=1.60 min, m/z=451.7 [M+H]$^+$; Purity (AUC) ≥95%.

Example HCH-24 (HCH-3-80-2) 3-((5-Bromo-3-chloro-2-hydroxyphenyl)sulfonamido)-2-hydroxy-5-(trifluoromethoxy)benzoic acid

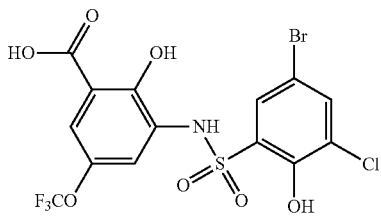 [SMILES: O=C(O)c1cc(OC(F)(F)F)cc(NS(=O)(=O)c2cc(Br)cc(Cl)c2O)c1O]

Step A. Methyl 3-((5-bromo-3-chloro-2-hydroxyphenyl)sulfonamido)-2-hydroxy-5-(trifluoromethoxy)benzoate (HCH-3-77-3). Using a procedure analogous to General Procedure E, starting from 5-bromo-3-chloro-2-hydroxybenzenesulfonyl chloride (50.0 mg, 0.16 mmol, which was prepared by a procedure analogous to the procedure used to prepare Example J4 Step A, and methyl 3-amino-2-hydroxy-5-(trifluoromethoxy)benzoate (53.4 mg, 0.21 mmol, 1.3 eq), which was prepared by a procedure analogous to the procedure used to prepare Example HCH-1 Step C, methyl 3-((5-bromo-3-chloro-2-hydroxyphenyl)sulfonamido)-2-hydroxy-5-(trifluoromethoxy)benzoate was obtained as a solid (26.4 mg, 0.05 mmol, 31%). LCMS (Method A) $t_R$=1.80 min, m/z=521.7 [M+H]$^+$.

Step B. 3-((5-Bromo-3-chloro-2-hydroxyphenyl)sulfonamido)-2-hydroxy-5-(trifluoromethoxy)benzoic acid. Using a procedure analogous to General Procedure F, starting from methyl 3-((5-bromo-3-chloro-2-hydroxyphenyl)sulfonamido)-2-hydroxy-5-(trifluoromethoxy)benzoate (10.5 mg, 0.02 mmol) and 1M NaOH (0.5 mL)/THF (1.0 mL)/MeOH (0.5 mL), the title compound was obtained as a solid (7.0 mg, 0.01 mmol, 68%). 1H NMR (400 MHz, Methanol-d$_4$) δ 7.74 (q, J=2.4 Hz, 2H), 7.54 (d, J=2.3 Hz, 1H), 7.47 (d, J=2.2 Hz, 1H). $^{19}$F NMR (376 MHz, Methanol-d$_4$) δ −60.27. LCMS (Method A) $t_R$=1.66 min, m/z=507.6 [M+H]$^+$; Purity (AUC) ≥95% (HCH-3-80-2)

Example HCH-27 (HCH-4-14-1) 3-((5-Bromo-2-hydroxy-3-(3-hydroxypropyl)phenyl)sulfonamido)-2-hydroxy-5-(trifluoromethoxy)benzoic acid (HCH-4-14-1)

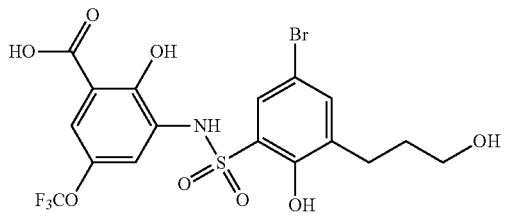 [SMILES: O=C(O)c1cc(OC(F)(F)F)cc(NS(=O)(=O)c2cc(Br)cc(CCCO)c2O)c1O]

Using a procedure analogous to General Procedure F, starting from methyl 3-((5-bromo-2-hydroxy-3-(3-hydroxypropyl)phenyl)sulfonamido)-2-hydroxy-5-(trifluoromethoxy)benzoate (10.0 mg, 0.02 mmol), which was prepared by a procedure analogous to the procedure used to prepare Example HCH-4 Step D, and 1M NaOH (0.5 mL)/THF (1.0 mL)/MeOH (0.5 mL), the title compound was obtained as a solid (4.7 mg, 0.009 mmol, 48%). 1H NMR (400 MHz, Methanol-d$_4$) δ 7.68 (d, J=2.3 Hz, 1H), 7.55 (d, J=2.2 Hz, 1H), 7.42 (s, 2H), 4.28-4.21 (m, 2H), 2.77 (t, J=6.4 Hz, 2H), 1.96 (p, J=6.3 Hz, 2H). $^{19}$F NMR (376 MHz, Methanol-d$_4$) δ −60.26. LCMS (Method A) $t_R$=1.68 min, m/z=531.3 [M+H]$^+$; Purity (AUC) ≥95%.

Example J13: 3-((6-Bromoquinoline)-8-sulfonamido)-5-chloro-2-hydroxybenzoic acid

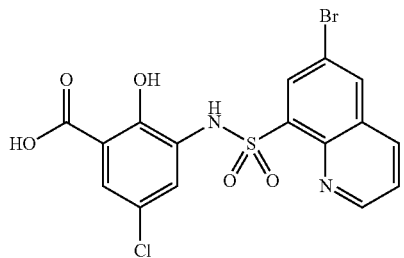 [SMILES: O=C(O)c1cc(Cl)cc(NS(=O)(=O)c2cc(Br)cc3cccnc23)c1O]

Step A: Methyl 3-((6-bromoquinoline)-8-sulfonamido)-5-chloro-2-hydroxybenzoate. Using a procedure analogous to General Procedure E, starting with methyl 3-amino-5-chloro-2-hydroxybenzoate (20 mg, 0.10 mmol) and 6-bromoquinoline-8-sulfonyl chloride, methyl 3-((6-bromoquinoline)-8-sulfonamido)-5-chloro-2-hydroxybenzoate was obtained as a colorless solid (45 mg, 0.095 mmol, 95%). LCMS (Method A) $t_R$=1.80 min, m/z=471, 473 [M+H]$^+$; Purity (AUC)=87%; taken forward without further purification.

Step B: 3-((6-Bromoquinoline)-8-sulfonamido)-5-chloro-2-hydroxybenzoic acid. Using a procedure analogous to General Procedure F, starting with methyl 3-((6-bromoquinoline)-8-sulfonamido)-5-chloro-2-hydroxybenzoate (45 mg, 0.095 mmol), which was prepared by a procedure analogous to the procedure used to prepare Example J13 Step A, the title compound was obtained as a colorless solid (29 mg, 0.063 mmol, 67%). $^1$H NMR (400 MHz, DMSO-d$_6$) δ$_H$ 9.50 (s, 1H), 9.06 (dd, J=4.3, 1.8 Hz, 1H), 8.65 (d, J=2.3 Hz, 1H), 8.52 (dd, J=8.5, 1.8 Hz, 1H), 8.33 (d, J=2.3 Hz, 1H), 7.77 (dd, J=8.5, 4.3 Hz, 1H), 7.58 (d, J=2.6 Hz, 1H), 7.46 (d, J=2.6 Hz, 1H); LCMS (Method A) $t_R$=1.57 min, m/z=456.7, 458.7 [M+H]$^+$; Purity (AUC) ≥95%.

Example J14: 3-((5-Bromo-2-hydroxyphenyl)sulfonamido)-5-chloro-2-hydroxy-N-methylbenzamide

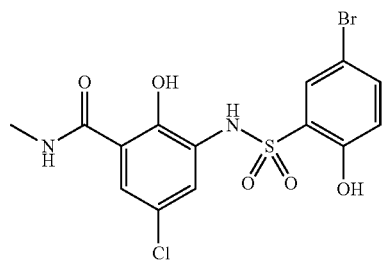 [SMILES: CNC(=O)c1cc(Cl)cc(NS(=O)(=O)c2cc(Br)ccc2O)c1O]

Using a procedure analogous to General Procedure G, starting with methyl 3-((5-bromo-2-hydroxyphenyl)sulfonamido)-5-chloro-2-hydroxybenzoate (109 mg, 0.25 mmol), which was prepared by a procedure analogous to the procedure used to prepare Example J1 Step B, and methylamine, the title compound was obtained as a colorless solid (89 mg, 82%). $^1$H NMR (400 MHz, DMSO-d$_6$) δ$_H$ 7.80 (d, J=2.5 Hz, 1H), 7.54 (d, J=2.4 Hz, 1H), 7.53 (dd, J=8.8, 2.5 Hz, 1H), 7.47 (d, J=2.4 Hz, 1H), 6.87 (d, J=8.8 Hz, 1H), 2.88 (s, 3H); LCMS (Method A) $t_R$=1.57 min, m/z=434.8, 436.8 [M+H]$^+$; Purity (AUC) ≥95%.

Example J15: 3-((5-Bromo-2-hydroxyphenyl)sulfonamido)-5-chloro-2-hydroxy-N-(2-methoxyethyl)benzamide

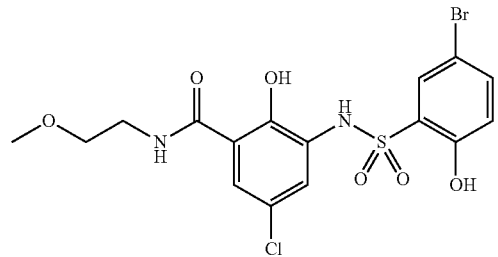 [SMILES: COCCNC(=O)c1cc(Cl)cc(NS(=O)(=O)c2cc(Br)ccc2O)c1O]

Using a procedure analogous to General Procedure J, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 2-methoxyethylamine, the title compound was obtained as a colorless solid (9 mg, 37%). LCMS (Method A) $t_R$=1.52 min, m/z=478.8, 480.8 [M+H]$^+$; Purity (AUC) ≥95%.

Example J16: 3-((5-Bromo-2-hydroxyphenyl)sulfonamido)-5-chloro-2-hydroxy-N-(2-hydroxyethyl)benzamide

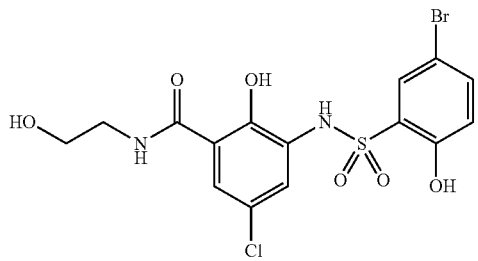 [SMILES: O=C(NCCO)c1cc(Cl)cc(NS(=O)(=O)c2cc(Br)ccc2O)c1O]

Using a procedure analogous to General Procedure J, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and ethanolamine, the title compound was obtained as a colorless solid (8 mg, 34%). LCMS (Method A) $t_R$=1.51 min, m/z=464.8, 466.8 [M+H]$^+$; Purity (AUC) ≥95%.

Example J17: 3-((5-Bromo-2-hydroxyphenyl)sulfonamido)-5-chloro-2-hydroxy-N-(3-hydroxypropyl)benzamide

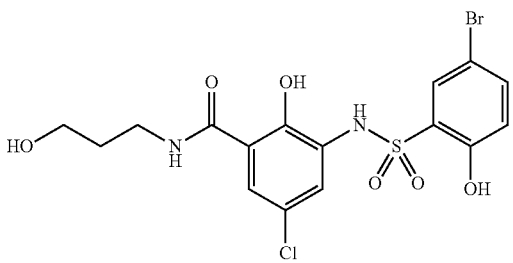 [SMILES: O=C(NCCCO)c1cc(Cl)cc(NS(=O)(=O)c2cc(Br)ccc2O)c1O]

Using a procedure analogous to General Procedure J, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 3-aminopropanol, the title compound was obtained as a colorless solid (9 mg, 37%). LCMS (Method A) $t_R$=1.44 min, m/z=478.8, 480.8 [M+H]$^+$; Purity (AUC) ≥95%.

Example J18: 3-((5-Bromo-2-hydroxyphenyl)sulfonamido)-5-chloro-2-hydroxy-N-(tetrahydrofuran-3-yl)benzamide

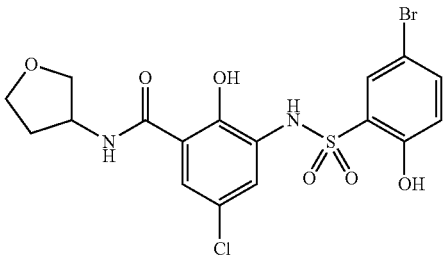 [SMILES: O=C(NC1CCOC1)c1cc(Cl)cc(NS(=O)(=O)c2cc(Br)ccc2O)c1O]

Using a procedure analogous to General Procedure J, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 3-aminotetrahydrofuran, the title compound was obtained as a colorless solid (7 mg, 28%). LCMS (Method A) $t_R$=1.52 min, m/z=490.8, 492.8 [M+H]$^+$; Purity (AUC) ≥95%.

Example J19: 3-((5-Bromo-2-hydroxyphenyl)sulfonamido)-5-chloro-2-hydroxy-N-(2-morpholinoethyl)benzamide

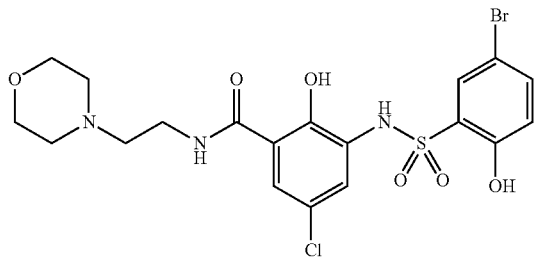 [SMILES: O=C(NCCN1CCOCC1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 2-morpholinoethan-1-amine, the title compound was obtained as a as an off-white gum (24 mg, 90%—as free base). $^1$H NMR (400 MHz, MeOH-d$_4$) $\delta_H$ 7.80 (d, J=2.5 Hz, 1H), 7.58-7.50 (m, 3H), 6.87 (d, J=8.7 Hz, 1H), 3.84-3.76 (m, 4H), 3.62 (t, J=6.2 Hz, 2H), 2.98-2.82 (m, 6H); LCMS (Method A) $t_R$=1.32 min, m/z=533.8, 535.8 [M+H]$^+$; Purity (AUC) ≥95%.

Example J21: 3-((5-Bromo-2-hydroxyphenyl)sulfonamido)-5-chloro-2-hydroxy-N-(oxetan-3-yl)benzamide

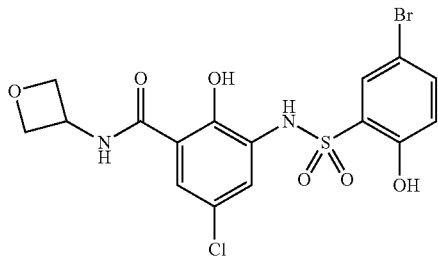 [SMILES: O=C(NC1COC1)c1cc(Cl)cc(NS(=O)(=O)c2cc(Br)ccc2O)c1O]

Using a procedure analogous to General Procedure I, starting with 3-((5-bromo-2-hydroxyphenyl)sulfonamido)-5-chloro-2-hydroxybenzoic acid (21 mg, 0.05 mmol) which was prepared by a procedure analogous to the procedure used to prepare Example J1 Step C, and 3-oxetanamine, the title compound was obtained as a colorless solid (7 mg, 29%). LCMS (Method A) $t_R$=1.52 min, m/z=476.7, 478.8 [M+H]$^+$; Purity (AUC) ≥95%.

Example J22: (S)-3-((5-Bromo-2-hydroxyphenyl)sulfonamido)-5-chloro-2-hydroxy-N-(tetrahydrofuran-3-yl)benzamide

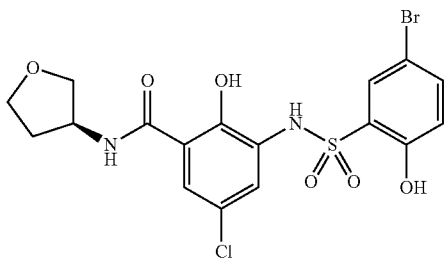 [SMILES: O=C(N[C@H]1CCOC1)c1cc(Cl)cc(NS(=O)(=O)c2cc(Br)ccc2O)c1O]

Using a procedure analogous to General Procedure I, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and (S)-3-aminotetrahydrofuran the title compound was obtained as a colorless solid (15 mg, 61%). LCMS (Method A) $t_R$=1.60 min, m/z=490.8, 492.7 [M+H]$^+$; Purity (AUC) ≥95%.

Example J23: 3-((5-Bromo-2-hydroxyphenyl)sulfonamido)-5-chloro-2-hydroxy-N-((tetrahydrofuran-3-yl)methyl)benzamide

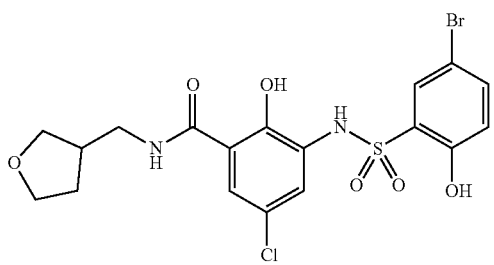 [SMILES: O=C(NCC1CCOC1)c1cc(Cl)cc(NS(=O)(=O)c2cc(Br)ccc2O)c1O]

Using a procedure analogous to General Procedure 1, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and (tetrahydrofuran-3-yl)methanamine, the title compound was obtained as a colorless solid (14 mg, 55%). LCMS (Method A) $t_R$=1.61 min, m/z=504.7, 506.7 [M+H]$^+$; Purity (AUC) ≥95%.

Example J24: 5-Bromo-N-(5-chloro-2-hydroxy-3-(3-methoxypyrrolidine-1-carbonyl)phenyl)-2-hydroxybenzenesulfonamide

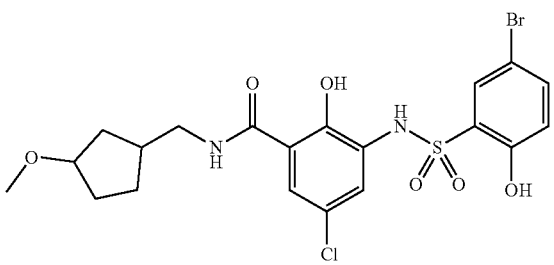 [SMILES: COC1CCC(CNC(=O)c2cc(Cl)cc(NS(=O)(=O)c3cc(Br)ccc3O)c2O)C1]

Using a procedure analogous to General Procedure 1, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 3-methoxypyrrolidine, the title compound was obtained as a colorless solid (16 mg, 63%). LCMS (Method A) $t_R$=1.55 min, m/z=504.7, 506.8 [M+H]$^+$; Purity (AUC) ≥95%.

Example J25: 3-((5-Bromo-2-hydroxyphenyl)sulfonamido)-5-chloro-2-hydroxy-N-((tetrahydrofuran-2-yl)methyl)benzamide

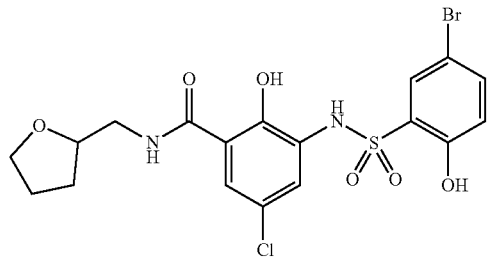 [SMILES: O=C(NCC1CCCO1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and (tetrahydrofuran-2-yl)methanamine, the title compound was obtained as a colorless solid (22 mg, 87%). $^1$H NMR (400 MHz, MeOH-d$_4$) $\delta_H$ 7.80 (d, J=2.5 Hz, 1H), 7.57-7.51 (m, 3H), 6.86 (d, J=8.8 Hz, 1H), 4.15-4.03 (m, 1H), 3.94-3.84 (m, 1H), 3.77 (q, J=7.3 Hz, 1H), 3.52-3.37 (m, 3H), 2.10-1.97 (m, 1H), 1.92 (dt, J=14.7, 7.4 Hz, 1H), 1.72-1.59 (m, 1H); LCMS (Method A) $t_R$=1.66 min, m/z=504.7, 506.8 [M+H]$^+$; Purity (AUC) ≥95%.

Example J26: (R)-3-((5-Bromo-2-hydroxyphenyl)sulfonamido)-5-chloro-2-hydroxy-N-((tetrahydrofuran-2-yl)methyl)benzamide

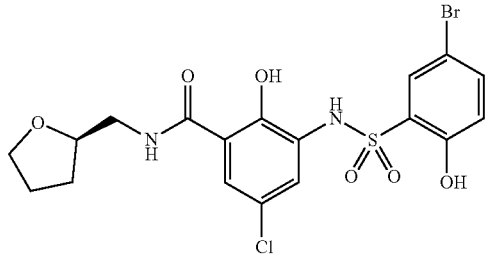 [SMILES: O=C(NC[C@H]1CCCO1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and (R)-(tetrahydrofuran-2-yl)methanamine, the title compound was obtained as a colorless solid (18 mg, 71%). LCMS (Method A) $t_R$=1.66 min, m/z=504.7, 506.8 [M+H]$^+$; Purity (AUC) ≥95%.

Example J27: (S)-3-((5-Bromo-2-hydroxyphenyl)sulfonamido)-5-chloro-2-hydroxy-N-((tetrahydrofuran-2-yl)methyl)benzamide

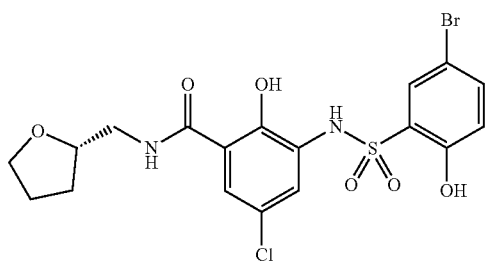 [SMILES: O=C(NC[C@@H]1CCCO1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and (S)-(tetrahydrofuran-2-yl)methanamine, the tide compound was obtained as a colorless solid (11 mg, 43%). LCMS (Method A) $t_R$=1.66 min, m/z=504.7, 506.8 [M+H]$^+$; Purity (AUC) ≥95%.

Example J28: (R)-5-Bromo-N-(5-chloro-2-hydroxy-3-(2-(methoxymethyl)pyrrolidine-1-carbonyl)phenyl)-2-hydroxybenzenesulfonamide

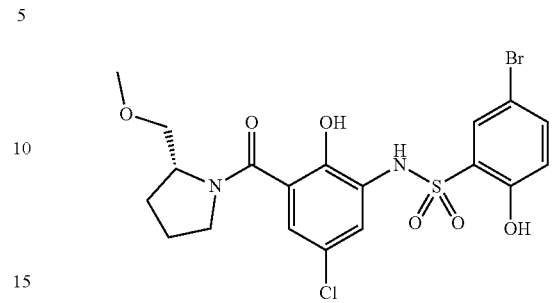

Using a procedure analogous to General Procedure 1, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and (R)-2-(methoxymethyl)pyrrolidine, the tide compound was obtained as a colorless solid (9 mg, 35%). LCMS (Method A) $t_R$=1.64 min, m/z=518.8, 520.8 [M+H]$^+$; Purity (AUC) ≥95%.

Example J29: (S)-5-Bromo-N-(5-chloro-2-hydroxy-3-(2-(methoxymethyl)pyrrolidine-1-carbonyl)phenyl)-2-hydroxybenzenesulfonamide

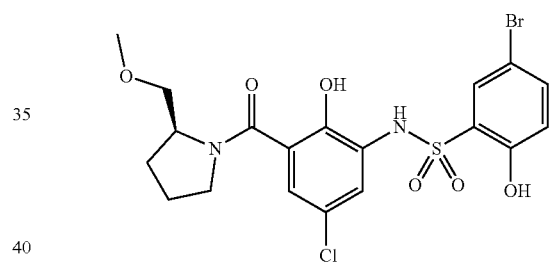

Using a procedure analogous to General Procedure 1, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and (S)-2-(methoxymethyl)pyrrolidine, the title compound was obtained as a colorless solid (15 mg, 58%). LCMS (Method A) $t_R$=1.64 min, m/z=518.8, 520.8 [M+H]$^+$; Purity (AUC) ≥95%.

Example J30: 5-Bromo-N-(5-chloro-2-hydroxy-3-(morpholine-4-carbonyl)phenyl)-2-hydroxybenzenesulfonamide

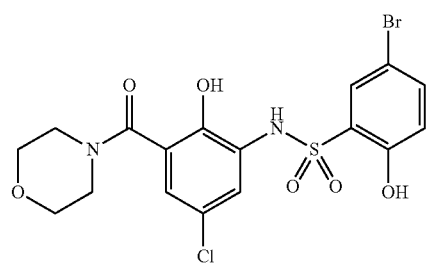 [SMILES: O=C(c1cc(Cl)cc(NS(=O)(=O)c2cc(Br)ccc2O)c1O)N1CCOCC1]

Using a procedure analogous to General Procedure I, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and morpholine, the title compound was obtained as a colorless solid (13 mg, 53%). $^1$H NMR (400 MHz, MeOH-d$_4$) δ$_H$ 7.72 (d, J=2.5 Hz, 1H), 7.57 (dd, J=8.7, 2.5 Hz, 1H), 7.29 (d, J=2.5 Hz, 1H), 7.03 (d, J=2.5 Hz, 1H), 6.91 (d, J=8.8 Hz, 1H), 3.67 (br s, 4H); LCMS (Method A) t$_R$=1.44 min, m/z=490.8, 492.7 [M+H]$^+$; Purity (AUC) ≥95%.

Example J31: 3-((5-Bromo-2-hydroxyphenyl)sulfonamido)-5-chloro-2-hydroxy-N-(pyridin-2-ylmethyl)benzamide

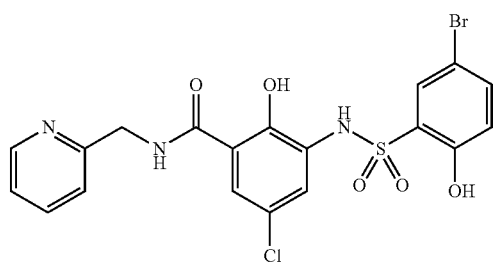 [SMILES: O=C(NCc1ccccn1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 2-picoloylamine, the title compound was obtained as a colorless solid (14 mg, 55%). LCMS (Method A) t$_R$=1.49 min, m/z=511.8, 513.7 [M+H]$^+$; Purity (AUC) ≥95%.

Example J32: 3-((5-Bromo-2-hydroxyphenyl)sulfonamido)-5-chloro-2-hydroxy-N-(pyrimidin-2-ylmethyl)benzamide

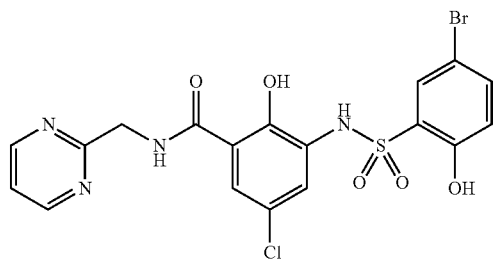 [SMILES: O=C(NCc1ncccn1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 2-pyrimidinmethanamine, the title compound was obtained as a colorless solid (8 mg, 31%). LCMS (Method A) t$_R$=1.50 min, m/z=512.7, 514.8 [M+H]$^+$; Purity (AUC) ≥95%.

Example J33: 3-((5-Bromo-2-hydroxyphenyl)sulfonamido)-5-chloro-2-hydroxy-N-(pyrimidin-5-ylmethyl)benzamide

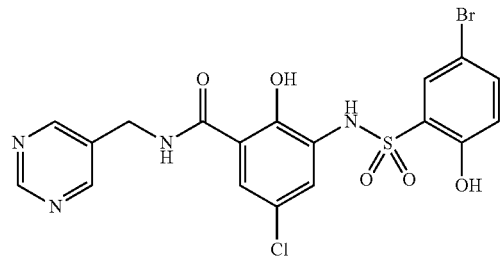 [SMILES: O=C(NCc1cncnc1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 5-pyrimidinmethanamine, the title compound was obtained as a colorless solid (7 mg, 27%). LCMS (Method A) t$_R$=1.50 min, m/z=512.7, 514.8 [M+H]$^+$; Purity (AUC) ≥95%.

Example J34: 3-((5-Bromo-2-hydroxyphenyl)sulfonamido)-5-chloro-N-(furan-2-ylmethyl)-2-hydroxybenzamide

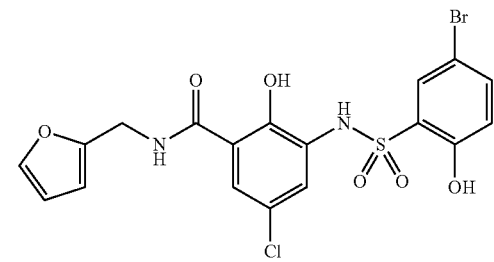 [SMILES: O=C(NCc1ccco1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and furfurylamine, the title compound was obtained as a colorless solid (15 mg, 60%). $^1$H NMR (400 MHz, MeOH-d$_4$) δ$_H$ 7.80 (d, J=2.5 Hz, 1H), 7.54 (s, 2H), 7.53 (dd, J=8.8, 2.5 Hz, 1H), 7.44 (dd, J=1.9, 0.8 Hz, 1H), 6.86 (d, J=8.8 Hz, 1H), 6.36 (dd, J=3.2, 1.9 Hz, 1H), 6.29 (dd, J=3.3, 0.9 Hz, 1H), 4.52 (s, 2H); LCMS (Method A) t$_R$=1.73 min, m/z=500.7, 502.8 [M+H]$^+$; Purity (AUC) ≥95%.

Example J35: 3-((5-Bromo-2-hydroxyphenyl)sulfonamido)-5-chloro-2-hydroxy-N-((6-oxo-1,6-dihydropyridin-3-yl)methyl)benzamide

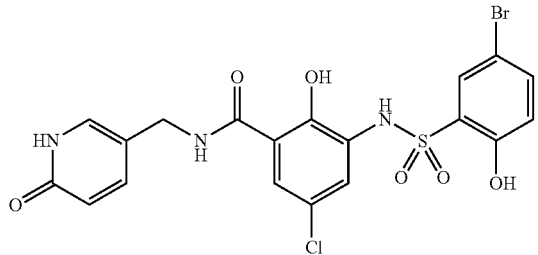 [SMILES: O=C(NCc1ccc(=O)[nH]c1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 5-aminomethyl-1H-pyridine-2-one, the title compound was obtained as a colorless solid (12 mg, 45%). $^1$H NMR (400 MHz, MeOH-d$_4$) $\delta_H$ 7.81 (d, J=2.5 Hz, 1H), 7.58 (s, 2H), 7.54 (dd, J=8.8, 2.5 Hz, 1H), 7.40 (dd, J=6.8, 0.8 Hz, 1H), 6.87 (d, J=8.8 Hz, 1H), 6.42 (dd, J=1.8, 0.8 Hz, 1H), 6.39 (dd, J=6.8, 1.8 Hz, 1H), 4.44 (d, J=1.2 Hz, 2H); LCMS (Method A) t$_R$=1.42 min, m/z=527.7, 539.7 [M+H]$^+$; Purity (AUC) ≥95%.

Example J36: 3-((5-Bromo-2-hydroxyphenyl)sulfonamido)-5-chloro-2-hydroxy-N-((2-oxo-1,2-dihydropyridin-4-yl)methyl)benzamide

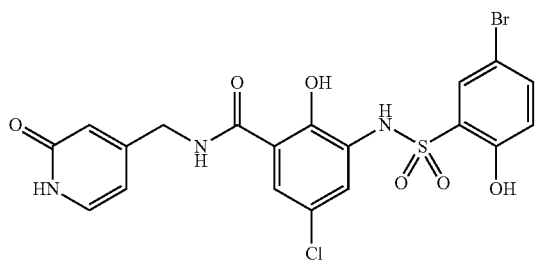 [SMILES: O=C(NCc1cc[nH]c(=O)c1)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and 4-aminomethyl-1H-pyridine-2-one, the title compound was obtained as a colorless solid (14 mg, 53%). $^1$H NMR (400 MHz, MeOH-d$_4$) $\delta_H$ 7.80 (d, J=2.5 Hz, 1H), 7.63 (dd, J=9.4, 2.6 Hz, 1H), 7.55-7.49 (m, 3H), 7.43 (d, J=2.6 Hz, 1H), 6.86 (d, J=8.8 Hz, 1H), 6.54 (d, J=9.4 Hz, 1H), 4.32 (s, 2H); LCMS (Method A) t$_R$=1.42 min, m/z=527.7, 539.7 [M+H]$^+$; Purity (AUC) ≥95%.

Example J37: 3-((5-Bromo-2-hydroxyphenyl)sulfonamido)-5-chloro-2-hydroxy-N-methyl-N-((tetrahydrofuran-2-yl)methyl)benzamide

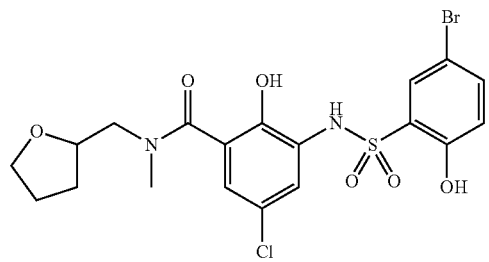 [SMILES: CN(CC1CCCO1)C(=O)c1cc(Cl)cc(NS(=O)(=O)c2cc(Br)ccc2O)c1O]

Using a procedure analogous to General Procedure H, starting with methyl 3-((5-bromo-2-hydroxyphenyl)sulfonamido)-5-chloro-2-hydroxybenzoate (22 mg, 0.05 mmol), which was prepared by a procedure analogous to the procedure used to prepare Example J1 Step B, and N-methyl-1-(tetrahydrofuran-2-yl)methanamine, the title compound was obtained as a colorless solid (13 mg, 50%). LCMS (Method A) t$_R$=1.48 min, m/z=518.8, 520.8 [M+H]$^+$; Purity (AUC) ≥95%.

Example J38: 3-((5-Bromo-2-hydroxyphenyl)sulfonamido)-5-chloro-N-(3,3-difluorocyclobutyl)-2-hydroxybenzamide

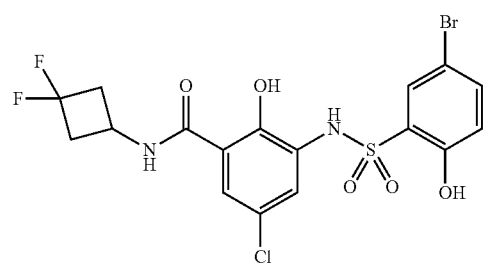 [SMILES: O=C(NC1CC(F)(F)C1)c1cc(Cl)cc(NS(=O)(=O)c2cc(Br)ccc2O)c1O]

Using a procedure analogous to General Procedure I, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 3,3-difluorocyclobutylamine hydrochloride, the title compound was obtained as a colorless solid (12 mg, 47/c). $^1$H NMR (400 MHz, DMSO-d$_6$) $\delta_H$ 7.80 (d, J=2.5 Hz, 1H), 7.59 (d, J=2.4 Hz, 1H), 7.56 (d, J=2.4 Hz, 1H), 7.53 (dd, J=8.8, 2.5 Hz, 1H), 6.86 (d, J=8.8 Hz, 1H), 4.39-4.25 (m, 1H), 3.04-2.89 (m, 2H), 2.82-2.63 (m, 1H); $^{19}$F NMR (376 MHz, MeOH-d$_4$) $\delta_F$ −85.44 (d, J=199.0 Hz, 1F), −100.59 (d, J=199.0 Hz, 1F); LCMS (Method A) t$_R$=1.75 min, m/z=510.7, 512.7 [M+H]$^+$; Purity (AUC) ≥95%.

Example J39: 3-((5-Bromo-2-hydroxyphenyl)sulfonamido)-5-chloro-N-(2,2-difluoroethyl)-2-hydroxybenzamide

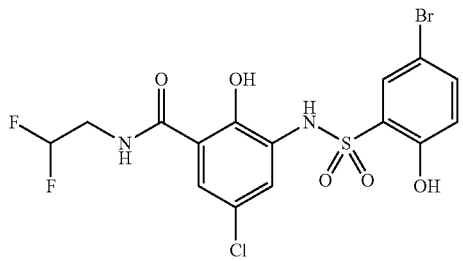 [SMILES: O=C(NCC(F)F)c1cc(Cl)cc(NS(=O)(=O)c2cc(Br)ccc2O)c1O]

Using a procedure analogous to General Procedure I, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J1 Step C, and 2,2-difluoroethanamine hydrochloride, the title compound was obtained as a colorless solid (15 mg, 60%). $^1$H NMR (400 MHz, MeOH-d$_4$) $\delta_H$ 7.81 (d, J=2.5 Hz, 1H), 7.56-7.51 (m, 3H), 6.86 (d, J=8.8 Hz, 1H), 5.99 (tt, J=56.1, 4.1 Hz, 1H), 3.72 (td, J=14.7, 4.1 Hz, 2H); $^{19}$F NMR (376 MHz, MeOH-d$_4$) $\delta_F$ −124.2; LCMS (Method A) $t_R$=1.64 min, m/z=486.7 [M+H]$^+$; Purity (AUC) ≥95%.

Example HCH-25: 3-((5-Bromo-3-chloro-2-hydroxyphenyl)sulfonamido)-5-chloro-2-hydroxybenzamide (HCH-3-81)

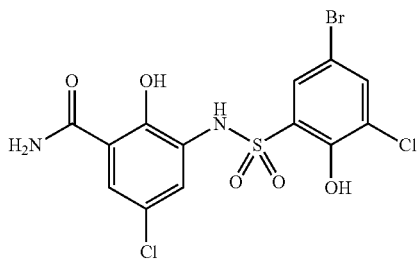 [SMILES: NC(=O)c1cc(Cl)cc(NS(=O)(=O)c2cc(Br)cc(Cl)c2O)c1O]

Using a procedure analogous to General Procedure K, starting with methyl 3-((5-bromo-3-chloro-2-hydroxyphenyl)sulfonamido)-5-chloro-2-hydroxybenzoate (10.6 mg, 0.02 mmol), which was prepared utilizing a procedure analogous to the procedure used to prepare which was prepared by a procedure analogous to the procedure used to prepare Example HCH-4 Step E, the title compound was prepared as a solid (8.2 mg, 0.02 mmol, 79%). LCMS (Method A) $t_R$=1.76 min, m/z=472.1 [M+H]$^+$; Purity (AUC) ≥95%.

Example J40: 3-((5-Bromo-3-chloro-2-hydroxyphenyl)sulfonamido)-5-chloro-2-hydroxy-N-methylbenzamide

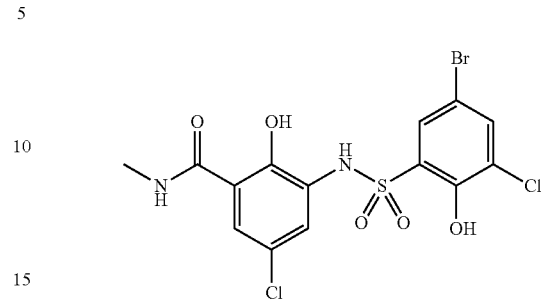

Using a procedure analogous to General Procedure I, 3-((5-bromo-3-chloro-2-hydroxyphenyl)sulfonamido)-5-chloro-2-hydroxybenzoic acid (23 mg, 0.05 mmol), which was prepared by a procedure analogous to the procedure used to prepare Example J4 Step C, and methylamine, the title compound was obtained as a colorless solid (5 mg, 21%). LCMS (Method A) $t_R$=1.69 min, m/z=470.7 [M+H]$^+$; Purity (AUC) ≥95%.

Example J41: 3-((5-Bromo-3-chloro-2-hydroxyphenyl)sulfonamido)-5-chloro-2-hydroxy-N-(2-hydroxyethyl)benzamide

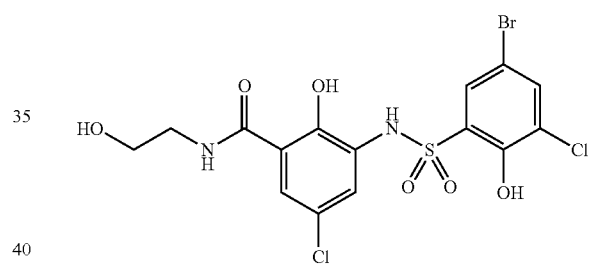

Using a procedure analogous to General Procedure I, 3-((5-bromo-3-chloro-2-hydroxyphenyl)sulfonamido)-5-chloro-2-hydroxybenzoic acid (23 mg, 0.05 mmol), which was prepared by a procedure analogous to the procedure used to prepare Example J4 Step C, and ethanolamine, the title compound was obtained as a colorless solid (5 mg, 20%). LCMS (Method A) $t_R$=1.54 min, m/z=500.7 [M+H]$^+$; Purity (AUC) ≥95%.

Example J42: 3-((5-Bromo-3-chloro-2-hydroxyphenyl)sulfonamido)-5-chloro-2-hydroxy-N-(2-methoxyethyl)benzamide

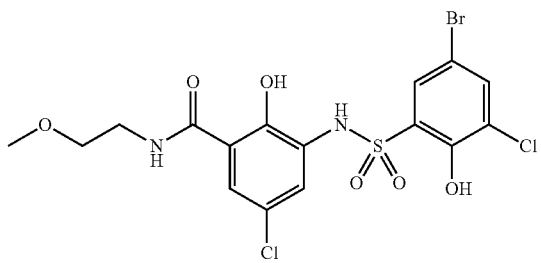 [SMILES: COCCNC(=O)c1cc(Cl)cc(NS(=O)(=O)c2cc(Br)cc(Cl)c2O)c1O]

Using a procedure analogous to General Procedure I, 3-((5-bromo-3-chloro-2-hydroxyphenyl)sulfonamido)-5-chloro-2-hydroxybenzoic acid (23 mg, 0.05 mmol), which was prepared by a procedure analogous to the procedure used to prepare Example J4 Step C, and 2-methoxyethylamine, the title compound was obtained as a colorless solid (8 mg, 31%). LCMS (Method A) $t_R$=1.72 min, m/z=514.6 [M+H]$^+$; Purity (AUC) ≥95%.

Example J43: 3-((5-Bromo-2-methoxyphenyl)sulfonamido)-5-chloro-2-hydroxybenzamide

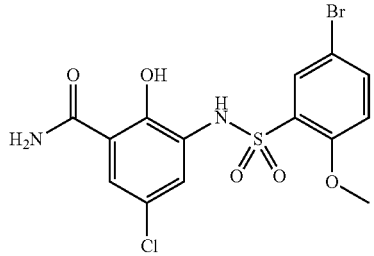 [SMILES: COc1ccc(Br)cc1S(=O)(=O)Nc1cc(Cl)cc(C(N)=O)c1O]

A sealed tube containing a mixture of methyl 3-((5-bromo-2-methoxyphenyl)sulfonamido)-5-chloro-2-hydroxybenzoate (45 mg, 0.10 mmol), which was prepared by a procedure analogous to the procedure used to prepare Example J2 Step A, and 1 mL of a 7 N solution of NH$_3$ in MeOH was heated at reflux for 16 h. Upon cooling, the mixture was concentrated and purified by flash column chromatography to afford the title compound as a colorless solid (42 mg, 96%). $^1$H NMR (400 MHz, DMSO-d$_6$) δ$_H$ 9.44 (s, 1H), 8.59 (s, 1H), 8.20 (s, 1H), 7.83-7.73 (m, 3H), 7.39 (d, J=2.4 Hz, 1H), 7.22-7.15 (m, 1H), 3.77 (s, 3H); LCMS (Method A) $t_R$=1.51 min, m/z=435.0, 436.9 [M+H]$^+$; Purity (AUC) ≥95%.

Example J44: 3-((5-Bromo-2-methoxyphenyl)sulfonamido)-5-chloro-2-hydroxy-N-methylbenzamide

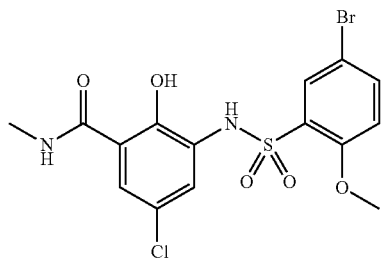

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and a 2.0 M solution of methylamine in THF, the title compound was obtained as a colorless solid (7 mg, 32%). $^1$H NMR (400 MHz, DMSO-d$_6$) δ$_H$ 9.45 (s, 1H), 9.06 (s, 1H), 7.81-7.71 (m, 3H), 7.38 (s, 1H), 7.17 (d, J=9.5 Hz, 1H), 3.77 (s, 3H), 2.78 (d, J=4.4 Hz, 3H); LCMS (Method A) $t_R$=1.58 min, m/z=449.0, 451.0 [M+H]$^+$; Purity (AUC) ≥95%.

Example J45: 3-((5-Bromo-2-methoxyphenyl)sulfonamido)-5-chloro-2-hydroxy-N-(2-methoxyethyl)benzamide

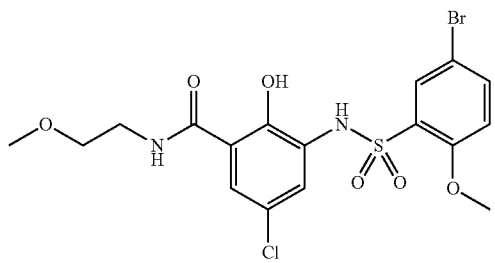

Using a procedure analogous to General Procedure J, starting with 3-((5-bromo-2-methoxyphenyl)sulfonamido)-5-chloro-2-hydroxybenzoic acid (44 mg, 0.10 mmol), which was prepared by a procedure analogous to the procedure used to prepare Example J2 Step B, and 2-methoxyethylamine, the title compound was obtained as a colorless solid (41 mg, 83%). $^1$H NMR (400 MHz, DMSO-d$_6$) δ$_H$ 9.46 (s, 1H), 9.12 (s, 1H), 7.87-7.77 (m, 2H), 7.76 (d, J=2.2 Hz, 1H), 7.38 (s, 1H), 7.18 (d, J=9.3 Hz, 1H), 3.77 (s, 3H), 3.49-3.38 (m, 4H), 3.25 (s, 3H); LCMS (Method A) $t_R$=1.63 min, m/z=493.0, 495.0 [M+H]$^+$; Purity (AUC) ≥95%.

Example J46: 3-((5-Bromo-2-methoxyphenyl)sulfonamido)-N-butyl-5-chloro-2-hydroxybenzamide

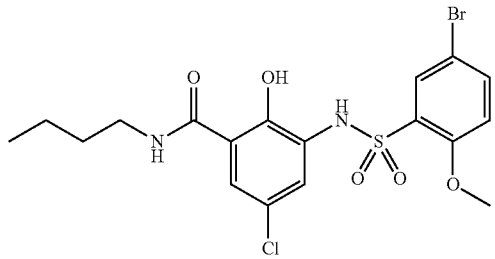 [SMILES: CCCCNC(=O)c1cc(Cl)cc(NS(=O)(=O)c2cc(Br)ccc2OC)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and n-butylamine, the title compound was obtained as a colorless solid (19 mg, 76%). $^1$H NMR (400 MHz, DMSO-d$_6$) δ$_H$ 9.44 (s, 1H), 9.02 (s, 1H), 7.83-7.74 (m, 3H), 7.38 (d, J=2.4 Hz, 1H), 7.18 (d, J=9.6 Hz, 1H), 3.77 (s, 3H), 3.25 (q, J=6.7 Hz, 2H), 1.50 (pent, J=7.2 Hz, 2H), 1.30 (sxt, J=7.4 Hz, 2H), 0.88 (t, J=7.3 Hz, 3H); LCMS (Method A) $t_R$=1.86 min, m/z=491.1, 493.0 [M+H]$^+$; Purity (AUC) ≥95%.

Example J47: N-Benzyl-3-((5-bromo-2-methoxyphenyl)sulfonamido)-5-chloro-2-hydroxybenzamide

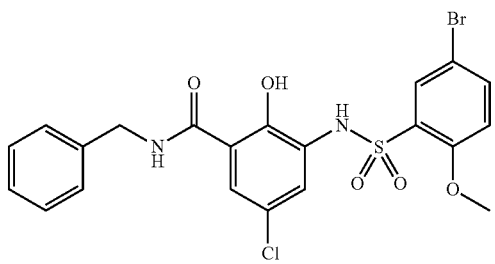 [SMILES: COc1ccc(Br)cc1S(=O)(=O)Nc1cc(Cl)cc(C(=O)NCc2ccccc2)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and benzylamine, the title compound was obtained as a colorless solid (15 mg, 56%). $^1$H NMR (400 MHz, DMSO-d$_6$) $\delta_H$ 9.61 (s, 1H), 9.48 (s, 1H), 7.86 (s, 1H), 7.77 (dt, J=3.8, 2.1 Hz, 2H), 7.43-7.23 (m, 5H), 7.17 (d, J=9.5 Hz, 1H), 4.47 (d, J=5.8 Hz, 2H), 3.77 (s, 3H); LCMS (Method A) $t_R$=1.84 min, m/z=525.0, 527.1 [M+H]$^+$; Purity (AUC) ≥95%.

Example J48: 5-Bromo-N-(5-chloro-2-hydroxy-3-(morpholine-4-carbonyl)phenyl)-2-methoxybenzenesulfonamide

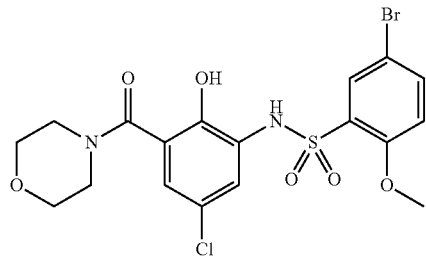 [SMILES: COc1ccc(Br)cc1S(=O)(=O)Nc1cc(Cl)cc(C(=O)N2CCOCC2)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and morpholine, the title compound was obtained as a colorless solid (15 mg, 58%). $^1$H NMR (400 MHz, DMSO-d$_6$) $\delta_H$ 9.64 (s, 1H), 9.32 (s, 1H), 7.79 (dd, J=8.9, 2.6 Hz, 1H), 7.67 (d, J=2.5 Hz, 1H), 7.21 (d, J=8.9 Hz, 1H), 7.17 (d, J=2.6 Hz, 1H), 6.99 (d, J=2.6 Hz, 1H), 3.84 (s, 3H), 3.74-3.40 (m, 8H); LCMS (Method A) $t_R$=1.43 min, m/z=505.0, 507.0 [M+H]$^+$; Purity (AUC) ≥95%.

Example J49: 3-((5-Bromo-2-methoxyphenyl)sulfonamido)-5-chloro-2-hydroxy-N-phenethylbenzamide

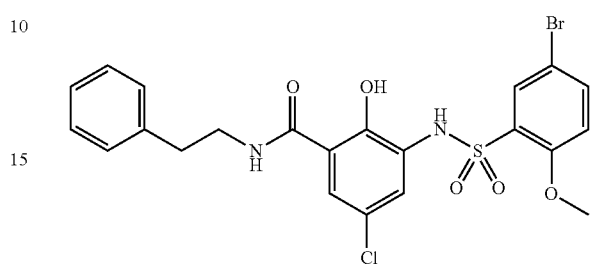

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and phenethylamine, the title compound was obtained as a colorless solid (22 mg, 82%). $^1$H NMR (400 MHz, DMSO-d$_6$) $\delta_H$ 9.46 (s, 1H), 9.15 (s, 1H), 7.77 (d, J=7.8 Hz, 3H), 7.38 (s, 1H), 7.32-7.25 (m, 2H), 7.24-7.15 (m, 4H), 3.74 (s, 3H), 3.49 (q, J=6.8 Hz, 2H), 2.84 (t, J=7.4 Hz, 2H); LCMS (Method A) $t_R$=1.88 min, m/z=539.1, 541.0 [M+H]$^+$; Purity (AUC) ≥95%.

Example J50: 3-((5-Bromo-2-methoxyphenyl)sulfonamido)-5-chloro-2-hydroxy-N,N-dimethylbenzamide

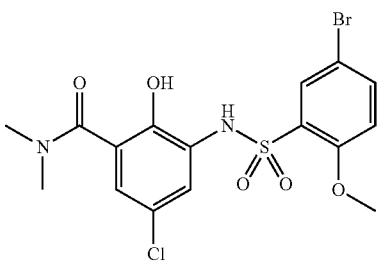

A sealed tube containing a mixture of methyl 3-((5-bromo-2-methoxyphenyl)sulfonamido)-5-chloro-2-hydroxybenzoate (23 mg, 0.05 mmol), which was prepared by a procedure analogous to the procedure used to prepare Example J2 Step A, and 1 mL of a 2 M solution of dimethylamine in THF was heated at reflux for 16 h. Upon cooling, the mixture was concentrated and purified by flash column chromatography to afford the title compound as a pale brown oily solid (15 mg, 64%). $^1$H NMR (400 MHz, DMSO-d$_6$) $\delta_H$ 7.80 (d, J=2.5 Hz, 1H), 7.69 (dd, J=8.8, 2.6 Hz, 1H), 7.28 (d, J=2.6 Hz, 1H), 7.12 (d, J=8.9 Hz, 1H), 6.98 (d, J=2.6 Hz, 1H), 3.95 (s, 3H), 2.92 (s, 6H); LCMS (Method A) $t_R$=1.48 min, m/z=463.0, 465.0 [M+H]$^+$; Purity (AUC) ≥95%.

Example J51: 3-((5-Bromo-2-methoxyphenyl)sulfonamido)-5-chloro-2-hydroxy-N-(3-methoxypropyl)benzamide

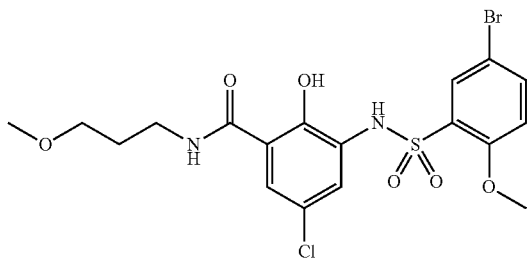

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-methoxypropylamine, the title compound was obtained as a colorless solid (12 mg, 47%). LCMS (Method A) $t_R$=1.68 min, m/z=506.9, 508.9 [M+H]$^+$; Purity (AUC) ≥95%.

Example J52: 3-((5-Bromo-2-methoxyphenyl)sulfonamido)-5-chloro-2-hydroxy-N-(tetrahydro-2H-pyran-4-yl)benzamide

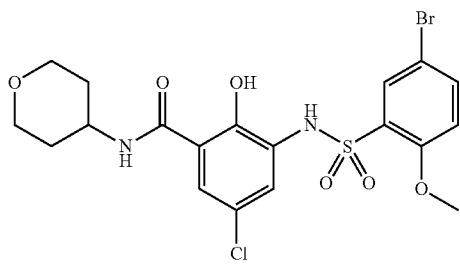 [SMILES: COc1ccc(Br)cc1S(=O)(=O)Nc1cc(Cl)cc(C(=O)NC2CCOCC2)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 4-aminotetrahydropyran hydrochloride, the title compound was obtained as a colorless solid (8 mg, 31%). LCMS (Method A) $t_R$=1.63 min, m/z=518.8, 520.8 [M+H]$^+$; Purity (AUC) ≥95%.

Example J53: 3-((5-Bromo-2-methoxyphenyl)sulfonamido)-5-chloro-2-hydroxy-N-(3-hydroxypropyl)benzamide

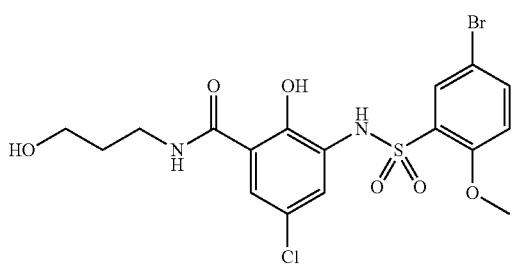 [SMILES: COc1ccc(Br)cc1S(=O)(=O)Nc1cc(Cl)cc(C(=O)NCCCO)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-aminopropanol, the title compound was obtained as a colorless solid (5 mg, 21%). LCMS (Method A) $t_R$=1.48 min, m/z=492.9, 494.8 [M+H]$^+$; Purity (AUC) ≥95%.

Example J54: (S)-5-Bromo-N-(5-chloro-2-hydroxy-3-(2-(hydroxymethyl)pyrrolidine-1-carbonyl)phenyl)-2-methoxybenzenesulfonamide

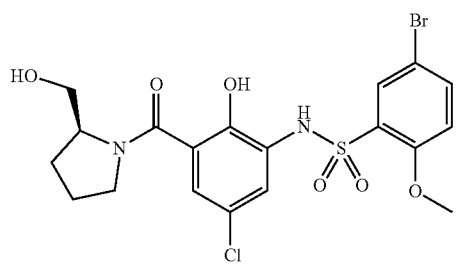 [SMILES: COc1ccc(Br)cc1S(=O)(=O)Nc1cc(Cl)cc(C(=O)N2CCC[C@H]2CO)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and (S)-Prolinol, the title compound was obtained as a colorless solid (11 mg, 41%). LCMS (Method A) $t_R$=1.45 min, m/z=518.8, 520.9 [M+H]$^+$; Purity (AUC) ≥95%.

Example J55: (R)-5-Bromo-N-(5-chloro-2-hydroxy-3-(2-(hydroxymethyl)pyrrolidine-1-carbonyl)phenyl)-2-methoxybenzenesulfonamide

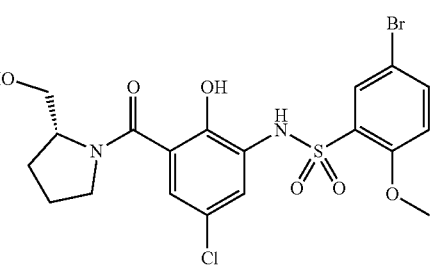

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and (R)-Prolinol, the title compound was obtained as a colorless solid (15 mg, 58%). LCMS (Method A) $t_R$=1.45 min, m/z=518.9, 520.9 [M+H]$^+$; Purity (AUC) ≥95%.

Example J56: (S)-5-Bromo-N-(5-chloro-2-hydroxy-3-(2-(methoxymethyl)pyrrolidine-1-carbonyl)phenyl)-2-methoxybenzenesulfonamide

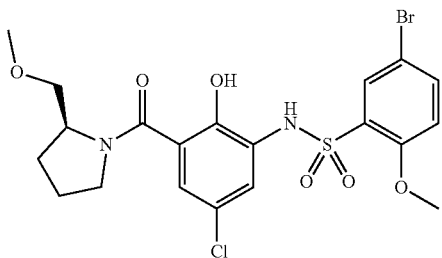

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and (S)-Prolinol methyl ether, the title compound was obtained as a colorless solid (19 mg, 71%). LCMS (Method A) $t_R$=1.63 min, m/z=532.9, 534.9 [M+H]$^+$; Purity (AUC) ≥95%.

Example J57: (R)-5-Bromo-N-(5-chloro-2-hydroxy-3-(2-(methoxymethyl)pyrrolidine-1-carbonyl)phenyl)-2-methoxybenzenesulfonamide

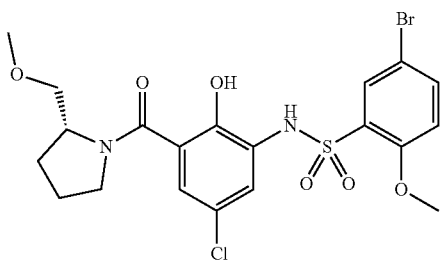

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and (R)-Prolinol methyl ether, the title compound was obtained as a colorless solid (21 mg, 78%). LCMS (Method A) $t_R$=1.63 min, m/z=532.9, 534.9 [M+H]$^+$; Purity (AUC) ≥95%.

Example J58: 3-((5-Bromo-2-methoxyphenyl)sulfonamido)-5-chloro-2-hydroxy-N-(2-methoxyethyl)-N-methylbenzamide

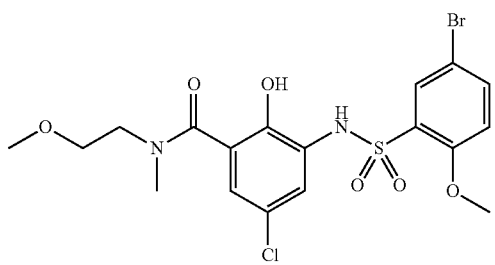

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and (2-methoxymethyl) methyl amine, the title compound was obtained as a colorless solid (17 mg, 68%). LCMS (Method A) $t_R$=1.48 min, m/z=506.9, 508.9 [M+H]$^+$; Purity (AUC) ≥95%.

Example J59: 3-((5-Bromo-2-methoxyphenyl)sulfonamido)-5-chloro-2-hydroxy-N-(2-hydroxyethyl)benzamide

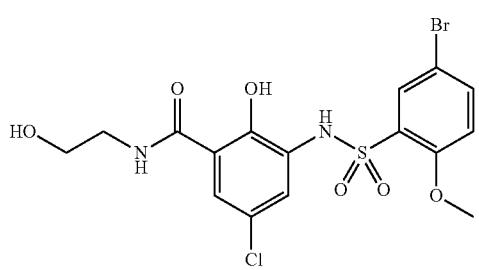 [SMILES: COc1ccc(Br)cc1S(=O)(=O)Nc1cc(Cl)cc(C(=O)NCCO)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and ethanolamine, the title compound was obtained as a colorless solid (12 mg, 52%). LCMS (Method A) $t_R$=1.44 min, m/z=478.9, 480.9 [M+H]$^+$; Purity (AUC) ≥95%.

Example J60: 3-((5-Bromo-2-methoxyphenyl)sulfonamido)-5-chloro-2-hydroxy-N-(tetrahydrofuran-3-yl)benzamide

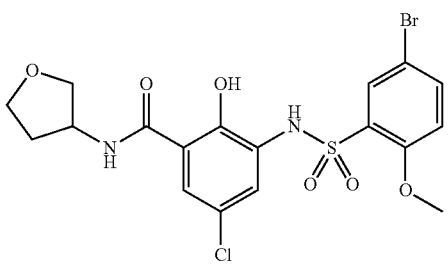 [SMILES: COc1ccc(Br)cc1S(=O)(=O)Nc1cc(Cl)cc(C(=O)NC2CCOC2)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-aminotetrahydrofuran, the title compound was obtained as a colorless solid (18 mg, 73%). LCMS (Method A) $t_R$=1.60 min, m z=504.9, 506.8 [M+H]$^+$; Purity (AUC) ≥95%.

Example J61: N-(2-Aminoethyl)-3-((5-bromo-2-methoxyphenyl)sulfonamido)-5-chloro-2-hydroxybenzamide

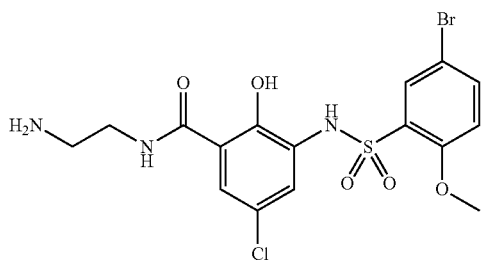 [SMILES: COc1ccc(Br)cc1S(=O)(=O)Nc1cc(Cl)cc(C(=O)NCCN)c1O]

Step A: tert-Butyl (2-(3-((5-bromo-2-methoxyphenyl)sulfonamido)-5-chloro-2-hydroxybenzamido)ethyl)carbamate. Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and N-Boc-1,2-diaminoethane, tert-butyl (2-(3-((5-bromo-2-methoxyphenyl)sulfonamido)-5-chloro-2-hydroxybenzamido)ethyl)carbamate was obtained as a brown oil (50 mg, 43%).

Step B: N-(2-Aminoethyl)-3-((5-bromo-2-methoxyphenyl)sulfonamido)-5-chloro-2-hydroxybenzamide. tert-Butyl (2-(3-((5-bromo-2-methoxyphenyl)sulfonamido)-5-chloro-2-hydroxybenzamido)ethyl)carbamate (50 mg, 0.09 mmol) which was prepared by a procedure analogous to the procedure used to prepare Example J62 Step A was dissolved in $CH_2Cl_2$ (1 mL) and stirred with TFA (1 mL) for 1 h at r.t. The mixture was washed with saturated aqueous $NaHCO_3$ and the organic extracts purified by SCX-chromatography (eluting with a 1 N solution of $NH_3$ in MeOH), the title compound was obtained as a colorless solid (38 mg, 0.08 mmol, 93%). $^1$H NMR (400 MHz, DMSO-$d_6$) $\delta_H$ 7.82 (d, J=2.6 Hz, 1H), 7.74 (dd, J=8.9, 2.6 Hz, 1H), 7.22 (d, J=3.0 Hz, 1H), 7.17 (d, J=8.9 Hz, 1H), 7.00 (d, J=3.0 Hz, 1H), 3.88 (s, 3H), 3.46 (q, J=5.9 Hz, 2H), 2.92 (t, J=6.1 Hz, 2H); LCMS (Method A) $t_R$=1.25 min, m/z=477.8, 479.8 [M+H]$^+$; Purity (AUC) ≥95%.

Example J62: 5-Bromo-N-(5-chloro-2-hydroxy-3-(3-methoxyazetidine-1-carbonyl)phenyl)-2-methoxybenzenesulfonamide

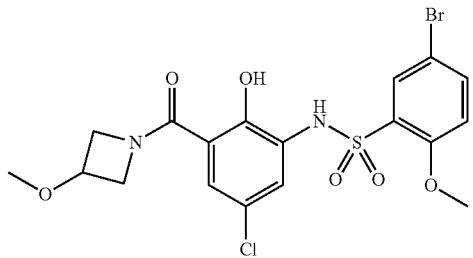

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-methoxyazetidine hydrochloride, the title compound was obtained as a colorless solid (47 mg, 46%). LCMS (Method A) $t_R$=1.67 min, m/z=504.8, 506.8 [M+H]$^+$; Purity (AUC) ≥95%.

Example J63: 5-Bromo-N-(5-chloro-2-hydroxy-3-(3-hydroxyazetidine-1-carbonyl)phenyl)-2-methoxybenzenesulfonamide

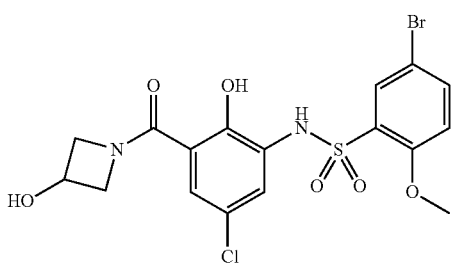 [SMILES: COc1ccc(Br)cc1S(=O)(=O)Nc1cc(Cl)cc(C(=O)N2CC(O)C2)c1O]

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-hydroxyazetidine hydrochloride, the title compound was obtained as a colorless solid (45 mg, 46%). $^1$H NMR (400 MHz, MeOH-$d_4$) $\delta_H$ 7.87 (d, J=2.5 Hz, 1H), 7.70 (dd, J=8.8, 2.5 Hz, 1H), 7.54 (d, J=2.5 Hz, 1H), 7.18 (d, J=2.5 Hz, 1H), 7.11 (d, J=8.8 Hz, 1H), 4.62 (t, J=4.7 Hz, 1H), 3.47-3.38 (m, 1H), 3.28-3.22 (m, 1H), 2.11-1.97 (m, 2H); LCMS (Method A) $t_R$=1.50 min, m/z=490.8, 492.7 [M+H]$^+$; Purity >90%.

Example J64: 5-Bromo-N-(5-chloro-2-hydroxy-3-(3-(methylsulfonyl)azetidine-1-carbonyl)phenyl)-2-methoxybenzenesulfonamide

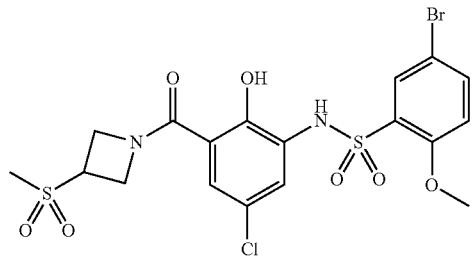

Using a procedure analogous to General Procedure J, starting with 3-((5-bromo-2-methoxyphenyl)sulfonamido)-5-chloro-2-hydroxybenzoic acid (22 mg, 0.05 mmol), which was prepared by a procedure analogous to the procedure used to prepare Example J2 Step B, and 3-(methylsulfonyl)azetidine, the title compound was obtained as a colorless solid (7 mg, 25%). $^1$H NMR (400 MHz, MeOH-$d_4$) $\delta_H$ 7.87 (d, J=2.5 Hz, 1H), 7.69 (dd, J=8.9, 2.5 Hz, 1H), 7.56 (d, J=2.4 Hz, 1H), 7.18 (d, J=2.4 Hz, 1H), 7.10 (d, J=8.9 Hz, 1H), 4.91-4.83 (m, 4H), 4.32 (td, J=8.5, 4.2 Hz, 1H), 3.91 (s, 3H), 3.02 (s, 3H); LCMS (Method A) $t_R$=1.52 min, m/z=552.7, 554.7 [M+H]$^+$; Purity (AUC) ≥95%.

Example J65: 3-((5-Bromo-2-methoxyphenyl)sulfonamido)-5-chloro-2-hydroxy-N-((tetrahydrofuran-2-yl)methyl)benzamide

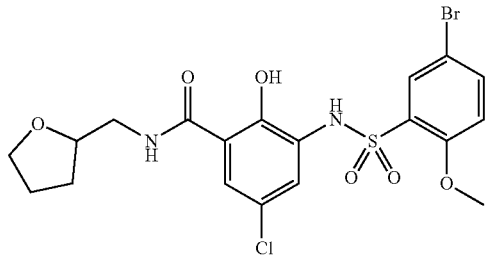 [SMILES: COc1ccc(Br)cc1S(=O)(=O)Nc1cc(Cl)cc(C(=O)NCC2CCCO2)c1O]

Using a procedure analogous to General Procedure H, starting with methyl 3-((5-bromo-2-methoxyphenyl)sulfonamido)-5-chloro-2-hydroxybenzoate (23 mg, 0.05 mmol), which was prepared by a procedure analogous to the procedure used to prepare Example J2 Step A, and tetrahydrofurylamine, the title compound was obtained as a colorless solid solid (23 mg, 88%). $^1$H NMR (400 MHz, MeOH-d$_4$) $\delta_H$ 7.88 (d, J=2.5 Hz, 1H), 7.69 (dd, J=8.8, 2.5 Hz, 1H), 7.56 (d, J=2.4 Hz, 1H), 7.54 (d, J=2.5 Hz, 1H), 7.10 (d, J=8.9 Hz, 1H), 4.13-4.04 (m, 1H), 3.91 (s, 3H), 3.92-3.85 (m, 1H), 3.77 (td, J=7.8, 6.4 Hz, 1H), 3.42 (qd, J=13.7, 5.9 Hz, 2H), 2.09-1.98 (m, 1H), 1.98-1.86 (m, 2H), 1.70-1.59 (m, 1H); LCMS (Method A) $t_R$=1.79 min, m/z=518.8, 520.8 [M+H]$^+$; Purity (AUC) ≥95%.

Example J66: 3-((5-Bromo-2-hydroxyphenyl)sulfonamido)-5-chlorobenzoic acid

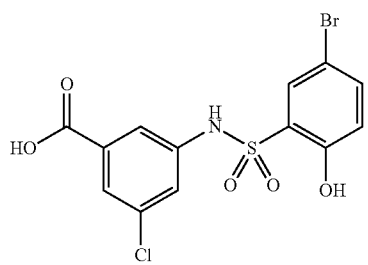 [SMILES: O=C(O)c1cc(Cl)cc(NS(=O)(=O)c2cc(Br)ccc2O)c1]

Using a procedure analogous to General Procedure E. starting with methyl 3-amino-5-chlorobenzoate (143 mg, 0.5 mmol) and 5-bromo-2-hydroxybenzenesulfonyl chloride, methyl 3-((5-bromo-2-hydroxyphenyl)sulfonamido)-5-chlorobenzoate was obtained. Without purification, methyl 3-((5-bromo-2-hydroxyphenyl)sulfonamido)-5-chlorobenzoate was hydrolyzed following General Procedure F, the title compound was obtained as a colorless solid (86 mg, 0.21 mmol, 42% over two steps). LCMS (Method A) $t_R$=1.31 min, m/z=427.8, 429.7 [M+Na]$^+$; Purity (AUC) ≥95%.

Example J67: 3-((5-Bromo-2-hydroxyphenyl)sulfonamido)-5-chloro-N-(1H-1,2,4-triazol-3-yl)benzamide [JRA-02-076]

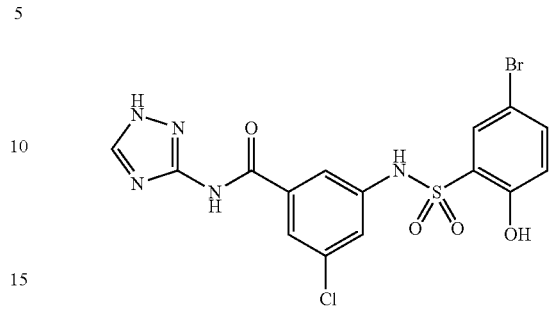

Using a procedure analogous to General Procedure 1, starting with 3-((5-bromo-2-hydroxyphenyl)sulfonamido)-5-chloro-2-hydroxybenzoic acid (21 mg, 0.05 mmol), which was prepared by a procedure analogous to the procedure used to prepare Example J66, and 1H-1,2,4-triazol-3-amine, to afford the title compound as a colorless solid. LCMS (Method A) $t_R$=1.54 min, m/z=474.1 [M+H]$^+$; Purity (AUC) ≥95%.

Example HCH-1: (3-((5-Bromo-2-hydroxyphenyl)sulfonamido)-2-hydroxy-5-(trifluoromethoxy)benzoyl)glycine (HCH-4-137-F76)

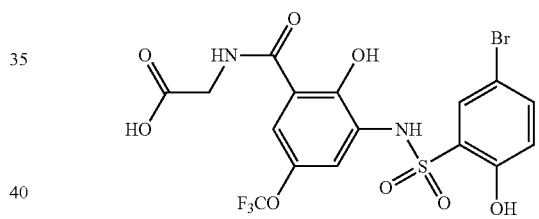

Step A. Methyl 2-hydroxy-5-(trifluoromethoxy)benzoate (HCH-3-39). To a round bottom flask containing a magnetic stir bar was added 2-hydroxy-5-(trifluoromethoxy)benzoic acid (2000.0 mg, 9.00 mmol), followed by CH$_2$Cl$_2$ (30.0 mL)/MeOH (30.0 mL). Using an ice bath, the mixture was cooled to 0° C. while stirring. To this reaction mixture was added EDCI (2590.0 mg, 13.5 mmol, 1.5 eq), followed by DMAP (220.0 mg, 1.80 mmol, 0.2 eq). The reaction temperature was allowed to increase up to room temperature while stirring overnight. Upon completion by LCMS analysis, the reaction mixture was concentrated under reduced pressure. The reaction mixture was partitioned between CH$_2$Cl$_2$ (30.0 mL) and H$_2$O (20.0 mL). The product was extracted with CH$_2$Cl$_2$ (3×30.0 mL) and the combined organics were dried over Na$_2$SO$_4$, filtered, and concentrated under reduced pressure. Purification by ISCO flash chromatography (0-100% EtOAc in hexanes) afforded methyl 2-hydroxy-5-(trifluoromethoxy)benzoate (1356.1 mg, 5.74 mmol, 63%). LCMS (Method A) $t_R$=1.62 min, m/z=237.2 [M+H]$^+$.

Step B. Methyl 2-hydroxy-3-nitro-5-(trifluoromethoxy)benzoate (HCH-3-43). To a reaction vial containing a magnetic stir bar was added methyl 2-hydroxy-5-(trifluoromethoxy)benzoate (1356.0 mg, 5.74 mmol), followed by CH$_2$Cl$_2$ (30.0 mL). The mixture was cooled −20° C. while stirring. To this mixture was added nitric acid (0.374 mL, 8.96 mmol, 1.51 eq), followed by sulfuric acid (0.839 mL, 15.73 mmol, 1.84 eq). The reaction mixture was stirred at −20° C. for 30 min. Then, the reaction temperature was allowed to increase up to room temperature while stirring, and stirred at room temperature for 8 h. Upon completion by LCMS analysis, H$_2$O (10.0 mL) was added to quench the reaction. The organics were separated by a phase separator and concentrated under reduced pressure. Purification by ISCO flash chromatography (0-100% EtOAc in hexanes) afforded methyl 2-hydroxy-3-nitro-5-(trifluoromethoxy) benzoate (1614.0 mg, quantitative). LCMS (Method A) t$_R$=1.51 min, m/z=252.1 [M+H]$^+$.

Step C. Methyl 3-amino-2-hydroxy-5-(trifluoromethoxy) benzoate (HCH-3-46). To a round bottom flask containing a magnetic stir bar was added methyl 2-hydroxy-3-nitro-5-(trifluoromethoxy)benzoate (1614.0 mg, 5.74 mmol), followed by EtOAc (40.0 mL). To this mixture was added 10% Pd/C (122.0 mg) and the mixture was purged with H$_2$ gas. Then, the reaction mixture was stirred for 2 h at room temperature. Upon completion by LCMS analysis, the reaction mixture was filtered through Celite and the combined organics were concentrated under reduced pressure to give methyl 3-amino-2-hydroxy-5-(trifluoromethoxy)benzoate. The crude product was used for the next step without further purification (1405.5 mg, 5.59 mmol, 97% over 2 steps). LCMS (Method A) t$_R$=1.42 min, m/z=251.2 [M+H]$^+$.

Step D. Methyl 3-((5-bromo-2-hydroxyphenyl)sulfonamido)-2-hydroxy-5-(trifluoromethoxy)benzoate (HCH-3-48-2). To a reaction vial containing a magnetic stir bar was added 5-bromo-2-hydroxybenzenesulfonyl chloride (60.0 mg, 0.22 mmol), which was prepared by a procedure analogous to the procedure used to prepare Example J1 Step A, followed by CH$_2$Cl$_2$ (1.5 mL). To this mixture was added methyl 3-amino-2-hydroxy-5-(trifluoromethoxy)benzoate (83.2 mg, 0.33 mmol, 1.5 eq). The reaction mixture was cooled 0° C. while stirring and pyridine (54.0 µL, 0.66 mmol, 3.0 eq) was added. Then, the reaction mixture was stirred overnight. The reaction temperature was allowed to increase up to room temperature while stirring. Upon completion by LCMS analysis, the reaction mixture was concentrated and purified by reverse phase chromatography (20-95% CH$_3$CN in H$_2$O containing 0.1% TFA) to afford methyl 3-((5-bromo-2-hydroxyphenyl)sulfonamido)-2-hydroxy-5-(trifluoromethoxy)benzoate as a solid (24.8 mg, 0.05 mmol, 23%). 1H NMR (400 MHz, Methanol-d$_4$) δ 7.80 (d, J=2.4 Hz, 1H), 7.58 (d, J=2.2 Hz, 1H), 7.51 (dd, J=8.8, 2.5 Hz, 1H), 7.43 (d, J=2.3 Hz, 1H), 6.84 (d, J=8.8 Hz, 1H), 3.95 (s, 3H). $^{19}$F NMR (376 MHz, Methanol-d$_4$) δ −60.28. LCMS (Method A) t$_R$=1.73 min, m/z=487.2 [M+H]$^+$.

Step E. tert-Butyl (3-((5-bromo-2-hydroxyphenyl)sulfonamido)-2-hydroxy-5-(trifluoromethoxy)benzoyl)glycinate (HCH-4-135-2). To a reaction vial containing a magnetic stir bar was added methyl 3-((5-bromo-2-hydroxyphenyl)sulfonamido)-2-hydroxy-5-(trifluoromethoxy)benzoate (50.0 mg, 0.10 mmol), followed by THF (0.5 mL). To this mixture was added tert-butyl glycinate (0.21 mL, 1.54 mmol, 15.0 eq) and Hunig's base (0.54 mL, 3.09 mmol, 30.0 eq). The reaction temperature was heated at 90° C. overnight. Upon completion by LCMS analysis, the reaction temperature was cooled to room temperature. The reaction mixture was concentrated and purified by reverse phase chromatography (20-95% CH$_3$CN in H$_2$O containing 0.1% TFA) to afford tert-butyl (3-((5-bromo-2-hydroxyphenyl)sulfonamido)-2-hydroxy-5-(trifluoromethoxy)benzoyl)glycinate as a solid (44.8 mg, 0.07 mmol, 74%). LCMS (Method A) t$_R$=1.91 min, m/z=259.4 [M+H]$^+$.

Step F. (3-((5-Bromo-2-hydroxyphenyl)sulfonamido)-2-hydroxy-5-(trifluoromethoxy)benzoyl)glycine (HCH-4-137-F76). To a reaction vial containing a magnetic stir bar was added tert-butyl (3-((5-bromo-2-hydroxyphenyl)sulfonamido)-2-hydroxy-5-(trifluoromethoxy)benzoyl)glycinate (44.8 mg, 0.08 mmol) followed by CH$_2$Cl$_2$ (1.0 mL). To this mixture were added TFA (0.1 mL) and 1 drop of concentrated HCl. The reaction mixture was stirred overnight at room temperature. Upon completion by LCMS analysis, the reaction mixture was diluted with MeOH, concentrated, and purified by reverse phase chromatography (20-95% CH$_3$CN in H$_2$O containing 0.1% TFA) to afford the title compound as a solid (24.1 mg, 0.05 mmol, 59%). $^1$H NMR (400 MHz, Methanol-d$_4$) δ 7.80 (d, J=2.4 Hz, 1H), 7.51 (d, J=2.5 Hz, 1H), 7.49 (s, 1H), 7.44 (d, J=2.4 Hz, 1H), 6.83 (d, J=8.8 Hz, 1H), 4.05 (s, 2H). $^{19}$F NMR (376 MHz, Methanol-d$_4$) δ −60.20. LCMS (Method A) t$_R$=1.64 min, m/z=530.2 [M+H]$^+$ Purity (AUC) ≥95%.

Example HCH-2 (HCH-5-64-4-F84) 3-((5-Bromo-3-ethyl-2-hydroxyphenyl)sulfonamido)-5-chloro-2-hydroxy-N-((4-hydroxy-1-methylpiperidin-4-yl)methyl)benzamide

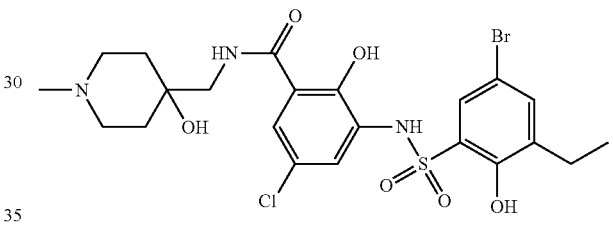

Step A. 5-Bromo-3-ethyl-2-hydroxybenzenesulfonyl chloride. 5-Bromo-3-ethyl-2-hydroxybenzenesulfonyl chloride (150.0 mg, 0.75 mmol) was reacted with neat chlorosulfonic acid (3.0 mL) for 1.5 h at room temperature. The reaction mixture was slowly poured into a flask that contained an ice and CH$_2$Cl$_2$ mixture. The reaction mixture was partitioned between CH$_2$Cl$_2$ (30.0 mL) and H$_2$O (10.0 mL). The product was extracted with CH$_2$Cl$_2$ (3×30.0 mL) and the combined organics were dried over Na$_2$SO$_4$, filtered, and concentrated in vacuo. The crude material was used for the next step without further purification.

Step B. Methyl 3-((5-bromo-3-ethyl-2-hydroxyphenyl) sulfonamide)-5-chloro-2-hydroxybenzoate (HCH-2-77-2). Methyl 3-amino-5-chloro-2-hydroxybenzoate (334.0 mg, 1.66 mmol, 1.5 eq) was reacted with 5-bromo-3-ethyl-2-hydroxybenzenesulfonyl chloride (331.2 mg, 1.11 mmol) using a procedure analogous to General Procedure E, to afford methyl 3-((5-bromo-3-ethyl-2-hydroxyphenyl) sulfonamide)-5-chloro-2-hydroxybenzoate as a solid (242.5 mg, 0.52 mmol, 47%). LCMS (Method A) t$_R$=1.88 min, m/z=465.7 [M+H]$^+$.

Step C. 3-((5-Bromo-3-ethyl-2-hydroxyphenyl)sulfonamido)-5-chloro-2-hydroxy-N-((4-hydroxy-1-methylpiperidin-4-yl)methyl)benzamide (HCH-5-64-4). Using a procedure analogous to General Procedure H, except that DMSO (0.5 mL) was added to aid dissolution and Hunig's base (0.14 mL, 0.81 mmol, 15 eq) was used, starting with methyl 3-((5-bromo-3-ethyl-2-hydroxyphenyl)sulfonamido)-5-chloro-2-hydroxybenzoate (25.0 mg, 0.05 mmol) and 4-(aminomethyl)-1-methylpiperidin-4-ol (38.8 mg, 0.27 mmol, 5.0 eq), 3-((5-bromo-3-ethyl-2-hydroxyphenyl)sulfonamido)-5-chloro-2-hydroxy-N-((4-hydroxy-1-methylpiperidin-4-yl)methyl)benzamide was obtained as a solid (7.5 mg, 0.01 mmol, 24%). LCMS (Method A) $t_R$=1.44 min, m/z=577.9 [M+H]$^+$; Purity (AUC) ≥95%.

Example HCH-3 (HCH-5-71-1-F4) 3-((5-Bromo-2-hydroxyphenyl)sulfonamido)-2-hydroxy-N-(3-hydroxycyclobutyl)-5-(trifluoromethoxy)benzamide (HCH-5-71-1-F4)

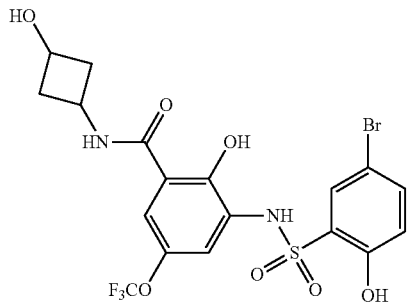 [SMILES: O=C(NC1CC(O)C1)c1cc(OC(F)(F)F)cc(NS(=O)(=O)c2cc(Br)ccc2O)c1O]

Using a procedure analogous to General Procedure H, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-1 Step E, and 3-aminocyclobutan-1-ol (40.0 μL, 0.49 mmol, 8.0 eq) the title compound was obtained as a solid (7.1 mg, 0.01 mmol, 21%). $^1$H NMR (400 MHz, Methanol-d$_4$) δ 7.78 (d, J=2.4 Hz, 1H), 7.55-7.46 (m, 3H), 6.83 (d, J=8.8 Hz, 1H), 4.59-4.37 (m, 1H), 4.07-3.89 (m, 1H), 2.70 (dtt, J=13.2, 6.8, 3.3 Hz, 1H), 2.39 (ddd, J=12.5, 8.0, 4.6 Hz, 1H), 2.31 (ddd, J=12.8, 8.3, 4.5 Hz, 1H), 1.98 (qd, J=9.0, 2.8 Hz, 1H). $^{19}$F NMR (376 MHz, Methanol-d$_4$) δ −60.19, −60.20. (* Mixture of cis and trans) LCMS (Method A) $t_R$=1.56 min, m/z=542.3 [M+H]$^+$; Purity (AUC) ≥93%.

Example HCH-9 (HCH-5-45) 3-((5-Bromo-2-hydroxyphenyl)sulfonamido)-2-hydroxy-N-(oxetan-3-yl)-5-(trifluoromethoxy)benzamide

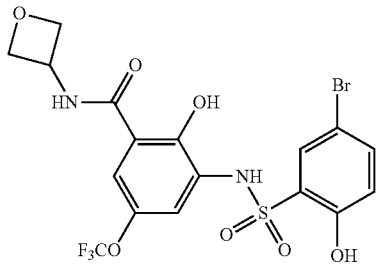 [SMILES: O=C(NC1COC1)c1cc(OC(F)(F)F)cc(NS(=O)(=O)c2cc(Br)ccc2O)c1O]

Using a procedure analogous to General Procedure H, except that DMSO (1.0 mL) was added to aid dissolution and Hunig's base (1.07 ML, 6.17 mmol, 15.0 eq) was used, starting from methyl 3-((5-bromo-2-hydroxyphenyl)sulfonamido)-2-hydroxy-5-(trifluoromethoxy)benzoate (200.0 mg, 0.41 mmol), which was prepared by a procedure analogous to the procedure used to prepare Example HCH-1 Step E, and oxetan-3-amine (0.14 μL, 2.06 mmol, 5.0 eq), the title compound was obtained as a solid (166.4 mg, 0.31 mmol, 76%). $^1$H NMR (400 MHz, Methanol-d$_4$) δ 7.78 (d, J=2.5 Hz, 1H), 7.56 (d, J=2.3 Hz, 1H), 7.51 (ddd, J=5.3, 4.3, 2.6 Hz, 2H), 6.83 (d, J=8.8 Hz, 1H), 5.09 (p, J=6.7 Hz, 1H), 4.89 (t, J=7.1 Hz, 2H), 4.70 (t, J=6.7 Hz, 2H). $^{19}$F NMR (376 MHz, Methanol-d$_4$) δ-63.26. LCMS (Method B) $t_R$=1.08 min, m/z=528.3 [M+H]$^+$; Purity (AUC) ≥95%.

Example HCH-26 (HCH-3-151-2) 3-((5-Bromo-2-hydroxyphenyl)sulfonamido)-2-hydroxy-N-(2-hydroxyethyl)-5-(trifluoromethoxy)benzamide (HCH-3-151-2)

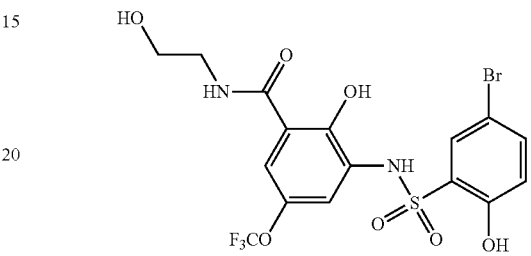

To a reaction vial containing a magnetic stir bar was added 3-((5-bromo-2-hydroxyphenyl)sulfonamido)-2-hydroxy-5-(trifluoromethoxy)benzoic acid (20.0 mg 0.04 mmol), followed by CH$_2$Cl$_2$ (1.0 mL). To this reaction mixture was added PyBroP (19.7 mg, 0.04 mmol), 2-aminoethan-1-ol (4.0 μL, 0.06 mmol), and Hunig's base (22.0 μL, 0.13 mmol). The reaction mixture was stirred at room temperature overnight. Upon completion by LCMS analysis, the reaction mixture was quenched with MeOH (0.5 mL). The reaction mixture was concentrated and purified by reverse phase chromatography (20-95% CH$_3$CN in H$_2$O containing 0.1% TFA) to afford the title compound as a solid (4.6 mg, 0.009 mmol, 21%). LCMS (Method A) $t_R$=1.44 min, m/z=516.3 [M+H]$^+$; Purity (AUC) ≥95%.

Example HCH-4 (HCH-4-14-2) 3-((5-Bromo-2-hydroxy-3-(3-hydroxypropyl)phenyl)sulfonamido)-2-hydroxy-5-(trifluoromethoxy)benzamide

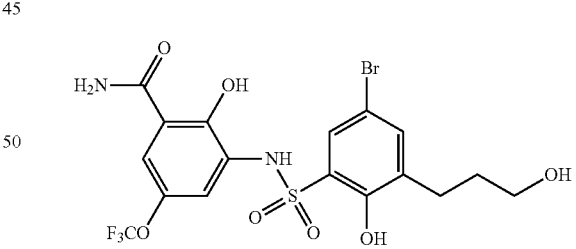

Step A. 2-(3-Hydroxypropyl)phenol (HCH-3-10). To a round bottom flask containing a magnetic stir bar was added methyl 3-(2-hydroxyphenyl)propanoate (1000.0 mg, 5.55 mmol), followed by THF (30.0 mL). To this reaction mixture was slowly added LiAlH$_4$ (351.9 mg, 8.32 mmol, 1.5 eq). The reaction mixture was stirred for 6 h at room temperature. Upon completion by TLC analysis, the reaction mixture was quenched with acetone (10.0 mL) and concentrated under reduced pressure. The crude reaction mixture was used for the next step without further purification.

Step B. 4-Bromo-2-(3-hydroxypropyl)phenol (HCH-3-11). To a round bottom flask containing a magnetic stir bar was added 2-(3-hydroxypropyl)phenol (844.6 mg, 5.55 mmol), followed by CHCl$_3$ (50.0 mL). To this reaction mixture was added tetrabutyl ammonium tribromide (3211.0 mg, 6.66 mmol, 1.2 eq). The reaction mixture was stirred overnight at room temperature. Upon completion by LCMS analysis, the reaction mixture was poured into a round bottom flask containing silica gel. The solvent was evaporated under reduced pressure and the residue was purified by ISCO flash chromatography (0-100% EtOAc in hexanes) to afford 4-bromo-2-(3-hydroxypropyl)phenol (780.8 mg, 3.37 mmol, 60% over 2 steps). $^1$H NMR (400 MHz, Chloroform-d) δ 7.22-7.17 (m, 2H), 6.74 (d, J=8.3 Hz, 1H), 4.31 (br s, 1H), 3.65 (t, J=5.8 Hz, 2H), 2.80-2.66 (m, 2H), 1.93-1.78 (m, 2H). LCMS (Method A) t$_R$=1.18 min, m/z=214.1 [M+H–H$_2$O]$^+$.

Step C. 5-Bromo-2-hydroxy-3-(3-hydroxypropyl)benzenesulfonyl chloride (HCH-4-12). Using a procedure analogous to General Procedure A, 4-bromo-2-(3-hydroxypropyl)phenol (333.9 mg, 1.44 mmol) was reacted with chlorosulfonic acid (3.0 mL). The reaction mixture was stirred for 1 h at room temperature. The crude material was used for the next step without further purification.

Step D. Methyl 3-((5-bromo-2-hydroxy-3-(3-hydroxypropyl)phenyl)sulfonamido)-2-hydroxy-5-(trifluoromethoxy)benzoate (HCH-4-13-2). Using a procedure analogous to General Procedure E, starting with 5-bromo-2-hydroxy-3-(3-hydroxypropyl)benzenesulfonyl chloride (297.4 mg, 0.90 mmol) and methyl 3-amino-2-hydroxy-5-(trifluoromethoxy)benzoate (294.6 mg, 1.17 mmol, 1.3 eq) (which was prepared by a procedure analogous to the procedure used to prepare Example HCH-1 Step C) methyl 3-((5-bromo-2-hydroxy-3-(3-hydroxypropyl)phenyl)sulfonamido)-2-hydroxy-5-(trifluoromethoxy)benzoate was obtained as a solid (53.2 mg, 0.09 mmol, 10%). LCMS (Method A) t$_R$=1.81 min, m/z=545.3 [M+H]$^+$ Step E. 3-((5-Bromo-2-hydroxy-3-(3-hydroxypropyl)phenyl)sulfonamido)-2-hydroxy-5-(trifluoromethoxy)benzamide (HCH-4-14-2). Methyl 3-((5-bromo-2-hydroxy-3-(3-hydroxypropyl)phenyl)sulfonamido)-2-hydroxy-5-(trifluoromethoxy)benzoate (10.0 mg, 0.02 mmol) was reacted with 25%-30% aq NH$_4$OH (0.5 mL). The reaction mixture was stirred at room temperature overnight. Upon completion by LCMS analysis, the reaction mixture was concentrated under reduced pressure and purified by reverse phase chromatography (20-95% CH$_3$CN in H$_2$O containing 0.1% TFA) to afford the title compound as a solid (5.7 mg, 0.01 mmol, 58%). $^1$H NMR (400 MHz, Methanol-d$_4$) δ 7.67 (d, J=2.2 Hz, 1H), 7.49 (s, 1H), 7.46 (s, 1H), 7.42 (d, J=1.9 Hz, 1H), 4.30-4.21 (m, 2H), 2.77 (t, J=6.3 Hz, 2H), 1.96 (dt, J=11.4, 6.1 Hz, 2H). $^{19}$F NMR (376 MHz, Methanol-d$_4$) δ −60.24. LCMS (Method A) t$_R$=1.57 min, m/z=512.3 [M+H–H$_2$O]$^+$; Purity (AUC) ≥95%.

Example HCH-39 (HCH-4-130-3-F15) 3-((5-Bromo-3-fluoro-2-hydroxyphenyl)sulfonamido)-2-hydroxy-N-(2-hydroxybutyl)-5-(trifluoromethoxy)benzamide

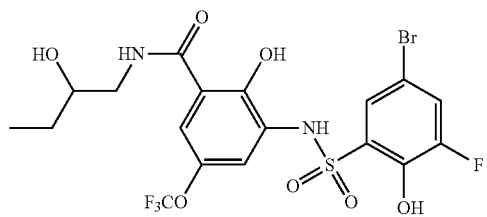 [SMILES: CCC(O)CNC(=O)c1cc(OC(F)(F)F)cc(NS(=O)(=O)c2cc(Br)cc(F)c2O)c1O]

Step A. Methyl 3-((5-bromo-3-fluoro-2-hydroxyphenyl)sulfonamido)-2-hydroxy-5-(trifluoromethoxy)benzoate (HCH-4-100-4-F50). Using a procedure analogous to General Procedure E, starting from 5-bromo-3-fluoro-2-hydroxybenzenesulfonyl chloride (25.0 mg, 0.09 mmol), which was prepared by a procedure analogous to the procedure used to prepare Example J4 Step A, and methyl 3-amino-2-hydroxy-5-(trifluoromethoxy)benzoate (26.0 mg, 0.10 mmol, 1.2 eq), which was prepared by a procedure analogous to the procedure used to prepare Example HCH-1 Step C, methyl 3-((5-bromo-3-fluoro-2-hydroxyphenyl)sulfonamido)-2-hydroxy-5-(trifluoromethoxy)benzoate was obtained as a solid (5.6 mg, 0.01 mmol, 12%). LCMS (Method A) t$_R$=1.90 min, m/z=505.3 [M+H]$^+$.

Step B. 3-((5-Bromo-3-fluoro-2-hydroxyphenyl)sulfonamido)-2-hydroxy-N-(2-hydroxybutyl)-5-(trifluoromethoxy)benzamide (HCH-4-130-3). Using a procedure analogous to General Procedure H, starting from methyl 3-((5-bromo-3-fluoro-2-hydroxyphenyl)sulfonamido)-2-hydroxy-5-(trifluoromethoxy)benzoate (5.6 mg, 0.01 mmol), 1-aminobutan-2-ol (24.0 μL, 0.22 mmol, 20.0 eq), and Hunig's base (58.0 μL, 0.33 mmol, 30.0 eq) the tide compound was obtained as a solid (5.3 mg, 0.009 mmol, 85%). $^1$H NMR (400 MHz, Methanol-d$_4$) δ 7.63 (s, 1H), 7.52 (d, J=10.3 Hz, 2H), 7.48 (s, 1H), 3.66 (tt, J=7.9, 4.4 Hz, 1H), 3.45 (dd, J=13.6, 4.2 Hz, 1H), 3.29-3.24 (m, 1H), 1.54 (dqt, J=15.6, 8.4, 4.2 Hz, 1H), 1.42 (dq, J=14.5, 7.3 Hz, 1H), 0.98 (t, J=7.4 Hz, 3H). $^{19}$F NMR (376 MHz, Methanol-d$_4$) δ −60.20, −133.08 (d, J=10.1 Hz). LCMS (Method A) t$_R$=1.73 min, m/z=562.3 [M+H]$^+$; Purity (AUC) ≥90%.

Example HCH-40 (HCH-4-130-2-F13) 3-((5-Bromo-3-ethyl-2-hydroxyphenyl)sulfonamido)-2-hydroxy-N-(2-hydroxybutyl)-5-(trifluoromethoxy)benzamide

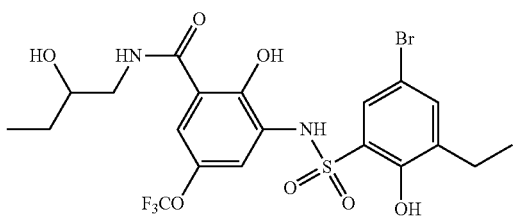 [SMILES: CCc1cc(Br)cc(S(=O)(=O)Nc2cc(OC(F)(F)F)cc(C(=O)NCC(O)CC)c2O)c1O]

Using a procedure analogous to General Procedure H, starting from methyl 3-((5-bromo-3-ethyl-2-hydroxyphenyl)sulfonamido)-2-hydroxy-5-(trifluoromethoxy)benzoate (21.0 mg, 0.04 mmol), which was prepared by a procedure analogous to the procedure used to prepare Example HCH-14 Step A, 1-aminobutan-2-ol (0.09 mL, 0.82 mmol, 20.0 eq), and Hunig's base (0.21 mL, 1.23 mmol, 30.0 eq), the title compound was obtained as a solid (19.0 mg, 0.03 mmol, 81%). $^1$H NMR (400 MHz, Methanol-d$_4$) δ 7.55 (t, J=3.1 Hz, 2H), 7.50-7.46 (m, 1H), 7.43 (d, J=2.3 Hz, 1H), 3.65 (tt, J=8.0, 4.5 Hz, 1H), 3.43 (dd, J=13.6, 4.2 Hz, 1H), 3.30-3.24 (m, 1H), 2.60 (q, J=7.5 Hz, 2H), 1.52 (dtt, J=11.1, 8.5, 4.3 Hz, 1H), 1.42 (dt, J=14.1, 7.5 Hz, 1H), 1.12 (t, J=7.5 Hz, 3H), 0.98 (t, J=7.4 Hz, 3H). $^{19}$F NMR (376 MHz, Methanol-d$_4$) δ −60.17. LCMS (Method A) t$_R$=1.90 min, m/z=572.4 [M+H]$^+$; Purity (AUC) ≥95%.

Example HCH-41 (HCH-4-130-4-F19) 3-((5-Bromo-3-chloro-2-hydroxyphenyl)sulfonamido)-2-hydroxy-N-(2-hydroxybutyl)-5-(trifluoromethoxy)benzamide (HCH-4-130-4)

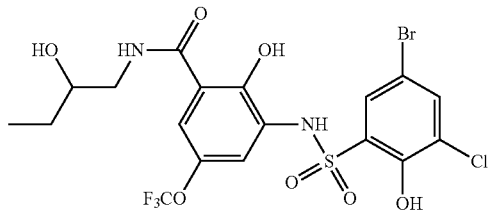 [SMILES: CCC(O)CNC(=O)c1cc(OC(F)(F)F)cc(NS(=O)(=O)c2cc(Br)cc(Cl)c2O)c1O]

Using a procedure analogous to General Procedure H, starting from methyl 3-((5-bromo-3-chloro-2-hydroxyphenyl)sulfonamido)-2-hydroxy-5-(trifluoromethoxy)benzoate (14.4 mg, 0.03 mmol), which was prepared by a procedure analogous to the procedure used to prepare Example HCH-24 Step A, 1-aminobutan-2-ol (0.06 mL, 0.55 mmol, 20.0 eq), and Hunig's base (0.15 mL, 0.83 mmol, 30.0 eq), the title compound was obtained as a solid (14.8 mg, 0.03 mmol, 92%). LCMS (Method A) $t_R$=1.81 min, m/z=578.8 [M+H]$^+$; Purity (AUC) ≥95%.

Example HCH-43 (HCH-5-23-2-F26) 3-((5-Bromo-2-hydroxyphenyl)sulfonamido)-2-hydroxy-N-(2-hydroxy-2-(thiophen-3-yl)ethyl)-5-(trifluoromethoxy)benzamide (HCH-5-23-2)

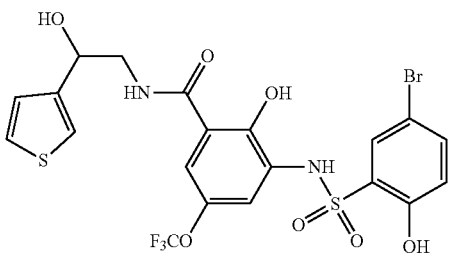 [SMILES: O=C(NCC(O)c1ccsc1)c1cc(OC(F)(F)F)cc(NS(=O)(=O)c2cc(Br)ccc2O)c1O]

Using a procedure analogous to General Procedure H, starting from methyl 3-((5-bromo-2-hydroxyphenyl)sulfonamido)-2-hydroxy-5-(trifluoromethoxy)benzoate (30.0 mg, 0.06 mmol, which was prepared by a procedure analogous to the procedure used to prepare Example HCH-19 Step A, 2-amino-1-(thiophen-3-yl)ethan-1-ol (44.0 µL, 0.31 mmol, 5.0 eq), and Hunig's base (0.16 mL, 0.93 mmol, 15.0 eq), the title compound was obtained as a solid (26.3 mg, 0.04 mmol, 71%). $^1$H NMR (400 MHz, Methanol-d$_4$) δ 7.79 (d, J=2.4 Hz, 1H), 7.51 (dd, J=8.8, 2.5 Hz, 1H), 7.49-7.46 (m, 1H), 7.43 (d, J=2.4 Hz, 1H), 7.37 (dd, J=4.9, 3.0 Hz, 1H), 7.31 (d, J=2.7 Hz, 1H), 7.15-7.09 (m, 1H), 6.84 (d, J=8.8 Hz, 1H), 4.96 (dd, J=8.1, 4.6 Hz, 1H), 3.65 (dd, J=13.5, 4.6 Hz, 1H), 3.54 (dd, J=13.5, 8.2 Hz, 1H). $^{19}$F NMR (376 MHz, Methanol-d$_4$) δ -60.17. LCMS (Method A) $t_R$=1.82 min, m/z=597.4 [M+H]$^+$; Purity (AUC) ≥95%.

Example HCH-44 (HCH-5-23-3-F34) 3-((5-Bromo-2-hydroxyphenyl)sulfonamido)-N-(2-cyclopropyl-2-hydroxypropyl)-2-hydroxy-5-(trifluoromethoxy)benzamide (HCH-5-23-3)

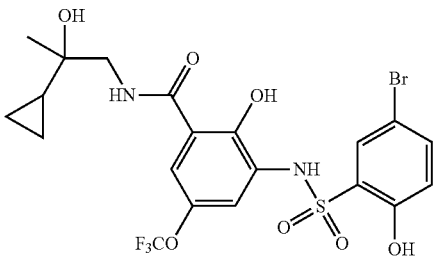 [SMILES: CC(O)(CNC(=O)c1cc(OC(F)(F)F)cc(NS(=O)(=O)c2cc(Br)ccc2O)c1O)C1CC1]

Using a procedure analogous to General Procedure H, starting from methyl 3-((5-bromo-2-hydroxyphenyl)sulfonamido)-2-hydroxy-5-(trifluoromethoxy)benzoate (30.0 mg, 0.06 mmol, which was prepared by a procedure analogous to the procedure used to prepare Example HCH-19 Step A, 1-amino-2-cyclopropylpropan-2-ol (36.0 µL, 0.31 mmol, 5.0 eq), and Hunig's base (0.16 mL, 0.93 mmol, 15.0 eq), the title compound was obtained as a solid (28.3 mg, 0.05 mmol, 80%). $^1$H NMR (400 MHz, Methanol-d$_4$) δ 7.78 (d, J=2.4 Hz, 1H), 7.53-7.46 (m, 3H), 6.84 (d, J=8.8 Hz, 1H), 3.53-3.41 (m, 2H), 1.11 (s, 3H), 0.95-0.84 (m, 1H), 0.50-0.40 (m, 1H), 0.32 (m, 3H). $^{19}$F NMR (376 MHz, Methanol-d$_4$) δ -60.16. LCMS (Method A) $t_R$=1.87 min, m/z=552.4 [M+H-H$_2$O]$^+$; Purity (AUC) ≥95%.

Example HCH-45 (HCH-5-23-4-F41) 3-((5-Bromo-2-hydroxyphenyl)sulfonamido)-2-hydroxy-N-(2-hydroxy-2-methylbutyl)-5-(trifluoromethoxy)benzamide (HCH-5-23-4)

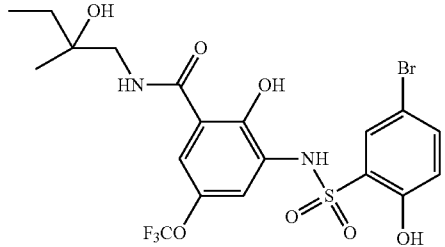 [SMILES: CCC(C)(O)CNC(=O)c1cc(OC(F)(F)F)cc(NS(=O)(=O)c2cc(Br)ccc2O)c1O]

Using a procedure analogous to General Procedure H, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A), -amino-2-methylbutan-2-ol (32.0 µL, 0.31 mmol, 5.0 eq), and Hunig's base (0.16 mL, 0.93 mmol, 15.0 eq), the title compound was obtained as a solid (29.0 mg, 0.05 mmol, 84%). $^1$H NMR (400 MHz, Methanol-d$_4$) δ 7.78 (d, J=2.4 Hz, 1H), 7.54-7.45 (m, 3H), 6.84 (d, J=8.8 Hz, 1H), 3.39 (s, 2H), 1.51 (q, J=7.4 Hz, 2H), 1.13 (s, 3H), 0.94 (t, J=7.5 Hz, 3H). $^{19}$F NMR (376 MHz, Methanol-d$_4$) δ -60.13. LCMS (Method A) $t_R$=1.78 min, m/z=558.3 [M+H]$^+$; Purity (AUC) ≥95%.

Example HCH-46 (HCH-5-31-F3) 3-((5-Bromo-2-hydroxyphenyl)sulfonamido)-2-hydroxy-N-(3-hydroxy-1-(methylamino)-1-oxopropan-2-yl)-5-(trifluoromethoxy)benzamide (HCH-5-37-1-F3)

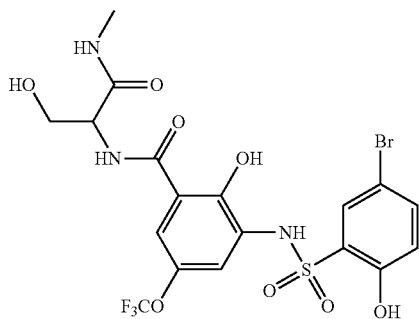 [SMILES: CNC(=O)C(CO)NC(=O)c1cc(OC(F)(F)F)cc(NS(=O)(=O)c2cc(Br)ccc2O)c1O]

Using a procedure analogous to General Procedure H, except that THF (0.5 mL) and DMSO (0.5 mL) were used as reaction solvents, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A, 2-amino-3-hydroxy-N-methylpropanamide (36.5 mg, 0.31 mmol, 5.0 eq), and Hunig's base (0.16 mL, 0.93 mmol, 15.0 eq), the title compound was obtained as a solid (15.1 mg, 0.03 mmol, 42%). LCMS (Method A) $t_R$=1.56 min, m/z=573.3 [M+H]$^+$; Purity (AUC) ≥95%.

Example HCH-47 (HCH-5-37-3-F19) (S)—N-(1-Amino-3-hydroxy-1-oxopropan-2-yl)-3-((5-bromo-2-hydroxyphenyl)sulfonamido)-2-hydroxy-5-(trifluoromethoxy)benzamide (HCH-5-37-3)

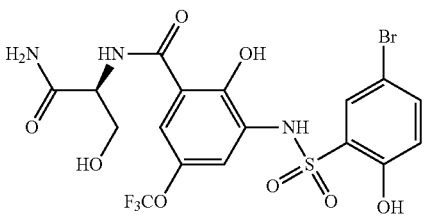 [SMILES: NC(=O)[C@H](CO)NC(=O)c1cc(OC(F)(F)F)cc(NS(=O)(=O)c2cc(Br)ccc2O)c1O]

Using a procedure analogous to General Procedure H, except that THF (0.5 mL) and DMSO (0.5 mL) were used as reaction solvents, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A, (S)-2-amino-3-hydroxypropanamide hydrochloride (43.4 mg, 0.31 mmol, 5.0 eq), and Hunig's base (0.16 mL, 0.93 mmol, 15.0 eq), the title compound was obtained as a solid (12.4 mg, 0.02 mmol, 35%). $^1$H NMR (400 MHz, Methanol-$d_4$) δ 7.79 (d, J=2.5 Hz, 1H), 7.59 (d, J=2.5 Hz, 1H), 7.51 (m, 2H), 6.84 (d, J=8.8 Hz, 1H), 4.62 (t, J=5.4 Hz, 1H), 3.89 (d, J=5.7 Hz, 2H). $^{19}$F NMR (376 MHz, Methanol-$d_4$) δ −60.12. LCMS (Method A) $t_R$=1.56 min, m/z=559.3 [M+H]$^+$; Purity (AUC) ≥95%.

Example HCH-48 (HCH-5-37-4-F29) N-(1-Amino-1-oxopropan-2-yl)-3-((5-bromo-2-hydroxyphenyl)sulfonamido)-2-hydroxy-5-(trifluoromethoxy)benzamide (HCH-5-37-4)

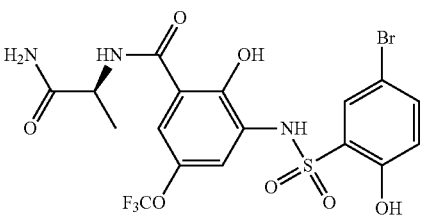 [SMILES: C[C@H](NC(=O)c1cc(OC(F)(F)F)cc(NS(=O)(=O)c2cc(Br)ccc2O)c1O)C(N)=O]

Using a procedure analogous to General Procedure H, except that THF (0.5 mL) and DMSO (0.5 mL) were used as reaction solvents, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A, 2-aminopropanamide (27.2 mg, 0.31 mmol, 5.0 eq), and Hunig's base (0.16 mL, 0.93 mmol, 15.0 eq), the title compound was obtained as a solid (7.3 mg, 0.01 mmol, 21%). THF (0.5 mL) and DMSO (0.5 mL) were used as reaction solvents. $^1$H NMR (400 MHz, Methanol-$d_4$) δ 7.78 (d, J=2.4 Hz, 1H), 7.61 (d, J=2.5 Hz, 1H), 7.53-7.46 (m, 2H), 6.83 (d, J=8.8 Hz, 1H), 4.52 (q, J=7.2 Hz, 1H), 1.46 (d, J=7.3 Hz, 3H). $^{19}$F NMR (376 MHz, Methanol-$d_4$) δ −60.15. LCMS (Method A) $t_R$=1.65 min, m/z=543.3 [M+H]$^+$; Purity (AUC) ≥95%.)

Example HCH-49 (HCH-5-37-2-F11) N-(2-Amino-2-oxo-1-(pyridin-2-yl)ethyl)-3-((5-bromo-2-hydroxyphenyl)sulfonamido)-2-hydroxy-5-(trifluoromethoxy)benzamide (HCH-5-37-2)

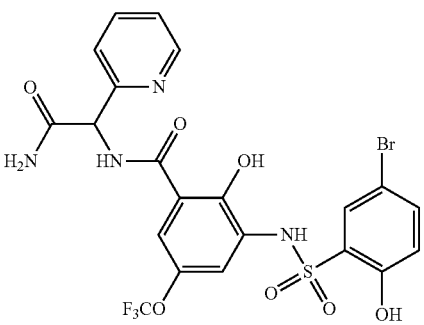 [SMILES: NC(=O)C(NC(=O)c1cc(OC(F)(F)F)cc(NS(=O)(=O)c2cc(Br)ccc2O)c1O)c1ccccn1]

Using a procedure analogous to General Procedure H, except that THE (0.5 mL) and DMSO (0.5 mL) were used as reaction solvents, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A, 2-amino-2-(pyridin-2-yl)acetamide (46.6 mg, 0.31 mmol, 5.0 eq), and Hunig's base (0.16 mL, 0.93 mmol, 15.0 eq) the title compound was obtained as a solid (4.0 mg, 0.007 mmol, 10%). THE (0.5 mL) and DMSO (0.5 mL) were used as reaction solvents. LCMS (Method A) $t_R$=1.63 min, m/z=606.3 [M+H]$^+$; Purity (AUC) ≥95%.

Example HCH-50 (HCH-5-43-4-F23) 3-((5-Bromo-3-chloro-2-hydroxyphenyl)sulfonamido)-2-hydroxy-N-((4-hydroxy-1-methylpiperidin-4-yl)methyl)-5-(trifluoromethoxy)benzamide (HCH-5-43-4)

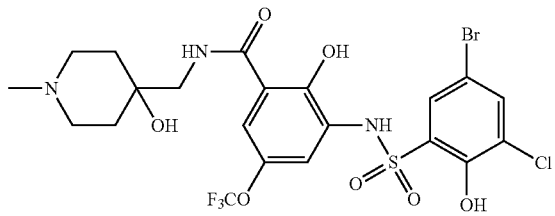 [SMILES: CN1CCC(O)(CNC(=O)c2cc(OC(F)(F)F)cc(NS(=O)(=O)c3cc(Br)cc(Cl)c3O)c2O)CC1]

Using a procedure analogous to General Procedure H, except that THF (0.5 mL) and DMSO (0.5 mL) were used as reaction solvents, starting from methyl 3-((5-bromo-3-chloro-2-hydroxyphenyl)sulfonamido)-2-hydroxy-5-(trifluoromethoxy)benzoate (19.0 mg, 0.04 mmol), which was prepared by a procedure analogous to the procedure used to prepare Example HCH-24 Step A, 4-(aminomethyl)-1-methylpiperidin-4-ol (30.0 μL, 0.18 mmol, 5.0 eq), and Hunig's base (0.10 mL, 0.55 mmol, 15.0 eq), the title compound was obtained as a solid (10.1 mg, 0.02 mmol, 43%). LCMS (Method A) $t_R$=1.43 min, m/z=633.8 [M+H]$^+$; Purity (AUC) ≥95%.

Example HCH-51 (HCH-5-43-1-F4) 3-((5-Bromo-3-chloro-2-hydroxyphenyl)sulfonamido)-N-(2-cyclopropyl-2-hydroxypropyl)-2-hydroxy-5-(trifluoromethoxy)benzamide (HCH-5-43-1)

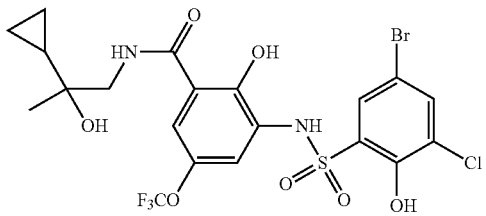 [SMILES: CC(O)(CNC(=O)c1cc(OC(F)(F)F)cc(NS(=O)(=O)c2cc(Br)cc(Cl)c2O)c1O)C1CC1]

Using a procedure analogous to General Procedure H, except that THF (0.5 mL) and DMSO (0.5 mL) were used as reaction solvents, starting from methyl 3-((5-bromo-3-chloro-2-hydroxyphenyl)sulfonamido)-2-hydroxy-5-(trifluoromethoxy)benzoate (19.0 mg, 0.04 mmol), which was prepared by a procedure analogous to the procedure used to prepare Example HCH-24 Step A, 1-amino-2-cyclopropylpropan-2-ol (20.0 μL, 0.18 mmol, 5.0 eq), and Hunig's base (0.10 mL, 0.55 mmol, 15.0 eq), the title compound was obtained as a solid (8.0 mg, 0.01 mmol, 36%). $^1$H NMR (400 MHz, Methanol-d$_4$) δ 7.72 (t, J=1.6 Hz, 2H), 7.54 (d, J=2.4 Hz, 1H), 7.49 (s, 1H), 3.52-3.42 (m, 2H), 1.11 (s, 3H), 0.95-0.84 (m, 1H), 0.43 (m, 1H), 0.32 (m, 3H). $^{19}$F NMR (376 MHz, Methanol-d$_4$) δ −60.17. LCMS (Method A) $t_R$=1.84 min, m/z=586.8 [M+H]$^+$; Purity (AUC) ≥95%.

Example HCH-52 (HCH-5-43-2-F12) 3-((5-Bromo-3-chloro-2-hydroxyphenyl)sulfonamido)-2-hydroxy-N-(2-hydroxy-3-methylbutyl)-5-(trifluoromethoxy)benzamide (HCH-5-43-2)

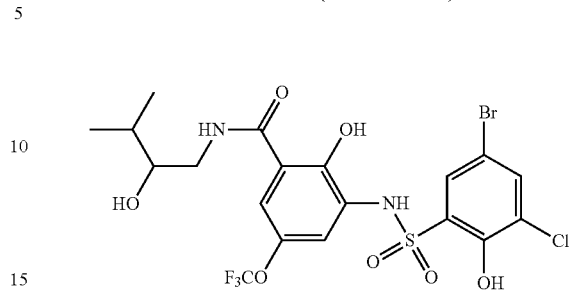

Using a procedure analogous to General Procedure H, except that THF (0.5 mL) and DMSO (0.5 mL) were used as reaction solvents, starting from methyl 3-((5-bromo-3-chloro-2-hydroxyphenyl)sulfonamido)-2-hydroxy-5-(trifluoromethoxy)benzoate (19.0 mg, 0.04 mmol), which was prepared by a procedure analogous to the procedure used to prepare Example HCH-24 Step A, 1-amino-3-methylbutan-2-ol (20.0 μL, 0.18 mmol, 5.0 eq), and Hunig's base (0.10 mL, 0.55 mmol, 15.0 eq), the title compound was obtained as a solid (9.3 mg, 0.02 mmol, 43%). $^1$H NMR (400 MHz, Methanol-d$_4$) δ 7.73 (q, J=2.3 Hz, 2H), 7.53 (d, J=2.4 Hz, 1H), 7.49 (s, 1H), 3.57-3.47 (m, 2H), 3.26 (m, 1H), 1.69 (dq, J=13.4, 6.7 Hz, 1H), 0.97 (dd, J=6.8, 1.3 Hz, 6H). $^{19}$F NMR (376 MHz, Methanol-d$_4$) δ −60.18. LCMS (Method A) $t_R$=1.85 min, m/z=592.8 [M+H]$^+$; Purity (AUC) ≥95%.

Example HCH-53 (HCH-5-43-3-F18) 3-((5-Bromo-3-chloro-2-hydroxyphenyl)sulfonamido)-2-hydroxy-N-((4-hydroxytetrahydro-2H-pyran-4-yl)methyl)-5-(trifluoromethoxy)benzamide (HCH-5-43-3)

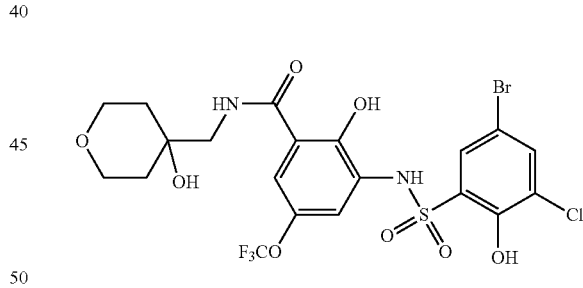

Using a procedure analogous to General Procedure H, except that THF (0.5 mL) and DMSO (0.5 mL) were used as reaction solvents, starting from methyl 3-((5-bromo-3-chloro-2-hydroxyphenyl)sulfonamido)-2-hydroxy-5-(trifluoromethoxy)benzoate (19.0 mg, 0.04 mmol), which was prepared by a procedure analogous to the procedure used to prepare Example HCH-24 Step A. 4-(aminomethyl)tetrahydro-2H-pyran-4-ol hydrochloride (30.6 mg, 0.18 mmol, 5.0 eq), and Hunig's base (0.10 mL, 0.55 mmol, 15.0 eq), the title compound was obtained as a solid (5.8 mg, 0.009 mmol, 25%). 1H NMR (400 MHz, Methanol-d$_4$) δ 7.73 (s, 2H), 7.57 (d, J=2.4 Hz, 1H), 7.51-7.47 (m, 1H), 3.74 (dd, J=6.1, 3.8 Hz, 4H), 3.42 (s, 2H), 1.69 (m, 2H), 1.51 (d, J=12.6 Hz, 2H). $^{19}$F NMR (376 MHz, Methanol-d$_4$) δ −60.15. LCMS (Method A) $t_R$=1.67 min, m/z=620.8 [M+H]$^+$; Purity (AUC) ≥95%.

Example HCH-54 (HCH-5-46-F5P) 3-((5-Bromo-3-chloro-2-hydroxyphenyl)sulfonamido)-2-hydroxy-N-(oxetan-3-yl)-5-(trifluoromethoxy)benzamide (HCH-5-46)

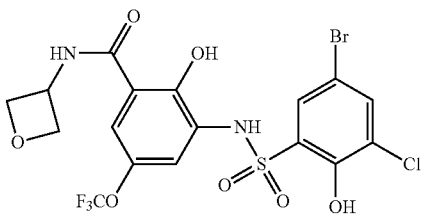 [SMILES: O=C(NC1COC1)c1cc(OC(F)(F)F)cc(NS(=O)(=O)c2cc(Br)cc(Cl)c2O)c1O]

Using a procedure analogous to General Procedure H, except that DMSO (0.5 mL) was added to aid dissolution, starting from methyl 3-((5-bromo-3-chloro-2-hydroxyphenyl)sulfonamido)-2-hydroxy-5-(trifluoromethoxy)benzoate (20.0 mg, 0.04 mmol), which was prepared by a procedure analogous to the procedure used to prepare Example HCH-24 Step A, oxetan-3-amine (10.0 µL, 0.19 mmol, 5.0 eq), and Hunig's base (0.10 mL, 0.58 mmol, 15.0 eq), the title compound was obtained as a solid (16.1 mg, 0.03 mmol, 74%). LCMS (Method A) $t_R$=1.98 min, m/z=562.7 [M+H]$^+$; Purity (AUC) ≥95%.

Example HCH-55 (HCH-5-53-3-F54) 3-((5-Bromo-2-hydroxyphenyl)sulfonamido)-N-(3,3-difluorocyclobutyl)-2-hydroxy-5-(trifluoromethoxy)benzamide (HCH-5-53-3)

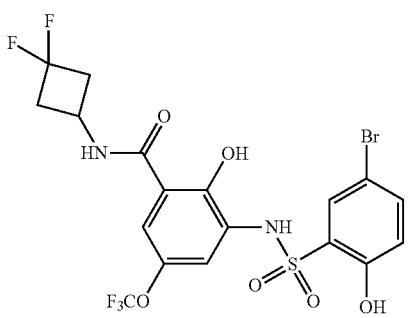 [SMILES: O=C(NC1CC(F)(F)C1)c1cc(OC(F)(F)F)cc(NS(=O)(=O)c2cc(Br)ccc2O)c1O]

Using a procedure analogous to General Procedure H, except that DMSO (0.5 mL) was added to aid dissolution, starting from methyl 3-((5-bromo-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-19 Step A, 3,3-difluorocyclobutan-1-amine hydrochloride (44.3 mg, 0.31 mmol, 5.0 eq), and Hunig's base (0.16 mL, 0.93 mmol, 15.0 eq), the title compound was obtained as a solid (10.8 mg, 0.02 mmol, 31%). LCMS (Method A) $t_R$=1.80 min, m/z=562.3 [M+H]$^+$; Purity (AUC) ≥95%.

Example HCH-56 (HCH-5-58-1-F1) (S)—N-(1-Amino-3-hydroxy-1-oxopropan-2-yl)-3-((5-bromo-3-chloro-2-hydroxyphenyl)sulfonamido)-2-hydroxy-5-(trifluoromethoxy)benzamide (HCH-5-58-1)

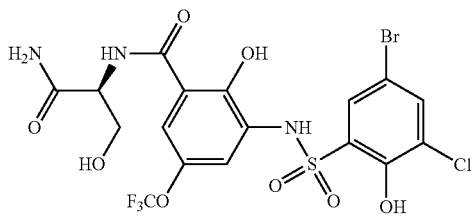 [SMILES: NC(=O)[C@H](CO)NC(=O)c1cc(OC(F)(F)F)cc(NS(=O)(=O)c2cc(Br)cc(Cl)c2O)c1O]

Using a procedure analogous to General Procedure H, except that DMSO (0.5 mL) was added to aid dissolution, starting from methyl 3-((5-bromo-3-chloro-2-hydroxyphenyl)sulfonamido)-2-hydroxy-5-(trifluoromethoxy)benzoate (16.0 mg, 0.03 mmol), which was prepared by a procedure analogous to the procedure used to prepare Example HCH-24 Step A), (S)-2-amino-3-hydroxypropanamide hydrochloride (21.6 mg, 0.15 mmol, 5.0 eq), and Hunig's base (0.08 mL, 0.46 mmol, 15.0 eq), the title compound was obtained as a solid (10.2 mg, 0.02 mmol, 56%). LCMS (Method A) $t_R$=1.48 min, m/z=593.7 [M+H]$^+$; Purity (AUC) ≥95%.

Example HCH-57 (HCH-5-58-2-F8) N-(1-Amino-1-oxopropan-2-yl)-3-((5-bromo-3-chloro-2-hydroxyphenyl)sulfonamido)-2-hydroxy-5-(trifluoromethoxy)benzamide (HCH-5-58-2)

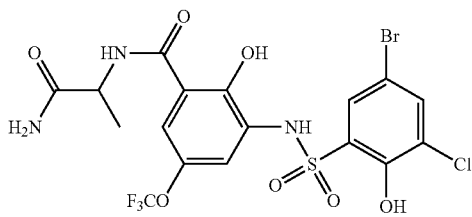 [SMILES: CC(NC(=O)c1cc(OC(F)(F)F)cc(NS(=O)(=O)c2cc(Br)cc(Cl)c2O)c1O)C(N)=O]

Using a procedure analogous to General Procedure H, except that DMSO (0.5 mL) was added to aid dissolution, starting from methyl 3-((5-bromo-3-chloro-2-hydroxyphenyl)sulfonamido)-2-hydroxy-5-(trifluoromethoxy)benzoate (16.0 mg, 0.03 mmol), which was prepared by a procedure analogous to the procedure used to prepare Example HCH-24 Step A, 2-aminopropanamide (10.0 µL, 0.15 mmol, 5.0 eq), and Hunig's base (0.08 mL, 0.46 mmol, 15.0 eq), the title compound was obtained as a solid (6.0 mg, 0.01 mmol, 33%). $^1$H NMR (400 MHz, Methanol-d$_4$) δ 7.76-7.70 (m, 2H), 7.66 (d, J=2.5 Hz, 1H), 7.52-7.47 (m, 1H), 4.53 (q, J=7.2 Hz, 1H), 1.46 (d, J=7.3 Hz, 3H). $^{19}$F NMR (376 MHz, Methanol-d$_4$) δ −60.15. LCMS (Method A) $t_R$=1.59 min, m/z=577.7 [M+H]$^+$; Purity (AUC) ≥95%.

Example HCH-58 (HCH-5-63-1-F42) 3-((5-Bromo-3-ethyl-2-hydroxyphenyl)sulfonamido)-5-chloro-2-hydroxy-N-(oxetan-3-yl)benzamide (HCH-5-63-1)

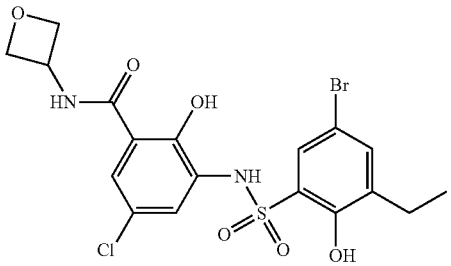 [SMILES: CCc1cc(Br)cc(S(=O)(=O)Nc2cc(Cl)cc(C(=O)NC3COC3)c2O)c1O]

Using a procedure analogous to General Procedure H, except that DMSO (0.5 mL) was added to aid dissolution, starting from methyl 3-((5-bromo-3-ethyl-2-hydroxyphenyl)sulfonamido)-5-chloro-2-hydroxybenzoate (25.0 mg, 0.05 mmol), which was prepared by a procedure analogous to the procedure used to prepare Example HCH-11 Step A, oxetan-3-amine (20.0 μL, 0.27 mmol, 5.0 eq), and Hunig's base (0.14 mL, 0.81 mmol, 15.0 eq), the title compound was obtained as a solid (11.3 mg, 0.02 mmol, 41%). LCMS (Method A) $t_R$=1.74 min, m/z=506.8 [M+H]$^+$; Purity (AUC) ≥95%.

Example HCH-59 (HCH-5-69) N-(1-Amino-1-oxopropan-2-yl)-3-((5-bromo-3-ethyl-2-hydroxyphenyl)sulfonamido)-5-chloro-2-hydroxybenzamide (HCH-5-69)

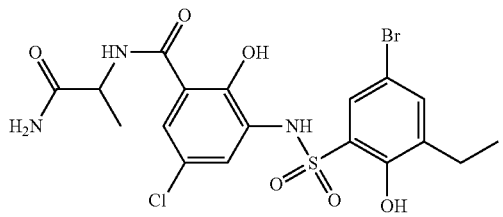 [SMILES: CCc1cc(Br)cc(S(=O)(=O)Nc2cc(Cl)cc(C(=O)NC(C)C(N)=O)c2O)c1O]

Using a procedure analogous to General Procedure H, except that DMSO (0.5 mL) was added to aid dissolution, starting from methyl 3-((5-bromo-3-ethyl-2-hydroxyphenyl)sulfonamido)-5-chloro-2-hydroxybenzoate (55.6 mg, 0.12 mmol), which was prepared by a procedure analogous to the procedure used to prepare Example HCH-11 Step A, 2-aminopropanamide (16.0 μL, 1.79 mmol, 5.0 eq), and Hunig's base (0.31 mL, 1.79 mmol, 15.0 eq), the title compound was obtained as a solid (22.3 mg, 0.04 mmol, 35%). $^1$H NMR (400 MHz, Methanol-d$_4$) δ 7.74 (s, 1H), 7.54 (d, J=13.4 Hz, 2H), 7.43 (s, 1H), 4.51 (q, J=6.5 Hz, 1H), 2.60 (q, J=6.5 Hz, 2H), 1.45 (d, J=6.9 Hz, 3H), 1.13 (t, J=7.2 Hz, 3H). LCMS (Method A) $t_R$=1.60 min, m/z=520.8 [M+H]$^+$; Purity (AUC) ≥95%.

Example HCH-60 (HCH-5-71-4-F26) 3-((5-Bromo-3-chloro-2-hydroxyphenyl)sulfonamido)-2-hydroxy-N-(3-methoxycyclobutyl)-5-(trifluoromethoxy)benzamide (HCH-5-71-4)

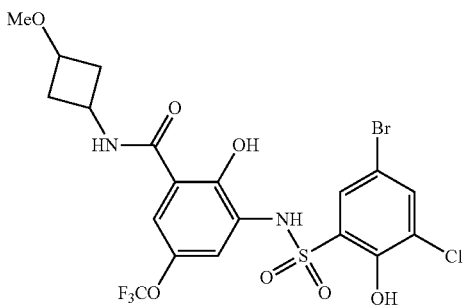 [SMILES: COC1CC(NC(=O)c2cc(OC(F)(F)F)cc(NS(=O)(=O)c3cc(Br)cc(Cl)c3O)c2O)C1]

Using a procedure analogous to General Procedure H, except that DMSO (0.5 mL) was added to aid dissolution, starting from methyl 3-((5-bromo-3-chloro-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-24 Step A, 3-methoxycyclobutan-1-amine hydrochloride (63.4 mg, 0.46 mmol, 8.0 eq), and Hunig's base (0.15 mL, 0.86 mmol, 15.0 eq), the title compound was obtained as a solid (12.7 mg, 0.02 mmol, 37%). LCMS (Method A) $t_R$=1.56 min, m/z=542.3 [M+H]$^+$; Purity (AUC) ≥95%.

Example HCH-61 (HCH-5-71-3-F1) 3-((5-Bromo-3-chloro-2-hydroxyphenyl)sulfonamido)-2-hydroxy-N-(3-hydroxycyclobutyl)-5-(trifluoromethoxy)benzamide (HCH-5-71-3)

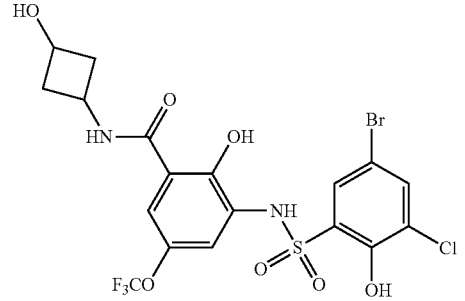 [SMILES: O=C(NC1CC(O)C1)c1cc(OC(F)(F)F)cc(NS(=O)(=O)c2cc(Br)cc(Cl)c2O)c1O]

Using a procedure analogous to General Procedure H, except that DMSO (0.5 mL) was added to aid dissolution, starting from methyl 3-((5-bromo-3-chloro-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-24 Step A, 3-aminocyclobutan-1-ol (30.0 μL, 0.46 mmol, 8.0 eq), and Hunig's base (0.15 mL, 0.86 mmol, 15.0 eq), the title compound was obtained as a solid (19.1 mg, 0.03 mmol, 57%). LCMS (Method A) $t_R$=1.65 min, m/z=576.7 [M+H]$^+$; Purity (AUC) ≥93%.

Example HCH-62 (HCH-7-42-2) 3-((5-Bromo-3-chloro-2-hydroxyphenyl)sulfonamido)-2-hydroxy-5-(trifluoromethoxy)benzamide (HCH-7-42-2)

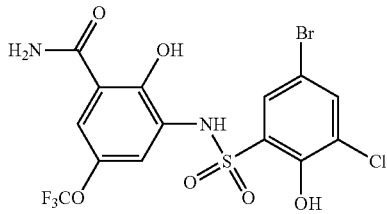 [SMILES: NC(=O)c1cc(OC(F)(F)F)cc(NS(=O)(=O)c2cc(Br)cc(Cl)c2O)c1O]

Using a procedure analogous to the procedure used to prepare Example HCH-4 Step E, starting from methyl 3-((5-bromo-3-chloro-2-hydroxyphenyl)sulfonamido)-2-hydroxy-5-(trifluoromethoxy)benzoate (30.0 mg, 0.06 mmol), the title compound was obtained as a solid (24.9 mg, 0.05 mmol, 85%). $^1$H NMR (400 MHz, Methanol-$d_4$) δ 7.74 (d, J=2.4 Hz, 1H), 7.72 (d, J=2.4 Hz, 1H), 7.51 (s, 2H). $^{19}$F NMR (376 MHz, Methanol-$d_4$) δ −60.23. LCMS (Method A) $t_R$=1.69 min, m/z=506.6 [M+H]$^+$; Purity (AUC) ≥95%.

Example HCH-63 (HCH-7-42-1) 3-((5-Bromo-3-chloro-2-hydroxyphenyl)sulfonamido)-2-hydroxy-N-methyl-5-(trifluoromethoxy)benzamide (HCH-7-42-1)

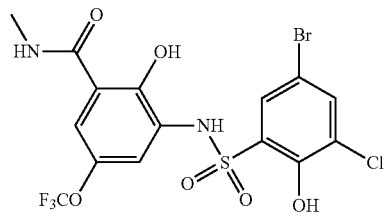 [SMILES: CNC(=O)c1cc(OC(F)(F)F)cc(NS(=O)(=O)c2cc(Br)cc(Cl)c2O)c1O]

Using a procedure analogous to General Procedure H, starting from methyl 3-((5-bromo-3-chloro-2-hydroxyphenyl)sulfonamido)-2-hydroxy-5-(trifluoromethoxy)benzoate (30.0 mg, 0.06 mmol), which was prepared by a procedure analogous to the procedure used to prepare Example HCH-24 Step, 2.0 M methanamine in THF (0.5 mL), and Hunig's base (0.10 mL, 0.58 mmol, 10.0 eq), the title compound was obtained as a solid (27.2 mg, 0.05 mmol, 90%). $^1$H NMR (400 MHz, Methanol-$d_4$) δ 7.73 (d, J=2.4 Hz, 1H), 7.71 (d, J=2.4 Hz, 1H), 7.50-7.46 (m, 1H), 7.42 (d, J=2.4 Hz, 1H), 2.87 (s, 3H). $^{19}$F NMR (376 MHz, Methanol-$d_4$) δ −60.21. LCMS (Method A) $t_R$=1.78 min, m/z=520.7 [M+H]$^+$; Purity (AUC) ≥95%.

Example J68: 3-((5-Bromo-2-hydroxyphenyl)sulfonamido)-5-cyclopropyl-2-hydroxybenzoic acid

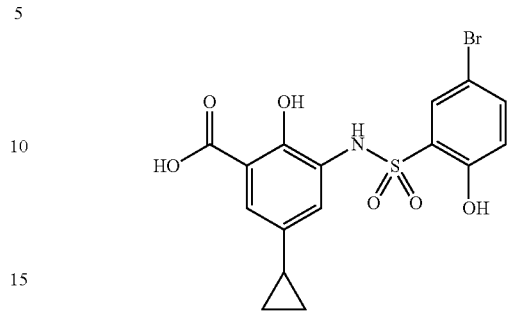

Step A: Methyl 5-bromo-2-hydroxy-3-nitrobenzoate. Using a procedure analogous to General Procedure B, starting with methyl 2-hydroxy-4-bromobenzoate (9.24 g, 40 mmol), methyl 5-bromo-2-hydroxy-3-nitrobenzoate was obtained as a crude yellow solid (10.3 g, 37.3 mmol, 93%), which was used without purification. $^1$H NMR (400 MHz, CDCl$_3$) $δ_H$ 8.27 (d, J=2.5 Hz, 1H), 8.24 (d, J=2.5 Hz, 1H), 4.03 (s, 3H); LCMS (Method A) $t_R$=1.02 min, m/z=276, 278 [M+H]$^+$; Purity (AUC) ≥95%.

Step B: Methyl 2-(benzyloxy)-5-bromo-3-nitrobenzoate. Using a procedure analogous to General Procedure Q, methyl 5-bromo-2-hydroxy-3-nitrobenzoate (8.9 g, 32.2 mmol), methyl 2-(benzyloxy)-5-bromo-3-nitrobenzoate was obtained as a yellow solid (10.6 g, 28.8 mmol, 89%). LCMS (Method A) $t_R$=1.23 min; Purity (AUC) ≥95%.

Step C: Methyl 2-(benzyloxy)-5-cyclopropyl-3-nitrobenzoate. Using a procedure analogous to General Procedure M, methyl 2-(benzyloxy)-5-bromo-3-nitrobenzoate (1.1 g, 3.0 mmol), methyl 2-(benzyloxy)-5-cyclopropyl-3-nitrobenzoate was obtained as a brown oil (895 mg, 2.73 mmol, 91%). $^1$H NMR (400 MHz, CDCl$_3$) $δ_H$ 7.77 (d, J=2.4 Hz, 1H), 7.64 (d, J=2.5 Hz, 1H), 7.52-7.47 (m, 2H), 7.46-7.35 (m, 3H), 3.91 (s, 3H), 2.03-1.94 (m, 1H), 1.13-1.07 (m, 2H), 0.83-0.74 (m, 2H); LCMS (Method A) $t_R$=1.27 min; Purity (AUC) ≥95%.

Step D: Methyl 3-amino-5-cyclopropyl-2-hydroxybenzoate. Using a procedure analogous to General Procedure C, methyl 2-(benzyloxy)-5-cyclopropyl-3-nitrobenzoate (895 mg, 2.73 mmol), methyl 3-amino-5-cyclopropyl-2-hydroxybenzoate was obtained as an off-white solid (495 mg, 2.39 mmol, 88%). $^1$H NMR (400 MHz, CDCl$_3$) $δ_H$ 10.78 (s, 1H), 7.15 (d, J=2.1 Hz, 1H), 6.94 (d, J=2.1 Hz, 1H), 3.96 (s, 3H), 1.83 (tt, J=8.4, 5.1 Hz, 1H), 0.96-0.86 (m, 2H), 0.68-0.59 (m, 2H); LCMS (Method A) $t_R$=1.28 min, m/z=208.2 [M+H]$^+$; Purity (AUC) ≥95%.

Step E: Methyl 3-((5-bromo-2-hydroxyphenyl)sulfonamido)-5-cyclopropyl-2-hydroxybenzoate. Using a procedure analogous to General Procedure E, starting with methyl 3-amino-5-cyclopropyl-2-hydroxybenzoate (207 mg, 1.0 mmol) and 5-bromo-2-hydroxybenzenesulfonyl chloride 326 mg, 1.2 mmol), which was prepared by a procedure analogous to the procedure used to prepare Example J1 Step A, methyl 3-((5-bromo-2-hydroxyphenyl)sulfonamido)-5-cyclopropyl-2-hydroxybenzoate was obtained as a a cream solid (395 mg, 0.89 mmol, 89%). $^1$H NMR (400 MHz, MeOH-$d_4$) $δ_H$ 7.76 (d, J=2.5 Hz, 1H), 7.51 (dd, J=8.8, 2.5 Hz, 1H), 7.36 (d, J=2.3 Hz, 1H), 7.31 (d, J=2.3 Hz, 1H), 6.84 (d, J=8.8 Hz, 1H), 3.93 (s, 3H), 1.84 (tt, J=8.4, 5.1 Hz, 11H), 0.98-0.90 (m, 2H), 0.54 (dt, J=6.5, 4.7 Hz, 2H); LCMS (Method A) $t_R$=1.67 min, m/z=442, 444 [M+H]$^+$; Purity (AUC) ≥95%.

Step F: 3-((5-Bromo-2-hydroxyphenyl)sulfonamido)-5-cyclopropyl-2-hydroxybenzoic acid. Using a procedure analogous to General Procedure F, starting with methyl 3-((5-bromo-2-hydroxyphenyl)sulfonamido)-5-cyclopropyl-2-hydroxybenzoate (44 mg, 0.10 mmol), the title compound was obtained as a colorless solid (33 mg, 0.078 mmol, 78%). $^1$H NMR (400 MHz, DMSO-d$_6$) δ$_H$ 11.25 (s, 1H), 8.85 (s, 1H), 7.68 (d, J=2.6 Hz, 1H), 7.59 (dd, J=8.7, 2.6 Hz, 1H), 7.30 (d, J=2.3 Hz, 1H), 7.06 (d, J=2.3 Hz, 1H), 6.94 (d, J=8.8 Hz, 1H), 1.84 (tt, J=8.4, 5.1 Hz, 1H), 0.97-0.77 (m, 2H), 0.51-0.37 (m, 2H); LCMS (Method A) $t_R$=1.51 min, m/z=427.8, 429.8 [M+H]$^+$; Purity (AUC) ≥95%.

Example J69: 3-((5-Bromo-2-methoxyphenyl)sulfonamido)-5-cyclopropyl-2-hydroxybenzoic acid

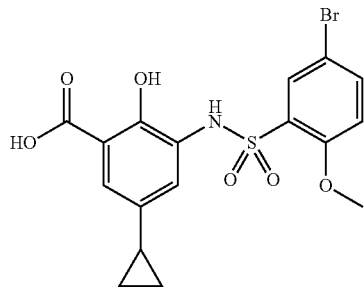 [SMILES: COc1ccc(Br)cc1S(=O)(=O)Nc1cc(C2CC2)cc(C(=O)O)c1O]

Using a procedure analogous to General Procedure E followed by General Procedure F, starting with methyl 3-amino-5-cyclopropyl-2-hydroxybenzoate, which was prepared by a procedure analogous to the procedure used to prepare Example J68 Step D, and 5-bromo-4-chloro-2-methoxybenzenesulfonyl chloride, which was prepared by a procedure analogous to the procedure used to prepare Example J2 Step A, the title compound was obtained. $^1$H NMR (400 MHz, DMSO-d$_6$) δ$_H$ 9.18 (s, 1H), 7.77 (dd, J=8.8, 2.6 Hz, 1H), 7.73 (d, J=2.6 Hz, 1H), 7.32 (d, J=2.3 Hz, 1H), 7.18 (d, J=8.9 Hz, 1H), 7.08 (d, J=2.3 Hz, 1H), 3.82 (s, 3H), 1.92-1.81 (m, 1H), 0.95-0.85 (m, 2H), 0.53-0.41 (m, 2H); LCMS (Method A) $t_R$=1.68 min, m/z=441.9, 443.8 [M+H]$^+$; Purity (AUC) ≥95%.

Example J70: 3-((5-Bromo-3-chloro-2-hydroxyphenyl)sulfonamido)-5-cyclopropyl-2-hydroxybenzoic acid

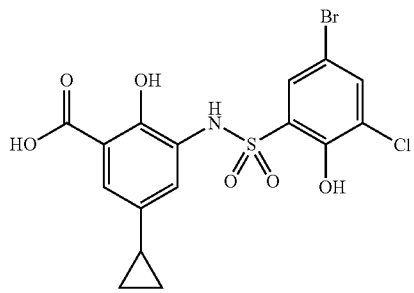 [SMILES: O=C(O)c1cc(C2CC2)cc(NS(=O)(=O)c2cc(Br)cc(Cl)c2O)c1O]

Step A: Methyl 3-((5-bromo-3-chloro-2-hydroxyphenyl)sulfonamido)-5-cyclopropyl-2-hydroxybenzoate. Using a procedure analogous to General Procedure E, starting with methyl 3-amino-5-cyclopropyl-2-hydroxybenzoate, which was prepared by a procedure analogous to the procedure used to prepare Example J68 Step D (41 mg, 0.20 mmol) and 5-bromo-4-chloro-2-methoxybenzenesulfonyl chloride, which was prepared by a procedure analogous to the procedure used to prepare Example J4 Step A, methyl 3-((5-bromo-3-chloro-2-hydroxyphenyl)sulfonamido)-5-cyclopropyl-2-hydroxybenzoate was obtained as a colorless solid (76 mg, 0.16 mmol, 80%). $^1$H NMR (400 MHz, DMSO-d$_6$) δ$_H$ 10.62 (s, 1H), 9.42 (s, 1H), 7.93 (d, J=2.5 Hz, 1H), 7.67 (d, J=2.4 Hz, 1H), 7.34 (d, J=2.3 Hz, 1H), 7.09 (d, J=2.3 Hz, 1H), 3.88 (s, 3H), 1.89 (ddt, J=13.5, 8.5, 4.3 Hz, 1H), 1.03-0.76 (m, 2H), 0.61-0.32 (m, 2H); LCMS (Method A) $t_R$=1.76 min, m/z=475.8, 477.7 [M+H]$^+$; Purity (AUC) ≥95%.

Step B: 3-((5-Bromo-3-chloro-2-hydroxyphenyl)sulfonamido)-5-cyclopropyl-2-hydroxybenzoic acid. Using a procedure analogous to General Procedure F, starting with methyl 3-((5-bromo-3-chloro-2-hydroxyphenyl)sulfonamido)-5-cyclopropyl-2-hydroxybenzoate (24 mg, 0.05 mmol), the tide compound was obtained as a colorless solid (19 mg, 82%). $^1$H NMR (400 MHz, MeOH-d$_4$) δ$_H$ 7.61 (dd, J=2.4, 1.7 Hz, 1H), 7.53 (dd, J=10.1, 2.4 Hz, 1H), 7.39 (d, J=2.1 Hz, 1H), 7.30 (d, J=2.3 Hz, 1H), 1.85 (tt, J=8.4, 5.1 Hz, 1H), 0.98-0.90 (m, 2H), 0.59-0.52 (m, 2H); LCMS (Method A) $t_R$=1.53 min, m/z=462.8, 464.8 [M+H]$^+$; Purity (AUC) ≥95%.

Example J71: 3-((5-Bromo-4-chloro-2-methoxyphenyl)sulfonamido)-5-cyclopropyl-2-hydroxybenzoic acid

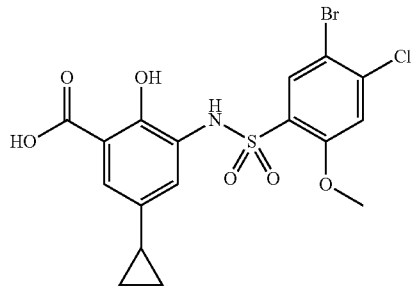 [SMILES: COc1cc(Cl)c(Br)cc1S(=O)(=O)Nc1cc(C2CC2)cc(C(=O)O)c1O]

Using a procedure analogous to General Procedure E followed by General Procedure F, starting with methyl 3-amino-5-cyclopropyl-2-hydroxybenzoate, which was prepared by a procedure analogous to the procedure used to prepare Example J68 Step D, and 5-bromo-4-chloro-2-methoxybenzenesulfonyl chloride, which was prepared by a procedure analogous to the procedure used to prepare Example J7 Step A, the title compound was obtained. LCMS (Method A) $t_R$=1.67 min, m/z=475.8, 477.7 [M+H]$^+$; Purity (AUC) ≥95%.

Example J72: 3-((5-Bromo-4-fluoro-2-methoxyphenyl)sulfonamido)-5-cyclopropyl-2-hydroxybenzoic acid

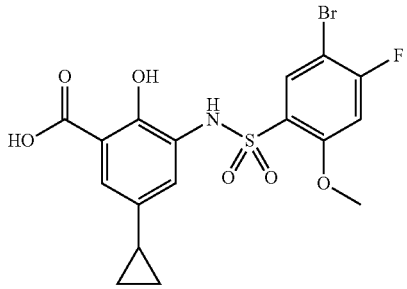 [SMILES: COc1cc(F)c(Br)cc1S(=O)(=O)Nc1cc(C2CC2)cc(C(=O)O)c1O]

Using a procedure analogous to General Procedure E followed by General Procedure F, starting with methyl 3-amino-5-cyclopropyl-2-hydroxybenzoate, which was prepared by a procedure analogous to the procedure used to prepare Example J68 Step D, and 5-bromo-4-chloro-2-methoxybenzenesulfonyl chloride, which was prepared by a procedure analogous to the procedure used to prepare Example J8 Step A, the title compound was obtained. LCMS (Method A) $t_R$=1.62 min, m/z=459.7, 461.8 [M+H]$^+$; Purity (AUC) ≥95%.

Example J73: 3-((5-Bromo-2-(cyclopropylamino)phenyl)sulfonamido)-5-cyclopropyl-2-hydroxybenzoic acid

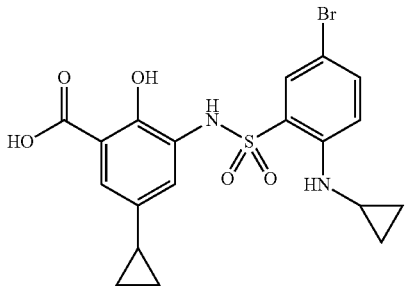 [SMILES: O=C(O)c1cc(C2CC2)cc(NS(=O)(=O)c2cc(Br)ccc2NC2CC2)c1O]

Step A: Methyl 3-amino-2-(benzyloxy)-5-cyclopropylbenzoate. Methyl 2-(benzyloxy)-5-cyclopropyl-3-nitrobenzoate, which was prepared by a procedure analogous to the procedure used to prepare Example J68 Step C (972 mg, 2.97 mmol) was dissolved in a mixture of MeOH (15 mL) and glacial acetic acid (1.5 mL), and Zinc powder (971 mg, 14.85 mmol) was added. The mixture was stirred at r.t. for 16 h, then filtered and concentrated. The concentrated was re-dissolved in $CH_2Cl_2$ and washed with saturated aqueous $NaHCO_3$ to afford methyl 3-amino-2-(benzyloxy)-5-cyclopropylbenzoate as a crude yellow oil (880 mg, quant.), which was used without purification. LCMS (Method A) $t_R$=1.49 min, m/z=298.1 [M+H]$^+$; Purity (AUC) ≥95%.

Step B: Methyl 2-(benzyloxy)-3-((5-bromo-2-fluorophenyl)sulfonamido)-5-cyclopropylbenzoate. Using a procedure analogous to General Procedure E, starting with the crude methyl 3-amino-2-(benzyloxy)-5-cyclopropylbenzoate (880 mg, 2.97 mmol) and 5-bromo-2-fluorobenzenesulfonyl chloride, methyl 2-(benzyloxy)-3-((5-bromo-2-fluorophenyl)sulfonamido)-5-cyclopropylbenzoate was obtained as a pale orange solid (1.42 g, 2.65 mmol, 89%).

Step C: 3-((5-Bromo-2-((cyclopropylmethyl)amino)phenyl)sulfonamido)-5-cyclopropyl-2-hydroxybenzoic acid. Methyl 2-(benzyloxy)-3-((5-bromo-2-fluorophenyl)sulfonamido)-5-cyclopropylbenzoate (53 mg, 0.10 mmol), cyclopropylamine (35 µL, 0.50 mmol) and triethylamine (70 µL, 0.50 mmol) were combined in 1,4-dioxane and heated at 110° C. in a sealed tube for 16 h. Upon cooling, the reaction was concentrated in vacuo and re-dissolved in anhydrous $CH_2Cl_2$, under an inert atmosphere, and cooled to −78° C. in an acetone/dry ice bath. $BBr_3$ (1.0 M in DCM, 0.2 mL, 0.2 mmol) was added drop-wise, and the mixture stirred for 1 h, then warmed to r.t. The mixture was washed with $H_2O$ and concentrated. The resultant crude oil was dissolved in THF (1 mL) and LiOH (2 M, 1 mL) added, the mixture was stirred for 16 h at 65° C. The solution was acidified to pH ~1 with 1M HCl and extracted with EtOAc. Purification by reverse-phase HPLC afforded the title compound was obtained as a colorless solid (5 mg, 0.01 mmol, 10/6); LCMS (Method A) $t_R$=1.73 min, m/z=465.8, 467.8 [M+H]$^+$; Purity (AUC) ≥95%.

Example J74: 3-((5-Bromo-2-(isobutylamino)phenyl)sulfonamido)-5-cyclopropyl-2-hydroxybenzoic acid

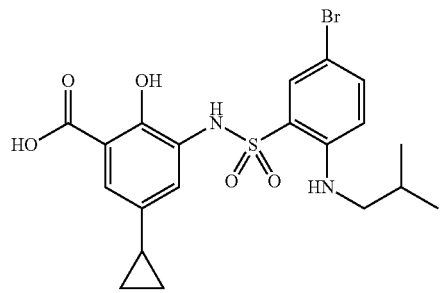 [SMILES: CC(C)CNc1ccc(Br)cc1S(=O)(=O)Nc1cc(C2CC2)cc(C(=O)O)c1O]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and sec-butylamine, the title compound (5 mg, 10%) was obtained. LCMS (Method A) $t_R$=1.82 min, m/z=482.8, 484.9 [M+H]$^+$; Purity (AUC) ≥95%.

Example J75: (R)-3-((5-Bromo-2-((3-methylbutan-2-yl)amino)phenyl)sulfonamido)-5-cyclopropyl-2-hydroxybenzoic acid

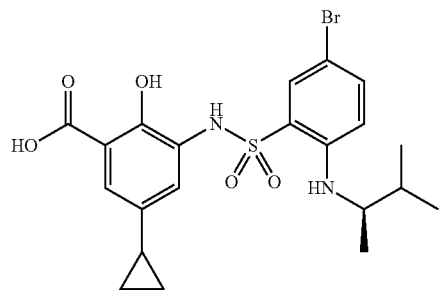 [SMILES: CC(C)[C@@H](C)Nc1ccc(Br)cc1S(=O)(=O)Nc1cc(C2CC2)cc(C(=O)O)c1O]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and (R)-2-amino-3-methylbutane, The title compound (3 mg, 6%) was obtained. LCMS (Method A) $t_R$=1.88 min, m/z=496.9, 498.9 [M+H]$^+$; Purity (AUC) ≥95%.

Example J76: (S)-3-((5-Bromo-2-((3-methylbutan-2-yl)amino)phenyl)sulfonamido)-5-cyclopropyl-2-hydroxybenzoic acid

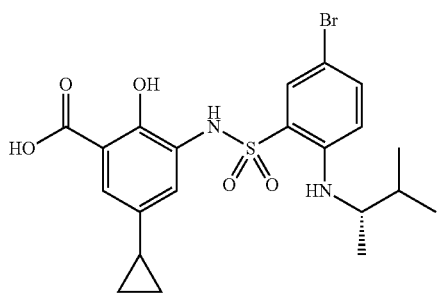 [SMILES: CC(C)[C@H](C)Nc1ccc(Br)cc1S(=O)(=O)Nc1cc(C2CC2)cc(C(=O)O)c1O]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and (S)-2-amino-3-methylbutane, the title compound (6 mg, 12%) was obtained. LCMS (Method A) $t_R$=1.88 min, m/z=496.9, 498.9 [M+H]$^+$; Purity (AUC) ≥95%.

Example J77: (R)-3-((5-Bromo-2-((1-cyclopropylethyl)amino)phenyl)sulfonamido)-5-cyclopropyl-2-hydroxybenzoic acid

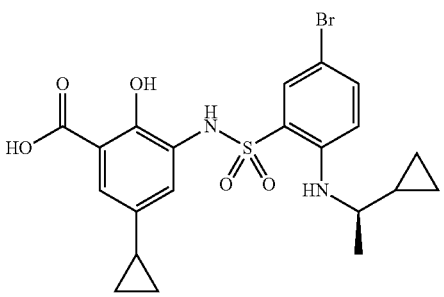 [SMILES: C[C@@H](Nc1ccc(Br)cc1S(=O)(=O)Nc1cc(C2CC2)cc(C(=O)O)c1O)C1CC1]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and (R)-1-cyclopropylethylamine, the title compound (7 mg, 14%) was obtained. LCMS (Method A) $t_R$=1.82 min, m/z=494.8, 496.9 [M+H]$^+$; Purity (AUC) ≥95%.

Example J78: (R)-3-((5-Bromo-2-(2-(methoxymethyl)pyrrolidin-1-yl)phenyl)sulfonamido)-5-cyclopropyl-2-hydroxybenzoic acid

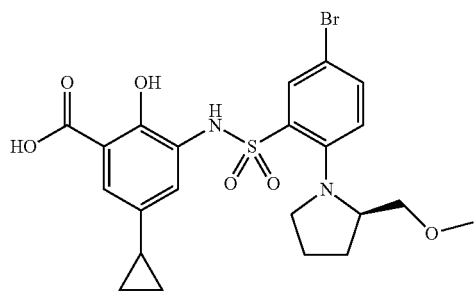 [SMILES: COC[C@H]1CCCN1c1ccc(Br)cc1S(=O)(=O)Nc1cc(C2CC2)cc(C(=O)O)c1O]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and D-prolinol methyl ether, the title compound (2 mg, 4%) was prepared. LCMS (Method A) $t_R$=1.76 min, m/z=524.8, 526.9 [M+H]$^+$; Purity (AUC) ≥95%.

Example J79: 3-((5-Bromo-2-((cyclopropylmethyl)amino)phenyl)sulfonamido)-5-cyclopropyl-2-hydroxybenzoic acid

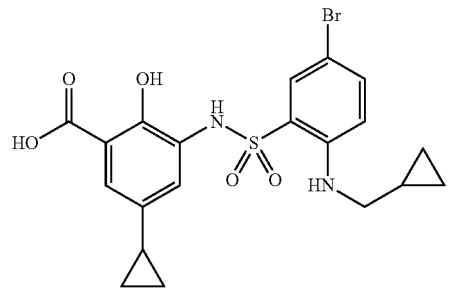 [SMILES: O=C(O)c1cc(C2CC2)cc(NS(=O)(=O)c2cc(Br)ccc2NCC2CC2)c1O]

Using a procedure analogous to the procedure used to prepare Example J73 Step C, starting from methyl 2-(benzyloxy)-3-((5-bromo-2-fluorophenyl)sulfonamido)-5-cyclopropylbenzoate (53 mg, 0.10 mmol) and cyclopropylmethanamine, the title compound (5 mg, 10%) was prepared. LCMS (Method A) $t_R$=1.78 min, m/z=480.9, 482.8 [M+H]$^+$; Purity (AUC) ≥95%.

Example J80: 3-((5-Bromo-2-hydroxyphenyl)sulfonamido)-5-cyclopropyl-2-hydroxybenzamide

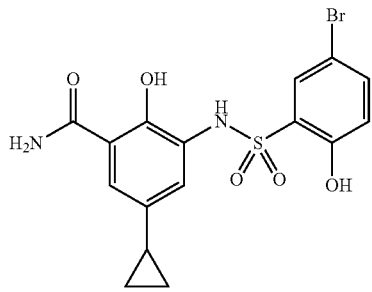 [SMILES: NC(=O)c1cc(C2CC2)cc(NS(=O)(=O)c2cc(Br)ccc2O)c1O]

Methyl 3-((5-bromo-2-hydroxyphenyl)sulfonamido)-5-cyclopropyl-2-hydroxybenzoate, which was prepared by a procedure analogous to the procedure used to prepare example J68 Step E: 22 mg, 0.05 mmol) was dissolved in ammonia (7 N in MeOH, 0.5 mL) and heated under microwave irradiation at 110° C. for 1 h, then heated at reflux for 16 h. The solvent was concentrated and crude material purified by preparative HPLC to afford the title compound as a colorless solid (8 mg, 37%). $^1$H NMR (400 MHz, MeOH-d$_4$) δ$_H$ 7.76 (d, J=2.5 Hz, 1H), 7.50 (dd, J=8.7, 2.5 Hz, 1H), 7.26 (d, J=2.1 Hz, 1H), 7.23 (d, J=2.1 Hz, 1H), 6.84 (d, J=8.7 Hz, 1H), 1.87-1.78 (m, 1H), 0.96-0.89 (m, 2H), 0.62-0.54 (m, 2H); LCMS (Method A) t$_R$=1.42 min, m/z=426.8, 428.8 [M+H]$^+$; Purity (AUC) ≥95%.

Example J81: 3-((5-Bromo-2-hydroxyphenyl)sulfonamido)-5-cyclopropyl-2-hydroxy-N-methylbenzamide

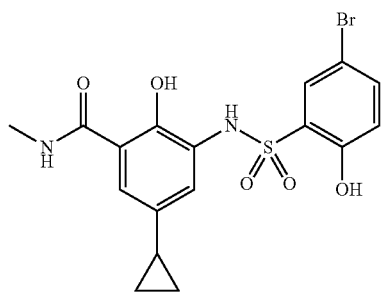 [SMILES: CNC(=O)c1cc(C2CC2)cc(NS(=O)(=O)c2cc(Br)ccc2O)c1O]

Using a procedure analogous to General Procedure G, starting with methyl 3-((5-bromo-2-hydroxyphenyl)sulfonamido)-5-cyclopropyl-2-hydroxybenzoate, which was prepared by a procedure analogous the procedure used to prepare Example J68 Step E (22 mg, 0.05 mmol) and methylamine, the title compound was obtained as an off-white solid (15 mg, 68%). 1H NMR (400 MHz, MeOH-d$_4$) δ$_H$ 7.76 (d, J=2.5 Hz, 1H), 7.51 (dd, J=8.8, 2.5 Hz, 1H), 7.22 (d, J=2.1 Hz, 1H), 7.18 (d, J=2.0 Hz, 1H), 6.84 (d, J=8.8 Hz, 1H), 2.88 (s, 3H), 1.88-1.76 (m, 1H), 0.95-0.89 (m, 2H), 0.61-0.55 (m, 2H); LCMS (Method A) t$_R$=1.52 min, m/z=440.8, 442.8 [M+H]$^+$; Purity (AUC) ≥95%.

Example J82: 3-((5-Bromo-2-hydroxyphenyl)sulfonamido)-5-cyclopropyl-2-hydroxy-N-(2-hydroxyethyl)-N-methylbenzamide

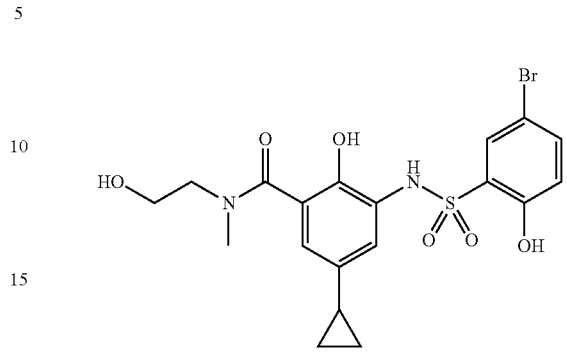

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to to the procedure used to prepare Example J68 Step E (22 mg, 0.05 mmol) and (2-methylamine)ethanol, the title compound was obtained as a colorless solid (18 mg, 74%). $^1$H NMR (400 MHz, MeOH-d$_4$) δ$_H$ 7.70 (d, J=2.5 Hz, 1H), 7.55 (dd, J=8.7, 2.5 Hz, 1H), 6.90 (d, J=8.7 Hz, 1H), 6.90 (d, J=2.3 Hz, 1H), 6.80 (d, J=2.3 Hz, 1H), 3.68 (s, 3H), 3.16-2.88 (m, 4H), 1.78 (tt, J=8.4, 5.1 Hz, 1H), 0.93-0.83 (m, 2H), 0.52-0.43 (m, 2H); LCMS (Method A) t$_R$=1.33 min, m/z=484.8, 486.8 [M+H]$^+$; Purity (AUC) ≥95%.

Example J83: 3-((5-Bromo-2-hydroxyphenyl)sulfonamido)-5-cyclopropyl-2-hydroxy-N-(2-methoxyethyl)-N-methylbenzamide

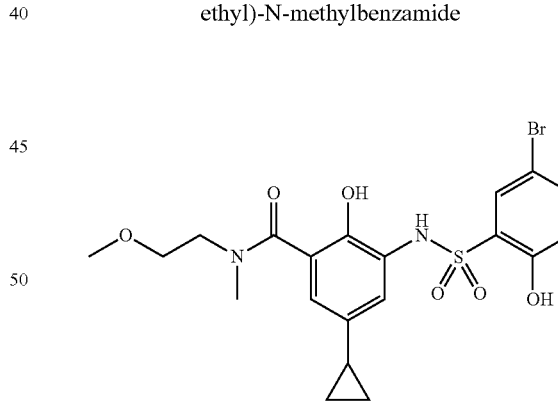

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and 2-methoxy-N-methylethan-1-amine, the title compound was obtained as a colorless solid (12 mg, 45%). LCMS (Method A) t$_R$=1.42 min, m/z=498.9, 500.8 [M+H]$^+$; Purity (AUC) ≥95%.

Example J84: 3-((5-Bromo-2-hydroxyphenyl)sulfonamido)-5-cyclopropyl-2-hydroxy-N-(2-morpholinoethyl)benzamide

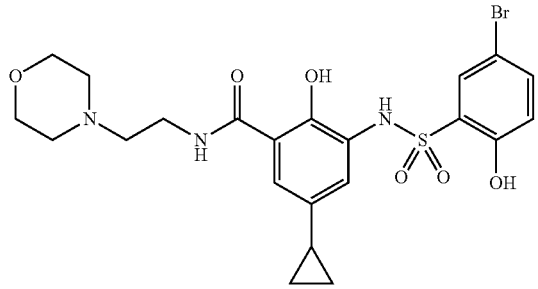 [SMILES: O=C(NCCN1CCOCC1)c1cc(C2CC2)cc(NS(=O)(=O)c2cc(Br)ccc2O)c1O]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and 2-morpholinoethan-1-amine, the title compound was obtained as a colorless solid (15 mg, 55%) as free base. $^1$H NMR (400 MHz, MeOH-d$_4$) $\delta_H$ 7.75 (d, J=2.5 Hz, 1H), 7.49 (dd, J=8.8, 2.5 Hz, 1H), 7.24 (d, J=2.1 Hz, 1H), 7.22 (d, J=2.1 Hz, 1H), 6.83 (d, J=8.8 Hz, 1H), 3.77-3.67 (m, 4H), 3.52 (t, J=6.7 Hz, 2H), 2.60 (t, J=6.6 Hz, 2H), 2.58-2.50 (m, 4H), 1.90-1.77 (m, 1H), 0.97-0.87 (m, 2H), 0.63-0.54 (m, 2H); LCMS (Method A) t$_R$=1.33 min, m/z=539.8, 541.8 [M+H]$^+$; Purity (AUC) ≥95%.

Example J85: 5-Bromo-N-(5-cyclopropyl-2-hydroxy-3-(morpholine-4-carbonyl)phenyl)-2-hydroxybenzenesulfonamide

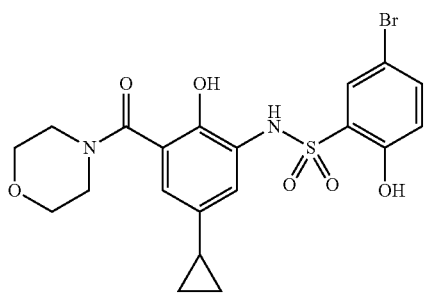 [SMILES: O=C(c1cc(C2CC2)cc(NS(=O)(=O)c2cc(Br)ccc2O)c1O)N1CCOCC1]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and morpholine, the title compound was obtained as a colorless solid (14 mg, 56%). LCMS (Method A) t$_R$=1.34 min, m/z=496.8, 498.8 [M+H]$^+$; Purity (AUC) ≥95%.

Example J86: 3-((5-Bromo-2-hydroxyphenyl)sulfonamido)-5-cyclopropyl-2-hydroxy-N-(2-methoxyethyl)benzamide

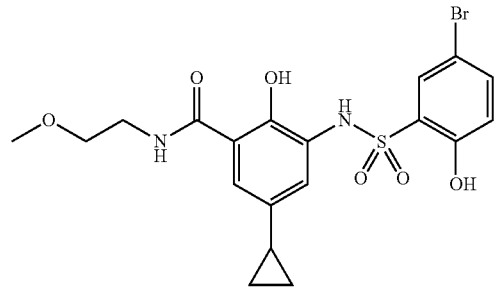 [SMILES: COCCNC(=O)c1cc(C2CC2)cc(NS(=O)(=O)c2cc(Br)ccc2O)c1O]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and 2-methoxyethylamine, the title compound was obtained as a colorless solid (16 mg, 66%). $^1$H NMR (400 MHz, MeOH-d$_4$) $\delta_H$ 7.76 (d, J=2.5 Hz, 1H), 7.51 (dd, J=8.7, 2.5 Hz, 1H), 7.24 (d, J=2.1 Hz, 1H), 7.22 (d, J=2.1 Hz, 1H), 6.85 (d, J=8.7 Hz, 1H), 3.56-3.52 (m, 4H), 3.38 (s, 3H), 1.83 (tt, J=8.5, 5.1 Hz, 1H), 0.96-0.88 (m, 2H), 0.58 (dt, J=6.5, 4.6 Hz, 2H); LCMS (Method A) t$_R$=1.54 min, m/z=484.8, 486.8 [M+H]$^+$; Purity (AUC) ≥95%.

Example J87: 3-((5-Bromo-2-hydroxyphenyl)sulfonamido)-5-cyclopropyl-2-hydroxy-N-(2-hydroxyethyl)benzamide

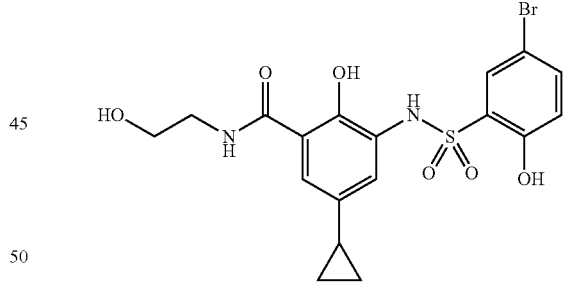

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and ethanolamine, the title compound was obtained as a colorless solid (13 mg, 55%). $^1$H NMR (400 MHz, MeOH-d$_4$) $\delta_H$ 7.75 (d, J=2.5 Hz, 1H), 7.49 (dd, J=8.8, 2.6 Hz, 1H), 7.27 (d, J=2.1 Hz, 1H), 7.22 (d, J=2.1 Hz, 1H), 6.83 (d, J=8.8 Hz, 1H), 3.69 (t, J=5.8 Hz, 2H), 3.48 (t, J=5.8 Hz, 2H), 1.91-1.76 (m, 1H), 0.96-0.87 (m, 2H), 0.65-0.53 (m, 2H); LCMS (Method A) t$_R$=1.42 min, m/z=470.8, 472.8 [M+H]$^+$; Purity (AUC) ≥95%.

Example J88: 3-((5-Bromo-2-hydroxyphenyl)sulfonamido)-5-cyclopropyl-2-hydroxy-N-(3-methoxypropyl)benzamide

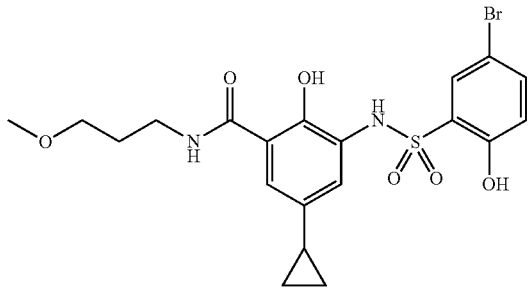 [SMILES: COCCCNC(=O)c1cc(C2CC2)cc(NS(=O)(=O)c2cc(Br)ccc2O)c1O]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and 3-methoxypropylamine, the title compound was obtained as a colorless solid (14 mg, 56%). $^1$H NMR (400 MHz, MeOH-d$_4$) $\delta_H$ 7.76 (d, J=2.5 Hz, 1H), 7.51 (dd, J=8.8, 2.5 Hz, 1H), 7.22 (d, J=2.1 Hz, 1H), 7.20 (d, J=2.1 Hz, 1H), 6.85 (d, J=8.8 Hz, 1H), 3.47 (t, J=6.1 Hz, 2H), 3.42 (t, J=7.0 Hz, 2H), 3.35 (s, 3H), 1.90-1.78 (m, 3H), 0.95-0.88 (m, 2H), 0.62-0.53 (m, 2H); LCMS (Method A) t$_R$=1.59 min, m/z=498.9, 500.8 [M+H]$^+$; Purity (AUC) ≥95%.

Example J89: 5-Bromo-2-hydroxyphenyl)sulfonamido)-5-cyclopropyl-N-(2-(dimethylamino)ethyl)-2-hydroxybenzamide

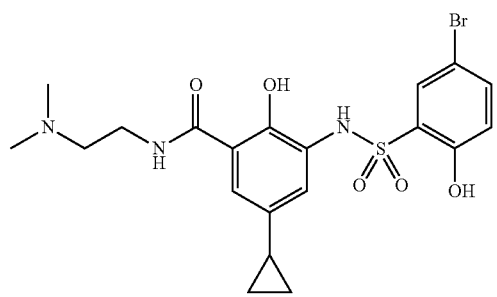 [SMILES: CN(C)CCNC(=O)c1cc(C2CC2)cc(NS(=O)(=O)c2cc(Br)ccc2O)c1O]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and dimethylamine ethylamine, the title compound was obtained as a colorless solid (13 mg, 52%) as free base. $^1$H NMR (400 MHz, MeOH-d$_4$) $\delta_H$ 7.75 (d, J=2.5 Hz, 1H), 7.48 (dd, J=8.8, 2.5 Hz, 1H), 7.27 (d, J=2.1 Hz, 1H), 7.22 (d, J=2.1 Hz, 1H), 6.82 (d, J=8.8 Hz, 1H), 3.62 (t, J=6.2 Hz, 2H), 2.95 (t, J=6.2 Hz, 2H), 2.63 (s, 6H), 1.88-1.76 (m, 1H), 0.97-0.87 (m, 2H), 0.66-0.51 (m, 2H); LCMS (Method A) t$_R$=1.35 min, m/z=497.8, 499.8 [M+H]$^+$; Purity (AUC) ≥95%.

Example J90: 3-((5-Bromo-2-hydroxyphenyl)sulfonamido)-5-cyclopropyl-2-hydroxy-N-(tetrahydrofuran-3-yl)benzamide

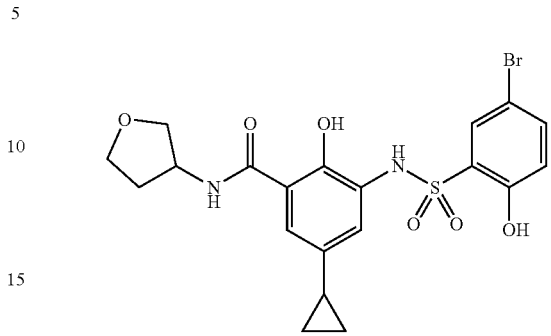

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and 3-aminotetrahydrofuran, the title compound was obtained as a colorless solid (15 mg, 60%). $^1$H NMR (400 MHz, MeOH-d$_4$) $\delta_H$ 7.76 (d, J=2.5 Hz, 1H), 7.51 (dd, J=8.8, 2.5 Hz, 1H), 7.33 (d, J=2.1 Hz, 1H), 7.21 (d, J=2.1 Hz, 1H), 6.85 (d, J=8.8 Hz, 1H), 4.57 (ddt, J=8.2, 6.0, 4.2 Hz, 1H), 4.03-3.92 (m, 2H), 3.83 (td, J=8.2, 6.0 Hz, 1H), 3.71 (dd, J=9.2, 4.2 Hz, 1H), 2.29 (dtd, J=12.9, 8.0, 6.6 Hz, 1H), 2.05-1.96 (m, 1H), 1.83 (tt, J=8.4, 5.1 Hz, 1H), 1.01-0.84 (m, 3H), 0.75-0.48 (m, 3H); LCMS (Method A) t$_R$=1.54 min, m/z=496.8, 498.8 [M+H]$^+$; Purity (AUC) ≥95%.

Example J91: 3-((5-Bromo-2-hydroxyphenyl)sulfonamido)-5-cyclopropyl-2-hydroxy-N-(3-hydroxypropyl)benzamide

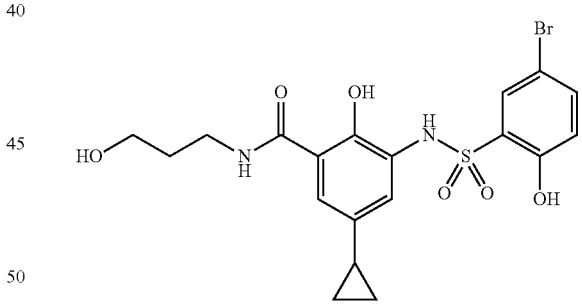

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (22 mg, 0.05 mmol) and propanolamine, the title compound was obtained as a colorless solid (12 mg, 49%). $^1$H NMR (400 MHz, DMSO-d$_6$) $\delta_H$ 11.30 (s, 1H), 8.92 (t, J=5.6 Hz, 1H), 8.63 (s, 1H), 7.69 (d, J=2.6 Hz, 1H), 7.58 (dd, J=8.8, 2.6 Hz, 1H), 7.31 (d, J=2.1 Hz, 1H), 7.09 (d, J=2.1 Hz, 1H), 6.92 (d, J=8.8 Hz, 1H), 4.49 (s, 1H), 4.03 (s, 1H), 3.45 (t, J=6.2 Hz, 2H), 3.34-3.30 (m, 2H), 1.83-1.74 (m, 1H), 1.73-1.63 (m, 2H), 0.92-0.85 (m, 2H), 0.55-0.48 (m, 2H); LCMS (Method A) t$_R$=1.45 min, m/z=484.8, 486.8 [M+H]$^+$; Purity (AUC) ≥95%.

Example J92: 5-Bromo-N-(5-cyclopropyl-2-hydroxy-3-(4-methylpiperazine-1-carbonyl)phenyl)-2-hydroxybenzenesulfonamide

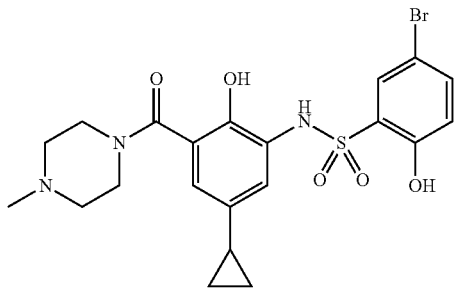 [SMILES: CN1CCN(C(=O)c2cc(C3CC3)cc(NS(=O)(=O)c3cc(Br)ccc3O)c2O)CC1]

Using a procedure analogous to General Procedure H, starting with methyl 3-((5-bromo-2-hydroxyphenyl)sulfonamido)-5-cyclopropyl-2-hydroxybenzoate, which was prepared by a procedure analogous to the procedure used to prepare Example J68 Step E (21 mg, 0.05 mmol) and N-methylpiperazine, the title compound was obtained as a colorless solid (10 mg, 39%). LCMS (Method A) $t_R$=1.21 min, m/z=509.8, 511.8 [M+H]$^+$; Purity (AUC) ≥95%.

Example J93: 3-((5-Bromo-2-hydroxyphenyl)sulfonamido)-5-cyclopropyl-2-hydroxy-N-(oxetan-3-yl)benzamide

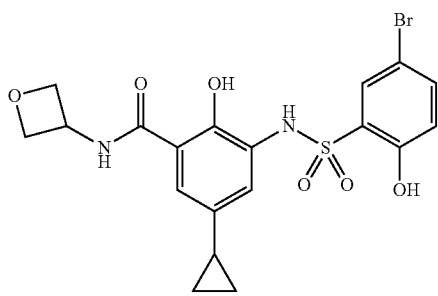 [SMILES: O=C(NC1COC1)c1cc(C2CC2)cc(NS(=O)(=O)c2cc(Br)ccc2O)c1O]

Using a procedure analogous to General Procedure H, starting with 3-((5-bromo-2-hydroxyphenyl)sulfonamido)-5-cyclopropyl-2-hydroxybenzoic acid, which was prepared by a procedure analogous to the procedure used to prepare Example J68 (21 mg, 0.05 mmol) and 3-aminooxetane, the title compound was obtained as a colorless solid (10 mg, 41%). $^1$H NMR (400 MHz, MeOH-d$_4$) $\delta_H$ 7.73 (d, J=2.6 Hz, 1H), 7.45 (dd, J=8.8, 2.6 Hz, 1H), 7.36 (d, J=2.2 Hz, 1H), 7.21 (d, J=2.2 Hz, 1H), 6.79 (d, J=8.8 Hz, 1H), 5.11 (p, J=7.0 Hz, 1H), 4.92 (t, J=7.0 Hz, 2H), 4.71 (t, J=7.0 Hz, 2H), 1.89-1.78 (m, 1H), 0.96-0.87 (m, 2H), 0.62-0.56 (m, 2H); LCMS (Method A) $t_R$=1.56 min, m/z=482.8, 484.8 [M+H]$^+$; Purity (AUC) ≥95%.

Example J94: 3-((5-Bromo-3-chloro-2-hydroxyphenyl)sulfonamido)-5-cyclopropyl-2-hydroxybenzamide

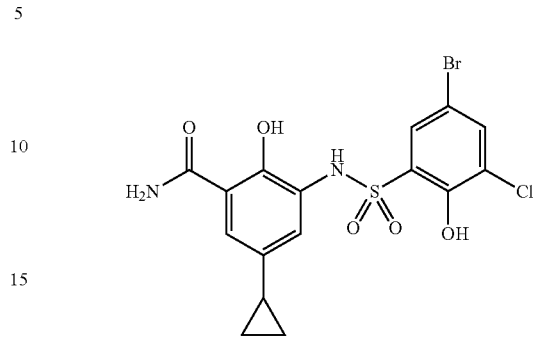

Methyl 3-((5-bromo-3-chloro-2-hydroxyphenyl)sulfonamido)-5-cyclopropyl-2-hydroxybenzoate, which was prepared by a procedure analogous to the procedure used to prepare Example J70 Step A (20 mg, 0.04 mmol) was dissolved in ammonia (7 N in MeOH, 0.5 mL) and heated at reflux in a sealed tube for 16 h. The solvent was concentrated and crude material purified by preparative HPLC to afford the title compound as a colorless solid (8 mg, 37%). $^1$H NMR (400 MHz, MeOH-d$_4$) $\delta_H$ 7.72 (d, J=2.4 Hz, 1H), 7.69 (d, J=2.4 Hz, 1H), 7.31 (d, J=2.1 Hz, 1H), 7.26 (d, J=2.1 Hz, 1H), 1.92-1.82 (m, 1H), 1.00-0.87 (m, 2H), 0.70-0.55 (m, 2H); LCMS (Method A) $t_R$=1.55 min, m/z=460.8, 462.8 [M+H]$^+$; Purity (AUC) ≥95%.

Example J95: 3-((5-Bromo-3-chloro-2-hydroxyphenyl)sulfonamido)-5-cyclopropyl-2-hydroxy-N-methylbenzamide

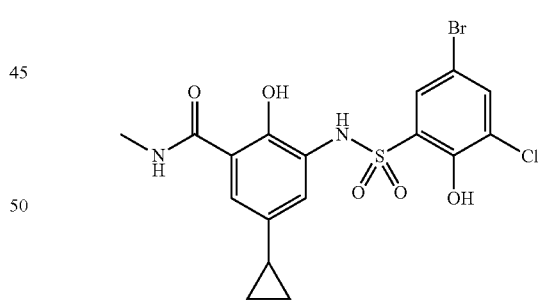

Using a procedure analogous to General Procedure G, starting with methyl 3-((5-bromo-3-chloro-2-hydroxyphenyl)sulfonamido)-5-cyclopropyl-2-hydroxybenzoate, which was prepared by a procedure analogous to the procedure used to prepare Example J70 Step A (20 mg, 0.04 mmol) and methylamine, the title compound was obtained as a colorless solid (17 mg, 72%). $^1$H NMR (400 MHz, MeOH-d$_4$) $\delta_H$ 7.70 (d, J=2.4 Hz, 1H), 7.68 (d, J=2.5 Hz, 1H), 7.25 (d, J=2.1 Hz, 1H), 7.23 (d, J=2.1 Hz, 1H), 2.88 (s, 3H), 1.91-1.79 (m, 1H), 1.01-0.87 (m, 2H), 0.60 (dt, J=6.5, 4.6 Hz, 2H); LCMS (Method A) $t_R$=1.63 min, m/z=474.7, 476.7 [M+H]$^+$; Purity (AUC) ≥95%.

Example J96: 3-((5-Bromo-3-chloro-2-hydroxyphenyl)sulfonamido)-5-cyclopropyl-2-hydroxy-N-(2-methoxyethyl)benzamide

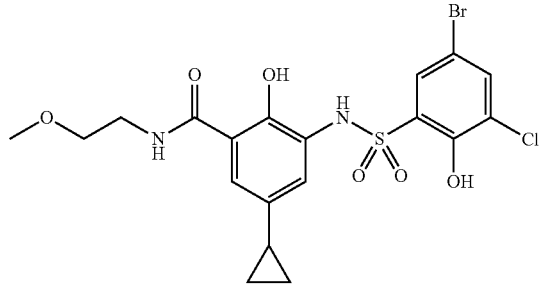 [SMILES: COCCNC(=O)c1cc(C2CC2)cc(NS(=O)(=O)c2cc(Br)cc(Cl)c2O)c1O]

Using a procedure analogous to General Procedure H, starting with methyl 3-((5-bromo-3-chloro-2-hydroxyphenyl)sulfonamido)-5-cyclopropyl-2-hydroxybenzoate, which was prepared by a procedure analogous to the procedure used to prepare Example J70 Step A (20 mg, 0.04 mmol) and 2-methoxyethylamine, the title compound was obtained as a colorless solid (16 mg, 62%). $^1$H NMR (400 MHz, MeOH-d$_4$) $\delta_H$ 7.71 (d, J=2.5 Hz, 1H), 7.68 (d, J=2.5 Hz, 1H), 7.31 (d, J=2.1 Hz, 1H), 7.23 (d, J=2.1 Hz, 1H), 3.57-3.52 (m, 4H), 3.38 (s, 3H), 1.86 (tt, J=8.4, 5.1 Hz, 1H), 0.98-0.89 (m, 2H), 0.65-0.59 (m, 2H); LCMS (Method A) t$_R$=1.65 min, m/z=518.8, 520.8 [M+H]$^+$; Purity (AUC) ≥95%.

Example J97: (S)-3-((5-Bromo-3-chloro-2-hydroxyphenyl)sulfonamido)-5-cyclopropyl-2-hydroxy-N-(tetrahydrofuran-3-yl)benzamide

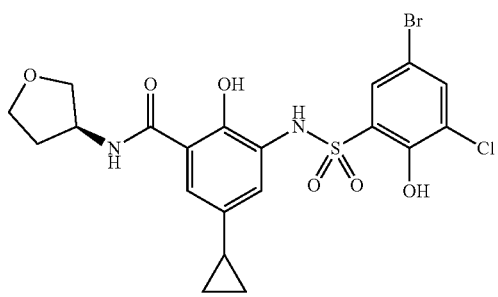 [SMILES: O=C(N[C@H]1CCOC1)c1cc(C2CC2)cc(NS(=O)(=O)c2cc(Br)cc(Cl)c2O)c1O]

Using a procedure analogous to General Procedure H, starting with 3-((5-bromo-3-chloro-2-hydroxyphenyl)sulfonamido)-5-cyclopropyl-2-hydroxybenzoic acid, which was prepared by a procedure analogous to the procedure used to prepare Example J70 (23 mg, 0.05 mmol) and 3-aminotetrahydrofuran, the title compound was obtained as a colorless solid (9 mg, 34%). $^1$H NMR (400 MHz, MeOH-d$_4$) $\delta_H$ 7.71 (d, J=2.5 Hz, 1H), 7.67 (d, J=2.4 Hz, 1H), 7.39 (d, J=2.1 Hz, 1H), 7.23 (d, J=2.1 Hz, 1H), 4.61-4.53 (m, 1H), 4.04-3.92 (m, 2H), 3.83 (td, J=8.3, 6.0 Hz, 1H), 3.72 (dd, J=9.2, 4.1 Hz, 1H), 2.36-2.23 (m, 1H), 2.07-1.96 (m, 1H), 1.91-1.82 (m, 1H), 0.97-0.88 (m, 2H), 0.66-0.58 (m, 2H); LCMS (Method A) t$_R$=1.74 min, m/z=530.7 532.8 [M+H]$^+$; Purity (AUC) ≥95%.

Example J98: 3-((5-Bromo-3-fluoro-2-hydroxyphenyl)sulfonamido)-5-cyclopropyl-2-hydroxy-N-methylbenzamide

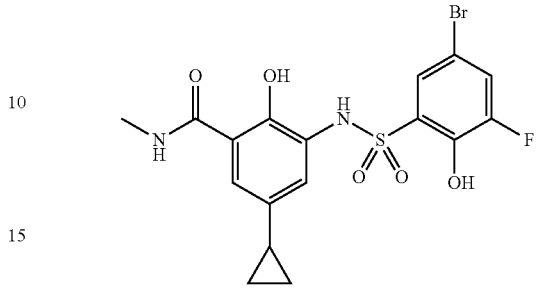 [SMILES: COCCNC(=O)c1cc(C2CC2)cc(NS(=O)(=O)c2cc(Br)cc(F)c2O)c1O]

Step A: Methyl 3-((5-bromo-3-fluoro-2-hydroxyphenyl)sulfonamido)-5-cyclopropyl-2-hydroxybenzoate. Using a procedure analogous to General Procedure E, starting with methyl 3-amino-5-cyclopropyl-2-hydroxybenzoate, which was prepared by a procedure analogous to the procedure used to prepare Example J68 Step D (41 mg, 0.20 mmol) and 5-bromo-3-fluoro-2-hydroxybenzenesulfonyl chloride, which was prepared by a procedure analogous to the procedure used to prepare Example J5 Step A, methyl 3-((5-bromo-3-fluoro-2-hydroxyphenyl)sulfonamido)-5-cyclopropyl-2-hydroxybenzoate was obtained as a colorless solid (69 mg, 0.15 mmol, 75%). $^1$H NMR (400 MHz, MeOH-d$_4$) $\delta_H$ 7.60 (dd, J=2.4, 1.7 Hz, 1H), 7.51 (dd, J=10.1, 2.4 Hz, 1H), 7.36 (dd, J=2.2, 0.5 Hz, 1H), 7.32 (d, J=2.2 Hz, 1H), 3.93 (s, 3H), 1.89-1.78 (m, 1H), 1.00-0.87 (m, 2H), 0.63-0.51 (m, 2H); $^{19}$F NMR (376 MHz, DMSO-d$_6$) $\delta_F$ −113.1; LCMS (Method A) t$_R$=1.67 min, m/z=460,462 [M+H]$^+$; Purity (AUC) ≥95%.

Step B: 3-((S-Bromo-3-fluoro-2-hydroxyphenyl)sulfonamido)-5-cyclopropyl-2-hydroxy-N-methylbenzamide.

Using a procedure analogous to General Procedure G, starting with methyl 3-((5-bromo-3-fluoro-2-hydroxyphenyl)sulfonamido)-5-cyclopropyl-2-hydroxybenzoate (23 mg, 0.05 mmol) and methylamine, the title compound was obtained as a colorless solid (14 mg, 61%). $^1$H NMR (400 MHz, DMSO-d$_6$) $\delta_H$ 7.60 (dd, J=2.4, 1.7 Hz, 1H), 7.52 (d, J=2.4 Hz, 0H), 7.50 (d, J=2.4 Hz, 0H), 7.23 (d, J=2.1 Hz, 1H), 7.21 (d, J=2.1 Hz, 1H), 2.88 (s, 3H), 1.89-1.78 (m, 1H), 0.96-0.89 (m, 2H), 0.62-0.56 (m, 2H); $^{19}$F NMR (376 MHz, DMSO-d$_6$) $\delta_F$ −133.2; LCMS (Method A) t$_R$=1.54 min, m/z=458.8, 460.8 [M+H]$^+$; Purity (AUC) ≥95%.

Example J99: 3-((5-Bromo-3-fluoro-2-hydroxyphenyl)sulfonamido)-5-cyclopropyl-2-hydroxy-N-(2-methoxyethyl)benzamide

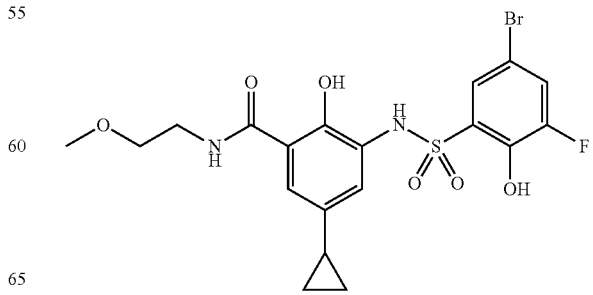

Using a procedure analogous to General Procedure H, starting with methyl 3-((5-bromo-3-fluoro-2-hydroxyphenyl)sulfonamido)-5-cyclopropyl-2-hydroxybenzoate (23 mg, 0.05 mmol), prepared by a procedure analogous to the procedure used to prepare Example J98 Step B, and 2-methoxyethylamine, the title compound was obtained as a colorless solid (16 mg, 64%). $^1$H NMR (400 MHz, DMSO-$d_6$) $\delta_H$ 9.02 (br s, 1H), 7.77 (d, J=10.1 Hz, 1H), 7.56-7.52 (m, 1H), 7.37 (d, J=2.1 Hz, 1H), 7.09 (d, J=2.1 Hz, 1H), 3.49-3.40 (m, 4H), 3.26 (s, 3H), 1.86-1.74 (m, 1H), 0.92-0.86 (m, 2H), 0.57-0.51 (m, 2H); $^{19}$F NMR (376 MHz, DMSO-$d_6$) $\delta_F$ −129.3; LCMS (Method A) $t_R$=1.55 min, m/z=502.8, 504.7 [M+H]$^+$; Purity (AUC) ≥95%.

Example J100: 3-((5-Bromo-2-(isobutylamino)phenyl)sulfonamido)-5-cyclopropyl-2-hydroxy-N-methylbenzamide

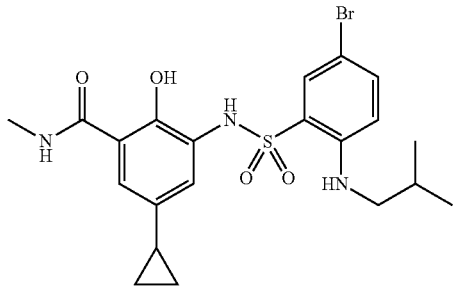 [SMILES: CNC(=O)c1cc(C2CC2)cc(NS(=O)(=O)c2cc(Br)ccc2NCC(C)C)c1O]

Using a procedure analogous to General Procedure I, starting with 3-((5-bromo-2-(isobutylamino)phenyl)sulfonamido)-5-cyclopropyl-2-hydroxybenzoic acid, which was prepared by a procedure analogous to the procedure used to prepare Example J74 (24 mg, 0.05 mmol) and methylamine, the title compound was obtained as a colorless solid (8 mg, 0.016 mmol, 32%). LCMS (Method A) $t_R$=1.81 min, m/z=495.9, 497.8 [M+H]$^+$; Purity (AUC) ≥95%.

Example J101: (R)-3-((5-Bromo-2-((3-methylbutan-2-yl)amino)phenyl)sulfonamido)-5-cyclopropyl-2-hydroxy-N-methylbenzamide

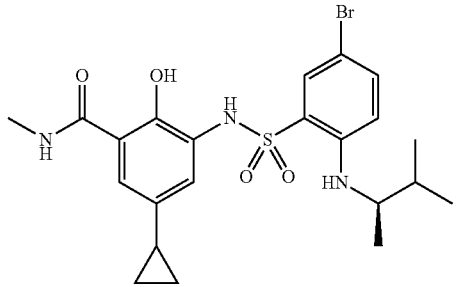 [SMILES: CNC(=O)c1cc(C2CC2)cc(NS(=O)(=O)c2cc(Br)ccc2N[C@H](C)C(C)C)c1O]

Using a procedure analogous to General Procedure I, starting with (R)-3-((5-bromo-2-((3-methylbutan-2-yl)amino)phenyl)sulfonamido)-5-cyclopropyl-2-hydroxybenzoic acid, which was prepared by a procedure analogous to the procedure used to prepare Example J75 (26 mg, 0.05 mmol) and methylamine, the title compound was obtained as a colorless solid (6 mg, 24%). LCMS (Method A) $t_R$=1.87 min, m/z=509.8, 511.8 [M+H]$^+$; Purity (AUC) ≥95%.

Example J102: (S)-3-((5-Bromo-2-((3-methylbutan-2-yl)amino)phenyl)sulfonamido)-5-cyclopropyl-2-hydroxy-N-methylbenzamide

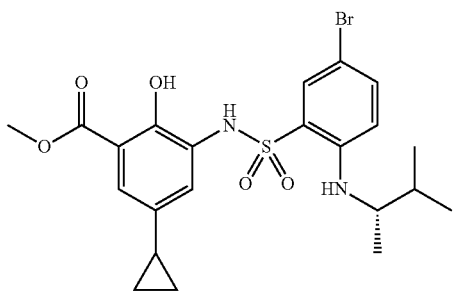 [SMILES: COC(=O)c1cc(C2CC2)cc(NS(=O)(=O)c2cc(Br)ccc2N[C@@H](C)C(C)C)c1O]

Using a procedure analogous to General Procedure 1, starting with (S)-3-((5-Bromo-2-((3-methylbutan-2-yl)amino)phenyl)sulfonamido)-5-cyclopropyl-2-hydroxybenzoic acid, which was prepared by a procedure analogous to the procedure used to prepare Example J76 (26 mg, 0.05 mmol), and methylamine, the title compound was obtained as a colorless solid (6 mg, 24%). LCMS (Method A) $t_R$=1.87 min, m/z=509.8, 511.8 [M+H]$^+$; Purity (AUC) ≥95%.

Example J103: 3-((5-Bromo-2-(cyclopropylamino)phenyl)sulfonamido)-5-cyclopropyl-2-hydroxy-N-methylbenzamide

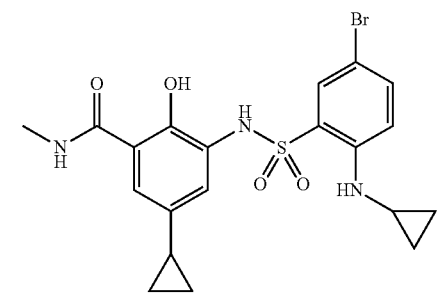 [SMILES: CNC(=O)c1cc(C2CC2)cc(NS(=O)(=O)c2cc(Br)ccc2NC2CC2)c1O]

Using a procedure analogous to General Procedure 1, starting with 3-((5-bromo-2-(cyclopropylamino)phenyl)sulfonamido)-5-cyclopropyl-2-hydroxybenzoic acid, which was prepared by a procedure analogous to the procedure used to prepare Example J73 (24 mg, 0.05 mmol) and methylamine, the title compound was obtained as a colorless solid (7 mg, 29%). LCMS (Method A) $t_R$=1.70 min, m/z=479.8, 481.8 [M+H]$^+$; Purity (AUC) ≥95%.

Example J104: 3-((5-Bromo-2-hydroxy-3-nitrophenyl)sulfonamido)-5-cyclopropyl-2-hydroxybenzamide

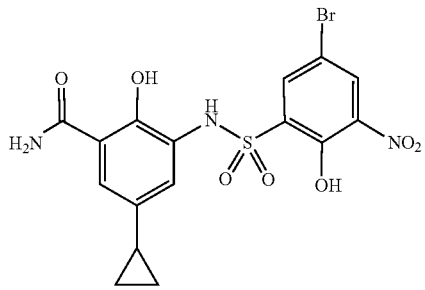 [SMILES: NC(=O)c1cc(C2CC2)cc(NS(=O)(=O)c2cc(Br)cc([N+](=O)[O-])c2O)c1O]

Step A: Methyl 3-((5-bromo-2-hydroxy-3-nitrophenyl)sulfonamido)-5-cyclopropyl-2-hydroxybenzoate. Using a procedure analogous to General Procedure E, starting with methyl 3-amino-5-cyclopropyl-2-hydroxybenzoate, which was prepared by a procedure analogous to the procedure used to prepare Example J68 Step D; 41 mg, 0.20 mmol) and 5-bromo-3-nitro-2-hydroxybenzenesulfonyl chloride, which was prepared by a procedure analogous to the procedure used to prepare Example J6 Step A), methyl 3-((5-bromo-2-hydroxy-3-nitrophenyl)sulfonamido)-5-cyclopropyl-2-hydroxybenzoate was obtained as a yellow solid (48 mg, 0.10 mmol, 49%). LCMS (Method A) $t_R$=1.73 min, m/z=487,489 [M+H]$^+$; Purity (AUC) ≥95%.

Step B: 3-((5-Bromo-2-hydroxy-3-nitrophenyl)sulfonamido)-5-cyclopropyl-2-hydroxybenzamide. Methyl 3-((5-bromo-2-hydroxy-3-nitrophenyl)sulfonamido)-5-cyclopropyl-2-hydroxybenzoate (37 mg, 0.08 mmol) was dissolved in ammonia (7 N in MeOH, 0.5 mL) and heated at reflux in a sealed tube for 16 h. The solvent was concentrated and crude material purified by preparative HPLC to afford the title compound as a yellow solid (16 mg, 68%). $^1$H NMR (400 MHz, MeOH-d$_4$) δ$_H$ 8.44 (d, J=2.5 Hz, 1H), 8.15 (d, J=2.5 Hz, 1H), 7.31 (d, J=2.1 Hz, 1H), 7.30 (d, J=2.1 Hz, 1H), 1.91-1.81 (m, 1H), 0.97-0.91 (m, 2H), 0.66-0.60 (m, 2H); LCMS (Method A) $t_R$=1.52 min, m/z=471.7, 473.8 [M+H]$^+$; Purity (AUC) ≥95%.

Example J105: 3-((5-Bromo-4-chloro-2-methoxyphenyl)sulfonamido)-5-cyclopropyl-2-hydroxybenzamide

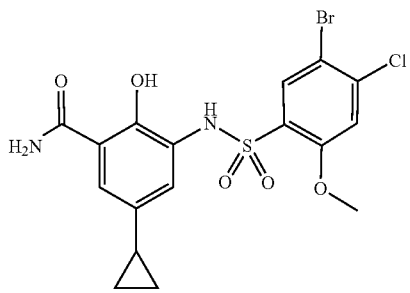 [SMILES: COc1cc(Cl)c(Br)cc1S(=O)(=O)Nc1cc(C2CC2)cc(C(N)=O)c1O]

Step A: Methyl 3-((5-bromo-4-chloro-2-methoxyphenyl)sulfonamido)-5-cyclopropyl-2-hydroxybenzoate. Using a procedure analogous to General Procedure E, starting with methyl 3-amino-5-cyclopropyl-2-hydroxybenzoate, which was prepared by a procedure analogous to the procedure used to prepare Example J68 Step D (41 mg, 0.20 mmol) and 5-bromo-4-chloro-2-methoxybenzenesulfonyl chloride, which was prepared by a procedure analogous to the procedure used to prepare Example J7 Step A, methyl 3-((5-bromo-4-chloro-2-methoxyphenyl)sulfonamido)-5-cyclopropyl-2-hydroxybenzoate was obtained as a colorless solid (95 mg, 0.19 mmol, 97%). LCMS (Method A) $t_R$=1.85 min, m/z=490, 492 [M+H]$^+$; Purity (AUC) ≥95%.

Step B: 3-((5-Bromo-4-chloro-2-methoxyphenyl)sulfonamido)-5-cyclopropyl-2-hydroxybenzamide. Methyl 3-((5-bromo-4-chloro-2-methoxyphenyl)sulfonamido)-5-cyclopropyl-2-hydroxybenzoate (29 mg, 0.06 mmol) was dissolved in ammonia (7 N in MeOH, 0.5 mL) and heated at reflux in a sealed tube for 16 h. The solvent was concentrated and crude material purified by preparative HPLC to afford the title compound as a colorless solid (20 mg, 71%). $^1$H NMR (400 MHz, MeOH-d$_4$) δ$_H$ 7.97 (s, 1H), 7.35 (s, 1H), 7.28 (d, J=2.1 Hz, 1H), 7.25 (d, J=2.1 Hz, 1H), 3.91 (s, 4H), 1.84 (ddd, J=13.5, 8.5, 5.1 Hz, 1H), 0.96-0.89 (m, 2H), 0.59 (dt, J=6.5, 4.6 Hz, 2H); LCMS (Method A) $t_R$=1.63 min, m/z=474.7, 476.7 [M+H]$^+$; Purity (AUC) ≥95%.

Example J106: 3-((5-Bromo-4-fluoro-2-methoxyphenyl)sulfonamido)-5-cyclopropyl-2-hydroxybenzamide

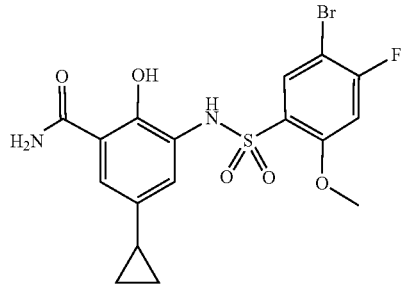 [SMILES: COc1cc(F)c(Br)cc1S(=O)(=O)Nc1cc(C2CC2)cc(C(N)=O)c1O]

Step A: Methyl 3-((5-bromo-4-fluoro-2-methoxyphenyl)sulfonamido)-5-cyclopropyl-2-hydroxybenzoate. Using a procedure analogous to General Procedure E, starting with methyl 3-amino-5-cyclopropyl-2-hydroxybenzoate, which was prepared by a procedure analogous to the procedure used to prepare Example J68 Step D (41 mg, 0.20 mmol) and 5-bromo-4-fluoro-2-methoxybenzenesulfonyl chloride, which was prepared by a procedure analogous to the procedure used to prepare Example J8 Step A, methyl 3-((5-bromo-4-fluoro-2-methoxyphenyl)sulfonamido)-5-cyclopropyl-2-hydroxybenzoate was obtained as a colorless solid (92 mg, 0.19 mmol, 97%). LCMS (Method A) $t_R$=1.80 min, m/z=476,478 [M+H]$^+$; Purity (AUC) ≥95%.

Step B: 3-((5-Bromo-4-fluoro-2-methoxyphenyl)sulfonamido)-5-cyclopropyl-2-hydroxybenzamide. Methyl 3-((5-bromo-4-fluoro-2-methoxyphenyl)sulfonamido)-5-cyclopropyl-2-hydroxybenzoate (43 mg, 0.09 mmol) was dissolved in ammonia (7 N in MeOH, 0.5 mL) and heated at reflux in a sealed tube for 16 h. The solvent was concentrated and crude material purified by preparative HPLC to afford the title compound as a colorless solid (31 mg, 74%). $^1$H NMR (400 MHz, MeOH-d$_4$) δ$_H$ 7.95 (d, J=7.7 Hz, 1H), 7.27 (d, J=2.1 Hz, 1H), 7.25 (d, J=2.1 Hz, 1H), 7.10 (d, J=10.5 Hz, 1H), 3.92 (s, 3H), 1.89-1.77 (m, 1H), 0.97-0.88 (m, 2H), 0.65-0.54 (m, 2H); $^{19}$F NMR (376 MHz, MeOH-d$_4$) δ$_F$ −97.9; LCMS (Method A) $t_R$=1.55 min, m/z=458.8, 460.8 [M+H]$^+$; Purity (AUC) ≥95%.

Example J107: 3-((5-Bromo-2-hydroxyphenyl)sulfonamido)-5-fluoro-2-hydroxybenzoic acid

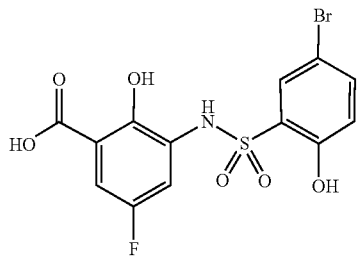 [SMILES: O=C(O)c1cc(F)cc(NS(=O)(=O)c2cc(Br)ccc2O)c1O]

Step A: Methyl 5-fluoro-2-hydroxy-3-nitrobenzoate. Using a procedure analogous to General Procedure B, starting with methyl 5-fluoro-2-hydroxybenzoate (1.01 g, 5.94 mmol), methyl 5-fluoro-2-hydroxy-3-nitrobenzoate was obtained as a pale yellow solid (1.25 g, 98%), which was used without further purification. $^1$H NMR (400 MHz, DMSO-d$_6$) $\delta_H$ 1.19 (s, 1H), 8.21 (dd, J=8.0, 3.3 Hz, 1H), 7.94 (dd, J=8.3, 3.3 Hz, 1H), 3.93 (s, 3H); $^{19}$F NMR (376 MHz, DMSO-d$_6$) $\delta_F$ −121.8; LCMS (Method A) $t_R$=1.19 min, m/z=216.1 [M+H]$^+$; Purity (AUC) ≥95%.

Step B: Methyl 3-amino-5-fluoro-2-hydroxybenzoate. Using a procedure analogous to General Procedure C, starting from methyl 5-fluoro-2-hydroxy-3-nitrobenzoate (740 mg, 3.44 mmol), methyl 3-amino-5-fluoro-2-hydroxybenzoate was obtained as a pale brown oil (631 mg, 99%), which was used without further purification. LCMS (Method A) $t_R$=0.89 min, m/z=186.1 [M+H]$^+$; Purity (AUC) ≥95%.

Step C: Methyl 3-((5-bromo-2-hydroxyphenyl)sulfonamido)-5-fluoro-2-hydroxybenzoate. Using a procedure analogous to General Procedure E, starting with methyl 3-amino-5-fluoro-2-hydroxybenzoate (631 mg, 3.41 mmol) and 5-bromo-2-hydroxybenzenesulfonyl chloride, which was prepared by a procedure analogous to the procedure used to prepare Example J1 Step A, methyl 3-((5-bromo-2-hydroxyphenyl)sulfonamido)-5-fluoro-2-hydroxybenzoate was obtained as a pale brown solid (675 mg, 1.61 mmol, 47%). $^1$H NMR (400 MHz, DMSO-d$_6$) $\delta_H$ 7.75 (d, J=2.6 Hz, 1H), 7.60 (dd, J=8.8, 2.6 Hz, 1H), 7.37 (dd, J=9.8, 3.1 Hz, 1H), 7.28 (dd, J=8.7, 3.1 Hz, 1H), 6.93 (d, J=8.8 Hz, 1H), 3.89 (s, 3H); $^{19}$F NMR (376 MHz, DMSO-d$_6$) $\delta_F$ −122.3; LCMS (Method A) $t_R$=1.60 min, m/z=420, 422 [M+H]$^+$; Purity (AUC) ≥95%.

Step D: 3-((5-Bromo-2-hydroxyphenyl)sulfonamido)-5-fluoro-2-hydroxybenzoic acid. Using a procedure analogous to General Procedure F, starting with methyl 3-((5-bromo-2-hydroxyphenyl)sulfonamido)-5-fluoro-2-hydroxybenzoate (315 mg, 0.75 mmol), the title compound was obtained as a colorless solid (211 mg, 0.52 mmol, 69%). $^1$H NMR (400 MHz, DMSO-d$_6$) $\delta_H$ 11.31 (br s, 1H), 9.19 (br s, 1H), 7.75 (d, J=2.5 Hz, 1H), 7.60 (dd, J=8.8, 2.5 Hz, 1H), 7.33 (dd, J=9.9, 3.2 Hz, 1H), 7.26 (dd, J=8.6, 3.2 Hz, 1H), 6.94 (d, J=8.8 Hz, 1H); $^{19}$F NMR (376 MHz, DMSO-d$_6$) $\delta_F$ −123.1; LCMS (Method A) $t_R$=1.43 min, m/z=427.8, 429.7 [M+Na]$^+$; Purity (AUC) ≥95%.

Example J108: 3-((5-Bromo-2-hydroxyphenyl)sulfonamido)-5-fluoro-2-hydroxybenzamide

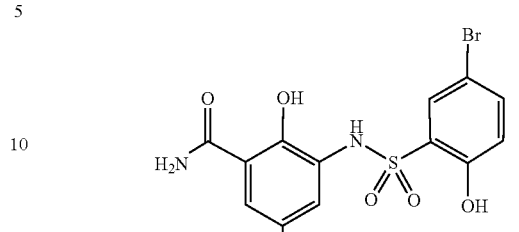

Methyl 3-((5-bromo-2-hydroxyphenyl)sulfonamido)-5-fluoro-2-hydroxybenzoate, which was prepared by a procedure analogous to the procedure used to prepare example J107 Step C (21 mg, 0.05 mmol) was dissolved in ammonia (7 N in MeOH, 0.5 mL) and heated at reflux in a sealed tube for 16 h. The solvent was concentrated and crude material purified by preparative HPLC to afford the title compound as a colorless solid (31 mg, 74%). $^1$H NMR (400 MHz, MeOH-d$_4$) $\delta_H$ 7.82 (d, J=2.5 Hz, 1H), 7.53 (dd, J=8.8, 2.5 Hz, 1H), 7.37 (dd, J=9.8, 3.0 Hz, 1H), 7.27 (dd, J=9.2, 3.0 Hz, 1H), 6.87 (d, J=8.8 Hz, 1H); $^{19}$F NMR (376 MHz, MeOH-d$_4$) $\delta_F$ −124.9; LCMS (Method A) $t_R$=1.36 min, m/z=404.8, 406.8 [M+H]$^+$; Purity (AUC) ≥95%.

Example J109: 3-((5-Bromo-2-hydroxyphenyl)sulfonamido)-5-fluoro-2-hydroxy-N-methylbenzamide

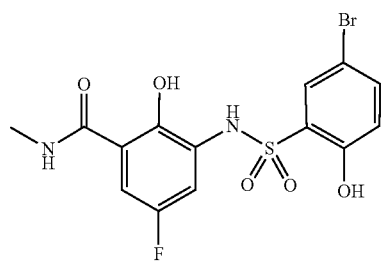 [SMILES: CNC(=O)c1cc(F)cc(NS(=O)(=O)c2cc(Br)ccc2O)c1O]

Using a procedure analogous to General Procedure G, starting with methyl 3-((5-bromo-2-hydroxyphenyl)sulfonamido)-5-fluoro-2-hydroxybenzoate, which was prepared by a procedure analogous to the procedure used to prepare example J107 Step C (21 mg, 0.05 mmol) and methylamine, the title compound was obtained as a colorless solid (18 mg, 43%). $^1$H NMR (400 MHz, DMSO-d$_6$) $\delta_H$ 11.35 (s, 1H), 8.99 (d, J=4.6 Hz, 1H), 7.74 (d, J=2.6 Hz, 1H), 7.60 (dd, J=8.8, 2.6 Hz, 1H), 7.47 (dd, J=9.6, 3.0 Hz, 1H), 7.27 (dd, J=9.9, 3.0 Hz, 1H), 6.93 (d, J=8.8 Hz, 1H), 2.80 (d, J=4.6 Hz, 3H); $^{19}$F NMR (376 MHz, DMSO-d$_6$) $\delta_F$ −123.4; LCMS (Method A) $t_R$=1.44 min, m/z=418.8, 420.7 [M+H]$^+$; Purity (AUC) ≥95%.

Example J110: 3-((5-Bromo-2-hydroxyphenyl) sulfonamido)-5-fluoro-2-hydroxy-N-(2-methoxy-ethyl)benzamide

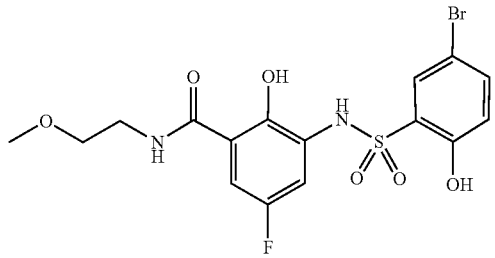 [SMILES: COCCNC(=O)c1cc(F)cc(NS(=O)(=O)c2cc(Br)ccc2O)c1O]

Using a procedure analogous to General Procedure G, starting with methyl 3-((5-bromo-2-hydroxyphenyl)sulfonamido)-5-fluoro-2-hydroxybenzoate, which was prepared by a procedure analogous to the procedure used to prepare example J107 Step C (21 mg, 0.05 mmol) and 2-methoxyethylamine, the title compound was obtained as a colorless solid (15 mg, 65%). $^1$H NMR (400 MHz, MeOH-d$_4$) $\delta_H$ 7.82 (d, J=2.5 Hz, 1H), 7.53 (dd, J=8.8, 2.5 Hz, 1H), 7.36 (dd, J=9.7, 2.9 Hz, 1H), 7.26 (dd, J=9.3, 2.9 Hz, 1H), 6.87 (d, J=8.8 Hz, 1H), 3.56-3.52 (m, 4H), 3.37 (s, 3H); $^{19}$F NMR (376 MHz, MeOH-d$_4$) $\delta_F$ −124.8; LCMS (Method A) t$_R$=1.43 min, m/z=462.7, 464.8 [M+H]$^+$; Purity (AUC) ≥95%.

Example J11: 3-((5-Bromo-2-hydroxyphenyl)sulfonamido)-5-fluoro-2-hydroxy-N-(2-hydroxyethyl) benzamide

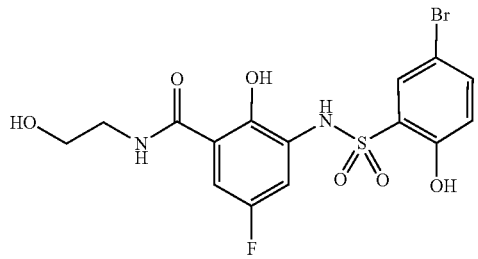 [SMILES: O=C(NCCO)c1cc(F)cc(NS(=O)(=O)c2cc(Br)ccc2O)c1O]

Using a procedure analogous to General Procedure G, starting with methyl 3-((5-bromo-2-hydroxyphenyl)sulfonamido)-5-fluoro-2-hydroxybenzoate, which was prepared by a procedure analogous to the procedure used to prepare example J107 Step C (21 mg, 0.05 mmol) and ethanolamine, the title compound was obtained as a colorless solid (16 mg, 71%). $^1$H NMR (400 MHz, MeOH-d$_4$) $\delta_H$ 7.81 (d, J=2.5 Hz, 1H), 7.53 (dd, J=8.8, 2.5 Hz, 1H), 7.36 (dd, J=9.7, 3.0 Hz, 1H), 7.27 (dd, J=9.3, 2.9 Hz, 1H), 6.86 (d, J=8.8 Hz, 1H), 3.69 (t, J=5.8 Hz, 2H), 3.48 (t, J=5.8 Hz, 2H); $^{19}$F NMR (376 MHz, MeOH-d$_4$) $\delta_F$ −124.9; LCMS (Method A) t$_R$=1.34 min, m/z=448.8, 450.7 [M+H]$^+$; Purity (AUC) ≥95%.

Example J112: 3-((5-Bromo-2-hydroxyphenyl) sulfonamido)-5-cyclopropyl-2-fluorobenzoic acid

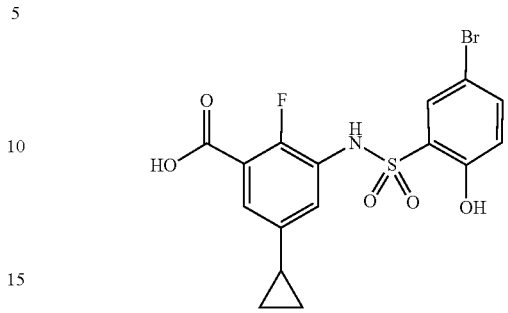

Step A: Methyl 3-amino-5-cyclopropyl-2-fluorobenzoate. Using a procedure analogous to General Procedure M, starting with methyl 3-amino-5-bromo-2-fluorobenzoate (496 mg, 2.0 mmol) and cyclopropylboronic acid, methyl 3-amino-5-cyclopropyl-2-fluorobenzoate was obtained as an off-white solid (301 mg, 72%). $^1$H NMR (400 MHz, CDCl$_3$) $\delta_H$ 6.99 (dd, J=6.0, 2.3 Hz, 1H), 6.68 (dd, J=7.7, 2.3 Hz, 1H), 3.93 (s, 2H), 1.88-1.79 (m, 1H), 1.00-0.89 (m, 2H), 0.71-0.62 (m, 2H); $^{19}$F NMR (376 MHz, CDCl$_3$) $\delta_F$ −137.6; LCMS (Method B) t$_R$=0.87 min, m/z=210.2 [M+H]$^+$; Purity (AUC) ≥95%.

Step B: Methyl 3-((5-bromo-2-hydroxyphenyl)sulfonamido)-5-cyclopropyl-2-fluorobenzoate. Using a procedure analogous to General Procedure E, starting with methyl 3-amino-5-cyclopropyl-2-fluorobenzoate (105 mg, 0.5 mmol) and 5-bromo-2-hydroxybenzenesulfonyl chloride, which was prepared by a procedure analogous to the procedure used to prepare Example J1 Step A, methyl 3-((5-bromo-2-hydroxyphenyl)sulfonamido)-5-cyclopropyl-2-fluorobenzoate was obtained as a cream solid (143 mg, 0.32 mmol, 64%). $^1$H NMR (400 MHz, CDCl$_3$) $\delta_H$ 8.34 (s, 1H), 7.66 (d, J=2.4 Hz, 1H), 7.54 (dd, J=8.9, 2.4 Hz, 1H), 7.48 (dd, =6.4, 2.4 Hz, 1H), 7.35 (dd, J=6.6, 2.4 Hz, 1H), 6.90 (d, J=8.9 Hz, 1H), 3.91 (s, 3H), 1.97-1.85 (m, 1H), 1.08-0.99 (m, 2H), 0.75-0.67 (m, 2H); $^{19}$F NMR (376 MHz, CDCl$_3$) $\delta_F$ −130.8; LCMS (Method A) t$_R$=1.67 min, m/z=444,446 [M+H]$^+$; Purity (AUC) ≥95%.

Step C: 3-((5-Bromo-2-hydroxyphenyl)sulfonamido)-5-cyclopropyl-2-fluorobenzoic acid. Using a procedure analogous to General Procedure F, starting with methyl 3-((5-bromo-2-hydroxyphenyl)sulfonamido)-5-cyclopropyl-2-fluorobenzoate (22 mg, 0.05 mmol) the title compound was obtained as a colorless solid (12 mg, 56%). $^1$H NMR (400 MHz, DMSO-d$_6$) $\delta_H$ 11.28 (s, 1H), 9.92 (s, 1H), 7.64 (d, J=2.5 Hz, 1H), 7.61 (dd, J=8.6, 2.6 Hz, 1H), 7.31 (dd, J=5.9, 2.4 Hz, 1H), 7.06 (dd, J=6.7, 2.5 Hz, 1H), 6.96 (d, J=8.6 Hz, 1H), 2.05-1.79 (m, 1H), 1.05-0.84 (m, 2H), 0.55-0.44 (m, 2H); $^{19}$F NMR (376 MHz, DMSO-d$_6$) $\delta_F$ −126.1; LCMS (Method A) t$_R$=1.47 min, m/z=446.8, 448.8 [M+NH$_4$]$^+$; Purity (AUC) ≥95%.

Example J113: 3-((6-Bromoquinoline)-8-sulfonamido)-5-cyclopropyl-2-fluorobenzoic acid

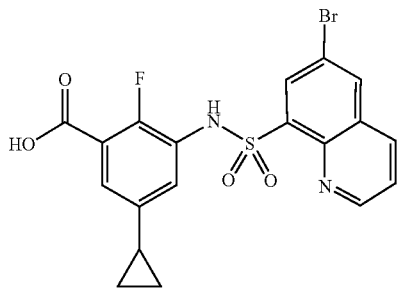 [SMILES: O=C(O)c1cc(C2CC2)cc(NS(=O)(=O)c2cc(Br)cc3cccnc23)c1F]

Step A: Methyl 3-((6-bromoquinoline)-8-sulfonamido)-5-cyclopropyl-2-fluorobenzoate. Using a procedure analogous to General Procedure E, starting with methyl 3-amino-5-cyclopropyl-2-fluorobenzoate, which was prepared by a procedure analogous to the procedure used to prepare Example J112 Step B (21 mg, 0.10 mmol) and 6-bromoquinoline-8-sulfonyl chloride (37 mg, 0.12 mmol), methyl 3-((6-bromoquinoline)-8-sulfonamido)-5-cyclopropyl-2-fluorobenzoate was obtained as an off-white solid (38 mg, 0.08 mmol, 79%). LCMS (Method A) $t_R$=2.12 min, m/z=479,481 [M+H]$^+$; Purity (AUC) ≥95%.

Step B: 3-((6-Bromoquinoline)-8-sulfonamido)-5-cyclopropyl-2-fluorobenzoic acid. Using a procedure analogous to General Procedure F, starting with methyl 3-((6-bromoquinoline)-8-sulfonamido)-5-cyclopropyl-2-fluorobenzoate (19 mg, 0.04 mmol) the title compound was obtained as a colorless solid (4 mg, 22%). $^1$H NMR (400 MHz, DMSO-d$_6$) $\delta_H$ 10.00 (s, 1H), 9.07 (dd, J=4.2, 1.8 Hz, 1H), 8.67 (d, J=2.3 Hz, 1H), 8.54 (dd, J=8.5, 1.8 Hz, 1H), 8.25 (d, J=2.2 Hz, 1H), 7.79 (dd, J=8.4, 4.2 Hz, 1H), 7.29 (dd, J=6.0, 2.5 Hz, 1H), 7.08 (dd, J=6.6, 2.5 Hz, 1H), 1.97-1.84 (m, 1H), 0.98-0.88 (m, 2H), 0.52-0.42 (m, 2H); $^{19}$F NMR (376 MHz, DMSO-d$_6$) $\delta_F$ −126.0; LCMS (Method A) $t_R$=1.61 min, m/z=464.8, 466.8 [M+H]$^+$; Purity (AUC) ≥95%.

Example J114: 5-((5-Bromo-2-hydroxyphenyl)sulfonamido)-3-cyclopropyl-2-fluorobenzoic acid

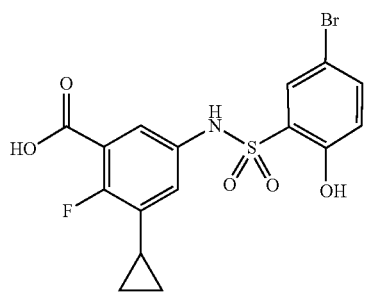 [SMILES: O=C(O)c1cc(NS(=O)(=O)c2cc(Br)ccc2O)cc(C2CC2)c1F]

Step A: Methyl 3-bromo-2-fluoro-5-nitrobenzoate. Methyl 2-fluoro-5-nitrobenzoate (2.99 g, 15 mmol) was dissolved in conc. sulfuric acid (60 mL), N-bromosuccinimide (3.20 g, 18 mmol) was added, and the mixture was stirred for 18 h at 60° C. Further NBS (320 mg, 1.8 mmol) was added and stirring was continued at 60° C. for 2 h. The mixture was poured over ice, extracted with CH$_2$Cl$_2$, and purified by ISCO flash chromatography to afford methyl 3-bromo-2-fluoro-5-nitrobenzoate as a pale-yellow solid (3.26 g, 11.7 mmol, 78%). $^1$H NMR (400 MHz, CDCl$_3$) $\delta_H$ 8.78 (dd, J=5.6, 2.9 Hz, 1H), 8.64 (dd, J=5.2, 2.9 Hz, 1H), 4.01 (s, 3H); $^{19}$F NMR (376 MHz, CDCl$_3$) $\delta_F$ −91.5; LCMS (Method A) $t_R$=1.56 min; Purity (AUC) ≥95%.

Step B: Methyl 5-amino-3-cyclopropyl-2-fluorobenzoate. Using a procedure analogous to General Procedure M, starting with methyl 3-bromo-2-fluoro-5-nitrobenzoate (556 mg, 2.0 mmol), crude nitro intermediate was produced, which, without purification, was hydrogenated using a procedure analogous to General Procedure C, to afford methyl 5-amino-3-cyclopropyl-2-fluorobenzoate as a colorless solid (251 mg, 1.2 mmol, 60%). $^1$H NMR (400 MHz, CDCl$_3$) $\delta_H$ 7.00 (dd, J=5.4, 3.0 Hz, 1H), 6.40 (dd, J=5.7, 3.0 Hz, 1H), 3.93 (s, 3H), 2.14-2.03 (m, 1H), 1.05-0.94 (m, 2H), 0.75-0.63 (m, 2H); $^{19}$F NMR (376 MHz, CDCl$_3$) $\delta_F$ 130.3; LCMS (Method A) $t_R$=1.18 min, m/z=210.1 [M+H]$^+$; Purity (AUC) ≥95%.

Step C: Methyl 5-((5-bromo-2-hydroxyphenyl)sulfonamido)-3-cyclopropyl-2-fluorobenzoate. Using a procedure analogous to General Procedure M, starting with methyl 5-amino-3-cyclopropyl-2-fluorobenzoate (68 mg, 0.33 mmol) and 5-bromo-2-hydroxybenzenesulfonyl chloride, which was prepared by a procedure analogous to the procedure used to prepare Example J1 Step A, methyl 5-amino-3-cyclopropyl-2-fluorobenzoate was obtained as a brown solid (127 mg, 0.28 mmol, 88%). $^1$H NMR (400 MHz, CDCl$_3$) $\delta_H$ 8.33 (br s, 1H), 7.60 (d, J=2.4 Hz, 1H), 7.54 (dd, J=8.8, 2.4 Hz, 1H), 7.35 (dd, J=5.7, 2.9 Hz, 1H), 6.88 (d, J=8.8 Hz, 1H), 6.79 (dd, J=5.8, 2.9 Hz, 1H), 6.60 (br s, 1H), 3.92 (s, 3H), 2.21-2.01 (m, 1H), 1.12-0.97 (m, 2H), 0.70-0.52 (m, 2H); $^{19}$F NMR (376 MHz, CDCl$_3$) $\delta_F$ −117.2; LCMS (Method A) $t_R$=1.79 min, m/z=444,446 [M+H]$^+$; Purity (AUC) ≥95%.

Step D: 5-((5-Bromo-2-hydroxyphenyl)sulfonamido)-3-cyclopropyl-2-fluorobenzoic acid. Using a procedure analogous to General Procedure M, starting with methyl 5-((5-bromo-2-hydroxyphenyl)sulfonamido)-3-cyclopropyl-2-fluorobenzoate (22 mg, 0.05 mmol), the title compound was obtained as a colorless solid (12 mg, 56%). $^1$H NMR (400 MHz, DMSO-d$_6$) $\delta_H$ 7.68 (d, J=2.5 Hz, 1H), 7.57 (dd, J=8.7, 2.6 Hz, 1H), 7.35 (dd, J=5.9, 2.8 Hz, 1H), 6.90 (d, J=8.8 Hz, 1H), 6.85 (dd, J=6.0, 2.9 Hz, 1H), 2.06-1.95 (m, 1H), 1.07-0.94 (m, 2H), 0.59-0.41 (m, 2H); $^{19}$F NMR (376 MHz, DMSO-d$_6$) $\delta_F$ −124.1; LCMS (Method A) $t_R$=1.53 min, m/z=446.8, 448.8 [M+NH$_4$]$^+$; Purity (AUC) ≥95%.

Example J114-2: 5-((5-Bromo-3-chloro-2-hydroxyphenyl)sulfonamido)-3-cyclopropyl-2-fluorobenzoic acid

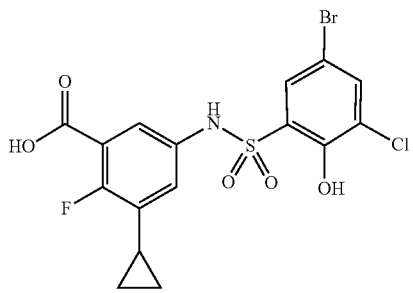 [SMILES: O=C(O)c1cc(NS(=O)(=O)c2cc(Br)cc(Cl)c2O)cc(C2CC2)c1F]

Using procedures analogous to General Procedures E and then F, starting with methyl 3-amino-5-cyclopropyl-2-fluorobenzoate, which was prepared by a procedure analogous to the procedure used to prepare Example J114 Step B (209 mg, 1.0 mmol), and 5-bromo-3-chloro-2-hydroxybenzenesulfonyl chloride, which was prepared by a procedure analogous to the procedure used to prepare Example J4 Step A, the title compound was obtained as a pale-brown solid (306 mg, 0.64 mmol, 64% over two steps). $^1$H NMR (400 MHz, MeOH-$d_4$) $\delta_H$ 7.73 (d, J=2.5 Hz, 1H), 7.70 (d, J=2.5 Hz, 1H), 7.45 (dd, J=5.8, 2.8 Hz, 1H), 6.87 (dd, J=5.9, 2.8 Hz, 1H), 2.12-2.01 (m, 1H), 1.05-0.98 (m, 2H), 0.64-0.56 (m, 2H); $^{19}$F NMR (376 MHz, MeOH-$d_4$) $\delta_F$ −123.5; LCMS (Method A) $t_R$=1.49 min, m/z=480.7, 482.7 [M+NH$_4$]$^+$; Purity (AUC) ≥95%.

Example J115: 5-((6-Bromoquinoline)-8-sulfonamido)-3-cyclopropyl-2-fluorobenzoic acid

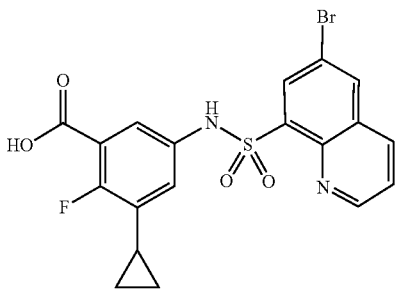 [SMILES: O=C(O)c1cc(NS(=O)(=O)c2cc(Br)cc3cccnc23)cc(C2CC2)c1F]

Step A: Methyl 5-((6-bromoquinoline)-8-sulfonamido)-3-cyclopropyl-2-fluorobenzoate. Using a procedure analogous to General Procedure E, starting with methyl 3-amino-5-cyclopropyl-2-fluorobenzoate, which was prepared by a procedure analogous to the procedure used to prepare Example J114 Step B (21 mg, 0.10 mmol) and 6-bromoquinoline-8-sulfonyl chloride (37 mg, 0.12 mmol), methyl 5-((6-bromoquinoline)-8-sulfonamido)-3-cyclopropyl-2-fluorobenzoate was obtained as an off-white solid (34 mg, 0.07 mmol, 71%). $^1$H NMR (400 MHz, DMSO-de) $\delta_H$ 10.38 (s, 1H), 9.13 (dd, J=4.3, 1.8 Hz, 1H), 8.63 (d, J=2.3 Hz, 1H), 8.49 (dd, J=8.5, 1.8 Hz, 1H), 8.32 (d, J=2.3 Hz, 1H), 7.78 (dd, J=8.4, 4.2 Hz, 1H), 7.31 (dd, J=5.8, 2.8 Hz, 1H), 6.79 (dd, J=6.1, 2.8 Hz, 1H), 3.78 (s, 3H), 1.92 (dq, J=7.2, 3.5 Hz, 1H), 1.02-0.79 (m, 2H), 0.35 (dd, J=5.0, 1.9 Hz, 2H); $^{19}$F NMR (376 MHz, DMSO-$d_6$) $\delta_F$ −123.2; LCMS (Method A) $t_R$=1.80 min, m/z=479, 481 [M+H]$^+$; Purity (AUC) ≥95%.

Step B: 5-((6-Bromoquinoline)-8-sulfonamido)-3-cyclopropyl-2-fluorobenzoic acid. Using a procedure analogous to General Procedure F, starting with methyl 5-((6-bromoquinoline)-8-sulfonamido)-3-cyclopropyl-2-fluorobenzoate (24 mg, 0.05 mmol), the title compound was obtained as a colorless solid (9 mg, 39%). $^1$H NMR (400 MHz, DMSO-$d_6$) $\delta_H$ 10.32 (s, 1H), 9.14 (dd, J=4.2, 1.8 Hz, 1H), 8.63 (d, J=2.3 Hz, 1H), 8.50 (dd, J=8.5, 1.8 Hz, 1H), 8.31 (d, J=2.3 Hz, 1H), 7.78 (dd, J=8.4, 4.2 Hz, 1H), 7.28 (dd, J=5.9, 2.8 Hz, 1H), 6.77 (dd, J=5.9, 2.8 Hz, 1H), 2.00-1.85 (m, 1H), 1.05-0.83 (m, 2H), 0.48-0.29 (m, 2H); $^{19}$F NMR (376 MHz, DMSO-$d_6$) $\delta_F$ −123.4; LCMS (Method A) $t_R$=1.56 min, m/z=464.8, 466.8 [M+H]$^+$; Purity (AUC) ≥95%.

Example J117: 3-((5-Bromo-2-hydroxyphenyl)sulfonamido)-5-cyclopropyl-6-fluoro-2-hydroxybenzoic acid

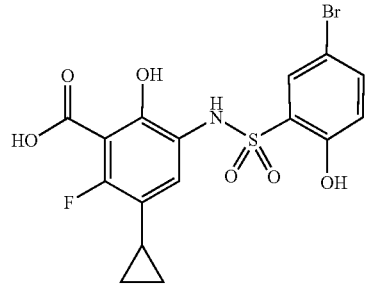 [SMILES: O=C(O)c1c(O)c(NS(=O)(=O)c2cc(Br)ccc2O)cc(C2CC2)c1F]

Step A: Methyl 2-fluoro-6-hydroxybenzoate. Using a procedure analogous to General Procedure P, starting with 2-fluoro-6-hydroxybenzoic acid (5.0 g, 32 mmol), methyl 2-fluoro-6-hydroxybenzoate was obtained as a colorless liquid (3.80 g, 70%). $^1$H NMR (400 MHz, CDCl$_3$) $\delta_H$ 11.26 (s, 1H), 7.40-7.36 (m, 1H), 6.79 (br d, 1H), 6.63-6.58 (m, 1H), 3.99 (s, 3H); $^{19}$F NMR (376 MHz, CDCl$_3$) $\delta_F$ −105.1; LCMS (Method A) $t_R$=1.33 min, m/z=171.1 [M+H]$^+$; Purity (AUC) ≥95%.

Step B: Methyl 3-bromo-2-fluoro-6-hydroxybenzoate. Methyl 2-fluoro-6-hydroxybenzoate (3.8 g, 22.3 mmol) was dissolved in MeCN (144 mL) and cooled to −10° C. in a salt/ice bath. HBF$_4$·Et$_2$O (3.37 mL, 24.6 mmol) was added, followed by N-bromosuccinimide (4.8 g, 26.8 mmol) portion-wise, and the reaction mixture was stirred for 1 h at −10° C. The mixture was concentrated under reduced pressure, then redissolved in EtOAc and washed with saturated aqueous Na$_2$S$_2$O$_8$ and saturated aqueous NaCl, and dried (MgSO$_4$). Purification by ISCO flash chromatography afforded a cream solid, partly contaminated with di-brominated by-product which is inseparable by chromatography, but is readily removed after Step C. (2.49 g, 10 mmol, 45%). $^1$H NMR (400 MHz, CDCl$_3$) $\delta_H$ 11.26 (s, 1H), 7.58 (dd, 1H, 9.1, 7.5 Hz), 6.76 (dt, 7.5, 0.9 Hz), 4.01 (s, 3H); $^{19}$F NMR (376 MHz, CDCl$_3$) $\delta_F$ −86.7; LCMS (Method A) $t_R$=1.59 min, m/z=249, 251 [M+H]$^+$.

Step C: Methyl 3-bromo-2-fluoro-6-hydroxy-5-nitrobenzoate. Using a procedure analogous to General Procedure B, starting with methyl 3-bromo-2-fluoro-6-hydroxybenzoate (2.49 g, 10 mmol), methyl 3-bromo-2-fluoro-6-hydroxy-5-nitrobenzoate was obtained as a pale-yellow solid (1.92 mg, 65%). 1H NMR (400 MHz, CDCl$_3$) $\delta_H$ 8.44 (d, 1H, J=7.0 Hz), 4.03 (s, 3H); $^{19}$F NMR (376 MHz, CDCl$_3$) $\delta_F$ −88.1; LCMS (Method A) $t_R$=1.55 min, m/z=294, 296 [M+H]$^+$; Purity (AUC) ≥95%.

Step D: Methyl 2-(benzyloxy)-5-bromo-6-fluoro-3-nitrobenzoate. Using a procedure analogous to General Procedure Q, starting with methyl 3-bromo-2-fluoro-6-hydroxy-5-nitrobenzoate (588 mg, 2.0 mmol) and benzyl bromide, methyl 2-(benzyloxy)-5-bromo-6-fluoro-3-nitrobenzoate was obtained as a pale-yellow solid (615 mg, 80%). $^1$H NMR (400 MHz, CDCl$_3$) $\delta_H$ 8.25 (d, 1H, J=7.0 Hz), 7.42-7.38 (m, 5H), 5.16 (s, 2H), 3.88 (s, 3H); $^{19}$F NMR (376 MHz, CDCl$_3$) $\delta_F$ −86.8; LCMS (Method A) $t_R$=1.75 min, m/z=406,408 [M+Na]$^+$; Purity (AUC) ≥95%.

Step E: Methyl 2-(benzyloxy)-5-cyclopropyl-6-fluoro-3-nitrobenzoate. Using a procedure analogous to General Procedure M, starting with methyl 2-(benzyloxy)-5-bromo- 6-fluoro-3-nitrobenzoate (103 mg, 1.2 mmol), methyl 2-(benzyloxy)-5-cyclopropyl-6-fluoro-3-nitrobenzoate was obtained as a cream solid (150 mg, 43%). $^1$H NMR (400 MHz, CDCl$_3$) $\delta_H$ 7.59 (d, 1H, J=7.6 Hz), 7.45-7.37 (m, 5H), 5.12 (s, 2H), 3.88 (s, 3H), 2.09-2.06 (m, 1H), 1.11-1.07 (m, 2H), 0.81-0.77 (m, 2H); $^{19}$F NMR (376 MHz, CDCl$_3$) $\delta_F$ −108.7; LCMS (Method A) $t_R$=1.85 min, m/z=363.1 [M+H]$^+$; Purity (AUC) ≥95%.

Step F: Methyl 3-amino-5-cyclopropyl-6-fluoro-2-hydroxybenzoate. Using a procedure analogous to General Procedure C, starting with methyl 2-(benzyloxy)-5-cyclopropyl-6-fluoro-3-nitrobenzoate (145 mg, 0.42 mmol), methyl 3-amino-5-cyclopropyl-6-fluoro-2-hydroxybenzoate was obtained as an off-white solid (66 mg, 70%). $^1$H NMR (400 MHz, CDCl$_3$) $\delta_H$ 11.17 (s, 1H), 6.46 (d, J=7.1 Hz, 1H), 4.01 (s, 3H), 2.12-1.92 (m, 1H), 1.07-0.82 (m, 2H), 0.70-0.50 (m, 2H); $^{19}$F NMR (376 MHz, CDCl$_3$) $\delta_F$ −125.0; LCMS (Method A) $t_R$=1.04 min, m/z=226.1 [M+H]$^+$; Purity (AUC) ≥95%.

Step G: Methyl 3-((5-bromo-2-hydroxyphenyl)sulfonamido)-5-cyclopropyl-6-fluoro-2-hydroxybenzoate. Using a procedure analogous to General Procedure E, starting with methyl 3-amino-5-cyclopropyl-6-fluoro-2-hydroxybenzoate (45 mg, 0.2 mmol) and 5-bromo-2-hydroxybenzenesulfonyl chloride, which was prepared by a procedure analogous to the procedure used to prepare Example J1 Step A, methyl 3-((5-bromo-2-hydroxyphenyl)sulfonamido)-5-cyclopropyl-6-fluoro-2-hydroxybenzoate was obtained as a pale-brown solid (69 mg, 0.15 mmol, 75%). $^1$H NMR (400 MHz, MeOH-d$_4$) $\delta_H$ 11.34 (s, 1H), 10.13 (s, 1H), 9.00 (s, 1H), 7.61 (dd, J=8.7, 2.6 Hz, 1H), 7.57 (d, J=2.5 Hz, 1H), 6.97 (d, J=8.7 Hz, 1H), 6.62 (d, J=8.0 Hz, 1H), 3.82 (s, 3H), 1.90-1.78 (m, 1H), 0.95-0.77 (m, 2H), 0.39-0.24 (m, 2H); LCMS (Method A) $t_R$=1.82 min, m/z=460,462 [M+H]$^+$; Purity (AUC) ≥95%.

Step H: 3-((5-Bromo-2-hydroxyphenyl)sulfonamido)-5-cyclopropyl-6-fluoro-2-hydroxybenzoic acid. Using a procedure analogous to General Procedure F, starting with methyl 3-((5-bromo-2-hydroxyphenyl)sulfonamido)-5-cyclopropyl-6-fluoro-2-hydroxybenzoate (23 mg, 0.05 mmol), the title compound was obtained as a colorless solid (9 mg, 40%). $^1$H NMR (400 MHz, MeOH-d$_4$) $\delta_H$ 7.71 (d, J=2.5 Hz, 1H), 7.53 (dd, J=8.8, 2.5 Hz, 1H), 7.13 (d, J=7.4 Hz, 1H), 6.87 (d, J=8.8 Hz, 1H), 3.96 (s, 3H), 2.01-1.93 (m, 1H), 0.99-0.91 (m, 2H), 0.59-0.51 (m, 2H); $^{19}$F NMR (376 MHz, MeOH-d$_4$) $\delta_F$ −116.6; LCMS (Method A) $t_R$=1.53 min, m/z=467.7.8, 469.7 [M+NH$_4$]$^+$; Purity (AUC) ≥95%.

Example J118: 3-((5-Bromo-3-chloro-2-hydroxyphenyl)sulfonamido)-5-cyclopropyl-6-fluoro-2-hydroxybenzoic acid

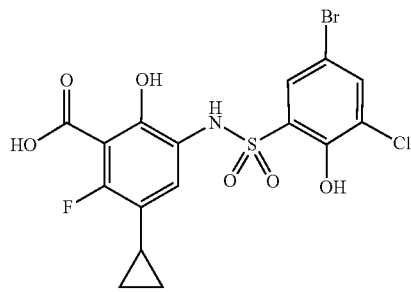 [SMILES: O=C(O)c1c(O)c(NS(=O)(=O)c2cc(Br)cc(Cl)c2O)cc(C2CC2)c1F]

Step A: Methyl 3-((5-bromo-3-chloro-2-hydroxyphenyl)sulfonamido)-5-cyclopropyl-6-fluoro-2-hydroxybenzoate. Using a procedure analogous to General Procedure E, starting with methyl 3-amino-5-cyclopropyl-6-fluoro-2-hydroxybenzoate (45 mg, 0.2 mmol) and 5-bromo-3-chloro-2-hydroxybenzenesulfonyl chloride, which was prepared by a procedure analogous to the procedure used to prepare Example J4 Step A, methyl 3-((5-bromo-3-chloro-2-hydroxyphenyl)sulfonamido)-5-cyclopropyl-6-fluoro-2-hydroxybenzoate was obtained as a pale-brown solid (69 mg, 0.15 mmol, 75%). 1H NMR (400 MHz, MeOH-d$_4$) $\delta_H$ 7.73 (d, J=2.4 Hz, 1H), 7.63 (d, J=2.4 Hz, 1H), 7.14 (d, J=7.4 Hz, 1H), 3.97 (s, 3H), 2.03-1.94 (m, 1H), 1.01-0.93 (m, 2H), 0.63-0.55 (m, 2H); $^{19}$F NMR (376 MHz, MeOH-d$_4$ $\delta_F$ −115.5; LCMS (Method A) $t_R$=1.94 min, m/z=494, 496 [M+H]$^+$; Purity (AUC) ≥95%.

Step B: 3-((5-Bromo-3-chloro-2-hydroxyphenyl)sulfonamido)-5-cyclopropyl-6-fluoro-2-hydroxybenzoic acid. Using a procedure analogous to General Procedure F, starting with methyl 3-((5-bromo-3-chloro-2-hydroxyphenyl)sulfonamido)-5-cyclopropyl-6-fluoro-2-hydroxybenzoate (23 mg, 0.05 mmol), the title compound was obtained as a colorless solid (10 mg, 42%). $^1$H NMR (400 MHz, DMSO-d$_6$) $\delta_H$ 7.94 (d, J=2.5 Hz, 1H), 7.61 (d, J=2.5 Hz, 1H), 6.78 (d, J=7.7 Hz, 1H), 1.89 (td, J=8.4, 4.2 Hz, 1H), 1.00-0.83 (m, 2H), 0.48-0.37 (m, 2H); $^{19}$F NMR (376 MHz, DMSO-d$_6$) $\delta_F$ −116.3; LCMS (Method A) $t_R$=1.74 min, m/z=477.7, 479.7 [M+H]$^+$; Purity (AUC) ≥95%.

Example J119: 3-((5-Bromo-3-fluoro-2-hydroxyphenyl)sulfonamido)-5-cyclopropyl-6-fluoro-2-hydroxybenzoic acid

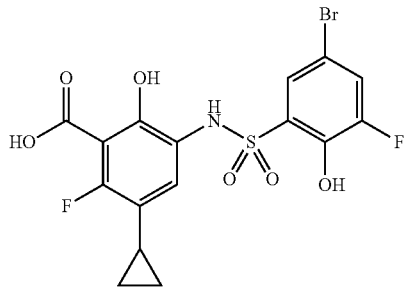 [SMILES: O=C(O)c1c(O)c(NS(=O)(=O)c2cc(Br)cc(F)c2O)cc(C2CC2)c1F]

Step A: Methyl 3-((5-bromo-3-fluoro-2-hydroxyphenyl)sulfonamido)-5-cyclopropyl-6-fluoro-2-hydroxybenzoate. Using a procedure analogous to General Procedure E, starting with methyl 3-amino-5-cyclopropyl-6-fluoro-2-hydroxybenzoate (45 mg, 0.2 mmol) and 5-bromo-3-chloro-2-hydroxybenzenesulfonyl chloride, which was prepared by a procedure analogous to the procedure used to prepare Example J5 Step A, methyl 3-((5-bromo-3-fluoro-2-hydroxyphenyl)sulfonamido)-5-cyclopropyl-6-fluoro-2-hydroxybenzoate was obtained as a pale-brown solid (65 mg, 0.14 mmol, 68%). $^1$H NMR (400 MHz, MeOH-d$_4$) $\delta_H$ 7.55 (s, 1H), 7.54 (dd, J=11.7, 2.4 Hz, 1H), 7.15 (dd, J=7.4, 2.4 Hz, 1H), 3.97 (s, 3H), 2.03-1.91 (m, 1H), 1.01-0.90 (m, 2H), 0.63-0.51 (m, 2H); $^{19}$F NMR (376 MHz, MeOH-d$_4$) $\delta_F$ −115.9, −133.1; LCMS (Method A) $t_R$=1.85 min, m/z=477.7, 479.7 [M+H]$^+$; Purity (AUC) ≥95%.

Step B: 3-((5-Bromo-3-fluoro-2-hydroxyphenyl)sulfonamido)-5-cyclopropyl-6-fluoro-2-hydroxybenzoic acid. Using a procedure analogous to General Procedure F, starting with methyl 3-((5-bromo-3-fluoro-2-hydroxyphenyl)

sulfonamido)-5-cyclopropyl-6-fluoro-2-hydroxybenzoate (23 mg, 0.05 mmol), the title compound was obtained as a colorless solid (12 mg, 52%). $^1$H NMR (400 MHz, MeOH-d$_4$) $\delta_H$ 7.55 (s, 1H), 7.54 (dd, J=13.0, 2.4 Hz, 1H), 7.15 (d, J=7.4 Hz, 1H), 1.99 (ddd, J=13.7, 8.6, 5.2 Hz, 1H), 1.01-0.91 (m, 2H), 0.57 (dt, J=6.4, 4.6 Hz, 2H); $^{19}$F NMR (376 MHz, MeOH-d$_4$) $\delta_F$ −115.9, −133.2; LCMS (Method A) t$_R$=1.66 min, m/z=485.7, 487.6 [M+Na]$^+$; Purity (AUC) ≥95%.

Example J120: 3-((5-Chloro-4-fluoro-2-hydroxyphenyl)sulfonamido)-5-cyclopropyl-6-fluoro-2-hydroxybenzoic acid

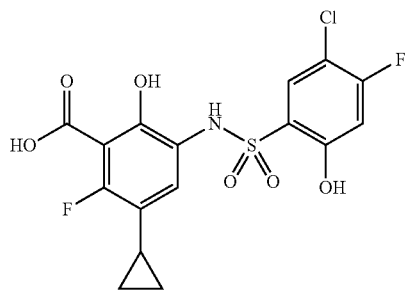

Step A: Methyl 3-((5-chloro-4-fluoro-2-hydroxyphenyl)sulfonamido)-5-cyclopropyl-6-fluoro-2-hydroxybenzoate. Using a procedure analogous to General Procedure E, starting with methyl 3-amino-5-cyclopropyl-6-fluoro-2-hydroxybenzoate (45 mg, 0.2 mmol) and 5-chloro-4-fluoro-2-hydroxybenzenesulfonyl chloride, which was prepared by a procedure analogous to the procedure used to prepare Example J10 Step A, methyl 3-((5-chloro-4-fluoro-2-hydroxyphenyl)sulfonamido)-5-cyclopropyl-6-fluoro-2-hydroxybenzoate was obtained as a pale-brown solid (69 mg, 0.16 mmol, 80%). $^1$H NMR (400 MHz, MeOH-d$_4$) $\delta_H$ 7.68 (d, J=8.2 Hz, 1H), 7.14 (d, J=7.4 Hz, 1H), 6.78 (d, J=10.4 Hz, 1H), 3.94 (s, 3H), 2.00-1.92 (m, 1H), 1.01-0.90 (m, 2H), 0.59-0.47 (m, 2H); $^{19}$F NMR (376 MHz, MeOH-d$_4$) $\delta_F$ −107.9, −116.2; LCMS (Method A) t$_R$=1.92 min, m/z=435.9 [M+H]$^+$; Purity (AUC) ≥95%.

Step B: 3-((5-Chloro-4-fluoro-2-hydroxyphenyl)sulfonamido)-5-cyclopropyl-6-fluoro-2-hydroxybenzoic acid. Using a procedure analogous to General Procedure F, starting with methyl 3-((5-chloro-4-fluoro-2-hydroxyphenyl)sulfonamido)-5-cyclopropyl-6-fluoro-2-hydroxybenzoate (22 mg, 0.05 mmol), the title compound was obtained as a colorless solid (12 mg, 57%). $^1$H NMR (400 MHz, MeOH-d$_4$) $\delta_H$ 7.70 (d, J=8.2 Hz, 1H), 7.16 (d, J=7.4 Hz, 1H), 6.80 (d, J=10.4 Hz, 1H), 2.02-1.94 (m, 1H), 1.01-0.92 (m, 2H), 0.60-0.53 (m, 2H); $^{19}$F NMR (376 MHz, MeOH-d$_4$) $\delta_F$ −107.8, −115.6; LCMS (Method A) t$_R$=1.56 min, m/z=417.8 [M+H]$^+$; Purity (AUC) ≥95%.

Example J121: 3-((6-Bromoquinoline)-8-sulfonamido)-5-cyclopropyl-6-fluoro-2-hydroxybenzoic acid

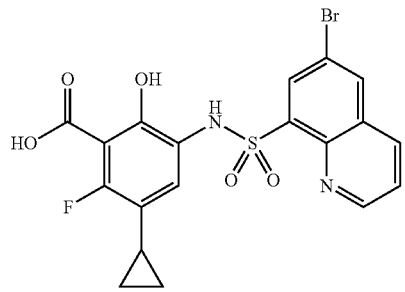 [SMILES: O=C(O)c1c(O)c(NS(=O)(=O)c2cc(Br)cc3cccnc23)cc(C2CC2)c1F]

Step A: Methyl 3-((6-bromoquinoline)-8-sulfonamido)-5-cyclopropyl-6-fluoro-2-hydroxybenzoate. Using a procedure analogous to General Procedure E, starting with methyl 3-amino-5-cyclopropyl-6-fluoro-2-hydroxybenzoate (45 mg, 0.2 mmol) and 6-bromoquinoline-8-sulfonyl chloride, methyl 3-((6-bromoquinoline)-8-sulfonamido)-5-cyclopropyl-6-fluoro-2-hydroxybenzoate was obtained as a colorless solid (84 mg, 85%). $^1$H NMR (400 MHz, DMSO-d$_6$) $\delta_H$ 9.11 (dd, J=4.3, 1.8 Hz, 1H), 8.68 (d, J=2.3 Hz, 1H), 8.55 (dd, J=8.4, 1.8 Hz, 1H), 8.26 (d, J=2.3 Hz, 1H), 7.80 (dd, J=8.4, 4.3 Hz, 1H), 6.70 (d, J=8.0 Hz, 1H), 3.78 (s, 3H), 1.94-1.74 (m, 1H), 0.91-0.74 (m, 2H), 0.39-0.24 (m, 2H); $^{19}$F NMR (376 MHz, DMSO-d$_6$) $\delta_F$ −120.7; LCMS (Method A) t$_R$=2.08 min, m/z=495,497 [M+H]$^+$; Purity (AUC) ≥95%.

Step B: 3-((6-Bromoquinoline)-8-sulfonamido)-5-cyclopropyl-6-fluoro-2-hydroxybenzoic acid. Using a procedure analogous to General Procedure F, starting with methyl 3-((6-bromoquinoline)-8-sulfonamido)-5-cyclopropyl-6-fluoro-2-hydroxybenzoate (25 mg, 0.05 mmol), the title compound was obtained as a colorless solid (17 mg, 71%). $^1$H NMR (400 MHz, MeOH-d$_4$) $\delta_H$ 9.07 (dd, J=4.3, 1.7 Hz, 1H), 8.41 (d, J=2.2 Hz, 1H), 8.37 (dd, J=8.4, 1.7 Hz, 1H), 8.31 (d, J=2.2 Hz, 1H), 7.67 (dd, J=8.4, 4.3 Hz, 1H), 7.23 (d, J=7.4 Hz, 1H), 2.04-1.86 (m, 1H), 1.01-0.87 (m, 2H), 0.63-0.48 (m, 2H); $^{19}$F NMR (376 MHz, MeOH-d$_4$) $\delta_F$ −116.0; LCMS (Method A) t$_R$=1.87 min, m/z=480.7, 482.7 [M+H]$^+$; Purity (AUC) ≥95%.

Example J123: 3-((5-Bromo-2-hydroxyphenyl)sulfonamido)-5-cyclopropyl-6-fluoro-2-hydroxybenzamide

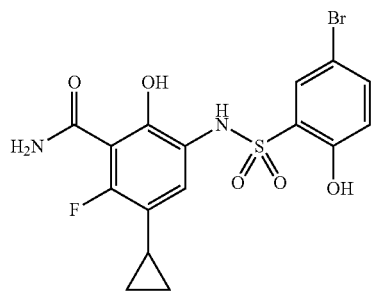 [SMILES: NC(=O)c1c(O)c(NS(=O)(=O)c2cc(Br)ccc2O)cc(C2CC2)c1F]

Methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G: 23 mg, 0.05 mmol) was dissolved in ammonia (7 N in MeOH, 0.5 mL) and heated at reflux in a sealed tube for 16 h. The solvent was concentrated and the crude material was purified by preparative HPLC to afford the title compound as a colorless solid (12 mg, 54%). $^1$H NMR (400 MHz, DMSO-d$_6$) δ$_H$ 11.24 (s, 1H), 8.86 (s, 1H), 8.30 (s, 1H), 7.89 (d, J=8.0 Hz, 1H), 7.65-7.53 (m, 2H), 6.94 (d, J=8.6 Hz, 1H), 6.81 (d, J=8.0 Hz, 1H), 1.88 (td, J=8.5, 4.3 Hz, 1H), 0.99-0.83 (m, 2H), 0.50-0.32 (m, 2H); $^{19}$F NMR (376 MHz, DMSO-d$_6$) δ$_F$ −118.9; LCMS (Method A) t$_R$=1.62 min, m/z=444.7, 446.8 [M+H]$^+$; Purity (AUC) ≥95%.

Example J124: 3-((5-Bromo-2-hydroxyphenyl) sulfonamido)-5-cyclopropyl-6-fluoro-2-hydroxy-N-methylbenzamide

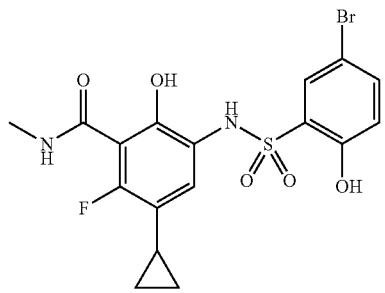

Using a procedure analogous to General Procedure G, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and methylamine, the title compound was obtained as a colorless solid (21 mg, 91%). $^1$H NMR (400 MHz, DMSO-d$_6$) δ$_H$ 11.27 (s, 1H), 8.88 (s, 1H), 8.44-8.35 (m, 1H), 7.60 (d, J=8.0 Hz, 2H), 6.95 (d, J=8.3 Hz, 1H), 6.75 (d, J=8.1 Hz, 1H), 2.79 (d, J=4.2 Hz, 3H), 1.94-1.79 (m, 1H), 0.95-0.81 (m, 2H), 0.45-0.34 (m, 2H); $^{19}$F NMR (376 MHz, DMSO-d$_6$) δ$_F$ −120.4; LCMS (Method A) t$_R$=1.69 min, m/z=458.8, 460.8 [M+H]$^+$; Purity (AUC) ≥95%.

Example J125: 3-((5-Bromo-2-hydroxyphenyl) sulfonamido)-5-cyclopropyl-6-fluoro-2-hydroxy-N-(2-morpholinoethyl)benzamide

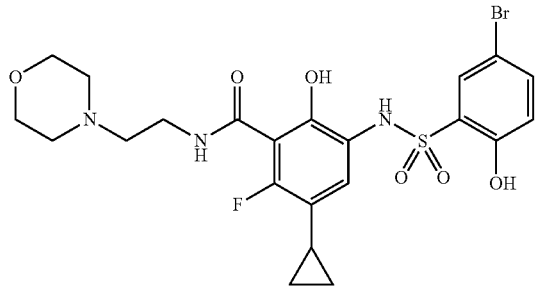 [SMILES: O=C(NCCN1CCOCC1)c1c(O)c(NS(=O)(=O)c2cc(Br)ccc2O)cc(C2CC2)c1F]

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol), and 2-morpholinoethan-1-amine, the title compound was obtained as a colorless solid (15 mg, 55%). $^1$H NMR (400 MHz, MeOH-d$_4$) δ$_H$ 7.70 (d, J=2.5 Hz, 1H), 7.53 (dd, J=8.8, 2.5 Hz, 1H), 7.10 (d, J=8.1 Hz, 1H), 6.87 (d, J=8.8 Hz, 1H), 4.15-3.97 (m, 2H), 3.86-3.78 (m, 6H), 3.43 (t, J=5.9 Hz, 2H), 2.05-1.93 (m, 1H), 1.03-0.91 (m, 2H), 0.63-0.50 (m, 2H); $^{19}$F NMR (376 MHz, MeOH-d$_4$) δ$_F$ −121.9; LCMS (Method A) t$_R$=1.37 min, m/z=457.8, 459.8 [M+H]$^+$; Purity (AUC) ≥95%.

Example J126: 3-((5-Bromo-2-hydroxyphenyl) sulfonamido)-5-cyclopropyl-6-fluoro-2-hydroxy-N-(2-hydroxyethyl)benzamide

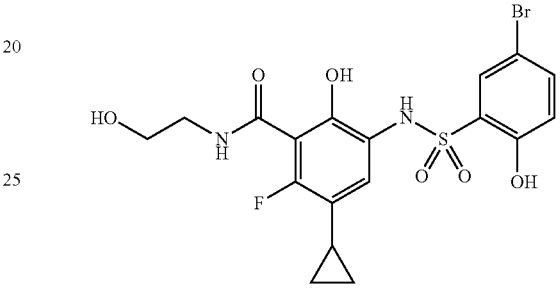

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and ethanolamine, the title compound was obtained as a colorless solid (8 mg, 33%). $^1$H NMR (400 MHz, MeOH-d$_4$) δ$_H$ 7.71 (d, J=2.5 Hz, 1H), 7.52 (dd, J=8.8, 2.5 Hz, 1H), 7.09 (d, J=8.2 Hz, 1H), 6.86 (d, J=8.7 Hz, 1H), 3.61-3.54 (m, 4H), 3.39 (s, 3H), 2.02-1.92 (m, 1H), 1.01-0.91 (m, 2H), 0.64-0.51 (m, 2H); $^{19}$F NMR (376 MHz, MeOH-d$_4$) δ$_F$ −122.8; LCMS (Method A) t$_R$=1.57 min, m/z=488.8, 490.8 [M+H]$^+$; Purity (AUC) ≥95%.

Example J127: 3-((5-Bromo-2-hydroxyphenyl) sulfonamido)-5-cyclopropyl-6-fluoro-2-hydroxy-N-(2-methoxyethyl)benzamide

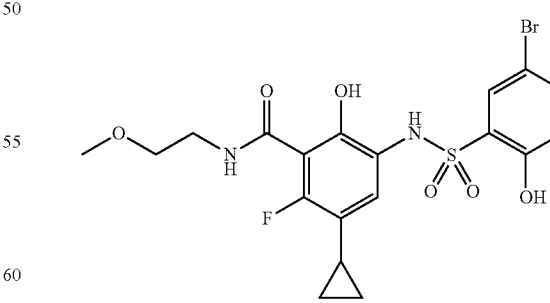

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol)

and 2-methoxyethylamine, the title compound was obtained as a colorless solid (12 mg, 48%). $^1$H NMR (400 MHz, MeOH-d$_4$) $\delta_H$ 7.71 (d, J=2.5 Hz, 1H), 7.52 (dd, J=8.8, 2.5 Hz, 1H), 7.09 (d, J=8.2 Hz, 1H), 6.86 (d, J=8.7 Hz, 1H), 3.61-3.54 (m, 4H), 3.39 (s, 3H), 2.02-1.92 (m, 1H), 1.01-0.91 (m, 2H), 0.64-0.51 (m, 2H); $^{19}$F NMR (376 MHz, MeOH-d$_4$) $\delta_F$ −122.8; LCMS (Method A) t$_R$=1.78 min, m/z=502.8, 504.7 [M+H]$^+$; Purity (AUC) ≥95%.

Example J128: 3-((5-Bromo-2-hydroxyphenyl)sulfonamido)-5-cyclopropyl-6-fluoro-2-hydroxy-N-(oxetan-3-yl)benzamide

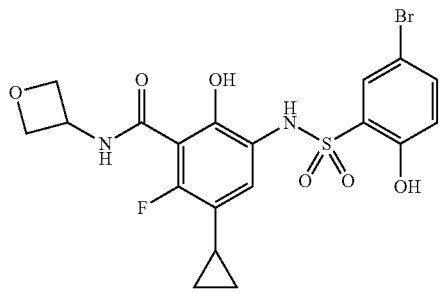 [SMILES: O=C(NC1COC1)c1c(O)c(NS(=O)(=O)c2cc(Br)ccc2O)cc(C2CC2)c1F]

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and 3-aminooxetane, the title compound was obtained as a colorless solid (12 mg, 48%). $^1$H NMR (400 MHz, DMSO-d$_6$) $\delta_H$ 11.35 (s, 1H), 10.82 (s, 1H), 9.08 (dd, J=6.4, 3.7 Hz, 1H), 8.94 (s, 1H), 7.66-7.59 (m, 2H), 6.98 (d, J=8.4 Hz, 1H), 6.63 (d, J=8.1 Hz, 1H), 4.95 (q, J=6.9 Hz, 1H), 4.74 (t, J=6.9 Hz, 2H), 4.54 (t, J=6.4 Hz, 2H), 1.94-1.81 (m, 1H), 0.93-0.82 (m, 2H), 0.40-0.28 (m, 2H); $^{19}$F NMR (376 MHz, DMSO-d$_6$) $\delta_F$ −121.6; LCMS (Method A) t$_R$=1.57 min, m/z=500.8, 502.8 [M+H]$^+$; Purity (AUC) ≥95%.

Example J131: 3-((5-Bromo-2-hydroxyphenyl)sulfonamido)-5-cyclopropyl-6-fluoro-2-hydroxy-N-(tetrahydrofuran-3-yl)benzamide

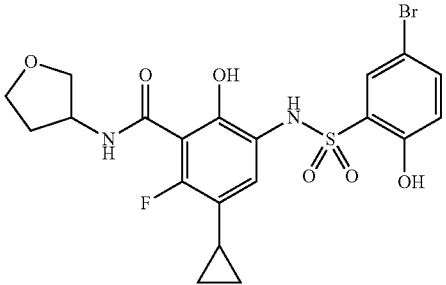 [SMILES: O=C(NC1CCOC1)c1c(O)c(NS(=O)(=O)c2cc(Br)ccc2O)cc(C2CC2)c1F]

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and 3-aminotetrahydrofuran, the title compound was obtained as a colorless solid (11 mg, 43%). LCMS (Method A) t$_R$=1.46 min, m/z=514.8, 516.7 [M+H]$^+$; Purity (AUC) ≥95%.

Example J132: (R)-3-((5-Bromo-2-hydroyphenyl)sulfonamido)-5-cyclopropyl-6-fluoro-2-hydroxy-N-(tetrahydrofuran-3-yl)benzamide

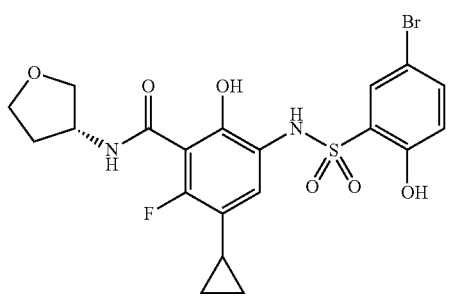 [SMILES: O=C(N[C@@H]1CCOC1)c1c(O)c(NS(=O)(=O)c2cc(Br)ccc2O)cc(C2CC2)c1F]

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and (R)-3-aminotetrahydrofuran, the title compound was obtained as a colorless solid (13 mg, 50%). LCMS (Method A) t$_R$=1.46 min, m/z=514.8, 516.7 [M+H]$^+$; Purity (AUC) ≥95%.

Example J133: (S)-3-((5-Bromo-2-hydroxyphenyl)sulfonamido)-5-cyclopropyl-6-fluoro-2-hydroxy-N-(tetrahydrofuran-3-yl)benzamide

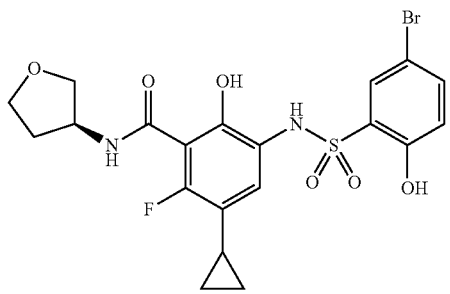 [SMILES: O=C(N[C@H]1CCOC1)c1c(O)c(NS(=O)(=O)c2cc(Br)ccc2O)cc(C2CC2)c1F]

Using a procedure analogous to General Procedure H, starting with methyl 3-((5-bromo-2-hydroxyphenyl)sulfonamido)-5-cyclopropyl-6-fluoro-2-hydroxybenzoate, which was prepared by a procedure analogous to the procedure used to prepare Example J117 Step G (23 mg, 0.05 mmol) and (S)-3-aminotetrahydrofuran, the title compound was obtained as a colorless solid (12 mg, 47%). LCMS (Method A) t$_R$=1.46 min, m/z=514.8, 516.7 [M+H]$^+$; Purity (AUC) ≥95%.

Example J134: 3-((6-Bromoquinoline)-8-sulfonamido)-5-cyclopropyl-6-fluoro-2-hydroxy-N-methylbenzamide

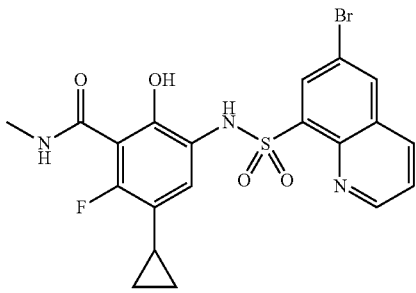 [SMILES: CNC(=O)c1c(O)c(NS(=O)(=O)c2cc(Br)cc3cccnc23)cc(C2CC2)c1F]

Using a procedure analogous to General Procedure G, starting with methyl 3-((6-bromoquinoline)-8-sulfonamido)-5-cyclopropyl-6-fluoro-2-hydroxybenzoate, which was prepared by a procedure analogous to the procedure used to prepare Example J121 Step A (25 mg, 0.05 mmol) and methylamine, the title compound was obtained as a colorless solid (23 mg, 93%). $^1$H NMR (400 MHz, DMSO-$d_6$) $\delta_H$ 9.11 (dd, J=4.3, 1.8 Hz, 1H), 8.64 (d, J=2.3 Hz, 1H), 8.52 (dd, J=8.5, 1.8 Hz, 1H), 8.39 (br s, 1H), 8.25 (d, J=2.2 Hz, 1H), 7.78 (dd, J=8.4, 4.3 Hz, 1H), 6.86 (d, J=8.0 Hz, 1H), 2.72 (d, J=4.4 Hz, 3H), 1.85 (td, J=8.5, 4.3 Hz, 1H), 0.94-0.83 (m, 2H), 0.48-0.36 (m, 2H); $^{19}$F NMR (376 MHz, DMSO-$d_6$) $\delta_F$ −120.0; LCMS (Method A) $t_R$=1.99 min, m/z=493.8, 495.7 [M+H]$^+$; Purity (AUC) ≥95%.

Example J135: 5-((5-Bromo-2-hydroxyphenyl)sulfonamido)-3-cyclopropyl-2-fluoro-N-methylbenzamide

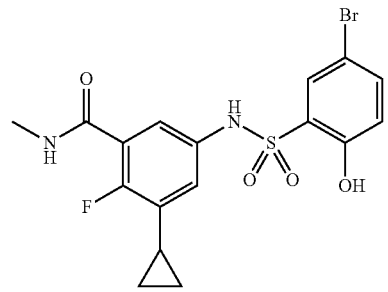 [SMILES: CNC(=O)c1cc(NS(=O)(=O)c2cc(Br)ccc2O)cc(C2CC2)c1F]

Using a procedure analogous to General Procedure H starting with methyl 5-((5-bromo-2-hydroxyphenyl)sulfonamido)-3-cyclopropyl-2-fluorobenzoate, which was prepared by a procedure analogous to the procedure used to prepare Example J114 Step C (22 mg, 0.05 mmol) and methylamine, the title compound was obtained as a colorless solid (19 mg, 86%). $^1$H NMR (400 MHz, MeOH-$d_4$) $\delta_H$ 7.71 (d, J=2.5 Hz, 1H), 7.49 (dd, J=8.8, 2.5 Hz, 1H), 7.23 (dd, J=5.8, 2.8 Hz, 1H), 6.87-6.82 (m, 2H), 2.88 (s, 3H), 2.13-1.96 (m, 2H), 1.12-0.95 (m, 2H), 0.70-0.52 (m, 2H); $^{19}$F NMR (376 MHz, MeOH-$d_4$) $\delta_F$ −128.4; LCMS (Method A) $t_R$=1.47 min, m/z=442.8, 444.8 [M+H]$^+$; Purity (AUC) ≥95%.

Example J136: 5-((5-Bromo-2-hydroxyphenyl)sulfonamido)-3-cyclopropyl-2-fluoro-N-(2-methoxyethyl)benzamide

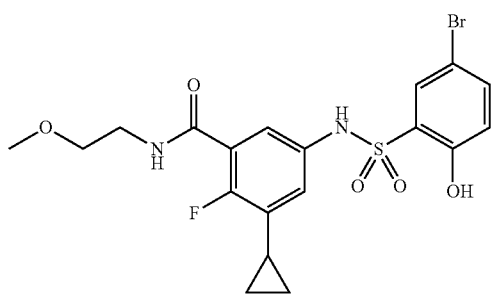 [SMILES: COCCNC(=O)c1cc(NS(=O)(=O)c2cc(Br)ccc2O)cc(C2CC2)c1F]

Using a procedure analogous to General Procedure I, starting with 5-((5-bromo-2-hydroxyphenyl)sulfonamido)-3-cyclopropyl-2-fluorobenzoic acid, which was prepared by a procedure analogous to the procedure used to prepare Example J114 Step D (22 mg, 0.05 mmol) and 2-methoxyethlamine, the title compound was obtained as a colorless solid (12 mg, 49%). LCMS (Method A) $t_R$=1.36 min, m/z=486.8, 488.8 [M+H]$^+$; Purity (AUC) ≥95%.

Example J137: 5-((5-Bromo-2-hydroxyphenyl)sulfonamido)-3-cyclopropyl-2-fluoro-N-(2-morpholinoethyl)benzamide

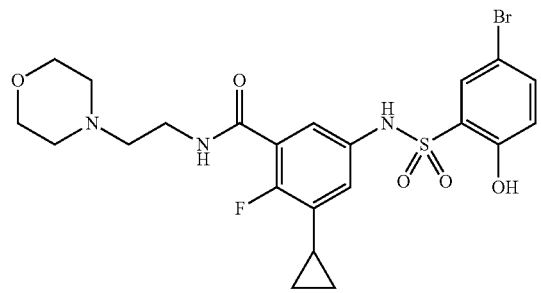 [SMILES: O=C(NCCN1CCOCC1)c1cc(NS(=O)(=O)c2cc(Br)ccc2O)cc(C2CC2)c1F]

Using a procedure analogous to General Procedure I, starting with methyl 5-((5-bromo-2-hydroxyphenyl)sulfonamido)-3-cyclopropyl-2-fluorobenzoate, which was prepared by a procedure analogous to the procedure used to prepare Example J114 Step C (22 mg, 0.05 mmol) and 2-morpholinoethan-1-amine, the title compound was obtained as a colorless solid (19 mg, 70%) as free base. LCMS (Method A) $t_R$=1.29 min, m/z=541.8 543.9 [M+H]$^+$; Purity (AUC) ≥95%.

Example J138: 5-((5-Bromo-2-hydroxyphenyl)sulfonamido)-3-cyclopropyl-2-fluoro-N-(oxetan-3-yl)benzamide

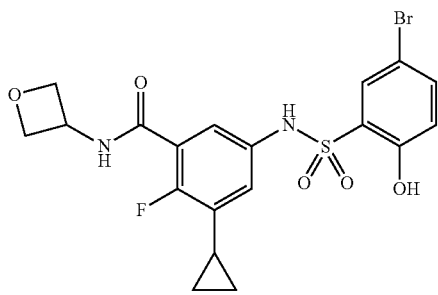 [SMILES: O=C(NC1COC1)c1cc(NS(=O)(=O)c2cc(Br)ccc2O)cc(C2CC2)c1F]

Using a procedure analogous to General Procedure 1, starting with methyl 5-((5-bromo-2-hydroxyphenyl)sulfonamido)-3-cyclopropyl-2-fluorobenzoate, which was prepared by a procedure analogous to the procedure used to prepare Example J114 Step C (22 mg, 0.05 mmol) and 3-aminooxetane hydrochloride, the title compound was obtained as a colorless solid (13 mg, 49%). LCMS (Method A) $t_R$=1.38 min, m/z=484.8, 486.7 [M+H]$^+$; Purity (AUC) ≥95%.

Example J139: 5-((5-Bromo-2-hydroxyphenyl)sulfonamido)-3-cyclopropyl-2-fluoro-N-(tetrahydrofuran-3-yl)benzamide

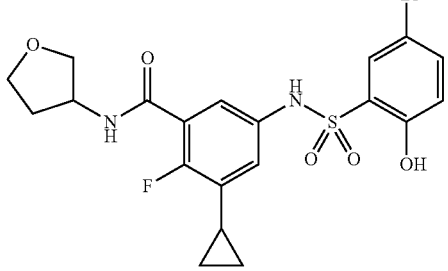

Using a procedure analogous to General Procedure 1, starting with methyl 5-((5-bromo-2-hydroxyphenyl)sulfonamido)-3-cyclopropyl-2-fluorobenzoate, which was prepared by a procedure analogous to the procedure used to prepare Example J114 Step C (22 mg, 0.05 mmol), and 3-aminotetrahydrofuran, the title compound was obtained as a colorless solid (9 mg, 36%). LCMS (Method A) $t_R$=1.20 min, m/z=498.8, 500.8 [M+H]$^+$; Purity (AUC) ≥95%.

Example J140: 5-((6-Bromoquinoline)-8-sulfonamido)-3-cyclopropyl-2-fluoro-N-methylbenzamide

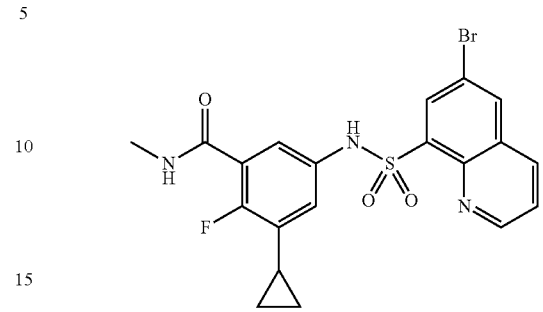

Using a procedure analogous to General Procedure G, starting with methyl 5-((6-bromoquinoline)-8-sulfonamido)-3-cyclopropyl-2-fluorobenzoate, which was prepared by a procedure analogous to the procedure used to prepare Example J115 Step A (24 mg, 0.05 mmol), and methylamine, the title compound was obtained as a colorless solid (18 mg, 75%). $^1$H NMR (400 MHz, DMSO-d$_6$) $\delta_H$ 10.37 (s, 1H), 9.13 (dd, J=4.2, 1.8 Hz, 1H), 8.63 (d, J=2.3 Hz, 1H), 8.50 (dd, J=8.4, 1.8 Hz, 1H), 8.32 (d, J=2.3 Hz, 1H), 7.78 (dd, J=8.4, 4.2 Hz, 1H), 7.31 (dd, J=6.0, 2.8 Hz, 1H), 6.79 (dd, J=6.0, 2.8 Hz, 1H), 3.78 (s, 3H), 2.05-1.84 (m, 1H), 1.04-0.87 (m, 2H), 0.45-0.27 (m, 2H); $^{19}$F NMR (376 MHz, DMSO-d$_6$) $\delta_F$ −123.2; LCMS (Method A) $t_R$=1.80 min, m/z=478.8, 480.7 [M+H]$^+$; Purity (AUC) ≥95%.

Example J141: 3-((5-Bromo-2-hydroxyphenyl)sulfonamido)-5-cyclopropyl-2-fluoro-N-methylbenzamide

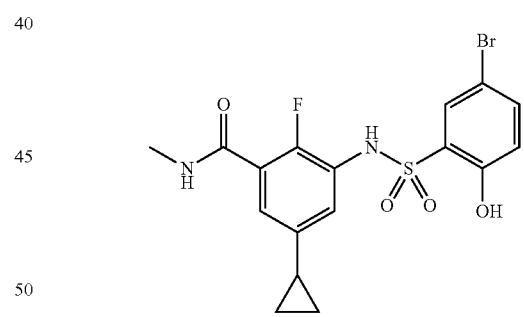

Using a procedure analogous to General Procedure I, starting with methyl 3-((5-bromo-2-hydroxyphenyl)sulfonamido)-5-cyclopropyl-2-fluorobenzoate, which was prepared by a procedure analogous to the procedure used to prepare Example J113 Step A (22 mg, 0.05 mmol), and methylamine, the title compound was obtained as a colorless solid (16 mg, 72%). $^1$H NMR (400 MHz, DMSO-d$_6$) $\delta_H$ 11.30 (s, 1H), 9.89 (s, 1H), 8.21 (d, J=5.2 Hz, 1H), 7.65 (d, J=2.5 Hz, 1H), 7.61 (dd, J=8.7, 2.6 Hz, 1H), 7.03-6.97 (m, 1H), 6.97 (d, J=8.7 Hz, 1H), 6.91 (dd, J=7.0, 2.4 Hz, 1H), 1.85 (td, J=8.4, 4.3 Hz, 1H), 0.96-0.85 (m, 2H), 0.53-0.43 (m, 2H); $^{19}$F NMR (376 MHz, DMSO-d$_6$) $\delta_F$ −130.4; LCMS (Method A) $t_R$=1.42 min, m/z=442.8, 444.8 [M+H]$^+$; Purity (AUC) ≥95%.

Example J142: 3-((5-Bromo-2-hydroxyphenyl)sulfonamido)-5-cyclopropyl-2-fluoro-N-(2-methoxyethyl)benzamide

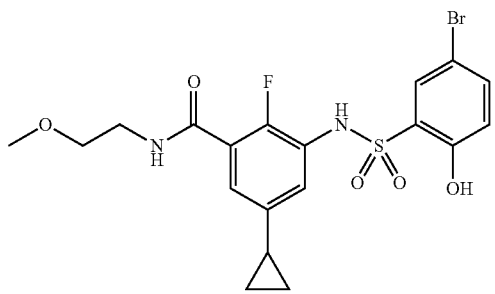 [SMILES: COCCNC(=O)c1cc(C2CC2)cc(NS(=O)(=O)c2cc(Br)ccc2O)c1F]

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J113 (22 mg, 0.05 mmol), and 2-methoxyethlamine, the title compound was obtained as a colorless solid (17 mg, 70%). LCMS (Method A) $t_R$=1.36 min, m/z=486.9, 488.8 [M+H]$^+$; Purity (AUC) ≥95%.

Example J143: 3-((5-Bromo-2-hydroxyphenyl)sulfonamido)-5-cyclopropyl-2-fluoro-N-(2-morpholinoethyl)benzamide

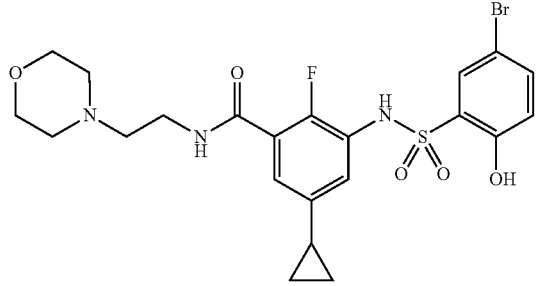 [SMILES: O=C(NCCN1CCOCC1)c1cc(C2CC2)cc(NS(=O)(=O)c2cc(Br)ccc2O)c1F]

Using a procedure analogous to General Procedure I, starting with 3-((5-Bromo-2-hydroxyphenyl)sulfonamido)-5-cyclopropyl-2-fluorobenzoic acid, which was prepared by a procedure analogous to the procedure used to prepare Example J113 (22 mg, 0.05 mmol), and (2-morpholino)ethanamine, the title compound was obtained as a colorless solid (21 mg, 77%) as free base. LCMS (Method A) $t_R$=1.29 min, m/z=541.8, 543.9 [M+H]$^+$; Purity (AUC) ≥95%.

Example J144: 3-((5-Bromo-2-hydroxyphenyl)sulfonamido)-5-cyclopropyl-2-fluoro-N-(oxetan-3-yl)benzamide

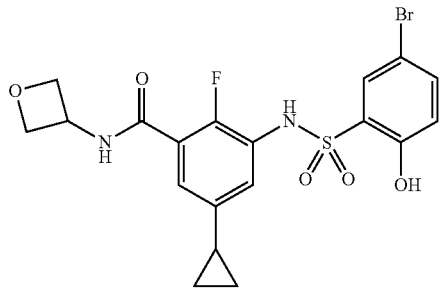 [SMILES: O=C(NC1COC1)c1cc(C2CC2)cc(NS(=O)(=O)c2cc(Br)ccc2O)c1F]

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J113 (22 mg, 0.05 mmol), and 3-aminooxetane, the title compound was obtained as a colorless solid (16 mg, 66%). LCMS (Method A) $t_R$=1.32 min, m/z=484.8, 486.8 [M+H]$^+$; Purity (AUC) ≥95%.

Example J145: 3-((5-Bromo-2-hydroxyphenyl)sulfonamido)-5-cyclopropyl-4-fluoro-2-hydroxy-N-methylbenzamide

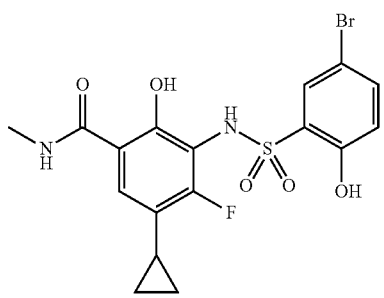 [SMILES: CNC(=O)c1cc(C2CC2)c(F)c(NS(=O)(=O)c2cc(Br)ccc2O)c1O]

Using a procedure analogous to General Procedure 1, starting with 3-((5-bromo-2-hydroxyphenyl)sulfonamido)-5-cyclopropyl-4-fluoro-2-hydroxybenzoic acid, which was prepared by a procedure analogous to the procedure used to prepare Example J122 (22 mg, 0.05 mmol), and methylamine, the title compound was obtained as a colorless solid (11 mg, 48%). LCMS (Method A) $t_R$=1.29 min, m/z=458.8, 460.8 [M+H]$^+$; Purity (AUC) ≥95%.

Example J146: 3-((5-Bromo-3-chloro-2-hydroxyphenyl)sulfonamido)-5-cyclopropyl-6-fluoro-2-hydroxy-N-methylbenzamide

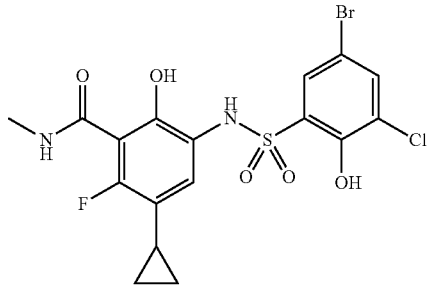 [SMILES: CNC(=O)c1c(O)c(NS(=O)(=O)c2cc(Br)cc(Cl)c2O)cc(C2CC2)c1F]

Using a procedure analogous to General Procedure G, starting with methyl 3-((5-bromo-3-chloro-2-hydroxyphenyl)sulfonamido)-5-cyclopropyl-6-fluoro-2-hydroxybenzoate, which was prepared by a procedure analogous to the procedure used to prepare Example J118 Step A (49 mg, 0.1 mmol), and methylamine, the title compound was obtained as a colorless solid (36 mg, 73%). $^1$H NMR (400 MHz, MeOH-d$_4$) $\delta_H$ 7.73 (d, J=2.4 Hz, 1H), 7.63 (d, J=2.4 Hz, 1H), 7.09 (d, J=8.1 Hz, 1H), 2.93 (s, 3H), 2.21-1.86 (m, 1H), 1.05-0.87 (m, 2H), 0.70-0.51 (m, 2H); $^{19}$F NMR (376 MHz, MeOH-d$_4$) $\delta_F$ −121.7; LCMS (Method A) $t_R$=1.83 min, m/z=492.7, 494.7 [M+H]$^+$; Purity (AUC) ≥95%.

Example J147: 3-((5-Bromo-3-chloro-2-hydroxyphenyl)sulfonamido)-5-cyclopropyl-6-fluoro-2-hydroxy-N-(2-methoxyethyl)benzamide

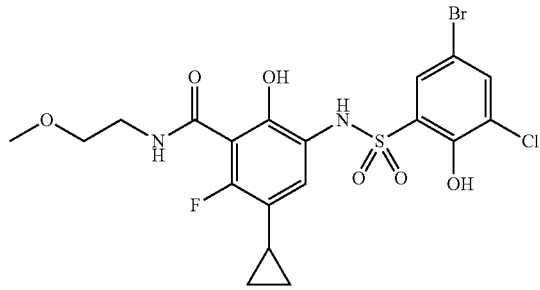

Using a procedure analogous to General Procedure I, starting with methyl 3-((5-bromo-3-chloro-2-hydroxyphenyl)sulfonamido)-5-cyclopropyl-6-fluoro-2-hydroxybenzoate, which was prepared by a procedure analogous to the procedure used to prepare Example J118 Step A (25 mg, 0.05 mmol), and 2-methoxyethlamine, the title compound was obtained as a colorless solid (7 mg, 26%). LCMS (Method A) $t_R$=1.78 min, m/z=536.7, 538.8 [M+H]$^+$; Purity (AUC) ≥95%.

Example J148: 3-((5-Bromo-3-chloro-2-hydroxyphenyl)sulfonamido)-5-cyclopropyl-6-fluoro-2-hydroxy-N-(2-morpholinoethyl)benzamide

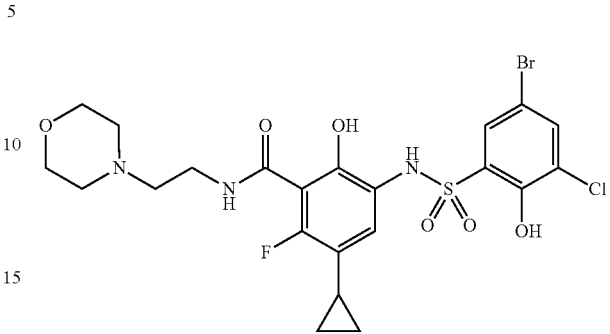

Using a procedure analogous to General Procedure I, starting with methyl 3-((5-bromo-3-chloro-2-hydroxyphenyl)sulfonamido)-5-cyclopropyl-6-fluoro-2-hydroxybenzoate, which was prepared by a procedure analogous to the procedure used to prepare Example J118 Step A (25 mg, 0.05 mmol), and (2-morpholino)ethanamine, the title compound was obtained as a pale brown solid (20 mg, 67%) as its trifluoroacetate salt. $^1$H NMR (400 MHz, MeOH-d$_4$) $\delta_H$ 7.47-7.38 (m, 2H), 6.92 (d, J=8.2 Hz, 1H), 3.72 (t, J=4.7 Hz, 4H), 3.54 (t, J=6.5 Hz, 2H), 2.60 (t, J=6.6 Hz, 2H), 2.55 (t, J=4.8 Hz, 4H), 2.01-1.87 (m, 1H), 0.96-0.85 (m, 2H), 0.58-0.48 (m, 2H); $^{19}$F NMR (376 MHz, MeOH-d$_4$) $\delta_F$ −125.4, −76.9 (TFA); LCMS (Method A) $t_R$=1.27 min, m/z=591.7, 593.7 [M+H]$^+$; Purity (AUC) ≥95%.

Example J149: 3-((5-Bromo-3-chloro-2-hydroxyphenyl)sulfonamido)-5-cyclopropyl-6-fluoro-2-hydroxy-N-(oxetan-3-yl)benzamide

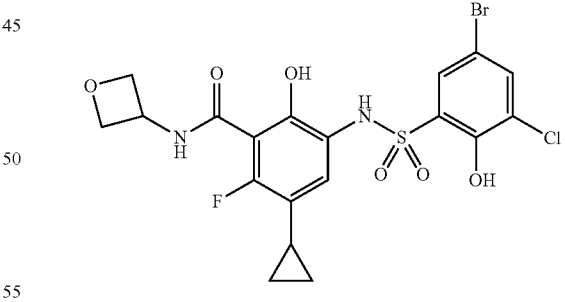

Using a procedure analogous to General Procedure I, starting with methyl 3-((5-bromo-3-chloro-2-hydroxyphenyl)sulfonamido)-5-cyclopropyl-6-fluoro-2-hydroxybenzoate, which was prepared by a procedure analogous to the procedure used to prepare Example J118 Step A (25 mg, 0.05 mmol), and 3-aminooxetane, the title compound was obtained as a pale brown solid (15 mg, 56%). LCMS (Method A) $t_R$=1.53 min, m/z=534.7, 536.7 [M+H]$^+$; Purity (AUC) ≥95%.

Example J150: 3-((5-Bromo-3-fluoro-2-hydroxyphenyl)sulfonamido)-5-cyclopropyl-6-fluoro-2-hydroxy-N-methylbenzamide

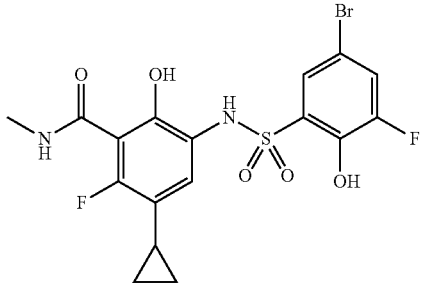 [SMILES: CNC(=O)c1c(O)c(NS(=O)(=O)c2cc(Br)cc(F)c2O)cc(C2CC2)c1F]

Using a procedure analogous to General Procedure G, starting with methyl 3-((5-bromo-3-fluoro-2-hydroxyphenyl)sulfonamido)-5-cyclopropyl-6-fluoro-2-hydroxybenzoate, which was prepared by a procedure analogous to the procedure used to prepare Example J119 Step A (31 mg, 0.065 mmol), and methylamine, the title compound was obtained as a colorless solid (19 mg, 61%). $^1$H NMR (400 MHz, MeOH-d$_4$) δ$_H$ 7.53 (s, 1H), 7.55-7.49 (m, 1H), 7.09 (d, J=8.1 Hz, 1H), 2.93 (s, 3H), 2.10-1.91 (m, 1H), 1.08-0.87 (m, 2H), 0.63-0.48 (m, 2H); $^{19}$F NMR (376 MHz, MeOH-d$_4$) δ$_F$ −122.4, −133.2; LCMS (Method A) t$_R$=1.74 min, m/z=476.7, 478.8 [M+H]$^+$; Purity (AUC) ≥95%.

Example J151: 5-((5-Bromo-3-chloro-2-hydroxyphenyl)sulfonamido)-3-cyclopropyl-2-fluoro-N-methylbenzamide

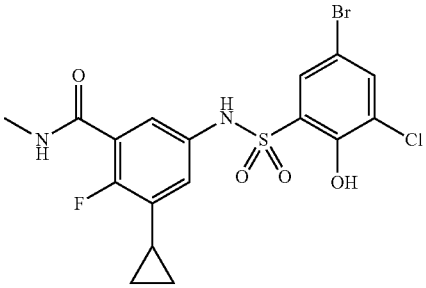 [SMILES: CNC(=O)c1cc(NS(=O)(=O)c2cc(Br)cc(Cl)c2O)cc(C2CC2)c1F]

Using a procedure analogous to General Procedure I, starting with 5-((5-bromo-3-chloro-2-hydroxyphenyl)sulfonamido)-3-cyclopropyl-2-fluorobenzoic acid, which was prepared by a procedure analogous to the procedure used to prepare Example J114-2 (23 mg, 0.05 mmol), and methylamine, the title compound was obtained as a colorless solid (7 mg, 29%). LCMS (Method A) t$_R$=1.43 min, m/z=476.7, 478.8 [M+H]$^+$; Purity (AUC) ≥95%.

Example J152: 5-((5-Bromo-3-chloro-2-hydroxyphenyl)sulfonamido)-3-cyclopropyl-2-fluoro-N-(2-methoxyethyl)benzamide

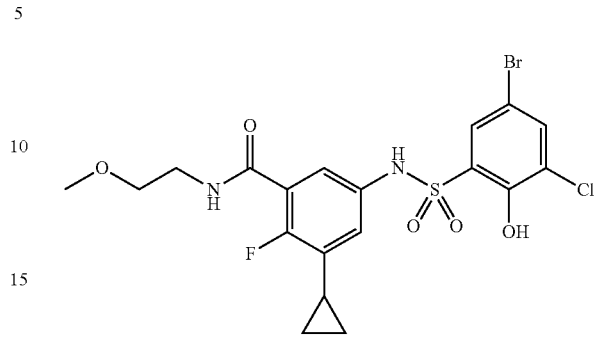

Using a procedure analogous to General Procedure I, starting with 5-((5-bromo-3-chloro-2-hydroxyphenyl)sulfonamido)-3-cyclopropyl-2-fluorobenzoic acid, which was prepared by a procedure analogous to the procedure used to prepare Example J114-2 (23 mg, 0.05 mmol) and 2-methoxyethlamine, the title compound was obtained as a colorless solid (24 mg, 92%). LCMS (Method A) t$_R$=1.58 min, m/z=520.8, 522.7 [M+H]$^+$; Purity (AUC) ≥95%.

Example J153: 5-((5-Bromo-3-chloro-2-hydroxyphenyl)sulfonamido)-3-cyclopropyl-2-fluoro-N-(2-morpholinoethyl)benzamide

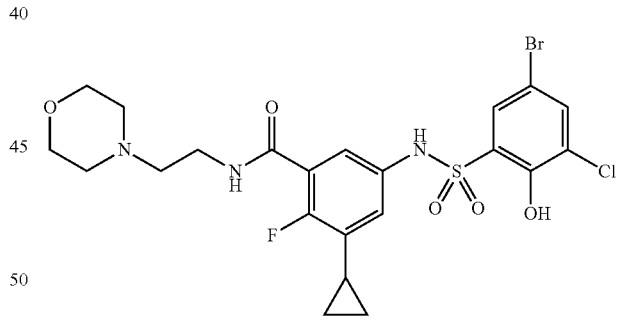

Using a procedure analogous to General Procedure I, starting with 5-((5-bromo-3-chloro-2-hydroxyphenyl)sulfonamido)-3-cyclopropyl-2-fluorobenzoic acid, which was prepared by a procedure analogous to the procedure used to prepare Example J114-2 (23 mg, 0.05 mmol), and (2-morpholino)ethanamine, the title compound was obtained as a pale brown solid (29 mg, 84%) as its trifluoroacetate salt. LCMS (Method A) t$_R$=1.37 min, m/z=575.8, 577.8 [M+H]$^+$; Purity (AUC) ≥95%.

Example J154: 5-((5-Bromo-3-chloro-2-hydroxyphenyl)sulfonamido)-3-cyclopropyl-2-fluoro-N-(1H-1,2,4-triazol-3-yl)benzamide

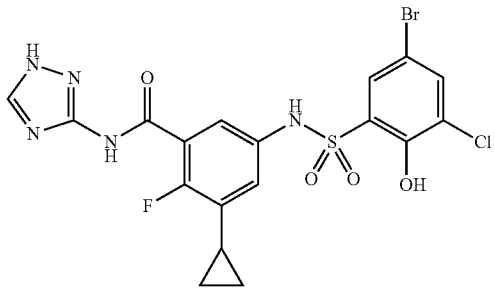 [SMILES: O=C(Nc1nc[nH]n1)c1cc(NS(=O)(=O)c2cc(Br)cc(Cl)c2O)cc(C2CC2)c1F]

Using a procedure analogous to General Procedure I, starting with 5-((5-bromo-3-chloro-2-hydroxyphenyl)sulfonamido)-3-cyclopropyl-2-fluorobenzoic acid, which was prepared by a procedure analogous to the procedure used to prepare Example J114-2 (23 mg, 0.05 mmol), and 3-amino-1,2,4-triazole, the title compound was obtained as a colorless solid (6 mg, 23%). LCMS (Method A) $t_R$=1.40 min, m/z=529.7, 531.7 [M+H]$^+$; Purity (AUC) ≥95%.

Example J155: 5-((5-Bromo-3-chloro-2-hydroxyphenyl)sulfonamido)-3-cyclopropyl-2-fluoro-N-(oxetan-3-yl)benzamide

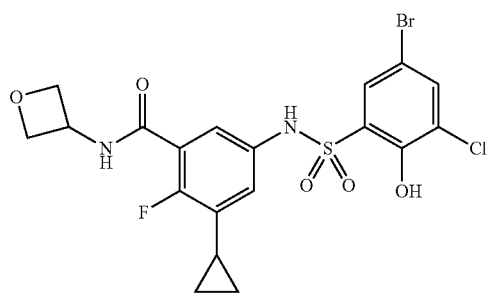 [SMILES: O=C(NC1COC1)c1cc(NS(=O)(=O)c2cc(Br)cc(Cl)c2O)cc(C2CC2)c1F]

Using a procedure analogous to General Procedure I, starting with 5-((5-bromo-3-chloro-2-hydroxyphenyl)sulfonamido)-3-cyclopropyl-2-fluorobenzoic acid, which was prepared by a procedure analogous to the procedure used to prepare Example J114-2 (23 mg, 0.05 mmol), and 3-aminooxetane, the title compound was obtained as a colorless solid (23 mg, 88%). LCMS (Method A) $t_R$=1.37 min, m/z=518.7, 520.7 [M+H]$^+$; Purity (AUC) ≥95%.

Example J156: 3-((5-Bromo-3-chloro-2-hydroxyphenyl)sulfonamido)-5-cyclopropyl-2-fluoro-N-methylbenzamide

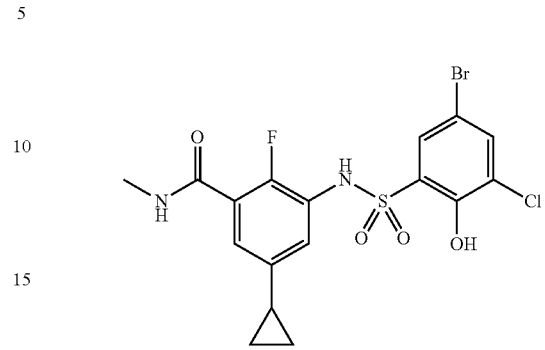

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J112 (23 mg, 0.05 mmol), and methylamine, the title compound was obtained as a colorless solid (19 mg, 80%). 1H NMR (400 MHz, MeOH-d$_4$) $\delta_H$ 7.75 (d, J=2.4 Hz, 1H), 7.72 (d, J=2.4 Hz, 1H), 7.18-7.12 (m, 2H), 2.87 (s, 3H), 1.93-1.83 (m, 1H), 1.02-0.93 (m, 2H), 0.62-0.54 (m, 2H); LCMS (Method A) $t_R$=1.41 min, m/z=476.8, 478.8 [M+H]$^+$; Purity (AUC) ≥95%.

Example J157: 3-((5-Bromo-3-chloro-2-hydroxyphenyl)sulfonamido)-5-cyclopropyl-2-fluoro-N-(2-methoxyethyl)benzamide

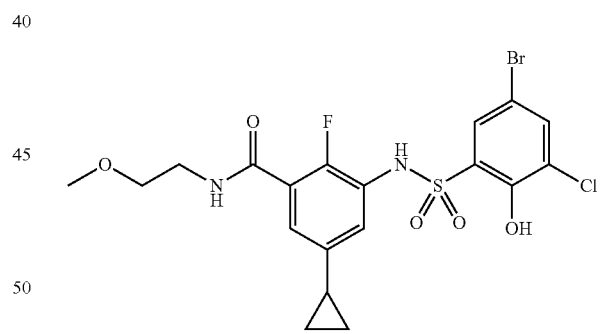

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J112 (23 mg, 0.05 mmol), and 2-methoxyethylamine, the title compound was obtained as a colorless solid (14 mg, 54%). $^1$H NMR (400 MHz, MeOH-d$_4$) $\delta_H$ 7.76 (d, J=2.5 Hz, 1H), 7.73 (d, J=2.5 Hz, 1H), 7.19-7.14 (m, 2H), 3.53-3.50 (m, 4H), 3.37 (s, 3H), 1.99-1.79 (m, 1H), 1.07-0.86 (m, 2H), 0.64-0.45 (m, 2H); LCMS (Method A) $t_R$=1.53 min, m/z=520.8, 522.7 [M+H]$^+$; Purity (AUC) ≥95%.

Example J158: 3-((5-Bromo-3-chloro-2-hydroxyphenyl)sulfonamido)-5-cyclopropyl-2-fluoro-N-(2-morpholinoethyl)benzamide

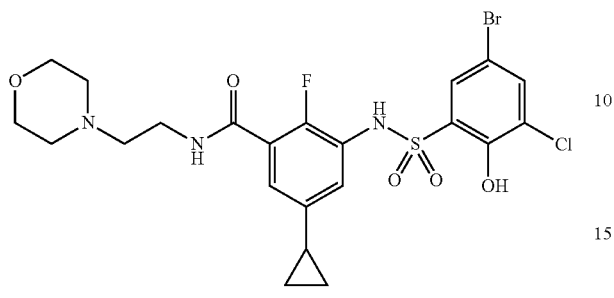

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J112 (23 mg, 0.05 mmol), and (2-morpholino)ethanamine, the title compound was obtained as an off-white solid (18 mg, 62%). $^1$H NMR (400 MHz, MeOH-d$_4$) $\delta_H$ 7.44 (d, J=2.6 Hz, 1H), 7.41 (d, J=2.6 Hz, 1H), 7.12 (dd, J=6.0, 2.4 Hz, 1H), 7.07 (dd, J=7.2, 2.4 Hz, 1H), 3.71 (t, J=4.7 Hz, 4H), 3.51 (t, J=6.7 Hz, 2H), 2.58 (t, J=6.7 Hz, 2H), 2.53 (t, J=4.7 Hz, 4H), 1.86-1.76 (m, 1H), 0.96-0.89 (m, 2H), 0.59-0.49 (m, 2H); LCMS (Method A) $t_R$=1.24 min, m/z=575.8, 577.8 [M+H]$^+$; Purity (AUC) ≥95%.

Example J159: 3-((5-Bromo-3-chloro-2-hydroxyphenyl)sulfonamido)-5-cyclopropyl-2-fluoro-N-(oxetan-3-yl)benzamide

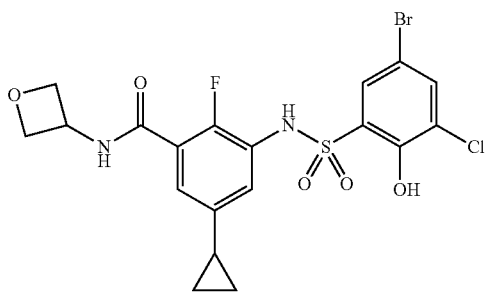 [SMILES: O=C(NC1COC1)c1cc(C2CC2)cc(NS(=O)(=O)c2cc(Br)cc(Cl)c2O)c1F]

Using a procedure analogous to General Procedure I, starting with 3-((5-bromo-2-hydroxyphenyl)sulfonamido)-5-cyclopropyl-2-fluorobenzoic acid, which was prepared by a procedure analogous to the procedure used to prepare Example J112 (23 mg, 0.05 mmol), and 3-aminooxetane, the title compound was obtained as an off-white solid (21 mg, 81%). $^1$H NMR (400 MHz, MeOH-d$_4$) $\delta_H$ 7.46 (d, J=2.7 Hz, 1H), 7.42 (d, J=2.7 Hz, 1H), 7.10 (dd, J=7.2, 2.4 Hz, 1H), 7.06 (dd, J=5.9, 2.4 Hz, 1H), 5.10 (p, J=6.8 Hz, 1H), 4.91 (t, J=6.8 Hz, 2H), 4.67 (t, J=6.8 Hz, 2H), 1.90-1.73 (m, 1H), 0.98-0.86 (m, 2H), 0.63-0.49 (m, 2H); LCMS (Method A) $t_R$=1.36 min, m/z=518.7, 520.8 [M+H]$^+$; Purity (AUC) ≥95%.

Example J160: 3-((5-Bromo-2-hydroxyphenyl)sulfonamido)-2-hydroxy-5-(trifluoromethoxy)benzoic acid

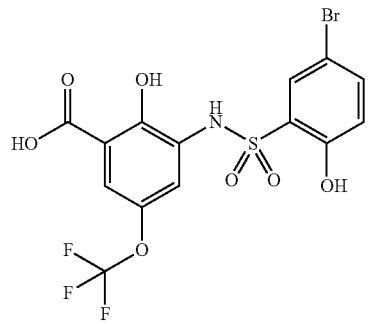 [SMILES: O=C(O)c1cc(OC(F)(F)F)cc(NS(=O)(=O)c2cc(Br)ccc2O)c1O]

Step A: Methyl 3-((5-bromo-2-hydroxyphenyl)sulfonamido)-2-hydroxy-5-(trifluoromethoxy)benzoate. Using a procedure analogous to General Procedure E, starting with methyl 3-amino-2-hydroxy-5-(trifluoromethoxy)benzoate, which was prepared by a procedure analogous to the procedure used to prepare Example HCH-1 Step C (1256 mg, 5.0 mmol), and 5-bromo-2-hydroxybenzenesulfonyl chloride, which was prepared by a procedure analogous to the procedure used to prepare Example J1 Step A, methyl 3-((5-bromo-2-hydroxyphenyl)sulfonamido)-2-hydroxy-5-(trifluoromethoxy)benzoate was obtained as a pale-brown solid (1020 mg, 2.2 mmol, 43%). $^1$H NMR (400 MHz, CDCl$_3$) $\delta_H$ 11.10 (s, 1H), 8.68 (s, 1H), 7.68 (d, J=2.4 Hz, 1H), 7.64-7.60 (m, 1H), 7.51-7.46 (m, 3H), 6.88 (d, J=8.9 Hz, 1H), 3.96 (s, 3H); $^{19}$F NMR (376 MHz, CDCl$_3$) $\delta_F$ −58.6; LCMS (Method B) $t_R$=1.20 min, m/z=485.8, 487.8 [M+H]$^+$; Purity (AUC) ≥95%.

Step B: 3-((5-Bromo-2-hydroxyphenyl)sulfonamido)-2-hydroxy-5-(trifluoromethoxy)benzoic acid. Using a procedure analogous to General Procedure F, starting with methyl 3-((5-bromo-2-hydroxyphenyl)sulfonamido)-2-hydroxy-5-(trifluoromethoxy)benzoate (1015 mg, 2.09 mmol), the title compound was obtained as a colorless solid (575 mg, 1.22 mmol, 58%). $^1$H NMR (400 MHz, MeOH-d$_4$) $\delta_H$ 7.82 (d, J=2.5 Hz, 1H), 7.58-7.55 (m, 1H), 7.54 (dd, J=8.8, 2.5 Hz, 1H), 7.45-7.41 (m, 1H), 6.86 (d, J=8.8 Hz, 1H); $^{19}$F NMR (376 MHz, MeOH-d$_4$) $\delta_F$ −60.3; LCMS (Method A) $t_R$=1.57 min, m/z=471.8, 473.8 [M+H]$^+$; Purity (AUC) ≥95%.

Example J161: 3-((6-Bromoquinoline)-8-sulfonamido)-2-hydroxy-5-(trifluoromethoxy)benzoic acid

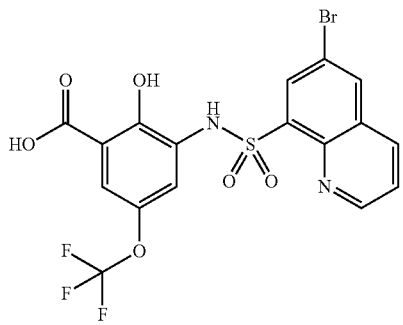 [SMILES: O=C(O)c1cc(OC(F)(F)F)cc(NS(=O)(=O)c2cc(Br)cc3cccnc23)c1O]

Step A: Methyl 3-((6-bromoquinoline)-8-sulfonamido)-2-hydroxy-5-(trifluoromethoxy)benzoate. Using a procedure analogous to General Procedure E, starting with methyl 3-amino-2-hydroxy-5-(trifluoromethoxy)benzoate (55 mg, 0.20 mmol), which was prepared by a procedure analogous to the procedure used to prepare Example HCH-1 Step C, and 6-bromoquinoline-8-sulfonyl chloride, methyl 3-((6-bromoquinoline)-8-sulfonamido)-2-hydroxy-5-(trifluoromethoxy)benzoate was obtained as a colorless solid (94 mg, 0.17 mmol, 86%). LCMS (Method A) $t_R$=1.93 min, m/z=546.7, 548.7 [M+H]$^+$; Purity (AUC) ≥95%.

Step B: 3-((6-Bromoquinoline)-8-sulfonamido)-2-hydroxy-5-(trifluoromethoxy)benzoic acid. Using a procedure analogous to General Procedure F, starting from methyl 3-((6-bromoquinoline)-8-sulfonamido)-2-hydroxy-5-(trifluoromethoxy)benzoate (26 mg, 0.05 mmol), the title compound was obtained as a colorless solid (16 mg, 63%) as free base. 1H NMR (400 MHz, MeOH-d$_4$) $\delta_H$ 9.09 (dd, J=4.3, 1.7 Hz, 1H), 8.45 (d, J=2.2 Hz, 1H), 8.43 (d, J=2.2 Hz, 1H), 8.39 (dd, J=8.4, 1.8 Hz, 1H), 7.71-7.66 (m, 2H), 7.41-7.36 (m, 1H); $^{19}$F NMR (376 MHz, MeOH-d$_4$) $\delta_F$ −60.3; LCMS (Method A) $t_R$=1.87 min, m/z=506.7, 508.7 [M+H]$^+$; Purity (AUC) ≥95%.

Example J162: 3-((5-Bromo-2-hydroxyphenyl)sulfonamido)-2-hydroxy-N-methyl-5-(trifluoromethoxy)benzamide

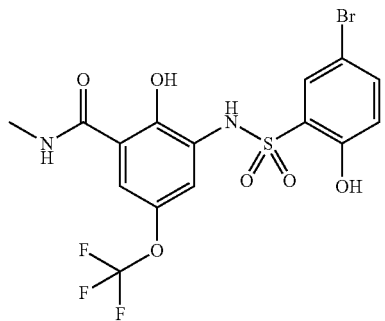 [SMILES: CNC(=O)c1cc(OC(F)(F)F)cc(NS(=O)(=O)c2cc(Br)ccc2O)c1O]

Using a procedure analogous to General Procedure G, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A), and methylamine, the title compound was obtained as a colorless solid (16 mg, 0.033 mmol, 66%). 1H NMR (400 MHz, MeOH-d$_4$) $\delta_H$ 7.81 (d, J=2.5 Hz, 1H), 7.53 (dd, J=8.8, 2.5 Hz, 1H), 7.48 (dd, J=2.7, 1.1 Hz, 1H), 7.38 (dd, J=2.7, 0.8 Hz, 1H), 6.86 (d, J=8.8 Hz, 1H), 2.89 (s, 3H); $^{19}$F NMR (376 MHz, MeOH-d$_4$) $\delta_F$ −60.2; LCMS (Method A) $t_R$=1.68 min, m/z=484.8, 486.7 [M+H]$^+$; Purity (AUC) ≥95%.

Example J163: 3-((5-Bromo-2-hydroxyphenyl)sulfonamido)-2-hydroxy-N-(2-methoxyethyl)-5-(trifluoromethoxy)benzamide

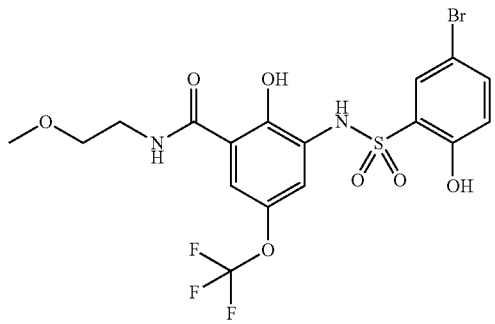 [SMILES: COCCNC(=O)c1cc(OC(F)(F)F)cc(NS(=O)(=O)c2cc(Br)ccc2O)c1O]

Using a procedure analogous to General Procedure 1, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160, and 2-methoxyethylamine, the title compound was obtained as a colorless solid (9 mg, 34%). LCMS (Method A) $t_R$=1.67 min, m/z=528.7, 530.7 [M+H]$^+$; Purity (AUC) >90%.

Example J164: 3-((5-Bromo-2-hydroxyphenyl)sulfonamido)-2-hydroxy-N-(2-morpholinoethyl)-(trifluoromethoxy)benzamide

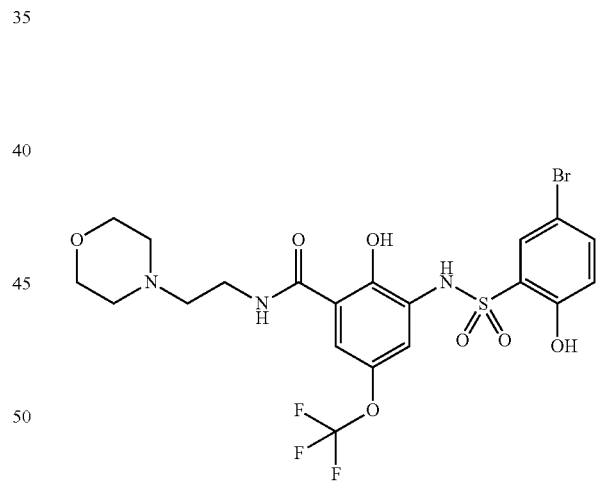

Using a procedure analogous to General Procedure I, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160 (24 mg, 0.05 mmol), and 2-morpholinoethan-1-amine, the title compound was obtained as a colorless solid (10 mg, 34%). LCMS (Method A) $t_R$=1.18 min, m/z=583.8, 585.7 [M+H]$^+$; Purity (AUC) ≥95%.

Example J165: 3-((5-Bromo-2-hydroxyphenyl)sulfonamido)-2-hydroxy-N-((tetrahydrofuran-2-yl)methyl)-5-(trifluoromethoxy)benzamide

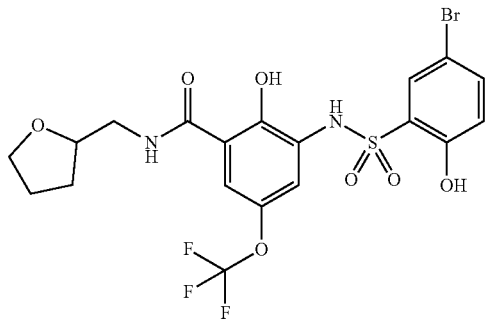 [SMILES: O=C(NCC1CCCO1)c1cc(OC(F)(F)F)cc(NS(=O)(=O)c2cc(Br)ccc2O)c1O]

Using a procedure analogous to General Procedure 1, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160, and tetrahydrofurfurylamine, the title compound was obtained as a colorless solid (15 mg, 54%). $^1$H NMR (400 MHz, MeOH-d$_4$) $\delta_H$ 7.81 (d, J=2.5 Hz, 1H), 7.53 (dd, J=8.8, 2.5 Hz, 1H), 7.52-7.45 (m, 2H), 6.86 (d, J=8.8 Hz, 1H), 4.14-4.03 (m, 1H), 3.92-3.85 (m, 1H), 3.81-3.73 (m, 1H), 3.52-3.36 (m, 2H), 2.11-1.98 (m, 1H), 1.98-1.87 (m, 2H), 1.64 (ddt, J=11.7, 7.9, 6.7 Hz, 1H); $^{19}$F NMR (376 MHz, MeOH-d$_4$) $\delta_F$ −60.2; LCMS (Method A) t$_R$=1.74 min, m/z=554.7, 556.7 [M+H]$^+$; Purity (AUC) ≥95%.

Example J166: 3-((5-Bromo-2-hydroxyphenyl)sulfonamido)-2-hydroxy-N-((tetrahydrofuran-3-yl)methyl)-5-(trifluoromethoxy)benzamide

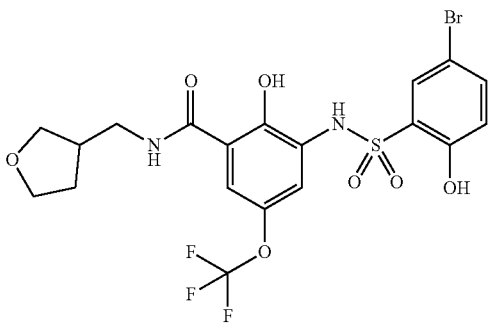 [SMILES: O=C(NCC1CCOC1)c1cc(OC(F)(F)F)cc(NS(=O)(=O)c2cc(Br)ccc2O)c1O]

Using a procedure analogous to General Procedure 1, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160, and (tetrahydrofuran-3-yl)methanamine, the title compound was obtained as a colorless solid (18 mg, 65%). $^1$H NMR (400 MHz, MeOH-d$_4$) $\delta_H$ 7.80 (d, J=2.5 Hz, 1H), 7.53 (dd, J=8.8, 2.5 Hz, 1H), 7.51-7.49 (m, 2H), 7.44 (d, J=2.6 Hz, 2H), 6.86 (d, J=8.8 Hz, 1H), 3.89 (td, J=8.2, 5.5 Hz, 1H), 3.81 (dd, J=8.7, 6.9 Hz, 1H), 3.75 (td, J=8.1, 6.9 Hz, 1H), 3.57 (dd, J=8.7, 5.4 Hz, 1H), 3.38 (dd, J=7.4, 2.7 Hz, 2H), 2.60 (hept, J=7.2 Hz, 1H), 2.12-2.00 (m, 1H), 1.76-1.64 (m, 1H); $^{19}$F NMR (376 MHz, MeOH-d$_4$) $\delta_F$ −60.2; LCMS (Method A) t$_R$=1.69 min, m/z=554.7, 556.7 [M+H]$^+$; Purity (AUC) ≥95%.

Example J167: 3-((5-Bromo-2-hydroxyphenyl)sulfonamido)-2-hydroxy-N-(tetrahydrofuran-3-yl)-5-(trifluoromethoxy)benzamide

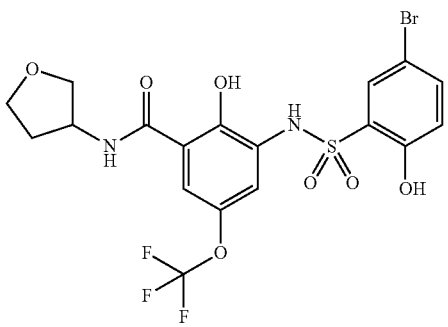 [SMILES: O=C(NC1CCOC1)c1cc(OC(F)(F)F)cc(NS(=O)(=O)c2cc(Br)ccc2O)c1O]

Using a procedure analogous to General Procedure I, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160, and 3-aminotetrahydrofuran, the title compound was obtained as a colorless solid (15 mg, 55%). $^1$H NMR (400 MHz, MeOH-d$_4$) $\delta_H$ 7.80 (d, J=2.5 Hz, 1H), 7.56 (d, J=2.8 Hz, 1H), 7.53 (dd, J=8.8, 2.5 Hz, 1H), 7.49 (dd, J=2.8, 1.1 Hz, 1H), 6.86 (d, J=8.8 Hz, 1H), 4.58 (ddt, J=8.1, 6.2, 4.1 Hz, 1H), 4.04-3.90 (m, 2H), 3.83 (td, J=8.3, 5.9 Hz, 1H), 3.72 (dd, J=9.3, 4.1 Hz, 1H), 2.29 (dtd, J=13.0, 8.0, 6.7 Hz, 1H), 2.07-1.94 (m, 1H); $^{19}$F NMR (376 MHz, MeOH-d$_4$) $\delta_F$ −60.2; LCMS (Method A) t$_R$=1.67 min, m/z=540.7, 542.7 [M+H]$^+$; Purity (AUC) ≥95%.

Example J168: (S)-3-((5-Bromo-2-hydroxyphenyl)sulfonamido)-2-hydroxy-N-(tetrahydrofuran-3-yl)-5-(trifluoromethoxy)benzamide

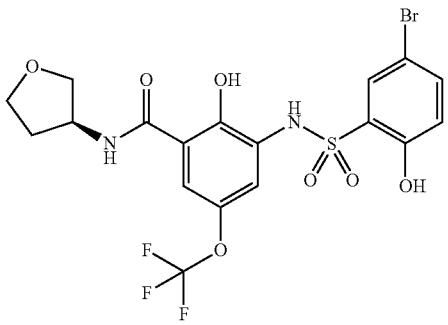 [SMILES: O=C(N[C@H]1CCOC1)c1cc(OC(F)(F)F)cc(NS(=O)(=O)c2cc(Br)ccc2O)c1O]

Using a procedure analogous to General Procedure I, starting from 3-((5-bromo-2-hydroxyphenyl)sulfonamido)-2-hydroxy-5-(trifluoromethoxy)benzoic (24 mg, 0.05 mmol), which was prepared by a procedure analogous to the procedure used to prepare Example J160, and (S)-3-aminotetrahydrofuran, the title compound was obtained as a colorless solid (20 mg, 74%). $^1$H NMR (400 MHz, MeOH-d$_4$) $\delta_H$ 7.80 (d, J=2.5 Hz, 1H), 7.56 (d, J=2.8 Hz, 1H), 7.53 (dd, J=8.8, 2.5 Hz, 1H), 7.49 (dd, J=2.8, 1.0 Hz, 2H), 6.86 (d, J=8.8 Hz, 1H), 4.58 (ddt, J=8.1, 6.1, 4.1 Hz, 1H), 4.03-3.90 (m, 2H), 3.83 (td, J=8.3, 5.9 Hz, 1H), 3.72 (dd, J=9.3, 4.1 Hz, 1H), 2.29 (dtd, J=13.0, 8.0, 6.6 Hz, 1H), 2.09-1.94 (m, 1H); $^{19}$F NMR (376 MHz, MeOH-d$_4$) $\delta_F$ −60.2; LCMS (Method A) $t_R$=1.67 min, m/z=540.7, 542.7 [M+H]$^+$; Purity (AUC) ≥95%.

Example J169: (S)-5-Bromo-2-hydroxy-N-(2-hydroxy-3-(2-(hydroxymethyl)pyrrolidine-1-carbonyl)-5-(trifluoromethoxy)phenyl)benzenesulfonamide

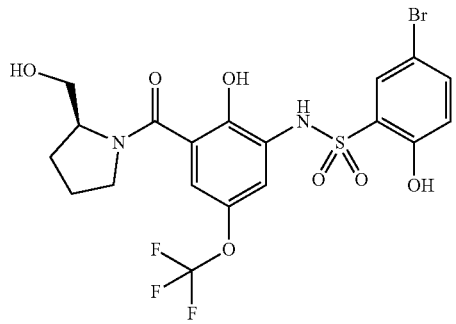 [SMILES: O=C(c1cc(OC(F)(F)F)cc(NS(=O)(=O)c2cc(Br)ccc2O)c1O)N1CCC[C@H]1CO]

Using a procedure analogous to General Procedure H, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A, and L-prolinol, the title compound was obtained as an off-white solid (19 mg, 68%). $^1$H NMR (400 MHz, MeOH-d$_4$) $\delta_H$ 7.74 (d, J=2.5 Hz, 1H), 7.55 (dd, J=8.8, 2.5 Hz, 1H), 7.31 (br s, 1H), 7.06 (d, J=2.9 Hz, 1H), 6.89 (d, J=8.8 Hz, 1H), 4.26 (br s, 1H), 3.93-3.58 (m, 2H), 2.23-1.65 (m, 5H); $^{19}$F NMR (376 MHz, MeOH-d$_4$) $\delta_F$ −60.1; LCMS (Method A) $t_R$=1.56 min, m/z=554.7, 556.8 [M+H]$^+$; Purity (AUC) ≥95%.

Example J170: (R)-5-Bromo-2-hydroxy-N-(2-hydroxy-3-(2-(hydroxymethyl)pyrrolidine-1-carbonyl)-5-(trifluoromethoxy)phenyl)benzenesulfonamide

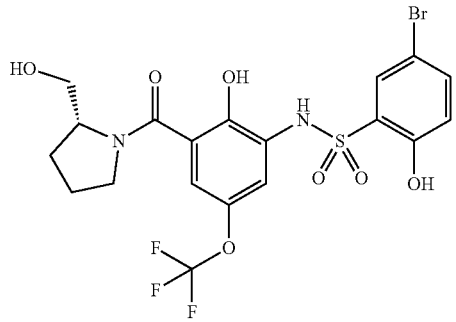 [SMILES: O=C(c1cc(OC(F)(F)F)cc(NS(=O)(=O)c2cc(Br)ccc2O)c1O)N1CCC[C@@H]1CO]

Using a procedure analogous to General Procedure H, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A, and D-prolinol, the title compound was obtained as an off-white solid (19 mg, 68%). $^1$H NMR (400 MHz, MeOH-d$_4$) $\delta_H$ 7.74 (d, J=2.5 Hz, 1H), 7.55 (dd, J=8.8, 2.5 Hz, 1H), 7.31 (br s, 1H), 7.06 (d, J=2.9 Hz, 1H), 6.89 (d, J=8.8 Hz, 1H), 4.26 (br s, 1H), 3.91-3.54 (m, 2H), 2.23-1.62 (m, 5H); $^{19}$F NMR (376 MHz, MeOH-d$_4$) $\delta_F$ −60.1; LCMS (Method A) $t_R$=1.56 min, m/z=554.7, 556.8 [M+H]$^+$; Purity (AUC) ≥95%.

Example J171: (S)-5-Bromo-2-hydroxy-N-(2-hydroxy-3-(2-(methoxymethyl)pyrrolidine-1-carbonyl)-5-(trifluoromethoxy)phenyl)benzenesulfonamide

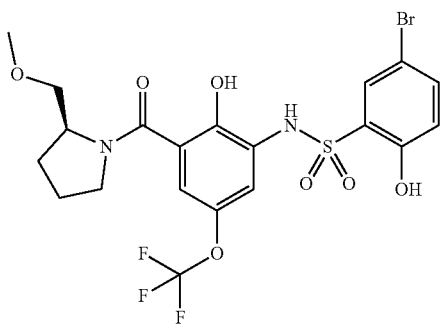 [SMILES: COC[C@@H]1CCCN1C(=O)c1cc(OC(F)(F)F)cc(NS(=O)(=O)c2cc(Br)ccc2O)c1O]

Using a procedure analogous to General Procedure H, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A, and O-methyl-L-prolinol, the title compound was obtained as an off-white solid (7 mg, 25%). LCMS (Method A) $t_R$=1.72 min, m/z=568.8, 570.7 [M+H]$^+$; Purity (AUC) ≥95%.

Example J172: (R)-5-Bromo-2-hydroxy-N-(2-hydroxy-3-(2-(methoxymethyl)pyrrolidine-1-carbonyl)-5-(trifluoromethoxy)phenyl)benzenesulfonamide

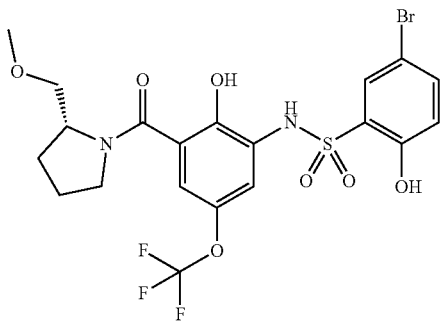

Using a procedure analogous to General Procedure H, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A, and O-methyl-D-prolinol, the title compound was obtained as an off-white solid (7 mg, 25%). LCMS (Method A) $t_R$=1.72 min, m/z=568.8, 570.7 [M+H]$^+$; Purity (AUC) ≥95%.

Example J173: (R)-5-Bromo-2-hydroxy-N-(2-hydroxy-3-(3-hydroxypyrrolidine-1-carbonyl)-5-(trifluoromethoxy)phenyl)benzenesulfonamide

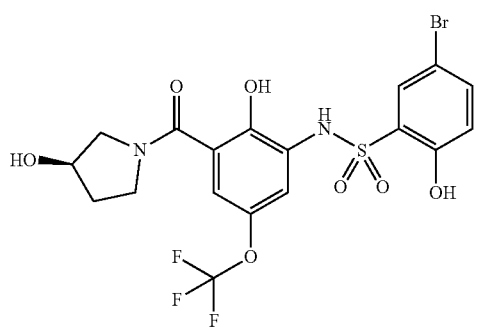 [SMILES: O=C(c1cc(OC(F)(F)F)cc(NS(=O)(=O)c2cc(Br)ccc2O)c1O)N1CC[C@@H](O)C1]

Using a procedure analogous to General Procedure H, starting from methyl 3-((5-bromo-2-hydroxyphenyl)sulfonamido)-2-hydroxy-5-(trifluoromethoxy)benzoate (24 mg, 0.05 mmol), which was prepared by a procedure analogous to the procedure used to prepare Example J160 Step A, and (R)-3-hydroxypyrrolidine, the title compound was obtained as an off-white solid (12 mg, 44%). LCMS (Method A) $t_R$=1.49 min, m/z=540.7, 542.7 [M+H]$^+$; Purity (AUC) ≥95%.

Example J174: 5-Bromo-2-hydroxy-N-(2-hydroxy-3-(3-methoxypyrrolidine-1-carbonyl)-5-(trifluoromethoxy)phenyl)benzenesulfonamide

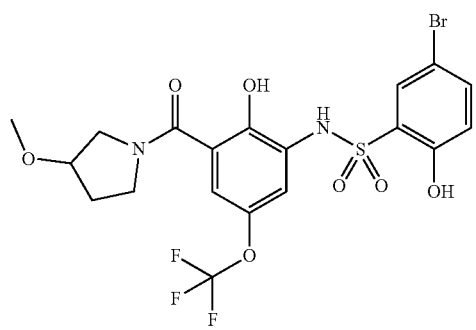 [SMILES: COC1CCN(C(=O)c2cc(OC(F)(F)F)cc(NS(=O)(=O)c3cc(Br)ccc3O)c2O)C1]

Using a procedure analogous to General Procedure I, starting from 3-((5-bromo-2-hydroxyphenyl)sulfonamido)-2-hydroxy-5-(trifluoromethoxy)benzoic acid (24 mg, 0.05 mmol), which was prepared by a procedure analogous to the procedure used to prepare Example J160, and 3-methoxypyrrolidine, the title compound was obtained as a colorless solid (20 mg, 72%). LCMS (Method A) $t_R$=1.64 min, m/z=554.7, 556.8 [M+H]$^+$; Purity (AUC) ≥95%.

Example J175: 3-((5-Chloro-2-hydroxyphenyl)sulfonamido)-2-hydroxy-N-methyl-5-(trifluoromethoxy)benzamide

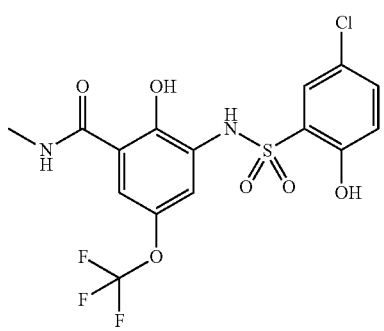

Step A: 5-Chloro-2-hydroxybenzenesulfonyl chloride. Using a procedure analogous to General Procedure A, starting from 4-chlorophenol (2.57 g, 20 mmol), 5-chloro-2-hydroxybenzenesulfonyl chloride was obtained as a pale brown oily solid (1.70 g, 7.49 mmol, 37%). $^1$H NMR (400 MHz, CDCl$_3$) $\delta_H$ 7.84 (d, J=2.6 Hz, 1H), 7.60 (dd, J=9.0, 2.6 Hz, 1H), 7.12 (d, J=9.0 Hz, 1H); LCMS (Method A) $t_R$=1.39 min; Purity (AUC) >90%.

Step B: Methyl 3-((5-chloro-2-hydroxyphenyl)sulfonamido)-2-hydroxy-5-(trifluoromethoxy)benzoate. Using a procedure analogous to General Procedure E, starting from methyl 3-amino-2-hydroxy-5-(trifluoromethoxy)benzoate (502 mg, 2.0 mmol), which was prepared by a procedure analogous to the procedure used to prepare Example HCH-1 Step C, and 5-chloro-2-hydroxybenzenesulfonyl chloride, methyl 3-((5-chloro-2-hydroxyphenyl)sulfonamido)-2-hydroxy-5-(trifluoromethoxy)benzoate was obtained as a pale brown solid (275 mg, 31%). LCMS (Method A) $t_R$=1.81 min, m/z=441.8 [M+H]$^+$; Purity (AUC) ≥95%.

Step C: 3-((5-Chloro-2-hydroxyphenyl)sulfonamido)-2-hydroxy-N-methyl-5-(trifluoromethoxy)benzamide. Using a procedure analogous to General Procedure G, starting with methyl 3-((5-chloro-2-hydroxyphenyl)sulfonamido)-2-hydroxy-5-(trifluoromethoxy)benzoate (22 mg, 0.05 mmol), and methylamine, the title compound was obtained as a colorless solid (12 mg, 54%). 1H NMR (400 MHz, MeOH-d$_4$) $\delta_H$ 7.68 (d, J=2.7 Hz, 1H), 7.49 (dd, J=2.8, 1.1 Hz, 1H), 7.40 (dd, J=8.8, 2.7 Hz, 1H), 7.38 (dd, J=2.8, 1.7 Hz, 1H), 6.91 (d, J=8.8 Hz, 1H), 2.89 (s, 3H); $^{19}$F NMR (376 MHz, MeOH-d$_4$) $\delta_F$ −60.3; LCMS (Method A) $t_R$=1.64 min, m/z=440.8 [M+H]$^+$; Purity (AUC) ≥95%.

Example J176: (S)-5-Chloro-2-hydroxy-N-(2-hydroxy-3-(2-(methoxymethyl)pyrrolidine-1-carbonyl)-5-(trifluoromethoxy)phenyl)benzenesulfonamide

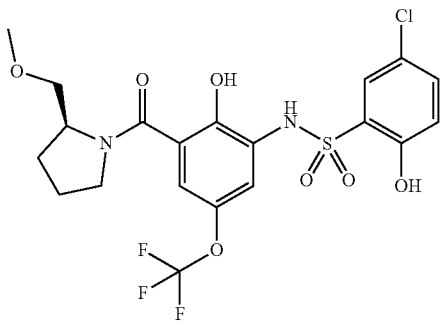

Using a procedure analogous to General Procedure H, starting from methyl 3-((5-chloro-2-hydroxyphenyl)sulfonamido)-2-hydroxy-5-(trifluoromethoxy)benzoate (22 mg, 0.05 mmol), which was prepared by a procedure analogous to the procedure used to prepare Example J175 Step B, and O-methyl-L-prolinol, the title compound was obtained as a colorless solid (5 mg, 19%). LCMS (Method A) $t_R$=1.70 min, m/z=524.8 [M+H]$^+$; Purity (AUC) ≥95%.

Example J177: (R)-5-Chloro-2-hydroxy-N-(2-hydroxy-3-(2-(methoxymethyl)pyrrolidine-1-carbonyl)-5-(trifluoromethoxy)phenyl)benzenesulfonamide

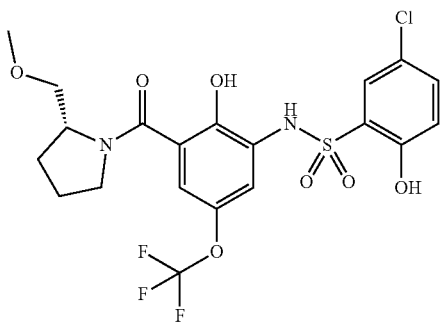

Using a procedure analogous to General Procedure H, starting from methyl 3-((5-chloro-2-hydroxyphenyl)sulfonamido)-2-hydroxy-5-(trifluoromethoxy)benzoate (22 mg, 0.05 mmol), which was prepared by a procedure analogous to the procedure used to prepare Example J175 Step B, and O-methyl-D-prolinol, the title compound was obtained as a colorless solid (5 mg, 19%). LCMS (Method A) $t_R$=1.70 min, m/z=524.8 [M+H]$^+$; Purity (AUC) ≥95%.

Example J178: 3-((5-Chloro-2-hydroxyphenyl)sulfonamido)-2-hydroxy-N-((tetrahydrofuran-2-yl)methyl)-5-(trifluoromethoxy)benzamide

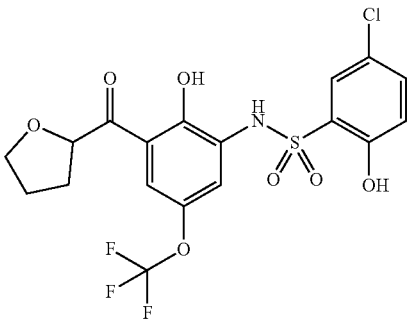 [SMILES: O=C(c1cc(OC(F)(F)F)cc(NS(=O)(=O)c2cc(Cl)ccc2O)c1O)C1CCCO1]

Using a procedure analogous to General Procedure H, starting from methyl 3-((5-chloro-2-hydroxyphenyl)sulfonamido)-2-hydroxy-5-(trifluoromethoxy)benzoate (22 mg, 0.05 mmol), which was prepared by a procedure analogous to the procedure used to prepare Example J175 Step B, and tetrahydrofurufrylamine, the title compound was obtained as a colorless solid (14 mg, 19%). $^1$H NMR (400 MHz, MeOH-d$_4$) $\delta_H$ 7.68 (d, J=2.6 Hz, 1H), 7.50-7.45 (m, 2H), 7.40 (dd, J=8.8, 2.7 Hz, 1H), 6.91 (d, J=8.8 Hz, 1H), 4.09 (td, J=6.9, 4.6 Hz, 1H), 3.89 (dt, J=8.3, 6.7 Hz, 1H), 3.77 (q, J=7.4 Hz, 1H), 3.52-3.37 (m, 2H), 2.10-1.99 (m, 1H), 1.99-1.88 (m, 2H), 1.70-1.59 (m, 1H); $^{19}$F NMR (376 MHz, MeOH-d$_4$) $\delta_F$ −60.2; LCMS (Method A) $t_R$=1.72 min, m/z=510.9 [M+H]$^+$; Purity (AUC) ≥95%.

Example J179: 3-((5-Bromo-2-methoxyphenyl)sulfonamido)-2-hydroxy-N-((tetrahydrofuran-2-yl)methyl)-5-(trifluoromethoxy)benzamide

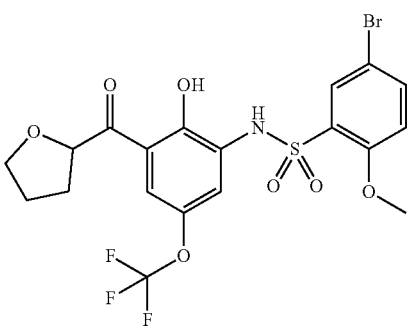 [SMILES: COc1ccc(Br)cc1S(=O)(=O)Nc1cc(OC(F)(F)F)cc(C(=O)C2CCCO2)c1O]

Step A: Methyl 3-((5-bromo-2-methoxyphenyl)sulfonamido)-2-hydroxy-5-(trifluoromethoxy)benzoate. Using a procedure analogous to General Procedure E, starting from methyl 3-amino-2-hydroxy-5-(trifluoromethoxy)benzoate (251 mg, 1.0 mmol), which was prepared by a procedure analogous to the procedure used to prepare Example HCH-1 Step C, and 5-bromo-2-methoxybenzenesulfonyl chloride, methyl 3-((5-bromo-2-methoxyphenyl)sulfonamido)-2-hydroxy-5-(trifluoromethoxy)benzoate was obtained as a pale brown solid (387 mg, 77%). $^1$H NMR (400 MHz, CDCl$_3$) $\delta_H$ 11.18 (s, 1H), 8.00 (d, J=2.5 Hz, 1H), 7.76 (s, 1H), 7.71 (d, J=2.9 Hz, 1H), 7.60 (dd, J=8.8, 2.5 Hz, 1H), 7.40 (d, J=2.9 Hz, 1H), 6.87 (d, J=8.8 Hz, 1H), 3.98 (s, 3H), 3.97 (s, 3H);

$^{19}$F NMR (376 MHz, CDCl$_3$) δ$_F$ −58.6; LCMS (Method A) t$_R$=1.93 min, m/z=499.8, 501.7 [M+H]$^+$; Purity (AUC) ≥95%.

Step B: 3-((5-bromo-2-methoxyphenyl)sulfonamido)-2-hydroxy-N-((tetrahydrofuran-2-yl)methyl)-5-(trifluoromethoxy)benzamide. Using a procedure analogous to General Procedure H, starting from methyl 3-((5-bromo-2-methoxyphenyl)sulfonamido)-2-hydroxy-5-(trifluoromethoxy)benzoate (25 mg, 0.05 mmol) and tetrahydrofurfurylamine, the title compound was obtained as a colorless solid (18 mg, 63%). $^1$H NMR (400 MHz, MeOH-d$_4$) δ$_H$ 7.89 (d, J=2.5 Hz, 1H), 7.68 (dd, J=8.8, 2.5 Hz, 1H), 7.47 (s, 2H), 7.09 (d, J=8.8 Hz, 1H), 4.15-4.04 (m, 1H), 3.91 (s, 3H), 3.93-3.85 (m, 1H), 3.81-3.72 (m, 1H), 3.44 (qd, J=13.7, 6.0 Hz, 2H), 2.10-1.98 (m, 1H), 1.98-1.86 (M, 2H), 1.71-1.58 (m, 1H); $^{19}$F NMR (376 MHz, MeOH-d$_4$) δ$_F$ −60.2; LCMS (Method A) t$_R$=1.86 min, m/z=568.8, 570.7 [M+H]$^+$; Purity (AUC) ≥95%.

Example J180: (S)-5-Bromo-N-(2-hydroxy-3-(2-(methoxymethyl)pyrrolidine-1-carbonyl)-5-(trifluoromethoxy)phenyl)-2-methoxybenzenesulfonamide

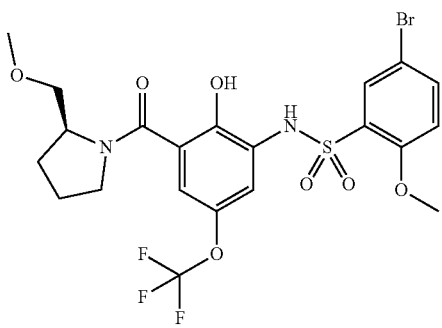

Using a procedure analogous to General Procedure H, starting from methyl 3-((5-bromo-2-methoxyphenyl)sulfonamido)-2-hydroxy-5-(trifluoromethoxy)benzoate (25 mg, 0.05 mmol), which was prepared by a procedure analogous to the procedure used to prepare Example J179 Step A, and O-methyl-L-prolinol, the title compound was obtained as a colorless solid (4 mg, 14%). LCMS (Method A) t$_R$=1.82 min, m/z=582.7, 584.8 [M+H]$^+$; Purity (AUC) ≥95%.

Example J181: (R)-5-bromo-N-(2-hydroxy-3-(2-(methoxymethyl)pyrrolidine-1-carbonyl)-5-(trifluoromethoxy)phenyl)-2-methoxybenzenesulfonamide

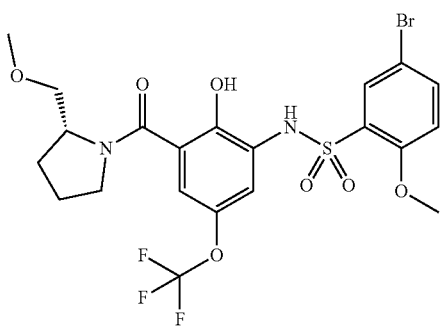

Using a procedure analogous to General Procedure H, starting from methyl 3-((5-bromo-2-methoxyphenyl)sulfonamido)-2-hydroxy-5-(trifluoromethoxy) (25 mg, 0.05 mmol), which was prepared by a procedure analogous to the procedure used to prepare Example J179 Step A, and O-methyl-D-prolinol, the title compound was obtained as a colorless solid (5 mg, 17%). LCMS (Method A) t$_R$=1.82 min, m/z=582.7, 584.8 [M+H]$^+$; Purity (AUC) ≥95%.

Example J182: 3-((6-Bromoquinoline)-8-sulfonamido)-2-hydroxy-N-methyl-5-(trifluoromethoxy)benzamide

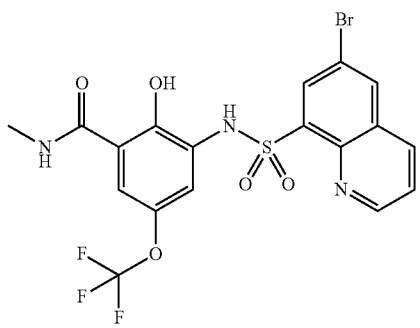 [SMILES: CNC(=O)c1cc(OC(F)(F)F)cc(NS(=O)(=O)c2cc(Br)cc3cccnc23)c1O]

Using a procedure analogous to General Procedure G, starting from methyl 3-((6-bromoquinoline)-8-sulfonamido)-2-hydroxy-5-(trifluoromethoxy)benzoate (26 mg, 0.05 mmol), which was prepared by a procedure analogous to the procedure used to prepare Example J161 Step A, and methylamine, the title compound was obtained as a colorless solid (14 mg, 54%). $^1$H NMR (400 MHz, MeOH-d$_4$) δ$_H$ 9.11 (dd, J=4.3, 1.7 Hz, 1H), 8.44 (d, J=2.3 Hz, 1H), 8.43 (d, J=2.3 Hz, 1H), 8.41-8.33 (m, 1H), 7.69 (dd, J=8.5, 4.3 Hz, 1H), 7.61-7.54 (m, 2H), 7.33 (d, J=2.7 Hz, 2H), 2.83 (s, 3H); $^{19}$F NMR (376 MHz, MeOH-d$_4$) δ$_F$ −60.2; LCMS (Method A) t$_R$=1.84 min, m/z=519.8, 521.8 [M+H]$^+$; Purity (AUC) ≥95%.

Example J183: 5-((5-Bromo-2-methoxyphenyl)sulfonamido)-4-hydroxy-[1,1'-biphenyl]-3-carboxylic acid

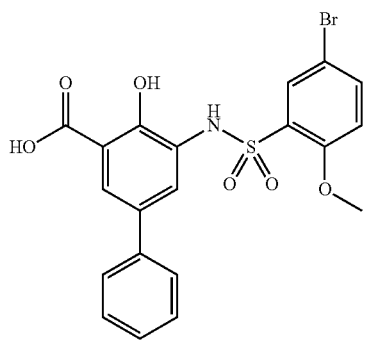 [SMILES: COc1ccc(Br)cc1S(=O)(=O)Nc1cc(-c2ccccc2)cc(C(=O)O)c1O]

Step A: Methyl 5-bromo-2-hydroxy-3-nitrobenzoate. Using a procedure analogous to General Procedure B, starting from methyl 5-bromo-2-hydroxybenzoate (2.31 g, 10 mmol), methyl 5-bromo-2-hydroxy-3-nitrobenzoate was obtained as a yellow-brown solid (2.35 g, 85%). $^1$H NMR (400 MHz, DMSO-d$_6$) $\delta_H$ 8.81 (d, J=3.1 Hz, 1H), 8.59 (d, J=3.1 Hz, 1H), 3.88 (s, 3H); LCMS (Method A) t$_R$=1.27 min; Purity (AUC) ≥95%.

Step B: Methyl 3-amino-5-bromo-2-hydroxybenzoate. Using a procedure analogous to General Procedure C, using 5% platinum on sulfided carbon as catalyst, starting from methyl 5-bromo-2-hydroxy-3-nitrobenzoate (690 mg, 2.5 mmol), methyl 3-amino-5-bromo-2-hydroxybenzoate was obtained as a pale brown solid (517 mg, 84%). LCMS (Method A) t$_R$=1.30 min, m/z=246.1, 248.1 [M+H]$^+$; Purity (AUC) ≥95%.

Step C: Methyl 5-amino-4-hydroxy-[1,1'-biphenyl]-3-carboxylate. Using a procedure analogous to General Procedure L, starting from methyl 3-amino-5-bromo-2-hydroxybenzoate (123 mg, 0.50 mmol) and phenylboronic acid, methyl 5-amino-4-hydroxy-[1,1'-biphenyl]-3-carboxylate was obtained as a pale brown solid (68 mg, 56%). %). LCMS (Method A) t$_R$=1.23 min, m/z=244.2 [M+H]$^+$; Purity (AUC) ≥95%.

Step D: Methyl 5-((5-bromo-2-methoxyphenyl)sulfonamido)-4-hydroxy-[1,1'-biphenyl]-3-carboxylate. Using a procedure analogous to General Procedure E, starting from methyl 5-amino-4-hydroxy-[1,1'-biphenyl]-3-carboxylate (29 mg, 0.12 mmol) and 5-bromo-2-methoxybenzenesulfonyl chloride, methyl 5-((5-bromo-2-methoxyphenyl)sulfonamido)-4-hydroxy-[1,1'-biphenyl]-3-carboxylate was obtained as an off-white solid (49 mg, 78%). LCMS (Method A) t$_R$=1.88 min, m/z=491.9, 493.9 [M+H]$^+$; Purity (AUC) ≥95%.

Step E: 5-((5-Bromo-2-methoxyphenyl)sulfonamido)-4-hydroxy-[1,1'-biphenyl]-3-carboxylic acid. Using a procedure analogous to General Procedure F, starting from methyl 5-((5-bromo-2-methoxyphenyl)sulfonamido)-4-hydroxy-[1,1'-biphenyl]-3-carboxylate (25 mg, 0.05 mmol), the title compound was obtained as a colorless solid (19 mg, 77%). $^1$H NMR (400 MHz, MeOH-d$_4$) $\delta_H$ 7.93 (d, J=2.5 Hz, 1H), 7.84-7.81 (m, 2H), 7.67 (dd, J=8.9, 2.6 Hz, 1H), 7.51-7.39 (m, 4H), 7.37-7.28 (m, 1H), 7.08 (d, J=8.9 Hz, 1H), 3.90 (s, 3H); LCMS (Method A) t$_R$=1.67 min, m/z=477.9, 479.9 [M+H]$^+$; Purity (AUC) ≥95%.

Example J184: 5-((5-Bromo-2-hydroxyphenyl)sulfonamido)-4-hydroxy-2-methyl-[1,1'-biphenyl]-3-carboxylic acid

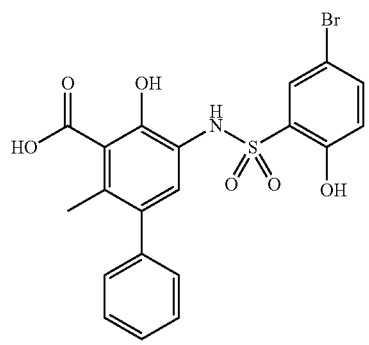 [SMILES: Cc1c(-c2ccccc2)cc(NS(=O)(=O)c2cc(Br)ccc2O)c(O)c1C(=O)O]

Step A: Methyl 3-bromo-6-hydroxy-2-methylbenzoate. Methyl 3-bromo-2-methylbenzoate (458 mg, 2.0 mmol), potassium persulfate (595 mg, 2.2 mmol) and [Ru(p-cymene)Cl]$_2$ (30.6 mg, 0.05 mmol) were combined in TFA (5 mL) and TFAA (2 mL) and heated at 80° C. for 24 h. After cooling, H$_2$O (5 mL) was added and the mixture extracted with CH$_2$Cl$_2$ (3×10 mL), dried (MgSO$_4$), and concentrated. Purification by ISCO flash column chromatography afforded a pale brown liquid (378 mg, 1.54 mmol, 77%). $^1$H NMR (400 MHz, CDCl$_3$) $\delta_H$ 10.83 (s, 1H), 7.60 (d, J=8.9 Hz, 1H), 6.78 (d, J=8.9 Hz, 1H), 4.01 (s, 3H), 2.65 (s, 3H); LCMS (Method A) t$_R$=1.33 min, m/z=245.0, 247.0 [M+H]$^+$; Purity (AUC) ≥95%.

Step B: Methyl 3-bromo-6-hydroxy-2-methyl-5-nitrobenzoate. Using a procedure analogous to General Procedure B, starting with methyl 3-bromo-6-hydroxy-2-methylbenzoate (371 mg, 1.51 mmol), methyl 3-bromo-6-hydroxy-2-methyl-5-nitrobenzoate was was obtained as a yellow solid (302 mg, 1.04 mmol, 69%). $^1$H NMR (400 MHz, DMSO-d$_6$) $\delta_H$ 11.0 (br s, 1H), 8.25 (s, 1H), 3.89 (s, 3H), 2.35 (s, 3H); LCMS (Method A) t$_R$=1.49 min; Purity (AUC) ≥95%.

Step C: Methyl 2-(benzyloxy)-5-bromo-6-methyl-3-nitrobenzoate. Using a procedure analogous to General Procedure Q, starting from methyl 3-bromo-6-hydroxy-2-methyl-5-nitrobenzoate (300 mg, 1.03 mmol), methyl 2-(benzyloxy)-5-bromo-6-methyl-3-nitrobenzoate was obtained as a yellow oil (383 mg, 1.01 mmol, 95%). $^1$H NMR (400 MHz, CDCl$_3$) $\delta_H$ 8.23 (s, 1H), 7.48-7.37 (m, 5H), 3.86 (s, 3H), 2.43 (s, 3H); LCMS (Method A) t$_R$=1.82 min, m/z=399.0 [M+NH$_4$]$^+$; Purity (AUC) ≥95%.

Step D: Methyl 4-(benzyloxy)-2-methyl-5-nitro-[1,1'-biphenyl]-3-carboxylate. Using a procedure analogous to General Procedure L, starting from methyl 2-(benzyloxy)-5-bromo-6-methyl-3-nitrobenzoate (76 mg, 0.2 mmol) and phenylboronic acid, methyl 4-(benzyloxy)-2-methyl-5-nitro-[1,1'-biphenyl]-3-carboxylate was obtained as a pale brown solid (51 mg, 0.14 mmol, 68%). LCMS (Method A) t$_R$=1.91 min, m/z=395.1[M+NH$_4$]$^+$; Purity (AUC) ≥95%.

Step E: Methyl 5-amino-4-hydroxy-2-methyl-[1,1'-biphenyl]-3-carboxylate. Using a procedure analogous to General Procedure C, starting from methyl 4-(benzyloxy)-2-methyl-5-nitro-[1,1'-biphenyl]-3-carboxylate (51 mg, 0.14 mmol), methyl 5-amino-4-hydroxy-2-methyl-[1,1'-biphenyl]-3-carboxylate was obtained as a brown solid (31 mg, 0.12 mmol, 86%). LCMS (Method A) t$_R$=1.19 min, m/z=258.1 [M+H]$^+$; Purity (AUC) >90%.

Step F: 5-((5-Bromo-2-hydroxyphenyl)sulfonamido)-4-hydroxy-2-methyl-[1,1'-biphenyl]-3-carboxylic acid. Using procedures analogous to General Procedures E and then F, starting with methyl 5-amino-4-hydroxy-2-methyl-[1,1'-biphenyl]-3-carboxylate (26 mg, 0.10 mmol) with and 5-bromo-2-hydroxybenzenesulfonyl chloride, which was prepared by a procedure analogous to the procedure used to prepare Example J1 Step A, the title compound was obtained as a colorless solid (22 mg, 46% over two steps). $^1$H NMR (400 MHz, DMSO-d$_6$) $\delta_H$ 7.67 (d, J=2.6 Hz, 1H), 7.64 (dd, J=8.6, 2.6 Hz, 1H), 7.45-7.30 (m, 3H), 7.10-7.04 (m, 2H), 6.97 (d, J=8.6 Hz, 1H), 6.89 (s, 1H), 2.11 (s, 3H); LCMS (Method A) t$_R$=1.60 min, m/z=477.8, 479.8 [M+H]$^+$; Purity (AUC) ≥95%.

Example J185: 3-((5-Bromo-2-hydroxyphenyl)sulfonamido)-5-cyclopropyl-2-hydroxy-6-methyl-benzoic acid

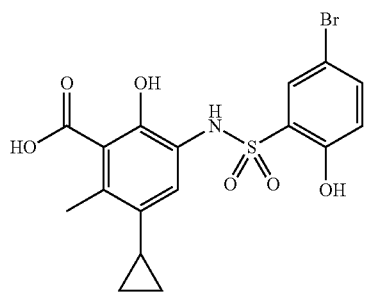 [SMILES: Cc1c(C2CC2)cc(NS(=O)(=O)c2cc(Br)ccc2O)c(O)c1C(=O)O]

Step A: Methyl 2-(benzyloxy)-5-cyclopropyl-6-methyl-3-nitrobenzoate. Using a procedure analogous to General Procedure M, starting from methyl 2-(benzyloxy)-5-bromo-6-methyl-3-nitrobenzoate (76 mg, 0.2 mmol), which was prepared by a procedure analogous to the procedure used to prepare Example J184 Step C, methyl 2-(benzyloxy)-5-cyclopropyl-6-methyl-3-nitrobenzoate was obtained as a brown oil (47 mg, 0.14 mmol, 69%). LCMS (Method A) $t_R$=1.83 min, m/z=359.1 [M+NH$_4$]$^+$; Purity (AUC) ≥95%.

Step B: Methyl 3-amino-5-cyclopropyl-2-hydroxy-6-methylbenzoate. Using a procedure analogous to General Procedure C, starting from methyl 2-(benzyloxy)-5-cyclopropyl-6-methyl-3-nitrobenzoate (47 mg, 0.14 mmol), methyl 3-amino-5-cyclopropyl-2-hydroxy-6-methylbenzoate was obtained as a brown oil (25 mg, 0.11 mmol, 81%). LCMS (Method A) $t_R$=0.18 min, m/z=222.1 [M+H]$^+$; Purity (AUC) ≥95%.

Step C: 3-((5-Bromo-2-hydroxyphenyl)sulfonamido)-5-cyclopropyl-2-hydroxy-6-methylbenzoic acid. Using procedures analogous to General Procedures E and then F, starting with methyl 3-amino-5-cyclopropyl-2-hydroxy-6-methylbenzoate (21 mg, 0.095 mmol) and 5-bromo-2-hydroxybenzenesulfonyl chloride, which was prepared by a procedure analogous to the procedure used to prepare Example J1 Step A, the title compound was obtained as a colorless solid (14 mg, 33%). $^1$H NMR (400 MHz, DMSO-d) $\delta_H$ 7.65-7.59 (m, 2H), 6.98 (d, J=8.4 Hz, 1H), 6.64 (s, 1H), 2.25 (s, 3H), 1.84-1.63 (m, 1H), 0.85-0.74 (m, 2H), 0.25-0.12 (m, 2H); LCMS (Method A) $t_R$=1.51 min, m/z=463.8, 465.7 [M+Na]$^+$; Purity (AUC) ≥95%.

Example J193: 3-((5-Bromo-2-methoxyphenyl)sulfonamido)-5-(3,6-dihydro-2H-pyran-4-yl)benzoic acid

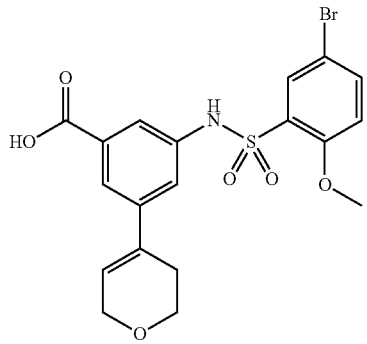 [SMILES: COc1ccc(Br)cc1S(=O)(=O)Nc1cc(C(=O)O)cc(C2=CCOCC2)c1]

Step A: Methyl 3-amino-5-(3,6-dihydro-2H-pyran-4-yl)benzoate. Using a procedure analogous to General Procedure L, starting with methyl 3-amino-5-bromobenzoate (230 mg, 1.0 mmol) and 2-(3,6-dihydro-2H-pyran-4-yl)-4,4,5,5-tetramethyl-1,3,2-dioxaborolane (315 mg, 1.5 mmol), methyl 3-amino-5-(3,6-dihydro-2H-pyran-4-yl)benzoate was obtained as a yellow oil (230 mg, 0.98 mmol, 98%). LCMS (Method A) $t_R$=0.88 min, m/z=234.2 [M+H]$^+$; Purity (AUC) ≥95%.

Step B: Methyl 3-((5-bromo-2-methoxyphenyl)sulfonamido)-5-(3,6-dihydro-2H-pyran-4-yl)benzoate. Using a procedure analogous to General Procedure E, starting with methyl 3-amino-5-(3,6-dihydro-2H-pyran-4-yl)benzoate (115 mg, 0.50 mmol) and 5-bromo-2-methoxybenzene sulfonyl chloride, methyl 3-((5-bromo-2-methoxyphenyl)sulfonamido)-5-(3,6-dihydro-2H-pyran-4-yl)benzoate was obtained as a colorless solid (141 mg, 0.28 mmol, 57%). LCMS (Method A) $t_R$=1.56 min, m/z=499.0, 501.0 [M+NH$_4$]$^+$; Purity (AUC) ≥95%.

Step C: 3-((5-Bromo-2-methoxyphenyl)sulfonamido)-5-(3,6-dihydro-2H-pyran-4-yl)benzoic acid. Using a procedure analogous to General Procedure F, starting from methyl 3-((5-bromo-2-methoxyphenyl)sulfonamido)-5-(3,6-dihydro-2H-pyran-4-yl)benzoate (78 mg, 0.16 mmol), 3-((5-bromo-2-methoxyphenyl)sulfonamido)-5-(3,6-dihydro-2H-pyran-4-yl)benzoic acid, the title compound was obtained as a colorless solid (20 mg, 27%). $^1$H NMR (400 MHz, DMSO-d$_6$) $\delta_H$ 10.43 (s, 1H), 7.84 (d, J=2.6 Hz, 1H), 7.75 (dd, J=8.9, 2.6 Hz, 1H), 7.61 (t, J=1.8 Hz, 1H), 7.57 (t, J=1.8 Hz, 1H), 7.34 (t, J=1.8 Hz, 1H), 7.15 (d, J=8.9 Hz, 1H), 6.18 (t, J=1.5 Hz, 1H), 4.20 (q, J=2.8 Hz, 2H), 3.83 (s, 3H), 3.79 (t, J=5.2 Hz, 2H), 2.32 (d, J=5.2 Hz, 2H); LCMS (Method A) $t_R$=1.86 min, m/z=491.9, 493.9 [M+NH$_4$]$^+$; Purity (AUC) ≥95%.

Example J194: 3-((5-Bromo-2-methoxyphenyl)sulfonamido)-2-hydroxy-5-morpholinobenzoic acid

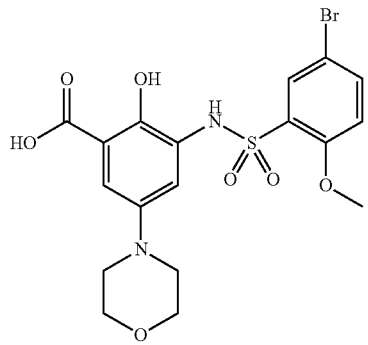 [SMILES: COc1ccc(Br)cc1S(=O)(=O)Nc1cc(N2CCOCC2)cc(C(=O)O)c1O]

Step A: Methyl 2-(benzyloxy)-5-morpholino-3-nitrobenzoate. Methyl 2-(benzyloxy)-5-bromo-3-nitrobenzoate, which was prepared by a procedure analogous to the procedure used to prepare Example J68 Step B (73 mg, 0.20 mmol), Pd(OAc)$_2$ (2.2 mg, 0.01 mmol), JohnPhos (6.0 mg, 0.02 mmol), and K$_3$PO$_4$ (106 mg, 0.50 mmol) were combined in DME (1 mL) and heated at 90° C. for 16 h. Upon cooling, the mixture was filtered, concentrated, redissolved in CH$_2$Cl$_2$ and washed with water. Purification by ISCO flash column chromatography afforded methyl 2-(benzyloxy)-5-morpholino-3-nitrobenzoate as a yellow solid (44 mg, 0.12 mmol, 59%). LCMS (Method A) $t_R$=1.77 min, m/z=373.0 [M+H]$^+$; Purity (AUC) ≥95%.

Step B: 3-((5-Bromo-2-methoxyphenyl)sulfonamido)-2-hydroxy-5-morpholinobenzoic acid. Using a procedure analogous to General Procedure C, starting from methyl 2-(benzyloxy)-5-morpholino-3-nitrobenzoate (44 mg, 0.12 mmol), a crude red-brown solid was obtained (assumed quantitative). Using a procedure analogous to General Procedure E with this crude material and 5-bromo-2-methoxybenzene sulfonyl chloride, a yellow solid was obtained (37 mg, 0.07 mmol). Using a procedure analogous to General Procedure F, this material was hydrolyzed to afford the title compound as a pale brown solid (16 mg, 0.03 mmol, 27% over 3 steps). LCMS (Method A) $t_R$=1.27 min, m/z=486.9, 488.8 [M+H]$^+$; Purity (AUC) ≥95%.

Example J195: 3-((5-Bromo-2-hydroxyphenyl)sulfonamido)-2-hydroxy-5-(thiophen-3-yl)benzoic acid

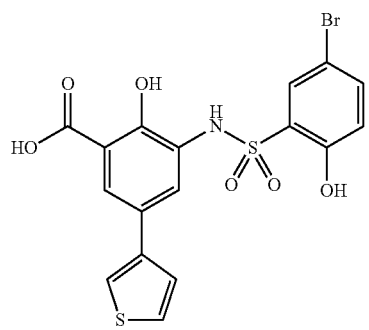 [SMILES: O=C(O)c1cc(-c2ccsc2)cc(NS(=O)(=O)c2cc(Br)ccc2O)c1O]

Step A: Methyl 2-(benzyloxy)-3-nitro-5-(thiophen-3-yl)benzoate. Using a procedure analogous to General Procedure L, starting with methyl 2-(benzyloxy)-5-bromo-3-nitrobenzoate, which was prepared by a procedure analogous to the procedure used to prepare Example J68 Step B (366 mg, 1.0 mmol), and thiophene-3-boronic acid (154 mg, 1.2 mmol), methyl 2-(benzyloxy)-3-nitro-5-(thiophen-3-yl)benzoate was obtained as a brown oil (303 mg, 0.82 mmol, 82%). LCMS (Method A) $t_R$=1.58 min, m/z=469.8, 471.7 [M+H]$^+$; Purity (AUC) ≥95%.

Step B: 3-((5-Bromo-2-hydroxyphenyl)sulfonamido)-2-hydroxy-5-(thiophen-3-yl)benzoic acid. Using a procedure analogous to General Procedure C, methyl 2-(benzyloxy)-3-nitro-5-(thiophen-3-yl)benzoate (37 mg, 0.1 mmol) was hydrogenated to afford a crude intermediate. Using procedures analogous to General Procedures E and then F, starting with this crude intermediate and 5-bromo-2-hydroxybenzenesulfonyl chloride, which was prepared by a procedure analogous to the procedure used to prepare Example J1 Step A, the title compound was obtained (8 mg, 17% over three steps). $^1$H NMR (400 MHz, DMSO-d$_6$) $\delta_H$ 7.79 (d, J=2.3 Hz, 1H), 7.75 (d, J=2.6 Hz, 1H), 7.68 (d, J=2.3 Hz, 1H), 7.63 (d, J=3.4 Hz, 2H), 7.59 (dd, J=8.7, 2.6 Hz, 1H), 7.36-7.30 (m, 1H), 6.95 (d, J=8.7 Hz, 1H); LCMS (Method A) $t_R$=1.58 min, m/z=469.8, 471.7 [M+H]$^+$; Purity (AUC) ≥95%.

Example J196: 3-((5-bromo-2-hydroxyphenyl)sulfonamido)-2-hydroxy-5-(thiophen-2-yl)benzoic acid

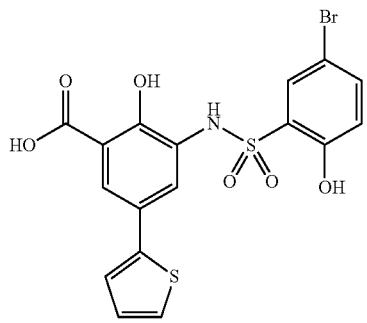 [SMILES: O=C(O)c1cc(-c2cccs2)cc(NS(=O)(=O)c2cc(Br)ccc2O)c1O]

Using a three-step sequence analogous to the procedure used to prepare Example J195, except using thiophene-2-boronic acid, the title compound was obtained as a colorless solid. $^1$H NMR (400 MHz, DMSO-d$_6$) $\delta_H$ 11.28 (s, 1H), 9.12 (s, 1H), 7.74 (s, 1H), 7.74 (s, 1H), 7.64 (d, J=2.3 Hz, 1H), 7.59 (dd, J=8.8, 2.6 Hz, 1H), 7.49 (dd, J=5.1, 1.1 Hz, 1H), 7.28 (dd, J=3.6, 1.2 Hz, 1H), 7.09 (dd, J=5.1, 3.6 Hz, 1H), 6.94 (d, J=8.8 Hz, 1H); LCMS (Method A) $t_R$=1.66 min, m/z=469.7, 471.7 [M+H]$^+$; Purity (AUC) ≥95%.

Example J197: 3-((5-Bromo-2-hydroxyphenyl)sulfonamido)-2-hydroxy-5-(3-methylthiophen-2-yl)benzoic acid

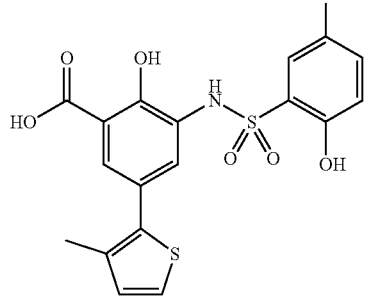

Using a three-step sequence analogous to the procedure used to prepare Example J195, except using 3-methylthiophene-2-boronic acid, the title compound was obtained as a colorless solid. $^1$H NMR (400 MHz, DMSO-d$_6$) $\delta_H$ 11.31 (s, 1H), 9.07 (s, 1H), 7.72 (d, J=2.5 Hz, 1H), 7.59 (dd, J=8.8, 2.5 Hz, 1H), 7.55 (d, J=2.3 Hz, 1H), 7.46 (d, J=2.3 Hz, 1H), 7.41 (d, J=5.1 Hz, 1H), 6.97-6.92 (m, 2H), 2.13 (s, 3H); LCMS (Method A) t$_R$=1.70 min, m/z=483.7 [M+H]$^+$; Purity (AUC) ≥95%.

Example J198: 3-((5-Bromo-2-hydroxyphenyl)sulfonamido)-2-hydroxy-5-(2-methylthiophen-3-yl)benzoic acid

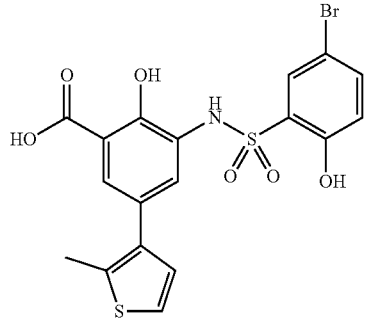 [SMILES: Cc1sccc1-c1cc(NS(=O)(=O)c2cc(Br)ccc2O)c(O)c(C(=O)O)c1]

Using a three-step sequence analogous to the procedure used to prepare Example J195, except using 2-methylthiophene-3-boronic acid, the title compound was obtained as a colorless solid. $^1$H NMR (400 MHz, MeOH-d$_4$) $\delta_H$ 7.81 (d, J=2.5 Hz, 1H), 7.63 (d, J=2.1 Hz, 1H), 7.59 (d, J=2.1 Hz, 1H), 7.52 (dd, J=8.8, 2.5 Hz, 1H), 7.18 (d, J=5.2 Hz, 1H), 6.93 (d, J=5.2 Hz, 1H), 6.86 (d, J=8.8 Hz, 1H), 2.41 (s, 3H); LCMS (Method A) t$_R$=1.74 min, m/z=483.7 [M+H]$^+$; Purity (AUC) ≥95%.

Example J199: 3-((5-Bromo-2-hydroxyphenyl)sulfonamido)-6-fluoro-2-hydroxy-5-(thiophen-3-yl)benzoic acid

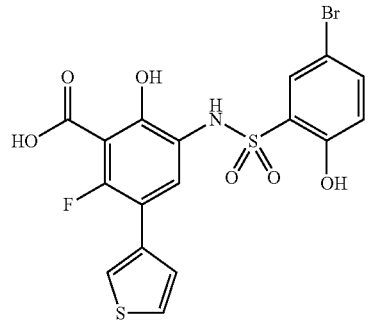 [SMILES: O=C(O)c1c(O)c(NS(=O)(=O)c2cc(Br)ccc2O)cc(-c2ccsc2)c1F]

Using a three-step sequence analogous to the procedure used to prepare Example J195, except reacting thiophene-3-boronic acid in the Step A reaction with methyl 2-(benzyloxy)-5-cyclopropyl-6-fluoro-3-nitrobenzoate, which was prepared by a procedure analogous to the procedure used to prepare Example J117 Step E, the title compound was obtained as a colorless solid. $^1$H NMR (400 MHz, MeOH-d$_4$) $\delta_H$ 7.55 (s, 1H), 7.54 (dd, J=13.0, 2.4 Hz, 1H), 7.15 (d, J=7.4 Hz, 1H), 1.99 (ddd, J=13.7, 8.6, 5.2 Hz, 1H), 1.01-0.91 (m, 2H), 0.57 (dt, J=6.4, 4.6 Hz, 2H): $^{19}$F NMR (376 MHz, MeOH-d$_4$) $\delta_F$ –113.4; LCMS (Method A) t$_R$=1.58 min, m/z=487.7 [M+H]$^+$; Purity (AUC) ≥95%.

Example J200: N-(3-((5-Bromo-2-methoxyphenyl)sulfonamido)-5-chloro-2-hydroxyphenyl)acetamide

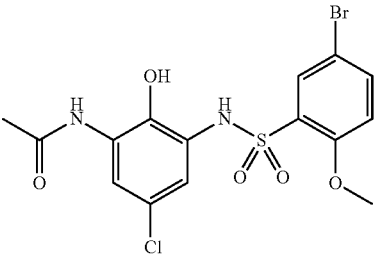 [SMILES: COc1ccc(Br)cc1S(=O)(=O)Nc1cc(Cl)cc(NC(C)=O)c1O]

2-Amino-4-chloro-6-nitrophenol (189 mg, 1.0 mmol) and acetic anhydride (104 μL, 1.1 mmol) were combined in CH$_2$Cl$_2$ (5 mL) and stirred at r.t. for 18 h. The mixture was washed with saturated aqueous NaHCO$_3$ (10 mL) and concentrated under reduced pressure to afford crude acetylated intermediate as an orange solid. This was dissolved in MeOH (10 mL), platinum (5% on sulfided carbon, 20 mg, 0.1 mmol) was added, and the mixture was stirred under an atmosphere of hydrogen at r.t. for 16 h. The mixture was filtered and concentrated under reduced pressure. Crude material was dissolved in CH$_2$Cl$_2$ (5 mL) and cooled to 0° C. before the addition of 5-bromo-2-methoxybenzene sulfonyl chloride (314 mg, 1.1 mmol) and pyridine (242 μL, 3.0 mmol). The mixture was stirred for 2 h, diluted with further CH$_2$Cl$_2$ (5 mL) and washed with 1M HCl (2×5 mL) and saturated aqueous NaCl (5 mL), then concentrated and purified by ISCO flash column chromatography to afford the title compound as a cream solid (124 mg, 0.28 mmol, 28%).

¹H NMR (400 MHz, DMSO-d₆) $δ_H$ 9.74 (s, 1H), 9.40 (br s, 2H), 7.77 (dd, J=8.8, 2.6 Hz, 1H), 7.73 (d, J=2.6 Hz, 1H), 7.32 (d, J=2.6 Hz, 1H), 7.19 (d, J=8.8 Hz, 1H), 6.93 (d, J=2.6 Hz, 1H), 3.82 (s, 3H), 2.07 (s, 3H); LCMS (Method A) $t_R$=1.48 min, m/z=448.9, 450.9 [M+H]⁺; Purity (AUC) ≥95%.

Example J201: 3-((5-Bromo-2-hydroxyphenyl) sulfonamido)-5-(tert-butyl)-2-hydroxybenzoic acid

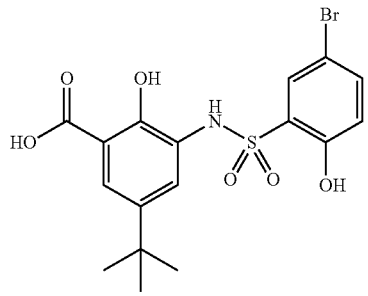 [SMILES: CC(C)(C)c1cc(NS(=O)(=O)c2cc(Br)ccc2O)c(O)c(C(=O)O)c1]

Step A: Methyl 5-(tert-butyl)-2-hydroxybenzoate. Using a procedure analogous to General Procedure P, starting with 5-(tert-butyl)-2-hydroxybenzoic acid (1.01 g, 5.2 mmol), methyl 5-(tert-butyl)-2-hydroxybenzoate was obtained as a straw-colored liquid (795 mg, 3.8 mmol, 73%). ¹H NMR (400 MHz, CDCl₃) $δ_H$ 10.59 (s, 1H), 7.82 (d, J=2.6 Hz, 1H), 7.51 (dd, J=8.7, 2.6 Hz, 1H), 6.93 (d, J=8.7 Hz, 1H), 3.96 (s, 3H), 1.30 (s, 9H); LCMS (Method B) $t_R$=1.20 min, m/z=209.2 [M+H]⁺; Purity (AUC) ≥95%.

Step B: Methyl 5-(tert-butyl)-2-hydroxy-3-nitrobenzoate. Using a procedure analogous to General Procedure B, starting from methyl 5-(tert-butyl)-2-hydroxybenzoate (790 mg, 3.8 mmol), methyl 5-(tert-butyl)-2-hydroxy-3-nitrobenzoate was obtained as a yellow solid (802 mg, 3.17 mmol, 83%). ¹H NMR (400 MHz, CDCl₃) $δ_H$ 8.20 (d, J=2.6 Hz, 1H), 8.17 (d, J=2.6 Hz, 1H), 4.04 (s, 3H), 1.37 (s, 9H); LCMS (Method B) $t_R$=1.14 min, m/z=254.1 [M+H]⁺; Purity (AUC) ≥95%.

Step C: Methyl 3-amino-5-(tert-butyl)-2-hydroxybenzoate. Using a procedure analogous to General Procedure C, starting from methyl 5-(tert-butyl)-2-hydroxy-3-nitrobenzoate (253 mg, 1.0 mmol), methyl 3-amino-5-(tert-butyl)-2-hydroxybenzoate was obtained as a brown solid (220 mg, quant.). ¹H NMR (400 MHz, CDCl₃) $δ_H$ 10.72 (s, 1H), 7.23 (d, J=2.3 Hz, 1H), 6.95 (d, J=2.3 Hz, 1H), 3.94 (s, 3H), 1.27 (s, 9H); LCMS (Method B) $t_R$=0.79 min, m/z=224.2 [M+H]⁺; Purity (AUC) ≥95%.

Step D: Methyl 3-((5-bromo-2-hydroxyphenyl)sulfonamido)-5-(tert-butyl)-2-hydroxybenzoate. Using a procedure analogous to General Procedure E, starting with methyl 3-amino-5-(tert-butyl)-2-hydroxybenzoate (112 mg, 0.5 mmol) and 5-bromo-2-hydroxybenzenesulfonyl chloride, which was prepared by a procedure analogous to the procedure used to prepare Example J1 Step A), methyl 3-((5-bromo-2-hydroxyphenyl)sulfonamido)-5-(tert-butyl)-2-hydroxybenzoate was obtained as a cream solid (215 mg, 0.47 mmol, 94%). ¹H NMR (400 MHz, MeOH-d₄) $δ_H$ 7.76 (d, J=2.5 Hz, 1H), 7.66 (d, J=2.4 Hz, 1H), 7.55 (d, J=2.4 Hz, 1H), 7.48 (dd, J=8.8, 2.5 Hz, 1H), 6.82 (d, J=8.8 Hz, 1H), 3.93 (s, 3H), 1.23 (s, 9H); LCMS (Method A) $t_R$=1.90 min, m/z=457.8, 459.9 [M+H]⁺; Purity (AUC) ≥95%.

Step E: 3-((5-Bromo-2-hydroxyphenyl)sulfonamido)-5-(tert-butyl)-2-hydroxybenzoic acid. Using a procedure analogous to General Procedure F, starting with methyl 3-((5-bromo-2-hydroxyphenyl)sulfonamido)-5-(tert-butyl)-2-hydroxybenzoate (23 mg, 0.05 mmol) the title compound was obtained as a colorless solid (8 mg, 36%). ¹H NMR (400 MHz, MeOH-d₄) $δ_H$ 7.79 (d, J=2.5 Hz, 1H), 7.64 (d, J=2.4 Hz, 1H), 7.59 (d, J=2.4 Hz, 1H), 7.51 (dd, J=8.8, 2.5 Hz, 1H), 6.84 (d, J=8.8 Hz, 1H), 1.25 (s, 9H); LCMS (Method A) $t_R$=1.70 min, m/z=443.8, 445.8 [M+H]⁺; Purity (AUC) ≥95%.

Example J202: 3-((5-Bromo-2-hydroxyphenyl) sulfonamido)-5-(tert-butyl)-2-hydroxy-N-methylbenzamide

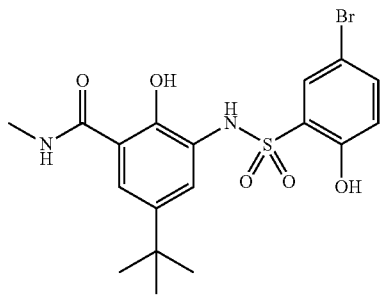 [SMILES: CNC(=O)c1cc(C(C)(C)C)cc(NS(=O)(=O)c2cc(Br)ccc2O)c1O]

Using a procedure analogous to General Procedure G, starting with methyl 3-((5-bromo-2-hydroxyphenyl)sulfonamido)-5-(tert-butyl)-2-hydroxybenzoate (23 mg, 0.05 mmol), the title compound was obtained as a colorless solid (12 mg, 53%). ¹H NMR (400 MHz, MeOH-d₄) $δ_H$ 7.76 (d, J=2.5 Hz, 1H), 7.54 (d, J=2.2 Hz, 1H), 7.48 (dd, J=8.8, 2.5 Hz, 1H), 7.38 (d, J=2.2 Hz, 1H), 6.82 (d, J=8.8 Hz, 1H), 2.88 (s, 3H), 1.25 (s, 9H); LCMS (Method A) $t_R$=1.71 min, m/z=456.9, 458.8 [M+H]⁺; Purity (AUC) ≥95%.

Example J203: 3-((5-Bromo-2-hydroxyphenyl) sulfonamido)-5-(1-cyanocyclobutyl)-2-hydroxybenzoic acid

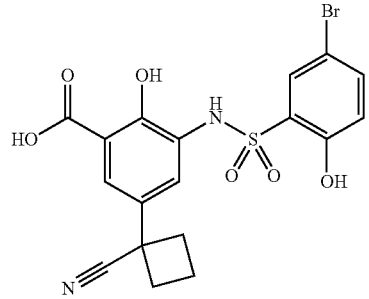 [SMILES: N#CC1(c2cc(NS(=O)(=O)c3cc(Br)ccc3O)c(O)c(C(=O)O)c2)CCC1]

Step A: 1-(3-Bromo-4-methoxyphenyl)cyclobutane-1-carbonitrile. To a mixture containing 2-(3-bromo-4-methoxyphenyl)acetonitrile (4.52 g, 20 mmol) and 1,3-dibromopropane (2.23 mL, 22 mmol) in DMSO (100 mL) was added NaH (60% dispersion in mineral oil, 2.0 g, 50 mmol) portion-wise. The reaction mixture was allowed to stir for 16 h at r.t., then diluted with EtOAc:Et₂O (200 mL, 1:1) and washed with water (3×400 mL). The combined aqueous layers were back-extracted with further EtOAc (200 mL). The combined organics were washed with saturated aqueous NaCl, concentrated and purified by ISCO flash column chromatography (120 g, 0-25% EtOAc in hexanes) to afford a colorless oil (3.65 g, 13.7 mmol, 68%). $^1$H NMR (400 MHz, CDCl$_3$) $\delta_H$ 7.61 (d, J=2.4 Hz, 1H), 7.34 (dd, J=8.6, 2.4 Hz, 1H), 6.93 (d, J=8.6 Hz, 1H), 3.93 (s, 3H), 2.88-2.78 (m, 2H), 2.66-2.54 (m, 2H), 2.44 (dt, J=11.6, 8.7 Hz, 1H), 2.16-2.04 (m, 1H); LCMS (Method B) $t_R$=1.10 min, no mass observed; Purity (AUC) ≥95%.

Step B: Phenyl 5-(1-cyanocyclobutyl)-2-methoxybenzoate. Using a procedure analogous to General Procedure N, starting from 1-(3-bromo-4-methoxyphenyl)cyclobutane-1-carbonitrile (531 µL, 3.43 mmol), phenyl 5-(1-cyanocyclobutyl)-2-methoxybenzoate was obtained as a a colorless solid. This reaction was performed in quadruplicate, with reaction products combined for purification to afford a total yield of 3.72 g, 12.1 mmol (88%.) $^1$H NMR (CDCl$_3$) $\delta_H$ 8.04 (d, J=2.6 Hz, 1H), 7.61 (dd, J=8.7, 2.6 Hz, 1H), 7.49-7.42 (m, 2H), 7.33-7.23 (m, 3H), 7.09 (d, J=8.7 Hz, 1H), 3.98 (s, 3H), 2.93-2.83 (m, 2H), 2.66 (dt, J=11.8, 9.0 Hz, 2H), 2.55-2.41 (m, 1H), 2.19-2.06 (m, 1H); LCMS (Method A): $t_R$=1.71 min, m/z=308.1 [M+H]$^+$; Purity (AUC) ≥95%.

Step C: Phenyl 5-(1-cyanocyclobutyl)-2-hydroxybenzoate. Using a procedure analogous to General Procedure O, starting from phenyl 5-(1-cyanocyclobutyl)-2-methoxybenzoate (3.72 g, 12.1 mmol), phenyl 5-(1-cyanocyclobutyl)-2-hydroxybenzoate was obtained as a colorless oil (3.47 g, 11.84 mmol, 98%). $^1$H NMR (400 MHz, CDCl$_3$) $\delta_H$ 10.55 (s, 1H), 8.09 (d, J=2.5 Hz, 1H), 7.59 (dd, J=8.7, 2.5 Hz, 1H), 7.52-7.43 (m, 2H), 7.34 (d, J=7.4 Hz, 1H), 7.25-7.20 (m, 2H), 7.09 (d, J=8.7 Hz, 1H), 2.91-2.81 (m, 2H), 2.72-2.59 (m, 2H), 2.53-2.38 (m, 1H), 2.16-2.05 (m, 1H) (Method A) LCMS: $t_R$=1.20 min, m/z=294.1 [M+H]$^+$; Purity (AUC) ≥95%.

Step D: Phenyl 5-(1-cyanocyclobutyl)-2-hydroxy-3-nitrobenzoate. A mixture containing phenyl 5-(1-cyanocyclobutyl)-2-hydroxybenzoate (2.93 g, 10 mmol) and DCE/H$_2$O (1:1, 20 mL) was cooled to 0° C. in an ice/water bath. Tetrabutylammonium bromide (161 mg, 0.50 mmol) was added, followed by HNO$_3$ (conc., 1.3 mL, 20 mmol). The mixture was stirred vigorously at 60° C. for 16 h, then cooled, diluted with CH$_2$Cl$_2$, and washed with water. Purification by ISCO flash chromatography (120 g, 0-40% EtOAc in hexanes) afforded phenyl 5-(1-cyanocyclobutyl)-2-hydroxy-3-nitrobenzoate as a pale yellow solid (2.71 g, 8.0 mmol, 80%). $^1$H NMR (400 MHz, CDCl$_3$) $\delta_H$ 8.42 (d, J=2.5 Hz, 1H), 8.31 (d, J=2.6 Hz, 1H), 7.55-7.48 (m, 2H), 7.43-7.35 (m, 1H), 7.32-7.24 (m, 3H), 3.00-2.89 (m, 2H), 2.76-2.63 (m, 2H), 2.61-2.49 (m, 1H), 2.25-2.11 (m, 1H); LCMS (Method A) $t_R$=1.18 min, m/z=339.0 [M+H]$^+$; Purity (AUC) ≥95%.

Step E: Phenyl 3-amino-5-(1-cyanocyclobutyl)-2-hydroxybenzoate. Using a procedure analogous to General Procedure C, starting with phenyl 5-(1-cyanocyclobutyl)-2-hydroxy-3-nitrobenzoate (2.71 g, 8.0 mmol), phenyl 3-amino-5-(1-cyanocyclobutyl)-2-hydroxybenzoate was obtained, after purification by ISCO flash chromatography (80 g, 0-50% EtOAc in hexanes), as a cream solid (2.15 g, 7.0 mmol, 87%). $^1$H NMR (400 MHz, CDCl$_3$) $\delta_H$ 10.70 (d, J=0.7 Hz, 1H), 7.52-7.46 (m, 2H), 7.48 (d, J=2.3 Hz, 1H), 7.38-7.32 (m, 1H), 7.27-7.22 (m, 2H), 6.98 (dd, J=2.3, 0.7 Hz, 1H), 2.90-2.77 (m, 2H), 2.71-2.58 (m, 2H), 2.54-2.39 (m, 1H), 2.16-2.07 (m, 1H); LCMS (Method B) $t_R$=1.08 min, m/z=309.2 [M+H]$^+$; Purity (AUC) ≥95%.

Step F: Phenyl 3-((5-bromo-2-hydroxyphenyl)sulfonamido)-5-(1-cyanocyclobutyl)-2-hydroxybenzoate. Using a procedure analogous to General Procedure E, starting with phenyl 3-amino-5-(1-cyanocyclobutyl)-2-hydroxybenzoate (308 mg, 1.0 mmol) and 5-bromo-2-hydroxybenzenesulfonyl chloride, (326 mg, 1.2 mmol, which was prepared by a procedure analogous to the procedure used to prepare Example 1 Step A, phenyl 3-((5-bromo-2-hydroxyphenyl)sulfonamido)-5-(1-cyanocyclobutyl)-2-hydroxybenzoate was obtained, after purification by ISCO flash chromatography (24 g, 0-40% EtOAc in hexanes), as a colorless solid (393 mg, 0.72 mmol, 72%). $^1$H NMR (400 MHz, CDCl$_3$) $\delta_H$ 8.63 (dt, J=4.4, 1.7 Hz, 2H), 7.90 (d, J=2.3 Hz, 1H), 7.82 (d, J=2.3 Hz, 1H), 7.77 (d, J=2.5 Hz, 1H), 7.49-7.45 (m, 2H), 7.38-7.35 (m, 2H), 7.23-7.17 (m, 2H), 6.88 (d, J=8.8 Hz, 1H), 2.94-2.84 (m, 3H), 2.68-2.56 (m, 2H), 2.55-2.43 (m, 1H), 2.21-2.09 (m, 1H); LCMS (Method A) $t_R$=1.86 min, m/z=559.8, 561.7 [M+NH$_4$]$^+$; Purity (AUC) ≥95%.

Step G: 3-((5-Bromo-2-hydroxyphenyl)sulfonamido)-5-(1-cyanocyclobutyl)-2-hydroxybenzoic acid. Using a procedure analogous to General Procedure F, starting with phenyl 3-((5-bromo-2-hydroxyphenyl)sulfonamido)-5-(1-cyanocyclobutyl)-2-hydroxybenzoate (108 mg, 0.20 mmol), the title compound was obtained as a colorless solid (61 mg, 0.16 mmol, 80%). $^1$H NMR (400 MHz, CDCl$_3$) $\delta_H$ 7.85 (d, J=2.5 Hz, 1H), 7.68 (d, J=2.4 Hz, 1H), 7.64 (d, J=2.4 Hz, 1H), 7.53 (dd, J=8.8, 2.5 Hz, 1H), 6.86 (d, J=8.8 Hz, 1H), 2.82-2.72 (m, 2H), 2.60-2.49 (m, 2H), 2.46-2.32 (m, 1H), 2.16-2.03 (m, 1H); LCMS (Method A) $t_R$=1.44 min, m/z=466.8, 468.7 [M+H]$^+$. Purity (AUC) ≥95%.

Example J205: 3-((5-Bromo-2-methoxyphenyl) sulfonamido)-5-(1-cyanocyclobutyl)-2-hydroxybenzoic acid

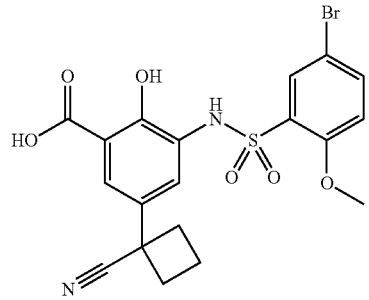 [SMILES: COc1ccc(Br)cc1S(=O)(=O)Nc1cc(C2(C#N)CCC2)cc(C(=O)O)c1O]

Step A: Phenyl 3-((5-bromo-2-methoxyphenyl)sulfonamido)-5-(1-cyanocyclobutyl)-2-hydroxybenzoate. Using a procedure analogous to General Procedure E, starting with phenyl 3-amino-5-(1-cyanocyclobutyl)-2-hydroxybenzoate (31 mg, 0.10 mmol), which was prepared by a procedure analogous to the procedure used to prepare Example J203 Step E, and 2-methoxy-5-bromophenylsulfonyl chloride, phenyl 3-((5-bromo-2-methoxyphenyl)sulfonamido)-5-(1-cyanocyclobutyl)-2-hydroxybenzoate was obtained as a colorless solid (56 mg, quant.). LCMS (Method B) $t_R$=1.26 min, m/z=574.3, 576.3 [M+NH$_4$]$^+$; Purity (AUC) >80%.

Step B: 3-((5-Bromo-2-methoxyphenyl)sulfonamido)-5-(1-cyanocyclobutyl)-2-hydroxybenzoic acid. Using a procedure analogous to General Procedure F, except the reaction was run at room temperature, starting with phenyl 3-((5-bromo-2-methoxyphenyl)sulfonamido)-5-(1-cyanocyclobutyl)-2-hydroxybenzoate (28 mg, 0.05 mmol), the title compound was obtained as a colorless solid (12 mg, 50%). $^1$H NMR (400 MHz, MeOH-d$_4$) $\delta_H$ 7.90 (d, J=2.5 Hz, 1H), 7.70-7.63 (m, 2H), 7.63 (d, J=2.4 Hz, 1H), 7.07 (d, J=8.9 Hz, 1H), 3.89 (s, 3H), 2.82-2.70 (m, 2H), 2.60-2.47 (m, 2H), 2.45-2.31 (m, 1H), 2.13-2.02 (m, 1H); LCMS (Method A) $t_R$=1.65 min, m/z=480.7, 482.8 [M+H]$^+$; Purity (AUC) ≥95%.

Example J206: 3-((S-Bromo-3-chloro-2-hydroxyphenyl)sulfonamido)-5-(1-cyanocyclobutyl)-2-hydroxybenzoic acid

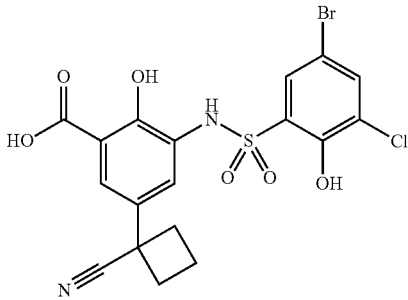 [SMILES: N#CC1(c2cc(NS(=O)(=O)c3cc(Br)cc(Cl)c3O)c(O)c(C(=O)O)c2)CCC1]

Step A: Phenyl 3-((5-bromo-3-chloro-2-hydroxyphenyl)sulfonamido)-5-(1-cyanocyclobutyl)-2-hydroxybenzoate. Using a procedure analogous to General Procedure E, starting with phenyl 3-amino-5-(1-cyanocyclobutyl)-2-hydroxybenzoate (154 mg, 0.50 mmol), which was prepared by a procedure analogous to the procedure used to prepare Example J203 Step E, and 5-bromo-3-chloro-2-hydroxybenzenesulfonyl chloride, which was prepared by a procedure analogous to the procedure used to prepare Example J4 Step A, phenyl 3-((5-bromo-3-chloro-2-hydroxyphenyl)sulfonamido)-5-(1-cyanocyclobutyl)-2-hydroxybenzoate was obtained as a brown solid (208 mg, 72%). LCMS (Method A) $t_R$=1.97 min, m/z=595.7, 597.7 [M+H]$^+$; Purity (AUC) ≥95%.

Step B: 3-((5-Bromo-3-chloro-2-hydroxyphenyl)sulfonamido)-5-(1-cyanocyclobutyl)-2-hydroxybenzoic acid. Using a procedure analogous to General Procedure F, except the reaction was run at room temperature, starting with phenyl 3-((5-bromo-3-chloro-2-hydroxyphenyl)sulfonamido)-5-(1-cyanocyclobutyl)-2-hydroxybenzoate (58 mg, 0.10 mmol), the title compound was obtained as a colorless solid (12 mg, 48%). $^1$H NMR (400 MHz, MeOH-d$_4$) $\delta_H$ 7.76 (d, J=2.4 Hz, 1H), 7.73 (d, J=2.4 Hz, 1H), 7.69 (d, J=2.4 Hz, 1H), 7.67 (d, J=2.4 Hz, 1H), 2.82-2.72 (m, 2H), 2.62-2.51 (m, 2H), 2.46-2.32 (m, 1H), 2.14-2.03 (m, 1H); LCMS (Method A) $t_R$=1.56 min, m/z=500.7, 502.8 [M+H]$^+$; Purity (AUC) ≥95%.

Example J207: 3-((5-Bromo-4-chloro-2-methoxyphenyl)sulfonamido)-5-(1-cyanocyclobutyl)-2-hydroxybenzoic acid

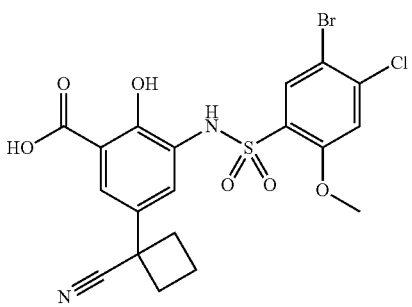 [SMILES: COc1cc(Cl)c(Br)cc1S(=O)(=O)Nc1cc(C2(C#N)CCC2)cc(C(=O)O)c1O]

Step A: Phenyl 3-((5-bromo-4-chloro-2-methoxyphenyl)sulfonamido)-5-(1-cyanocyclobutyl)-2-hydroxybenzoate. Using a procedure analogous to General Procedure E, starting with phenyl 3-amino-5-(1-cyanocyclobutyl)-2-hydroxybenzoate (31 mg, 0.10 mmol), which was prepared by a procedure analogous to the procedure used to prepare Example J203 Step E, and 2-methoxy-4-chloro-5-bromophenylsulfonyl chloride, which was prepared by a procedure analogous to the procedure used to prepare Example J7 Step A, phenyl 3-((5-bromo-4-chloro-2-methoxyphenyl)sulfonamido)-5-(1-cyanocyclobutyl)-2-hydroxybenzoate was obtained as a brown gum (37 mg, 0.063 mmol, 63%). LCMS (Method B) $t_R$=1.32 min, m/z=610.2 [M+NH$_4$]$^+$; Purity (AUC) >90%.

Step B: 3-((5-Bromo-4-chloro-2-methoxyphenyl)sulfonamido)-5-(1-cyanocyclobutyl)-2-hydroxybenzoic acid. Using a procedure analogous to General Procedure F, except the reaction was run at room temperature, starting with phenyl 3-((5-bromo-4-chloro-2-methoxyphenyl)sulfonamido)-5-(1-cyanocyclobutyl)-2-hydroxybenzoate (18 mg, 0.03 mmol), the title compound was obtained as a colorless solid (8 mg, 52%). $^1$H NMR (400 MHz, MeOH-d$_4$) $\delta_H$ 8.01 (s, 1H), 7.67 (s, 1H), 7.66 (s, 1H), 7.35 (s, 1H), 3.89 (s, 3H), 2.83-2.71 (m, 2H), 2.62-2.47 (m, 2H), 2.45-2.28 (m, 1H), 2.08 (ddt, J=11.8, 9.2, 4.6 Hz, 1H); LCMS (Method A) $t_R$=1.77 min, m/z=532.6, 534.7 [M+NH$_4$]$^+$; Purity (AUC) ≥95%.

Example J208: 3-((5-Bromo-2-hydroxyphenyl)sulfonamido)-5-(1-cyanocyclobutyl)-2-hydroxy-N-methylbenzamide

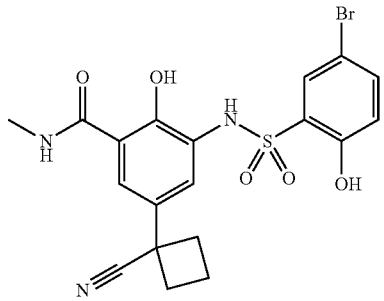 [SMILES: CNC(=O)c1cc(C2(C#N)CCC2)cc(NS(=O)(=O)c2cc(Br)ccc2O)c1O]

Using a procedure analogous to General Procedure G, starting with phenyl 3-((5-bromo-3-chloro-2-hydroxyphenyl)sulfonamido)-5-(1-cyanocyclobutyl)-2-hydroxybenzoate (31 mg, 0.05 mmol), which was prepared by a procedure analogous to the procedure used to prepare Example J203 Step F, and methylamine, the title compound was obtained as a colorless solid (18 mg, 75%). $^1$H NMR (400 MHz, MeOH-d$_4$) $\delta_H$ 7.82 (d, J=2.5 Hz, 1H), 7.56-7.47 (m, 3H), 6.84 (d, J=8.8 Hz, 1H), 2.91 (s, 3H), 2.81-2.71 (m, 2H), 2.65-2.51 (m, 2H), 2.38 (dt, J=11.5, 8.6 Hz, 1H), 2.12-2.02 (m, 1H); LCMS (Method A) $t_R$=1.54 min, m/z=479.8, 481.8 [M+H]$^+$; Purity (AUC) ≥95%.

Example J210: 3-((5-Bromo-2-methoxyphenyl)sulfonamido)-5-(1-cyanocyclobutyl)-2-hydroxy-N-methylbenzamide

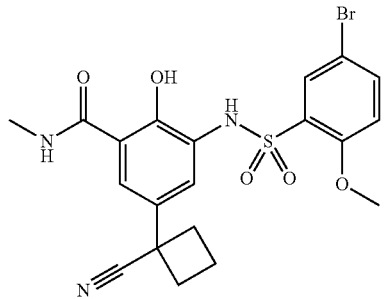

Using a procedure analogous to General Procedure G, starting with phenyl 3-((5-bromo-2-methoxyphenyl)sulfonamido)-5-(1-cyanocyclobutyl)-2-hydroxybenzoate (28 mg, 0.05 mmol) and methylamine, the title compound was obtained as a colorless solid (14 mg, 57%). $^1$H NMR (400 MHz, MeOH-d$_4$) $\delta_H$ 7.88 (d, J=2.5 Hz, 1H), 7.65 (dd, J=8.9, 2.5 Hz, 1H), 7.56 (d, J=2.2 Hz, 1H), 7.47 (d, J=2.2 Hz, 1H), 7.06 (d, J=8.9 Hz, 1H), 3.90 (s, 3H), 2.89 (s, 3H), 2.81-2.70 (m, 2H), 2.62-2.50 (m, 2H), 2.38 (dq, J=11.5, 8.5 Hz, 1H), 2.12-1.98 (m, 1H); LCMS (Method A) t$_R$=1.74 min, m/z=493.8, 495.8 [M+H]$^+$; Purity (AUC) ≥95%.

Example J211: 3-((5-Bromo-3-chloro-2-hydroxyphenyl)sulfonamido)-5-(1-cyanocyclobutyl)-2-hydroxy-N-methylbenzamide

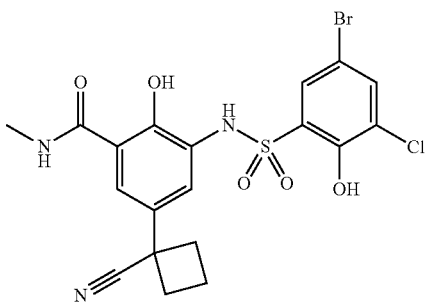 [SMILES: CNC(=O)c1cc(C2(C#N)CCC2)cc(NS(=O)(=O)c2cc(Br)cc(Cl)c2O)c1O]

Using a procedure analogous to General Procedure G, starting with phenyl 3-((5-bromo-3-chloro-2-hydroxyphenyl)sulfonamido)-5-(1-cyanocyclobutyl)-2-hydroxybenzoate 929 mg, 0.05 mmol), which was prepared by a procedure analogous to the procedure used to prepare Example J206 Step A, and methylamine, the title was obtained compound as a colorless solid (13 mg, 54%). $^1$H NMR (400 MHz, DMSO-d$_6$) $\delta_H$ 11.07 (br s, 1H), 9.39 (br s, 2H), 9.12 (d, J=4.6 Hz, 1H), 7.93 (d, J=2.5 Hz, 1H), 7.71 (d, J=2.1 Hz, 1H), 7.71 (d, J=2.5 Hz, 1H), 7.35 (d, J=2.1 Hz, 1H), 2.83 (d, J=4.6 Hz, 3H), 2.75-2.65 (m, 2H), 2.58-2.46 (m, 2H), 2.25 (dt, J=11.3, 8.6 Hz, 1H), 2.05-1.88 (m, 1H); LCMS (Method A) t$_R$=1.66 min, m/z=513.7, 515.8 [M+H]$^+$; Purity (AUC) ≥95%.

Example J212: 3-((5-Bromo-2-hydroxy-3-methylphenyl)sulfonamido)-5-(1-cyanocyclobutyl)-2-hydroxy-N-methylbenzamide

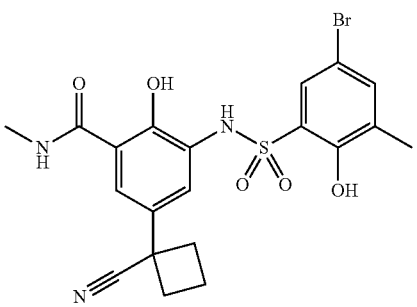

Step A: 5-Bromo-2-hydroxy-3-methylbenzenesulfonyl chloride. Using a procedure analogous to General Procedure A, starting with 2-methyl-4-bromophenol (1.87 g, 10 mmol), 5-bromo-2-hydroxy-3-methylbenzenesulfonyl chloride was obtained a colorless solid (1.66 g, 5.8 mmol, 58%). $^1$H NMR (400 MHz, DMSO-d$_6$) $\delta_H$ 7.36-7.34 (d, J=2.6 Hz, 1H), 7.29 (d, J=2.69 Hz, 1H), 2.13 (s, 3H); LCMS (Method B) t$_R$=1.06 min: Purity (AUC) >90%.

Step B: Phenyl 3-((5-bromo-2-hydroxy-3-methylphenyl)sulfonamido)-5-(1-cyanocyclobutyl)-2-hydroxybenzoate. Using a procedure analogous to General Procedure E, starting from phenyl 3-amino-5-(1-cyanocyclobutyl)-2-hydroxybenzoate (62 mg, 0.20 mmol), which was prepared by a procedure analogous to the procedure used to prepare Example J203 Step E, and 5-bromo-2-hydroxy-3-methylbenzenesulfonyl chloride, phenyl 3-((5-bromo-2-hydroxy-3-methylphenyl)sulfonamido)-5-(1-cyanocyclobutyl)-2-hydroxybenzoate was obtained as a a colorless solid (84 mg, 0.96 mmol, 96%). LCMS (Method A) t$_R$=2.00 min, m/z=573.7, 757.8 [M+NH$_4$]$^+$; Purity (AUC) ≥95%.

Step C: 3-((5-Bromo-2-hydroxy-3-methylphenyl)sulfonamido)-5-(1-cyanocyclobutyl)-2-hydroxy-N-methylbenzamide. Using a procedure analogous to General Procedure F, starting from phenyl 3-((5-bromo-2-hydroxy-3-methylphenyl)sulfonamido)-5-(1-cyanocyclobutyl)-2-hydroxybenzoate (22 mg, 0.05 mmol) and methylamine, the title compound was obtained as a colorless solid (14 mg, 57%). $^1$H NMR (400 MHz, DMSO-d$_6$) $\delta_H$ 7.59 (dd, J=2.6, 0.8 Hz, 1H), 7.55 (d, J=2.2 Hz, 1H), 7.54 (d, J=2.2 Hz, 1H), 7.46 (dd, J=2.6, 0.8 Hz, 1H), 2.91 (s, 3H), 2.83-2.73 (m, 2H), 2.66-2.56 (m, 2H), 2.46-2.34 (m, 1H), 2.20 (s, 2H), 2.14-2.06 (m, 1H); LCMS (Method A) t$_R$=1.69 min, m/z=493.8, 495.8 [M+H]$^+$; Purity (AUC) ≥95%.

Example J213: 3-((5-Bromo-3-ethyl-2-hydroxyphenyl)sulfonamido)-5-(1-cyanocyclobutyl)-2-hydroxy-N-methylbenzamide

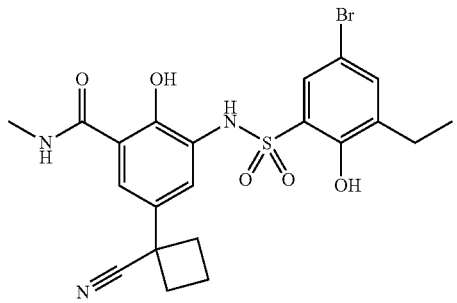 [SMILES: CCc1cc(Br)cc(S(=O)(=O)Nc2cc(C3(C#N)CCC3)cc(C(=O)NC)c2O)c1O]

Step A: 4-Bromo-2-ethylphenol. To a mixture containing 2-ethylphenol (5.4 mL, 50 mmol) in THF (125 mL) was added concentrated sulfuric acid (0.14 mL, 2.5 mmol) and NBS (9.8 g, 55 mmol). The mixture was allowed to stir at r.t. for 18 h. The mixture was concentrated under reduced pressure, re-dissolved in EtOAc (100 mL) and washed with water (2×50 mL) and saturated aqueous NaCl (50 mL) to afford 4-bromo-2-ethylphenol as a crude brown oil (9.89 g, 49.2 mmol), which was used without further purification. $^1$H NMR (400 MHz, CDCl$_3$) $\delta_H$ 7.27 (d, J=8.4 Hz, 1H), 7.27 (s, 1H), 6.67 (d, J=8.4 Hz, 1H), 2.62 (q, J=7.6 Hz, 2H), 1.24 (t, J=7.6 Hz, 3H).

Step B: 5-Bromo-3-ethyl-2-hydroxybenzenesulfonyl chloride. Using a procedure analogous to General Procedure A, starting with 4-bromo-2-ethylphenol (2.01 g, 10 mmol), 5-bromo-3-ethyl-2-hydroxybenzenesulfonyl chloride was obtained as a pale brown solid (525 mg, 1.75 mmol, 18%). $^1$H NMR (400 MHz, DMSO-d$_6$) $\delta_H$ 7.50 (d, J=2.1 Hz, 1H), 7.32 (d, J=2.1 Hz, 1H), 2.62 (q, J=7.6 Hz, 2H), 1.12 (t, J=7.5 Hz, 3H).

Step C: Phenyl 3-((5-bromo-3-ethyl-2-hydroxyphenyl)sulfonamido)-5-(1-cyanocyclobutyl)-2-hydroxybenzoate. Using a procedure analogous to General Procedure E, starting from phenyl 3-amino-5-(1-cyanocyclobutyl)-2-hydroxybenzoate (62 mg, 0.20 mmol), which was prepared by a procedure analogous to the procedure used to prepare Example J203 Step E, and 5-bromo-3-ethyl-2-hydroxybenzenesulfonyl chloride, phenyl 3-((5-bromo-3-ethyl-2-hydroxyphenyl)sulfonamido)-5-(1-cyanocyclobutyl)-2-hydroxybenzoate was obtained as a colorless solid (56 mg, 0.12 mmol, 62%). LCMS (Method A) t$_R$=1.87 min, m/z=570.8, 572.7 [M+H]$^+$; Purity (AUC) ≥95%.

Step D: 3-((5-Bromo-3-ethyl-2-hydroxyphenyl)sulfonamido)-5-(1-cyanocyclobutyl)-2-hydroxy-N-methylbenzamide. Using a procedure analogous to General Procedure G, starting from phenyl 3-((5-bromo-3-ethyl-2-hydroxyphenyl)sulfonamido)-5-(1-cyanocyclobutyl)-2-hydroxybenzoate (23 mg, 0.05 mmol) and methylamine, the title compound was obtained as a colorless solid (16 mg, 56%). $^1$H NMR (400 MHz, MeOH-d$_4$) $\delta_H$ 7.76 (d, J=2.3 Hz, 1H), 7.60 (d, J=2.3 Hz, 1H), 7.54 (d, J=2.3 Hz, 1H), 7.46 (d, J=2.3 Hz, 1H), 2.90 (s, 3H), 2.85-2.74 (m, 2H), 2.64 (q, J=7.5 Hz, 2H), 2.69-2.57 (m, 2H), 2.48-2.34 (m, 1H), 2.17-2.03 (m, 1H), 1.12 (t, J=7.5 Hz, 3H); LCMS (Method A) t$_R$=1.58 min, m/z=507.8, 509.8 [M+H]$^+$; Purity (AUC) ≥95%.

Example J214: 3-((5-Bromo-2-hydroxy-3-(trifluoromethoxy)phenyl)sulfonamido)-5-(1-cyanocyclobutyl)-2-hydroxy-N-methylbenzamide

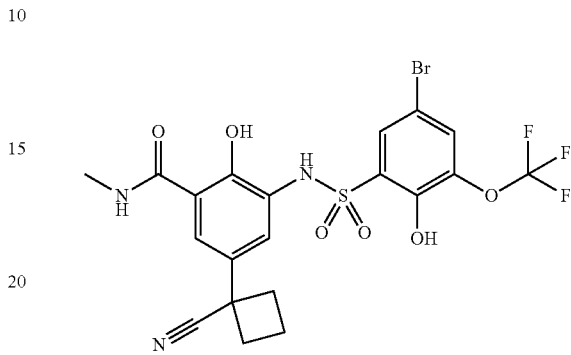

Step A: 5-Bromo-2-hydroxy-3-(trifluoromethoxy)benzenesulfonyl chloride. Using a procedure analogous to General Procedure A, starting with 2-(trifluoromethoxy)-4-bromophenol (2.57 g, 10 mmol), 5-bromo-2-hydroxy-3-(trifluoromethoxy)benzenesulfonyl chloride was obtained as a pale brown liquid (2.48 g, 6.98 mmol, 70%). $^1$H NMR (400 MHz, DMSO-d$_6$) $\delta_H$ 7.61-7.59 (m, 1H), 7.57 (s, 1H); $^{19}$F NMR (376 MHz, DMSO-d$_6$) $\delta_F$ −57.4; LCMS (Method B) t$_R$=1.10 min; Purity (AUC) >90%.

Step B: Phenyl 3-((5-bromo-2-hydroxy-3-(trifluoromethoxy)phenyl)sulfonamido)-5-(1-cyanocyclobutyl)-2-hydroxybenzoate. Using a procedure analogous to General Procedure E, starting from phenyl 3-amino-5-(1-cyanocyclobutyl)-2-hydroxybenzoate (62 mg, 0.20 mmol), which was prepared by a procedure analogous to the procedure used to prepare Example J203 Step E, and 5-bromo-2-hydroxy-3-(trifluoromethoxy)benzenesulfonyl chloride, phenyl 3-((5-bromo-2-hydroxy-3-(trifluoromethoxy)phenyl)sulfonamido)-5-(1-cyanocyclobutyl)-2-hydroxybenzoate was obtained as a colorless solid (48 mg, 0.095 mmol, 47%). LCMS (Method A) t$_R$=2.02 min, m/z=643.6, 645.7 [M+NH$_4$]$^+$; Purity (AUC) ≥95%.

Step C: 3-((5-Bromo-2-hydroxy-3-(trifluoromethoxy)phenyl)sulfonamido)-5-(1-cyanocyclobutyl)-2-hydroxy-N-methylbenzamide. Using a procedure analogous to General Procedure G, starting from phenyl 3-((5-bromo-2-hydroxy-3-(trifluoromethoxy)phenyl)sulfonamido)-5-(1-cyanocyclobutyl)-2-hydroxybenzoate (15 mg, 0.03 mmol) and methylamine, the title compound was obtained as a colorless solid (9 mg, 74%). $^1$H NMR (400 MHz, MeOH-d$_4$) $\delta_H$ 7.80 (d, J=2.5 Hz, 1H), 7.62 (dd, J=2.5, 1.3 Hz, 1H), 7.57 (d, J=2.2 Hz, 1H), 7.55 (d, J=2.2 Hz, 1H), 2.91 (s, 3H), 2.84-2.73 (m, 2H), 2.66-2.55 (m, 2H), 2.39 (dp, J=11.4, 8.7 Hz, 1H), 2.16-2.02 (m, 1H); $^{19}$F NMR (376 MHz, MeOH-d$_4$) $\delta_F$ −60.2; LCMS (Method A) t$_R$=1.72 min, m/z=563.7, 565.7 [M+H]$^+$; Purity (AUC) ≥95%.

Example J215: 3-((5-Bromo-4-chloro-2-methoxyphenyl)sulfonamido)-5-(1-cyanocyclobutyl)-2-hydroxy-N-methylbenzamide

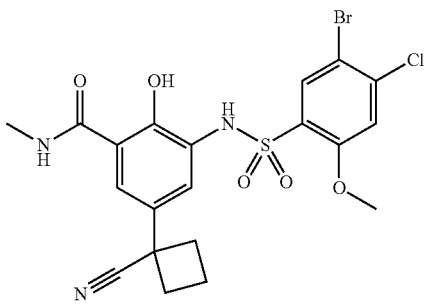 [SMILES: CNC(=O)c1cc(C2(C#N)CCC2)cc(NS(=O)(=O)c2cc(Br)c(Cl)cc2OC)c1O]

Using a procedure analogous to General Procedure G, starting from phenyl 3-((5-bromo-4-chloro-2-methoxyphenyl)sulfonamido)-5-(1-cyanocyclobutyl)-2-hydroxybenzoate (18 mg, 0.03 mmol), which was prepared by a procedure analogous to the procedure used to prepare Example J207 Step A, and methylamine, the title compound was obtained as a colorless solid (11 mg, 68%). $^1$H NMR (400 MHz, MeOH-d$_4$) $\delta_H$ 8.00 (s, 1H), 7.54 (d, J=2.2 Hz, 1H), 7.50 (d, J=2.2 Hz, 1H), 7.34 (s, 1H), 3.90 (s, 3H), 2.89 (s, 3H), 2.81-2.70 (m, 2H), 2.62-2.52 (m, 2H), 2.44-2.29 (m, 1H), 2.12-1.99 (m, 1H); LCMS (Method A) $t_R$=1.83 min, m/z=562.6 [M+H]$^+$; Purity (AUC) ≥95%.

Example J216: 5-(1-Cyanocyclobutyl)-3-((3,5-dichloro-2-hydroxyphenyl)sulfonamido)-2-hydroxy-N-methylbenzamide

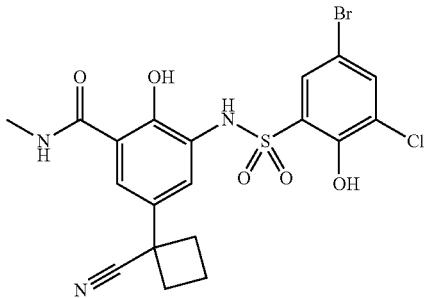 [SMILES: CNC(=O)c1cc(C2(C#N)CCC2)cc(NS(=O)(=O)c2cc(Br)cc(Cl)c2O)c1O]

Step A: 3,5-Dichloro-2-hydroxybenzenesulfonyl chloride. Using a procedure analogous to General Procedure A, starting with 2,4-dichlorophenol (1.0 g, 6.1 mmol), 3,5-dichloro-2-hydroxybenzenesulfonyl chloride was obtained as a colorless solid (1.37 g, 5.2 mmol, 85%). $^1$H NMR (400 MHz, DMSO-d$_6$) $\delta_H$ 7.55 (d, J=2.6 Hz, 1H), 7.38 (d, J=2.6 Hz, 1H).

Step B: Phenyl 5-(1-cyanocyclobutyl)-3-((3,5-dichloro-2-hydroxyphenyl)sulfonamido)-2-hydroxybenzoate. Using a procedure analogous to General Procedure E, starting from phenyl 3-amino-5-(1-cyanocyclobutyl)-2-hydroxybenzoate (62 mg, 0.20 mmol), which was prepared by a procedure analogous to the procedure used to prepare Example J203 Step E, and 3,5-dichloro-2-hydroxybenzenesulfonyl chloride, phenyl 5-(1-cyanocyclobutyl)-3-((3,5-dichloro-2-hydroxyphenyl)sulfonamido)-2-hydroxybenzoate was obtained as a colorless solid (71 mg, 0.17 mmol, 86%). LCMS (Method A) $t_R$=1.91 min, m/z=549.8, 551.8 [M+NH$_4$]$^+$; Purity (AUC) ≥95%.

Step C: 5-(1-Cyanocyclobutyl)-3-((3,5-dichloro-2-hydroxyphenyl)sulfonamido)-2-hydroxy-N-methylbenzamide. Using a procedure analogous to General Procedure G, starting from phenyl 5-(1-cyanocyclobutyl)-3-((3,5-dichloro-2-hydroxyphenyl)sulfonamido)-2-hydroxybenzoate (21 mg, 0.05 mmol) and methylamine, the title compound was obtained as a colorless solid (14 mg, 60%). $^1$H NMR (400 MHz, MeOH-d$_4$) $\delta_H$ 7.63 (d, J=2.6 Hz, 1H), 7.61 (d, J=2.6 Hz, 1H), 7.58 (d, J=2.2 Hz, 1H), 7.55 (d, J=2.2 Hz, 1H), 2.91 (s, 3H), 2.83-2.74 (m, 2H), 2.68-2.55 (m, 2H), 2.47-2.32 (m, 1H), 2.14-2.02 (m, 1H); LCMS (Method A) $t_R$=1.64 min, m/z=469.8, 471.8 [M+H]$^+$; Purity (AUC) ≥95%.

Example J217: 3-((6-Bromoquinoline)-8-sulfonamido)-5-(1-cyanocyclobutyl)-2-hydroxy-N-methylbenzamide

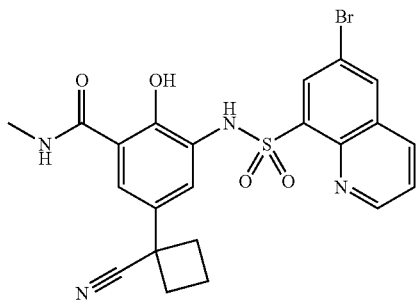 [SMILES: CNC(=O)c1cc(C2(C#N)CCC2)cc(NS(=O)(=O)c2cc(Br)cc3cccnc23)c1O]

Step A: Phenyl 3-((6-bromoquinoline)-8-sulfonamido)-5-(1-cyanocyclobutyl)-2-hydroxybenzoate. Using a procedure analogous to General Procedure E, starting from phenyl 3-amino-5-(1-cyanocyclobutyl)-2-hydroxybenzoate (31 mg, 0.10 mmol), which was prepared by a procedure analogous to the procedure used to prepare Example J203 Step E, and 6-bromoquinoline-8-sulfonyl chloride, phenyl 3-((6-bromoquinoline)-8-sulfonamido)-5-(1-cyanocyclobutyl)-2-hydroxybenzoate was obtained as a colorless solid (22 mg, 0.04 mmol, 38%). LCMS (Method B) $t_R$=1.18 min, m/z=578.3, 580.3 [M+H]$^+$; Purity (AUC) ≥95%.

Step B: 3-((6-Bromoquinoline)-8-sulfonamido)-5-(1-cyanocyclobutyl)-2-hydroxy-N-methylbenzamide. Using a procedure analogous to General Procedure G, starting from phenyl 3-((6-bromoquinoline)-8-sulfonamido)-5-(1-cyanocyclobutyl)-2-hydroxybenzoate (22 mg, 0.04 mmol) and methylamine, the title compound was obtained as a colorless solid (7 mg, 36%). $^1$H NMR (400 MHz, MeOH-d$_4$) $\delta_H$ 9.09 (dd, J=4.3, 1.7 Hz, 1H), 8.42 (d, J=2.2 Hz, 1H), 8.40 (d, J=2.2 Hz, 1H), 8.37 (dd, J=8.4, 1.8 Hz, 1H), 7.70-7.66 (m, 1H), 7.68 (d, J=2.3 Hz, 1H), 7.42 (d, J=2.2 Hz, 1H), 2.82 (s, 3H), 2.79-2.71 (m, 2H), 2.63-2.52 (m, 2H), 2.43-2.32 (m, 1H), 2.11-2.00 (m, 1H); LCMS (Method A) $t_R$=1.19 min, m/z=514.8, 516.7 [M+H]$^+$; Purity (AUC) ≥95%.

Example J218: 3-((5-Bromo-2-hydroxyphenyl)sulfonamido)-5-(1-cyanocyclobutyl)-2-hydroxybenzamide

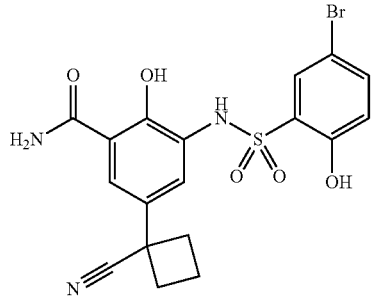 [SMILES: N#CC1(c2cc(NS(=O)(=O)c3cc(Br)ccc3O)c(O)c(C(N)=O)c2)CCC1]

Phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, was dissolved in ammonia (7 N in MeOH, 0.5 mL) and heated at reflux in a sealed tube for 16 h. The solvent was concentrated and crude material was purified by preparative HPLC to afford the title compound as a colorless solid (14 mg, 58%). $^1$H NMR (400 MHz, MeOH-d$_4$) $\delta_H$ 7.83 (d, J=2.5 Hz, 1H), 7.57 (d, J=2.3 Hz, 1H), 7.55 (d, J=2.3 Hz, 1H), 7.51 (dd, J=8.8, 2.5 Hz, 1H), 6.85 (d, J=8.8 Hz, 1H), 2.81-2.72 (m, 2H), 2.64-2.52 (m, 2H), 2.45-2.31 (m, 1H), 2.13-2.00 (m, 1H); LCMS (Method A) t$_R$=1.46 min, m/z=465.7, 467.8 [M+H]$^+$; Purity (AUC) ≥95%.

Example J219: 3-((5-Bromo-2-hydroxyphenyl)sulfonamido)-5-(1-cyanocyclobutyl)-2-hydroxy-N-(2-methoxyethyl)benzamide

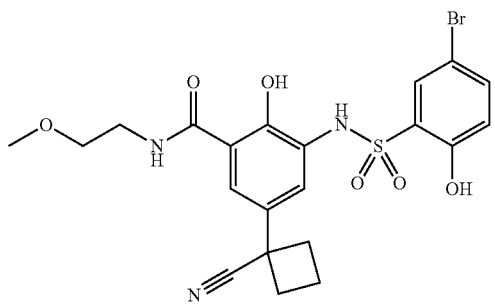 [SMILES: COCCNC(=O)c1cc(C2(C#N)CCC2)cc(NS(=O)(=O)c2cc(Br)ccc2O)c1O]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and (2-methoxyethyl)ethylamine, the title compound was obtained as a colorless solid (16 mg, 61%). $^1$H NMR (400 MHz, MeOH-d$_4$) $\delta_H$ 7.80 (d, J=2.5 Hz, 1H), 7.54 (d, J=2.2 Hz, 1H), 7.53 (d, J=2.2 Hz, 1H), 7.50 (dd, J=8.7, 2.5 Hz, 1H), 6.84 (d, J=8.8 Hz, 1H), 3.55 (d, J=1.4 Hz, 4H), 3.36 (s, 3H), 2.81-2.70 (m, 2H), 2.62-2.51 (m, 2H), 2.44-2.30 (m, 1H), 2.11-1.97 (m, 1H); LCMS (Method A) t$_R$=1.57 min, m/z=523.8, 525.7 [M+H]$^+$; Purity (AUC) ≥95%.

Example J220: 3-((5-Bromo-2-hydroxyphenyl)sulfonamido)-5-(1-cyanocyclobutyl)-2-hydroxy-N-((tetrahydrofuran-2-yl)methyl)benzamide

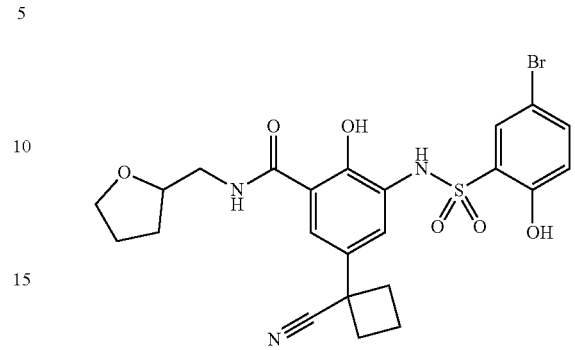

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and tetrahydrofurfurylamine, the title compound was obtained as a colorless solid (15 mg, 55%). $^1$H NMR (400 MHz, MeOH-d$_4$) $\delta_H$ 7.82 (d, J=2.5 Hz, 1H), 7.57 (d, J=2.2 Hz, 1H), 7.55 (d, J=2.2 Hz, 1H), 7.52 (dd, J=8.8, 2.5 Hz, 1H), 6.85 (d, J=8.8 Hz, 1H), 4.11 (td, J=7.0, 4.5 Hz, 1H), 3.90 (dt, J=8.2, 6.6 Hz, 1H), 3.82-3.74 (m, 1H), 3.55-3.37 (m, 2H), 2.83-2.71 (m, 2H), 2.66-2.53 (m, 2H), 2.40 (dq, J=11.4, 8.6 Hz, 1H), 2.14-1.99 (m, 1H), 1.99-1.87 (m, 2H), 1.75-1.58 (m, 1H); LCMS (Method A) t$_R$=1.62 min, m/z=549.8, 551.8 [M+H]$^+$; Purity (AUC) ≥95%.

Example J221: 5-Bromo-N-(5-(1-cyanocyclobutyl)-2-hydroxy-3-(3-methoxypyrrolidine-1-carbonyl)phenyl)-2-hydroxybenzenesulfonamide

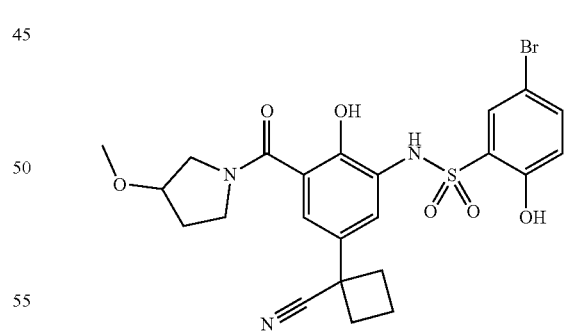

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 3-methoxypyrrolidine hydrochloride, the title compound was obtained as a colorless solid (9 mg, 33%). LCMS (Method A) t$_R$=1.49 min, m/z=549.9, 551.8 [M+H]$^+$; Purity (AUC) ≥95%.

Example J222: 3-((5-Bromo-2-hydroxyphenyl)sulfonamido)-5-(1-cyanocyclobutyl)-2-hydroxy-N-((2-oxo-1,2-dihydropyridin-4-yl)methyl)benzamide

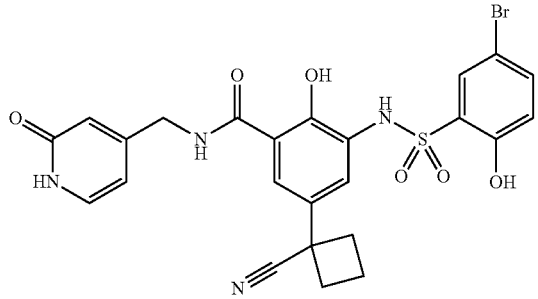 [SMILES: N#CC1(c2cc(NS(=O)(=O)c3cc(Br)ccc3O)c(O)c(C(=O)NCc3cc[nH]c(=O)c3)c2)CCC1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 4-(aminomethyl)pyridin-2(1H)-one, the title compound was obtained as a colorless solid (17 mg, 59%). $^1$H NMR (400 MHz, MeOH-$d_4$) $\delta_H$ 7.83 (d, J=2.5 Hz, 1H), 7.60 (d, J=2.2 Hz, 1H), 7.59 (d, J=2.2 Hz, 1H), 7.52 (dd, J=8.8, 2.5 Hz, 1H), 7.41 (dd, J=6.7, 0.7 Hz, 1H), 6.86 (d, J=8.8 Hz, 1H), 6.46-6.41 (m, 1H), 6.40 (dd, J=6.8, 1.7 Hz, 1H), 4.47 (s, 2H), 2.83-2.72 (m, 2H), 2.65-2.53 (m, 2H), 2.47-2.31 (m, 1H), 2.14-1.99 (m, 1H); LCMS (Method A) $t_R$=1.41 min, m/z=572.8, 574.8 [M+H]$^+$; Purity (AUC) ≥95%.

Example J223: 5-Bromo-N-(5-(1-cyanocyclobutyl)-2-hydroxy-3-(3-methoxyazetidine-1-carbonyl)phenyl)-2-hydroxybenzenesulfonamide

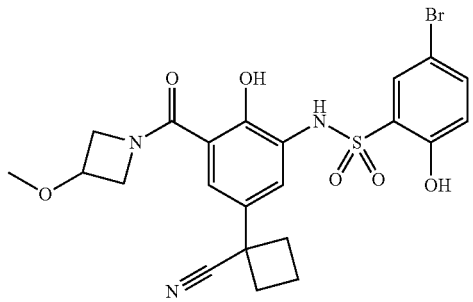 [SMILES: COC1CN(C(=O)c2cc(C3(C#N)CCC3)cc(NS(=O)(=O)c3cc(Br)ccc3O)c2O)C1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 3-methoxyazetidine hydrochloride, the title compound was obtained as a colorless solid (16 mg, 60%). $^1$H NMR (400 MHz, MeOH-$d_4$) $\delta_H$ 7.81 (d, J=2.5 Hz, 1H), 7.60 (d, J=2.2 Hz, 1H), 7.52 (dd, J=8.8, 2.5 Hz, 1H), 7.23 (d, J=2.3 Hz, 1H), 6.86 (d, J=8.8 Hz, 1H), 4.74-4.40 (m, 4H), 4.36-4.25 (m, 1H), 2.82-2.72 (m, 2H), 2.60-2.48 (m, 2H), 2.46-2.34 (m, 1H), 2.17-2.03 (m, 1H); LCMS (Method A) $t_R$=1.59 min, m/z=535.8, 537.7 [M+H]$^+$; Purity (AUC) ≥95%.

Example J224: 5-Bromo-N-(5-(1-cyanocyclobutyl)-2-hydroxy-3-(3-hydroxyazetidine-1-carbonyl)phenyl)-2-hydroxybenzenesulfonamide

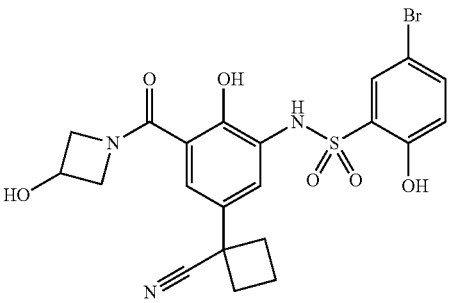 [SMILES: N#CC1(c2cc(NS(=O)(=O)c3cc(Br)ccc3O)c(O)c(C(=O)N3CC(O)C3)c2)CCC1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 3-hydroxyazetidine hydrochloride, the title compound was obtained as a colorless solid (10 mg, 38%). LCMS (Method A) $t_R$=1.43 min, m/z=521.8, 523.8 [M+H]$^+$; Purity (AUC) ≥95%.

Example J225: 3-((5-Bromo-2-hydroxyphenyl)sulfonamido)-5-(1-cyanocyclobutyl)-2-hydroxy-N-(2-morpholinoethyl)benzamide

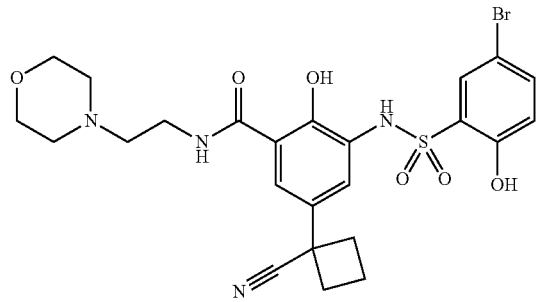 [SMILES: N#CC1(c2cc(NS(=O)(=O)c3cc(Br)ccc3O)c(O)c(C(=O)NCCN3CCOCC3)c2)CCC1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 2-morpholinoethan-1-amine, the title compound was obtained as an off-white solid (20 mg, 69%) as a free base. $^1$H NMR (400 MHz, MeOH-$d_4$) $\delta_H$ 7.78 (d, J=2.6 Hz, 1H), 7.59 (d, J=2.6 Hz, 1H), 7.43-7.36 (m, 2H), 6.74 (d, J=8.8 Hz, 1H), 3.74 (t, J=4.7 Hz, 4H), 3.56 (t, J=6.7 Hz, 2H), 3.10 (d, J=23.0 Hz, 3H), 2.78-2.66 (m, 2H), 2.62 (t, J=6.7 Hz, 2H), 2.59-2.48 (m, 6H), 2.42-2.27 (m, 1H), 2.11-1.98 (m, 1H); LCMS (Method A) $t_R$=1.20 min, m/z=578.8, 580.8 [M+H]$^+$; Purity (AUC) ≥95%.

Example J226: 3-((5-Bromo-2-hydroxyphenyl)sulfonamido)-5-(1-cyanocyclobutyl)-N-(2-(dimethylamino)ethyl)-2-hydroxybenzamide

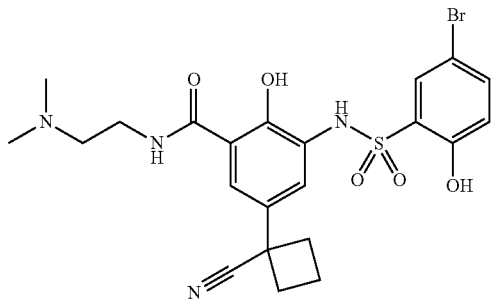 [SMILES: CN(C)CCNC(=O)c1cc(C2(C#N)CCC2)cc(NS(=O)(=O)c2cc(Br)ccc2O)c1O]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and N,N-dimethylethan-1,2-diamine, the title compound was obtained as a pale brown solid (18 mg, 67%). $^1$H NMR (400 MHz, MeOH-$d_4$) $\delta_H$ 7.77 (d, J=2.6 Hz, 1H), 7.58 (d, J=2.6 Hz, 1H), 7.39-7.32 (m, 2H), 6.70 (d, J=8.9 Hz, 1H), 3.57 (t, J=6.9 Hz, 2H), 2.77-2.63 (m, 4H), 2.60-2.47 (m, 2H), 2.39 (s, 6H), 2.38-2.27 (m, 1H), 2.12-1.98 (m, 1H); LCMS (Method A) $t_R$=1.24 min, m/z=536.8, 538.8 [M+H]$^+$; Purity (AUC) ≥95%.

Example J227: 3-((5-Bromo-2-hydroxyphenyl)sulfonamido)-5-(1-cyanocyclobutyl)-2-hydroxy-N-(1H-1,2,4-triazol-3-yl)benzamide

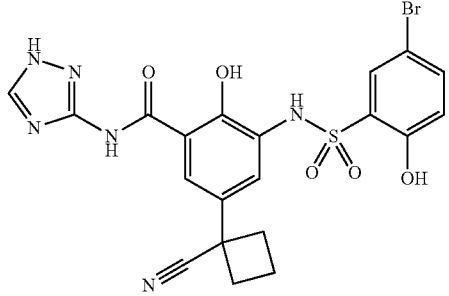 [SMILES: N#CC1(c2cc(NS(=O)(=O)c3cc(Br)ccc3O)c(O)c(C(=O)Nc3nc[nH]n3)c2)CCC1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 3-amino-1,2,4-triazole, the title compound was obtained as a colorless solid (15 mg, 56%). LCMS (Method A) $t_R$=1.41 min, m/z=532.8, 534.7 [M+H]$^+$; Purity (AUC) ≥95%.

Example J228: 3-((5-Bromo-2-hydroxyphenyl)sulfonamido)-5-(1-cyanocyclobutyl)-2-hydroxy-N-(2-hydroxyethyl)benzamide

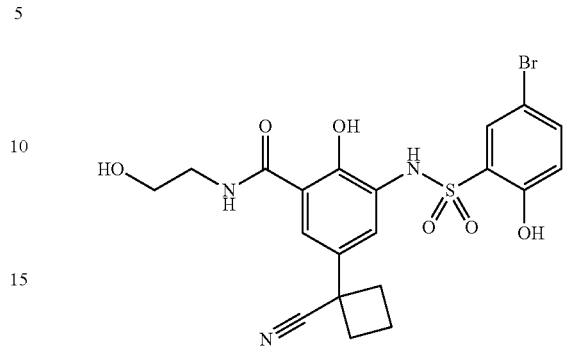

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and ethanolamine, the title compound was obtained as a colorless solid (19 mg, 74%). $^1$H NMR (400 MHz, MeOH-$d_4$) $\delta_H$ 7.82 (d, J=2.5 Hz, 1H), 7.56 (s, 2H), 7.51 (dd, J=8.8, 2.5 Hz, 1H), 6.85 (d, J=8.8 Hz, 1H), 3.71 (t, J=5.7 Hz, 2H), 3.51 (t, J=5.7 Hz, 2H), 2.82-2.72 (m, 2H), 2.59 (dt, J=12.1, 8.9 Hz, 2H), 2.38 (dp, J=11.5, 8.7 Hz, 1H), 2.13-1.99 (m, 1H); LCMS (Method A) $t_R$=1.43 min, m/z=509.8, 511.8 [M+H]$^+$; Purity (AUC) ≥95%.

Example J229: 3-((5-Bromo-2-hydroxyphenyl)sulfonamido)-5-(1-cyanocyclobutyl)-2-hydroxy-N-((tetrahydro-2H-pyran-2-yl)methyl)benzamide

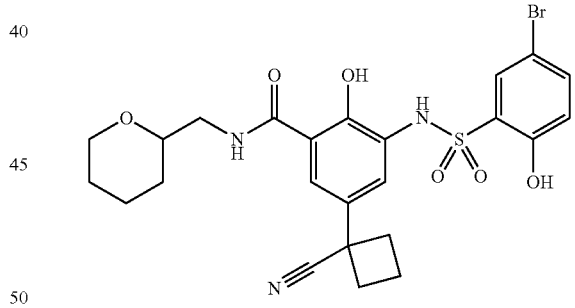

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and (tetrahydropyran-2-yl)methanamine, the title compound was obtained as a colorless solid (23 mg, 81%). $^1$H NMR (400 MHz, MeOH-$d_4$) $\delta_H$ 7.82 (d, J=2.5 Hz, 1H), 7.56 (d, J=2.2 Hz, 1H), 7.55 (d, J=2.2 Hz, 1H), 7.51 (dd, J=8.7, 2.5 Hz, 1H), 6.85 (d, J=8.8 Hz, 1H), 3.97 (dd, J=11.1, 3.3 Hz, 1H), 3.60-3.51 (m, 1H), 3.50-3.40 (m, 2H), 3.37 (d, J=7.6 Hz, 1H), 2.84-2.72 (m, 2H), 2.65-2.53 (m, 2H), 2.47-2.32 (m, 1H), 2.12-1.98 (m, 1H), 1.73-1.64 (m, 1H), 1.63-1.49 (m, 4H), 1.39-1.25 (m, 1H); LCMS (Method A) $t_R$=1.72 min, m/z=563.8, 565.8 [M+H]$^+$; Purity (AUC) ≥95%.

Example J230: 3-((5-Bromo-2-hydroxyphenyl)sulfonamido)-5-(1-cyanocyclobutyl)-2-hydroxy-N-((6-oxo-1,6-dihydropyridin-3-yl)methyl)benzamide

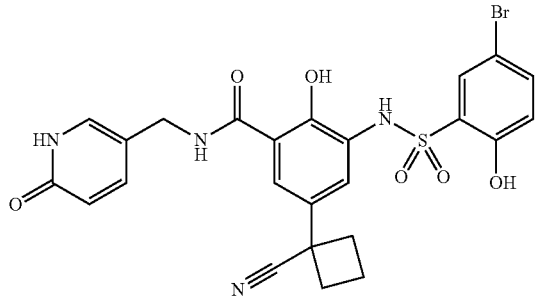 [SMILES: N#CC1(c2cc(NS(=O)(=O)c3cc(Br)ccc3O)c(O)c(C(=O)NCc3ccc(=O)[nH]c3)c2)CCC1]

Using a procedure analogous to General Procedure H, starting from phenyl 3-((5-bromo-3-chloro-2-hydroxyphenyl)sulfonamido)-5-(1-cyanocyclobutyl)-2-hydroxybenzoate (27 mg, 0.05 mmol), which was prepared by a procedure analogous to the procedure used to prepare Example J203 Step F, and 5-(aminomethyl)pyridin-2(1H)-one, the title compound was obtained as a colorless solid (18 mg, 63%). LCMS (Method A) $t_R$=1.41 min, m/z=572.7, 574.8 [M+H]$^+$; Purity (AUC) ≥95%.

Example J231: 3-((5-Bromo-2-hydroxyphenyl)sulfonamido)-5-(1-cyanocyclohexyl)-2-hydroxybenzoic acid

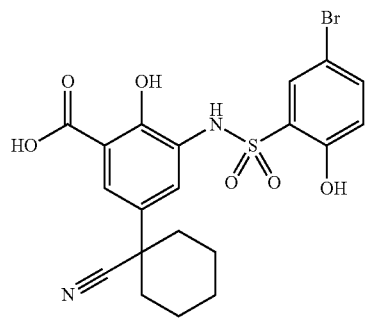 [SMILES: N#CC1(c2cc(NS(=O)(=O)c3cc(Br)ccc3O)c(O)c(C(=O)O)c2)CCCCC1]

The title compound was synthesized using a sequence of procedures analogous to the sequence of procedures used to prepare Example J203, except that Step A involved the synthesis of 1-(3-bromo-4-methoxyphenyl)cyclohexane-1-carbonitrile, using 1,5-dibromopentane. $^1$H NMR (400 MHz, MeOH-d$_4$) δ$_H$ 7.85 (d, J=2.5 Hz, 1H), 7.73 (d, J=2.4 Hz, 1H), 7.70 (d, J=2.4 Hz, 1H), 7.52 (dd, J=8.8, 2.5 Hz, 1H), 6.84 (d, J=8.8 Hz, 1H), 2.08-1.87 (m, 4H), 1.88-1.77 (m, 1H), 1.74 (td, J=12.9, 10.5, 6.3 Hz, 4H), 1.46-1.31 (m, 1H); LCMS (Method A) $t_R$=1.65 min, m/z=494.8, 496.8 [M+H]$^+$; Purity (AUC) ≥95%.

Example J232: 3-((5-Bromo-2-hydroxyphenyl)sulfonamido)-5-(1-cyanocyclohexyl)-2-hydroxybenzamide

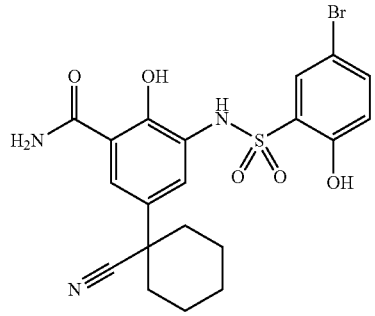 [SMILES: N#CC1(c2cc(NS(=O)(=O)c3cc(Br)ccc3O)c(O)c(C(N)=O)c2)CCCCC1]

Phenyl 3-((5-bromo-2-hydroxyphenyl)sulfonamido)-5-(1-cyanocyclohexyl)-2-hydroxybenzoate (29 mg, 0.05 mmol), which was prepared by a procedure analogous to the procedure used to prepare Example J231, was dissolved in ammonia (7 N in MeOH, 0.5 mL) and heated at reflux in a sealed tube for 16 h. The solvent was concentrated and crude material purified by preparative HPLC to afford the tide compound as a colorless solid (15 mg, 61%). $^1$H NMR (400 MHz, DMSO-d$_6$) δ$_H$ 11.30 (s, 1H), 8.68 (s, 1H), 8.10 (s, 1H), 7.71 (d, J=2.6 Hz, 1H), 7.69 (d, J=2.3 Hz, 1H), 7.58 (dd, J=8.8, 2.6 Hz, 1H), 7.50 (d, J=2.2 Hz, 1H), 6.92 (d, J=8.7 Hz, 1H), 4.03 (s, 3H), 1.99 (d, J=12.2 Hz, 2H), 1.87-1.52 (m, 7H), 1.34-1.17 (m, 1H); LCMS (Method A) $t_R$=1.64 min, m/z=493.8, 495.8 [M+H]$^+$; Purity (AUC) ≥95%.

Example J233: 3-((5-Bromo-2-hydroxyphenyl)sulfonamido)-5-(1-cyanocyclohexyl)-2-hydroxy-N-methylbenzamide

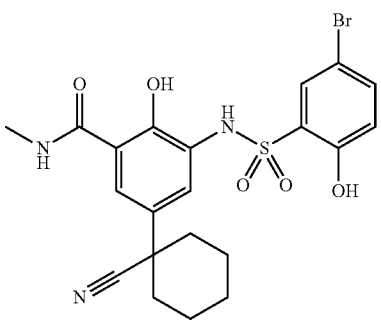 [SMILES: CNC(=O)c1cc(C2(C#N)CCCCC2)cc(NS(=O)(=O)c2cc(Br)ccc2O)c1O]

Using a procedure analogous to General Procedure G, starting from phenyl 3-((5-bromo-2-hydroxyphenyl)sulfonamido)-5-(1-cyanocyclohexyl)-2-hydroxybenzoate (29 mg, 0.05 mmol), which was prepared by a procedure analogous to the procedure used to prepare Example J231, and methylamine, the tide compound was obtained as a colorless solid (16 mg, 63%). $^1$H NMR (400 MHz, DMSO-d$_6$) δ$_H$ 11.30 (s, 1H), 9.09 (s, 1H), 8.88 (s, 1H), 7.71 (d, J=2.6 Hz, 1H), 7.65 (d, J=2.1 Hz, 1H), 7.58 (dd, J=8.7, 2.1 Hz, 1H), 7.50-7.45 (m, 3H), 6.91 (d, J=8.7 Hz, 1H), 2.81 (d, J=4.3 Hz, 3H), 1.99 (d, J=11.7 Hz, 2H), 1.90-1.51 (m, 8H); LCMS (Method A) $t_R$=1.72 min, m/z=507.8, 509.8 [M+H]$^+$; Purity (AUC) ≥95%.

Example J234: 3-((5-Bromo-3-chloro-2-hydroxyphenyl)sulfonamido)-5-(1-cyanocyclohexyl)-2-hydroxybenzoic acid

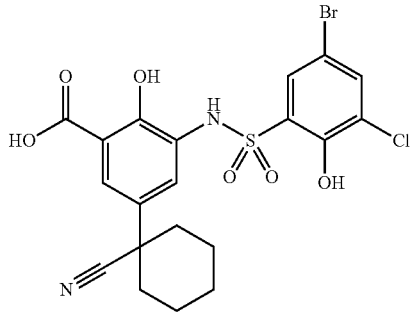 [SMILES: N#CC1(c2cc(NS(=O)(=O)c3cc(Br)cc(Cl)c3O)c(O)c(C(=O)O)c2)CCCCC1]

Using procedures analogous to General Procedures E and then F, starting with phenyl 3-((5-bromo-2-hydroxyphenyl)sulfonamido)-5-(1-cyanocyclohexyl)-2-hydroxybenzoate (29 mg, 0.05 mmol), which was prepared by a procedure analogous to the procedure used to prepare Example J231, and 5-bromo-3-chloro-2-hydroxybenzenesulfonyl chloride, which was prepared by a procedure analogous to the procedure used to prepare Example J4 Step A, the title compound was obtained. $^1$H NMR (400 MHz, MeOH-d$_4$) $\delta_H$ 7.79 (d, J=2.5 Hz, 1H), 7.78 (d, J=2.5 Hz, 1H), 7.75 (d, J=2.4 Hz, 1H), 7.72 (d, J=2.5 Hz, 1H), 2.05 (dd, J=8.3, 3.5 Hz, 2H), 1.99-1.87 (m, 2H), 1.89-1.78 (m, 1H), 1.80-1.69 (m, 3H), 1.46-1.31 (m, 1H); LCMS (Method A) t$_R$=1.74 min, m/z=530.7 [M+H]$^+$; Purity (AUC) ≥95%.

Example J235: 3-((5-Bromo-3-chloro-2-hydroxyphenyl)sulfonamido)-5-(1-cyanocyclohexyl)-2-hydroxybenzamide

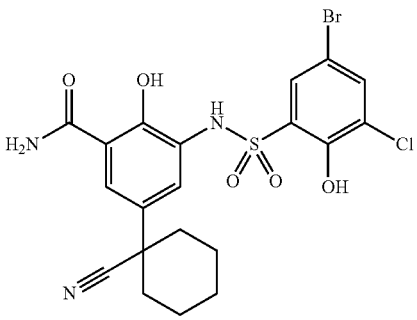 [SMILES: N#CC1(c2cc(NS(=O)(=O)c3cc(Br)cc(Cl)c3O)c(O)c(C(N)=O)c2)CCCCC1]

Phenyl 3-((5-bromo-3-chloro-2-hydroxyphenyl)sulfonamido)-5-(1-cyanocyclohexyl)-2-hydroxybenzoate (30 mg, 0.05 mmol), which was prepared by a procedure analogous to the procedure used to prepare Example J234, was dissolved in ammonia (7 N in MeOH, 0.5 mL) and heated at reflux in a sealed tube for 16 h. The solvent was concentrated and crude material purified by preparative HPLC to afford the title compound as a colorless solid (19 mg, 72%). $^1$H NMR (400 MHz, DMSO-d$_6$) $\delta_H$ 8.67 (s, 1H), 8.12 (s, 1H), 7.92 (d, J=2.5 Hz, 1H), 7.76 (d, J=2.2 Hz, 1H), 7.70 (d, J=2.5 Hz, 1H), 7.48 (d, J=2.2 Hz, 1H), 2.02 (d, J=12.7 Hz, 2H), 1.89-1.47 (m, 7H), 1.36-1.16 (m, 1H); LCMS (Method A) t$_R$=1.74 min, m/z=529.7 [M+H]$^+$; Purity (AUC) ≥95%.

Example J236: 3-((5-Bromo-3-chloro-2-hydroxyphenyl)sulfonamido)-5-(1-cyanocyclohexyl)-2-hydroxy-N-methylbenzamide

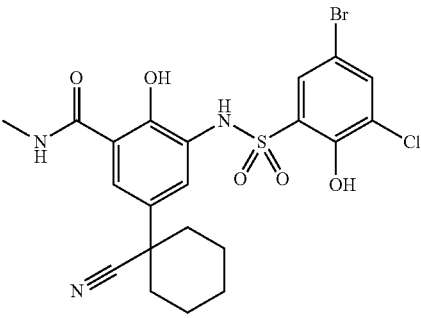 [SMILES: CNC(=O)c1cc(C2(C#N)CCCCC2)cc(NS(=O)(=O)c2cc(Br)cc(Cl)c2O)c1O]

Using a procedure analogous to General Procedure G, starting from phenyl 3-((5-bromo-3-chloro-2-hydroxyphenyl)sulfonamido)-5-(1-cyanocyclohexyl)-2-hydroxybenzoate (30 mg, 0.05 mmol), which was prepared by a procedure analogous to the procedure used to prepare Example J234, the title compound was obtained as a colorless solid (21 mg, 77%). $^1$H NMR (400 MHz, DMSO-d$_6$) $\delta_H$ 9.09 (d, J=4.4 Hz, 1H), 7.92 (d, J=2.3 Hz, 1H), 7.72 (d, J=2.4 Hz, 1H), 7.70 (d, J=2.4 Hz, 1H), 7.46 (d, J=2.2 Hz, 1H), 2.82 (d, J=4.4 Hz, 3H), 2.02 (d, J=12.7 Hz, 2H), 1.88-1.51 (m, 7H), 1.26 (d, J=12.7 Hz, 1H); LCMS (Method A) t$_R$=1.84 min, m/z=543.7 [M+H]$^+$; Purity (AUC) ≥95%.

Example SN-3: 3-((5-bromo-3-chloro-2-methoxyphenyl)sulfonamido)-5-(1-cyanocyclobutyl)-2-hydroxy-N-methylbenzamide

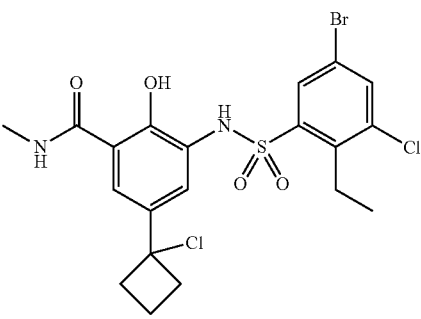 [SMILES: CCc1c(Cl)cc(Br)cc1S(=O)(=O)Nc1cc(C2(Cl)CCC2)cc(C(=O)NC)c1O]

Step A: 5-bromo-3-chloro-2-methoxybenzenesulfonyl chloride. To a stirred solution of HBF$_4$ (21 μL, 0.2 mmol, 60%) and DCM (2 mL) was added 5-bromo-3-chloro-2-hydroxybenzenesulfonyl chloride (30 mg, 0.09 mmol) at 0° C. TMSCHN$_2$ (0.34 mmol, 0.2 mL, 2 M hexane solution) was added dropwise in three portions at intervals of 30 min, and the reaction mixture was stirred for further 40 min at the same temperature after the additions were complete. The mixture was diluted with water, extracted with DCM, dried (Na$_2$SO$_4$), and concentrated. Purification by ISCO flash chromatography (12 g, 0-10% EtOAc in hexanes) afforded 5-bromo-3-chloro-2-methoxybenzenesulfonyl chloride as a white solid (23 mg, 0.07 mmol, 73%). $^1$H NMR (400 MHz, CDCl$_3$) $\delta_H$ 8.003 (d, J=2.4 Hz, 1H), 7.88 (d, J=2.4 Hz, 1H), 4.12 (s, 3H).

Step B: Phenyl-3-((5-bromo-3-chloro-2-methoxyphenyl)sulfonamido)-5-(1-cyanocyclobutyl)-2-hydroxybenzoate. Using a procedure analogous to General Procedure E, starting with phenyl-3-amino-5-(1-cyanocyclobutyl)-2-hydroxybenzoate (25 mg, 0.08 mmol) and 5-bromo-3-chloro-2-methoxybenzenesulfonyl chloride (23 mg, 0.08 mmol), phenyl 3-((5-bromo-3-chloro-2-methoxyphenyl)sulfonamido)-5-(1-cyanocyclobutyl)-2-hydroxybenzoate was obtained, after purification by preparative HPLC, as a white liquid (22 mg, 0.04 mmol, 46%). $^1$H NMR (400 MHz, CDCl$_3$) $\delta_H$ 10.82 (s, 1H), 7.88 (d, J=2.4 Hz, 1H), 7.84-7.82 (m, 2H), 7.70 (d, J=2.4 Hz, 1H), 7.68 (s, 1H), 7.47-7.43 (m, 2H), 7.34-7.30 (m, 1H), 7.17 (d, J=7.6 Hz, 2H), 4.10 (s, 3H), 2.89-2.82 (m, 2H), 2.62-2.54 (m, 2H), 2.51-2.42 (m, 1H), 2.15-2.06 (m, 1H); LCMS (Method B) $t_R$=1.36 min; m/z=609.3, 611.3 [M+H]$^+$; Purity (AUC) 85%.

Step C: 3-((5-bromo-3-chloro-2-methoxyphenyl)sulfonamido)-5-(1-cyanocyclobutyl)-2-hydroxy-N-methylbenzamide. Using a procedure analogous to General Procedure G, starting with phenyl-3-((5-bromo-3-chloro-2-methoxyphenyl)sulfonamido)-5-(1-cyanocyclobutyl)-2-hydroxybenzoate (22 mg, 0.04 mmol) and methylamine, the title compound was obtained as a white solid (13 mg, 0.02 mmol, 66%). $^1$H NMR (400 MHz, CDCl$_3$) $\delta_H$ 7.86 (d, J=2.4 Hz, 1H), 7.72-7.67 (m, 3H), 7.12 (d, J=2.0 Hz, 1H), 6.49 (d, J=4.4 Hz, 1H), 4.10 (s, 3H), 2.98 (d, J=4.8 Hz, 3H), 2.83-2.76 (m, 2H), 2.57-2.48 (m, 2H), 2.46-2.36 (m, 1H), 2.16-2.06 (m, 1H); LCMS (Method B) $t_R$=1.17 min; m/z=628.2, 629.3 [M+H]$^+$; Purity (AUC) ≥95%.

Example SN-4: 3-((5-bromo-3-chloro-2-methoxyphenyl)sulfonamido)-5-(1-cyanocyclobutyl)-2-hydroxybenzoic acid

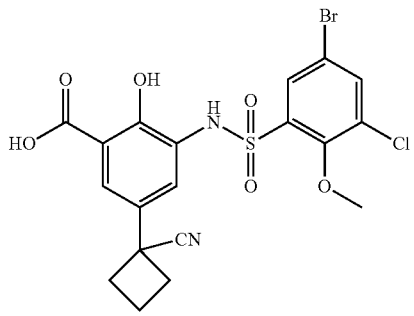 [SMILES: COc1c(Cl)cc(Br)cc1S(=O)(=O)Nc1cc(C2(C#N)CCC2)cc(C(=O)O)c1O]

Using a procedure analogous to General Procedure F, starting with phenyl 3-((5-bromo-3-chloro-2-methoxyphenyl)sulfonamido)-5-(1-cyanocyclobutyl)-2-hydroxybenzoate (100 mg, 0.17 mmol), the title compound was obtained as a pale pink solid (20 mg, 0.04 mmol, 23%). $^1$H NMR (400 MHz, CD$_3$OD) $\delta_H$ 7.87 (d, J=2.4 Hz, 1H), 7.85 (d, J=2.8 Hz, 1H), 7.69 (d, J=2.4 Hz, 1H), 7.65 (d, J=2.4 Hz, 1H), 3.96 (s, 3H), 2.79-2.73 (m, 2H), 2.60-2.53 (m, 2H), 2.43-2.31 (m, 1H), 2.12-2.03 (m, 1H); LCMS (Method B) $t_R$=1.10 min; m/z=532.2, 534.2 [M+H]$^+$; Purity (AUC) ≥95%.

Example SN-5: 3-((5-bromo-4-fluoro-2-methoxyphenyl)sulfonamido)-5-(1-cyanocyclobutyl)-2-hydroxy-N-methylbenzamide

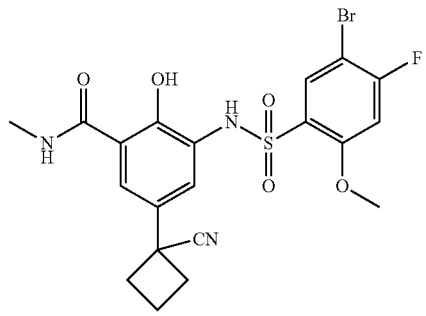 [SMILES: CNC(=O)c1cc(C2(C#N)CCC2)cc(NS(=O)(=O)c2cc(Br)c(F)cc2OC)c1O]

Step A: 5-bromo-4-fluoro-2-methoxybenzenesulfonyl chloride. Using a procedure analogous to General Procedure A, starting with 1-bromo-2-fluoro-4-methoxybenzene (500 mg, 2.15 mmol), 5-bromo-4-fluoro-2-methoxybenzenesulfonyl chloride was obtained as a white solid (681 mg, 2.44 mmol, 92%). $^1$H NMR (400 MHz, CDCl$_3$) $\delta_H$ 8.17 (d, J=7.2 Hz, 1H), 6.91 (d, J=9.6 Hz, 1H), 4.05 (s, 3H).

Step B: Phenyl-3-((5-bromo-4-fluoro-2-methoxyphenyl)sulfonamido)-5-(1-cyanocyclobutyl)-2-hydroxybenzoate. Using a procedure analogous to General Procedure E, starting with phenyl-3-amino-5-(1-cyanocyclobutyl)-2-hydroxybenzoate (25 mg, 0.08 mmol) and 5-bromo-4-fluoro-2-methoxybenzenesulfonyl chloride (37 mg, 0.12 mmol), phenyl-3-((5-bromo-4-fluoro-2-methoxyphenyl)sulfonamido)-5-(1-cyanocyclobutyl)-2-hydroxybenzoate was obtained, after purification by preparative HPLC, as a pale orange solid (39 mg, 0.07 mmol, 84%). $^1$H NMR (400 MHz, CDCl$_3$) $\delta_H$ 10.93 (s, 1H), 8.06 (d, J=7.2 Hz, 1H), 7.84 (dd, J=19.2 Hz, 2.4 Hz, 2H), 7.69 (s, 1H), 7.47-7.43 (m, 2H), 7.33 (t, J=7.6 Hz, 1H), 7.17 (d, J=7.6 Hz, 2H), 6.76 (d, J=9.6 Hz, 1H), 2.88-2.81 (m, 2H), 2.60-2.53 (m, 2H), 2.50-2.38 (m, 1H), 2.15-2.05 (m, 1H); LCMS (Method B) $t_R$=1.28 min; m/z=592.3, 594.3 [M+H]$^+$; Purity (AUC) ≥95%.

Step C: 3-((5-bromo-4-fluoro-2-methoxyphenyl)sulfonamido)-5-(1-cyanocyclobutyl)-2-hydroxy-N-methylbenzamide. Using a procedure analogous to General Procedure G, starting with phenyl-3-((5-bromo-4-fluoro-2-methoxyphenyl)sulfonamido)-5-(1-cyanocyclobutyl)-2-hydroxybenzoate (39 mg, 0.07 mmol) and methylamine, the title compound was obtained as a white solid (19 mg, 0.04 mmol, 55%). $^1$H NMR (400 MHz, CDCl$_3$) $\delta_H$ 8.01 (d, J=7.2 Hz, 1H), 7.75 (s, 1H), 7.72 (d, J=2.0 Hz, 1H), 7.13 (d, J=2 Hz, 1H), 6.73 (d, J=10 Hz, 1H), 6.62 (d, J=4.4 Hz, 1H), 3.95 (s, 3H), 2.98 (d, J=4.8 Hz, 3H), 2.81-2.74 (m, 2H), 2.56-2.37 (m, 3H), 2.15-2.07 (m, 1H); $^{19}$F NMR (376 MHz, CDCl$_3$) $\delta_F$ −94.5; LCMS (Method B) $t_R$=1.09 min; m/z=512.3, 514.4 [M+H]$^+$; Purity (AUC) ≥95%.

Example SN-6: 3-((6-bromoquinoline)-8-sulfonamido)-5-(1-cyanocyclobutyl)-2-hydroxybenzoic acid

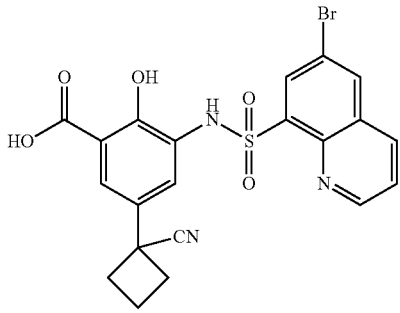 [SMILES: N#CC1(c2cc(NS(=O)(=O)c3cc(Br)cc4cccnc34)c(O)c(C(=O)O)c2)CCC1]

Step A: Phenyl-3-((6-bromoquinoline)-8-sulfonamido)-5-(1-cyanocyclobutyl)-2-hydroxybenzoate. Using a procedure analogous to General Procedure E, starting with phenyl 3-amino-5-(1-cyanocyclobutyl)-2-hydroxybenzoate (60 mg, 0.19 mmol) and 6-bromoquinoline-8-sulfonyl chloride (89 mg, 0.29 mmol), phenyl 3-((6-bromoquinoline)-8-sulfonamido)-5-(1-cyanocyclobutyl)-2-hydroxybenzoate was obtained, after purification by ISCO flash chromatography (12 g, 0-30% EtOAc in hexanes), as a white solid (71 mg, 0.12 mmol, 63%). $^1$H NMR (400 MHz, CDCl$_3$) $\delta_H$ 10.37 (s, 1H), 8.96 (dd, J=4.0, 1.2 Hz, 1H), 8.86 (s, 1H), 8.30 (d, J=2.0 Hz, 1H), 8.03-7.99 (m, 2H), 7.86 (d, J=2.4 Hz, 1H), 7.62 (d, J=2.4 Hz, 1H), 7.44-7.41 (m, 1H), 7.28-7.24 (m, 2H), 7.16-7.12 (m, 1H), 6.95 (d, J=7.6 Hz, 2H), 2.74-2.67 (m, 2H), 2.50-2.43 (m, 2H), 2.36-2.24 (m, 1H), 2.02-1.92 (m, 1H); LCMS (Method B) $t_R$=1.24 min; m/z=578.3, 580.3 [M+H]$^+$; Purity (AUC) >60%.

Step B: 3-((6-bromoquinoline)-8-sulfonamido)-5-(1-cyanocyclobutyl)-2-hydroxybenzoic acid. Using a procedure analogous to General Procedure F, starting with phenyl-3-((6-bromoquinoline)-8-sulfonamido)-5-(1-cyanocyclobutyl)-2-hydroxybenzoate (71 mg, 0.12 mmol), the title compound was obtained as a white solid (40 mg, 0.08 mmol, 65%). $^1$H NMR (400 MHz, CD$_3$OD) $\delta_H$ 9.06 (dd, J=4.4, 2 Hz, 1H), 8.40-8.39 (m, 2H), 8.34 (dd, J=8.4, 1.6 Hz, 1H), 7.79 (d, J=2.4 Hz, 1H), 7.67-7.64 (m, 1H), 7.56 (d, J=2.4 Hz, 1H), 2.77-2.71 (m, 2H), 2.57-2.49 (m, 2H), 2.42-2.30 (m, 1H), 2.10-2.01 (m, 1H); LCMS (Method B) $t_R$=1.04 min; m/z=502.3, 504.2 [M+H]$^+$; Purity (AUC) ≥95%.

Example SN-9: 3-((5-bromo-2,3-dihydrobenzofuran)-7-sulfonamido)-5-(1-cyanocyclobutyl)-2-hydroxy-N-methylbenzamide

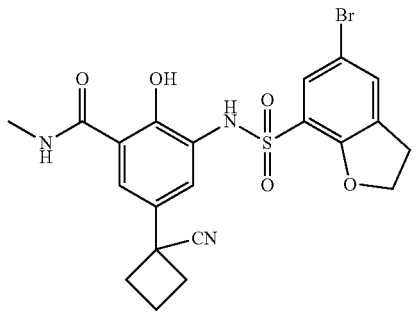 [SMILES: CNC(=O)c1cc(C2(C#N)CCC2)cc(NS(=O)(=O)c2cc(Br)cc3c2OCC3)c1O]

Step A: Phenyl-3-((5-bromo-2,3-dihydrobenzofuran)-7-sulfonamido)-5-(1-cyanocyclobutyl)-2-hydroxybenzoate. Using a procedure analogous to General Procedure E, starting with phenyl-3-amino-5-(1-cyanocyclobutyl)-2-hydroxybenzoate (60 mg, 0.19 mmol) and 5-bromo-2,3-dihydrobenzofuran-7-sulfonyl chloride (87 mg, 0.29 mmol), phenyl-3-((5-bromo-2,3-dihydrobenzofuran)-7-sulfonamido)-5-(1-cyanocyclobutyl)-2-hydroxybenzoate was obtained, after purification by ISCO flash chromatography (12 g, 0-35% EtOAc in hexanes), as a white solid (58 mg, 0.10 mmol, 52%). $^1$H NMR (400 MHz, CDCl$_3$) $\delta_H$ 10.87 (s, 1H), 7.85 (d, J=2.4 Hz, 1H), 7.80 (d, J=2.4 Hz, 1H), 7.68 (s, 1H), 7.61 (s, 1H), 7.47-7.43 (m, 3H), 7.34-7.30 (m, 1H), 7.17 (d, J=7.6 Hz, 2H), 4.75 (t, J=8.8 Hz, 2H), 3.22 (t, J=8.8 Hz, 2H), 2.87-2.81 (m, 2H), 2.61-2.54 (m, 2H), 2.50-2.38 (m, 1H), 2.15-2.06 (m, 1H); LCMS (Method B) $t_R$=1.22 min; m/z=586.3, 588.3 [M+H]$^+$; Purity (AUC) >50%.

Step B: 3-((5-bromo-2,3-dihydrobenzofuran)-7-sulfonamido)-5-(1-cyanocyclobutyl)-2-hydroxy-N-methylbenzamide. Using a procedure analogous to General Procedure G, starting with phenyl-3-((5-bromo-2,3-dihydrobenzofuran)-7-sulfonamido)-5-(1-cyanocyclobutyl)-2-hydroxybenzoate (25 mg, 0.04 mmol) and methylamine, the title compound was obtained as a white solid (20 mg, 0.04 mmol, 90%). $^1$H NMR (400 MHz, CDCl$_3$) $\delta_H$ 7.71-7.58 (m, 3H), 7.39 (d, J=2.0 Hz, 1H), 7.13 (d, J=2.0 Hz, 1H), 6.66 (d, J=4.4 Hz, 1H), 4.75 (t, J=8.8 Hz, 2H), 3.21 (t, J=8.8 Hz, 2H), 2.97 (d, J=4.8 Hz, 3H), 2.81-2.75 (m, 2H), 2.57-2.49 (m, 2H), 2.46-2.37 (m, 1H), 2.16-2.10 (m, 1H); LCMS (Method B) $t_R$=1.07 min; m/z=506.3, 508.2 [M+H]$^+$; Purity (AUC) ≥95%.

Example SN-10: 3-((5-bromo-2,3-dihydrobenzofuran)-7-sulfonamido)-5-(1-cyanocyclobutyl)-2-hydroxybenzoic acid

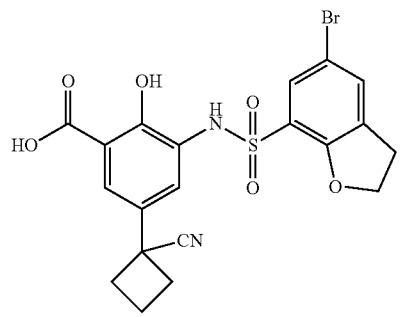 [SMILES: N#CC1(c2cc(NS(=O)(=O)c3cc(Br)cc4c3OCC4)c(O)c(C(=O)O)c2)CCC1]

Using a procedure analogous to General Procedure F, starting with phenyl-3-((5-bromo-2,3-dihydrobenzofuran)-7-sulfonamido)-5-(1-cyanocyclobutyl)-2-hydroxybenzoate (58 mg, 0.10 mmol), the title compound was obtained as a white solid (30 mg, 0.06 mmol, 60%). $^1$H NMR (400 MHz, CD$_3$OD) $\delta_H$ 7.65 (dd, J=8.8, 2.4 Hz, 2H), 7.59 (d, J=2.0 Hz, 1H), 7.51 (d, J=1.6 Hz, 1H), 4.64 (t, J=8.8 Hz, 2H), 3.21 (t, J=8.8 Hz, 2H), 2.79-2.72 (m, 2H), 2.58-2.51 (m, 2H), 2.43-2.31 (m, 1H), 2.12-2.03 (m, 1H); LCMS (Method B) $t_R$=1.02 min; m/z=510.3, 512.3 [M+H]$^+$; Purity (AUC) >95%.

Example S63: 3-((5-Bromo-3-chloro-2-hydroxyphenyl)sulfonamido)-2-hydroxy-N-methyl-5-(pentafluoro-λ⁶-sulfaneyl)benzamide

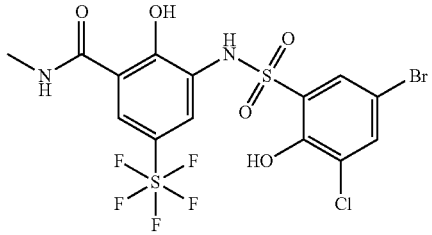 [SMILES: CNC(=O)c1cc(S(F)(F)(F)(F)F)cc(NS(=O)(=O)c2cc(Br)cc(Cl)c2O)c1O]

Step A: Phenyl 2-hydroxy-5-(pentafluoro-λ⁶-sulfaneyl)benzoate. Using a procedure analogous to General Procedure O, starting with phenyl-2-methoxy-5-(pentafluoro-λ⁶-sulfaneyl)benzoate (2.80 g, 7.90 mmol, limiting reagent), phenyl 2-hydroxy-5-(pentafluoro-λ6-sulfaneyl)benzoate was obtained (1.805 g, 5.30 mmol, 67% yield). $^1$H NMR (400 MHz, Chloroform-d) δ 10.88 (s, 1H), 8.50 (d, J=2.8 Hz, 1H), 7.92 (dd, J=9.2, 2.8 Hz, 1H), 7.53-7.45 (m, 2H), 7.40-7.31 (m, 1H), 7.29-7.20 (m, 3H), 7.11 (d, J=9.4 Hz, 1H). $^{19}$F NMR (376 MHz, Chloroform-d) δ 85.37, 84.98 (d, J=6.4 Hz), 84.57 (d, J=3.1 Hz), 84.18 (d, J=5.9 Hz), 83.77, 64.10, 64.09-64.03 (m), 63.70, 63.66 (d, J=5.1 Hz). LCMS (Method B) $t_R$=1.288 min, m/z=341.2 [M+H]⁺, ≥95% pure by H-NMR.

Step B: 2-Hydroxy-5-(pentafluoro-λ⁶-sulfaneyl)benzoic acid. Using a procedure analogous to General Procedure F, starting with phenyl-2-hydroxy-5-(pentafluoro-λ⁶-sulfaneyl)benzoate (1.81 g, 5.32 mmol, limiting reagent), 2-hydroxy-5-(pentafluoro-λ⁶-sulfaneyl)benzoic acid was obtained (1.15 g, 4.35 mmol, 82% yield). $^1$H NMR (400 MHz, Methanol-d₄) δ 8.27 (d, J=2.9 Hz, 1H), 7.91 (dd, J=9.2, 2.9 Hz, 1H), 7.07 (d, J=9.2 Hz, 1H). $^{19}$F NMR (376 MHz, Methanol-d₄) δ 84.46, 84.07 (d, J=5.6 Hz), 83.68 (d, J=5.8 Hz), 83.29 (d, J=5.6 Hz), 82.89, 62.55, 62.16. LCMS (Method B) $t_R$=0.944 min, ≥95% pure by H-NMR.

Step C: 2-Hydroxy-3nitro-5-(pentafluoro-λ⁶-sulfaneyl)benzoic acid. Using a procedure analogous to General Procedure F, starting with 2-hydroxy-5-(pentafluoro-λ⁶-sulfaneyl)benzoic acid (300 mg) 2-hydroxy-3-nitro-5-(pentafluoro-λ⁶-sulfaneyl)benzoic acid was obtained (159 mg, 0.514 mmol, 45% yield). $^{13}$C NMR (101 MHz, Methanol-d₄) δ 171.32, 158.79, 143.72, 138.99, 133.54, 129.73, 117.45. $^1$H NMR (400 MHz, Methanol-d₄) δ 8.60 (d, J=2.8 Hz, 4H), 8.53 (d, J=2.9 Hz, 4H). $^{19}$F NMR (376 MHz, Methanol-d₄) δ 81.67, 81.27, 80.88 (d, J=6.1 Hz), 80.87, 80.47, 80.08, 62.56, 62.52, 62.17. LCMS (Method B) $t_R$=0.807 min, ≥95% (AUC).

Step D: Methyl 2-hydroxy-3nitro-5-(pentafluoro-λ⁶-sulfaneyl)benzoate. To a mixture containing 2-hydroxy-3-nitro-5-(pentafluoro-λ⁶-sulfaneyl)benzoic acid (60 mg, 0.19 mmol, 1 eq) in MeOH ([1.3 M]), two drops of H₂SO₄ were added. The reaction mixture was heated at reflux and stirred overnight. Then, the reaction mixture was allowed to cool to rt and concentrated under reduced pressure. DCM was added to the residue and mixture was washed with water. The organic phase was dried over a phase separator and the solvent removed under reduced pressure to afford methyl 2-hydroxy-3-nitro-5-(pentafluoro-λ6-sulfaneyl)benzoate (60 mg, 0.19 mmol, 96% yield) which was used with no further purification. $^1$H NMR (400 MHz, Chloroform-d) δ 8.55 (d, J=2.9 Hz, 1H), 8.51 (d, J=2.8 Hz, 1H), 4.09 (s, 3H). LCMS (Method B) $t_R$=1.093 min, ≥95% (AUC).

Step E: Methyl 3-amino-2-hydroxy-5-(pentafluoro-λ⁶-sulfaneyl)benzoate. Using a procedure analogous to General Procedure C, starting with methyl 2-hydroxy-3nitro-5-(pentafluoro-λ⁶-sulfaneyl)benzoate (223 mg, 0.690 mmol, limiting reagent), which was prepared by a procedure analogous to the procedure Example S63, Step D, methyl 3-amino-2-hydroxy-5-(pentafluoro-λ⁶-sulfaneyl)benzoate was obtained (170 mg, 0.580 mmol, 84% yield). $^1$H NMR (400 MHz, Chloroform-d) δ 8.40 (d, J=2.4 Hz, 1H), 8.32 (d, J=2.5 Hz, 1H), 3.33 (d, J=1.6 Hz, 3H), 2.88 (dddd, J=12.6, 6.8, 3.9, 1.4 Hz, 2H), 2.69-2.56 (m, 2H), 2.56-2.42 (m, 1H), 2.12 (dtd, J=11.6, 8.8, 4.4 Hz, 1H). $^{19}$F NMR (376 MHz, Chloroform-d) δ 86.07 (d, J=5.5 Hz), 85.67 (d, J=6.5 Hz), 85.27 (d, J=5.7 Hz), 84.87, 63.91, 63.87, 63.51, 63.47. LCMS (Method B) $t_R$=1.056 min, m/z=294.2, 295.1 [M+H]⁺, ≥94% pure by H-NMR Step F: Methyl 3-((5-bromo-3-chloro-2-hydroxyphenyl)sulfonamido)-2-hydroxy-5-(pentafluoro-λ⁶-sulfaneyl)benzoate. Using a procedure analogous to General Procedure E, starting with methyl 3-amino-2-hydroxy-5-(pentafluoro-λ⁶-sulfaneyl)benzoate (50 mg, 0.17 mmol) and 5-bromo-3-chloro-2-hydroxy-benzenesulfonyl chloride, which was prepared by a procedure analogous to the procedure used to prepare Example S7 Step A, methyl 3-((5-bromo-3-chloro-2-hydroxyphenyl)sulfonamido)-2-hydroxy-5-(pentafluoro-6-sulfaneyl)benzoate was obtained after ISCO flash chromatography (21 mg) as a mixture that also contains residual impurities. $^1$H NMR (400 MHz, Chloroform-d) δ 8.72-8.67 (m, 1H), 8.11 (d, J=2.6 Hz, 1H), 8.02 (d, J=2.6 Hz, 1H), 7.74 (d, J=2.4 Hz, 1H), 7.63 (d, J=2.4 Hz, 1H), 3.99 (s, 3H). $^{19}$F NMR (376 MHz, Chloroform-d) δ 83.92 (d, J=6.6 Hz), 83.51, 83.12 (d, J=6.9 Hz), 63.90, 63.50. LC-MS: $t_R$=1.191 min, m/z=562.1 [M+H]⁺.

Step G: 3-((5-Bromo-3-chloro-2-hydroxyphenyl)sulfonamido)-2-hydroxy-N-methyl-5-(pentafluoro-λ⁶-sulfaneyl)benzamide. Using a procedure analogous to General Procedure H, starting with the mixture containing methyl 3-amino-2-hydroxy-5-(pentafluoro-λ⁶-sulfaneyl)benzoate (18 mg) and methanamine (0.53 mmol the title compound was obtained (3 mg, 0.005 mmol). 1H NMR (400 MHz, Chloroform-d) δ 8.04 (d, J=2.4 Hz, 1H), 7.72 (d, J=2.4 Hz, 1H), 7.64 (d, J=2.3 Hz, 1H), 7.53 (d, J=2.6 Hz, 2H), 6.42 (s, 1H), 3.04 (d, J=4.9 Hz, 3H). $^{19}$F NMR (376 MHz, Chloroform-d) δ 84.77, 84.37 (d, J=5.9 Hz), 83.96, 83.56, 64.28, 63.88. LCMS (Method B) $t_R$=1.159 min, m/z=561.1, 563.1 [M+H]⁺, ≥95% (AUC).

Example S64: 3-((5-Bromo-3-chloro-2-hydroxyphenyl)sulfonamido)-2-hydroxy-5-(pentafluoro-λ⁶-sulfaneyl)benzoic acid

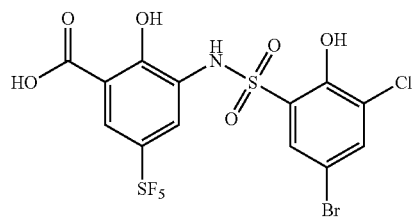

Using a procedure analogous to General Procedure F, starting with a mixture containing methyl 3-amino-2-hydroxy-5-(pentafluoro-λ⁶-sulfaneyl)benzoate (20 mg), which was prepared by a procedure analogous to the procedure used to prepare Example S63 Step F, the title compound was obtained (8 mg, 0.015 mmol). ¹H NMR (400 MHz, Acetone-d₆) δ 8.12 (d, J=2.7 Hz, 1H), 8.09 (d, J=2.8 Hz, 1H), 7.86 (d, J=2.4 Hz, 1H), 7.81 (d, J=2.4 Hz, 1H). ¹⁹F NMR (376 MHz, Methanol-d₄) δ 83.73, 83.34 (d, J=5.6 Hz), 82.94, 82.55 (d, J=5.9 Hz), 82.15, 62.41, 62.01. LCMS (Method B) t$_R$=1.111 min, m/z=548.1, 550.1 [M+H]⁺, ≥95% (AUC).

Example S65: 3-((5-Bromo-2-hydroxyphenyl)sulfonamido)-2-hydroxy-5-(pentafluoro-λ⁶-sulfaneyl) benzoic acid

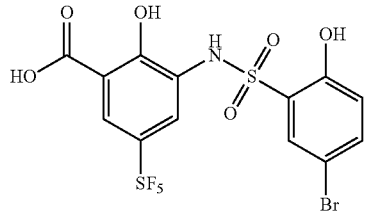

Step A: Methyl 3-((5-bromo-3-2-hydroxyphenyl)sulfonamido)-2-hydroxy-5-(pentafluoro-4'-sulfaneyl)benzoate
Using a procedure analogous to General Procedure E, starting with methyl 3-amino-2-hydroxy-5-(pentafluoro-λ⁶-sulfaneyl)benzoate (50 mg, 0.17 mmol), which was prepared by a procedure analogous to the procedure used to prepare Example S63 Step E, and 5-bromo-2-hydroxy-benzenesulfonyl chloride, which was prepared by a procedure analogous to the procedure used to prepare Example S6 Step A, the title compound was obtained after purification by flash chromatography (54 mg), as a mixture that also contains impurities. ¹H NMR (400 MHz, Chloroform-d) δ 8.06 (d, J=2.7 Hz, 1H), 8.03 (d, J=2.8 Hz, 1H), 7.70 (d, J=2.5 Hz, 1H), 7.48 (dd, J=8.8, 2.5 Hz, 1H), 6.86 (d, J=8.8 Hz, 1H), 3.99 (s, 3H). ¹⁹F NMR (376 MHz, Chloroform-d) 83.84 (d, J=6.4 Hz), 83.43, 83.04 (d, J=6.8 Hz), 82.63, 63.90, 63.49. LC-MS: t$_R$=1.243 min.

Step B: Methyl 3-((5-bromo-2-hydroxyphenyl)sulfonamido)-2-hydroxy-5-(pentafluoro-λ⁶-sulfaneyl)benzoate
Using a procedure analogous to General Procedure E, starting with a mixture containing impure methyl 3-amino-2-hydroxy-5-(pentafluoro-λ⁶-sulfaneyl)benzoate (27 mg) and methanamine (0.53 mmol), the title compound was obtained (6 mg, 0.012 mmol). ¹H NMR (400 MHz, Methanol-d₄) δ 8.02 (d, J=2.7 Hz, 1H), 7.97 (d, J=2.7 Hz, 1H), 7.81 (d, J=2.5 Hz, 1H), 7.52 (dd, J=8.8, 2.5 Hz, 1H), 6.85 (d, J=8.8 Hz, 1H). ¹⁹F NMR (376 MHz, Methanol-d₄) δ 83.44 (d, J=5.7 Hz), 83.04, 82.65 (d, J=6.0 Hz), 82.26, 62.37, 61.97. LCMS (Method B) t$_R$=1.065 min, m/z=537.3 [M+Na]⁺, ≥95% (AUC).

Example S66: 3-((5-Bromo-2-hydroxyphenyl)sulfonamido)-2-hydroxy-N-methyl-5-(pentafluoro-λ⁶-sulfaneyl)benzamide

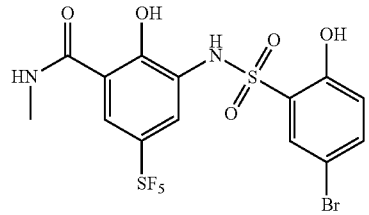

Using a procedure analogous to General Procedure H, starting with a mixture containing impure methyl 3-amino-2-hydroxy-5-(pentafluoro-λ⁶-sulfaneyl)benzoate (28 mg), which was prepared by a procedure analogous to the procedure used to prepare Example S65 Step A, and methanamine (0.53 mmol), the title compound was obtained (7 mg, 0.013 mmol). ¹H NMR (400 MHz, Chloroform-d) 8.34 (s, 1H), 8.05 (s, 2H), 7.68 (d, J=2.4 Hz, 1H), 7.50 (dd, J=8.9, 2.4 Hz, 1H), 7.28 (s, 1H), 6.87 (d, J=8.8 Hz, 1H), 4.00 (s, 3H). ¹⁹F NMR (376 MHz, Chloroform-d) δ 84.12, 83.72 (d, J=6.0 Hz), 83.31, 82.92 (d, J=6.3 Hz), 82.51, 63.90, 63.50. LCMS (Method B) t$_R$=1.176 min, m/z=n/a, ≥95% (AUC).

Example S67: 3-((6-Bromoquinoline)-8-sulfonamido)-2-hydroxy-N-methyl-5-pentafluoro-λ⁶-sulfaneyl)benzamide

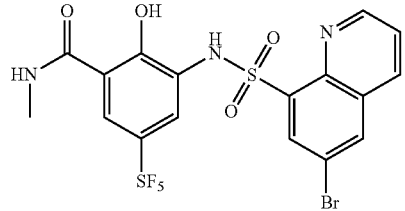

Step A: Methyl 3-((5-bromo-3-2-hydroxyphenyl)sulfonamido)-2-hydroxy-5-(pentafluoro-λ⁶-sulfaneyl)benzoate.
Using a procedure analogous to General Procedure E, starting with methyl 3-amino-2-hydroxy-5-(pentafluoro-λ⁶-sulfaneyl)benzoate (35 mg, 0.12 mmol), which was prepared by a procedure analogous to the procedure used to prepare Example S63 Step E, and 6-bromoquinoline-8-sulfonyl chloride, methyl 3-((5-bromo-3-2-hydroxyphenyl)sulfonamido)-2-hydroxy-5-(pentafluoro-λ6-sulfaneyl)benzoate was obtained after purification by flash chromatography (28 mg), as a mixture that also contains an impurity. LCMS: t$_R$=1.229 min, m/z=563.2 [M+H]⁺.

Step B: 3-((6-Bromoquinoline)-8-sulfonamido)-2-hydroxy-N-methyl-5-pentafluoro-λ⁶-sulfaneyl)benzamide.
Using a procedure analogous to General Procedure H, starting with a mixture containing impure methyl 3-amino-2-hydroxy-5-(pentafluoro-λ⁶-sulfaneyl)benzoate (14 mg) and methanamine (0.25 mmol), the tide compound was obtained (9 mg, 0.016 mmol). ¹H NMR (400 MHz, Chloroform-d) δ 9.11 (dd, J=4.4, 1.7 Hz, 1H), 8.43 (d, J=2.2 Hz, 1H), 8.22 (d, J=2.4 Hz, 1H), 8.20-8.12 (m, 2H), 7.58 (dd, J=8.4, 4.3 Hz, 1H), 7.41 (d, J=2.5 Hz, 1H), 6.41-6.36 (m, 1H), 2.94 (d, J=4.8 Hz, 3H). ¹⁹F NMR (376 MHz, Chloroform-d) δ 84.98 (d, J=5.8 Hz), 84.57, 84.18 (d, J=6.3 Hz), 64.28, 63.88. LCMS (Method B) $t_R$=1.193 min, m/z=562.2, 563.2 [M+H]$^+$, ≥95% (AUC).

Example S68: 3-((6-Bromoquinoline)-8-sulfonamido)-2-hydroxy-5-pentafluoro-λ$^6$-sulfaneyl)benzoic acid

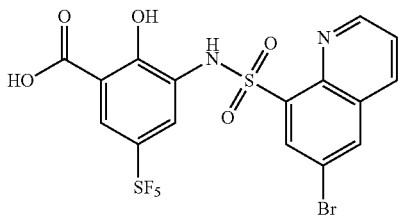

Using a procedure analogous to General Procedure F, starting with a mixture containing impure methyl 3-amino-2-hydroxy-5-(pentafluoro-λ$^6$-sulfaneyl)benzoate (14 mg), which was prepared by a procedure analogous to the procedure used to prepare Example S67 Step A, the title compound was obtained (8 mg, 0.015 mmol). $^1$H NMR (400 MHz, Methanol-$d_4$) δ 9.04 (dd, J=4.3, 1.7 Hz, 1H), 8.45-8.39 (m, 2H), 8.37 (dd, J=8.5, 1.7 Hz, 1H), 8.15 (d, J=2.8 Hz, 1H), 7.92 (d, J=2.7 Hz, 1H), 7.67 (dd, J=8.4, 4.3 Hz, 1H). $^{19}$F NMR (376 MHz, Methanol-$d_4$) δ 83.41, 83.01, 82.62, 62.36, 61.97. LCMS (Method B) $t_R$=1.133 min, m/z=549.1, 551.2 [M+H]$^+$, ≥95% (AUC).

Example S69: 3-((5-Bromo-3-chloro-2-hydroxyphenyl)sulfonamido)-5-chloro-N-methylbenzamide

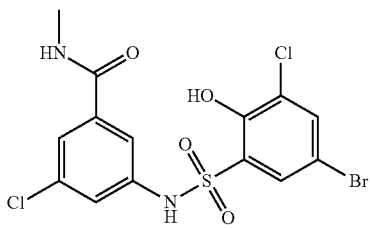 [SMILES: CNC(=O)c1cc(Cl)cc(NS(=O)(=O)c2cc(Br)cc(Cl)c2O)c1]

Step A: Methyl 3-((5-bromo-3-chloro-2-hydroxyphenyl)sulfonamido)-5-chlorobenzoate Using a procedure analogous to General Procedure E, starting with methyl 3-amino-5-chlorobenzoate with 5-bromo-3-chloro-2-hydroxy-benzenesulfonyl chloride (50 mg, 0.27 mmol, limiting reagent), which was prepared by a procedure analogous to the procedure used to prepare Example S7 Step A, methyl 3-((5-bromo-3-chloro-2-hydroxyphenyl)sulfonamido)-5-chlorobenzoate was obtained after flash chromatography (64 mg) as a mixture that also contains an impurity. LCMS (Method B) $t_R$=1.103 min, m/z=471.1 [M+NH$_4$]$^+$, ≥60% pure by H-NMR.

Step B: 3-((5-Bromo-3-chloro-2-hydroxyphenyl)sulfonamido)-5-chloro-N-methylbenzamide. Using a procedure analogous to General Procedure H, starting with a mixture containing impure methyl 3-((5-bromo-3-chloro-2-hydroxyphenyl)sulfonamido)-5-chlorobenzoate (64 mg) and methanamine (0.14 mmol), the title compound was obtained (15 mg, 0.033 mmol, 12% yield). $^1$H NMR (400 MHz, Chloroform-d) δ 8.62 (s, 1H), 7.70 (d, J=2.4 Hz, 1H), 7.64-7.54 (m, 2H), 7.52 (t, J=1.9 Hz, 1H), 7.40 (t, J=1.7 Hz, 1H), 6.32 (d, J=5.1 Hz, 1H), 3.06 (d, J=4.8 Hz, 3H). LCMS (Method B) $t_R$=0.984 min, m/z=453.1 [M+H]$^+$, ≥95% (AUC).

Example S70: 3-((5-Bromo-2-hydroxyphenyl)sulfonamido)-5-chloro-N-methylbenzamide

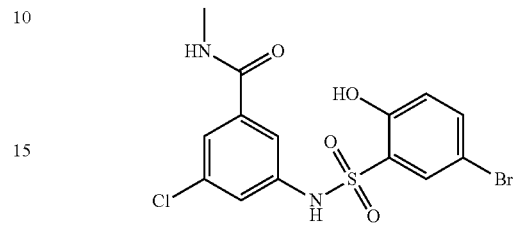

Step A: Methyl 3-((5-bromo-3-2-hydroxyphenyl)sulfonamido)-5-chlorobenzoate. Using a procedure analogous to General Procedure E, starting with methyl 3-amino-5-chlorobenzoate with 5-bromo-2-hydroxy-benzenesulfonyl chloride (50 mg, 0.27 mmol, limiting reagent), which was prepared by a procedure analogous to the procedure used to prepare Example S6 Step A, methyl 3-((5-bromo-3-2-hydroxyphenyl)sulfonamido)-5-chlorobenzoate was obtained after flash chromatography (86 mg) as a mixture that also contains impurities. LCMS (Method B) $t_R$=1.052 min, m/z=552.2 [M+CH$_3$OH+H]$^+$, ≥38% (AUC).

Step B: 3-((5-Bromo-2-hydroxyphenyl)sulfonamido)-5-chloro-N-methylbenzamide. Using a procedure analogous to General Procedure E, starting with a mixture containing impure methyl 3-((5-bromo-2-hydroxyphenyl)sulfonamido)-5-chlorobenzoate (86 mg) and methanamine (0.20 mmol), the title compound was obtained (18 mg, 0.043 mmol, 16% yield). $^1$H NMR (400 MHz, Methanol-$d_4$) δ 7.83 (d, J=2.6 Hz, 1H), 7.53 (t, J=1.8 Hz, 1H), 7.49 (dd, J=8.7, 2.5 Hz, 1H), 7.44 (t, J=1.7 Hz, 1H), 7.34 (t, J=2.0 Hz, 1H), 6.84 (d, J=8.8 Hz, 1H), 3.31 (t, J=1.7 Hz, 2H). LCMS (Method B) $t_R$=0.907 min, m/z=419.2 [M+H]$^+$, ≥95% (AUC).

Example S71: 3-((5-Bromo-3-chloro-2-hydroxyphenyl)sulfonamido)-5-(1-cyanocyclobutyl)benzoic acid

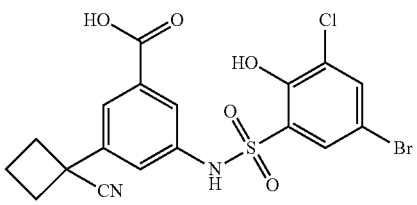 [SMILES: N#CC1(c2cc(NS(=O)(=O)c3cc(Br)cc(Cl)c3O)cc(C(=O)O)c2)CCC1]

Step A: Methyl 3-((5-bromo-3-chloro-2-hydroxyphenyl)sulfonamido)-5-(1-cyanocyclobutyl)benzoate Using a procedure analogous to General Procedure E, starting with methyl 3-amino-5-(1-cyanocyclobutyl)benzoate (50 mg, 0.22 mmol, limiting reagent) and 5-bromo-3-chloro-2-hydroxy-benzenesulfonyl chloride, which was prepared by a procedure analogous to the procedure used to prepare Example S7 Step A, methyl 3-((5-bromo-3-chloro-2-hydroxyphenyl)sulfonamido)-5-(1-cyanocyclobutyl)benzoate was obtained after flash chromatography (45 mg, 0.081 mmol, 37% yield) as a mixture that also contains impurities.

LCMS (Method B) $t_R$=1.082 min, m/z=516.3, 517.3 [M+NH$_4$]$^+$, ≥90% pure by $^1$H-NMR.

Step B: 3-((5-Bromo-3-chloro-2-hydroxyphenyl)sulfonamido)-5-(1-cyanocyclobutyl)benzoic acid. Using a procedure analogous to General Procedure F, starting with a mixture containing impure methyl 3-((5-bromo-3-chloro-2-hydroxyphenyl)sulfonamido)-5-(1-cyanocyclobutyl)benzoate (45 mg), the title compound was obtained (15 mg, 0.031 mmol, 38% yield). $^1$H NMR (400 MHz, Methanol-d$_4$) δ 7.83 (d, J=2.5 Hz, 1H), 7.79-7.74 (m, 2H), 7.72 (d, J=2.4 Hz, 1H), 7.46 (t, J=2.0 Hz, 1H), 2.83-2.71 (m, 2H), 2.63-2.50 (m, 2H), 2.47-2.33 (m, 1H), 2.15-2.01 (m, 1H). LCMS (Method B) $t_R$=0.994 min, m/z=502.2 [M+NH$_4$]$^+$, ≥95% (AUC).

Example S1: 5-Bromo-2-hydroxy-N-(3-(methylsulfonyl)phenyl)-3-(trifluoromethoxy)benzenesulfonamide

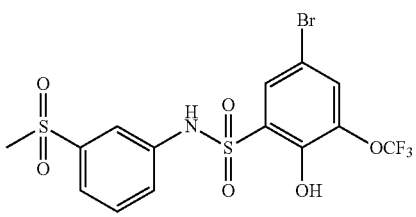 [SMILES: CS(=O)(=O)c1cccc(NS(=O)(=O)c2cc(Br)cc(OC(F)(F)F)c2O)c1]

Step A: 3-(Methylsulfonyl)aniline. Using a procedure analogous to General Procedure A, starting with 3-iodoaniline (300 mg, 1.37 mmol), 3-(methylsulfonyl)aniline was obtained, after purification by preparative HPLC, as a green oil (102.9 mg, 0.60 mmol, 44%). $^1$H NMR (400 MHz, Methanol-d$_4$) δ$_H$ 7.30 (t, J=7.9 Hz, 1H), 7.21 (d, J=2.2 Hz, 1H), 7.20-7.13 (m, 1H), 7.00-6.93 (m, 1H), 5.48 (s, 1H), 3.06 (s, 3H); LCMS (Method A) $t_R$=0.157 min, m/z=172.1 [M+H]$^+$; (AUC) ≥95%.

Step B: 5-Bromo-2-hydroxy-N-(3-(methylsulfonyl)phenyl)-3-(trifluoromethoxy)benzenesulfonamide. Using a procedure analogous to General Procedure E, starting with 3-(methylsulfonyl)aniline (14 mg, 0.08 mmol, limiting reagent) and 5-bromo-2-hydroxy-3-(trifluoromethoxy)benzenesulfonyl chloride, which was prepared by a procedure analogous to the procedure used to prepare Example S3 Step B, 5-bromo-2-hydroxy-N-(3-(methylsulfonyl)phenyl)-3-(trifluoromethoxy)benzenesulfonamide, was obtained, after purification by preparative HPLC, as a colorless solid (20 mg, 0.041 mmol, 50%). $^1$H NMR (400 MHz, Chloroform-d) δ$_H$ 7.91 (s, 1H), 7.75 (d, J=2.3 Hz, 1H), 7.73 (dt, J=6.7, 2.0, 1.6 Hz, 1H), 7.65 (s, 1H), 7.55-7.51 (m, 3H), 3.07 (s, 3H); 19F NMR (376 MHz, Chloroform-d) δ$_F$ −61.43 (s, 3F), −79.69 (s, TFA); LCMS (Method A): $t_R$=1.652 min, m/z=506.7, 508.7 [M+NH$_4$]$^+$; ≥95% (AUC).

Example S3: 5-Bromo-N-(3-bromo-5-(methylsulfonyl)phenyl)-2-hydroxy-3-(trifluoromethoxy)benzenesulfonamide

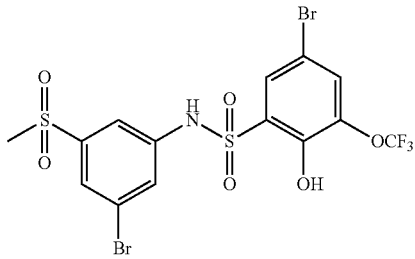 [SMILES: CS(=O)(=O)c1cc(Br)cc(NS(=O)(=O)c2cc(Br)cc(OC(F)(F)F)c2O)c1]

Step A: 3-Bromo-5-(methylsulfonyl)aniline. Using a procedure analogous to General Procedure S, except that the reaction was heated at 60° C., starting with 3-bromo-5-iodoaniline (400 mg, 1.34 mmol), 3-bromo-5-(methylsulfonyl)aniline was obtained, after purification by ISCO flash chromatography, as a mixture, along with 3-iodo-5-(methylsulfonyl)aniline (142 mg, 0.568 mmol, 42% desired product). LCMS (Method B) $t_R$=0.629 min, m/z=250.0, 252.0 [M+H]$^+$.

Step B: 5-Bromo-2-hydroxy-3-(trifluoromethoxy)benzenesulfonyl chloride. Using a procedure analogous to General Procedure A, starting with 4-bromo-2-(trifluoromethoxy)phenol (200 mg, 0.78 mmol), 5-bromo-2-hydroxy-3-(trifluoromethoxy)benzenesulfonyl chloride was obtained. The crude material was used without further purification. LCMS (Method A) $t_R$=1.754 min; (AUC) >51%.

Step C: 5-Bromo-N-(3-bromo-5-(methylsulfonyl)phenyl)-2-hydroxy-3-(trifluoromethoxy)benzenesulfonamide. Using a procedure analogous to General Procedure E, starting with 3-bromo-5-(methylsulfonyl)aniline (27 mg, 0.11 mmol, limiting reagent) and 5-bromo-2-hydroxy-3-(trifluoromethoxy)benzenesulfonyl chloride, which was prepared by a procedure analogous to the procedure used to prepare Example S3 Step B, the title compound was obtained, after purification by preparative HPLC (4.2 mg, 0.0074 mmol, 7%). $^1$H NMR (400 MHz, Chloroform-d) δ$_H$ 7.87 (t, J=1.5 Hz, 1H), 7.78 (d, J=2.3 Hz, 1H), 7.64 (t, J=1.82 Hz, 1H), 7.58-7.56 (m, 2H), 3.04 (s, 1H); $^{19}$F NMR (376 MHz, Chloroform-d) δ$_F$ −58.25 LCMS (Method A): $t_R$=LC-MS: $t_R$=1.749 min, m/z=584.5, 586.5 [M+NH$_4$]$^+$; ≥86% (AUC).

Example S4: 5-Bromo-N-(3-chloro-5-(methylsulfonyl)phenyl)-2-hydroxy-3-(trifluoromethoxy)benzenesulfonamide

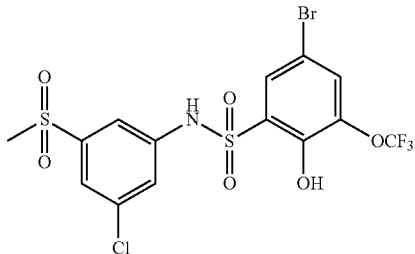 [SMILES: CS(=O)(=O)c1cc(Cl)cc(NS(=O)(=O)c2cc(Br)cc(OC(F)(F)F)c2O)c1]

Step A: 3-Chloro-5-(methylsulfonyl)aniline. Using a procedure analogous to General Procedure S, starting with 1-chloro-3-iodo-5-nitrobenzene (400 mg, 1.41 mmol), 1-chloro-3-(methylsulfonyl)-5-nitrobenzene was obtained. The crude material was carried forward without further purification. Using a procedure analogous to General Procedure C, starting from the crude 1-chloro-3-(methylsulfonyl)-5-nitrobenzene, 3-chloro-5-(methylsulfonyl)aniline was obtained, after purification by ISCO flash chromatography, as a yellow solid (108.4 mg, 0.53 mmol, 55% yield). $^1$H NMR (400 MHz, Chloroform-d) $\delta_H$ 7.23 (s, 1H), 7.08 (s, 1H), 6.86 (s, 1H), 4.11 (s, 2H), 3.04 (s, 3H). LCMS (Method A) $t_R$=0.210 min, m/z=247.9 [M+ACN+H]$^+$; ≥95% (AUC).

Step B: 5-Bromo-N-(3-chloro-5-(methylsulfonyl)phenyl)-2-hydroxy-3-(trifluoromethoxy)benzenesulfonamide. Using a procedure analogous to General Procedure E, starting with 3-chloro-5-(methylsulfonyl)aniline (24 mg, 0.12 mmol, limiting reagent) and 5-bromo-2-hydroxy-3-(trifluoromethoxy)benzenesulfonyl chloride, which was prepared by a procedure analogous to the procedure used to prepare Example S3 Step B, the title compound was obtained, after purification by preparative HPLC (11.9 mg, 0.023 mmol, 20%). $^1$H NMR (400 MHz, Chloroform-d) $\delta_H$ 7.90 (s, 1H), 7.78 (d, J=2.3 Hz, 1H), 7.72 (t, J=1.5 Hz, 1H), 7.58 (t, J=1.1 Hz, 1H), 7.52 (t, J=1.5 Hz, 1H), 7.50 (t, J=1.6 Hz, 1H), 7.28 (s, 1H), 3.04 (s, 1H); $^{19}$F NMR (376 MHz, Chloroform-d) $\delta_F$ −61.31; LCMS (Method B): $t_R$=1.126 min, m/z=542.8 [M+NH$_4$]$^+$; ≥95% (AUC).

Example S5: 5-Bromo-N-(3-chloro-5-(methylsulfonyl)phenyl)-3-ethyl-2-hydroxybenzenesulfonamide

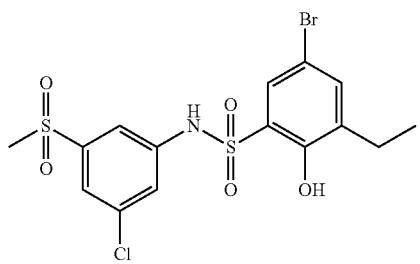 [SMILES: CCc1cc(Br)cc(S(=O)(=O)Nc2cc(Cl)cc(S(C)(=O)=O)c2)c1O]

Step A: 5-Bromo-3-ethyl-2-hydroxybenzenesulfonyl chloride. Using a procedure analogous to General Procedure A, starting with 4-bromo-2-ethylphenol (200 mg, 0.78 mmol), 5-bromo-3-ethyl-2-hydroxybenzenesulfonyl chloride was obtained as a crude material that was used without further purification. LCMS (Method A) $t_R$=1.848 min, ≥55% (AUC).

Step B: 5-Bromo-N-(3-chloro-5-(methylsulfonyl)phenyl)-3-ethyl-2-hydroxybenzenesulfonamide. Using a procedure analogous to General Procedure E, starting with 3-chloro-5-(methylsulfonyl)aniline (25 mg, 0.12 mmol, limiting reagent), which was prepared by a procedure analogous to the procedure use to prepare Example S4 Step A, and 5-bromo-3-ethyl-2-hydroxybenzenesulfonyl chloride, the title compound was obtained, after purification by preparative HPLC (30.6 mg, 0.12 mmol, 54%). $^1$H NMR (400 MHz, Methanol-d$_4$) $\delta_H$ 7.67 (d, J=2.5, 1H), 7.62 (t, J=1.7 Hz, 1H), 7.61 (t, J=1.7 Hz, 1H), 7.48 (d, 2.45 Hz, 1H), 7.44 (t, 1.9 Hz, 1H), 4.88 (s, H2O) 3.07 (s, 3H), 2.62 (q, J=7.5 Hz, 2H), 1.14 (t, J=7.5, 3H); $^{19}$F NMR (376 MHz, Methanol-d$_4$) $\delta_F$ −79.69 (s, TFA); LCMS (Method A): $t_R$=1.652 min, m/z=467.7, 471.7 [M+H]$^+$; ≥95% (AUC).

Example S6: 5-Bromo-N-(3-chloro-5-(methylsulfonyl)phenyl)-2-hydroxybenzenesulfonamide

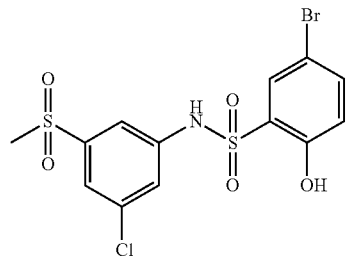 [SMILES: CS(=O)(=O)c1cc(Cl)cc(NS(=O)(=O)c2cc(Br)ccc2O)c1]

Step A: 5-Bromo-2-hydroxybenzenesulfonyl chloride. Using a procedure analogous to General Procedure A, starting with 4-bromophenol (1.73 g, 10 mmol), 5-bromo-2-hydroxybenzenesulfonyl chloride was obtained as a pale brown oily solid (1.50 g, 5.53 mmol, 55%). 1H NMR (400 MHz, Chloroform-d) $\delta_H$ 7.95 (d, J=2.4 Hz, 1H), 7.71 (dd, J=8.9, 2.4 Hz, 1H), 7.04 (d, J=8.9 Hz, 1H); LCMS (Method A) $t_R$=1.39 min; Purity (AUC) >90%.

Step B: 5-Bromo-N-(3-chloro-5-(methylsulfonyl)phenyl)-3-ethyl-2-hydroxybenzenesulfonamide. Using a procedure analogous to General Procedure E, starting with 5-bromo-2-hydroxybenzenesulfonyl chloride and 3-chloro-5-(methylsulfonyl)aniline (20 mg, 0.10 mmol, limiting reagent), which was prepared by a procedure analogous to Example S4 Step A, the title compound was obtained after purification by preparative HPLC (20.4 mg, 0.046 mmol, 48%). $^1$H NMR (400 MHz, Methanol-d$_4$) $\delta_H$ 7.88 (d, J=2.5, 1H), 7.65 (t, J=1.7 Hz, 1H), 7.58 (t, J=1.7 Hz, 1H), 7.52 (dd, 8.8, 2.6 Hz, 1H), 7.47 (t, 1.9 Hz, 1H), 6.85 (d, J=8.8 Hz, 1H), 4.84 (s, H2O) 3.06 (s, 3H); $^{19}$F NMR (376 MHz, Methanol-d$_4$) $\delta_F$ −80.12 (s, TFA); LCMS (Method A): $t_R$=1.626 min, m/z=458.7 [M+NH4]+; ≥95% (AUC).

Example S8: 5-Bromo-3-chloro-N-(3-chloro-5-(methylsulfonyl)phenyl)-2-hydroxybenzenesulfonamide

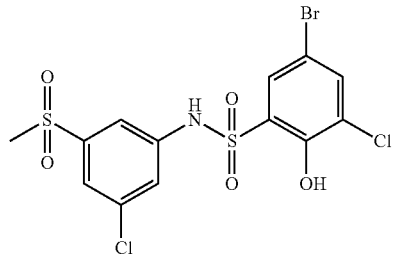 [SMILES: CS(=O)(=O)c1cc(Cl)cc(NS(=O)(=O)c2cc(Br)cc(Cl)c2O)c1]

Using a procedure analogous to General Procedure E, starting with 3-chloro-5-(methylsulfonyl)aniline (50 mg, 0.24 mmol, limiting reagent), which was prepared by a procedure analogous to the procedure used to prepare Example S4 Step A, and 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (37.6 mg, 0.085 mmol, 35%). $^1$H NMR (400 MHz, Chloroform-d) $\delta_H$ 7.79 (t, J=1.8

Hz, 1H), 7.70 (d, J=2.2 Hz, 2H), 7.52 (d, J=1.9 Hz, 2H), 3.05 (s, 3H); LCMS (Method B): $t_R$=1.072 min, m/z=492.8 [M+NH$_4$]$^+$; ≥95% (AUC).

Example S9: 5-Bromo-N-(3-cyclopropyl-5-(methylsulfonyl)phenyl)-2-hydroxybenzenesulfonamide

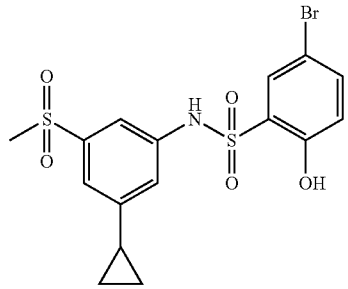 [SMILES: CS(=O)(=O)c1cc(NS(=O)(=O)c2cc(Br)ccc2O)cc(C2CC2)c1]

Step A: 3-Cyclopropyl-5-(methylsulfonyl)aniline. Using a procedure analogous to General Procedure M, starting with 3-bromo-5-(methylsulfonyl)aniline (149 mg, 0.60 mmol, limiting reagent), which was prepared by a procedure analogous to the procedure used to prepare Example S3 Step A, 3-cyclopropyl-5-(methylsulfonyl)aniline was obtained (101.1 mg, 0.48 mmol, 80%). $^1$H NMR (400 MHz, Chloroform-d) δ 6.97 (d, J=2.0 Hz, 2H), 6.58 (d, J=1.9 Hz, 1H), 3.93 (d, J=7.3 Hz, 2H), 3.00 (d, J=1.2 Hz, 3H), 1.86 (ddd, J=8.3, 5.3, 3.2 Hz, 1H), 1.03-0.94 (m, 2H), 0.70 (dt, J=4.6, 2.2 Hz, 2H); LCMS (Method B): $t_R$=0.421 min, m/z=212.2 [M+H]$^+$; ≥89% (AUC).

Step B: 5-Bromo-N-(3-cyclopropyl-5-(methylsulfonyl)phenyl)-2-hydroxybenzenesulfonamide. Using a procedure analogous to General Procedure E, starting with 3-cyclopropyl-5-(methylsulfonyl)aniline (50 mg, 0.24 mmol, limiting reagent) and 5-bromo-2-hydroxybenzenesulfonyl chloride, which was prepared by a procedure analogous to the procedure used to prepare Example S6 Step A, the title compound was obtained, after purification by preparative HPLC, as a white solid (56.6 mg, 0.71 mmol, 54%). $^1$H NMR (400 MHz, Chloroform-d) $δ_H$ 7.65 (d, J=2.7 Hz, 1H), 7.51 (dd, J=8.8, 2.5 Hz, 1H), 7.47-7.42 (m, 1H), 7.33-7.23 (m, 4H), 7.17 (s, 1H), 7.14-7.09 (m, 1H), 6.88 (d, J=8.7 Hz, 1H), 3.00 (s, 3H), 1.93 (dq, J=8.7, 5.0, 4.1 Hz, 1H), 1.08 (ddd, J=9.8, 7.0, 5.1 Hz, 2H), 0.77-0.68 (m, 2H); LCMS (Method B): $t_R$=1.036 min, m/z=462.9, 464.9 [M+NH$_4$]$^+$; ≥95% (AUC).

Example S10: 5-Bromo-3-chloro-N-(3-cyclopropyl-5-(methylsulfonyl)phenyl)-2-hydroxybenzenesulfonamide

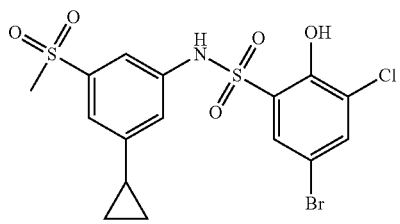 [SMILES: CS(=O)(=O)c1cc(NS(=O)(=O)c2cc(Br)cc(Cl)c2O)cc(C2CC2)c1]

Using a procedure analogous to General Procedure E, starting with 3-cyclopropyl-5-(methylsulfonyl)aniline (23 mg, 0.11 mmol, limiting reagent), which was prepared by a procedure analogous to the procedure used to prepare Example S9 Step A, and 5-bromo-2-hydroxybenzenesulfonyl chloride 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (22.5 mg, 0.047 mmol, 44%). $^1$H NMR (400 MHz, Chloroform-d) δ 7.71 (d, J=2.4 Hz, 1H), 7.66 (d, J=2.4 Hz, 1H), 7.42 (d, J=1.7 Hz, 1H), 7.39-7.32 (m, 2H), 7.15 (t, J=1.9 Hz, 1H), 3.01 (s, 3H), 1.93 (td, J=8.4, 4.2 Hz, 1H), 1.12-1.06 (m, 2H), 0.73 (dt, J=6.7, 4.9 Hz, 2H); LCMS (Method B): $t_R$=1.119 min, m/z=479.8 [M+NH$_4$]$^+$; ≥95% (AUC).

Example S11: 5-Bromo-2-hydroxy-N-(3-(methylsulfonyl)-5-(trifluoromethoxy)phenyl)benzenesulfonamide

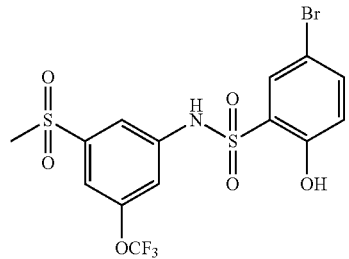 [SMILES: CS(=O)(=O)c1cc(NS(=O)(=O)c2cc(Br)ccc2O)cc(OC(F)(F)F)c1]

Step A: Methyl 3-(methylsulfonyl)-5-(trifluoromethoxy)benzoate. Using a procedure analogous to General Procedure S, starting with methyl 3-bromo-5-(trifluoromethoxy)benzoate (600 mg, 2.01 mmol), methyl 3-(methylsulfonyl)-5-(trifluoromethoxy)benzoate was obtained as a white solid (270.1 mg, 0.91 mmol, 45% yield). $^1$H NMR (400 MHz, Chloroform-d) $δ_H$ 8.50 (t, J=1.5 Hz, 1H), 8.12 (dt, J=2.4, 1.2 Hz, 1H), 7.99-7.93 (m, 1H), 5.28 (s, 1H), 3.97 (s, 3H), 3.10 (s, 3H). LCMS (Method B): $t_R$=0.977 min; ≥95% (AUC).

Step B: 3-(Methylsulfonyl)-5-(trifluoromethoxy)benzoic acid. Using a procedure analogous to General Procedure F, starting with methyl 3-(methylsulfonyl)-5-(trifluoromethoxy)benzoate (64 mg, 0.21 mmol, limiting reagent), 3-(methylsulfonyl)-5-(trifluoromethoxy)benzoic acid was obtained as a white solid (57.7 mg, 0.20 mmol, 97%). $^1$H NMR (400 MHz, Chloroform-d) $δ_H$ 8.60 (d, J=1.6 Hz, 1H), 8.24-8.18 (m, 1H), 8.05 (s, 1H), 3.15 (s, 3H). $^{19}$F NMR (376 MHz, Chloroform-d) $δ_F$ −57.98. LCMS (Method B): $t_R$=0.824 min; ≥95% (AUC).

Step C: 3-(Methylsulfonyl)-5-(trifluoromethoxy)aniline. Using a procedure analogous to General Procedure X, starting with 3-(methylsulfonyl)-5-(trifluoromethoxy)benzoic acid (55 mg, 0.19 mmol, limiting reagent), 3-(methylsulfonyl)-5-(trifluoromethoxy)aniline was obtained as a white solid (18.2 mg, 0.071 mmol, 37%). $^1$H NMR (400 MHz, Chloroform-d) $δ_H$ 7.11 (dt, J=15.6, 1.5 Hz, 2H), 6.71 (td, J=2.2, 1.1 Hz, 1H), 4.22 (s, 1H), 3.05 (s, 3H). $^{19}$F NMR (376 MHz, Chloroform-d) $δ_F$ −60.82; LCMS (Method B): $t_R$=0.807 min, m/z=256.1 [M+H]$^+$; ≥95% (AUC).

Step D: 5-bromo-2-hydroxy-N-(3-(methylsulfonyl)-5-(trifluoromethoxy)phenyl)benzenesulfonamide. Using a procedure analogous to General Procedure E, starting with 3-(methylsulfonyl)-5-(trifluoromethoxy)aniline (18 mg, 0.07 mmol, limiting reagent) and 5-bromo-2-hydroxybenzenesulfonyl chloride, which was prepared by a procedure analogous to the procedure used to prepare Example S6 Step A, the title compound was obtained, after purification by preparative HPLC, as a white solid (21 mg, 0.04 mmol, 57%). $^1$H NMR (400 MHz, Chloroform-d) $\delta_H$ 8.35 (s, 1H), 7.86 (s, 1H), 7.75 (d, J=2.4 Hz, 1H), 7.52 (dd, J=12.2, 2.3 Hz, 3H), 7.43 (s, 1H), 6.89 (d, J=8.8 Hz, 1H), 3.09 (s, 3H); $^{19}$F NMR (376 MHz, Chloroform-d) $\delta_F$ −61.02; LC-MS: $t_R$=1.084 min, m/z=506.8, 508.8 [M+NH$_4$]$^+$; 95% (AUC).

Example S12: 5-Bromo-3-chloro-2-hydroxy-N-(3-(methylsulfonyl)-5-(trifluoromethoxy)phenyl)benzenesulfonamide

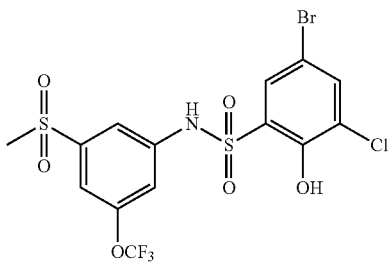 [SMILES: CS(=O)(=O)c1cc(NS(=O)(=O)c2cc(Br)cc(Cl)c2O)cc(OC(F)(F)F)c1]

Using a procedure analogous to General Procedure E, starting with 3-(methylsulfonyl)-5-(trifluoromethoxy)aniline (20 mg, 0.07 mmol, limiting reagent), which was prepared by a procedure analogous to the procedure used to prepare Example S13 Steps A-C, and 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (15.3 mg, 0.027 mmol, 40%). $^1$H NMR (400 MHz, Chloroform-d) $\delta_H$ 7.80 (d, J=2.3 Hz, 1H), 7.70 (d, J=2.4 Hz, 1H), 7.55 (d, J=2.2 Hz, 2H), 7.42 (s, 1H), 3.07 (s, 3H); $^{19}$F NMR (376 MHz, Chloroform-d) $\delta_F$ −57.96; LC-MS: $t_R$=1.166 min, m/z=542.8 [M+NH$_4$]$^+$; 95% (AUC).

Example S13: 5-Bromo-2-hydroxy-N-(3-(methylsulfonyl)-5-(pentafluoro-λ$^6$-sulfaneyl)phenyl)benzenesulfonamide

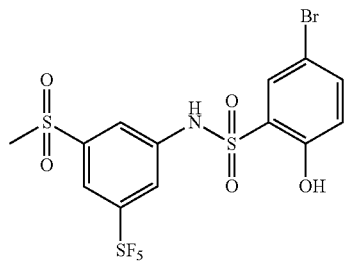

Step A: Methyl 3-(methylsulfonyl)-5-(pentafluoro-λ$^6$-sulfaneyl)benzoate. Using a procedure analogous to General Procedure S, starting with methyl 3-bromo-5-(pentafluoro-λ$^6$-sulfaneyl)benzoate (600 mg, 1.91 mmol), methyl 3-(methylsulfonyl)-5-(pentafluoro-λ$^6$-sulfaneyl)benzoate was obtained as a white solid (164.1 mg, 0.48 mmol, 25% yield). $^1$H NMR (400 MHz, Chloroform-d) $\delta_H$ 8.74 (d, J=1.6 Hz, 1H), 8.68 (t, J=1.7 Hz, 1H), 8.50 (t, J=1.8 Hz, 1H), 4.02 (s, 3H), 3.15 (s, 3H); $^{19}$F NMR (376 MHz, Chloroform-d) $\delta$ 80.84 (d, J=6.8 Hz), 80.44 (d, J=6.9 Hz), 80.04 (d, J=7.0 Hz), 79.63, 63.21, 63.14 (d, J=19.6 Hz), 62.81, 62.74 (d, J=19.5 Hz). LC-MS: $t_R$=0.978 min, m/z=341 [M+H]$^+$; ≥95% (AUC).

Step B: 3-(methylsulfonyl)-5-(pentafluoro-λ$^6$-sulfaneyl)benzoic acid. Using a procedure analogous to General Procedure F, starting with methyl 3-(methylsulfonyl)-5-(pentafluoro-λ$^6$-sulfaneyl)benzoate (162 mg, 0.54 mmol, limiting reagent), 3-(methylsulfonyl)-5-(pentafluoro-λ$^6$-sulfaneyl)benzoic acid was obtained as a white solid (117.7 mg, 0.36 mmol, 67%). $^1$H NMR (400 MHz, Chloroform-d) 8.79 (s, 1H), 8.73 (s, 1H), 8.56 (d, J=1.9 Hz, 1H), 7.26 (s, 4H), 3.17 (d, J=0.8 Hz, 3H); $^{19}$F NMR (376 MHz, Chloroform-d) $\delta_F$ 80.64, 80.24, 79.84, 63.23, 62.83; LCMS (Method B): $t_R$=0.766 min; ≥95% (AUC).

Step C: 3-(Methylsulfonyl)-5-(pentafluoro-λ$^6$-sulfaneyl) aniline. Using a procedure analogous to General Procedure X, starting with 3-(methylsulfonyl)-5-(pentafluoro-λ$^6$-sulfaneyl)benzoic acid (117 mg, 0.36 mmol, limiting reagent), 3-(methylsulfonyl)-5-(pentafluoro-λ$^6$-sulfaneyl)aniline was obtained as a white solid (51.2 mg, 0.17 eq, 48%). 1H NMR (400 MHz, Chloroform-d) $\delta_H$ 7.11 (dt, J=15.6, 1.5 Hz, 2H), 6.71 (td, J=2.2, 1.1 Hz, 1H), 4.22 (s, 1H), 3.05 (s, 3H). $^{19}$F NMR (376 MHz, Chloroform-d) $\delta_F$ −60.82; LCMS (Method B): $t_R$=1.184 min; ≥90% (AUC).

Step D: 5-Bromo-2-hydroxy-N-(3-(methylsulfonyl)-5-(pentafluoro-λ$^6$-sulfaneyl)phenyl)benzenesulfonamide. Using a procedure analogous to General Procedure E, starting with 3-(methylsulfonyl)-5-(pentafluoro-λ$^6$-sulfaneyl)aniline (20 mg, 0.07 mmol, limiting reagent) and 5-bromo-2-hydroxybenzenesulfonyl chloride, which was prepared by a procedure analogous to the procedure used to prepare Example S6 Step A, the title compound was obtained, after purification by preparative HPLC, as a white solid (8.4 mg, 0.016 mmol, 23%). $^1$H NMR (400 MHz, Chloroform-d) $\delta_H$; LC-MS: $t_R$=1.128 min, m/z=548.8 [M+NH$_4$]$^+$; ≥95% (AUC); $^{19}$F NMR (376 MHz, Chloroform-d) $\delta_F$ 80.91, 80.51, 80.11, 63.13, 62.80, 62.73, 62.40, −75.69.

Example S14: 5-Bromo-3-chloro-2-hydroxy-N-(3-(methylsulfonyl)-5-(pentafluoro-λ$^6$-sulfaneyl)phenyl)benzenesulfonamide

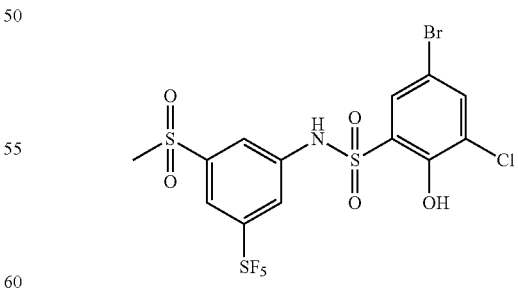

Using a procedure analogous to General Procedure E, starting with 3-(methylsulfonyl)-5-(pentafluoro-λ$^6$-sulfaneyl)aniline (20 mg, 0.07 mmol, limiting reagent), which was prepared using a procedure analogous to the procedure used to prepare Example S12 Steps A-C, and 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (7.3 mg, 0.013 mmol, 19%). $^1$H NMR (400 MHz, Chloroform-d) $\delta_H$ 8.08 (s, 1H), 7.82 (s, 1H), 7.77 (s, 1H), 7.73 (d, J=2.5 Hz, 1H), 7.65 (s, 1H), 6.90 (d, J=8.8 Hz, 1H), 3.08 (s, 3H); $^{19}$F NMR (376 MHz, Chloroform-d) $\delta_F$ −80.86, 80.46, 80.06, 63.12, 62.72, −57.94, −75.73; LC-MS: $t_R$=1.201 min, m/z=584.7 [M+NH$_4$]$^+$; ≥95% (AUC).

Example S15: 5-Bromo-N-(3-bromo-5-((tetrahydrofuran-2-yl)sulfonyl)phenyl)-3-chloro-2-hydroxybenzenesulfonamide

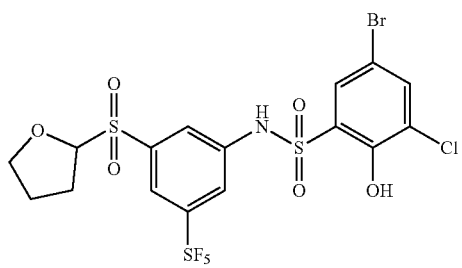

Step A: 3-Bromo-5-((tetrahydrofuran-2-yl)sulfonyl)aniline. Using a procedure analogous to General Procedure S, except that reaction temperature was set to 95° C., starting with 3-bromo-5-iodoaniline (60 mg, 0.24 mmol), 3-bromo-5-((tetrahydrofuran-2-yl)sulfonyl)aniline was obtained (27.9 mg, 0.10 mmol, 42%). $^1$H NMR (400 MHz, Chloroform-d) $\delta_H$ 7.30 (s, 1H), 7.07 (s, 1H), 7.02 (s, 1H), 4.31-4.17 (m, 2H), 3.97-3.87 (m, 3H), 3.78 (tdd, J=10.6, 7.4, 4.9 Hz, 2H), 2.43-2.30 (m, 1H), 2.23-2.10 (m, 1H); LCMS (Method B) $t_R$=0.732 min, m/z=306.1, 308.1 [M+H]$^+$.

Step B: 5-Bromo-N-(3-bromo-5-(methylsulfonyl)phenyl)-2-hydroxy-3-chlorobenzenesulfonamide. Using a procedure analogous to General Procedure E, starting with 3-bromo-5-((tetrahydrofuran-2-yl)sulfonyl)aniline (16 mg, 0.05 mmol, limiting reagent) and 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (18.2 mg, 0.032 mmol, 63%). $^1$H NMR (400 MHz, Chloroform-d) $\delta_H$ 8.02 (s, 1H), 7.80 (d, J=2.4 Hz, 1H), 7.78 (t, J=1.6 Hz, 1H), 7.75 (t, J=1.8 Hz, 1H), 7.66 (d, J=2.3 Hz, 1H), 7.60 (t, J=1.8 Hz, 1H), 4.24 (dd, J=10.5, 4.2 Hz, 1H), 3.98 (td, J=8.2, 5.3 Hz, 1H), 3.88 (dd, J=10.5, 7.7 Hz, 1H), 3.77 (dt, J=8.9, 6.9 Hz, 2H), 2.40-2.27 (m, 1H), 2.23-2.11 (m, 1H).); $^{19}$F NMR (376 MHz, Chloroform-d) $\delta_F$ −78.60; LCMS (Method B): $t_R$=1.022 min, m/z=538.2, 540.2 [M+H]$^+$; ≥84% (AUC).

Example S16: 5-Bromo-3-chloro-N-(3-cyclopropyl-5-((tetrahydrofuran-2-yl)sulfonyl)phenyl)-2-hydroxybenzenesulfonamide

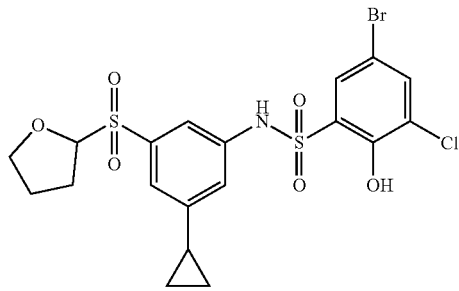 [SMILES: O=S(=O)(Nc1cc(C2CC2)cc(S(=O)(=O)C2CCCO2)c1)c1cc(Br)cc(Cl)c1O]

Step A: 3-Cyclopropyl-5-((tetrahydrofuran-2-yl)sulfonyl)aniline. Using a procedure analogous to General Procedure M, starting with 3-bromo-5-((tetrahydrofuran-2-yl)sulfonyl)aniline (60 mg, 0.20 mmol, limiting reagent), which was prepared by a procedure analogous to the procedure used to prepare Example S14 Step A, 3-cyclopropyl-5-((tetrahydrofuran-2-yl)sulfonyl)aniline was obtained (27.9 mg, 0.10 eq, 43%). LCMS (Method B): $t_R$=0.113 min, m/z=268.3 [M+NH$_4$]$^+$; ≥86% (AUC).

Step B: 5-Bromo-N-(3-bromo-5-(methylsulfonyl)phenyl)-2-hydroxy-3-chlorobenzenesulfonamide. Using a procedure analogous to General Procedure E, starting with 3-cyclopropyl-5-((tetrahydrofuran-2-yl)sulfonyl)aniline (13 mg, 0.05 mmol, limiting reagent) and 5-bromo-3-chloro-2-hydroxybenzenesulfonyl chloride, which was prepared by a procedure analogous to the procedure used to prepare Example S7 Step A, the title compound was obtained, after purification by preparative HPLC, as a white solid (17.7 mg, 0.033 mmol, 66%). $^1$H NMR (400 MHz, Chloroform-d) $\delta_H$ 7.73 (d, J=2.4 Hz, 1H), 7.66 (d, J=2.1 Hz, 1H), 7.64 (d, J=2.4 Hz, 1H), 7.37 (p, J=1.7 Hz, 2H), 7.21 (t, J=1.8 Hz, 1H), 4.18 (dd, J=10.3, 4.7 Hz, 1H), 3.94 (td, J=8.2, 5.5 Hz, 1H), 3.86 (dd, J=10.3, 7.9 Hz, 1H), 3.82-3.67 (m, 2H), 2.32 (dtd, J=14.6, 7.2, 5.4 Hz, 1H), 2.19-2.07 (m, 1H), 1.94 (tt, J=8.4, 5.0 Hz, 1H), 1.14-1.05 (m, 2H), 0.77-0.68 (m, 2H); $^{19}$F NMR (376 MHz, Chloroform-d) $\delta_F$ −78.59. LCMS (Method B): $t_R$=1.045 min, m/z=538.2, 539.2 [M+H]$^+$; ≥95% (AUC).

Example S15-2: 5-Bromo-N-(3-bromo-5-((tetrahydrofuran-2-yl)sulfonyl)phenyl)-2-hydroxybenzenesulfonamide

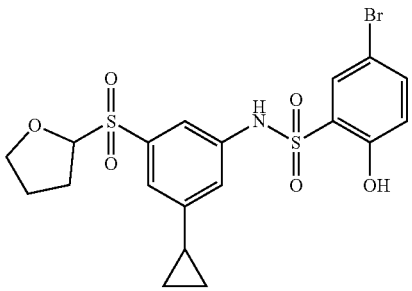 [SMILES: O=S(=O)(Nc1cc(C2CC2)cc(S(=O)(=O)C2CCCO2)c1)c1cc(Br)ccc1O]

Using a procedure analogous to General Procedure E, starting with 3-cyclopropyl-5-((tetrahydrofuran-2-yl)sulfonyl)aniline (13 mg, 0.05 mmol, limiting reagent), which was prepared by a procedure analogous to the procedure used to prepare Example S14 Step A, and 5-bromo-2-hydroxybenzenesulfonyl chloride, which was prepared by a procedure analogous to the procedure used to prepare Example S6 Step A, the title compound was obtained, after purification by preparative HPLC, as a white solid (15.2 mg, 0.030 mmol, 61%). $^1$H NMR (400 MHz, Chloroform-d) $\delta_H$ 7.72-7.65 (m, 2H), 7.48 (dd, J=8.8, 2.5 Hz, 1H), 7.38 (t, J=1.6 Hz, 1H), 7.33 (t, J=1.9 Hz, 1H), 7.17 (t, J=1.8 Hz, 1H), 6.85 (d, J=8.8 Hz, 1H), 4.11 (dd, J=10.3, 4.9 Hz, 1H), 3.97-3.67 (m, 5H), 2.35-2.23 (m, 1H), 2.12 (dddd, J=13.5, 9.4, 7.4, 5.9 Hz, 1H), 2.02 (s, 1H), 1.93 (tt, J=8.3, 5.0 Hz, 1H), 1.15-1.02 (m, 2H), 0.71 (dt, J=6.7, 4.9 Hz, 2H); $^{19}$F NMR (376 MHz, Chloroform-d) $\delta_F$ -78.62; LCMS (Method B): $t_R$=0.954 min, m/z=502.2, 504.2 [M+H]$^+$; ≥88% (AUC).

Example S16-2: 5-Bromo-3-chloro-N-(5-chloro-2-hydroxy-3-(methylsulfonyl)phenyl)-2-hydroxybenzenesulfonamide

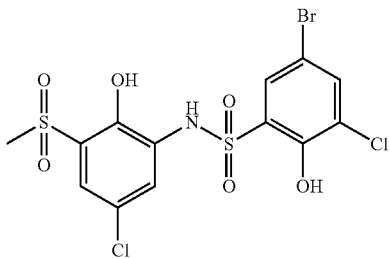

Step A: 4-Chloro-2-(methylthio)-6-nitrophenol. Using a procedure analogous to General Procedure T, starting with 2-bromo-4-chloro-6-nitrophenol (1000 mg, 3.96 mmol), 4-chloro-2-(methylthio)-6-nitrophenol was obtained (630 mg, 2.87 mmol, 72%). LCMS (Method B): $t_R$=0.098 min, m/z=221.2 [M+H]$^+$; ≥58% (AUC).

Step B: 4-Chloro-2-(methylsulfonyl)-6-nitrophenol. Using a procedure analogous to General Procedure U, starting with 4-chloro-2-(methylthio)-6-nitrophenol (1024 mg, 4.66 mmol, limiting reagent), which was prepared using a procedure analogous to the procedure used to prepare Example S16-2 Step A, 4-chloro-2-(methylsulfonyl)-6-nitrophenol was obtained as a a yellow solid (1155 mg, 4.58 eq, 98%), which was used without further purification. $^1$H NMR (400 MHz, Chloroform-d) $\delta_H$ 11.40 (s, 1H), 8.39 (d, J=2.7 Hz, 1H), 8.31 (d, J=2.7 Hz, 1H), 7.26 (s, 1H), 3.34 (s, 3H); LCMS (Method B): $t_R$=0.730 min, ≥92% (AUC).

Step C: 2-Amino-4-chloro-6-(methylsulfonyl)phenol. Using a procedure analogous to General Procedure C, starting with 4-chloro-2-(methylsulfonyl)-6-nitrophenol (68 mg, 0.20 mmol, limiting reagent, 2-amino-4-chloro-6-(methylsulfonyl)phenol was obtained (60 mg, 0.2 eq, 98%) and used without further purification. $^1$H NMR (400 MHz, Chloroform-d) $\delta_H$ 7.00 (d, J=2.3 Hz, 1H), 6.86 (d, J=2.4 Hz, 1H), 3.12 (s, 3H); LCMS (Method B): $t_R$=0.0.95 min, ≥95% (AUC).

Step D: 5-Bromo-3-chloro-N-(5-chloro-2-hydroxy-3-(methylsulfonyl)phenyl)-2-hydroxybenzenesulfonamide. Using a procedure analogous to General Procedure E, starting with amino-4-chloro-6-(methylsulfonyl)phenol (21 mg, 0.09 mmol, limiting reagent) and 5-bromo-3-chloro-2-hydroxy-benzenesulfonyl chloride, which was prepared by a procedure analogous to the procedure used to prepare Example S7 Step A, the title compound was obtained, after purification by preparative HPLC (12.2 mg, 0.024 mmol, 28%). $^1$H NMR (400 MHz, Chloroform-d) $\delta_H$ 7.76 (d, J=2.5 Hz, 1H), 7.74 (d, J=2.4 Hz, 1H), 7.69 (d, J=2.3 Hz, 1H), 7.45 (d, J=2.5 Hz, 1H), 3.11 (s, 3H); LC-MS (Method B): $t_R$=1.71 min, m/z=509.1 [M+NH$_4$]$^+$; ≥95% (AUC).

Example S17: 5-Bromo-N-(5-chloro-2-hydroxy-3-(methylsulfonyl)phenyl)-2-hydroxybenzenesulfonamide

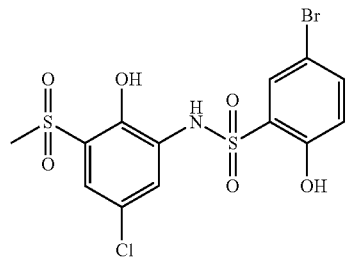 [SMILES: CS(=O)(=O)c1cc(Cl)cc(NS(=O)(=O)c2cc(Br)ccc2O)c1O]

Using a procedure analogous to General Procedure E, starting with amino-4-chloro-6-(methylsulfonyl)phenol (21 mg, 0.09 mmol, limiting reagent), which was prepared by a procedure analogous to the procedure used to prepare Example S16-2 Steps A-C, and 5-bromo-2-hydroxy-benzenesulfonyl chloride, which was prepared by a procedure analogous to the procedure used to prepare Example S6 Step A, the title compound was obtained, after purification by preparative HPLC (0.8 mg, 0.024 mmol, 26%). $^1$H NMR (400 MHz, Chloroform-d) $\delta_H$ 9.13 (s, 1H), 8.33 (s, 1H), 7.72 (d, J=2.5 Hz, 1H), 7.63 (d, J=2.4 Hz, 1H), 7.54 (dd, J=8.9, 2.4 Hz, 1H), 7.48 (d, J=2.5 Hz, 1H), 7.18 (s, 1H), 6.91 (d, J=8.9 Hz, 1H), 3.08 (s, 3H); LCMS (Method B): $t_R$=1.71 min, m/z=0.993 min, m/z=475.1 [M+NH$_4$]$^+$; ≥95% (AUC).

Example S18: 5-Bromo-3-chloro-2-hydroxy-N-(2-hydroxy-3-(methylsulfonyl)-5-(pentafluoro-$\lambda^6$-sulfaneyl)phenyl)benzenesulfonamide

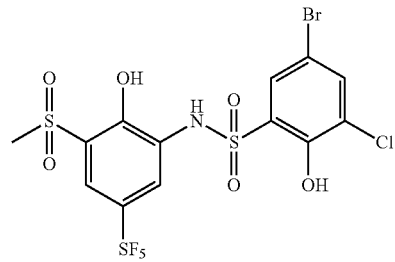

Step A: 2-Bromo-4-(pentafluoro-$\lambda^6$-sulfaneyl)phenol. To a mixture containing 4-(pentafluoro-$\lambda^6$-sulfaneyl)phenol (800 mg, 3.63 mmol, 1 eq) and acetic acid (at [0.9 M]) was added FeCl$_3$ (59 mg, 0.36 mmol, 0.10 eq). The mixture was cooled to 0° C. and then Br$_2$ (812 mg, 5.45 mmol, 1.5 eq) was added. The mixture was allowed to reach room temperature and stirred for 2 h. Then, the solvent was removed under reduced pressure and the crude material was purified by ISCO flash chromatography to afford 2-bromo-4-(pentafluoro-$\lambda^6$-sulfaneyl)phenol (439 mg, 1.5 mmol, 41%). $^1$H NMR (400 MHz, Chloroform-d) $\delta_H$ 7.90 (d, J=2.6 Hz, 1H), 7.63 (dd, J=9.0, 2.6 Hz, 1H), 7.06 (dt, J=9.0, 1.1 Hz, 1H); LC-MS (Method A): $t_R$=1.571 min; ≥74% (AUC).

Step B: 2-(methylthio)-4-(pentafluoro-$\lambda^6$-sulfaneyl)phenol. Using a procedure analogous to General Procedure T, starting with 2-bromo-4-(pentafluoro-$\lambda^6$-sulfaneyl)phenol (439 mg, 1.47 mmol, limiting reagent), 2-(methylthio)-4-(pentafluoro-$\lambda^6$-sulfaneyl)phenol was obtained (84 mg, 0.32 mmol, 32%). $^1$H NMR (400 MHz, Chloroform-d) $\delta_H$ 7.89 (d, J=2.7 Hz, 1H), 7.63 (dd, J=9.0, 2.7 Hz, 1H), 7.05-6.97 (m, 2H), 2.37 (s, 3H); LC-MS (Method A): $t_R$=0.156 min, m/z=266.0 [M+H]$^+$; ≥80% (AUC).

Step C: 2-(Methylsulfonyl)-4-(pentafluoro-$\lambda^6$-sulfaneyl)phenol. Using a procedure analogous to General Procedure U, starting with 2-(methylthio)-4-(pentafluoro-$\lambda^6$-sulfaneyl)phenol (84 mg, 0.32 mmol, limiting reagent), 2-(methylsulfonyl)-4-(pentafluoro-$\lambda^6$-sulfaneyl)phenol was obtained (44 mg, 0.25 mmol, 78%). $^1$H NMR (400 MHz, Chloroform-d) $\delta_H$ 9.25 (s, 1H), 8.11 (d, J=2.7 Hz, 1H), 7.91 (dd, J=9.2, 2.7 Hz, 1H), 7.13 (d, J=9.2 Hz, 1H), 3.18 (s, 3H); $^{19}$F NMR (376 MHz, Chloroform-d) $\delta_F$ 83.62 (d, J=6.3 Hz), 83.22 (d, J=7.0 Hz), 82.82 (d, J=6.5 Hz), 64.43 (d, J=14.0 Hz), 64.19, 64.15, 64.09-63.92 (m), 63.85, 63.79, 63.75; LC-MS (Method A): $t_R$=1.318 min, m/z=n/a; ≥86% (AUC).

Step D: 2-(Methylsulfonyl)-6-nitro-4-(pentafluoro-$\lambda^6$-sulfaneyl)phenol. Using a procedure analogous to General Procedure B, starting with 2-(methylsulfonyl)-4-(pentafluoro-$\lambda^6$-sulfaneyl)phenol (74 mg, 0.25 mmol, limiting reagent), 2-(methylsulfonyl)-6-nitro-4-(pentafluoro-$\lambda^6$-sulfaneyl)phenol was obtained (68.2 mg, 0.20 mmol, 80%). $^1$H NMR (400 MHz, Chloroform-d) $\delta_H$ 8.81 (s, 1H), 8.70 (s, 1H), 3.38 (s, 3H). $^{19}$F NMR (376 MHz, Chloroform-d) $\delta_F$ 80.81, 80.42 (d, J=7.1 Hz), 80.01 (t, J=5.6 Hz), 79.61 (d, J=7.9 Hz), 79.20, 64.17 (d, J=8.2 Hz), 64.12, 64.07, 63.97, 63.72, 63.57. LC-MS (Method B): $t_R$=0.762 min, m/z=n/a; ≥95% (AUC).

Step E: 2-Amino-6-(Methylsulfonyl)-4-(pentafluoro-$\lambda^6$-sulfaneyl)phenol. Using a procedure analogous to General Procedure C, starting with 2-(methylsulfonyl)-6-nitro-4-(pentafluoro-$\lambda^6$-sulfaneyl)phenol (235 mg. 0.68 mmol, limiting reagent), which was prepared by a procedure analogous to the procedure used to prepare Example S18 Step D, 2-amino-6-(Methylsulfonyl)-4-(pentafluoro-$\lambda^6$-sulfaneyl)phenol was obtained (214 mg, 0.68 mmol, 100%). LC-MS (Method B): $t_R$=0.118 min, m/z=314.1, 315.1 [M+H]$^+$; ≥95% (AUC).

Step F: 5-Bromo-3-chloro-2-hydroxy-N-(2-hydroxy-3-(methylsulfonyl)-5-(pentafluoro-$\lambda^6$-sulfaneyl)phenyl)benzenesulfonamide. Using a procedure analogous to General Procedure E, starting with 2-amino-6-(methylsulfonyl)-4-(pentafluoro-$\lambda^6$-sulfaneyl)phenol (21 mg, 0.09 mmol, limiting reagent) and 5-bromo-3-chloro-2-hydroxy-benzenesulfonyl chloride, which was prepared by a procedure analogous to the procedure used to prepare Example S7 Step A, the title compound was obtained after purification by preparative HPLC (32.2 mg, 0.055 mmol, 42%). $^1$H NMR (400 MHz, Chloroform-d) $\delta_H$ 8.16 (d, J=2.6 Hz, 1H), 7.85 (d, J=2.5 Hz, 1H), 7.78 (d, J=2.4 Hz, 1H), 7.71 (d, J=2.3 Hz, 1H), 3.17 (s, 3H); $^{19}$F NMR (376 MHz, Chloroform-d) $\delta_F$ 79.29 (d, J=6.9 Hz), 78.88, 78.48, 78.08, 60.92, 60.52; LC-MS (Method B): $t_R$=1.113 min; ≥95% (AUC).

Example S19: 5-Bromo-2-hydroxy-N-(2-hydroxy-3-(methylsulfonyl)-5-(pentafluoro-$\lambda^6$-sulfaneyl)phenyl)benzenesulfonamide

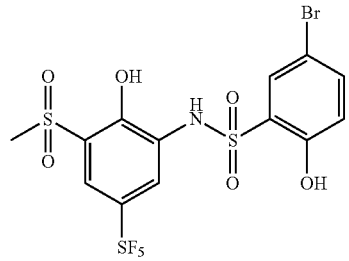

Using a procedure analogous to General Procedure E, starting with 2-amino-6-(methylsulfonyl)-4-(pentafluoro-$\lambda^6$-sulfaneyl)phenol (40 mg, 0.13 mmol, limiting reagent), which was prepared by a procedure analogous to the procedure used to prepare Example S18 Steps A-E, and 5-bromo-2-hydroxy-benzenesulfonyl chloride, which was prepared by a procedure analogous to the procedure used to prepare Example S6 Step A, the title compound was obtained, after purification by preparative HPLC (24 mg, 0.044 mmol, 34%). 1H NMR (400 MHz, Chloroform-d) $\delta_H$ 8.03 (d, J=2.8 Hz, 1H), 7.75 (d, J=2.5 Hz, 1H), 7.67 (d, J=2.8 Hz, 1H), 7.62 (dd, J=8.8, 2.5 Hz, 1H), 6.97 (d, J=8.8 Hz, 1H), 3.31 (s, 6H); $^{19}$F NMR (376 MHz, Chloroform-d) $\delta_F$ 79.46, 79.06, 78.66, 78.27, 59.55, 59.16, −80.13; LC-MS (Method B): $t_R$=1.077 min, m/z=565.2, 267.2 [M+NH$_4$]$^+$; ≥95% (AUC).

Example S20: 4-Bromo-2-hydroxy-N-(2-hydroxy-3-(methylsulfonyl)-5-(pentafluoro-$\lambda$6-sulfaneyl)phenyl)benzenesulfonamide

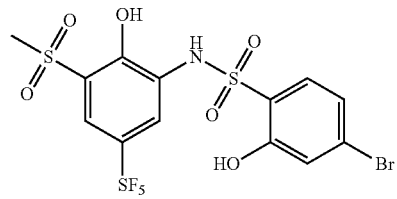

Step A: 4-Bromo-2-hydroxybenzenesulfonyl chloride. Using a procedure analogous to General Procedure A, starting with 3-bromophenol (1.1 mL, 10 mmol), 4-bromo-2-hydroxybenzenesulfonyl chloride was obtained as a crude mixture that was used without further purification. $^1$H NMR (400 MHz, Chloroform-d) $\delta$ 8.08 (d, J=8.9 Hz, 1H), 7.31 (d, J=2.5 Hz, 1H), 6.92 (dd, J=8.9, 2.5 Hz, 1H); LCMS (Method B) $t_R$=0.966 min; Purity (AUC) ≥84%.

Step B: 4-Bromo-2-hydroxy-N-(2-hydroxy-3-(methylsulfonyl)-5-(pentafluoro-$\lambda$6-sulfaneyl)phenyl)benzenesulfonamide. Using a procedure analogous to General Procedure A, starting with 2-amino-6-(methylsulfonyl)-4-(pentafluoro-$\lambda^6$-sulfaneyl)phenol (22 mg, 0.07 mmol, limiting reagent), which was prepared by a procedure analogous to the procedure used to prepare Example S18 Steps A-E, and 4-bromo-2-hydroxy-benzenesulfonyl chloride, the title compound was obtained, after purification by preparative HPLC, as a white solid (14 mg, 0.26 mmol, 36%). $^1$H NMR (400 MHz, Chloroform-d) δ 9.66 (s, 1H), 8.08 (d, J=2.5 Hz, 1H), 8.04 (dd, J=8.8, 1.2 Hz, 1H), 7.81 (s, 1H), 7.76-7.71 (m, 1H), 7.19 (dd, J=2.5, 1.2 Hz, 1H), 6.86 (ddd, J=8.7, 2.5, 1.2 Hz, 1H), 6.03 (s, 1H), 3.17 (s, 3H); LCMS (Method B) $t_R$=0.846 min, m/z=548.0, 550.1; Purity (AUC) ≥95%.

Example S21: 5-Bromo-3-Chloro-N-(5-chloro-3-(ethylsulfonyl)-2-hydroxyphenyl)-2-hydroxybenzenesulfonamide

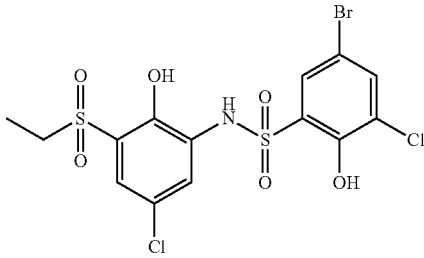 [SMILES: CCS(=O)(=O)c1cc(Cl)cc(NS(=O)(=O)c2cc(Br)cc(Cl)c2O)c1O]

Step A: 4-Chloro-2-(ethylthio)-6-nitrophenol. Using a procedure analogous to General Procedure T, starting with 2-bromo-4-chloro-6-nitrophenol (500 mg, 1.98 mmol), 4-chloro-2-(ethylthio)-6-nitrophenol was obtained as a crude material that was used without further purification (463 mg). $^1$H NMR (400 MHz, Chloroform-d) $δ_H$ 7.89 (s, 1H), 7.40 (s, 1H), 2.98 (d, J=7.5 Hz, 2H), 1.37 (t, J=7.4 Hz, 3H); LC-MS (Method A): $t_R$=1.137 min, m/z=n/a; ≥41% (AUC).

Step B: 4-Chloro-2-(ethylsulfonyl)-6-nitrophenol. Using a procedure analogous to General Procedure U, starting with 4-chloro-2-(ethylthio)-6-nitrophenol (463 mg, 1.98 mmol, limiting reagent), 4-chloro-2-(ethylsulfonyl)-6-nitrophenol was obtained (300 mg, 1.13 mmol, 57%). $^1$H NMR (400 MHz, Chloroform-d) $δ_H$ 11.35 (s, 1H), 8.38 (d, J=2.7 Hz, 1H), 8.27 (d, J=2.7 Hz, 1H), 3.49 (q, J=7.5 Hz, 2H), 1.33 (t, J=7.5 Hz, 3H); LCMS (Method B): 734 min, m/z=236.2 [M+H]$^+$.

Step C: 2-Amino-4-chloro-6-(ethylsulfonyl)-phenol. Using a procedure analogous to General Procedure C, starting with 4-chloro-2-(ethylsulfonyl)-6-nitrophenol (300 mg, 1.13 mmol, limiting reagent), 2-amino-4-chloro-6-(ethylsulfonyl)-phenol was obtained (238 mg, 1.01 mmol, 89%). $^1$H NMR (400 MHz, Chloroform-d) $δ_H$ 6.91 (d, J=3.0 Hz, 1H), 6.87-6.82 (m, 1H), 3.16 (qd, J=7.5, 2.3 Hz, 2H), 1.30 (ddd, J=7.4, 5.1, 2.3 Hz, 3H); LCMS (Method B): $t_R$=0.734 min, m/z=n/a; ≥50% (AUC).

Step D: 5-Bromo-3-chloro-N-(5-chloro-3-(ethylsulfonyl)-2-hydroxyphenyl)-2-hydroxybenzenesulfonamide. Using a procedure analogous to General Procedure E, starting with 2-amino-4-chloro-6-(ethylsulfonyl)-phenol (55 mg, 0.23 mmol, limiting reagent) and 5-bromo-3-chloro-2-hydroxy-benzenesulfonyl chloride, which was prepared by a procedure analogous to the procedure used to prepare Example S7 Step A, the title compound was obtained after purification by preparative HPLC (18 mg, 0.036 mmol, 16%). $^1$H NMR (400 MHz, Chloroform-d) $δ_H$ 7.74 (dd, J=11.1, 2.4 Hz, 2H), 7.68 (d, J=2.4 Hz, 1H), 7.41 (d, J=2.5 Hz, 1H), 3.15 (q, J=7.4 Hz, 3H), 1.24 (t, J=7.4 Hz, 3H); LC-MS (Method B): $t_R$=1.093 min, m/z=528.1 [M+Na]$^+$; 95% (AUC).

Example S22: 5-Bromo-N-(5-chloro-3-(ethylsulfonyl)-2-hydroxyphenyl)-2-hydroxybenzenesulfonamide

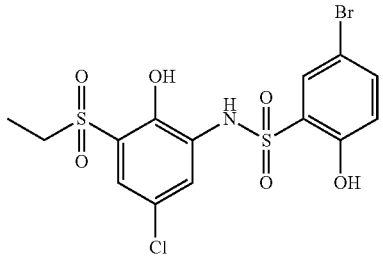 [SMILES: CCS(=O)(=O)c1cc(Cl)cc(NS(=O)(=O)c2cc(Br)ccc2O)c1O]

Using a procedure analogous to General Procedure E, starting with 2-amino-4-chloro-6-(ethylsulfonyl)-phenol (38 mg, 0.15 eq, limiting reagent), which was prepared by a procedure analogous to the procedure used to prepare Example S20 Steps A-C, and 5-bromo-2-hydroxy-benzenesulfonyl chloride, which was prepared by a procedure analogous to the procedure used to prepare Example S6 Step A, the title compound was obtained after purification by preparative HPLC (5 mg, 0.011 mmol, 7%). $^1$H NMR (400 MHz, Chloroform-d) $δ_H$ 9.27 (s, 1H), 8.34 (s, 1H), 7.73 (d, J=2.5 Hz, 1H), 7.64 (d, J=2.4 Hz, 1H), 7.52 (dd, J=8.8, 2.5 Hz, 1H), 7.42 (d, J=2.5 Hz, 1H), 7.15 (s, 1H), 6.89 (d, J=8.9 Hz, 1H), 3.12 (q, J=7.4 Hz, 2H), 1.21 (t, J=7.4 Hz, 3H); LC-MS: $t_R$ (Method B)=1.020 min, m/z=512.5 [M+ACN+H]$^+$; ≥95% (AUC).

Example S23.1: 5-Bromo-3-chloro-N-(5-chloro-2-hydroxy-3-(isopropylsulfonyl)phenyl)-2-hydroxybenzenesulfonamide

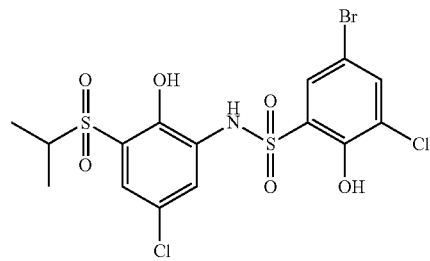 [SMILES: CC(C)S(=O)(=O)c1cc(Cl)cc(NS(=O)(=O)c2cc(Br)cc(Cl)c2O)c1O]

Step A: 4-Chloro-2-(isopropylthio)-6-nitrophenol. Using a procedure analogous to General Procedure T, starting with 2-bromo-4-chloro-6-nitrophenol (500 mg, 1.98 mmol), 4-chloro-2-(isopropylthio)-6-nitrophenol was obtained as a crude material that was used without further purification (661 mg). $^1$H NMR (400 MHz, Chloroform-d) $δ_H$ 7.95 (d, J=2.5 Hz, 1H), 7.54 (d, J=2.5 Hz, 1H), 3.57 (hept, J=6.7 Hz, 1H), 1.34 (d, J=6.7 Hz, 6H).

Step B: 4-Chloro-2-(isopropylsulfonyl)-6-nitrophenol. Using a procedure analogous to General Procedure U, starting with crude 4-chloro-2-(ethylsulfonyl)-6-nitrophenol, 4-chloro-2-(isopropylsulfonyl)-6-nitrophenol was obtained as a mixture with the corresponding sulfoxide (241 mg). $^1$H NMR (400 MHz, Chloroform-d) $δ_H$ 10.84 (s, 1H), 8.20 (d, J=2.6 Hz, 1H), 7.98 (d, J=2.7 Hz, 1H), 3.29 (p, J=6.9 Hz, 1H), 1.04 (d, J=6.8 Hz, 3H).

Step C: 2-Amino-4-chloro-6-(isopropylsulfonyl)phenol. Using a procedure analogous to General Procedure C, starting with a mixture of 4-chloro-2-(isopropylsulfonyl)-6-nitrophenol and the corresponding sulfoxide (241 mg), 2-amino-4-chloro-6-(isopropylsulfonyl)phenol was obtained as a mixture with the corresponding sulfoxide (81 mg) that was used without further purification.

Step D: 5-Bromo-3-chloro-N-(5-chloro-2-hydroxy-3-(isopropylsulfonyl)phenyl)-2-hydroxybenzenesulfonamide. Using a procedure analogous to General Procedure C, starting with a mixture of 2-amino-4-chloro-6-(isopropylsulfonyl)phenol and the corresponding sulfoxide (81 mg) and 5-bromo-3-chloro-2-hydroxy-benzenesulfonyl chloride, which was prepared by a procedure analogous to the procedure used to prepare Example S7 Step A, the title compound was obtained, after purification by preparative HPLC (7 mg, 0.013 mmol, 9%). $^1$H NMR (400 MHz, Chloroform-d) $\delta_H$ 9.41 (s, 1H), 7.77 (d, J=2.5 Hz, 1H), 7.72 (d, J=2.4 Hz, 1H), 7.67 (d, J=2.3 Hz, 1H), 7.37 (d, J=2.5 Hz, 1H), 7.36 (s, 1H), 3.20 (h, J=6.8 Hz, 1H), 1.26 (d, J=6.9 Hz, 6H); LC-MS (Method B): $t_R$=1.136 min, m/z=520.1 [M+H]$^+$; ≥89% (AUC).

Example S23.2: 5-Bromo-3-chloro-N-(5-chloro-2-hydroxy-3-(isopropylsulfinyl)phenyl)-2-hydroxybenzenesulfonamide

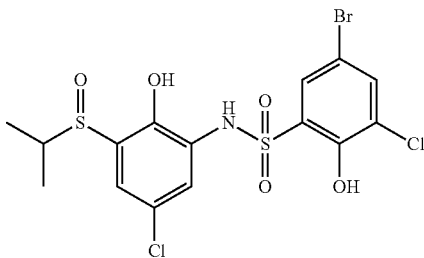 [SMILES: CC(C)S(=O)c1cc(Cl)cc(NS(=O)(=O)c2cc(Br)cc(Cl)c2O)c1O]

From the procedures in Example 23.1, Steps A-D, 5-bromo-3-chloro-N-(5-chloro-2-hydroxy-3-(isopropylsulfonyl)phenyl)-2-hydroxybenzenesulfonamide was also obtained (14 mg, 0.028 mmol, 2%). $^1$H NMR (400 MHz, Chloroform-d) $\delta_H$ 11.21 (s, 1H), 7.70 (d, J=2.4 Hz, 1H), 7.62 (dd, J=13.8, 2.4 Hz, 2H), 7.54 (s, 1H), 6.77 (d, J=2.4 Hz, 1H), 3.06 (hept, J=6.9 Hz, 1H), 1.23 (t, J=6.8 Hz, 6H). LC-MS (Method B): $t_R$=1.086 min, m/z=504.1 [M+H]$^+$; ≥95% (AUC).

Example S23.3: 5-Bromo-N-(5-chloro-2-hydroxy-3-(isopropylsulfinyl)phenyl)-2-hydroxybenzenesulfonamide

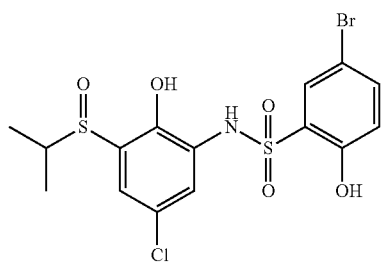 [SMILES: CC(C)S(=O)c1cc(Cl)cc(NS(=O)(=O)c2cc(Br)ccc2O)c1O]

From a procedure analogous to the procedure used to prepare Example S22.1, the title compound was obtained after purification by preparative HPLC (12 mg, 0.026 mmol, 1%). $^1$H NMR (400 MHz, Chloroform-d) $\delta_H$ 7.65 (t, J=2.7 Hz, 1H), 7.59 (d, J=2.4 Hz, 1H), 7.48 (dd, J=8.9, 2.4 Hz, 1H), 7.30 (s, 1H), 6.85 (d, J=8.8 Hz, 1H), 6.78 (d, J=2.4 Hz, 1H), 3.06 (hept, J=6.8 Hz, 1H), 1.21 (dd, J=6.9, 2.1 Hz, 6H); LC-MS (Method B): $t_R$=1.022 min, m/z=470.1 [M+H]$^+$; ≥84% (AUC).

Example S24: 5-Bromo-3-chloro-2-hydroxy-N-(2-hydroxy-3-(methylsulfinyl)-5-(trifluoromethyl)phenyl)benzenesulfonamide

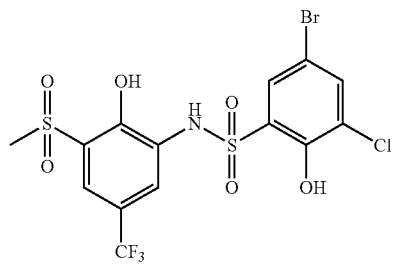 [SMILES: CS(=O)(=O)c1cc(C(F)(F)F)cc(NS(=O)(=O)c2cc(Br)cc(Cl)c2O)c1O]

Step A: 2-(methylthio)-4-(trifluoromethyl)phenol. Using a procedure analogous to General Procedure T, starting with 2-bromo-4-(trifluoromethyl)phenol (700 mg, 2.90 mmol), 2-(methylthio)-4-(trifluoromethyl)phenol was obtained as a crude mixture that was used without further purification (604 mg). LC-MS (Method A): $t_R$=1.509 min.

Step B: 2-(methylsulfonyl)-4-(trifluoromethyl)phenol. Using a procedure analogous to General Procedure U, starting with 2-(methylthio)-4-(trifluoromethyl)phenol (439 mg, 2.90 mmol, limiting reagent), 2-(methylsulfonyl)-4-(trifluoromethyl)phenol was obtained (220 mg, 0.92 mmol, 32%). $^1$H NMR (400 MHz, Chloroform-d) $\delta_H$ 7.89 (d, J=2.7 Hz, 1H), 7.63 (dd, J=9.0, 2.7 Hz, 1H), 7.05-6.97 (m, 2H), 2.37 (s, 3H). LC-MS (Method A): $t_R$=0.967 min, m/z=266.0 [M+H]$^+$; ≥80% (AUC).

Step C: 2-(Methylsulfonyl)-6-nitro-4-(trifluoromethyl)phenol. Using a procedure analogous to General Procedure B, except that the reaction mixture was heated at 50° C. and stirred overnight, starting with 2-(methylthio)-4-(trifluoromethyl)phenol (220 mg, 0.92 mmol, limiting reagent), 2-(methylsulfonyl)-6-nitro-4-(trifluoromethyl)phenol was obtained (211 mg, 0.74 mmol, 80%). 1H NMR (400 MHz, Chloroform-d) $\delta_H$ 8.71-8.66 (m, 1H), 8.59 (d, J=2.3 Hz, 1H), 3.37 (s, 3H); $^{19}$F NMR (376 MHz, Chloroform-d) $\delta_F$ −62.41; LC-MS (Method B): $t_R$=0.808 min.

Step D: 2-Amino-6-(methylsulfonyl)-4-(trifluoromethyl)phenol. Using a procedure analogous to General Procedure C, starting with 2-(methylsulfonyl)-6-nitro-4-(trifluoromethyl)phenol (211 mg, 0.74 mmol, limiting reagent), 2-amino-6-(methylsulfonyl)-4-(trifluoromethyl)phenol was obtained (171 mg. 1H NMR (400 MHz, Chloroform-d) $\delta_H$ 7.31 (dd, J=2.1, 1.0 Hz, 1H), 7.10 (d, J=2.1 Hz, 1H), 3.15 (s, 3H); $^{19}$F NMR (376 MHz, Chloroform-d) $\delta_F$ −62.37; LC-MS (Method B): $t_R$=0.748 min, m/z=256.1 [M+H]$^+$.

Step E: 5-Bromo-3-chloro-2-hydroxy-N-(2-hydroxy-3-(methylsulfonyl)-5-(trifluoromethyl)phenyl)benzenesulfonamide. Using a procedure analogous to General Procedure E, starting with 2-amino-6-(methylsulfonyl)-4-(trifluoromethyl)phenol (30 mg, 0.12 eq, limiting reagent) and 5-bromo-3-chloro-2-hydroxy-benzenesulfonyl, which was prepared by a procedure analogous to the procedure used to prepare Example S7 Step A, the title compound was obtained after purification by preparative HPLC (18 mg, 0.034 mmol, 5%). $^1$H NMR (400 MHz, Chloroform-d) $\delta_H$ 9.67 (s, 1H), 8.01 (d, J=2.1 Hz, 1H), 7.76 (d, J=2.4 Hz, 1H), 7.74 (s, 1H), 7.70 (d, J=2.3 Hz, 1H), 7.60 (s, 1H), 7.49 (s, 1H), 3.15 (s, 3H); $^{19}$F NMR (376 MHz, Chloroform-d) $\delta_F$ −65.42; LC-MS (Method B): $t_R$=1.062 min, m/z=548.1 [M+Na]+; ≥95% (AUC).

Example S25: 5-Bromo-3-2-hydroxy-N-(2-hydroxy-3-(methylsulfonyl)-5-(trifluoromethyl)phenyl)benzenesulfonamide

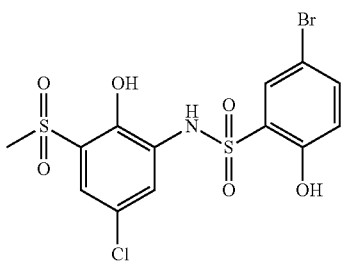 [SMILES: CS(=O)(=O)c1cc(Cl)cc(NS(=O)(=O)c2cc(Br)ccc2O)c1O]

Using a procedure analogous to General Procedure E, starting with 2-amino-6-(methylsulfonyl)-4-(trifluoromethyl)phenol (30 mg, 0.12 eq, limiting reagent), which was prepared by a procedure analogous to the procedure used to prepare Example S23 Steps A-D, and 5-bromo-2-hydroxy-benzenesulfonyl chloride, which was prepared by a procedure analogous to the procedure used to prepare Example S6 Step A, the title compound was obtained after purification by preparative HPLC (16 mg, 0.032 mmol, 4%). $^1$H NMR (400 MHz, Chloroform-d) $\delta_H$ 8.29 (s, 1H), 7.96 (s, 1H), 7.77 (s, 1H), 7.65 (d, J=2.4 Hz, 1H), 7.55 (dd, J=8.8, 2.5 Hz, 1H), 6.91 (d, J=8.9 Hz, 1H), 3.12 (s, 3H), 2.17 (s, 1H), 1.25 (s, 2H); $^{19}$F NMR (376 MHz, Chloroform-d) −65.45; LC-MS (Method A): $t_R$=1.624 min, m/z=489.7 [M+H]+; ≥95% (AUC).

Example S25-2: 5-Bromo-3-chloro-N-(5-cyclopropyl-2-hydroxy-3-(methylsulfonyl)phenyl)-2-hydroxybenzenesulfonamide

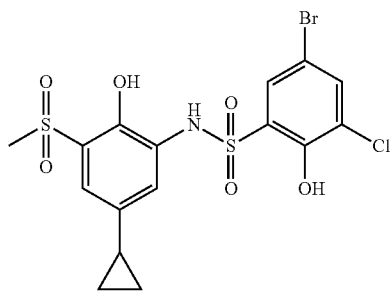 [SMILES: CS(=O)(=O)c1cc(C2CC2)cc(NS(=O)(=O)c2cc(Br)cc(Cl)c2O)c1O]

Step A: 2-(benzyloxy)-5-chloro-1-(methylsulfonyl)-3-nitrobenzene. Using a procedure analogous to General Procedure Q, starting with amino-4-chloro-6-(methylsulfonyl)phenol (150 mg, 0.60 mmol, limiting reagent), which was prepared by a procedure analogous to the procedure used to prepare Example S16 Steps A-B, 2-(benzyloxy)-5-chloro-1-(methylsulfonyl)-3-nitrobenzene was obtained after purification by preparative HPLC (57 mg, 0.17 mmol, 28%). $^1$H NMR (400 MHz, Chloroform-d) $\delta_H$ 8.27 (d, J=2.7 Hz, 1H), 8.16 (d, J=2.7 Hz, 1H), 7.63-7.53 (m, 2H), 7.49-7.36 (m, 3H), 5.24 (s, 2H), 3.22 (s, 3H); LCMS (Method B): $t_R$=1.109 min, m/z=359.3 [M+H]+.

Step B: 2-(Benzyloxy)-5-cyclopropyl-1-(methylsulfonyl)-3-nitrobenzene. Using a procedure analogous to General Procedure M, starting with 2-(benzyloxy)-5-chloro-1-(methylsulfonyl)-3-nitrobenzene (57 mg, 0.17 mmol, limiting reagent), 2-(benzyloxy)-5-cyclopropyl-1-(methylsulfonyl)-3-nitrobenzene was obtained (32 mg, 0.092 mmol, 54%). $^1$H NMR (400 MHz, Chloroform-d) $\delta_H$ 7.97 (d, J=2.4 Hz, 1H), 7.86 (d, J=2.4 Hz, 1H), 7.63-7.56 (m, 2H), 7.47-7.37 (m, 3H), 5.21 (s, 2H), 3.21 (s, 3H), 2.03 (dp, J=8.6, 5.0 Hz, 1H), 1.14 (td, J=7.0, 4.9 Hz, 2H), 0.82 (dt, J=6.9, 5.0 Hz, 2H).

Step C: 2-Amino-4-cyclopropyl-6-(methylsulfonyl)phenol. Using a procedure analogous to General Procedure C, starting with 2-(benzyloxy)-5-cyclopropyl-1-(methylsulfonyl)-3-nitrobenzene (32 mg, 0.092 mmol, limiting reagent), 2-amino-4-cyclopropyl-6-(methylsulfonyl)phenol was obtained (19 mg) as a crude material that was used without further purification.

Step D: 5-Bromo-3-chloro-N-(5-cyclopropyl-2-hydroxy-3-(methylsulfonyl)phenyl)-2-hydroxybenzenesulfonamide. Using a procedure analogous to General Procedure E, starting with crude 2-amino-4-cyclopropyl-6-(methylsulfonyl)phenol (10 mg) and 5-bromo-3-chloro-2-hydroxy-benzenesulfonyl chloride, which was prepared by a procedure analogous to the procedure used to prepare Example S7 Step A, the title compound was obtained, after purification by preparative HPLC (9 mg, 0.018 mmol, 20%). $^1$H NMR (400 MHz, Chloroform-d) $\delta_H$ 7.65 (q, J=2.4 Hz, 2H), 7.40 (d, J=2.2 Hz, 1H), 7.31 (s, 1H), 7.22 (d, J=2.2 Hz, 1H), 3.06 (s, 3H), 1.87 (tt, J=8.4, 5.1 Hz, 1H), 1.07-0.95 (m, 2H), 0.65 (dt, J=6.6, 4.9 Hz, 2H); LCMS (Method B): $t_R$=1.051 min, m/z=498.2 [M+H]+; ≥95% (AUC).

Example S26: 5-Bromo-N-(5-cyclopropyl-2-hydroxy-3-(methylsulfonyl)phenyl)-2-hydroxybenzenesulfonamide

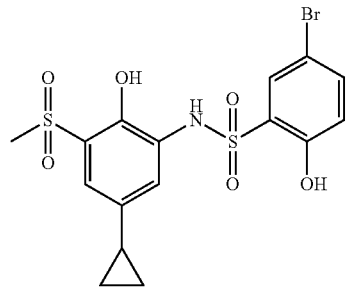 [SMILES: CS(=O)(=O)c1cc(C2CC2)cc(NS(=O)(=O)c2cc(Br)ccc2O)c1O]

Using a procedure analogous to General Procedure E, starting with crude 2-amino-4-cyclopropyl-6-(methylsulfonyl)phenol (9 mg), which was prepared using a procedure analogous to the procedure used to prepare Example S24 Steps A-D, and 5-bromo-2-hydroxy-benzenesulfonyl chloride, which was prepared by a procedure analogous to the procedure used to prepare Example S6 Step A, the title compound was obtained after purification by preparative HPLC (7 mg, 0.015 mmol, 16%). $^1$H NMR (400 MHz, Chloroform-d) $\delta_H$ 8.86 (s, 1H), 7.59 (d, J=2.4 Hz, 1H), 7.50 (dd, J=8.8, 2.4 Hz, 1H), 7.37 (d, J=2.2 Hz, 1H), 7.24 (d, J=2.2 Hz, 1H), 7.13 (s, 1H), 6.87 (d, J=8.9 Hz, 1H), 3.03 (s, 3H), 1.88 (ddd, J=13.5, 8.5, 5.0 Hz, 1H), 1.06-0.95 (m, 2H), 0.70-0.62 (m, 2H); LCMS (Method B): $t_R$=0.986 min, m/z=480.3 [M+H]$^+$; ≥95% (AUC).

Example S27: 5-Bromo-3-chloro-N-(5-chloro-2-hydroxy-3-sulfamoylphenyl)-2-hydroxybenzenesulfonamide

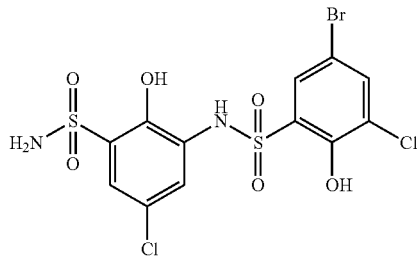 [SMILES: NS(=O)(=O)c1cc(Cl)cc(NS(=O)(=O)c2cc(Br)cc(Cl)c2O)c1O]

Step A: 5-chloro-2-hydroxy-3-nitrobenzenesulfonyl chloride. Using a procedure analogous to General Procedure B, starting with 5-chloro-2-hydroxybenzenesulfonyl chloride (1140 mg, 5 mmol, limiting reagent), which was prepared by a procedure analogous to the procedure used to prepare Example J175 Step A, 5-chloro-2-hydroxy-3-nitrobenzenesulfonyl chloride was obtained (1020 mg, 3.75 mmol, 75%). $^1$H NMR (400 MHz, Chloroform-d) $\delta_H$ 8.48 (d, J=2.7 Hz, 1H), 8.29 (d, J=2.7 Hz, 1H). LCMS (Method B): $t_R$=0.098 min; ≥95% (AUC).

Step B: 5-Chloro-2-hydroxy-3-nitrobenzenesulfonamide. Using a procedure analogous to General Procedure Y, starting with 5-chloro-2-hydroxy-3-nitrobenzenesulfonyl chloride (100 mg, 0.37 mmol, limiting reagent), and a 7 M solution of ammonia in MeOH, 5-chloro-2-hydroxy-3-nitrobenzenesulfonamide was obtained (41 mg) as an impure mixture. LCMS (Method B): $t_R$=1.030 min, m/z=505.2 [2M+H]$^+$.

Step C: 3-Amino-5-chloro-2-hydroxybenzenesulfonamide. Using a procedure analogous to General Procedure C, starting with 5-chloro-2-hydroxy-3-nitrobenzenesulfonamide (39 mg, 0.15 mmol, limiting reagent), 3-amino-5-chloro-2-hydroxybenzenesulfonamide was obtained (36 mg). $^1$H NMR (400 MHz, Methanol-d$_4$) $\delta_H$ 6.98 (d, J=2.5 Hz, 1H), 6.85 (d, J=2.6 Hz, 1H).

Step D: 5-Bromo-3-chloro-N-(5-chloro-2-hydroxy-3-sulfamoylphenyl)-2-hydroxybenzenesulfonamide. Using a procedure analogous to General Procedure E, starting with 3-amino-5-chloro-2-hydroxybenzenesulfonamide (18 mg, 0.08 mmol, limiting reagent) and 5-bromo-3-chloro-2-hydroxy-benzenesulfonyl chloride, which was prepared by a procedure analogous to the procedure used to prepare Example S7 Step A, the title compound was obtained after purification by preparative HPLC (7 mg, 0.014 mmol, 9%). $^1$H NMR (400 MHz, Chloroform-d) $\delta_H$ 7.98 (d, J=2.4 Hz, 1H), 7.85 (d, J=2.4 Hz, 1H), 7.37 (d, J=2.5 Hz, 1H), 7.00 (d, J=2.5 Hz, 1H), 5.33 (s, 2H); LCMS (Method B): $t_R$=0.970 min, m/z=493.1 [M+H]$^+$; ≥90% (AUC).

Example S27-2: 5-Bromos-N-(5-chloro-2-hydroxy-3-sulfamoylphenyl)-2-hydroxybenzenesulfonamide

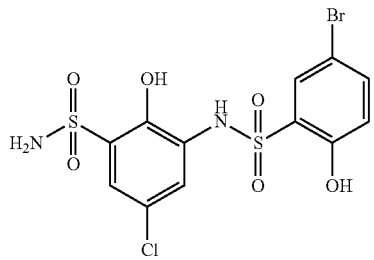 [SMILES: NS(=O)(=O)c1cc(Cl)cc(NS(=O)(=O)c2cc(Br)ccc2O)c1O]

Using a procedure analogous to General Procedure E, starting with 3-amino-5-chloro-2-hydroxybenzenesulfonamide (18 mg, 0.08 mmol, limiting reagent), which was prepared by a procedure analogous to the procedure used to prepare Example S26 Steps A-C, and 5-bromo-2-hydroxybenzenesulfonyl chloride, which was prepared by a procedure analogous to the procedure used to prepare Example S6 Step A, the title compound was obtained, after purification by preparative HPLC using the basic method (1 mg, 0.002 mmol, 1%). $^1$H NMR (400 MHz, Methanol-d$_4$) $\delta_H$ 7.83 (d, J=2.6 Hz, 1H), 7.55 (dd, J=9.0, 2.6 Hz, 1H), 7.12 (d, J=2.6 Hz, 1H), 7.01 (d, J=2.6 Hz, 1H), 6.85 (d, J=8.9 Hz, 1H); LCMS (Method B): $t_R$=0.902 min, m/z=459.1 [M+H]$^+$; ≥95% (AUC).

Example S28: 5-bromo-3-chloro-N-(5-chloro-2-hydroxy-3-(N-methylsulfamoyl)phenyl)-2-hydroxybenzenesulfonamide

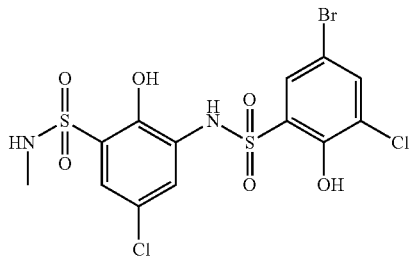 [SMILES: CNS(=O)(=O)c1cc(Cl)cc(NS(=O)(=O)c2cc(Br)cc(Cl)c2O)c1O]

Step A: 5-Chloro-2-hydroxy-N-methyl-3-nitrobenzenesulfonamide. Using a procedure analogous to General Procedure Y, starting with 3-amino-5-chloro-2-hydroxybenzenesulfonamide (100 mg, 0.37 mmol, limiting reagent), which was prepared by a procedure analogous to Example S26 Step C, and methylamine, 5-chloro-2-hydroxy-N-methyl-3-nitrobenzenesulfonamide was obtained (55 mg) as a mixture with impurities. $^1$H NMR (400 MHz, Chloroform-d) $\delta_H$ 8.33 (d, J=2.7 Hz, 1H), 8.23 (d, J=2.7 Hz, 1H), 5.02 (s, 1H), 2.73 (s, 3H); LCMS (Method B): $t_R$=0.817 min.

Step B: 3-Amino-5-chloro-2-hydroxy-N-methylbenzenesulfonamide. Using a procedure analogous to General Procedure C, starting with 5-chloro-2-hydroxy-N-methyl-3-nitrobenzenesulfonamide (55 mg), 3-amino-5-chloro-2-hydroxy-N-methylbenzenesulfonamide was obtained (48 mg) as a crude material that was used without further purification. LCMS (Method B): $t_R$=0.632, 237.1 [M+H]$^+$.

Step C: 5-Bromo-3-chloro-N-(5-chloro-2-hydroxy-3-(N-methylsulfamoyl)phenyl)-2-hydroxybenzenesulfonamide.

Using a procedure analogous to General Procedure E, starting with 3-amino-5-chloro-2-hydroxy-N-methylbenzenesulfonamide (24 mg) and 5-bromo-3-chloro-2-hydroxy-benzenesulfonyl chloride, which was prepared by a procedure analogous to the procedure used to prepare Example S7 Step A, the title compound was obtained after purification by preparative HPLC (4 mg, 0.008 mmol, 2%). $^1$H NMR (400 MHz, Chloroform-d) & 7.76 (d, J=2.5 Hz, 1H), 7.67 (d, J=2.5 Hz, 1H), 7.22 (d, J=2.4 Hz, 1H), 6.88 (d, J=2.4 Hz, 1H), 2.70 (s, 3H); LCMS (Method B): $t_R$=1.051 min, m/z=507.1 [M+H]$^+$; ≥95% (AUC).

Example S29: 5-bromo-N-(5-chloro-2-hydroxy-3-(N-methylsulfamoyl)phenyl)-2-hydroxybenzenesulfonamide

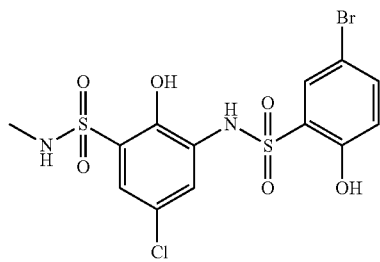 [SMILES: CNS(=O)(=O)c1cc(Cl)cc(NS(=O)(=O)c2cc(Br)ccc2O)c1O]

Using a procedure analogous to General Procedure E, starting with 3-amino-5-chloro-2-hydroxy-N-methylbenzenesulfonamide (24 mg), which was prepared by a procedure analogous to Example S27 Step B, and 5-bromo-2-hydroxybenzenesulfonyl chloride, which was prepared by a procedure analogous to the procedure used to prepare Example S6 Step A, the title compound was obtained after purification by preparative HPLC (3 mg, 0.006 mmol, 2%). $^1$H NMR (400 MHz, Chloroform-d) 7.93 (d, J=2.4 Hz, 1H), 7.59 (d, J=8.1 Hz, 1H), 6.95 (d, J=2.5 Hz, 2H), 3.13 (s, 1H), 2.69 (s, 3H); LCMS (Method B): $t_R$=0.991 min, m/z=473.1 [M+H]$^+$; ≥95% (AUC).

Example S30: 5-bromo-3-chloro-N-(5-chloro-2-hydroxy-3-(N-(2-methoxyethyl)sulfamoyl)phenyl)-2-hydroxybenzenesulfonamide

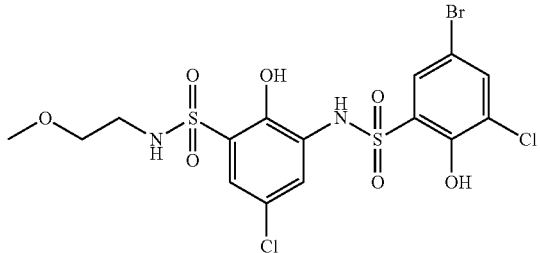 [SMILES: COCCNS(=O)(=O)c1cc(Cl)cc(NS(=O)(=O)c2cc(Br)cc(Cl)c2O)c1O]

Step A: 5-Chloro-2-hydroxy-N-(2-methoxyethyl)-nitrobenzenesulfonamide. Using a procedure analogous to General Procedure Y, starting with 3-amino-5-chloro-2-hydroxybenzenesulfonamide (100 mg, 0.37 mmol, limiting reagent), which was prepared by a procedure analogous to Example S26 Step C, and 2-methoxyethan-1-amine, 5-chloro-2-hydroxy-N-(2-methoxyethyl)-nitrobenzenesulfonamide was obtained (74 mg, 0.24 mmol, 64%). $^1$H NMR (400 MHz, Chloroform-d) $\delta_H$ 8.31 (d, J=2.7 Hz, 1H), 8.21 (d, J=2.7 Hz, 1H), 5.47 (t, J=5.9 Hz, 1H), 3.44 (dd, J=5.5, 4.5 Hz, 2H), 3.26 (s, 3H), 3.20 (td, J=5.6, 4.4 Hz, 2H); LCMS (Method B): $t_R$=0.810 min, m/z=311.2 [M+H]$^+$.

Step B: 3-Amino-5-chloro-2-hydroxy-N-(2-methoxyethyl)benzenesulfonamide. Using a procedure analogous to General Procedure C, starting with of 5-chloro-2-hydroxy-N-(2-methoxyethyl)-3-nitrobenzenesulfonamide (74 mg, 0.24 mmol, limiting reagent), 3-amino-5-chloro-2-hydroxy-N-(2-methoxyethyl)benzenesulfonamide was obtained (64 mg, 0.23 mmol, 95%) and used without further purification. $^1$H NMR (400 MHz, Methanol-d$_4$) $\delta_H$ 6.92 (d, J=2.5 Hz, 1H), 6.87 (d, J=2.5 Hz, 1H), 3.37 (t, J=5.4 Hz, 2H), 3.25 (s, 3H), 3.08 (t, J=5.4 Hz, 2H); LCMS (Method B): $t_R$=0.646 min, 281.1 [M+H]$^+$.

Step C: 5-Bromo-3-chloro-N-(5-chloro-2-hydroxy-3-(2-methoxyethylsulfamoyl)phenyl)-2-hydroxybenzenesulfonamide. Using a procedure analogous to General Procedure E, starting with 3-amino-5-chloro-2-hydroxy-N-(2-methoxyethyl)benzenesulfonamide (30 mg, 0.11 mmol, limiting reagent), and 5-bromo-3-chloro-2-hydroxy-benzenesulfonyl chloride, which was prepared by a procedure analogous to the procedure used to prepare Example S7 Step A, the title compound was obtained after purification by preparative HPLC (3 mg, 0.005 mmol, 5%). $^1$H NMR (400 MHz, Chloroform-d) $\delta_H$ 7.76 (d, J=2.3 Hz, 1H), 7.63 (d, J=2.3 Hz, 1H), 6.90 (s, 1H), 3.49 (s, 2H), 3.32 (s, 3H), 3.08 (s, 2H); LCMS (Method B): $t_R$=1.068 min, m/z=551.1 [M+H]$^+$; ≥95% (AUC).

Example S31: 5-bromo-N-(5-chloro-2-hydroxy-3-(N-(2-methoxyethyl)sulfamoyl)phenyl)-2-hydroxy-benzenesulfonamide

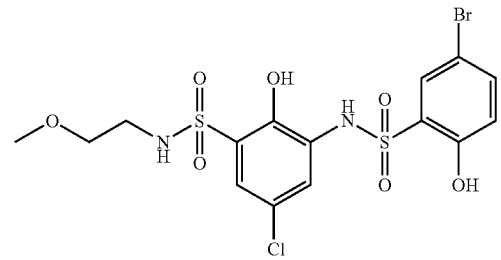 [SMILES: COCCNS(=O)(=O)c1cc(Cl)cc(NS(=O)(=O)c2cc(Br)ccc2O)c1O]

Using a procedure analogous to General Procedure E, starting with 3-amino-5-chloro-2-hydroxy-N-(2-methoxyethyl)benzenesulfonamide (35 mg, 0.12 mmol, limiting reagent), which was prepared by a procedure analogous to Example S29 Steps A-B, and 5-bromo-2-hydroxy-benzenesulfonyl chloride, which was prepared by a procedure analogous to the procedure used to prepare Example S6 Step A, the title compound was obtained after purification by preparative basic method HPLC (8 mg, 0.015 mmol, 13%). $^1$H NMR (400 MHz, Chloroform-d) $\delta_H$ 7.73 (d, J=2.4 Hz, 1H), 7.57 (s, 1H), 7.42-7.34 (m, 2H), 6.66 (d, J=8.7 Hz, 1H), 3.35 (s, 2H), 3.21 (s, 3H), 2.99 (d, J=5.4 Hz, 2H); LCMS (Method B): $t_R$=1 1.029 min, m/z=515.2 [M+H]$^+$; ≥93% (AUC).

Example S32: 5-Bromo-3-chloro-N-(5-chloro-2-hydroxy-3-(N-((tetrahydrofuran-2-yl)methyl)sulfamoyl)phenyl)-2-hydroxybenzenesulfonamide

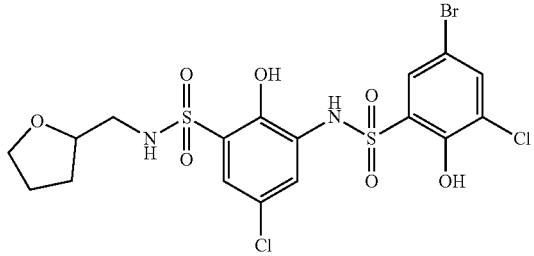 [SMILES: O=S(=O)(Nc1cc(Cl)cc(S(=O)(=O)NCC2CCCO2)c1O)c1cc(Br)cc(Cl)c1O]

Step A: 5-Chloro-2-hydroxy-3-nitro-N-((tetrahydrofuran-2-yl)methyl)benzenesulfonamide. Using a procedure analogous to General Procedure Y, starting with 3-amino-5-chloro-2-hydroxybenzenesulfonamide (100 mg, 0.37 mmol, limiting reagent), which was prepared by a procedure analogous to Example S26 Step C, and tetrahydrofurylamine, 5-chloro-2-hydroxy-3-nitro-N-((tetrahydrofuran-2-yl)methyl)benzenesulfonamide was obtained (75 mg, 0.22 mmol, 60%). $^1$H NMR (400 MHz, Chloroform-d) $\delta_H$ 11.31 (s, 1H), 8.30 (d, J=2.7 Hz, 1H), 8.20 (d, J=2.7 Hz, 1H), 5.48 (t, J=6.1 Hz, 1H), 3.94 (qd, J=6.9, 3.4 Hz, 1H), 3.77 (dt, J=8.4, 6.6 Hz, 1H), 3.68 (dt, J=8.3, 6.8 Hz, 1H), 3.21 (ddd, J=12.8, 6.5, 3.4 Hz, 1H), 2.96 (ddd, J=12.6, 6.8, 5.5 Hz, 1H), 2.00-1.93 (m, 1H), 1.91-1.83 (m, 2H), 1.68-1.55 (m, 1H); LCMS (Method B): $t_R$=0.896 min, m/z=337.2 [M+H]$^+$.

Step B: 3-Amino-5-chloro-2-hydroxy-N-((tetrahydrofuran-2-yl)methyl)benzenesulfonamide. Using a procedure analogous to General Procedure C, starting with 5-chloro-2-hydroxy-3-nitro-N-((tetrahydrofuran-2-yl)methyl)benzenesulfonamide (75 mg, 0.22 mmol, limiting reagent) was obtained (63 mg, 0.21 mmol, 93%) and used without further purification. LCMS (Method B): $t_R$=0.804 min, 307.1 [M+H]$^+$.

Step C: 5-Bromo-3-chloro-N-(5-chloro-2-hydroxy-3-(N-((tetrahydrofuran-2-yl)methyl)sulfamoyl)phenyl)-2-hydroxybenzenesulfonamide. Using a procedure analogous to General Procedure C, starting with 3-amino-5-chloro-2-hydroxy-N-((tetrahydrofuran-2-yl)methyl)benzenesulfonamide (31.5 mg, 0.10 mmol, limiting reagent), and 5-bromo-3-chloro-2-hydroxy-benzenesulfonyl chloride, which was prepared by a procedure analogous to the procedure used to prepare Example S7 Step A, the title compound was obtained after purification by preparative HPLC (12 mg, 0.021 mmol, 21%). $^1$H NMR (400 MHz, Chloroform-d) $\delta_H$ 7.54 (d, J=2.6 Hz, 1H), 7.50 (d, J=2.6 Hz, 1H), 7.48 (d, J=2.6 Hz, 1H), 7.44 (d, J=2.7 Hz, 1H), 3.89-3.79 (m, 1H), 3.71 (dt, J=8.3, 6.5 Hz, 1H), 3.61 (dt, J=8.1, 6.7 Hz, 1H), 2.82 (d, J=5.6 Hz, 2H), 1.91-1.71 (m, 3H), 1.59-1.47 (m, 1H); LCMS (Method B): $t_R$=1.110 min, m/z=577.1.1 [M+H]$^+$; ≥95% (AUC).

Example S32-2: 5-Bromo-N-(5-chloro-2-hydroxy-3-(N-((tetrahydrofuran-2-yl)methyl)sulfamoyl)phenyl)-2-hydroxybenzenesulfonamide

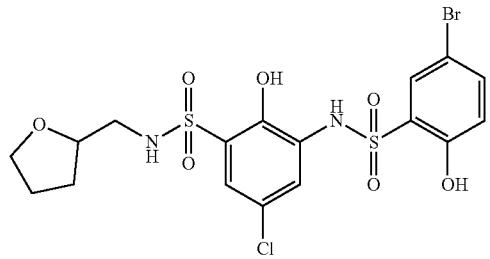 [SMILES: O=S(=O)(Nc1cc(Cl)cc(S(=O)(=O)NCC2CCCO2)c1O)c1cc(Br)ccc1O]

Using a procedure analogous to General Procedure E, starting with 3-amino-5-chloro-2-hydroxy-N-(2-methoxyethyl)benzenesulfonamide (31.5 mg, 0.10 mmol, limiting reagent), which was prepared by a procedure analogous to Example S31 Step B, and 5-bromo-2-hydroxy-benzenesulfonyl chloride, which was prepared by a procedure analogous to Example S6 Step A, the title compound was obtained after purification by preparative basic method HPLC (6 mg, 0.011 mmol, 11%). $^1$H NMR (400 MHz, Chloroform-d) $\delta_H$ 7.75 (d, J=2.5 Hz, 1H), 7.54-7.47 (m, 1H), 7.38 (dd, J=19.6, 2.6 Hz, 2H), 6.86 (d, J=8.7 Hz, 1H), 3.85 (td, J=6.5, 4.9 Hz, 1H), 3.77-3.61 (m, 2H), 2.83 (dd, J=13.3, 5.4 Hz, 2H), 1.84 (dt, J=13.3, 6.9 Hz, 3H), 1.64-1.50 (m, 1H); LCMS (Method B): $t_R$=1.056 min, m/z=543.2 [M+H]+; ≥93% (AUC).

Example S33: 5-Bromo-3-chloro-N-(5-chloro-2-hydroxy-3-(N-(2-(4-methylpiperazin-1-yl)ethyl)sulfamoyl)phenyl)-2-hydroxybenzenesulfonamide

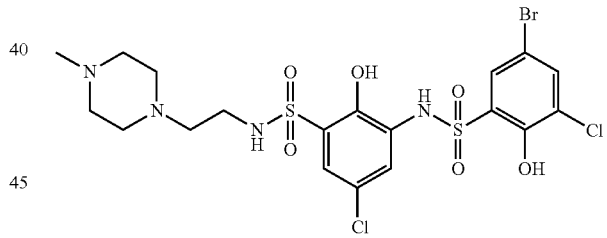

Step A: 5-Chloro-2-hydroxy-N-(2-(4-methylpiperazin-1-yl)ethyl)-3-nitrobenzenesulfonamide. Using a procedure analogous to General Procedure Y, starting with 3-amino-5-chloro-2-hydroxybenzenesulfonamide (100 mg, 0.37 mmol, limiting reagent), which was prepared by a procedure analogous to Example S26 Step C, and 2-(4-methylpiperazin))ethylamine, 5-chloro-2-hydroxy-N-(2-(4-methylpiperazin-1-yl)ethyl)-3-nitrobenzenesulfonamide was obtained and used without further purification. LCMS (Method B): $t_R$=0.116 min.

Step B: 3-Amino-5-chloro-2-hydroxy-N-(2-(4-methylpiperazin-1-yl)ethyl)benzenesulfonamide. Using a procedure analogous to General Procedure C, starting with the crude mixture containing 5-chloro-2-hydroxy-N-(2-(4-methylpiperazin-1-yl)ethyl)-3-nitrobenzenesulfonamide, 3-amino-5-chloro-2-hydroxy-N-(2-(4-methylpiperazin-1-yl)ethyl)benzenesulfonamide was obtained and used without further purification. LCMS (Method B): $t_R$=0.092 min, 349.3 [M+H]$^+$.

Step C: 5-Bromo-3-chloro-N-(5-chloro-2-hydroxy-3-(N-((tetrahydrofuran-2-yl)methyl)sulfamoyl)phenyl)-2-hydroxybenzenesulfonamide. Using a procedure analogous to General Procedure E, starting with the crude mixture containing 3-amino-5-chloro-2-hydroxy-N-((tetrahydrofuran-2-yl)methyl)benzenesulfonamide and 5-bromo-3-chloro-2-hydroxy-benzenesulfonyl chloride, which was prepared by a procedure analogous to the procedure used to prepare Example S7 Step A, the title compound was obtained, after purification by ISCO flash chromatography, filtration through a SCX column, and basic method HPLC (4 mg, 0.006 mmol, 4%). $^1$H NMR (400 MHz, Chloroform-d) $\delta_H$ 7.64 (d, J=2.7 Hz, 1H), 7.54 (d, J=2.7 Hz, 1H), 7.52 (d, J=2.7 Hz, 1H), 7.40 (d, =2.7 Hz, 1H), 3.39 (t, J=5.0 Hz, 4H), 2.99 (s, 2H), 2.84 (s, 7H), 2.71 (t, J=5.5 Hz, 2H); LCMS (Method B): $t_R$=1.356 min, m/z=618.7 [M+H]+; ≥93% (AUC).

Example S34: 5-Bromo-3-chloro-N-(3-chloro-5-((2-(diethylamino)ethyl)thio)phenyl)-2-hydroxybenzenesulfonamide

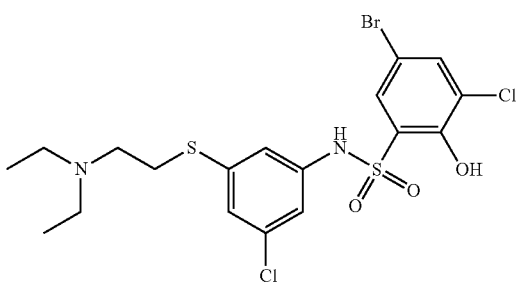 [SMILES: CCN(CC)CCSc1cc(Cl)cc(NS(=O)(=O)c2cc(Br)cc(Cl)c2O)c1]

Step A: 3-Chloro-5-((2-(diethylamino)ethyl)thio)aniline. Using a procedure analogous to General Procedure W, starting with 3-bromo-5-chloroaniline (250 mg, 1.21 mmol, limiting reagent) and 2-(diethylamino)ethyl bromide hydrobromide, 3-chloro-5-((2-(diethylamino)ethyl)thio)aniline was obtained (127 mg, 0.49 mmol, 40% yield). LCMS (Method B): $t_R$=0.101 min, m/z=259.2 [M+H]$^+$; ≥95% (AUC).

Step B: 5-Bromo-3-chloro-N-(3-chloro-5-((2-(diethylamino)ethyl)thio)phenyl)-2-hydroxybenzenesulfonamide. Using a procedure analogous to General Procedure E, starting with 3-chloro-5-((2-(diethylamino)ethyl)thio)aniline (50 mg, 0.19 mmol) and 5-bromo-3-chloro-2-hydroxy-benzenesulfonyl chloride, which was prepared by a procedure analogous to the procedure used to prepare Example S7 Step A, the title compound was obtained as a yellow oil after purification by ISCO flash chromatography (62 mg, 0.12 mmol, 63% yield). $^1$H NMR (400 MHz, Chloroform-d) δ 7.58 (d, J=2.6 Hz, 1H), 7.44 (d, J=2.6 Hz, 1H), 7.30 (s, 1H), 7.21 (s, 1H), 7.03 (d, J=1.8 Hz, 1H), 3.44-3.35 (m, 2H), 3.11 (q, J=8.4, 7.3 Hz, 6H), 1.12 (t, J=7.3 Hz, 6H). LCMS (Method B): $t_R$=0.955 min, m/z=529.2 [M+H]$^+$; ≥95% by H-NMR.

Example S35: 5-Bromo-3-chloro-N-(3-chloro-5-((2-(diethylamino)ethyl)sulfonyl)phenyl)-2-hydroxybenzenesulfonamide

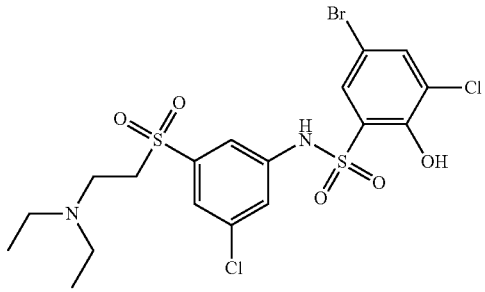 [SMILES: CCN(CC)CCS(=O)(=O)c1cc(Cl)cc(NS(=O)(=O)c2cc(Br)cc(Cl)c2O)c1]

Using a procedure analogous to General Procedure U, starting with 5-bromo-3-chloro-N-(3-chloro-5-((2-(diethylamino)ethyl)thio)phenyl)-2-hydroxybenzenesulfonamide (43 mg, 0.08 mmol, limiting reagent), which was prepared by a procedure analogous to Example S34 Step B, the title compound was obtained as its corresponding TFA salt (16 mg, 0.024 mmol, 30% yield). $^1$H NMR (400 MHz, Chloroform-d) δ 7.88 (s, 1H), 7.68 (s, 1H), 7.65 (s, 1H), 7.60 (d, J=2.4 Hz, 1H), 7.58 (s, 1H), 3.85-3.78 (m, 2H), 3.49-3.42 (m, 2H), 3.15 (d, J=7.5 Hz, 4H), 1.35 (t, J=7.3 Hz, 6H). LCMS (Method B): $t_R$=0.927 min, m/z=561.2 [M+H]$^+$; ≥95% (AUC).

Example S36: 5-Bromo-3-chloro-N-(3-chloro-5-((2-(diisopropylamino)ethyl)thio)phenyl)-2-hydroxybenzenesulfonamide

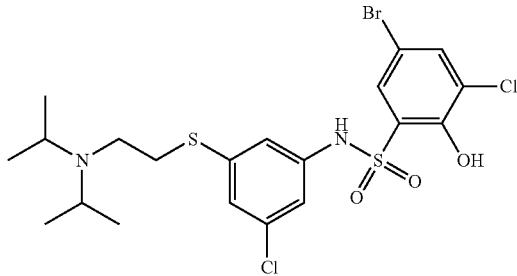 [SMILES: CC(C)N(CCSc1cc(Cl)cc(NS(=O)(=O)c2cc(Br)cc(Cl)c2O)c1)C(C)C]

Step A: 3-Chloro-5-((2-(diisopropylamino)ethyl)thio)aniline. Using a procedure analogous to General Procedure W, starting with 3-bromo-5-chloroaniline (250 mg, 1.21 mmol, limiting reagent) and 2-diisopropylaminoethylchloride hydrochloride, 3-chloro-5-((2-(diisopropylamino)ethyl)thio)aniline was obtained (100 mg, 0.38 mmol, 32% yield). LCMS (Method B): $t_R$=0.112 min, m/z=287.3, 289.4 [M+H]$^+$; ≥95% (AUC).

Step B: 5-Bromo-3-chloro-N-(3-chloro-5-((2-(diisopropylamino)ethyl)thio)phenyl)-2-hydroxybenzenesulfonamide. Using a procedure analogous to General Procedure E, starting with 3-chloro-5-((2-(diisopropylamino)ethyl)thio)aniline (50 mg, 0.17 mmol) and 5-bromo-3-chloro-2-hydroxy-benzenesulfonyl chloride, which was prepared by a procedure analogous to the procedure used to prepare Example S7 Step A, the title compound was obtained, after purification by ISCO flash chromatography, as a yellow oil (49 mg, 0.093 mmol, 55% yield). $^1$H NMR (400 MHz, Chloroform-d) δ 7.60 (d, J=2.6 Hz, 1H), 7.45 (d, J=2.6 Hz, 1H), 7.35 (s, 1H), 7.21 (s, 1H), 7.04 (s, 1H), 4.12 (q, J=7.2 Hz, 1H), 3.74-3.60 (m, 2H), 3.14-2.99 (m, 2H), 2.04 (s, 2H), 1.25 (d, J=6.7 Hz, 12H). LCMS (Method B): $t_R$=0.997 min, m/z=557.2, 559.2 [M+NH$_4$]$^+$; ≥95% pure by 1H-NMR.

Example S37: 5-Bromo-3-chloro-N-(3-chloro-5-((2-(diisopropylamino)ethyl)sulfonyl)phenyl)-2-hydroxybenzenesulfonamide

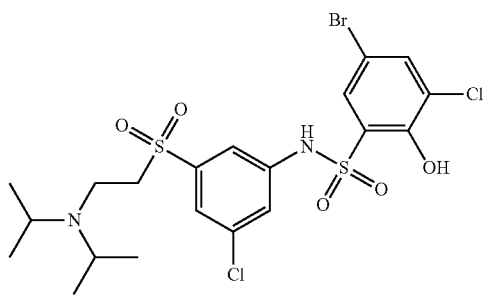 [SMILES: CC(C)N(CCS(=O)(=O)c1cc(Cl)cc(NS(=O)(=O)c2cc(Br)cc(Cl)c2O)c1)C(C)C]

Using a procedure analogous to General Procedure U, starting with 5-bromo-3-chloro-N-(3-chloro-5-((2-(diisopropylamino)ethyl)thio)phenyl)-2-hydroxybenzenesulfonamide (36 mg, 0.06 mmol, limiting reagent), which was prepared by a procedure analogous to Example S36 Step B, the title compound was obtained as its corresponding TFA salt (22 mg, 0.031 mmol, 52% yield). $^1$H NMR (400 MHz, Chloroform-d) δ 7.85 (d, J=2.4 Hz, 1H), 7.74 (d, J=1.9 Hz, 1H), 7.64 (t, J=1.7 Hz, 1H), 7.59 (d, J=2.4 Hz, 1H), 7.55 (t, J=1.8 Hz, 1H), 4.03-3.90 (m, 2H), 3.66 (p, J=6.6 Hz, 2H), 3.53-3.43 (m, 2H), 1.39 (d, J=6.6 Hz, 12H). LCMS (Method B): $t_R$=0.961 min, m/z=589.2 [M+H]$^+$; ≥95% (AUC).

Example S40: 5-Bromo-N-(3-chloro-5-((2-(diethylamino)ethyl)sulfonyl)phenyl)-2-hydroxybenzenesulfonamide

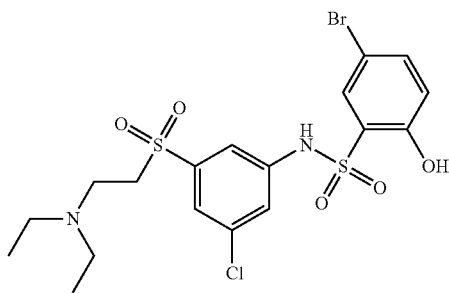 [SMILES: CCN(CC)CCS(=O)(=O)c1cc(Cl)cc(NS(=O)(=O)c2cc(Br)ccc2O)c1]

Step A: 5-Bromo-N-(3-chloro-5-((2-(diethylamino)ethyl)thio)phenyl)-2-hydroxybenzenesulfonamide. Using a procedure analogous to General Procedure E, starting with 3-chloro-5-((2-(diethylamino)ethyl)thio)aniline (50 mg, 0.19 mmol), which was prepared by a procedure analogous to Example S34 Step A, and 5-bromo-2-hydroxy-benzenesulfonyl chloride, which was prepared by a procedure analogous to the procedure used to prepare Example S6 Step A, the title compound was obtained (51 mg, 0.10 mmol, 53% yield). $^1$H NMR (400 MHz, Chloroform-d) δ 11.19 (s, 1H), 8.49 (s, 1H), 7.81 (d, J=2.5 Hz, 1H), 7.42 (dd, J=8.8, 2.5 Hz, 1H), 7.30 (d, J=1.9 Hz, 1H), 7.05-6.95 (m, 2H), 6.90 (d, J=8.8 Hz, 1H), 3.28-3.08 (m, 8H), 1.31 (s, 6H). LCMS (Method B): $t_R$=0.888 min, m/z=493.2 [M+H]$^+$; ≥95% (AUC).

Step B: 5-Bromo-N-(3-chloro-5-((2-(diethylamino)ethyl)sulfonyl)phenyl)-2-hydroxybenzenesulfonamide. Using a procedure analogous to General Procedure U, starting with 5-bromo-N-(3-chloro-5-((2-(diethylamino)ethyl)thio)phenyl)-2-hydroxybenzenesulfonamide (29 mg, 0.06 mmol, limiting reagent), the title compound was obtained as its corresponding TFA salt (11 mg, 0.017 mmol, 29% yield). $^1$H NMR (400 MHz, Chloroform-d) δ 7.94 (d, J=2.5 Hz, 1H), 7.68 (s, 1H), 7.62 (d, J=1.8 Hz, 1H), 7.57 (s, 1H), 7.41 (dd, J=8.7, 2.5 Hz, 1H), 6.84 (d, J=8.8 Hz, 1H), 3.71 (d, J=9.2 Hz, 2H), 3.57 (d, J=8.5 Hz, 2H), 3.17 (m, 4H), 1.35 (t, J=7.3 Hz, 6H). LCMS (Method B): $t_R$=0.878 min, m/z=525.2 [M+H]$^+$; ≥95% (AUC).

Example S41: 5-Bromo-N-(3-chloro-5-((2-(diisopropylamino)ethyl)sulfonyl)phenyl)-2-hydroxybenzenesulfonamide

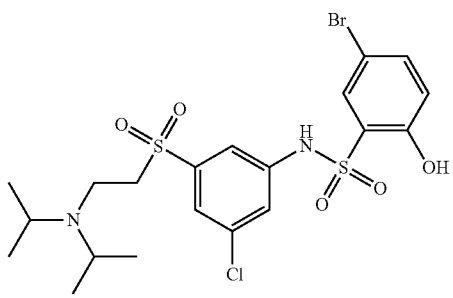 [SMILES: CC(C)N(CCS(=O)(=O)c1cc(Cl)cc(NS(=O)(=O)c2cc(Br)ccc2O)c1)C(C)C]

Step A: 5-Bromo-N-(3-chloro-5-((2-(diisopropylamino)ethyl)thio)phenyl)-2-hydroxybenzenesulfonamide. Using a procedure analogous to General Procedure E, starting with 3-chloro-5-((2-(diethylamino)ethyl)thio)aniline (50 mg, 0.19 mmol), which was prepared by a procedure analogous to Example S36 Step A, and 5-bromo-2-hydroxy-benzenesulfonyl chloride which was prepared by a procedure analogous to the procedure used to prepare Example S6 Step A, the title compound was obtained (51 mg, 0.080 mmol, 47% yield). $^1$H NMR (400 MHz, Chloroform-d) δ 10.06 (s, 1H), 8.39 (s, 1H), 7.79 (d, J=2.5 Hz, 1H), 7.41 (dd, J=8.8, 2.5 Hz, 1H), 7.35 (d, J=1.9 Hz, 1H), 6.99 (d, J=1.8 Hz, 1H), 6.97-6.89 (m, 2H), 3.64 (td, J=6.7, 3.3 Hz, 2H), 3.40-3.32 (m, 2H), 3.10 (dt, J=12.6, 4.3 Hz, 2H), 1.37 (dd, J=11.2, 6.6 Hz, 12H). LCMS (Method B): $t_R$=0.919 min, m/z=521.3 [M+H]$^+$; ≥95% (AUC).

Step B: 5-Bromo-N-(3-chloro-5-((2-(diisopropylamino)ethyl)sulfonyl)phenyl)-2-hydroxybenzenesulfonamide. Using a procedure analogous to General Procedure U, starting with 5-bromo-N-(3-chloro-5-((2-(diisopropylamino)ethyl)thio)phenyl)-2-hydroxybenzenesulfonamide (31 mg, 0.06 mmol, limiting reagent), the title compound was obtained as its corresponding TFA salt (22 mg, 0.033 mmol, 55% yield). $^1$H NMR (400 MHz, Chloroform-d) δ 10.53 (s, 1H), 7.95 (d, J=2.5 Hz, 1H), 7.88 (d, J=4.9 Hz, 1H), 7.74 (t, J=1.9 Hz, 1H), 7.63 (d, J=1.7 Hz, 1H), 7.56 (t, J=1.8 Hz, 1H), 7.42 (dd, J=8.8, 2.5 Hz, 1H), 6.86 (d, J=8.8 Hz, 1H), 3.92-3.84 (m, 2H), 3.69 (p, J=6.7 Hz, 2H), 3.58 (dd, J=10.5, 5.7 Hz, 2H), 1.43 (dd, J=6.8, 4.2 Hz, 12H). LCMS (Method B): $t_R$=0.817 min, m/z=553.3, 554.3 [M+H]$^+$; ≥90% pure by 1H-NMR

Example S43: 6-Bromo-N-(3-chloro-5-((2-(diethylamino)ethyl)sulfonyl)phenyl)quinoline-8-sulfonamide

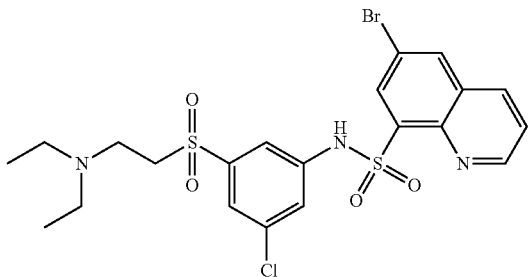 [SMILES: CCN(CC)CCS(=O)(=O)c1cc(Cl)cc(NS(=O)(=O)c2cc(Br)cc3cccnc23)c1]

Step A: 6-Bromo-N-(3-chloro-5-((2-(diisopropylamino)ethyl)thio)phenyl)quinoline-8-sulfonamide. Using a procedure analogous to General Procedure E, starting with 3-chloro-5-((2-(diethylamino)ethyl)thio)aniline (10 mg, 0.04 mmol), which was prepared by a procedure analogous to Example S34 Step A, and 6-bromoquinoline-8-sulfonyl chloride, the title compound was obtained as a yellow oil (5 mg, 0.01 mmol, 19% yield). $^1$H NMR (400 MHz, Chloroform-d) δ 9.15 (dd, J=4.3, 1.7 Hz, 1H), 8.38 (d, J=2.2 Hz, 1H), 8.24 (dd, J=8.9, 1.9 Hz, 2H), 7.66 (dd, J=8.4, 4.3 Hz, 1H), 7.06 (t, J=1.8 Hz, 1H), 7.01 (t, J=1.7 Hz, 1H), 6.82 (t, J=1.9 Hz, 1H), 3.28-3.09 (m, 8H), 1.31 (t, J=7.3 Hz, 6H). LCMS (Method B): $t_R$=0.967 min, m/z=530.2 [M+H]$^+$; ≥90% (AUC).

Step B: 6-Bromo-N-(3-chloro-5-((2-(diethylamino)ethyl)sulfonyl)phenyl)quinoline-8-sulfonamide. Using a procedure analogous to General Procedure U, starting with 6-bromo-N-(3-chloro-5-((2-(diisopropylamino)ethyl)thio)phenyl)quinoline-8-sulfonamide (10 mg, 0.02 mmol, limiting reagent), the title compound was obtained as its corresponding TFA salt (4 mg, 0.006 mmol, 30% yield). $^1$H NMR (400 MHz, Chloroform-d) 7.94 (d, J=2.5 Hz, 1H), 7.68 (s, 1H), 7.62 (d, J=1.8 Hz, 1H), 7.57 (s, 1H), 7.41 (dd, J=8.7, 2.5 Hz, 1H), 6.84 (d, J=8.8 Hz, 1H), 3.71 (d, J=9.2 Hz, 2H), 3.57 (d, J=8.5 Hz, 2H), 3.17 (m, 4H), 1.35 (t, J=7.3 Hz, 6H). LCMS (Method B): $t_R$=0.925 min, m/z=562.3 [M+H]$^+$; ≥95% (AUC).

Example S45: 6-Bromo-N-(3-chloro-5-((2-(diisopropylamino)ethyl)sulfonyl)phenyl)quinoline-8-sulfonamide

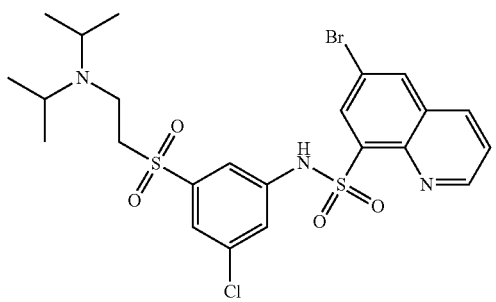 [SMILES: CC(C)N(CCS(=O)(=O)c1cc(Cl)cc(NS(=O)(=O)c2cc(Br)cc3cccnc23)c1)C(C)C]

Step A: 6-Bromo-N-(3-chloro-5-((2-(diisopropylamino)ethyl)thio)phenyl)quinoline-8-sulfonamide. Using a procedure analogous to General Procedure E, starting with 3-chloro-5-((2-(diethylamino)ethyl)thio)aniline (30 mg, 0.12 mmol), which was prepared by a procedure analogous to Example S36 Step A, and 6-bromoquinoline-8-sulfonyl chloride, the title compound was obtained (67 mg, 0.10 mmol, 83% yield). $^1$H NMR (400 MHz, Chloroform-d) δ 11.11 (s, 1H), 9.16 (dd, J=4.3, 1.7 Hz, 1H), 8.38 (d, J=2.2 Hz, 1H), 8.27-8.19 (m, 2H), 7.66 (dd, J=8.4, 4.3 Hz, 1H), 7.06 (d, J=1.9 Hz, 2H), 6.91 (t, J=1.9 Hz, 1H), 3.64 (p, J=6.6 Hz, 2H), 3.36-3.27 (m, 2H), 3.11-3.02 (m, 2H), 1.34 (dd, J=20.8, 6.6 Hz, 12H). LCMS (Method B): $t_R$=0.987 min, m/z=556.3 [M+H]$^+$; ≥95% (AUC).

Step B: 6-Bromo-N-(3-chloro-5-((2-(diisopropylamino)ethyl)sulfonyl)phenyl)quinoline-8-sulfonamide. Using a procedure analogous to General Procedure U, starting with 6-bromo-N-(3-chloro-5-((2-(diisopropylamino)ethyl)thio)phenyl)quinoline-8-sulfonamide (27 mg, 0.05 mmol, limiting reagent), the title compound was obtained as its corresponding TFA salt (10 mg, 0.01 mmol, 28% yield). $^1$H NMR (400 MHz, Chloroform-d) δ 9.16 (dd, J=4.3, 1.7 Hz, 1H), 8.42 (d, J=2.2 Hz, 1H), 8.24 (dt, J=5.3, 2.2 Hz, 2H), 7.66 (dd, J=8.4, 4.3 Hz, 1H), 7.58 (d, J=1.8 Hz, 1H), 7.49 (dt, J=8.9, 2.0 Hz, 2H), 3.79-3.71 (m, 2H), 3.69-3.62 (m, 2H), 3.39-3.30 (m, 2H), 1.36 (d, J=6.6 Hz, 12H). LCMS (Method B): $t_R$=0.952 min, m/z=590.3 [M+H]$^+$; ≥94% (AUC).

Example S46: 5-Bromo-N-(3-chloro-5-((2-(diethylamino)ethyl)sulfonyl)phenyl)-2-methoxybenzenesulfonamide

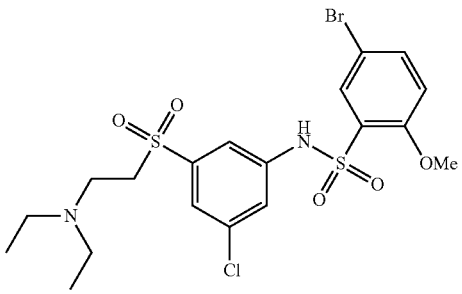 [SMILES: CCN(CC)CCS(=O)(=O)c1cc(Cl)cc(NS(=O)(=O)c2cc(Br)ccc2OC)c1]

Step A: 5-Bromo-N-(3-chloro-5-((2-(diethylamino)ethyl)thio)phenyl)-2-methoxybenzenesulfonamide. Using a procedure analogous to General Procedure E, starting with 3-chloro-5-((2-(diethylamino)ethyl)thio)aniline (7 mg, 0.03 mmol, limiting reagent), which was prepared by a procedure analogous to Example S34 Step A, and 5-bromo-2-methoxybenzenesulfonyl chloride, 5-bromo-N-(3-chloro-5-((2-(diethylamino)ethyl)thio)phenyl)-2-methoxybenzenesulfonamide was obtained as a crude material that was used without further purification. LCMS (Method B): $t_R$=0.953 min, m/z=507.3, 508.3 [M+H]$^+$; ≥73% (AUC).

Step B: 5-Bromo-N-(3-chloro-5-((2-(diethylamino)ethyl)sulfonyl)phenyl)-2-methoxybenzenesulfonamide. Using a procedure analogous to General Procedure U, starting with crude 5-bromo-N-(3-chloro-5-((2-(diethylamino)ethyl)thio)phenyl)-2-methoxybenzenesulfonamide, the title compound was obtained as its corresponding TFA salt (8 mg, 0.01 mmol, 40% yield). $^1$H NMR (400 MHz, Chloroform-d) δ 8.55 (s, 1H), 7.97 (d, J=2.5 Hz, 1H), 7.65-7.55 (m, 3H), 7.52 (t, J=1.8 Hz, 1H), 6.89 (d, J=8.9 Hz, 1H), 3.93 (s, 3H), 3.77-3.69 (m, 2H), 3.49-3.41 (m, 2H), 3.19 (d, J=7.6 Hz, 4H), 1.33 (t, J=7.3 Hz, 6H). LCMS (Method B): $t_R$=0.914 min, m/z=539.2, 541.2 [M+H]$^+$; ≥94% (AUC).

Example S47: 5-Bromo-N-(3-chloro-5-((2-(diisopropylamino)ethyl)sulfonyl)phenyl)-2-methoxybenzenesulfonamide

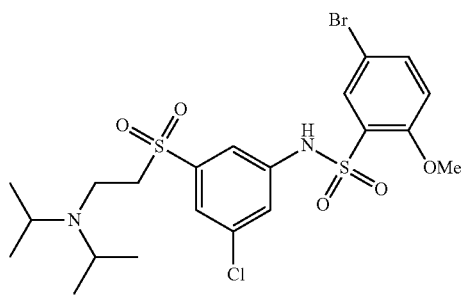 [SMILES: COc1ccc(Br)cc1S(=O)(=O)Nc1cc(Cl)cc(S(=O)(=O)CCN(C(C)C)C(C)C)c1]

Step A: 5-bromo-N-(3-chloro-5-((2-(diisopropylamino)ethyl)thio)phenyl)-2-methoxybenzenesulfonamide. Using a procedure analogous to General Procedure U, starting with 3-chloro-5-((2-(diisopropylamino)ethyl)thio)aniline (30 mg, 0.10 mmol, limiting reagent), which was prepared by a procedure analogous to Example S36 Step A, and 5-bromo-2-methoxybenzenesulfonyl chloride, 5-bromo-N-(3-chloro-5-((2-(diisopropylamino)ethyl)thio)phenyl)-2-methoxybenzenesulfonamide was obtained as an impure mixture (37 mg). LCMS (Method B): $t_R$=0.974 min, m/z=535.3, 537.3 [M+H]$^+$; ≥87% (AUC).

Step B: 5-Bromo-N-(3-chloro-5-((2-(diisopropylamino)ethyl)sulfonyl)phenyl)-2-methoxybenzenesulfonamide. Using a procedure analogous to General Procedure U, starting with impure 5-bromo-N-(3-chloro-5-((2-(diisopropylamino)ethyl)thio)phenyl)-2-methoxybenzenesulfonamide, the title compound was obtained as its corresponding TFA salt (14 mg, 0.01 mmol, 21% yield). $^1$H NMR (400 MHz, Chloroform-d) δ 8.41 (s, 1H), 7.98 (d, J=2.5 Hz, 1H), 7.70 (t, J=1.9 Hz, 1H), 7.61 (ddd, J=6.3, 4.0, 2.5 Hz, 2H), 7.52 (t, J=1.8 Hz, 1H), 6.90 (d, J=8.9 Hz, 1H), 3.97 (s, 3H), 3.94-3.86 (m, 2H), 3.70-3.62 (m, 2H), 3.43-3.35 (m, 2H), 1.38 (d, J=6.6 Hz, 12H). LCMS (Method B): $t_R$=0.959 min, m/z=567.3, 569.3 [M+H]$^+$; ≥95% (AUC).

Example S48: 5-Bromo-3-chloro-N-(5-chloro-2-hydroxy-3-(methylsulfonyl)phenyl)-2-methoxybenzenesulfonamide

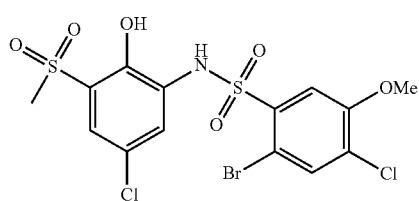 [SMILES: COc1cc(S(=O)(=O)Nc2cc(Cl)cc(S(C)(=O)=O)c2O)c(Br)cc1Cl]

Step A: 5-Bromo-3-chloro-2-methoxybenzenesulfonyl chloride. A mixture containing HBF$_4$ (6 µL, 0.098 mmol, 1 eq) and DCM ([0.5 M]) was cooled to 0° C. Then, 30 mg, 0.099 mmol, 1 eq) of 5-bromo-3-chloro-2-hydroxy-benzenesulfonyl chloride, which was prepared by a procedure analogous to the procedure used to prepare Example S7 Step A, was added. Three portions of a 2 M hexane solution of TMSCHN$_2$ [50 µL (0.099 mmol, 1 eq), 30 µL (0.059 mmol, 0.6 eq), 20 µL (0.039 mmol, 0.4 eq)] were added dropwise at intervals of 30 min. The reaction mixture was allowed to stir for an additional 40 min at 0° C., then poured into water and extracted with DCM. The organic phase was dried over a phase separator and the solvent removed under reduced pressure to afford 5-bromo-3-chloro-2-methoxybenzenesulfonyl chloride (23.0 mg, 0.072 mmol, 74%). $^1$H NMR (400 MHz, Chloroform-d) δ 8.00 (d, J=2.4 Hz, 1H), 7.88 (d, J=2.4 Hz, 1H), 4.12 (s, 3H). ≥95% pure by $^1$H-NMR.

Step B: 5-Bromo-3-chloro-N-(5-chloro-2-hydroxy-3-(methylsulfonyl)phenyl)-2-methoxybenzenesulfonamide. Using a procedure analogous to General Procedure E, starting with amino-4-chloro-6-(methylsulfonyl)phenol (21 mg, 0.239 mmol, limiting reagent), which was prepared by a procedure analogous to the procedure used to prepare Example S16 Step C, and 5-bromo-3-chloro-2-methoxybenzenesulfonyl chloride, the title compound was obtained after purification by preparative HPLC (24 mg, 0.048 mmol, 28%). $^1$H NMR (400 MHz, Chloroform-d) δ 7.72 (d, J=2.5 Hz, 1H), 7.70 (s, 1H), 7.66 (s, 1H), 7.35 (d, J=2.4 Hz, 1H), 3.96 (s, 3H), 3.12 (s, 3H). LCMS (Method B): $t_R$=1.090 min, m/z=523.1 [M+NH$_4$]$^+$; ≥95% (AUC).

Example S49: 5-Bromo-N-(5-chloro-2-hydroxy-3-(methylsulfonyl)phenyl)-2-methoxybenzenesulfonamide

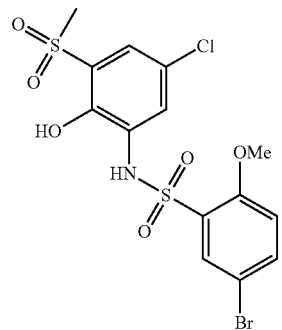 [SMILES: COc1ccc(Br)cc1S(=O)(=O)Nc1cc(Cl)cc(S(C)(=O)=O)c1O]

Using a procedure analogous to General Procedure E, starting with amino-4-chloro-6-(methylsulfonyl)phenol (50 mg, 0.23 mmol, limiting reagent), which was prepared by a procedure analogous to the procedure used to prepare Example S16 Step C, and 5-bromo-2-methoxybenzenesulfonyl chloride, the title compound was obtained after purification by preparative HPLC (3 mg, 0.006 mmol, 3%). $^1$H NMR (400 MHz, Chloroform-d) δ 9.24 (s, 1H), 8.00 (d, J=2.5 Hz, 1H), 7.82 (d, J=2.5 Hz, 1H), 7.68 (s, 1H), 7.63 (dd, J=8.8, 2.5 Hz, 1H), 7.34 (d, J=2.4 Hz, 1H), 6.89 (d, J=8.8 Hz, 1H), 3.96 (s, 3H), 3.11 (s, 3H). LCMS (Method B): $t_R$=1.055 min, m/z=489.2 [M+NH$_4$]$^+$; ≥95% (AUC).

Example S51: 5-Bromo-3-chloro-N-(3-chloro-5-((3-(dimethylamino)propyl)sulfonyl)phenyl)-2-hydroxybenzenesulfonamide

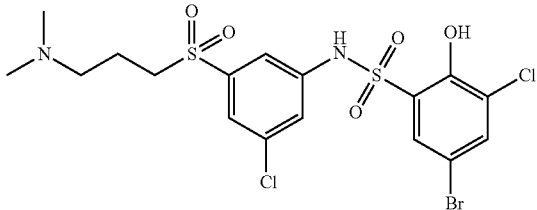 [SMILES: CN(C)CCCS(=O)(=O)c1cc(Cl)cc(NS(=O)(=O)c2cc(Br)cc(Cl)c2O)c1]

Step A: 3-Chloro-5-((3-(dimethylamino)propyl)thio)aniline. Using a procedure analogous to General Procedure W, starting with 3-bromo-5-chloroaniline (400 mg, 1.94 mmol, limiting reagent) and 3-bromo-N,N-dimethylpropan-1-amine hydrobromide, 3-chloro-5-((3-(dimethylamino)propyl)thio)aniline was obtained (168 mg, 0.69 mmol, 35% yield). $^1$H NMR (400 MHz, Chloroform-d) δ 6.66 (dt, J=2.5, 1.6 Hz, 1H), 6.48 (q, J=1.9 Hz, 1H), 6.44 (q, J=1.9 Hz, 1H), 3.73 (s, 2H), 2.91 (td, J=7.3, 1.7 Hz, 2H), 2.60 (d, J=1.7 Hz, 6H), 2.37 (td, J=7.1, 1.5 Hz, 3H), 1.79 (td, J=7.2, 1.6 Hz, 3H). LCMS (Method B): $t_R$=0.107 min, m/z=245.2, 246.4 [M+H]$^+$; ≥95 (AUC).

Step B: 5-Bromo-3-chloro-N-(3-chloro-5-((3-(dimethylamino)propyl)thio)phenyl)-2-hydroxybenzenesulfonamide. Using a procedure analogous to General Procedure E, starting with 3-chloro-5-((3-(dimethylamino)propyl)thio)aniline (50 mg, 0.20 mmol) and 5-bromo-3-chloro-2-hydroxy-benzenesulfonyl chloride, which was prepared by a procedure analogous to the procedure used to prepare Example S7 Step A, 5-bromo-3-chloro-N-(3-chloro-5-((3-(dimethylamino)propyl)thio)phenyl)-2-hydroxybenzenesulfonamide, was obtained as an impure mixture (57 mg). LCMS (Method B): $t_R$=0.957 min, m/z=515.2 [M+H]$^+$; ≥61% (AUC).

Step C: 5-Bromo-3-chloro-N-(3-chloro-5-((3-(dimethylamino)propyl)sulfonyl)phenyl)-2-hydroxybenzenesulfonamide. Using a procedure analogous to General Procedure U, starting with impure 5-bromo-3-chloro-N-(3-chloro-5-((3-(dimethylamino)propyl)thio)phenyl)-2-hydroxybenzenesulfonamide (57 mg), the title compound was obtained as its corresponding TFA salt (39 mg, 0.059 mmol, 30% yield). $^1$H NMR (400 MHz, Chloroform-d) δ 10.66 (s, 1H), 7.80 (d, J=2.4 Hz, 1H), 7.64 (d, J=2.4 Hz, 1H), 7.62-7.56 (m, 3H), 7.20 (s, 2H), 3.37 (s, 2H), 3.25 (t, J=6.9 Hz, 2H), 2.92 (d, J=2.5 Hz, 6H), 2.35-2.20 (m, 2H). LCMS (Method B): $t_R$=0.895 min, m/z=547.2 [M+H]$^+$; ≥95% (AUC).

Example S52: 5-Bromo-N-(3-chloro-5-((3-(dimethylamino)propyl)sulfonyl)phenyl)-2-hydroxybenzenesulfonamide

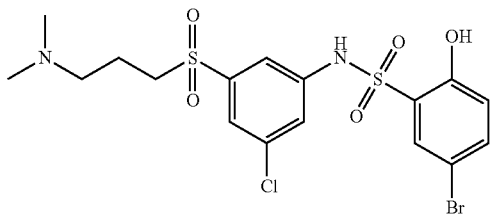 [SMILES: CN(C)CCCS(=O)(=O)c1cc(Cl)cc(NS(=O)(=O)c2cc(Br)ccc2O)c1]

Step A: 5-Bromo-N-(3-chloro-5-((3-(dimethylamino)propyl)thio)phenyl)-2-hydroxybenzenesulfonamide. Using a procedure analogous to General Procedure E, starting with 3-chloro-5-((3-(dimethylamino)propyl)thio)aniline (50 mg, 0.20 mmol), which was prepared by a procedure analogous to the procedure used to prepare Example S51 Step A, and 5-bromo-2-hydroxy-benzenesulfonyl chloride, which was prepared by a procedure analogous to the procedure used to prepare Example S6 Step A, 5-bromo-N-(3-chloro-5-((3-(dimethylamino)propyl)thio)phenyl)-2-hydroxybenzenesulfonamide was obtained as an impure mixture (35 mg, 0.073 mmol, 36% yield). LCMS (Method B): $t_R$=0.911 min, m/z=481.2 [M+H]$^+$; ≥95% (AUC).

Step B: 5-Bromo-N-(3-chloro-5-((3-(dimethylamino)propyl)sulfonyl)phenyl)-2-hydroxybenzenesulfonamide. Using a procedure analogous to General Procedure U, starting with impure 5-bromo-N-(3-chloro-5-((3-(dimethylamino)propyl)thio)phenyl)-2-hydroxybenzenesulfonamide (35 mg), the title compound was obtained as its corresponding TFA salt (6 mg, 0.0096 mmol, 14% yield). $^1$H NMR (400 MHz, Chloroform-d) δ 8.53 (s, 1H), 7.89 (d, J=2.5 Hz, 1H), 7.68 (t, J=1.4 Hz, 2H), 7.63 (t, J=1.7 Hz, 1H), 7.48 (dd, J=8.8, 2.5 Hz, 1H), 6.93 (d, J=8.8 Hz, 1H), 3.35 (t, J=7.6 Hz, 2H), 3.25 (t, J=6.9 Hz, 2H), 2.92 (s, 4H), 2.32-2.26 (m, 2H). LCMS (Method B): $t_R$=0.867 min, m/z=513.2 [M+H]$^+$; ≥95% (AUC).

Example S54: 5-Bromo-3-chloro-N-(5-chloro-2-fluoro-3-(methylsulfonyl)phenyl)-2-hydroxybenzenesulfonamide

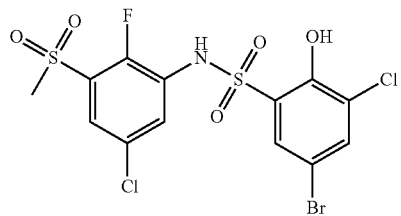 [SMILES: CS(=O)(=O)c1cc(Cl)cc(NS(=O)(=O)c2cc(Br)cc(Cl)c2O)c1F]

Step A: 3-Bromo-5-chloro-2-fluoroaniline. Using a procedure analogous to General Procedure D, starting with 1-bromo-5-chloro-2-fluoro-3-nitrobenzene (200 mg, 0.79 mmol, limiting reagent), 3-bromo-5-chloro-2-fluoroaniline was obtained (134 mg, 0.60 mmol, 76% yield). 1H NMR (400 MHz, Chloroform-d) δ 6.87 (dd, J=5.3, 2.5 Hz, 1H), 6.69 (dd, J=7.1, 2.5 Hz, 1H), 3.89 (s, 2H). LCMS (Method B): $t_R$=1.030 min, m/z=288.4 [M+CAN+Na]$^+$; ≥95% (AUC).

Step B: 5-Chloro-2-fluoro-3-(methylsulfonyl)aniline. Using a procedure analogous to General Procedure S, starting with 3-bromo-5-chloro-2-fluoroaniline (134 mg, 0.60 mmol, limiting reagent), 5-chloro-2-fluoro-3-(methylsulfonyl)aniline was obtained (6 mg, 0.045 mmol, 7% yield). $^1$H NMR (400 MHz, Chloroform-d) δ 7.23 (dd, J=5.1, 2.5 Hz, 1H), 7.01 (dd, J=7.3, 2.6 Hz, 1H), 4.07 (s, 2H), 3.24-3.18 (m, 3H). $^{19}$F NMR (376 MHz, Chloroform-d) δ −136.22. LCMS (Method B): $t_R$=0.116 min, m/z=224.2 [M+H]$^+$; ≥95% (AUC).

Step C: 5-Bromo-3-chloro-N-(5-chloro-2-fluoro-3-(methylsulfonyl)phenyl)-2-hydroxybenzenesulfonamide. Using a procedure analogous to General Procedure E except that DCM was substituted with more pyridine, starting with 5-chloro-2-fluoro-3-(methylsulfonyl)aniline (20 mg, 0.10 mmol) and 5-bromo-3-chloro-2-hydroxy-benzenesulfonyl chloride, which was prepared by a procedure analogous to the procedure used to prepare Example S7 Step A, the title compound was obtained (3 mg, 0.0061 mmol, 6% yield). $^1$H NMR (400 MHz, Chloroform-d) δ 7.85 (dd, J=6.4, 2.6 Hz, 1H), 7.82 (d, J=2.4 Hz, 1H), 7.73 (d, J=2.4 Hz, 1H), 7.70 (dd, J=5.6, 2.6 Hz, 1H), 7.30 (s, 1H), 3.16 (s, 3H). $^{19}$F NMR (376 MHz, Chloroform-d) δ −132.69 (t, J=6.4 Hz). LC-MS: $t_R$=1.070 min, m/z=510.2, 511.1 [M+NH$_4$]$^+$; ≥89% (AUC).

Example S55: 5-Bromo-N-(5-chloro-2-hydroxy-3-(methylsulfonyl)phenyl)-2,3-dihydrobenzofuran-7-sulfonamide

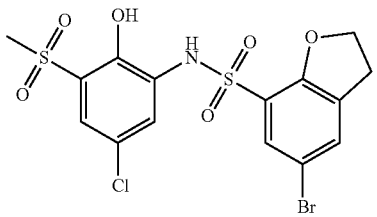 [SMILES: CS(=O)(=O)c1cc(Cl)cc(NS(=O)(=O)c2cc(Br)cc3c2OCC3)c1O]

Using a procedure analogous to General Procedure E, starting with amino-4-chloro-6-(methylsulfonyl)phenol (20 mg, 0.090 mmol, limiting reagent), which was prepared by a procedure analogous to the procedure used to prepare Example S16 Step C, and 5-bromo-2,3-dihydrobenzofuran-7-sulfonyl chloride, the title compound was obtained after purification by preparative HPLC (10 mg, 0.021 mmol, 23%). $^1$H NMR (400 MHz, Chloroform-d) δ 9.20 (s, 1H), 7.79 (d, J=2.4 Hz, 1H), 7.71 (d, J=2.0 Hz, 1H), 7.54 (s, 1H), 7.48 (d, J=1.8 Hz, 1H), 7.35 (d, J=2.4 Hz, 1H), 4.76 (t, J=8.8 Hz, 2H), 3.27 (t, J=8.8 Hz, 2H), 3.12 (s, 3H). LCMS (Method B): $t_R$=1.035 min, m/z=288.4 [M+ACN+Na]$^+$; ≥95% (AUC).

Example S59: 5-Bromo-N-(5-(1-cyanocyclobutyl)-2-hydroxy-3-(methylsulfonyl)phenyl)-2-methoxy-benzenesulfonamide

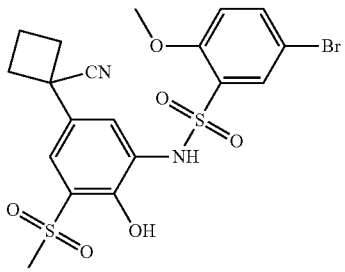 [SMILES: COc1ccc(Br)cc1S(=O)(=O)Nc1cc(C2(C#N)CCC2)cc(S(C)(=O)=O)c1O]

Step A: 1-(3-Bromo-4-methoxyphenyl)cyclobutane-1-carbonitrile (JDM-10-143). To a mixture containing 2-(3-bromo-4-methoxyphenyl)acetonitrile (4.52 g, 20 mmol) and 1,3-dibromopropane (2.23 mL, 22 mmol) in DMSO (100 mL) was added NaH (60% dispersion in mineral oil, 2.0 g, 50 mmol) portion-wise. The reaction mixture was allowed to stir for 16 h at r.t., then diluted with EtOAc:Et$_2$O (200 mL, 1:1) and washed with water (3×400 mL). The combined aqueous layers were back-extracted with further EtOAc (200 mL). The combined organics were washed with saturated aqueous. NaCl, concentrated, and purified by ISCO flash column chromatography (120 g, 0-25% EtOAc in hexanes) to afford a colorless oil (3.65 g, 13.7 mmol, 68%). $^1$H NMR (400 MHz, CDCl$_3$) δ$_H$ 7.61 (d, J=2.4 Hz, 1H), 7.34 (dd, J=8.6, 2.4 Hz, 1H), 6.93 (d, J=8.6 Hz, 1H), 3.93 (s, 3H), 2.88-2.78 (m, 2H), 2.66-2.54 (m, 2H), 2.44 (dt, J=11.6, 8.7 Hz, 1H), 2.16-2.04 (m, 1H); LCMS (Method A) $t_R$=1.10 min, no mass observed; ≥95% (AUC).

Step B: 1-(4-Methoxy-3-(methylthio)phenyl)cyclobutane-1-carbonitrile. Using a procedure analogous to General Procedure Z, starting with 1-(3-bromo-4-methoxyphenyl)cyclobutane-1-carbonitrile (200 mg, 0.751 mmol, limiting reagent), 1-(4-methoxy-3-(methylthio)phenyl)cyclobutane-1-carbonitrile was obtained as a yellow oil (174 mg, 0.746 mmol, 99% yield). $^1$H NMR (400 MHz, Chloroform-d) δ 7.21-7.13 (m, 2H), 6.87-6.80 (m, 1H), 3.90 (s, 3H), 2.81 (dddt, J=13.6, 7.0, 4.3, 2.6 Hz, 2H), 2.59 (dt, J=9.8, 8.0 Hz, 2H), 2.45 (s, 3H), 2.43-2.36 (m, 1H), 2.06 (tdd, J=9.1, 7.3, 4.5 Hz, 1H). LCMS (Method B) $t_R$=1.035 min, m/z=234.2 [M+H]$^+$; ≥90% (AUC).

Step C: 1-(4-Methoxy-3-(methylsulfonyl)phenyl)cyclobutane-1-carbonitrile. Using a procedure analogous to General Procedure U, starting with 1-(4-methoxy-3-(methylthio)phenyl)cyclobutane-1-carbonitrile (174 mg, 0.671 mmol, limiting reagent), 1-(4-methoxy-3-(methylsulfonyl)phenyl)cyclobutane-1-carbonitrile was obtained as a pale-yellow solid (188 mg, 0.58 mmol, 87% yield) that was used with no further purification. $^1$H NMR (400 MHz, Chloroform-d) δ 8.01 (d, J=2.5 Hz, 1H), 7.64 (dd, J=8.7, 2.6 Hz, 1H), 7.08 (d, J=8.7 Hz, 1H), 4.02 (s, 3H), 3.24 (s, 3H), 2.90-2.79 (m, 2H), 2.67-2.55 (m, 2H), 2.44 (dt, J=11.6, 8.7 Hz, 1H), 2.09 (ddt, J=11.7, 9.0, 4.5 Hz, 1H). LCMS (Method B) $t_R$=0.724 min, m/z=269.2 [M+NH$_4$]$^+$; ≥87% pure by H-NMR.

Step D: 1-(4-Hydroxy-3-(methylsulfonyl)phenyl)cyclobutane-1-carbonitrile. Using a procedure analogous to General Procedure O, starting with 1-(3-bromo-4-methoxyphenyl)cyclobutane-1-carbonitrile (188 mg, 0.58 mmol, limiting reagent), 1-(4-hydroxy-3-(methylsulfonyl)phenyl)cyclobutane-1-carbonitrile was obtained (170 mg) as a crude material that was used with no further purification. $^1$H NMR (400 MHz, Chloroform-d) δ 8.85 (s, 1H), 7.71 (d, J=2.5 Hz, 1H), 7.59 (dd, J=8.7, 2.5 Hz, 1H), 7.11 (d, J=8.7 Hz, 1H), 3.17 (s, 3H), 2.85 (ddd, J=14.5, 6.7, 3.5 Hz, 2H), 2.60 (qd, J=9.1, 2.5 Hz, 2H), 2.46 (dt, J=11.7, 8.8 Hz, 1H), 2.09 (ddt, J=11.6, 8.9, 4.6 Hz, 1H). LCMS (Method B) $t_R$=0.724 min, m/z=269.2 [M+H]$^+$; ≥85% pure by H-NMR.

Step E: 1-(4-Hydroxy-3-(methylsulfonyl)-5-nitrophenyl)cyclobutane-1-carbonitrile. Using a procedure analogous to General Procedure B, starting with crude 1-(4-hydroxy-3-(methylsulfonyl)phenyl)cyclobutane-1-carbonitrile (170 mg), 1-(4-hydroxy-3-(methylsulfonyl)-5-nitrophenyl)cyclobutane-1-carbonitrile obtained (145 mg, 0.489 mmol, 84% yield). $^1$H NMR (400 MHz, Chloroform-d) δ 8.41 (d, J=2.5 Hz, 1H), 8.33 (dt, J=2.2, 1.0 Hz, 1H), 3.34 (s, 3H), 2.95-2.84 (m, 2H), 2.63 (qd, J=9.2, 2.4 Hz, 2H), 2.50 (dq, J=11.8, 8.5 Hz, 1H), 2.19-2.06 (m, 1H). LCMS (Method B) $t_R$=0.654 min, m/z=314.3 [M+NH$_4$]$^+$, 95% (AUC).

Step F: 1-(3-Amino-4-hydroxy-5-(methylsulfonyl)phenyl)cyclobutane-1-carbonitrile. Using a procedure analogous to General Procedure C, starting with 1-(4-hydroxy-3-(methylsulfonyl)-5-nitrophenyl)cyclobutane-1-carbonitrile (145 mg, 0.489 mmol, limiting reagent), 1-(3-amino-4-hydroxy-5-(methylsulfonyl)phenyl)cyclobutane-1-carbonitrile was obtained (122 mg, 0.458 mmol, 94% yield). $^1$H NMR (400 MHz, Chloroform-d) δ 7.01 (d, J=2.2 Hz, 1H), 6.93 (d, J=2.2 Hz, 1H), 3.13 (s, 3H), 2.78 (ddt, J=10.9, 8.7, 3.3 Hz, 2H), 2.56 (qd, J=9.1, 2.5 Hz, 2H), 2.41 (dt, J=11.5, 8.8 Hz, 1H), 2.05 (tdd, J=9.0, 7.9, 4.4 Hz, 1H). LCMS (Method B) $t_R$=0.626 min, m/z=267.2 [M+H]$^+$, ≥95% pure by H-NMR.

Step G: 5-Bromo-N-(5-(1-cyanocyclobutyl)-2-hydroxy-3-(methylsulfonyl)phenyl)-2-methoxybenzenesulfonamide. Using a procedure analogous to General Procedure E, starting with 1-(3-amino-4-hydroxy-5-(methylsulfonyl)phenyl)cyclobutane-1-carbonitrile (20 mg, 0.075 mmol) and 5-bromo-2-methoxy-benzenesulfonyl chloride, the title compound was obtained (8 mg, 0.016 mmol, 21% yield). $^1$H NMR (400 MHz, Chloroform-d) δ 9.34 (s, 1H), 8.00 (d, J=2.5 Hz, 1H), 7.82 (d, J=2.3 Hz, 1H), 7.70 (s, 1H), 7.62 (dd, J=8.8, 2.5 Hz, 1H), 7.37 (d, J=2.3 Hz, 1H), 6.89 (d, J=8.9 Hz, 1H), 3.96 (s, 3H), 3.13 (s, 3H), 2.87-2.76 (m, 2H), 2.47 (ddt, J=17.4, 10.8, 8.9 Hz, 3H), 2.13-2.02 (m, 1H). LC-MS: $t_R$=1.008 min, m/z=515.2 [M+H]$^+$; ≥95% (AUC).

Example S60: 5-Bromo-3-chloro-N-(5-(1-cyanocyclobutyl)-2-hydroxy-3-(methylsulfonyl)phenyl)-2-hydroxybenzenesulfonamide

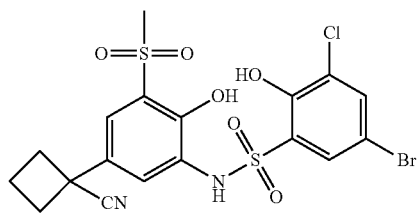 [SMILES: CS(=O)(=O)c1cc(C2(C#N)CCC2)cc(NS(=O)(=O)c2cc(Br)cc(Cl)c2O)c1O]

Using a procedure analogous to General Procedure E, starting with 1-(3-amino-4-hydroxy-5-(methylsulfonyl)phenyl)cyclobutane-1-carbonitrile (15 mg, 0.056 mmol), which was prepared by a procedure analogous to the procedure used to prepare Example S59 Step F, and 5-bromo-3-chloro-2-hydroxy-benzenesulfonyl chloride, which was prepared by a procedure analogous to the procedure used to prepare Example S7 Step A, the title compound was obtained (8 mg, 0.015 mmol, 27% yield). $^1$H NMR (400 MHz, Acetonitrile-d$_3$) δ 7.81 (d, J=2.4 Hz, 1H), 7.69 (d, J=2.4 Hz, 1H), 7.61 (d, J=2.4 Hz, 1H), 7.46 (d, J=2.4 Hz, 1H), 3.16 (s, 3H), 2.77-2.70 (m, 2H), 2.53-2.45 (m, 2H), 2.34 (dq, J=11.5, 8.6 Hz, 1H), 2.06-1.97 (m, 1H). LC-MS: $t_R$=1.015 min, m/z=552.2, 553.2 [M+NH$_4$]$^+$; ≥95% (AUC).

Example S61: 6-Bromo-N-(5-(1-cyanocyclobutyl)-2-hydroxy-3-(methylsulfonyl)phenyl)quinoline-8-sulfonamide

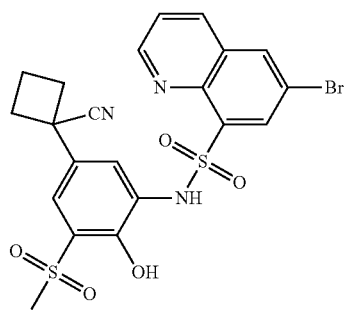 [SMILES: CS(=O)(=O)c1cc(C2(C#N)CCC2)cc(NS(=O)(=O)c2cc(Br)cc3cccnc23)c1O]

Using a procedure analogous to General Procedure E, starting with 1-(3-amino-4-hydroxy-5-(methylsulfonyl)phenyl)cyclobutane-1-carbonitrile (21 mg, 0.079 mmol), which was prepared by a procedure analogous to the procedure used to prepare Example S59 Step F, and 6-bromoquinoline-8-sulfonyl chloride, the title compound was obtained (16 mg, 0.030 mmol, 38% yield). $^1$H NMR (400 MHz, Chloroform-d) δ 9.11 (dd, J=4.4, 1.6 Hz, 1H), 8.46 (d, J=2.1 Hz, 1H), 8.25-8.17 (m, 2H), 7.93 (d, J=2.3 Hz, 1H), 7.62 (dd, J=8.4, 4.3 Hz, 1H), 7.37 (d, J=2.3 Hz, 1H), 3.06 (s, 3H), 2.82 (ddd, J=11.9, 8.5, 4.1 Hz, 2H), 2.59-2.51 (m, 2H), 2.44 (dq, J=11.5, 8.7, 8.1 Hz, 1H), 2.14-2.04 (m, 1H). LCMS (Method B): $t_R$=1.015 min, m/z=552.2, 553.2 [M+H]$^+$; ≥95% (AUC).

Example S62: 5-Bromo-3-chloro-N-(5-(1-cyanocyclobutyl)-2-hydroxy-3-(methylsulfonyl)phenyl)-2-methoxybenzenesulfonamide

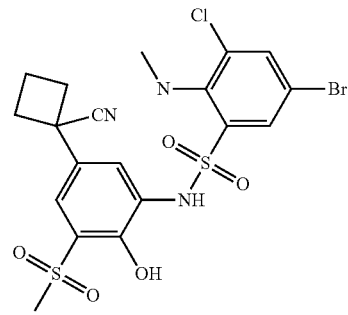 [SMILES: CNc1c(Cl)cc(Br)cc1S(=O)(=O)Nc1cc(C2(C#N)CCC2)cc(S(C)(=O)=O)c1O]

Using a procedure analogous to General Procedure E, starting with 1-(3-amino-4-hydroxy-5-(methylsulfonyl)phenyl)cyclobutane-1-carbonitrile (20 mg, 0.075 mmol), which was prepared by procedure analogous to the procedure used to prepare Example S59 Step F, and 5-bromo3-chloro-2-methoxy-benzenesulfonyl chloride, the title compound was obtained (2 mg, 0.004 mmol, 5% yield). $^1$H NMR (400 MHz, Chloroform-d) δ 7.96 (d, J=2.4 Hz, 1H), 7.86 (d, J=2.4 Hz, 1H), 7.33 (d, J=2.3 Hz, 1H), 7.10 (d, J=2.4 Hz, 1H), 4.13 (s, 3H), 3.01 (s, 3H), 2.85-2.77 (m, 2H), 2.65-2.57 (m, 3H), 2.49-2.40 (m, 2H), 2.08 (ddd, J=16.5, 9.1, 4.6 Hz, 2H). LCMS (Method B): $t_R$=1.146 min, m/z=549.2, 550.2 [M+H]$^+$; ≥95% (AUC).

Example S72: 5-Bromo-3-chloro-N-(3-(1-cyanocyclobutyl)-5-(methylsulfonyl)phenyl)-2-hydroxybenzenesulfonamide

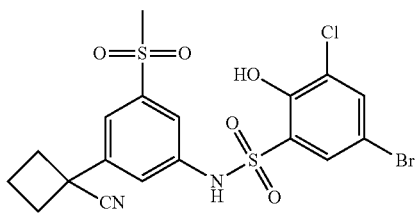 [SMILES: CS(=O)(=O)c1cc(NS(=O)(=O)c2cc(Br)cc(Cl)c2O)cc(C2(C#N)CCC2)c1]

Step A: 3-Methyl-5-(methylsulfonyl)aniline. Using a procedure analogous to General Procedure S, starting with 3-bromo-5-methylaniline (2000 mg, 10.75 mmol, limiting reagent) and sodium sulfonate, 3-methyl-5-(methylsulfonyl)

aniline was obtained (1196 mg, 6.46 mmol, 60% yield). $^{13}$C NMR (101 MHz, Chloroform-d) δ 147.39, 141.46, 140.94, 120.49, 117.65, 110.39, 44.55, 21.49. $^1$H NMR (400 MHz, Chloroform-d) δ 7.10 (dt, J=1.6, 0.8 Hz, 1H), 7.01 (t, J=2.2 Hz, 1H), 6.71 (ddd, J=2.3, 1.5, 0.8 Hz, 1H), 3.90 (s, 2H), 3.01 (s, 3H), 2.36-2.31 (m, 3H). LCMS (Method B) $t_R$=0.111 min, m/z=371.4 [2M+H]$^+$, ≥95% (AUC).

Step B: tert-Butyl (3-methyl-5-(methylsulfonyl)phenyl) carbamate. A mixture containing 3-methyl-5-(methylsulfonyl)aniline (1196 mg, 6.46 mmol, 1 eq) and di-tert-butyl decarbonate (1671 mg, 7.66 mmol, 1.2 eq) in MeOH ([0.30 M]) was allowed to stir overnight at room temperature. The solvent was removed under reduced pressure and the crude material was purified by ISCO flash chromatography to give 826 mg (2.89 mmol, 45% yield) of tert-butyl (3-methyl-5-(methylsulfonyl)phenyl) carbamate. $^1$H NMR (400 MHz, Chloroform-d) δ 7.71 (t, J=2.0 Hz, 1H), 7.56 (s, 1H), 7.39 (d, J=1.8 Hz, 1H), 6.86 (s, 1H), 3.03 (s, 3H), 2.39 (s, 3H), 1.51 (s, 9H). LCMS (Method B) $t_R$=0.916 min, m/z=303.2 [M+NH$_4$]$^+$, ≥95% (AUC).

Step C: tert-Butyl (3-(bromomethyl-5-(methylsulfonyl) phenyl) carbamate. A mixture containing tert-butyl (3-methyl-5-(methylsulfonyl)phenyl) carbamate (826 mg, 2.89 mmol, 1 eq) and NBS (618 mg, 3.47 mmol, 1.2 eq) was dissolved in CCl$_4$ ([0.13 M]) and the solution was bubbled with Ar for 10 min. To this mixture was added AIBN (119 mg, 724 mmol, 0.25 eq) and the reaction mixture was heated at 80° C. overnight. The reaction mixture was allowed to cool to rt and filtered. The filtrate was washed first with HCl [1 M] and then with a saturated solution of NaHCO$_3$. The organic phase was dried using a phase separator and the solvent was removed under reduced pressure. The crude material was purified using ISCO flash chromatography to give 961 mg of tert-butyl (3-(bromomethyl-5-(methylsulfonyl)phenyl) carbamate as a mixture that also contains dibrominated material. $^1$H NMR (400 MHz, Chloroform-d) δ 7.84 (d, J=1.8 Hz, 1H), 7.60 (s, 1H), 6.88 (s, 1H), 4.47 (s, 2H), 3.06 (s, 3H), 1.52 (s, 9H). LCMS (Method B) $t_R$=0.952 min, m/z=381.3, 383.2 [M+NH$_4$]$^+$.

Step D: tert-Butyl (3-(cyanomethyl-5-(methylsulfonyl) phenyl) carbamate. A mixture containing tert-butyl (3-(bromomethyl-5-(methylsulfonyl)phenyl) carbamate (961 mg) and 5.0 mL of MeCN was cooled to 0° C. Then, K$_2$CO$_3$ (438 mg, 3.17 mmol, 1.2 eq) and TMSCN (0.420 mL, 3.17 mmol, 1.2 eq) were added. The reaction mixture was heated at 50° C. overnight. The reaction mixture was allowed to cool to rt and NaOH [3 M] was added. The reaction mixture was extracted with EtOAc, and the organic phase was dried using a phase separator. The solvents were removed under reduced pressure and the residue was purified using ISCO flash chromatography to give 441 mg (1.42 mmol, 49% yield) of tert-butyl (3-(cyanomethyl-5-(methylsulfonyl)phenyl) carbamate. $^{13}$C NMR (101 MHz, Chloroform-d) δ 152.45, 142.18, 140.87, 132.85, 122.51, 120.43, 117.00, 116.67, 81.82, 44.39, 28.32, 23.65. $^1$H NMR (400 MHz, Chloroform-d) δ 7.89 (t, J=1.8 Hz, 1H), 7.77 (s, 1H), 7.55 (t, J=1.7 Hz, 1H), 6.82 (s, 1H), 3.81 (s, 2H), 3.07 (s, 3H), 1.53 (s, 9H). LCMS (Method B) $t_R$=0.849 min, m/z=328.3 [M+NH$_4$]$^+$, ≥95% (AUC).

Step E: tert-Butyl (3-(1-cyanocyclobutyl)-5-(methylsulfonyl)phenyl) carbamate. To a mixture containing tert-butyl (3-(cyanomethyl-5-(methylsulfonyl)phenyl) carbamate (421 mg, 1.36 mmol, 1 eq) and 1,3-dibromopropane (151 μL, 1.49 mmol, 1.1 eq) in 7.0 mL of DMSO ([0.2 M]) was added NaH (140 mg, 3.39 mmol, 2.5 eq). The reaction mixture was allowed to stir overnight at room temperature, then quenched by the addition of water and extracted with EtOAc. The organic phase was dried over a phase separator and the solvent was removed under reduced pressure. The crude material was purified using ISCO flash chromatography to give 311 mg, (0.887 mmol, 65% yield) of tert-butyl (3-(1-cyanocyclobutyl)-5-(methylsulfonyl)phenyl) carbamate. $^{13}$C NMR (101 MHz, Chloroform-d) δ 152.45, 142.54, 142.06, 140.80, 123.52, 120.57, 118.02, 116.51, 81.65, 44.40, 40.13, 34.57, 28.30, 17.14. $^1$H NMR (400 MHz, Chloroform-d) 67.93 (d, J=1.8 Hz, 1H), 7.79 (d, J=2.1 Hz, 1H), 7.57 (dt, J=3.3, 1.6 Hz, 1H), 7.30 (s, 1H), 3.06 (s, 3H), 2.87-2.76 (m, 2H), 2.62 (qd, J=9.2, 4.4 Hz, 2H), 2.43 (dt, J=11.9, 8.8 Hz, 1H), 2.13-2.04 (m, 1H), 1.50 (s, 9H). LCMS (Method B) $t_R$=0.994 min, m/z=368.3 [M+NH$_4$]$^+$, ≥95% (AUC).

Step F: 1-(3-Amino-5-(methylsulfonyl)phenyl)cyclobutene-1-carbonitrile. A mixture containing the with tert-butyl (3-(1-cyanocyclobutyl)-5-(methylsulfonyl)phenyl) carbamate (311 mg, 0.887 mmol, limiting reagent), and a 4 M solution of HCl in dioxane was heated at 50° C. for 1-4 hours. The solvent was removed under vacuum to obtain, 1-(3-amino-5-(methylsulfonyl)phenyl)cyclobutene-1-carbonitrile as a crude material that was used without further purification (253 mg). $^1$H NMR (400 MHz, Chloroform-d) δ 8.14 (s, 1H), 7.96 (s, 1H), 7.82 (s, 1H), 3.09 (s, 3H), 2.79 (s, 2H), 2.61 (d, J=11.4 Hz, 2H), 2.44-2.34 (m, 1H), 2.07 (s, 1H). LCMS (Method B) $t_R$=0.588 min, m/z=251.0 [M+H]$^+$, ≥83% (AUC).

Step G: 5-Bromo-3-chloro-N-(3-(1-cyanocyclobutyl)-5-(methylsulfonyl)phenyl)-2-hydroxybenzenesulfonamide. Using a procedure analogous to General Procedure E, starting with crude 1-(3-amino-5-(methylsulfonyl)phenyl)cyclobutene-1-carbonitrile (83 mg) and 5-bromo-3-chloro-2-hydroxy-benzenesulfonyl chloride, which was prepared by a procedure analogous to the procedure used to prepare Example S7 Step A, the title compound was obtained (55 mg, 0.11 mmol). $^1$H NMR (400 MHz, Chloroform-d) δ 7.90 (s, 1H), 7.78 (d, J=2.4 Hz, 1H), 7.73 (d, J=1.6 Hz, 1H), 7.67 (d, J=2.4 Hz, 1H), 7.62 (d, J=1.8 Hz, 1H), 7.53 (t, J=1.9 Hz, 1H), 3.08 (s, 3H), 2.86 (ddt, J=11.8, 8.1, 2.9 Hz, 2H), 2.64-2.52 (m, 2H), 2.52-2.42 (m, 1H), 2.12 (dp, J=11.3, 4.4 Hz, 1H). LCMS (Method A) $t_R$=1.812 min, m/z=518.9, 521.9 [M+NH$_4$]$^+$, ≥95% (AUC).

Example S73: 5-bromo-N-(3-(1-cyanocyclobutyl)-5-(methylsulfonyl)phenyl)-2-hydroxybenzenesulfonamide

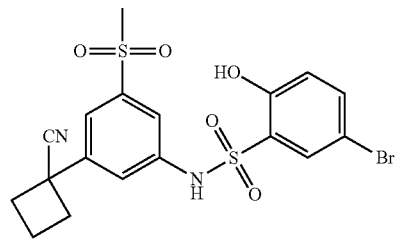 [SMILES: CS(=O)(=O)c1cc(NS(=O)(=O)c2cc(Br)ccc2O)cc(C2(C#N)CCC2)c1]

Using a procedure analogous to General Procedure E, starting with crude 1-(3-amino-5-(methylsulfonyl)phenyl) cyclobutene-1-carbonitrile (82 mg), which was prepared by a procedure analogous to the procedure used to prepare Example S72 Step F, and 5-bromo-2-hydroxy-benzenesulfonyl chloride, which was prepared by a procedure analogous to the procedure used to prepare Example S6 Step A, the title compound was obtained (62 mg, 0.13 mmol). $^1$H NMR (400 MHz, Chloroform-d) δ 8.32 (s, 1H), 7.77 (d, J=2.4 Hz, 1H), 7.71 (t, J=1.6 Hz, 1H), 7.64 (q, J=2.6, 1.8 Hz, 1H), 7.53 (t, J=1.9 Hz, 1H), 7.47 (dd, J=8.8, 2.5 Hz, 1H), 6.88 (d, J=8.8 Hz, 1H), 3.08 (s, 3H), 2.90-2.80 (m, 2H), 2.63-2.54 (m, 2H), 2.54-2.40 (m, 1H), 2.11 (ddq, J=11.5, 9.1, 4.7, 4.1 Hz, 1H). LCMS (Method A) $t_R$=1.715 min, m/z=484.9, 486.9 [M+H]$^+$, ≥95% (AUC).

Example NE1: 5-Bromo-N-(5-chloro-2-hydroxy-3-nitrophenyl)-2-methoxybenzenesulfonamide

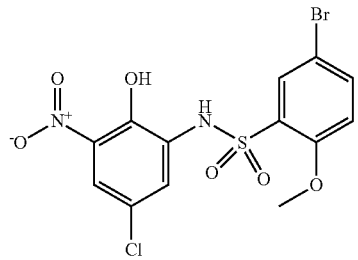

Using a procedure analogous to General Procedure E, starting with 5-bromo-2-methoxybenzenesulfonyl chloride and 2-amino-4-chloro-6-nitrophenol, the title compound was obtained. LCMS (Method A) $t_R$=1.679 min, m/z=438 [M+H]$^+$; Purity (AUC) ≥98%.

Example NE2: 5-Chloro-N-(5-chloro-2-hydroxy-3-nitrophenyl)-2-methoxybenzenesulfonamide

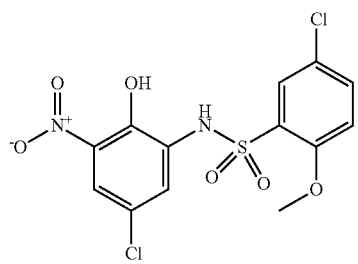

Using a procedure analogous to General Procedure E, starting with 5-chloro-2-methoxybenzenesulfonyl chloride and 2-amino-4-chloro-6-nitrophenol, the title compound was obtained. LCMS (Method A) $t_R$=1.658 min, m/z=394 [M+H]$^+$; Purity (AUC) ≥98%.

Example NE3: 2-Bromo-N-(5-chloro-2-hydroxy-3-nitrophenyl)-4-ethyl-5-hydroxybenzenesulfonamide

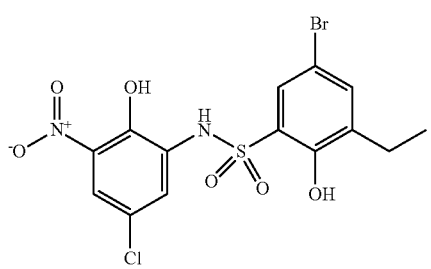

Using a procedure analogous to General Procedure E, starting with 2-amino-4-chloro-6-nitrophenol and 5-bromo-3-ethyl-2-hydroxybenzenesulfonyl chloride, which was prepared by a procedure analogous to the procedure used to prepare Example HCH-2 Step A, the title compound was obtained. LCMS (Method A) $t_R$=1.789 min, m/z=469 [M+H$_2$O]$^+$; Purity (AUC) ≥80%.

Example NE4: Methyl 4-chloro-2-(N-(5-chloro-2-hydroxy-3-nitrophenyl)sulfamoyl)benzoate

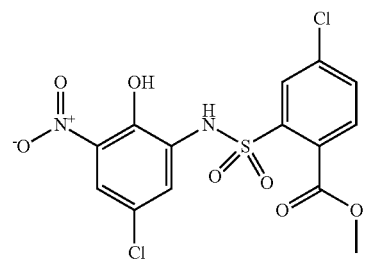

Using a procedure analogous to General Procedure E, starting with 2-amino-4-chloro-6-nitrophenol and methyl 4-bromo-2-(chlorosulfonyl)benzoate, the title compound was obtained. LCMS (Method A) $t_R$=1.782 min, m/z=452 [M+H]$^+$; Purity (AUC) ≥98%.

Example NE5: Methyl 4-chloro-2-(N-(5-chloro-2-hydroxy-3-nitrophenyl)sulfamoyl)benzoate

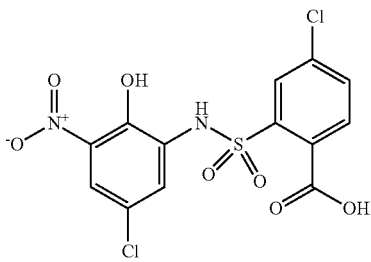

Using a procedure analogous to General Procedure F, starting from methyl 4-chloro-2-(N-(5-chloro-2-hydroxy-3-nitrophenyl)sulfamoyl)benzoate, which which was prepared by a procedure analogous to the procedure used to prepare Example NE4, the title compound was obtained. LCMS (Method A) $t_R$=1.716 min, m/z=422 [M+H]$^+$; Purity (AUC) ≥90%.

Example NE6: 5-Bromo-N-(5-chloro-2-hydroxy-3-nitrophenyl)-2-hydroxybenzenesulfonamide

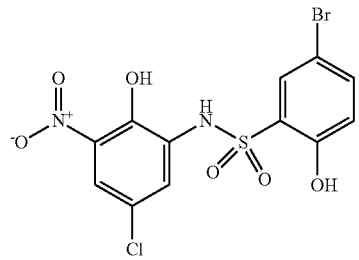

Using a procedure analogous to General Procedure E, starting with 2-amino-4-chloro-6-nitrophenol and 5-bromo-2-hydroxybenzenesulfonyl chloride, which was prepared by a procedure analogous to the procedure used to prepare Example J1 Step A, the title compound was obtained. LCMS (Method A) $t_R$=1.576 min, m/z=425 [M+H]$^+$; Purity (AUC) ≥98%.

Example NE7: 5-Bromo-N-(5-chloro-2-hydroxy-3-nitrophenyl)-2,3-dihydrobenzofuran-7-sulfonamide

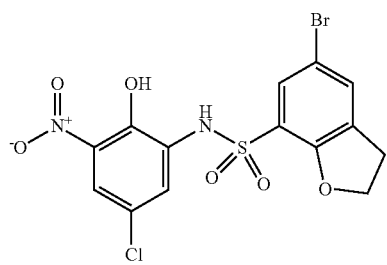

Using a procedure analogous to General Procedure E, starting with 2-amino-4-chloro-6-nitrophenol and 5-bromo-2,3-dihydrobenzofuran-7-sulfonyl chloride, the title compound was obtained. LCMS (Method A) $t_R$=1.48 min, m/z=449,451 [M+H]$^+$; Purity (AUC) ≥95%.

Example NE8: 5-Bromo-N-(5-chloro-2-hydroxy-3-nitrophenyl)-2,4-dimethoxybenzenesulfonamide

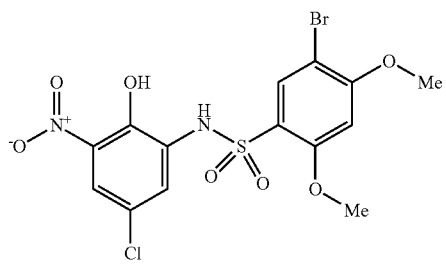

Using a procedure analogous to General Procedure E, starting with 2-amino-4-chloro-6-nitrophenol and 5-bromo-2,4-dimethoxybenzenesulfonyl chloride, the title compound was obtained. LCMS (Method A) $t_R$=1.661 min, m/z=450 [M+H]$^+$; Purity (AUC) 298%.

Example NE9: 5-Bromo-N-(5-chloro-2-hydroxy-3-nitrophenyl)-2-hydroxy-3-(trifluoromethoxy)benzenesulfonamide

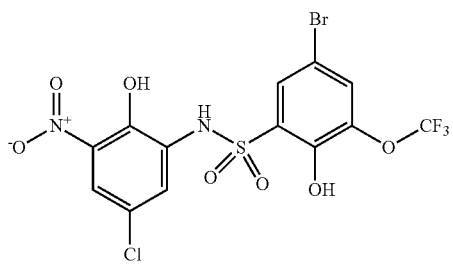

Using a procedure analogous to General Procedure E, starting with 2-amino-4-chloro-6-nitrophenol and 5-bromo-2-hydroxy-3-(trifluoromethoxy)benzenesulfonyl chloride, which was prepared by a procedure analogous to the procedure used to prepare Example J214 Step A, the title compound was obtained. LCMS (Method A) $t_R$=1.661 min, m/z=485 [M+H]$^+$; Purity (AUC) ≥98%.

Example NE10: 5-Bromo-N-(5-chloro-2-hydroxy-3-nitrophenyl)-2-hydroxy-3-propylbenzenesulfonamide

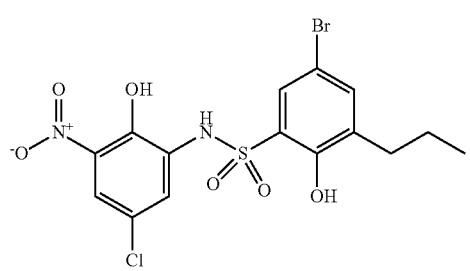

Using a procedure analogous to General Procedure E, starting with 2-amino-4-chloro-6-nitrophenol and 5-bromo-2-hydroxy-3-propylbenzenesulfonyl chloride which was prepared by a procedure analogous to the procedure used to prepare Example HCH-16 Step B, the title compound was obtained. LCMS (Method A) $t_R$=1.644 min, m/z=438 [M+H]$^+$; Purity (AUC) ≥98%.

Example NE12: 3-Bromo-5-(N-(5-chloro-2-hydroxy-3-nitrophenyl)sulfamoyl)benzoic acid

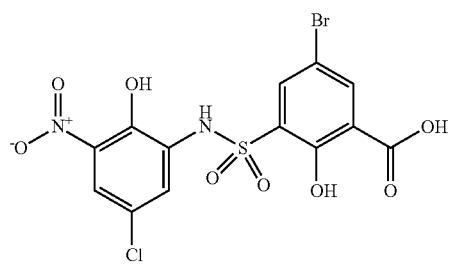

Step A: 5-Bromo-3-(chlorosulfonyl)-2-hydroxybenzoic acid. Using a procedure analogous to General Procedure A, starting from 5-bromo-2-hydroxybenzoic acid, 5-bromo-3-(chlorosulfonyl)-2-hydroxybenzoic acid was obtained (347 mg) as a crude mixture that was used with no further purification.

Step B: 3-Bromo-5-(N-(5-chloro-2-hydroxy-3-nitrophenyl)sulfamoyl)benzoic acid. Using a procedure analogous to General Procedure E, starting with 2-amino-4-chloro-6-nitrophenol, and 5-bromo-3-(chlorosulfonyl)-2-hydroxybenzoic acid, the title compound was obtained. LCMS (Method A) $t_R$=1.61 min, m/z=451, 453 [M+H]$^+$; Purity (AUC) ≥98%.

Example NE13: 5-Bromo-3-chloro-N-(3-chloro-5-(2-oxopyrrolidin-1-yl)phenyl)-2-hydroxybenzene-sulfonamide

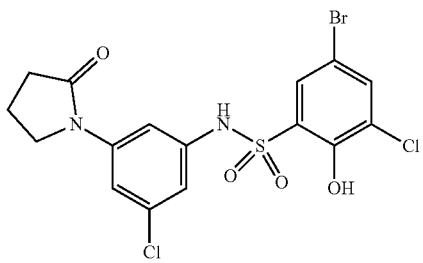 [SMILES: O=C1CCCN1c1cc(Cl)cc(NS(=O)(=O)c2cc(Br)cc(Cl)c2O)c1]

Step A: 1-(3-Chloro-5-nitrophenyl)pyrrolidin-2-one. A reaction mixture containing 1-bromo-3-chloro-5-nitrobenzene, pyrrolidinone, copper iodide, and potassium carbonate in n-butanol may be heated at reflux until LCMS analysis indicates the reaction is complete. The crude material may be purified by silica gel chromatography to give 1-(3-chloro-5-nitrophenyl)pyrrolidin-2-one.

Step B: 1-(3-Amino-5-chlorophenyl)pyrrolidin-2-one. Using a procedure analogous to General Procedure D, starting with 1-(3-chloro-5-nitrophenyl)pyrrolidin-2-one, 1-(3-amino-5-chlorophenyl)pyrrolidin-2-one may be obtained.

Step C: 5-Bromo-3-chloro-N-(3-chloro-5-(2-oxopyrrolidin-1-yl)phenyl)-2-hydroxybenzenesulfonamide. Using a procedure analogous to General Procedure E, starting with 1-(3-amino-5-chlorophenyl)pyrrolidin-2-one and 5-bromo-3-chloro-2-hydroxybenzenesulfonyl chloride, which may be prepared by a procedure analogous to the procedure used to prepare Example J4 Step A, the title compound may be obtained. LCMS (Method A) $t_R$=1.077 min, m/z=479 [M+H]$^+$; Purity (AUC) ≥95%.

Example NE14: 5-Bromo-3-chloro-N-(3-chloro-5-(2-oxoimidazolidin-1-yl)phenyl)-2-hydroxybenzene-sulfonamide

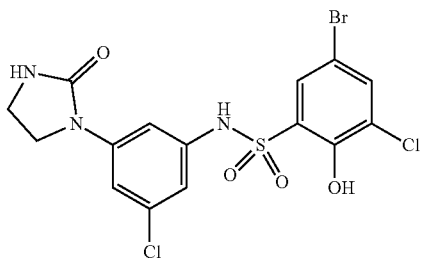 [SMILES: O=C1NCCN1c1cc(Cl)cc(NS(=O)(=O)c2cc(Br)cc(Cl)c2O)c1]

Step A: 1-(3-Chloro-5-nitrophenyl)imidazolidin-2-one. A reaction mixture containing 1-bromo-3-chloro-5-nitrobenzene, imidazolidin-2-one, copper iodide, and potassium carbonate in n-butanol may be heated at reflux until LCMS analysis indicates the reaction is complete. The crude material may be purified by silica gel chromatography to give 1-(3-chloro-5-nitrophenyl)imidazolidin-2-one.

Step B: 1-(3-Amino-5-chlorophenyl)imidazolidin-2-one. Using a procedure analogous to General Procedure D, starting with 1-(3-chloro-5-nitrophenyl)imidazolidin-2-one, 1-(3-amino-5-chlorophenyl)imidazolidin-2-one may be obtained.

Step C: 5-Bromo-3-chloro-N-(3-chloro-5-(2-oxoimidazolidin-1-yl)phenyl)-2-hydroxybenzenesulfonamide. Using a procedure analogous to General Procedure E, starting with 1-(3-amino-5-chlorophenyl)imidazolidin-2-one and 5-bromo-3-chloro-2-hydroxybenzenesulfonyl chloride, which may be prepared by a procedure analogous to the procedure used to prepare Example J4 Step A, the title compound may be obtained. LCMS (Method A) $t_R$=1.018 min, m/z=480 [M+H]$^+$; Purity (AUC) ≥95%.

Example HCH-1-9-4re: 3-Bromo-N-(5-chloro-2-hydroxyphenyl)benzenesulfonamide

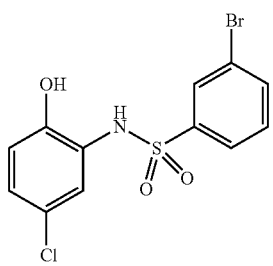 [SMILES: O=S(=O)(Nc1cc(Cl)ccc1O)c1cccc(Br)c1]

2-Amino-4-chlorophenol (17 mg, 0.12 mmol) was reacted with 3-bromobenzenesulfonyl chloride (46 mg, 0.18 mmol) following General Procedure E, affording the title compound as a colorless solid (22 mg, 0.72 mmol, 51%). $^1$H NMR (400 MHz, MeOH-d$_4$) $\delta_H$ 7.92 (t, J=1.8 Hz, 1H), 7.75-7.66 (m, 2H), 7.37 (t, J=8.0 Hz, 1H), 7.33 (d, J=2.6 Hz, 1H), 6.95 (dd, J=8.7, 2.6 Hz, 1H), 6.66 (d, J=8.7 Hz, 1H); LCMS $t_R$=1.50 min, m/z=363.6 [M+H]$^+$; Purity (AUC) ≥95%.

Example HCH-1-143-2: 5-Bromo-N-(5-chloro-2-hydroxyphenyl)-2-hydroxybenzenesulfonamide

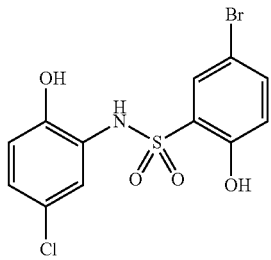 [SMILES: O=S(=O)(Nc1cc(Cl)ccc1O)c1cc(Br)ccc1O]

Step A: 5-Bromo-2-hydroxybenzenesulfonyl chloride. 4-Bromophenol, 17a (1.73 g, 10 mmol) was added portion wise to ice-cold chlorosulfonic acid (4.77 mL, 70 mmol) and the mixture stirred for 16 h, warming to rt. The mixture was carefully poured over a slurry of ice, DCM and brine, and extracted with DCM. Purification by flash chromatography affords 5-bromo-2-hydroxybenzenesulfonyl chloride as a pale brown oily solid (1.50 g, 5.53 mmol, 55%). $^1$H NMR (400 MHz, CDCl$_3$) NH 7.95 (d, J=2.4 Hz, 1H), 7.71 (dd, J=8.9, 2.4 Hz, 1H), 7.04 (d, J=8.9 Hz, 1H).

Step B: 5-Bromo-N-(5-chloro-2-hydroxyphenyl)-2-hydroxybenzenesulfonamide. Using a procedure analogous to General Procedure E, starting with 2-amino-4-chlorophenol (14 mg, 0.1 mmol) and 5-bromo-2-hydroxybenzenesulfonyl chloride (41 mg, 0.15 mmol), the title compound was obtained as a colorless solid (21 mg, 0.06 mmol, 55%). $^1$H NMR (400 MHz, CDCl$_3$) $\delta_H$ 7.66 (d, J=2.5 Hz, 1H), 7.53 (dd, JJ=8.8, 2.5 Hz, 1H), 7.08 (d, J=8.2 Hz, 2H), 6.88 (d, J=8.8 Hz, 1H), 6.80 (d, J=8.2 Hz, 1H); LCMS $t_R$=1.53 min, m/z=377.8, 379.8 [M+H]$^+$; Purity (AUC) ≥95%.

Example JDM-10-108A: 5-Bromo-N-(5-cyclopropyl-2-hydroxyphenyl)-2-hydroxybenzenesulfonamide

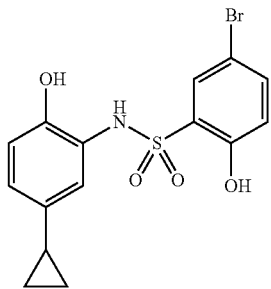 [SMILES: O=S(=O)(Nc1cc(C2CC2)ccc1O)c1cc(Br)ccc1O]

Step A: 1-(Benzyloxy)-4-bromo-2-nitrobenzene. Using a procedure analogous to General Procedure Q, starting with 2-nitro-4-bromophenol (10.9 g, 50 mmol), 1-(benzyloxy)-4-bromo-2-nitrobenzene was obtained as a yellow solid (14.2 g, 46.1 mmol, 92%). LCMS $t_R$=1.25 min, m/z=307.2 [M+H]$^+$.

Step B: 1-(Benzyloxy)-4-cyclopropyl-2-nitrobenzene. 1-(Benzyloxy)-4-bromo-2-nitrobenzene, (1.54 g, 5.0 mmol), cyclopropylboronic acid (515 mg, 6.0 mmol), Pd(OAc)$_2$ (56 mg, 0.25 mmol), PCy$_3$·HBF$_4$ (184 mg, 0.50 mmol), K$_3$PO$_4$ (2.65 g, 12.5 mmol) were taken up in toluene (25 mL) and water (5 mL) and stirred at 110° C. in a sealed tube for 16 h. The cooled mixture was filtered through celite, diluted with EtOAc and washed with water. Purification by flash chromatography affords a yellow solid (1.22 g, 4.53 mmol, 91%). LCMS $t_R$=1.27 min, does not ionize by ESI.

Step C: 2-Amino-4-cyclopropylphenol. Using a procedure analogous to General Procedure C, starting with 1-(benzyloxy)-4-cyclopropyl-2-nitrobenzene (539 mg, 2.0 mmol), 2-amino-4-cyclopropylphenol was obtained as a colorless solid (262 mg, 1.75 mmol, 88%). $^1$H NMR (400 MHz, MeOH-d$_4$) $\delta_H$ 6.59 (d, J=8.2 Hz, 1H), 6.50 (d, J=2.2 Hz, 1H), 6.36 (dd, J=8.2, 2.2 Hz, 1H), 1.80-1.70 (m, 1H), 0.87-0.78 (m, 2H), 0.58-0.49 (m, 2H); LCMS $t_R$=1.00 min, m/z=150.3 [M+H]$^+$.

Step D: 5-Bromo-N-(5-cyclopropyl-2-hydroxyphenyl)-2-hydroxybenzenesulfonamide. Using a procedure analogous to General Procedure E, starting with 2-amino-4-cyclopropylphenol (15 mg, 0.1 mmol) and 5-bromo-2-hydroxybenzenesulfonyl chloride (41 mg, 0.15 mmol), the title compound was obtained as a colorless solid (17 mg, 0.04 mmol, 44%). $^1$H NMR (400 MHz, CDCl$_3$) $\delta_H$ 8.40 (s, 1H), 7.61 (d, J=2.5 Hz, 1H), 7.52 (dd, J=8.8, 2.5 Hz, 1H), 6.90 (dd, J=8.4, 2.2 Hz, 1H), 6.86 (d, J=8.8 Hz, 1H), 6.77 (d, J=8.4 Hz, 1H), 6.60 (d, J=2.2 Hz, 1H), 6.56 (s, 1H), 5.53 (s, 1H), 1.80-1.68 (m, 1H), 0.91-0.81 (m, 2H), 0.46 (dt, J=6.6, 4.7 Hz, 2H); LCMS $t_R$=1.56 min, m/z=383.8, 385.8 [M+H]$^+$; Purity (AUC) ≥95%.

Example HCH-3-48-1: 5-Bromo-2-hydroxy-N-(2-hydroxy-5-(trifluoromethoxy)phenyl)benzenesulfonamide

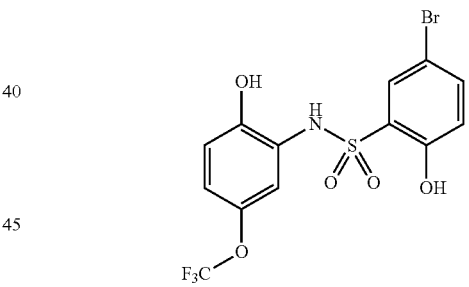

Step A. 2-Amino-4-(trifluoromethoxy)phenol. Using a procedure analogous to General Procedure C, starting with 2-nitro-4-(trifluoromethoxy)phenol (900 mg, 4.03 mmol), 2-amino-4-(trifluoromethoxy)phenol was obtained as a crude brown solid (693 mg, 3.59 mmol, 89%) that was taken forward without purification. LCMS $t_R$=0.83 min, m/z=194.1 [M+H]$^+$.

Step B. 5-Bromo-2-hydroxy-N-(2-hydroxy-5-(trifluoromethoxy)phenyl)benzenesulfonamide. Using a procedure analogous to General Procedure E, starting with 2-amino-4-(trifluoromethoxy)phenol (19 mg, 0.1 mmol) and 5-bromo-2-hydroxybenzenesulfonyl chloride (41 mg, 0.15 mmol), the title compound was obtained as a colorless solid (4 mg, 0.009 mmol, 9%). $^1$H NMR (400 MHz, MeOH-d$_4$) $\delta_H$ 7.80 (d, J=2.4 Hz, 1H), 7.58 (d, J=2.2 Hz, 1H), 7.51 (dd, J=8.8, 2.5 Hz, 1H), 7.43 (d, J=2.3 Hz, 1H), 6.84 (d, J=8.8 Hz, 1H); $^{19}$F NMR (376 MHz, MeOH-d$_4$) $\delta_F$ −60.3; LCMS $t_R$=1.57 min, m/z=429.2 [M+H]$^+$; Purity (AUC) ≥95%.

Example JDM-08-142A: 5-Bromo-2-hydroxy-N-(2-hydroxy-5-(pentafluorosulfanyl)phenyl)benzenesulfonamide

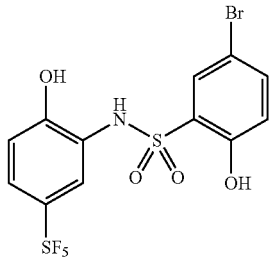

Step A: 2-Nitro-4-(pentafluorosulfanyl)phenol. 4-Hydroxyphenyl sulfur pentafluoride (1.1 g, 5 mmol) was dissolved in DCM (25 mL) and cooled to 0° C. before the addition of nitronium tetrafluoroborate (863 mg, 6.5 mmol) and stirred for 18 h. The mixture was neutralized with sat. aq. NaHCO$_3$ and extracted with DCM to afford a crude yellow oil (479 mg, 1.81 mmol, 36%) which was used without further purification. $^1$H NMR (400 MHz, CDCl$_3$) $\delta_H$ 10.78 (s, 1H), 8.57 (d, J=2.7 Hz, 1H), 7.96 (dd, J=9.2, 2.7 Hz, 1H), 7.27 (d, J=9.2 Hz, 1H); $^{19}$F NMR (376 MHz, CDCl$_3$) $\delta_F$ 82.43 (d, J=151 Hz, 1F), 63.76 (d, J=151 Hz, 4F); LCMS $t_R$=1.03 min, does not ionize by ESI.

Step B: 2-Amino-4-(pentafluorosulfanyl)phenol. Using a procedure analogous to General Procedure C, starting with 2-nitro-4-(pentafluorosulfanyl)phenol (479 mg, 1.81 mmol), 2-amino-4-(pentafluorosulfanyl)phenol was obtained as a brown gum (99 mg, 0.42 mmol, 23%). LCMS $t_R$=0.55 min, m/z=236.2 [M+H]$^+$.

Step C: 5-Bromo-2-hydroxy-N-(2-hydroxy-5-(pentafluorosulfanyl)phenyl)benzenesulfonamide. Using a procedure analogous to General Procedure E, starting with 2-amino-4-(pentafluorosulfanyl)phenol, (24 mg, 0.1 mmol) and 5-bromo-2-hydroxybenzenesulfonyl chloride (41 mg, 0.15 mmol), the title compound was obtained as a colorless solid (12 mg, 0.026 mmol, 26%). $^1$H NMR (400 MHz, CDCl$_3$) $\delta_H$ 7.63 (d, J=2.6 Hz, 1H), 7.59-7.54 (m, 1H), 7.57-7.52 (m, 1H), 7.31 (d, J=2.6 Hz, 1H), 6.96 (d, J=9.0 Hz, 1H), 6.89 (d, J=9.0 Hz, 1H), 6.70 (br s, 2H); $^{19}$F NMR (376 MHz, CDCl$_3$) $\delta_F$ 84.3 (p, J=151 Hz, 1F), 64.0 (d, J=151 Hz, 4F); LCMS $t_R$=1.66 min, m/z=471.2 [M+H]$^+$; Purity (AUC) ≥95%.

Example JDM-09-131: 5-Bromo-2-hydroxy-N-(2-hydroxy-5-(1-(trifluoromethyl)cyclopropyl)phenyl)benzenesulfonamide

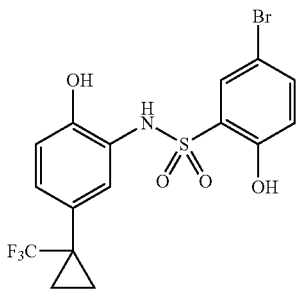 [SMILES: O=S(=O)(Nc1cc(C2(C(F)(F)F)CC2)ccc1O)c1cc(Br)ccc1O]

Step A: 2-(4-(Benzyloxy)-3-nitrophenyl)-4,4,5,5-tetramethyl-1,3,2-dioxaborolane. Using a procedure analogous to General Procedure Q, starting with 4-hydroxy-3-nitrophenylboronic acid, pinacol ester, (980 mg, 3.7 mmol), 2-(4-(benzyloxy)-3-nitrophenyl)-4,4,5,5-tetramethyl-1,3,2-dioxaborolane was obtained as a yellow solid (1215 mg, 3.4 mmol, 92%). MS (ESI) m/z=373.1 [M+NH$_4$]$^+$.

Step B: 1-(Benzyloxy)-2-nitro-4-(3,3,3-trifluoroprop-1-en-2-yl)benzene. 2-(4-(Benzyloxy)-3-nitrophenyl)-4,4,5,5-tetramethyl-1,3,2-dioxaborolane (710 mg, 2.0 mmol), 2-bromo-3,3,3-trifluoroprop-1-ene (830 μL, 8.0 mmol), Pd(dppf)Cl$_2$·DCM (163 mg, 0.2 mmol) and K$_2$CO$_3$ (553 mg, 4.0 mmol) were taken in dioxane:water (10:1, 10 mL) and heated to 70° C. for 3 h under an inert atmosphere. The cooled mixture was diluted with EtOAc and washed with water, brine. Purification by flash chromatography affords 1-(benzyloxy)-2-nitro-4-(3,3,3-trifluoroprop-1-en-2-yl)benzene as a straw-colored oil (433 mg, 1.34 mmol, 67%). $^1$H NMR (400 MHz, CDCl$_3$) $\delta_H$ 7.96 (d, J=2.4 Hz, 1H), 7.61-7.55 (m, 1H), 7.48-7.32 (m, 5H), 7.13 (d, J=8.8 Hz, 1H), 6.01 (d, J=1.6 Hz, 1H), 5.80 (d, J=1.6 Hz, 1H), 5.28 (s, 2H); $^{19}$F NMR (376 MHz, CDCl$_3$) $\delta_F$ −65.1; LCMS $t_R$=1.26 min, does not ionize by ESI.

Step C: 1-(Benzyloxy)-2-nitro-4-(1-(trifluoromethyl)cyclopropyl)benzene. To a mixture of 1-(benzyloxy)-2-nitro-4-(3,3,3-trifluoroprop-1-en-2-yl)benzene (65 mg, 0.20 mmol) and Ph$_2$MeSBF$_4$ (115 mg, 0.40 mmol) in anhydrous THF at −78° C., was added LiHMDS [1.0 M in THF] (0.8 mL, 0.8 mmol). The mixture was stirred for 12 h, warming to rt, then diluted with EtOAc and washed with water. Purification by flash chromatography affords 1-(benzyloxy)-2-nitro-4-(1-(trifluoromethyl)cyclopropyl)benzene as a pale-yellow gum (32 mg, 0.09 mmol, 47%). $^1$H NMR (400 MHz, CDCl$_3$) $\delta_H$ 7.96 (d, J=2.3 Hz, 1H), 7.61 (dd, J=8.7, 2.3 Hz, 1H), 7.51-7.35 (m, 5H), 7.11 (d, J=8.7 Hz, 1H), 5.27 (s, 2H), 1.45-1.39 (m, 2H), 1.09-1.01 (m, 1H); $^{19}$F NMR (376 MHz, CDCl$_3$) $\delta_F$ −70.3; LCMS $t_R$=1.26 min, does not ionize by ESI.

Step D: 5-Bromo-2-hydroxy-N-(2-hydroxy-5-(1-(trifluoromethyl)cyclopropyl)phenyl)benzenesulfonamide. Using a procedure analogous to General Procedure C, starting with 1-(benzyloxy)-2-nitro-4-(1-(trifluoromethyl)cyclopropyl)benzene (32 mg, 0.09 mmol), 1-(benzyloxy)-2-amino-4-(1-(trifluoromethyl)cyclopropyl)benzene was obtained as a crude colorless solid (20 mg, 0.09 mmol) that was reacted with 5-bromo-2-hydroxybenzenesulfonyl chloride (41 mg, 0.15 mmol) using a procedure analogous to General Procedure E, affording 5-bromo-2-hydroxy-N-(2-hydroxy-5-(1-(trifluoromethyl)cyclopropyl)phenyl)benzenesulfonamide as a colorless solid (13 mg, 0.029 mmol, 31%). $^1$H NMR (400 MHz, MeOH-d$_4$) $\delta_H$ 7.72 (d, J=2.5 Hz, 1H), 7.49 (dd, J=8.8, 2.5 Hz, 1H), 7.36 (d, J=2.2 Hz, 1H), 6.99 (dd, J=8.3, 2.2 Hz, 1H), 6.83 (d, J=8.8 Hz, 1H), 6.70 (d, J=8.3 Hz, 1H), 1.30-1.20 (m, 2H), 0.93-0.87 (m, 2H); $^{19}$F NMR (376 MHz, CDCl$_3$) $\delta_F$ −71.9; LCMS $t_R$=1.67 min, m/z=451.8 [M+H]$^+$; Purity (AUC) ≥95%.

Example JDM-10-107: 5-Bromo-N-(5-(1-cyanocyclopropyl)-2-hydroxyphenyl)-2-hydroxybenzenesulfonamide

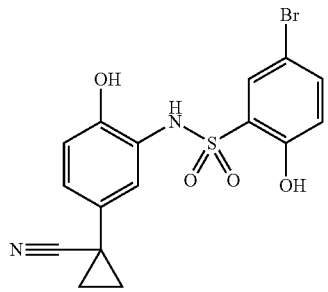 [SMILES: N#CC1(c2ccc(O)c(NS(=O)(=O)c3cc(Br)ccc3O)c2)CC1]

Step A: 1-(4-Methoxy-3-nitrophenyl)cyclopropane-1-carbonitrile. Using a procedure analogous to General Procedure B, starting with 1-(4-methoxyphenyl) cyclopropanecarbonitrile, (1 mL, 6.3 mmol), 1-(4-methoxy-3-nitrophenyl)cyclopropane-1-carbonitrile was obtained as a yellow solid (1178 mg, 5.40 mmol, 86%). $^1$H NMR (400 MHz, CDCl$_3$) $\delta_H$ 7.69 (d, J=2.5 Hz, 1H), 7.60 (dd, J=8.8, 2.5 Hz, 11H), 7.09 (d, J=8.8 Hz, 1H), 3.97 (s, 3H), 1.83-1.71 (m, 2H), 1.45-1.36 (m, 2H); LCMS $t_R$=0.87 min, does not ionize by ESI.

Step B: 1-(4-Hydroxy-3-nitrophenyl)cyclopropane-1-carbonitrile. Using a procedure analogous to General Procedure O, starting with 1-(4-methoxy-3-nitrophenyl)cyclopropane-1-carbonitrile (218 mg, 1.0 mmol), 1-(4-hydroxy-3-nitrophenyl)cyclopropane-1-carbonitrile was obtained as a cream solid (161 mg, 0.79 mmol, 79%). $^1$H NMR (400 MHz, CDCl$_3$) $\delta_H$ 10.54 (s, 1H), 8.01 (d, J=2.5 Hz, 1H), 7.60 (dd, J=8.8, 2.5 Hz, 1H), 7.19 (d, J=8.8 Hz, 1H), 1.87-1.71 (m, 2H), 1.48-1.32 (m, 2H). LCMS $t_R$=0.86 min, does not ionize by ESI.

Step C: 1-(3-Amino-4-hydroxyphenyl)cyclopropane-1-carbonitrile. Using a procedure analogous to General Procedure C, starting with 1-(4-hydroxy-3-nitrophenyl)cyclopropane-1-carbonitrile (102 mg, 0.5 mmol), 1-(3-amino-4-hydroxyphenyl)cyclopropane-1-carbonitrile was obtained as a cream solid (74 mg, 0.43 mmol, 85%). $^1$H NMR (400 MHz, CDCl$_3$) $\delta_H$ 6.73 (d, J=2.2 Hz, 1H), 6.67 (d, J=8.2 Hz, 1H), 6.57 (dd, J=8.2, 2.2 Hz, 1H), 4.72 (s, 1H), 3.71 (s, 2H), 1.65-1.58 (m, 2H), 1.32-1.27 (m, 2H); m/z (ESI)=175.3 [M+H]$^+$.

Step D: 5-Bromo-N-(5-(1-cyanocyclopropyl)-2-hydroxyphenyl)-2-hydroxybenzenesulfonamide. Using a procedure analogous to General Procedure E, starting with 1-(3-amino-4-hydroxyphenyl)cyclopropane-1-carbonitrile (27 mg, 0.16 mmol), and 5-bromo-2-hydroxybenzenesulfonyl chloride (41 mg, 0.15 mmol) following, the title compound was obtained as a colorless solid (47 mg, 0.12 mmol, 72%). $^1$H NMR (400 MHz, CDCl$_3$) $\delta_H$ 8.51 (s, 1H), 7.61 (d, J=2.4 Hz, 1H), 7.53 (dd, J=8.9, 2.4 Hz, 1H), 7.07 (d, J=8.5, 2.4 Hz, 1H), 6.92-6.85 (m, 3H), 6.80 (s, 1H), 1.67-1.61 (m, 2H), 1.26-1.20 (m, 2H); LCMS $t_R$=1.42 min, m/z=408.9, 410.8 [M+H]$^+$; Purity (AUC) ≥95%.

Example JDM-06-030B: 5-Bromo-N-(5-(1-cyanocyclobutyl)-2-hydroxyphenyl)-2-hydroxybenzenesulfonamide

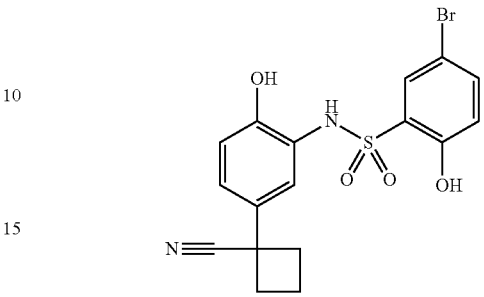

Step A: 2-(4-Hydroxy-3-nitrophenyl)acetonitrile. Using a procedure analogous to General Procedure B, starting from 4-hydroxybenzylacetontrile (2.66 g, 20 mmol), 2-(4-hydroxy-3-nitrophenyl)acetonitrile was obtained as a yellow-orange solid (3.42 g, 19.2 mmol, 96%). $^1$H NMR (400 MHz, CDCl$_3$) $\delta_H$ 10.57 (s, 1H), 8.10 (d, J=2.4 Hz, 1H), 7.57 (dd, J=8.7, 2.4 Hz, 1H), 7.22 (d, J=8.7 Hz, 1H), 3.76 (s, 2H).

Step B: 2-(4-(Benzyloxy)-3-nitrophenyl)acetonitrile. Using a procedure analogous to General Procedure Q, starting with 2-(4-hydroxy-3-nitrophenyl)acetonitrile (1.78 g, 10 mmol), 2-(4-(benzyloxy)-3-nitrophenyl)acetonitrile was obtained as a yellow-orange solid (2.31 g, 8.6 mmol, 86%). $^1$H NMR (400 MHz, CDCl$_3$) $\delta_H$ 7.82 (d, J=2.4 Hz, 1H), 7.49 (dd, J=8.7, 2.4 Hz, 1H), 7.47-7.30 (m, 6H), 7.15 (d, J=8.7 Hz, 1H), 5.26 (s, 2H), 3.74 (s, 2H).

Step C: 1-(4-(benzyloxy)-3-nitrophenyl)cyclobutane-1-carbonitrile. To a solution of 2-(4-(benzyloxy)-3-nitrophenyl)acetonitrile (134 mg, 0.5 mmol) and 1,3-dibromopropane (61 μL, 0.6 mmol) in DMSO (5 mL) was added carefully added NaH (60% in mineral oil, 60 mg, 1.5 mmol) and the mixture stirred for 16 h. The mixture was diluted with EtOAc:Et$_2$O (1:1, 50 mL) and washed with water (3×100 mL), brine (100 mL). Purification by flash chromatography affords 1-(4-(benzyloxy)-3-nitrophenyl)cyclobutane-1-carbonitrile as a yellow-brown oil (80 mg, 0.26 mmol, 52%); m/z (ESI)=309.0 [M+H]$^+$.

Step D: 1-(3-Amino-4-hydroxyphenyl)cyclobutane-1-carbonitrile, Using a procedure analogous to General Procedure C, starting with 1-(4-(benzyloxy)-3-nitrophenyl)cyclobutane-1-carbonitrile (80 mg, 0.26 mmol), 1-(3-amino-4-hydroxyphenyl)cyclobutane-1-carbonitrile was obtained as a colorless oil (26 mg, 0.14 mmol, 53%). $^1$H NMR (400 MHz, MeOH-d$_4$) $\delta_H$ 6.84 (d, J=2.3 Hz, 1H), 6.73 (d, J=8.2 Hz, 1H), 6.66 (dd, J=8.2, 2.3 Hz, 1H), 2.77-2.66 (m, 2H), 2.66-2.56 (m, 2H), 2.42-2.28 (m, 1H), 2.13-2.00 (m, 1H); m/z (ESI)=189.1 [M+H]$^+$.

Step E: 5-Bromo-N-(5-(1-cyanocyclobutyl)-2-hydroxyphenyl)-2-hydroxybenzenesulfonamide. Using a procedure analogous to General Procedure E, starting with 1-(3-amino-4-hydroxyphenyl)cyclobutane-1-carbonitrile (26 mg, 0.14 mmol) and with 5-bromo-2-hydroxybenzenesulfonyl chloride (41 mg, 0.15 mmol), the title compound was obtained as a colorless solid (22.5 mg, 0.05 mmol, 38%). $^1$H NMR (400 MHz, CDCl$_3$) $\delta_H$ 7.65 (d, J=2.4 Hz, 1H), 7.56 (dd, J=8.8, 2.4 Hz, 1H), 7.22 (dd, J=8.5, 2.4 Hz, 1H), 6.98 (d, J=2.4 Hz, 1H), 6.95 (d, J=8.5 Hz, 1H), 6.91 (d, J=8.8 Hz, 1H), 6.71 (s, 1H), 2.82-2.71 (m, 2H), 2.52-2.33 (m, 2H), 2.08-2.01 (m, 2H); LCMS $t_R$=1.60 min, m/z=439.8, 441.8 [M+H]$^+$; Purity (AUC) ≥95%.

Example JDM-06-030A: 5-Bromo-N-(5-(1-cyanocyclopentyl)-2-hydroxyphenyl)-2-hydroxybenzenesulfonamide

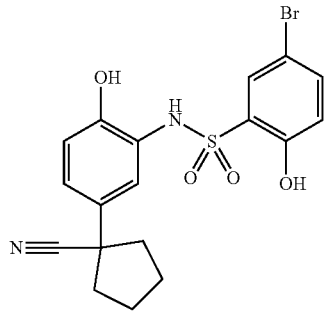 [SMILES: N#CC1(c2ccc(O)c(NS(=O)(=O)c3cc(Br)ccc3O)c2)CCCC1]

Step A: 1-(4-(Benzyloxy)-3-nitrophenyl)cyclopentane-1-carbonitrile. To a solution of 2-(4-(benzyloxy)-3-nitrophenyl)acetonitrile (134 mg, 0.5 mmol) and 1,4-dibromobutane (72 μL, 0.6 mmol) in DMSO (5 mL) was added carefully added NaH (60% in mineral oil, 60 mg, 1.5 mmol) and the mixture stirred for 16 h. The mixture was diluted with EtOAc:Et$_2$O (1:1, 50 mL) and washed with water (3×100 mL), brine (100 mL). Purification by flash chromatography affords 1-(4-(benzyloxy)-3-nitrophenyl)cyclopentane-1-carbonitrile as a yellow-brown oil (103 mg, 0.32 mmol, 64%). $^1$H NMR (400 MHz, CDCl$_3$) δ$_H$ 7.89 (d, J=2.5 Hz, 1H), 7.62 (dd, J=8.8, 2.5 Hz, 1H), 7.48-7.31 (m, 5H), 7.13 (d, J=8.8 Hz, 1H), 5.26 (s, 2H), 2.55-2.44 (m, 2H), 2.14-1.88 (m, 6H); LCMS $t_R$=1.96 min, m/z=323.1 [M+H]$^+$.

Step B: 1-(3-Amino-4-hydroxyphenyl)cyclopentane-1-carbonitrile. Using a procedure analogous to General Procedure C, starting with 1-(4-(benzyloxy)-3-nitrophenyl)cyclopentane-1-carbonitrile (103 mg, 0.32 mmol), 1-(3-amino-4-hydroxyphenyl)cyclopentane-1-carbonitrile was obtained as a colorless oil (50 mg, 0.25 mmol, 78%). $^1$H NMR (400 MHz, MeOH-d$_4$) δ$_H$ 6.86 (t, J=1.4 Hz, 1H), 6.68 (d, J=1.4 Hz, 2H), 2.44-2.29 (m, 2H), 2.13-2.00 (m, 2H), 2.00-1.89 (m, 4H); m/z (ESI)=203.2 [M+H]$^+$.

Step C: 5-Bromo-N-(5-(1-cyanocyclopentyl)-2-hydroxyphenyl)-2-hydroxybenzenesulfonamide. Using a procedure analogous to General Procedure E, starting with 1-(3-amino-4-hydroxyphenyl)cyclopentane-1-carbonitrile (50 mg, 0.25 mmol) and 5-bromo-2-hydroxybenzenesulfonyl chloride (41 mg, 0.15 mmol), the title compound was obtained as a colorless solid (12 mg, 0.04 mmol, 11%). $^1$H NMR (400 MHz, CDCl$_3$) δ$_H$ 7.61 (d, J=2.5 Hz, 1H), 7.50 (dd, J=8.8, 2.5 Hz, 1H), 7.17 (dd, J=8.5, 2.3 Hz, 1H), 6.98 (d, J=2.3 Hz, 2H), 6.90 (d, J=5.2 Hz, 1H), 6.87 (d, J=5.2 Hz, 1H), 2.40-2.26 (m, 2H), 2.01-1.81 (m, 6H); LCMS $t_R$=1.65 min, m/z=453.8, 455.8 [M+H]$^+$; Purity (AUC) ≥95%.

Example JDM-06-030C: 5-Bromo-N-(5-(1-cyanocyclohexyl)-2-hydroxyphenyl)-2-hydroxybenzenesulfonamide

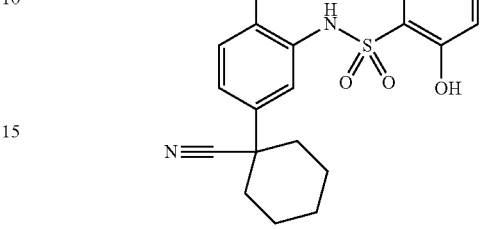

Step A: 1-(4-(Benzyloxy)-3-nitrophenyl)cyclohexane-1-carbonitrile. To a solution of 2-(4-(benzyloxy)-3-nitrophenyl)acetonitrile (134 mg, 0.5 mmol) and 1,5-dibromopentane (82 μL, 0.6 mmol) in DMSO (5 mL) was added carefully added NaH (60% in mineral oil, 60 mg, 1.5 mmol) and the mixture stirred for 16 h. The mixture was diluted with EtOAc:Et$_2$O (1:1, 50 mL) and washed with water (3×100 mL), brine (100 mL). Purification by flash chromatography affords 1-(4-(benzyloxy)-3-nitrophenyl)cyclohexane-1-carbonitrile as a yellow-brown oil (91 mg, 0.27 mmol, 54%). LCMS $t_R$=1.98 min, m/z=337.0 [M+H]$^+$.

Step B: 1-(3-Amino-4-hydroxyphenyl)cyclohexane-1-carbonitrile. Using a procedure analogous to General Procedure C, starting with 1-(4-(benzyloxy)-3-nitrophenyl)cyclohexane-1-carbonitrile (91 mg, 0.27 mmol), 1-(3-amino-4-hydroxyphenyl)cyclohexane-1-carbonitrile was obtained as a colorless oil (39 mg, 0.18 mmol, 67%). $^1$H NMR (400 MHz, MeOH-d$_4$) δ$_H$ 6.91 (d, J=1.9 Hz, 1H), 6.72 (d, J=1.9 Hz, 1H), 6.71 (s, 1H), 2.12-2.02 (m, 3H), 1.92-1.69 (m, 6H), 1.43-1.26 (m, 1H); m/z (ESI)=217.1 [M+H]$^+$.

Step C: 5-Bromo-N-(5-(1-cyanocyclohexyl)-2-hydroxyphenyl)-2-hydroxybenzenesulfonamide. Using a procedure analogous to General Procedure E, starting with 1-(3-amino-4-hydroxyphenyl)cyclohexane-1-carbonitrile (39 mg, 0.18 mmol), and 5-bromo-2-hydroxybenzenesulfonyl chloride (54 mg, 0.20 mmol), the title compound was obtained as a colorless solid (24 mg, 0.05 mmol, 30%). $^1$H NMR (400 MHz, MeOH-d$_4$) δ$_H$ 7.79 (d, J=2.5 Hz, 1H), 7.51 (dd, J=8.8, 2.5 Hz, 1H), 7.37 (d, J=2.4 Hz, 1H), 7.07 (dd, J=8.5, 2.4 Hz, 1H), 6.86 (d, J=8.8 Hz, 1H), 6.77 (d, J=8.5 Hz, 1H), 1.98 (dt, J=12.8, 1.9 Hz, 2H), 1.91-1.63 (m, 9H), 1.43-1.27 (m, 1H); LCMS $t_R$=1.72 min, m/z=467.8, 469.8 [M+H]$^+$; Purity (AUC) ≥95%.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I) or (II)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I) or (II), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch: cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *Theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I) or (II)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I) or (II)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I) or (II)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

The disclosed compounds and compositions may be used in methods for treatment of MYC-related cancers. The methods of treatment may comprise administering to a subject in need of such treatment a composition comprising a therapeutically effective amount of the compound of formula (I) or (II).

In one aspect, disclosed is a method of treating cancer, the method comprising administration of a therapeutically effective amount of a compound of formula (I) or (II), or a pharmaceutically acceptable salt thereof to a subject in need thereof.

In certain embodiments, the cancer being treated is associated with overexpression of MYC.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MYC, the method comprising administration of a therapeutically effective amount of a compound of formula (I) or (II), or a pharmaceutically acceptable salt thereof to a subject in need thereof.

The compositions can be administered to a subject in need thereof to bind WDR5 and modulate MYC, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL.

The compositions may be useful for treating certain cancers in humans and animals related to MYC overexpression. Treatment of such cancers may be effected by modulating MYC binding to WDR5 in a subject, by administering a compound or composition of the invention, either alone or in combination with another active agent as part of a therapeutic regimen to a subject in need thereof.

Disruption of the the interaction between WDR5 and its binding partners (such as MYC) may lead to treatment and reduction of cancer or tumor growth, and/or reduce metastasis of cancerous or tumor cells. Accordingly, the disclosed compositions may be used in methods that treat and/or prevent cancer or tumors in a subject administered the composition. The method can treat cancer or tumor-based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof may mediate reduction, clearance or prevention of additional growth of tumor cells by disrupting the ability of MYC, another transcription factor, or chromatin to associate with WDR5, thereby reducing growth/proliferation of tumor cells, but does not have an effect on normal cells.

In some embodiments, the administered composition may increase tumor free survival, reduce tumor mass, slow tumor growth, increase tumor survival, or a combination thereof in the subject. The administered composition may reduce tumor volume in the subject in need thereof. The administered composition may increase tumor free survival in the subject after administration of the composition.

In some embodiments, the composition may be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension, or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I) or (II). The above combinations include combinations of a compound of the present invention not only with one other active compound, but also with two or more other active compounds. For example, the compound of Formula (I) or (II) can be combined with a variety of different anti-cancer drugs such as chemotherapeutics, anti-tumor agents, and anti-proliferative agents.

Further, the compound of formula (I) or (II) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP) ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, γ-radiation, DOTIL inhibitors, agents targeting epigenetic mechanisms, or an additional chemotherapeutic agent such as N—Ac-Sar-Gly-Val-D-alloIle-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl}-N-(2-fluoro-5-methylphenyl)urea or a salt thereof, N-(4-(4-aminothieno[2,3-d]pyrimidin-5-yl)phenyl}-N-(2-fluoro-5-(trifluoromethyl)phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I) or (II)], a systemic or topical composition described above, or both; and information, instructions, or both that use of the kit will provide treatment for medical conditions in mammals (particularly humans). The information and instructions may be in the form of words, pictures, or both, and the like. In addition, or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

Biological Example 1. Fluorescence Polarization Anisotropy Assay

Compounds of the present invention were assessed for their ability to bind to WDr5 using a competition-based fluorescence polarization anisotropy assay, similar to the method previously described. (Thomas, Fesik, Tansey, et al, Molecular Cell 2015 (58): 440-452). Fluorescence polarization measurements were performed in 384-well plates (Greiner Bio One) using a Cytation 3 plate reader (BioTek). Fluorescein isothiocyanate (FITC)-labeled peptide probe (FITC-AHx-SEEEIDVVSV) was purchased from GenScript USA Inc and used without further purification. Fluorescein isothiocyanate (FITC)-labeled small molecule probes were synthesized using procedures analogous to the procedures described above. The assay buffer contained 200 mM phosphate, 300 mM NaCl, and 0.5 mM TCEP and 0.1% Chaps at pH 6.0. Compounds were serially diluted in assay buffer at a top concentration sufficient to yield a 9-point dose-response curve. The change in fluorescence anisotropy was measured and used to calculate an $IC_{50}$ (inhibitor concentration at which 50% of bound probe is displaced) by fitting the inhibition data using a single-site binding model implemented in the XL Fit software (XLfit). This was converted into a binding dissociation constant ($K_i$ value) according to the formula:

$$K_i = [I]50/([L]50/K_d + [P]0/K_d + 1)$$

where [I]50 is the concentration of the free inhibitor at 50% inhibition, [L]50 is the concentration of the free labeled ligand at 50% inhibition, [P]0 is the concentration of the free protein at 0% inhibition, and $K_d$ represents the dissociation constant of the FITC labeled probe (Nikolovska-Coleska et al., 2004).

Data shown in the table below represents a K; determined from this method for each Example, using either a fluorescently labeled small molecule probe analogous to Example J2 or Example HCH-25, or the peptide probe described above, in the assay.

| Example | $K_i$ (μM) | Example | $K_i$ (μM) | Example | $K_i$ (μM) | Example | $K_i$ (μM) |
|---|---|---|---|---|---|---|---|
| J1 | 0.09 | HCH-44 | 0.43 | J140 | 40.00 | J236 | 0.24 |
| J2 | 0.18 | HCH-45 | 0.44 | J141 | 0.96 | SN-3 | 13.69 |
| J4 | 0.06 | HCH-46 | 0.45 | J142 | 1.48 | SN-4 | 0.87 |
| J5 | 0.34 | HCH-47 | 0.26 | J143 | 2.54 | SN-5 | 2.62 |
| J6 | 0.11 | HCH-48 | 0.25 | J144 | 6.76 | SN-6 | 0.04 |
| J7 | 3.75 | HCH-49 | 0.32 | J145 | 40.00 | SN-9 | 0.99 |
| J8 | 2.77 | HCH-50 | 0.21 | J146 | 0.04 | SN-10 | 0.05 |
| J9 | 2.67 | HCH-51 | 0.12 | J147 | 0.23 | S63 | 0.16 |
| J10 | 21.93 | HCH-52 | 0.14 | J148 | 0.60 | S64 | 0.02 |
| J11 | 2.49 | HCH-53 | 0.17 | J149 | 0.71 | S65 | 0.03 |
| J12 | 11.11 | HCH-54 | 0.14 | J150 | 0.92 | S66 | 0.02 |
| HCH-11 | 0.46 | HCH-55 | 0.35 | J151 | 0.21 | S67 | 0.09 |
| HCH-12 | 0.20 | HCH-56 | 0.19 | J152 | 0.32 | S68 | 0.02 |
| HCH-13 | 0.22 | HCH-57 | 0.15 | J153 | 0.44 | S69 | 0.77 |
| HCH-14 | 0.13 | HCH-58 | 0.46 | J154 | 0.13 | S70 | 2.93 |
| HCH-15 | 0.17 | HCH-59 | 0.34 | J155 | 0.33 | S71 | 0.01 |
| HCH-16 | 0.11 | HCH-60 | 0.24 | J156 | 0.21 | S3 | 0.50 |
| HCH-17 | 0.32 | HCH-61 | 0.24 | J157 | 0.21 | S4 | 0.85 |
| HCH-18 | 0.06 | HCH-62 | 0.33 | J158 | 0.32 | S5 | 0.61 |
| HCH-21 | 0.46 | HCH-63 | 0.20 | J159 | 0.61 | S6 | 1.23 |
| HCH-22 | 0.09 | J68 | 0.05 | J160 | 0.06 | S8 | 0.17 |
| HCH-24 | 0.04 | J69 | 1.94 | J161 | 0.35 | S9 | 1.03 |
| HCH-27 | 0.40 | J70 | 0.13 | J162 | 0.41 | S10 | 0.17 |
| J13 | 0.78 | J71 | 2.72 | J163 | 0.57 | S11 | 0.82 |
| J14 | 0.37 | J72 | 1.11 | J164 | 1.44 | S12 | 0.07 |
| J15 | 0.61 | J73 | 5.98 | J165 | 0.42 | S13 | 0.42 |
| J16 | 0.54 | J74 | 3.93 | J166 | 0.68 | S14 | 0.03 |
| J17 | 2.69 | J75 | 5.17 | J167 | 0.36 | S15 | 4.49 |
| J18 | 1.35 | J76 | 3.24 | J168 | 0.46 | S16 | 0.20 |
| J19 | 1.18 | J77 | 2.87 | J169 | 1.71 | S15-2 | 8.62 |
| J21 | 0.58 | J78 | 3.99 | J170 | 2.84 | S16-2 | 0.02 |
| J22 | 0.47 | J79 | 5.27 | J171 | 1.04 | S17 | 0.09 |
| J23 | 0.49 | J80 | 1.64 | J172 | 0.68 | S18 | 0.03 |
| J24 | 5.44 | J81 | 0.75 | J173 | 1.56 | S19 | 0.10 |
| J25 | 0.23 | J82 | 3.76 | J174 | 4.69 | S20 | 4.30 |
| J26 | 0.74 | J83 | 6.38 | J175 | 0.81 | S21 | 0.24 |
| J27 | 0.78 | J84 | 1.07 | J176 | 7.01 | S22 | 0.25 |
| J28 | 8.29 | J85 | 1.44 | J177 | 4.86 | S23.1 | 0.13 |
| J29 | 4.00 | J86 | 0.56 | J178 | 0.70 | S23.2 | 0.33 |
| J30 | 2.36 | J87 | 0.59 | J179 | 0.74 | S23.3 | 0.36 |
| J31 | 0.79 | J88 | 0.60 | J180 | 4.02 | S24 | 0.06 |
| J32 | 40.00 | J89 | 1.31 | J181 | 5.88 | S25 | 0.09 |
| J33 | 40.00 | J90 | 0.74 | J182 | 1.06 | S25-2 | 0.10 |
| J34 | 0.32 | J91 | 0.94 | J183 | 2.38 | S26 | 0.24 |
| J35 | 0.23 | J92 | 4.44 | J184 | 1.62 | S27 | 0.36 |
| J36 | 0.24 | J93 | 0.54 | J185 | 0.58 | S27-2 | 40.00 |
| J37 | 3.78 | J94 | 0.40 | J193 | 69.23 | S28 | 20.69 |
| J38 | 0.40 | J95 | 0.39 | J194 | 10.31 | S29 | 15.53 |
| J39 | 0.79 | J96 | 0.61 | J195 | 0.94 | S30 | 3.05 |
| HCH-25 | 0.27 | J97 | 0.14 | J196 | 1.07 | S31 | 0.65 |
| J40 | 0.24 | J98 | 2.32 | J197 | 1.93 | S32 | 0.44 |
| J41 | 2.48 | J99 | 3.72 | J198 | 1.10 | S32-2 | 0.53 |
| J42 | 0.30 | J100 | 75.00 | J199 | 0.64 | S33 | 0.73 |
| J43 | 1.15 | J101 | 75.00 | J200 | 68.78 | S34 | 0.51 |
| J44 | 1.26 | J102 | 75.00 | J201 | 0.70 | S35 | 0.34 |
| J45 | 0.99 | J103 | 75.00 | J202 | 1.08 | S36 | 0.78 |
| J46 | 125.00 | J104 | 0.61 | J203 | 0.04 | S37 | 0.40 |

-continued

| | | | | | | | |
|---|---|---|---|---|---|---|---|
| J47 | 125.00 | J105 | 12.98 | J205 | 0.05 | S40 | 4.38 |
| J48 | 6.19 | J106 | 1.53 | J206 | 0.02 | S41 | 3.81 |
| J49 | 125.00 | J107 | 1.48 | J207 | 0.22 | S43 | 31.26 |
| J50 | 74.21 | J108 | 2.24 | J208 | 0.39 | S45 | 40.00 |
| J51 | 2.45 | J109 | 3.47 | J209 | 5.47 | S46 | 20.58 |
| J52 | 3.95 | J110 | 2.26 | J210 | 0.39 | S47 | 40.00 |
| J53 | 2.07 | J111 | 2.93 | J211 | 0.05 | S48 | 40.00 |
| J54 | 6.84 | J112 | 0.78 | J212 | 0.26 | S49 | 0.29 |
| J55 | 8.17 | J113 | 1.71 | J213 | 12.18 | S51 | 1.45 |
| J56 | 4.64 | J114 | 0.52 | J214 | 0.39 | S52 | 0.83 |
| J57 | 8.44 | J115 | 40.00 | J215 | 40.00 | S54 | 0.80 |
| J58 | 7.74 | J117 | 0.03 | J216 | 0.17 | S55 | 0.85 |
| J59 | 1.17 | J118 | 0.35 | J217 | 0.42 | S59 | 0.31 |
| J60 | 0.94 | J119 | 0.13 | J218 | 1.50 | S60 | 0.05 |
| J61 | 2.68 | J120 | 40.00 | J219 | 0.44 | S61 | 0.19 |
| J62 | 9.36 | J121 | 40.00 | J220 | 1.03 | S62 | 40.00 |
| J63 | 5.51 | J123 | 0.36 | J221 | 27.84 | S72 | 0.15 |
| J64 | 4.15 | J124 | 0.28 | J222 | 0.41 | S73 | 1.03 |
| J65 | 1.02 | J125 | 1.32 | J223 | 0.43 | NE1 | 1.78 |
| J66 | 3.51 | J126 | 0.77 | J224 | 0.29 | NE2 | 5.05 |
| J67 | 0.36 | J127 | 1.97 | J225 | 0.86 | NE3 | 0.06 |
| HCH-1 | 0.65 | J128 | 0.70 | J226 | 1.09 | NE4 | 1.81 |
| HCH-2 | 0.60 | J131 | 2.99 | J227 | 0.05 | NE5 | 0.46 |
| HCH-3 | 0.51 | J132 | 2.45 | J228 | 0.37 | NE6 | 12.44 |
| HCH-9 | 0.38 | J133 | 4.51 | J229 | 0.85 | NE7 | 1.11 |
| HCH-26 | 0.25 | J134 | 40.00 | J230 | 0.63 | NE8 | 7.24 |
| HCH-4 | 0.58 | J135 | 0.69 | J231 | 0.02 | NE9 | 0.39 |
| HCH-39 | 0.32 | J136 | 1.11 | J232 | 0.22 | NE10 | 11.71 |
| HCH-40 | 0.35 | J137 | 2.98 | J233 | 0.10 | NE12 | 0.61 |
| HCH-41 | 0.23 | J138 | 4.75 | J234 | 0.02 | NE13 | 1.42 |
| HCH-43 | 0.43 | J139 | 12.17 | J235 | 0.08 | NE14 | 0.37 |
| HCH-1-9-4re | 36.1 | HCH-3-48-1 | 0.55 | JDM-10-107 | 0.85 | JDM-06-030C | 0.23 |
| HCH-1-143-2 | 1.25 | JDM-08-142A | 0.11 | JDM-06-030B | 0.29 | | |
| JDM-10-108A | 0.82 | JDM-09-131 | 0.55 | JDM-06-030A | 0.61 | | |

Biological Example 2. Co-Immunoprecipitation Experiments

Some compounds of the present invention were also assessed for their ability to interrupt the binding between MYC and WDR5 in whole cells and/or cellular lysates.

To prepare the cells, procedures analogous to the following procedures were used. HEK293 cells stably expressing MYC2HA were made by retroviral transduction followed by selection in Hygromycin (50 μg/mL). The mixed population was then infected with pBabe-Puro expressing GFP or WDR5 with selection in puromycin (1 μg/mL). For retroviral transductions, HEK293T cells were transfected with the appropriate pBabe vector, the pCL10A packaging vector, and pMax-GFP to estimate transfection efficiency. Viral supernatant was collected and used to infect HEK293 class over three days. HEK293 cells were maintained in DMEM supplemented with 10% FBS. Hygromycin B (50 μg/mL) and puromycin (100 ng/mL) were added to media to maintain plasmid expression. Both cell lines were tested and confirmed negative of mycoplasma using the VenorGem PCR test kit (Sigma Aldrich). After thawing from liquid nitrogen, cells were passaged at least twice before use in experiments, and passaged for a maximum of 25 times.

To perform the experiments, procedures analogous to the following procedures were used. HEK293 cells were harvested and lysates were prepared on ice in lysis buffer (50 mM Tris-HCl pH 8.0, 150 mM NaCl, 5 mM EDTA, 1% Triton X100 and supplemented with protease and phosphatase inhibitors). Equal amounts of protein lysate were subject to immunoprecipitation with M2 agarose overnight (for WDR5-c-MYC) or for 2 hours with magnetic M2 beads (for WDR5-RbBP5) at 4° C. Immune complexes were recovered, washed in lysis buffer, and resolved by SDS-PAGE. Immunoblotting was performed using the indicated primary antibodies (the following primary antibodies were used for this study: α-c-MYC (#5605), α-RbBP5 (#13171), α-WDR5 (#13105), α-FLAG (#8146) all purchased from Cell Signaling), incubated with labeled secondary antibodies and membranes were scanned using the Odyssey imager (LiCor).

Figure 2:
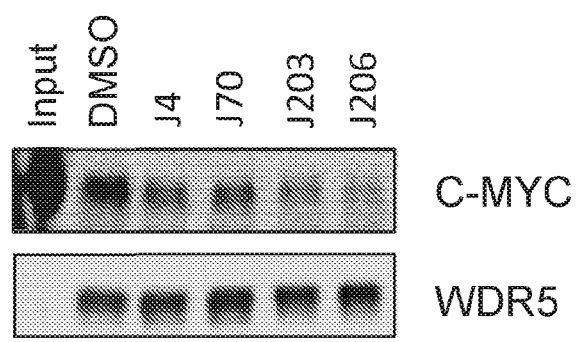
FIG. 2 shows the inhibition of binding between MYC and WDR5 for selected example compounds at a concentration of 30 µM, as described in Biological Example 2.
Figure 3:
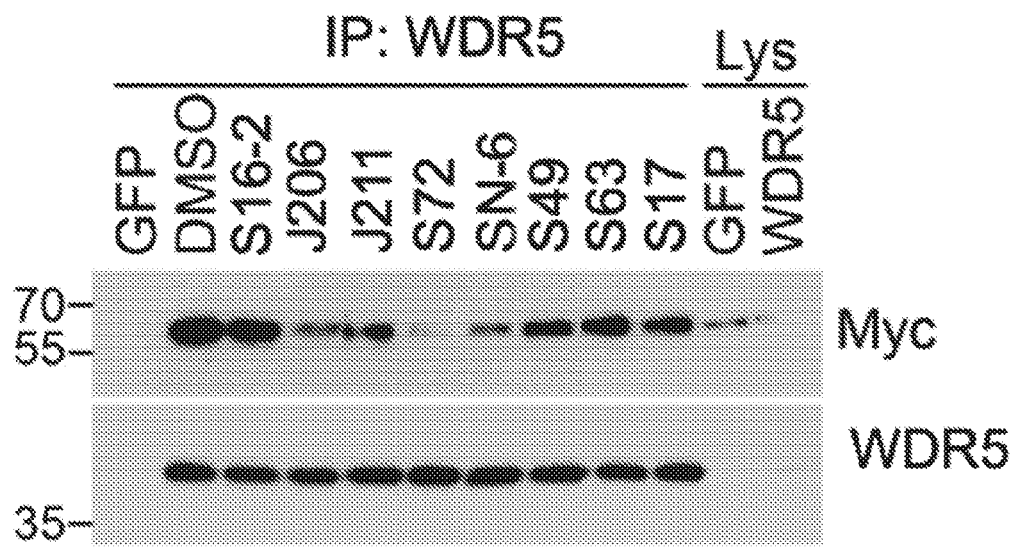
FIG. 3 shows the inhibition of binding between MYC and WDR5 for selected example compounds at a concentration of 50 µM, as described in Biological Example 2.

The results of co-immunoprecipitation experiments for selected compounds of the invention are shown in FIG. 1, FIG. 2, and FIG. 3. FIG. 1 shows selected compounds tested at 50 μM. FIG. 2. Shows selected compounds tested at 30 μM. FIG. 3. Shows selected compounds tested at 50 μM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

REFERENCES

Conacci-Sorrell M, McFerrin L, Eisenman R N. 2014. An overview of MYC and its interactome. *Cold Spring Harbor perspectives in medicine* 4: a014357.

Dang C V. 2011. Therapeutic targeting of Myc-reprogrammed cancer cell metabolism. Cold Spring Harbor symposia on quantitative biology 76: 369-374.

Delmore J E, Issa G C, Lemieux M E, Rahl P B, Shi J, Jacobs H M, Kastritis E, Gilpatrick T, Paranal R M, Qi J et al. 2011. BET bromodomain inhibition as a therapeutic strategy to target c-Myc. *Cell* 146: 904-917.

Lorenzin F, Benary U, Baluapuri A, Walz S, Jung L A, von Eyss B, Kisker C, Wolf J, Eilers M, Wolf E. 2016. Different promoter affinities account for specificity in MYC-dependent gene regulation. *eLife* 5:e15161.

Soucek L, Whitfield J R, Sodir N M, Masso-Valles D, Serrano E, Karnezis A N, Swigart L B, Evan G I. 2013. Inhibition of Myc family proteins eradicates KRas-driven lung cancer in mice. *Genes Dev* 27: 504-513.

Sun Y, Bell J L, Carter D R, Gherardi S, Poulos R C, Milazzo G, Wong J W, Al-Awar R, Tee A E, Liu P Y et al. 2015. WDR5 supports an N-Myc transcriptional complex that drives a pro-tumorigenic gene expression signature in neuroblastoma. *Cancer Res.* 75: 5143-5154.

Tansey W P. 2014. Mammalian MYC proteins and cancer. *New Journal of Science* 2014: 1-27.

Thomas L R, Wang Q, Grieb B C, Phan J, Foshage A M, Sun Q, Olejniczak E T, Clark T, Dey S, Lorey S et al. 2015. Interaction with WDR5 Promotes Target Gene Recognition and Tumorigenesis by MYC. *Mol Cell* 58: 440-452.

The invention claimed is:

1. A compound of formula (I), or a pharmaceutically acceptable salt thereof,

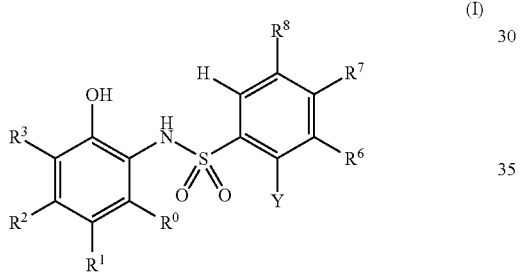

wherein

Y is —XR$^{5b}$, C(O)OH, or C(O)OC$_{1-4}$alkyl;

X is O, S, N, or NR$^{5a}$,

R$^0$ is hydrogen or halogen;

R$^1$ is halogen, cyano, SF$_5$, C$_{1-6}$alkyl, C$_{2-6}$alkenyl, C$_{1-4}$haloalkyl, —OC$_{1-4}$alkyl, —OC$_{1-4}$haloalkyl, or R$^{1G}$;

R$^{1G}$ is C$_{3-6}$cycloalkyl, C$_{5-6}$cycloalkenyl, phenyl, a 4- to 6-membered heterocyclyl, or a 5- to 6-membered heteroaryl, wherein R$^{1G}$ is optionally substituted with 1-4 substituents independently selected from the group consisting of halogen, cyano, oxo or a cyclic ketal thereof, C$_{1-4}$alkyl, and C$_{1-4}$haloalkyl;

R$^2$ is hydrogen, C$_{1-4}$alkyl, —OC$_{1-4}$alkyl, —OC$_{1-4}$haloalkyl, halogen, or OH;

R$^3$ is C(O)OR$^{3a}$, C(O)NR$^{3b}$R$^{3c}$, C(O)R$^{3a}$, SR$^{3d}$, S(O)R$^{3d}$, S(O)$_2$R$^{3d}$, S(O)$_2$NR$^{3b}$R$^{3c}$, NO$_2$, NR$^{3b}$C(O)R$^{3c}$, or NR$^{3b}$C(O)NR$^{3b}$R$^{3c}$,

R$^{3a}$ is hydrogen, C$_{1-8}$alkyl, C$_{1-8}$haloalkyl, -L$^1$-R$^{30}$, G$^1$, or -L$^1$-G$^2$;

R$^{3b}$ and R$^{3c}$ are independently hydrogen, C$_{1-8}$alkyl, C$_{1-8}$haloalkyl, -L$^1$-R$^{30}$, G$^1$, or -L$^1$-G$^2$, wherein R$^{3b}$ and R$^{3c}$ together with the nitrogen to which they attach optionally form a 3- to 8-membered heterocyclyl, the heterocyclyl being optionally substituted with 1-4 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, —C$_{1-6}$alkylene-OH, —C$_{1-6}$alkylene-OC$_{1-4}$alkyl, NH$_2$, —NHC$_{1-4}$alkyl, —N(C$_{1-4}$alkyl)$_2$, and —S(O)$_2$C$_{1-4}$alkyl; or R$^{3b}$ and R$^{3c}$ together with the intervening —NC(O)— or —NC(O)N(R$^{3b}$)—, optionally form a 5- to 8-membered heterocyclyl, the heterocyclyl being optionally substituted with 1-4 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, NH$_2$, —NHC$_{1-4}$alkyl, and —N(C$_{1-4}$alkyl)$_2$;

R$^{3d}$ is C$_{1-8}$alkyl, C$_{1-8}$haloalkyl, -L$^1$-R$^{30}$, G$^1$, or -L$^1$-G$^2$;

L$^1$ is C$_{1-6}$alkylene, wherein the C$_{1-6}$alkylene is optionally substituted with halogen, OH, COOH, —C(O)OC$_{1-4}$alkyl, C(O)NH$_2$, —C(O)NHC$_{1-4}$alkyl, or —C(O)N(C$_{1-4}$ alkyl)$_2$;

R$^{30}$ is —OR$^{30a}$, —SR$^{30a}$, —NR$^{30b}$R$^{30c}$, COOH, —C(O)OC$_{1-4}$alkyl, C(O)NH$_2$, —C(O)NHC$_{1-4}$alkyl, or —C(O)N(C$_{1-4}$alkyl)$_2$;

R$^{30a}$, R$^{30b}$, and R$^{30c}$ are independently hydrogen, C$_{1-4}$alkyl, C$_{1-4}$haloalkyl, G$^1$, or -L$^2$ G$^2$;

L$^2$ is C$_{1-3}$alkylene;

G$^1$, at each occurrence, is independently C$_{3-10}$carbocyclyl, a 6- to 12-membered aryl, a 5- to 12-membered heteroaryl, or a 4- to 12-membered heterocyclyl, wherein G$^1$ is attached to the parent molecular moiety at a carbon atom of G$^1$ and optionally substituted with 1-5 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, NH$_2$, —NHC$_{1-4}$alkyl, and —N(C$_{1-4}$alkyl)$_2$;

G$^2$, at each occurrence, is independently C$_{3-10}$carbocyclyl, a 6- to 12-membered aryl, a 5- to 12-membered heteroaryl, or a 4- to 12-membered heterocyclyl, wherein G$^2$ is optionally substituted with 1-5 substituents independently selected from the group consisting of halogen, cyano, C$_{1-4}$alkyl, C$_{1-4}$haloalkyl, oxo, OH, —OC$_{1-4}$alkyl, —OC$_{1-4}$haloalkyl, NH$_2$, —NHC$_{1-4}$alkyl, and —N(C$_{1-4}$alkyl)$_2$;

R$^4$ is hydrogen, halogen, OH, —OC$_{1-4}$alkyl, —OC$_{1-4}$haloalkyl, —OC$_{3-6}$cycloalkyl, NH$_2$, —NHC$_{1-4}$alkyl, —N(C$_{1-4}$alkyl)$_2$, —NHC$_{3-6}$cycloalkyl, —N(C$_{1-4}$alkyl)(C$_{3-6}$cycloalkyl), or —N(C$_{3-6}$cycloalkyl)$_2$;

R$^{5a}$ is hydrogen, C$_{1-6}$alkyl, C$_{1-6}$haloalkyl, C$_{3-6}$cycloalkyl, or —C$_{1-3}$alkylene-C$_{3-6}$cycloalkyl;

R$^{5b}$ is hydrogen, C$_{1-6}$alkyl, C$_{1-6}$haloalkyl, C$_{3-6}$cycloalkyl, or —C$_{1-3}$alkylene-C$_{3-6}$cycloalkyl;

alternatively, R$^{5a}$ and R$^{5b}$, together with the nitrogen to which they attach form a 3- to 8-membered heterocyclyl, the heterocyclyl being optionally substituted with 1-4 substituents independently selected from the group consisting of halogen, cyano, C$_{1-4}$alkyl, C$_{1-4}$haloalkyl, OH, —OC$_{1-4}$alkyl, —OC$_{1-4}$haloalkyl, —C$_{1-6}$alkylene-OH, and —C$_{1-6}$alkylene-OC$_{1-4}$alkyl;

R$^6$ is hydrogen, halogen, cyano, C(O)OH, SF$_5$, NO$_2$, C$_{1-4}$alkyl, C$_{1-4}$haloalkyl, —OC$_{1-4}$alkyl, —OC$_{1-4}$haloalkyl, —C$_{1-6}$alkylene-OH, —C$_{1-6}$alkylene-OC$_{1-4}$alkyl, C$_{3-6}$cycloalkyl, or a 4- to 7-membered heterocyclyl, wherein the cycloalkyl and heterocyclyl are optionally substituted with 1-4 substituents independently selected from the group consisting of halogen, cyano, C$_{1-4}$alkyl, and C$_{1-4}$haloalkyl;

alternatively, R$^{5b}$ and R$^6$, together with the intervening atoms form a 5- to 6-membered heteroaryl or a 5- to 7-membered heterocycle, wherein the heteroaryl and heterocycle are optionally substituted with 1-4 substituents independently selected from the group consisting of halogen, cyano, $C_{1-4}$alkyl, and $C_{1-4}$haloalkyl;

$R^7$ is hydrogen, halogen, cyano, $C_{1-4}$alkyl, $C_{1-4}$haloalkyl, —$OC_{1-4}$alkyl, or —$OC_{1-4}$haloalkyl; and $R^8$ is halogen, cyano, $C_{1-2}$alkyl, $C_{1-2}$haloalkyl, —$OC_{1-2}$alkyl, or —$OC_{1-2}$haloalkyl;

provided the compound of formula (I) is not
3-[[(6-methyl-8-quinolinyl)sulfonyl]amino]-5-(trifluoromethyl)-benzoic acid;
3-[[(5-bromo-2-methoxyphenyl)sulfonyl]amino]-5-(trifluoromethyl)-benzoic acid; or
3-[[(3-bromo-5-chloro-2-methoxyphenyl)sulfonyl]amino]-5-(trifluoromethyl)-benzoic acid.

2. The compound of claim 1, or a pharmaceutically acceptable salt thereof, wherein $R^4$ is OH or hydrogen.

3. The compound of claim 1, or a pharmaceutically acceptable salt thereof, wherein $R^2$ is OH, hydrogen, or $C_{1-4}$alkyl.

4. The compound of claim 1, or a pharmaceutically acceptable salt thereof, wherein $R^3$ is $C(O)OR^{3a}$, $C(O)NR^{3b}R^{3c}$, $S(O)R^{3d}$, $S(O)_2R^{3d}$, $NO_2$, $NR^{3b}C(O)R^{3c}$, or $NR^{3b}C(O)NR^{3b}R^{3c}$.

5. The compound of claim 4, or a pharmaceutically acceptable salt thereof, wherein $R^3$ is $C(O)OH$.

6. The compound of claim 4, or a pharmaceutically acceptable salt thereof, wherein $R^3$ is $C(O)NR^{3b}R^{3c}$.

7. The compound of claim 4, or a pharmaceutically acceptable salt thereof, wherein $R^3$ is $C(O)OH$, $C(O)NH_2$, $C(O)NHCH_3$, $C(O)NHCH_2CH_2OCH_3$, $C(O)NHCH_2CH_2N(CH_3)_2$, $NO_2$, $S(O)_2CH_3$, $S(O)_2CH_2CH_3$, $S(O)_2CH(CH_3)_2$, $S(O)_2CH_2CH_2N(CH_2CH_3)_2$, $S(O)_2CH_2CH_2N(CH(CH_3)_2)_2$, $S(O)_2CH_2CH_2CH_2N(CH(CH_3)_2)_2$, $S(O)CH_3$, $S(O)CH_2CH_3$,

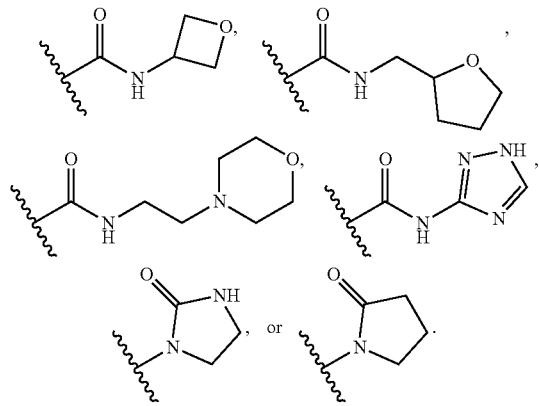

8. The compound of claim 1, or a pharmaceutically acceptable salt thereof, wherein $R^1$ is halogen, $SF_5$, $C_{1-4}$alkyl, $C_{1-4}$haloalkyl, —$OC_{1-4}$haloalkyl, or $R^{1G}$, wherein $R^{1G}$ is optionally substituted with 1-4 substituents independently selected from the group consisting of halogen, cyano, $C_{1-4}$alkyl, and $C_{1-4}$haloalkyl.

9. The compound of claim 1, or a pharmaceutically acceptable salt thereof, wherein Y is —$XR^{5b}$, X is O; and $R^{5b}$ is hydrogen of $C_{1-4}$alkyl.

10. The compound of claim 1, or a pharmaceutically acceptable salt thereof, wherein Y is —$XR^{5b}$; X is O; and $R^{5b}$ and $R^6$, together with the intervening atoms form a 5- to 7-membered heterocycle containing 1-2 oxygen atoms, the heterocycle being optionally substituted with 1-4 substituents independently selected from the group consisting of halogen, cyano, $C_{1-4}$alkyl, and $C_{1-4}$haloalkyl.

11. The compound of claim 1, or a pharmaceutically acceptable salt thereof, wherein Y is —$XR^{5b}$, X is N; and $R^{5b}$ and $R^6$, together with the intervening atoms form a 6-membered heteroaryl containing 1-2 nitrogen atoms, the heteroaryl being optionally substituted with 1-4 substituents independently selected from the group consisting of halogen, cyano, $C_{1-4}$alkyl, and $C_{1-4}$haloalkyl.

12. The compound of claim 1, or a pharmaceutically acceptable salt thereof, wherein Y is $C(O)OH$ or $C(O)OC_{1-4}$alkyl.

13. The compound of claim 1, or a pharmaceutically acceptable salt thereof, wherein $R^6$ is hydrogen, halogen, $C_{1-4}$alkyl, —$OC_{1-4}$alkyl, —$OC_{1-4}$haloalkyl, or $C(O)OH$.

14. The compound of claim 1, or a pharmaceutically acceptable salt thereof, wherein $R^7$ is hydrogen, $C_{1-4}$alkyl, or —$OC_{1-4}$alkyl.

15. The compound of claim 1, or a pharmaceutically acceptable salt thereof, wherein $R^8$ is halogen.

16. A compound of formula (II), or a pharmaceutically acceptable salt thereof,

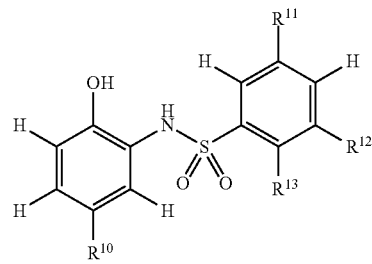

wherein
$R^{10}$ is cyano, —$C_{1-3}$alkylene-cyano, $SF_5$, $C_{1-4}$alkyl, $C_{1-4}$haloalkyl, —$OC_{1-4}$alkyl, —$OC_{1-4}$haloalkyl, or $C_{3-6}$cycloalkyl, wherein the cycloalkyl is optionally substituted with 1-4 substituents independently selected from the group consisting of halogen, cyano, $C_{1-4}$alkyl, and $C_{1-4}$haloalkyl;
$R^{11}$ is halogen;
$R^{12}$ is hydrogen or halogen; and
$R^{13}$ is hydrogen or OH.

17. The compound of claim 16, or a pharmaceutically acceptable salt thereof, wherein
$R^{10}$ is chloro, cyano, —$CH_2$-cyano, $SF_5$, $CF_3$, —$OCF_3$, or

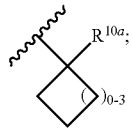

and
$R^{10a}$ is cyano or $CF_3$.

18. A pharmaceutical composition comprising the compound of claim 1, or a pharmaceutically acceptable salt thereof, and a pharmaceutically acceptable carrier.

* * * * *